(12) United States Patent
Akiyama et al.

(10) Patent No.: US 9,815,835 B2
(45) Date of Patent: *Nov. 14, 2017

(54) SUBSTITUTED POLYCYCLIC CARBAMOLYPYRIDONE DERIVATIVE

(71) Applicant: Shionogi & Co., Ltd., Osaka-Shi, Osaka (JP)

(72) Inventors: Toshiyuki Akiyama, Osaka (JP); Kenji Takaya, Osaka (JP); Makoto Kawai, Osaka (JP); Yoshiyuki Taoda, Osaka (JP); Minako Mikamiyama, Osaka (JP); Kenji Morimoto, Osaka (JP); Kenji Tomita, Osaka (JP); Hidenori Mikamiyama, Osaka (JP); Naoyuki Suzuki, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/252,791

(22) Filed: Aug. 31, 2016

(65) Prior Publication Data

US 2016/0368921 A1    Dec. 22, 2016

Related U.S. Application Data

(62) Division of application No. 14/536,079, filed on Nov. 7, 2014, now Pat. No. 9,469,638, which is a division of application No. 13/378,334, filed as application No. PCT/JP2010/060006 on Jun. 14, 2010, now Pat. No. 8,927,710.

(30) Foreign Application Priority Data

Jun. 15, 2009   (JP) ................................. 2009-142166

(51) Int. Cl.
| | |
|---|---|
| *C07D 487/14* | (2006.01) |
| *C07D 487/20* | (2006.01) |
| *A61K 31/53* | (2006.01) |
| *A61P 31/16* | (2006.01) |
| *C07D 471/04* | (2006.01) |
| *C07D 471/14* | (2006.01) |
| *C07D 498/14* | (2006.01) |

(52) U.S. Cl.
CPC ............ *C07D 471/04* (2013.01); *A61K 31/53* (2013.01); *C07D 471/14* (2013.01); *C07D 487/14* (2013.01); *C07D 487/20* (2013.01); *C07D 498/14* (2013.01)

(58) Field of Classification Search
CPC .... C07D 487/14; C07D 487/20; C07D 87/14; C07D 87/20; A61K 31/53
USPC ................. 544/183, 184; 514/243
See application file for complete search history.

(56) References Cited

U.S. PATENT DOCUMENTS

| 5,475,109 A | 12/1995 | Selnick et al. |
|---|---|---|
| 5,618,830 A | 4/1997 | Selnick et al. |
| 8,188,271 B2 | 5/2012 | Yoshida et al. |
| 8,927,710 B2 * | 1/2015 | Akiyama ............. C07D 471/04 544/111 |
| 8,987,441 B2 * | 3/2015 | Takahashi ............ C07D 471/04 544/112 |
| 2008/0161271 A1 | 7/2008 | Yoshida et al. |
| 2009/0143356 A1 | 6/2009 | Yoshida et al. |

FOREIGN PATENT DOCUMENTS

| EP | 1 544 199 A1 | 6/2005 |
|---|---|---|
| GB | 2 280 435 A | 2/1995 |
| WO | WO 2004/024078 A2 | 3/2004 |
| WO | WO 2005/087766 A1 | 9/2005 |
| WO | WO 2005/092099 A1 | 10/2005 |
| WO | WO 2006/066414 A1 | 6/2006 |
| WO | WO 2006/116764 A1 | 11/2006 |

OTHER PUBLICATIONS

International Search Report from the Japanese Patent Office for International Application No. PCT/JP2010/060006, dated Aug. 24, 2010.
Hensens et al.; "Isolation and Structure of Flutimide, A Novel Endonuclease Inhibitor of Influenza Virus", Tetrahedron Letters, vol. 36, No. 12, pp. 2005-2008, (1995).
Singh; "Total Synthesis of Flutimide, A Novel Endonuclease Inhibitor of Influenza Virus", Tetrahedron Letters, vol. 36, No. 12, pp. 2009-2012, (1995).
Tomassini et al.; "Inhibition of CAP ($M^7$GpppXm)—Dependent Endonuclease of Influenza Virus by 4-Substituted 2,4-Dioxobutanoic Acid Compounds", Antimicrobial Agents and Chemotherapy, vol. 38, No. 12, pp. 2827-2837, (1994).
Hastings et al.; "Anti-Influenza Virus Activities of 4-Substituted 2,4-Dioxobutanoic Acid Inhibitors", Antimicrobial Agents and Chemotherapy, vol. 40, No. 5, pp. 1304-1307, (1996).
Parkes et al.; "Use of a Pharmacophore Model to Discover a New Class of Influenza Endonuclease Inhibitors", Journal of Medicinal Chemistry, vol. 46, No. 7, pp. 1153-1164, (2003).
Wai et al.; "Dihydroxypyridopyrazine-1,6-Dione HIV-1 Integrase Inhibitors", Bioorganic & Medicinal Chemistry Letters, vol. 17, pp. 5595-5599, (2007).
Dias et al.; "The CAP-Snatching Endonuclease of Influenza Virus Polymerase Resides in the PA Subunit", Nature, pp. 1-5, (2009).

\* cited by examiner

*Primary Examiner* — Venkataraman Balasubramanian
(74) *Attorney, Agent, or Firm* — Finnegan, Henderson, Farabow, Garrett & Dunner, LLP

(57) ABSTRACT

This invention provides compounds having antiviral activities especially inhibiting activity for influenza virus, more preferably provides substituted 3-hydroxy-4-pyridone derivatives having cap-dependent endonuclease inhibitory activity.

12 Claims, No Drawings

SUBSTITUTED POLYCYCLIC CARBAMOLYPYRIDONE DERIVATIVE

This is a division of application Ser. No. 14/536,079, filed Nov. 7, 2014, which is a division of application Ser. No. 13/378,334, filed Mar. 2, 2012, which is the U.S. national stage application of International Application No. PCT/JP2010/060006, filed on Jun. 14, 2010, which claims the benefit of priority from Japanese Application No. 2009-142166, filed on Jun. 15, 2009. All of these applications are herein incorporated by reference in their entireties.

TECHNICAL FIELD

This invention relates to substituted polycyclic carbamoylpyridone derivatives having cap-dependent endonuclease inhibitory activity, and pharmaceutical compositions including thereof.

BACKGROUND ART

Influenza is an acute respiratory infectious disease caused by infection with an influenza virus. In Japan, there is a report of a few millions of influenza-like patients every winter, and influenza is accompanied with high morbidity and mortality. Influenza is a particularly important disease in a high risk population such as baby and elderly, a complication rate with pneumonia is high in elderly, and death with influenza is occupied with elderly in many cases.

As anti-influenza drugs, Symmetrel (trade name: Amantadine) and Flumadine (trade name: Rimantadine) which inhibit the denucleation process of a virus, and Oseltamivir (trade name: Tamiflu) and Zanamivir (trade name: Relenza) which are neuraminidase inhibitors suppressing virus budding and release from a cell are known. However, since problems of appearances of resistant strains and side effects, and worldwide epidemic of a new-type influenza virus having high pathogenicity and mortality are feared, development of an anti-influenza drug having a novel mechanism has been desired.

Since a cap-dependent endonuclease which is an influenza virus-derived enzyme is essential for virus proliferation, and has the virus-specific enzymatic activity which is not possessed by a host, it is believed that the endonuclease is suitable for a target of an anti-influenza drug. The cap-dependent endonuclease has a host mRNA precursor as a substrate, and has the endonuclease activity of producing a fragment of 9 to 13 bases including a cap structure (not including the number of bases of the cap structure). This fragment functions as a primer of a virus RNA polymerase, and is used in synthesizing mRNA encoding a virus protein. That is, it is believed that a substance which inhibits the cap-dependent endonuclease inhibits synthesis of a virus protein by inhibiting synthesis of virus mRNA and, as a result, inhibits virus proliferation.

As the substance which inhibits the cap-dependent endonuclease, flutamide (Patent Document 1 and Non-Patent Documents 1 and 2) and 4-substituted 2,4-dioxobutanoic acid (Non-Patent Documents 3 to 5) are reported, but they have not yet led to clinical use as anti-influenza drugs. In addition, Patent Documents 2 to 9 and Non-Patent Document 6 describe compounds having a similar structure to that of this invention, however, the documents do not describe cap-dependent endonuclease.

PRIOR ART DOCUMENTS

Patent Documents

[Patent Document 1] GB No. 2280435 specification
[Patent Document 2] International Publication No. 2007/049675 pamphlet
[Patent Document 3] International Publication No. 2006/088173 pamphlet
[Patent Document 4] International Publication No. 2006/066414 pamphlet
[Patent Document 5] International Publication No. 2005/092099 pamphlet
[Patent Document 6] International Publication No. 2005/087766 pamphlet
[Patent Document 7] International Publication No. 2005/016927 pamphlet
[Patent Document 8] International Publication No. 2004/024078 pamphlet
[Patent Document 9] International Publication No. 2006/116764 pamphlet Non-Patent Documents

[Non-Patent Document 1] Tetrahedron Lett 1995, 36(12), 2005
[Non-Patent Document 2] Tetrahedron Lett 1995, 36(12), 2009
[Non-Patent Document 3] Antimicrobial Agents And Chemotherapy, December 1994, p. 2827-2837
[Non-Patent Document 4] Antimicrobial Agents And Chemotherapy, May 1996, p. 1304-1307
[Non-Patent Document 5] J. Med. Chem. 2003, 46, 1153-1164
[Non-Patent Document 6] Bioorganic & Medicinal Chemistry Letters 17(2007)5595-5599

SUMMARY OF THE INVENTION

Problems to be Solved by the Invention

An object of the present invention is to provide compounds having antiviral activities especially inhibiting growth activity of influenza virus. More preferably, this invention provides compounds and medicament containing the same which inhibit increase of influenza virus by exhibiting cap-dependent endonuclease inhibitory activity.

Means for Solving the Problems

[Item 1']
A CAP dependent endonuclease inhibitor containing a compound represented by formula (I), a pharmaceutically acceptable salt, or a solvate thereof:

[Chemical formula 1]

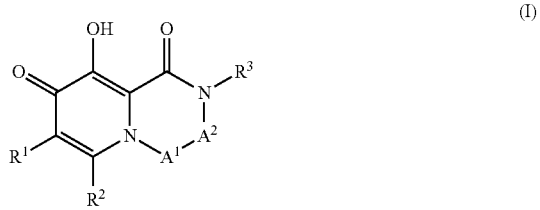

(wherein
$R^1$ is hydrogen, halogen, hydroxy, carboxy, cyano, formyl, lower alkyl optionally substituted by substituent group A, lower alkenyl optionally substituted by substituent group A, lower alkynyl optionally substituted by substituent group A, lower alkyloxy optionally substituted by substituent group A, lower alkenyloxy optionally substituted by substituent group A, lower alkylcarbonyl optionally substituted by substituent group A, lower alkyloxycarbonyl optionally substituted by substituent group A, carbocyclic group optionally substituted by substituent group A, carbocycle lower alkyl optionally substituted by substituent group A, carbocyclecarbonyl optionally substituted by substituent group A, carbocycleoxy optionally substituted by substituent group A, carbocycleoxycarbonyl optionally substituted by substituent group A, heterocyclic group optionally substituted by substituent group A, heterocycle lower alkyl optionally substituted by substituent group A, heterocyclecarbonyl optionally substituted by substituent group A, heterocycleoxy optionally substituted by substituent group A, heterocycleoxycarbonyl optionally substituted by substituent group A, —Z—N($R^{X1}$)($R^{X2}$),
—Z—N($R^{X3}$)—$SO_2$—($R^{X4}$),
—Z—C(=O)—N($R^{X5}$)—$SO_2$—($R^{X6}$),
—Z—N($R^{X7}$)—C(=O)—$R^{X8}$,
—Z—C(=O)—N($R^{X9}$)($R^{X10}$),
—Z—S—$R^{X11}$,
—Z—$SO_2$—$R^{X12}$,
—Z—S(=O)—$R^{X13}$,
—Z—N($R^{X14}$)—C(=O)—O—$R^{X15}$,
—Z—N($R^{X16}$)—C(=O)—N($R^{X17}$)($R^{X18}$),
—Z—C(=O)—N($R^{X19}$)—C(=O)—N($R^{X20}$)($R^{X21}$), or
—Z—N($R^{X22}$)—C(=O)—C(=O)—$R^{X23}$ (wherein $R^{X1}$, $R^{X2}$, $R^{X3}$, $R^{X5}$, $R^{X7}$, $R^{X8}$, $R^{X9}$, $R^{X10}$, $R^{X11}$, $R^{X14}$, $R^{X15}$, $R^{X16}$, $R^{X17}$, $R^{X18}$, $R^{X19}$, $R^{X20}$, $R^{X21}$, $R^{X22}$, and $R^{X23}$ are each independently selected from a substituent group consisting of hydrogen, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{X4}$, $R^{X6}$, $R^{X12}$, and $R^{X13}$ are each independently selected from a substituent group consisting of, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{X1}$ and $R^{X2}$, $R^{X9}$ and $R^{X10}$, $R^{X17}$ and $R^{X18}$, and $R^{X20}$ and $R^{X21}$ each may be taken together with an adjacent atom to form heterocycle, and Z is a bond or straight or branched lower alkylene);

$R^2$ is hydrogen, halogen, hydroxy, carboxy, cyano, formyl, lower alkyl optionally substituted by substituent group A, lower alkenyl optionally substituted by substituent group A, lower alkynyl optionally substituted by substituent group A, lower alkyloxy optionally substituted by substituent group A, lower alkenyloxy optionally substituted by substituent group A, lower alkylcarbonyl optionally substituted by substituent group A, lower alkyloxycarbonyl optionally substituted by substituent group A, carbocyclic group optionally substituted by substituent group A, carbocycle lower alkyl optionally substituted by substituent group A, carbocyclecarbonyl optionally substituted by substituent group A, carbocycleoxy optionally substituted by substituent group A, carbocycleoxycarbonyl optionally substituted by substituent group A, heterocyclic group optionally substituted by substituent group A, heterocycle lower alkyl optionally substituted by substituent group A, heterocyclecarbonyl optionally substituted by substituent group A, heterocycleoxy optionally substituted by substituent group A, heterocycleoxycarbonyl optionally substituted by substituent group A, —Z—N($R^{Y1}$)—$SO_2$—$R^{Y2}$,
—Z—N($R^{Y3}$)—C(=O)—$R^{Y4}$,
—Z—N($R^{Y5}$)—C(=O)—O—$R^{Y6}$,
—Z—C(=O)—N($R^{Y7}$)($R^{Y8}$),
—Z—N($R^{Y9}$)($R^{Y10}$), or
—Z—$SO_2$—$R^{Y11}$ (wherein $R^{Y1}$, $R^{Y3}$, $R^{Y4}$, $R^{Y5}$, $R^{Y6}$, $R^{Y7}$, $R^{Y8}$, $R^{Y9}$, and $R^{Y10}$ are each independently selected from a substituent group consisting of hydrogen, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{Y2}$ and $R^{Y11}$ are each independently selected from a substituent group consisting of lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{Y7}$ and $R^{Y8}$, and $R^{Y9}$ and $R^{Y10}$ may be taken together with an adjacent atom to form heterocycle and Z is a bond or straight or branched lower alkylene);

$R^3$ is hydrogen, hydroxy, carboxy, cyano, formyl, lower alkyl optionally substituted by substituent group A, lower alkenyl optionally substituted by substituent group A, lower alkynyl optionally substituted by substituent group A, lower alkyloxy optionally substituted by substituent group A, lower alkenyloxy optionally substituted by substituent group A, lower alkylcarbonyl optionally substituted by substituent group A, lower alkyloxycarbonyl optionally substituted by substituent group A, carbocyclic group optionally substituted by substituent group A, carbocycle lower alkyl optionally substituted by substituent group A, carbocycleoxy lower alkyl optionally substituted by substituent group A, carbocyclecarbonyl optionally substituted by substituent group A, carbocycleoxy optionally substituted by substituent group A, carbocycleoxycarbonyl optionally substituted by substituent group A, heterocyclic group optionally substituted by substituent group A, heterocycle lower alkyl optionally substituted by substituent group A, heterocycleoxy lower alkyl optionally substituted by substituent group A, heterocyclecarbonyl optionally substituted by substituent group A, heterocycleoxy optionally substituted by substituent group A, heterocycleoxycarbonyl optionally substituted by substituent group A, —Z—N($R^{Z1}$)—$SO_2$—$R^{Z2}$,
—Z—N($R^{Z3}$)—C(=O)—$R^{Z4}$,
—Z—N($R^{Z5}$)—C(=O)—O—$R^{Z6}$,
—Z—C(=O)—N($R^{Z7}$)($R^{Z8}$),
—Z—N($R^{Z9}$)($R^{Z10}$),
—Z—$SO_2$—$R^{Z11}$, or
—Z—N($R^{Z12}$)—O—C(=O)—$R^{Z13}$ (wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from a substituent group consisting of hydrogen, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{Z2}$ and $R^{Z11}$ are each independently selected from a substituent group consisting of lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{Z7}$ and $R^{Z8}$, and $R^{Z9}$ and $R^{Z10}$ each may be taken together with an adjacent atom to form heterocycle, and Z is a bond or straight or branched lower alkylene) and;

a) either $A^1$ or $A^2$ is $CR^5R^6$, and the other is $NR^7$, or b) $A^1$ is $CR^8R^9$, and $A^2$ is $CR^{10}R^{11}$, $R^5$, $R^6$, $R^7$, $R^8$, $R^9$, $R^{10}$, and $R^{11}$ are each independently selected from a substituent group consisting of hydrogen, carboxy, cyano, lower alkyl optionally substituted by substituent group A, lower alkenyl optionally substituted by substituent group A, lower alkynyl optionally substituted by substituent group A, lower alkyl carbonyl optionally substituted by substituent group A, lower alkyl oxycarbonyl optionally substituted by substituent group A, carbocyclic group optionally substituted by substituent group A, carbocycle lower alkyl optionally substituted by substituent group A, carbocycleoxy lower alkyl optionally substituted by substituent group A, carbocyclecarbonyl optionally substituted by substituent group A, carbocycleoxycarbonyl optionally substituted by substituent group A, heterocyclic group optionally substituted by substituent group A, heterocycle lower alkyl optionally substituted by substituent group A, heterocycleoxy lower alkyl optionally substituted by substituent group A, heterocyclecarbonyl optionally substituted by substituent group A, heterocycleoxycarbonyl optionally substituted by substituent group A, —Z—S—$R^{V1}$,
—Z—S(=O)—$R^{V2}$,
—Z—SO$_2$—$R^{V3}$,
—C(=O) C(=O)—$R^{V4}$,
—C(=O)—N($R^{V5}$)($R^{V6}$)
—Z—N($R^{V7}$)—C(=O)—O—$R^{V8}$, or
—Z—N($R^{V9}$)—C(=O)—$R^{V10}$ (wherein $R^{V1}$, $R^{V4}$, $R^{V5}$, $R^{V6}$, $R^{V7}$, $R^{V8}$, $R^{V9}$, and $R^{V10}$ are each independently selected from a substituent group consisting of hydrogen, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{V2}$ and $R^{V3}$ are each independently selected from a substituent group consisting of lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{V5}$ and $R^{V6}$ may be taken together with an adjacent atom to form heterocycle, and Z is a bond or straight or branched lower alkylene), and $R^5$ and $R^6$ may be taken together with an adjacent atom to form carbocycle;

1) when $A^1$ is $CR^5R^6$ and $A^2$ is $NR^7$,
$R^3$ and $R^7$ may be taken together with an adjacent atom to form heterocycle optionally substituted by substituent group B or may form a condensed ring, 2) when $A^1$ is $NR^{7a}$ and $A^2$ is $CR^{10}R^{11}$,
$R^3$ and $R^6$ may be taken together with an adjacent atom to form heterocycle optionally substituted by substituent group B or may form condensed ring, or 3) when $A^1$ is $CR^8R^9$, and $A^2$ is $CR^{10}R^{11}$,
$R^8$ and $R^{10}$ may be taken together with an adjacent atom to form a bond, and $R^8$ and $R^{10}$ may be taken together with an adjacent atom to form carbocycle or heterocycle, or
$R^3$ and $R^{11}$ may be taken together with an adjacent atom to form heterocycle optionally substituted by substituent group B or may form condensed ring;

with a proviso that the following case of c) and d) are excluded;

c) $R^5$, $R^6$, and $R^7$ are all hydrogens
d) $R^8$, $R^9$, $R^{10}$, and $R^{11}$ are all hydrogens;

Substituent group A: halogen, cyano, hydroxy, carboxy, formyl, amino, oxo, nitro, lower alkyl, halogeno lower alkyl, lower alkyloxy, lower alkylthio, hydroxy lower alkyl, carbocyclic group, heterocyclic group, heterocyclic group substituted by oxo, carbocycle lower alkyloxy, carbocycleoxy lower alkyl, carbocycle lower alkyloxy lower alkyl, heterocycle lower alkyloxy, heterocycleoxy lower alkyl, heterocycle lower alkyloxy lower alkyl, halogeno lower alkyloxy, lower alkyloxy lower alkyl, lower alkyloxy lower alkyloxy, lower alkylcarbonyl, lower alkylcarbonyloxy, lower alkyloxycarbonyl, lower alkylamino, lower alkylcarbonylamino, halogeno lower alkyl carbonylamino, lower alkylaminocarbonyl, lower alkylsulfonyl, lower alkylsulfinyl, and lower alkylsulfonylamino;

Substituent group B: halogen, cyano, hydroxy, carboxy, formyl, amino, oxo, nitro, lower alkyl, halogeno lower alkyl, lower alkyloxy, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, lower alkylsulfonylamino, carbocyclic group optionally substituted by substituent group A, heterocyclic group optionally substituted by substituent group A, carbocycle lower alkyl optionally substituted by substituent group A, and heterocycle lower alkyl optionally substituted by substituent group A).

[Item 2']

A CAP dependent endonuclease inhibitor according to item 1', wherein $R^1$ is hydrogen, halogen, hydroxy, carboxy, cyano, formyl, lower alkyl optionally substituted by substituent group A, lower alkenyl optionally substituted by substituent group A, lower alkynyl optionally substituted by substituent group A, lower alkyloxy optionally substituted by substituent group A, lower alkenyloxy optionally substituted by substituent group A, lower alkylcarbonyl optionally substituted by substituent group A, lower alkyloxycarbonyl optionally substituted by substituent group A, carbocyclic group optionally substituted by substituent group A, carbocycle lower alkyl optionally substituted by substituent group A, carbocyclecarbonyl optionally substituted by substituent group A, carbocycleoxy optionally substituted by substituent group A, carbocycleoxycarbonyl optionally substituted by substituent group A, heterocyclic group optionally substituted by substituent group A, heterocycle lower alkyl optionally substituted by substituent group A, heterocyclecarbonyl optionally substituted by substituent group A, heterocycleoxy optionally substituted by substituent group A, heterocycleoxycarbonyl optionally substituted by substituent group A,
—Z—N(R$^{X1}$)(R$^{X2}$),
—Z—N(R$^{X3}$)—SO$_2$—(R$^{X4}$),
—Z—C(=O)—N(R$^{X5}$)—SO$_2$—(R$^{X6}$),
—Z—N(R$^{X7}$)—C(=O)—R$^{X8}$,
—Z—S—R$^{X11}$,
—Z—SO$_2$—R$^{X12}$,
—Z—S(=O)—R$^{X13}$,
—Z—N(R$^{X14}$)—C(=O)—O—R$^{X8}$,
—Z—N(R$^{X16}$)—C(=O)—N(R$^{X17}$)(R$^{X18}$), or
—Z—N(R$^{X22}$)—C(=O)—C(=O)—R$^{X23}$
(Substituent group A, R$^{X1}$, R$^{X2}$, R$^{X3}$, R$^{X4}$, R$^{X5}$, R$^{X6}$, R$^{X7}$, R$^{X8}$, R$^{X11}$, R$^{X12}$, R$^{X13}$, R$^{X14}$, R$^{X15}$, R$^{X16}$, R$^{X17}$, R$^{X18}$, R$^{X22}$, R$^{X23}$, and Z are same meaning as those of item 1').

[Item 3']
A CAP dependent endonuclease inhibitor according to item 1', wherein
R$^1$ is hydrogen, halogen, hydroxy, carboxy, lower alkyl optionally substituted by substituent group A, lower alkenyl optionally substituted by substituent group A, lower alkyloxy optionally substituted by substituent group A, lower alkylcarbonyl optionally substituted by substituent group A, lower alkyloxycarbonyl optionally substituted by substituent group A, heterocyclic group optionally substituted by substituent group A,
—Z—N(R$^{X1}$)(R$^{X2}$),
—Z—N(R$^{X7}$)—C(=O)—R$^{X8}$, or
—Z—N(R$^{X14}$)—C(=O)—O—R$^{X15}$
(Substituent group A, R$^{X1}$, R$^{X2}$, R$^{X7}$, R$^{X8}$, R$^{X14}$, R$^{X15}$, and Z are same meaning as those of item 1').

[Item 4']
A CAP dependent endonuclease inhibitor according to item 1', wherein
R$^1$ is hydrogen, halogen, hydroxy, carboxy, lower alkyl optionally substituted by substituent group A, lower alkenyl optionally substituted by substituent group A, lower alkyloxy optionally substituted by substituent group A, lower alkyl carbonyl optionally substituted by substituent group A, lower alkyloxycarbonyl optionally substituted by substituent group A, heterocyclic group optionally substituted by substituent group A, or
—Z—N(R$^{X1}$)(R$^{X2}$)
(Substituent group A, R$^{X1}$, R$^{X2}$, and Z are same meaning as those of item 1').

[Item 5']
A CAP dependent endonuclease inhibitor according to item 1', wherein R$^1$ is hydrogen or carboxy.

[Item 6']
A CAP dependent endonuclease inhibitor according to any one of items 1' to 5', wherein
R$^2$ is hydrogen, lower alkyl optionally substituted by substituent group A, carbocycle lower alkyl optionally substituted by substituent group A, heterocycle lower alkyl optionally substituted by substituent group A, or
—Z—N(R$^{Y9}$)(R$^{Y10}$)
(Substituent group A, R$^{Y9}$, R$^{Y10}$, and Z are same meaning as those of item 1').

[Item 7']
A CAP dependent endonuclease inhibitor according to any one of items 1' to 5', wherein
R$^2$ is hydrogen or lower alkyl optionally substituted by substituent group A
(Substituent group A is same meaning as that of item 1').

[Item 8']
A CAP dependent endonuclease inhibitor according to any one of items 1' to 7', wherein
R$^3$ is hydrogen, lower alkyl optionally substituted by substituent group A, lower alkenyl optionally substituted by substituent group A, lower alkynyl optionally substituted by substituent group A, carbocyclic group optionally substituted by substituent group A, carbocycle lower alkyl optionally substituted by substituent group A, carbocycleoxy lower alkyl optionally substituted by substituent group A, heterocycle lower alkyl optionally substituted by substituent group A,
—Z—N(R$^{Z1}$)—SO$_2$—R$^{Z2}$,
—Z—N(R$^{Z3}$)—C(=O)—R$^{Z4}$,
—Z—N(R$^{Z5}$)—C(=O)O—R$^{Z6}$,
—Z—C(=O)—N(R$^{Z7}$)(R$^{Z8}$), or
—Z—N(R$^{Z9}$)(R$^{Z10}$)
(Substituent group A, R$^{Z1}$, R$^{Z2}$, R$^{Z3}$, R$^{Z4}$, R$^{Z5}$, R$^{Z6}$, R$^{Z7}$, R$^{Z8}$, R$^{Z9}$, R$^{Z10}$, and Z are same meaning as those of item 1')

[Item 9']
A CAP dependent endonuclease inhibitor according to any one of items 1' to 8', wherein
A$^1$ is CR$^8$R$^9$, A$^2$ is CR$^{10}$R$^{11}$,
R$^9$, R$^{10}$, and R$^{11}$ are hydrogen or lower alkyl optionally substituted by substituent group A, and
R$^8$ is lower alkyl optionally substituted by substituent group A, carbocyclic group optionally substituted by substituent group A, carbocycle lower alkyl optionally substituted by substituent group A, carbocycleoxy lower alkyl optionally substituted by substituent group A, heterocyclic group optionally substituted by substituent group A, heterocycle lower alkyl optionally substituted by substituent group A, heterocycleoxy lower alkyl optionally substituted by substituent group A,
—Z—S—R$^{V1}$,
—Z—S(=O)—R$^{V2}$, or
—Z—SO$_2$—R$^{V3}$
(Substituent group A, R$^{V1}$, R$^{V2}$, R$^{V3}$, and Z are same meaning as those of item 1').

[Item 10']
A CAP dependent endonuclease inhibitor according to any one of items 1' to 8', wherein
A is CR$^8$R$^9$, A$^2$ is CR$^{10}$R$^{11}$,
R$^8$, R$^9$, and R$^{11}$ are hydrogen, or lower alkyl optionally substituted by substituent group A, and
R$^{10}$ is lower alkyl optionally substituted by substituent group A, carbocyclic group optionally substituted by substituent group A, carbocycle lower alkyl optionally substituted by substituent group A, carbocycleoxy lower alkyl optionally substituted by substituent group A, heterocyclic group optionally substituted by substituent group A, heterocycle lower alkyl optionally substituted by substituent group A, heterocycleoxy lower alkyl optionally substituted by substituent group A,
—Z—S—R$^{V1}$,
—Z—S(=O)—R$^{V2}$, or
—Z—SO$_2$—R$^{V3}$
(Substituent group A, R$^{V1}$, R$^{V2}$, R$^{V3}$, and Z are same meaning as those of item 1').

[Item 11']
A CAP dependent endonuclease inhibitor according to any one of items 1' to 8', wherein
$A^1$ is $CR^8R^9$, $A^2$ is $CR^{10}R^{11}$,
$R^9$ and $R^{11}$ are hydrogen,
i) either $R^8$ or $R^{10}$ is a group shown below:

[Chemical formula 2]

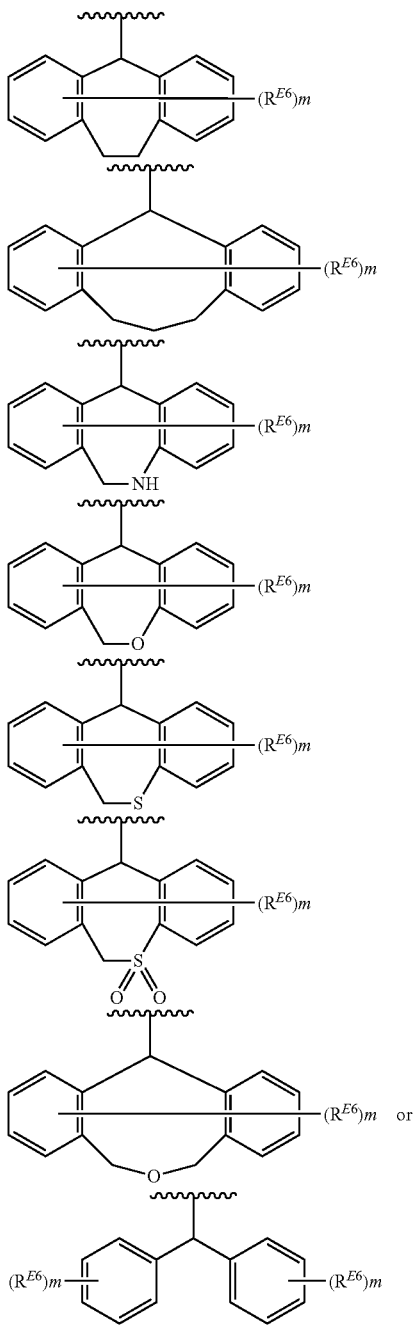

(wherein $R^{E6}$ is selected from substituent group A, m is an integer of 0 or more, and substituent group A is same meaning as those of item 1')
and;
ii) the other of $R^8$ or $R^{10}$ is hydrogen, or lower alkyl optionally substituted by substituent group A;

[Item 12']
CAP dependent endonuclease inhibitor according to item 11', wherein
$A^1$ is $CR^8R^9$, $A^2$ is $CR^{10}R^{11}$,
$R^9$ and $R^{11}$ are hydrogen,
i) either $R^8$ or $R^{10}$ is a group shown below:

[Chemical formula 3]

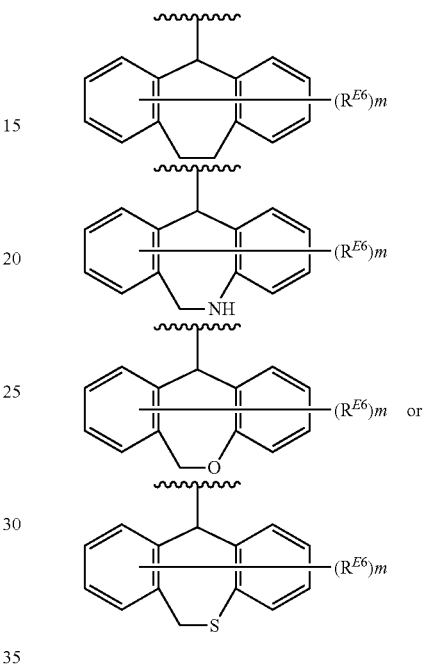

(wherein $R^{E6}$ is selected from substituent group A,
m is an integer of 0 or more, substituent group A is same meaning as that of item 1')
and;
ii) the other of $R^8$ or $R^{10}$ is hydrogen or lower alkyl optionally substituted by substituent group A.

[Item 13']
A compound represented by formula (II), or a pharmaceutically acceptable salt thereof or a solvate thereof:

[Chemical formula 4]

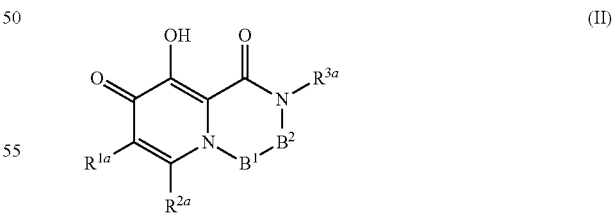

(II)

(wherein
$R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy optionally substituted by substituent group C, heterocycleoxycarbonyl optionally substituted by substituent group C, —Z—N($R^{A1}$)($R^{A2}$),
—Z—N($R^{A3}$)—SO$_2$—($R^{A4}$),
—Z—C(=O)—N($R^{A5}$)—SO$_2$—($R^{A6}$),
—Z—N($R^{A7}$)—C(=O)—$R^{A8}$,
—Z—S—$R^{A9}$,
—Z—SO$_2$—$R^{A10}$,
—Z—S(=O)—$R^{A11}$,
—Z—N($R^{A12}$)—C(=O)—O—$R^{A13}$,
—Z—N($R^{A14}$)—C(=O)—N($R^{A15}$)($R^{A16}$),
—Z—C(=O)—N($R^{A17}$)—C(=O)—N($R^{A18}$)($R^{A19}$), or
—Z—N($R^{A20}$)—C(=O)—$R^{A21}$ (wherein $R^{A1}$, $R^{A2}$, $R^{A3}$, $R^{A5}$, $R^{A7}$, $R^{A8}$, $R^{A9}$, $R^{A12}$, $R^{A13}$, $R^{A14}$, $R^{A15}$, $R^{A16}$, $R^{A17}$, $R^{A18}$, $R^{A19}$, $R^{A20}$, and $R^{A21}$ are each independently selected from substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{A4}$, $R^{A6}$, $R^{A1}$, and $R^{A11}$ are each independently selected from substituent group consisting of, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{A1}$ and $R^{A2}$, $R^{A15}$ and $R^{A16}$, and $R^{A18}$ and $R^{A19}$ each may be taken together with an adjacent atom to form heterocycle, and Z is a bond or straight or branched lower alkylene);

$R^{2a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{B1}$)—SO$_2$—$R^{B2}$,
—Z—N($R^{B3}$)—C(=O)—$R^{B4}$,
—Z—N($R^{B5}$)—C(=O)—O—$R^{B6}$,
—Z—C(=O)—N($R^{B7}$)($R^{B8}$),
—Z—N($R^{B9}$)($R^{B10}$), or
—Z—SO$_2$—$R^{B11}$ (wherein $R^{B1}$, $R^{B3}$, $R^{B4}$, $R^{B5}$, $R^{B6}$, $R^{B7}$, $R^{B8}$, $R^{B9}$, and $R^{B10}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B2}$ and $R^{B11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B7}$ and $R^{B8}$, and $R^{B9}$ and $R^{B10}$ each may be taken together with an adjacent atom to form heterocycle, and Z is a bond or straight or branched lower alkylene);

$R^{3a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$),
—Z—N($R^{C9}$)($R^{C10}$),
—Z—SO$_2$—$R^{C11}$, or
—Z—N($R^{C12}$)—O—C(=O)—$R^{C13}$ (wherein $R^{C1}$, $R^{C3}$, $R^{C4}$, $R^{C5}$, $R^{C6}$, $R^{C7}$, $R^{C8}$, $R^{C9}$, $R^{C10}$, $R^{C12}$ and, $R^{C13}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{C2}$, and $R^{C11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{C7}$ and $R^{C8}$, and $R^{C9}$ and $R^{C10}$ each may be taken together with an adjacent atom to form heterocycle, and Z is a bond or straight or branched lower alkylene) and;

a) either $B^1$ or $B^2$ is $CR^{5a}R^{6a}$, and the other is $NR^{7a}$, or b) $B^1$ is $CR^{8a}R^{9a}$ and $B^2$ is $CR^{10a}R^{11a}$, $R^{5a}$, $R^{6a}$, $R^{7a}$, $R^{8a}$, $R^{9a}$, $R^{10a}$ and $R^{11a}$ are each independently selected from a substituent group consisting of hydrogen, carboxy, cyano, lower alkyl optionally substituted by substituent group C, lower alkenyl optionally substituted by substituent group C, lower alkynyl optionally substituted by substituent group C, lower alkyl carbonyl optionally substituted by substituent group C, lower alkyl oxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C, —Y—S—$R^{D1}$,
—Z—S(=O)—$R^{D2}$,
—Z—SO$_2$—$R^{D3}$,
—C(=O)—C(=O)—$R^{D4}$,
—C(=O)—N($R^{D5}$)($R^{D6}$),
—Z—C($R^{D7}$)($R^{D8}$)($R^{D9}$),
—Z—CH$_2$—$R^{D10}$,
—Z—N($R^{D11}$)—C(=O)—O—$R^{D12}$, or
—Z—N($R^{D13}$)—C(=O)—$R^{D14}$ (wherein $R^{D1}$, $R^{D4}$, $R^{D5}$, $R^{D6}$, $R^{D9}$, $R^{D11}$, $R^{D12}$, $R^{D13}$, and $R^{D14}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D2}$ and $R^{D3}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D7}$, $R^{D8}$, and $R^{D10}$ are each independently selected from a substituent group consisting of carbocyclic group optionally substituted by substituent group C, heterocyclic group optionally substituted by substituent group C, $R^{D5}$ and $R^{D6}$ may be taken together with an adjacent atom to form heterocycle, Y is straight or branched lower alkylene, and Z is a bond or straight or branched lower alkylene);

$R^{D5}$ and $R^{D6}$ may be taken together with an adjacent atom to form carbocycle;

1) when $B^1$ is $CR^{5a}R^{6a}$ and $B^2$ is $NR^{7a}$, $R^{3a}$ and $R^{7a}$ may be taken together with an adjacent atom to form heterocycle optionally substituted by substituent group D, 2) when $B^1$ is $NR^{7a}$ and $B^2$ is $CR^{5a}R^{6a}$, $R^{3a}$ and $R^{6a}$ may be taken together with an adjacent atom to form heterocycle optionally substituted by substituent group D, or 3) when $B^1$ is $CR^{8a}R^{9a}$ and $B^2$ is $CR^{10a}R^{11a}$, $R^{8a}$ and $R^{10a}$ may be taken together with an adjacent atom to form carbocycle or heterocycle optionally substituted by substituent group D, or $R^{3a}$ and $R^{11a}$ may be taken together with an adjacent atom to form heterocycle optionally substituted by substituent group D, wherein when $B^1$ is $CR^{8a}R^{9a}$, and $B^2$ is $CR^{10a}R^{11a}$, and $R^{9a}$ is hydrogen, and $R^{11a}$ is hydrogen, i) either $R^{8a}$ or $R^{10a}$ is
—Z—C($R^{E1}$)($R^{E2}$)($R^{E3}$)
—Y—S—$R^{E4}$,
—Z—CH$_2$—$R^{E5}$, or
a group shown below:

[Chemical formula 5]

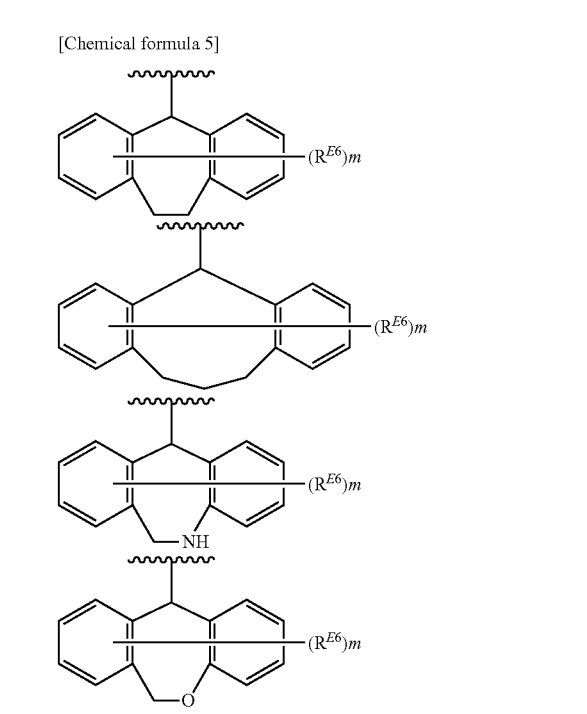

-continued

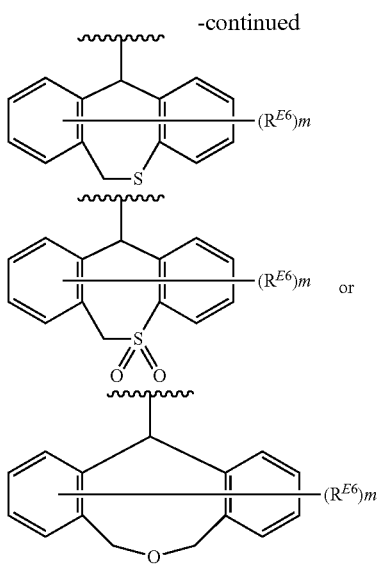

(wherein $R^{E1}$ and $R^{E2}$ are each independently, carbocycle optionally substituted by substituent group C, and heterocycle optionally substituted by substituent group C, $R^{E3}$ is selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{E4}$ is selected from a substituent group consisting of carbocycle lower alkyl optionally substituted by substituent group C, and heterocycle lower alkyl optionally substituted by substituent group C, $R^{E5}$ is aromatic heterocycle optionally substituted by substituent group C, $R^{E6}$ is selected from a substituent group C, m is an integer of 0 or more, provided that m of $R^{E6}$s is same or different groups selected from substituent group C Y is straight or branched lower alkylene, and Z is a bond or straight or branched lower alkylene); and ii) the other of $R^{8a}$ or $R^{10a}$ is hydrogen, carboxy, cyano, lower alkyl optionally substituted by substituent group C, lower alkenyl optionally substituted by substituent group C, lower alkynyl optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl, heterocycleoxycarbonyl optionally substituted by substituent group C, —Y—S—$R^{F1}$,
—C(=O)—C(=O)—$R^{F2}$, or
—C(=O)—N($R^{F3}$)($R^{F4}$)

(wherein $R^{F1}$, $R^{F2}$, $R^{F3}$, and $R^{F4}$ are each independently, hydrogen, lower alkyl optionally substituted by substituent group C, lower alkenyl optionally substituted by substituent group C, lower alkynyl optionally substituted by substituent group C, carbocyclic group optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, and Y is straight or branched lower alkylene);

with a proviso that the following c) and d) are excluded c) $R^{5a}$, $R^{6a}$, and $R^{7a}$ are all hydrogens d) $R^{8a}$, $R^{9a}$, $R^{10a}$, and $R^{11a}$ are all hydrogens;

Substituent group C: halogen, cyano, hydroxy, carboxy, formyl, amino, oxo, nitro, lower alkyl, halogeno lower alkyl, lower alkyloxy, lower alkylthio, hydroxy lower alkyl, carbocyclic group, heterocyclic group, heterocyclic group substituted by oxo, carbocycle lower alkyloxy, carbocycleoxy lower alkyl, carbocycle lower alkyloxy lower alkyl, heterocycle lower alkyloxy, heterocycleoxy lower alkyl, heterocycle lower alkyloxy lower alkyl, halogeno lower alkyloxy, lower alkyloxy lower alkyl, lower alkyloxy lower alkyloxy, lower alkylcarbonyl, lower alkylcarbonyloxy, lower alkyloxycarbonyl, lower alkylamino, lower alkylcarbonylamino, halogeno lower alkyl carbonylamino, lower alkylaminocarbonyl, lower alkylsulfonyl, lower alkylsulfinyl, and lower alkylsulfonylamino;

Substituent group D: halogen, cyano, hydroxy, carboxy, formyl, amino, oxo, nitro, lower alkyl, halogeno lower alkyl, lower alkyloxy, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, lower alkylsulfonylamino, carbocyclic group optionally substituted by substituent group C, heterocyclic group optionally substituted by substituent group C, carbocycle lower alkyl optionally substituted by substituent group C, and heterocycle lower alkyl optionally substituted by substituent group C).

[Item 14']

The compound according to item 13', or the pharmaceutically acceptable salt thereof or the solvate thereof, wherein $R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{A1}$)($R^{A2}$),
—Z—N($R^{A3}$)—SO$_2$—($R^{A4}$),
—Z—N($R^{A7}$)—C(=O)—$R^{A8}$,
—Z—S—$R^{A9}$,
—Z—SO$_2$—$R^{A10}$,
—Z—N($R^{A12}$)—C(=O)—O—$R^{A13}$, or
—Z—N($R^{A20}$)—C(=O)—C(=O)—$R^{A21}$
(substituent group C, $R^{A1}$, $R^{A2}$, $R^{A3}$, $R^{A4}$, $R^{A7}$, $R^{A8}$, $R^{A9}$, $R^{A10}$, $R^{A12}$, $R^{A13}$, $R^{A20}$, $R^{A21}$, and Z are same meaning as those of item 13).

[Item 15']
The compound according to item 13', or the pharmaceutically acceptable salt thereof or the solvate thereof,
wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C,
—Z—N($R^{A1}$)($R^{A2}$),
—Z—N($R^{A7}$)—C(=O)—$R^{A8}$, or
—Z—N($R^{A12}$)—C(=O)—O—$R^{A13}$
(substituent group C, $R^{A1}$, $R^{A2}$, $R^{A7}$, $R^{A8}$, $R^{A12}$, $R^{A13}$, and Z are same as those of item 13').

[Item 16']
The compound according to item 13', or the pharmaceutically acceptable salt thereof or the solvate thereof,
wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkyloxycarbonyl optionally substituted by substituent group C, heterocyclic group optionally substituted by substituent group C, or
—Z—N($R^{A1}$)($R^{A2}$)
(substituent group C, $R^{A1}$, $R^{A2}$, and Z are same as those of item 13').

[Item 17']
The compound according to item 13', or the pharmaceutically acceptable salt thereof or the solvate thereof,
wherein $R^{1a}$ is hydrogen, or carboxy.

[Item 18']
The compound according to any one of items 13' to 17', or the pharmaceutically acceptable salt thereof or the solvate thereof,
wherein $R^{2a}$ is hydrogen, lower alkyl optionally substituted by substituent group C, carbocycle lower alkyl optionally substituted by substituent group C, heterocycle lower alkyl optionally substituted by substituent group C, or
—Z—N($R^{B9}$)($R^{B10}$)
(substituent group C, $R^{B9}$, $R^{B10}$, and Z are same as those of item 13').

[Item 19']
The compound according to any one of items 13' to 17', or the pharmaceutically acceptable salt thereof or the solvate thereof,
wherein $R^{2a}$ is hydrogen or lower alkyl optionally substituted by substituent group C
(substituent group C is same as that of item 13').

[Item 20']
The compound according to any one of items 13' to 19', or the pharmaceutically acceptable salt thereof or the solvate thereof,
wherein $R^{3a}$ is hydrogen, lower alkyl optionally substituted by substituent group C, lower alkenyl optionally substituted by substituent group C, lower alkynyl optionally substituted by substituent group C, carbocyclic group optionally substituted by substituent group C, carbocycle lower alkyl optionally substituted by substituent group C, carbocycleoxy lower alkyl optionally substituted by substituent group C, heterocycle lower alkyl optionally substituted by substituent group C,
—Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$), or
—Z—N($R^{C9}$)($R^{C10}$)
(substituent group C, $R^{C1}$, $R^{C2}$, $R^{C3}$, $R^{C4}$, $R^{C5}$, $R^{C6}$, $R^{C7}$, $R^{C8}$, $R^{C9}$, $R^{C10}$, and Z are same as those of item 13').

[Item 21']
The compound according to any one of items 13' to 19', or the pharmaceutically acceptable salt thereof or the solvate thereof,
wherein $R^{3a}$ is hydrogen, lower alkyl optionally substituted by substituent group C, carbocyclic group optionally substituted by substituent group C, heterocyclic group optionally substituted by substituent group C, carbocycle lower alkyl optionally substituted by substituent group C,
(substituent group C, is same as that of item 13').

[Item 22']
The compound according to any one of items 13' to 21', or the pharmaceutically acceptable salt thereof or the solvate thereof,
wherein $B^1$ is NR$^{7a}$, and $B^2$ is CR$^{5a}$R$^{6a}$, and
$R^{5a}$, $R^{6a}$ and $R^{7a}$ are each independently hydrogen, carboxy, cyano, lower alkyl optionally substituted by substituent group C, lower alkenyl optionally substituted by substituent group C, lower alkynyl optionally substituted by substituent group C, lower alkyl carbonyl optionally substituted by substituent group C, lower alkyl oxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C,
—Y—S—$R^{D1}$,
—Z—S(=O)—$R^{D2}$,
—Z—SO$_2$—$R^{D3}$,
—C(=O)—C(=O)—$R^{D4}$,
—C(=O)—N($R^{D5}$)($R^{D6}$),
—Z—C($R^{D7}$)($R^{D8}$)($R^{D9}$)
—Z—N($R^{D11}$)—C(=O)—O—$R^{D12}$, or
—Z—N($R^{D13}$)—C(=O)—$R^{D14}$
(substituent group C, $R^{D1}$, $R^{D2}$, $R^{D3}$, $R^{D4}$, $R^{D5}$, $R^{D6}$, $R^{D7}$, $R^{D8}$, $R^{D9}$, $R^{D11}$, $R^{D12}$, $R^{D13}$, $R^{D14}$, Y and Z are same as those of item 13).

[Item 23']
The compound according to any one of items 13' to 21', or the pharmaceutically acceptable salt thereof or the solvate thereof,
wherein $B^1$ is NR$^{7a}$, and $B^2$ is CR$^{5a}$R$^{6a}$,
$R^{5a}$ is hydrogen,
$R^{6a}$ is hydrogen, or lower alkyl optionally substituted by substituent group C, and $R^{7a}$ is lower alkyl optionally substituted by substituent group C, carbocyclic group optionally substituted by substituent group C, carbocycleoxy lower alkyl optionally substituted by substituent group C, heterocyclic group optionally substituted by substituent group C, carbocycle lower alkyl optionally substituted by substituent group C, heterocycle lower alkyl optionally substituted by substituent group C, or
—Z—C($R^{D7}$)($R^{D8}$)($R^{D9}$)
(substituent group C, $R^{D7}$, $R^{D8}$, $R^{D9}$ and Z are same as item 13').

[Item 24']

The compound according to any one of items 13' to 21', or the pharmaceutically acceptable salt thereof or the solvate thereof,
wherein $B^1$ is $CR^{5a}R^{6a}$, and $B^2$ is $NR^{7a}$,
$R^{5a}$ is hydrogen,
$R^{6a}$ is hydrogen, or lower alkyl optionally substituted by substituent group C, and
$R^{7a}$ is lower alkyl optionally substituted by substituent group C, carbocyclic group optionally substituted by substituent group C, carbocycleoxy lower alkyl optionally substituted by substituent group C, heterocyclic group optionally substituted by substituent group C, carbocycle lower alkyl optionally substituted by substituent group C, heterocycle lower alkyl optionally substituted by substituent group C, or
—Z—C($R^{D7}$)($R^{D8}$)($R^{D9}$)
(Substituent group C, $R^{D7}$, $R^{D8}$, $R^{D9}$, and Z are same as item 13').

[Item 25']

The compound according to items 23' or 24', or the pharmaceutically acceptable salt thereof or the solvate thereof,
wherein $R^{7a}$ is a group shown below:

[Chemical formula 6]

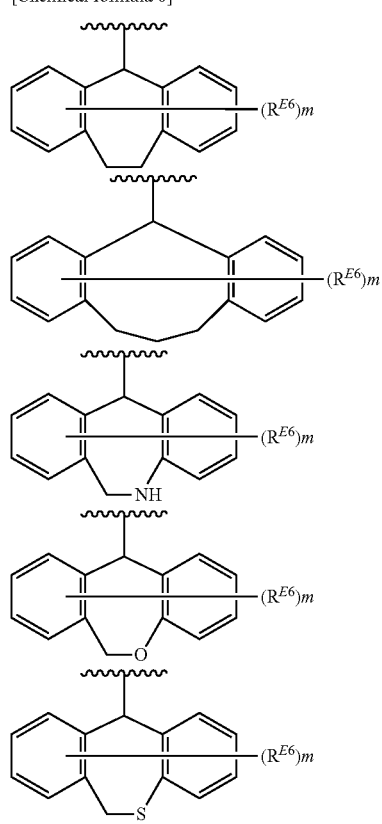

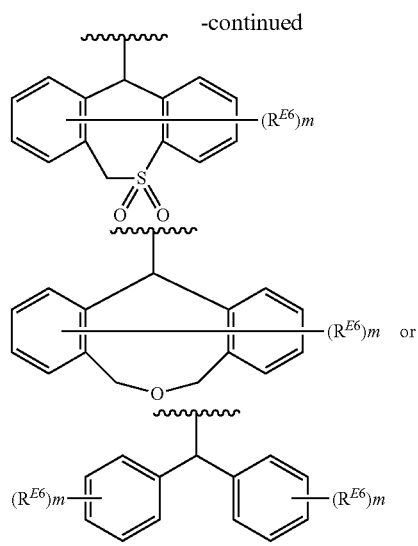

(wherein $R^{E6}$ and m are same as those of item 13').

[Item 26']

The compound according to items 13' or 21', or the pharmaceutically acceptable salt thereof or the solvate thereof,
wherein
$B^1$ is $CR^{8a}R^{9a}$, and $B^2$ is $CR^{10a}R^{11a}$,
$R^{9a}$ is hydrogen, and $R^{11a}$ is hydrogen, and
i) either $R^{8a}$ or $R^{10a}$ is a group shown below:

[Chemical formula 7]

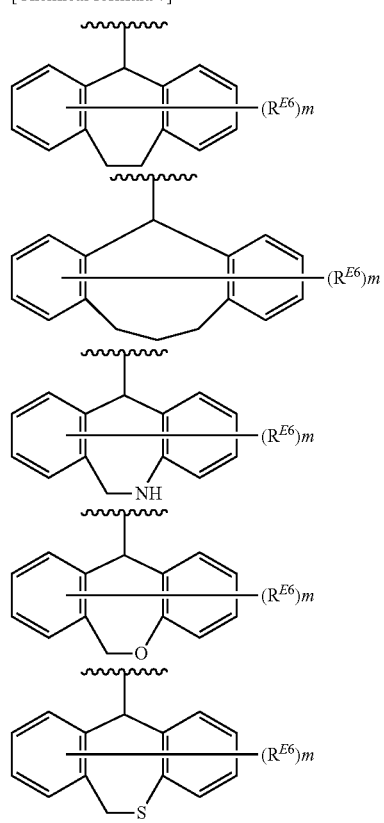

-continued

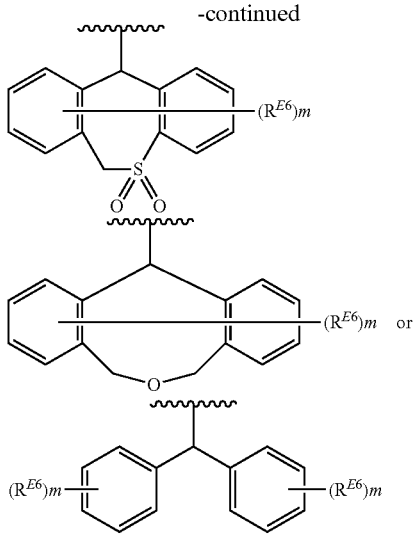

(wherein $R^{E6}$, and m are same as those of item 13'); and
ii) the other of $R^{8a}$ or $R^{10a}$ is
hydrogen, or lower alkyl optionally substituted by substituent group C,
(Substituent group C is same as those of item 13').

[Item 27']
The compound according to any one of items 13' to 19', or the pharmaceutically acceptable salt thereof or the solvate thereof,
wherein $B^1$ is $CR^{5a}R^{6a}$, and $B^2$ is $NR^{7a}$,
$R^{6a}$ is hydrogen,
$R^{3a}$ and $R^{7a}$ may be taken together with an adjacent atom to form heterocycle optionally substituted by substituent group D, and
$R^{5a}$ is hydrogen, lower alkyl optionally substituted by substituent group C, carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C, heterocycleoxy lower alkyl optionally substituted by substituent group C,
—Y—S—$R^{D1}$,
—C(=O)—C(=O)—$R^{D2}$, or
—C(=O)—N($R^{D3}$)($R^{D4}$)
(wherein $R^{D1}$, $R^{D2}$, $R^{D3}$, $R^{D4}$, Y, substituent group C and substituent group D are the same as item 13').

[Item 28']
The compound according to item 27', or the pharmaceutically acceptable salt thereof or the solvate thereof,
wherein $R^{5a}$ is hydrogen, carbocyclic group optionally substituted by substituent group C, carbocycle lower alkyl optionally substituted by substituent group C, heterocyclic group optionally substituted by substituent group C, or heterocycle lower alkyl optionally substituted by substituent group C
(wherein Substituent group C is same as item 13').

[Item 29']
The compound according to any one of items 13' to 19', or the pharmaceutically acceptable salt thereof or the solvate thereof,
wherein $B^1$ is $CR^{8a}R^{9a}$, and $B^2$ is $CR^{10a}R^{11a}$,
$R^{9a}$ is hydrogen, and $R^{10a}$ is hydrogen,
$R^{3a}$ and $R^{11a}$ are taken together with an adjacent atom to form heterocycle optionally substituted by substituent group D, and
$R^{8a}$ is hydrogen, lower alkyl optionally substituted by substituent group C, carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C, heterocycleoxy lower alkyl optionally substituted by substituent group C,
—Y—S—$R^{D1}$,
—C(=O)—C(=O)—$R^{D2}$, or
—C(=O)—N($R^{D3}$)($R^{D4}$)
(wherein $R^{D1}$, $R^{D2}$, $R^{D3}$, $R^{D4}$, Y, substituent group C and substituent group D is same as item 13').

[Item 30']
The compound according to item 29', or the pharmaceutically acceptable salt thereof or the solvate thereof,
wherein $R^{8a}$ is hydrogen, carbocyclic group optionally substituted by substituent group C, carbocycle lower alkyl optionally substituted by substituent group C, heterocyclic group optionally substituted by substituent group C, or heterocycle lower alkyl optionally substituted by substituent group C
(wherein substituent group C is same as that of item 13').

[Item 31']
The compound according to any one of items 27' to 30', or the pharmaceutically acceptable salt thereof or the solvate thereof,
wherein substituent group D is carbocyclic group optionally substituted by substituent group C, heterocyclic group optionally substituted by substituent group C, carbocycle lower alkyl optionally substituted by substituent group C, or heterocycle lower alkyl optionally substituted by substituent group C
(wherein substituent group C is same as that of item 13').

[Item 32']
A pharmaceutical composition containing a compound according to any one of items 13' to 31', or a pharmaceutically acceptable salt thereof or a solvate thereof.

[Item 33']
The pharmaceutical composition according to item 32' which exhibits anti influenza activity.

[Item 34']
The compound according to any one of items 13' to 31' for treating and/or preventing influenza infectious disease.

[Item 35']
The compound according to any one of items 13' to 31', or the pharmaceutically acceptable salt thereof or the solvate thereof, for treating and/or preventing influenza infectious disease.

[Item 36']
The pharmaceutical composition according to item 32' which exhibits CAP dependent endonuclease inhibitory activity.

This invention provides following items as another aspect.

[Item 1]
A CAP dependent endonuclease inhibitor containing a compound represented by formula (I), a pharmaceutically acceptable salt, or a solvate thereof:

[Chemical formula 8]

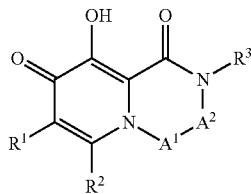

(I)

(wherein
$R^1$ is hydrogen, halogen, hydroxy, carboxy, cyano, formyl, lower alkyl optionally substituted by substituent group A, lower alkenyl optionally substituted by substituent group A, lower alkynyl optionally substituted by substituent group A, lower alkyloxy optionally substituted by substituent group A, lower alkenyloxy optionally substituted by substituent group A, lower alkylcarbonyl optionally substituted by substituent group A, lower alkyloxycarbonyl optionally substituted by substituent group A, carbocyclic group optionally substituted by substituent group A, carbocycle lower alkyl optionally substituted by substituent group A, carbocyclecarbonyl optionally substituted by substituent group A, carbocycleoxy optionally substituted by substituent group A, carbocycleoxycarbonyl optionally substituted by substituent group A, heterocyclic group optionally substituted by substituent group A, heterocycle lower alkyl optionally substituted by substituent group A, heterocyclecarbonyl optionally substituted by substituent group A, heterocycleoxy optionally substituted by substituent group A, heterocycleoxycarbonyl optionally substituted by substituent group A,
—Z—N($R^{X1}$)($R^{X2}$),
—Z—N($R^{X3}$)—SO$_2$—($R^{X4}$),
—Z—C(=O)—N($R^{X5}$)—SO$_2$—($R^{X6}$),
—Z—N($R^{X7}$)—C(=O)—$R^{X8}$,
—Z—C(=O)—N($R^{X9}$)($R^{X10}$),
—Z—S—$R^{X11}$,
—Z—SO$_2$—$R^{X12}$,
—Z—S(=O)—$R^{X13}$,
—Z—N($R^{X14}$)—C(=O)—O—$R^{X15}$,
—Z—N($R^{X16}$)—C(=O)—N($R^{X17}$)($R^{X18}$)
—Z—C(=O)—N($R^{X19}$)—C(=O)—N($R^{X20}$)($R^{X21}$), or
—Z—N($R^{X22}$)—C(=O)—C(=O)—$R^{X23}$
(wherein $R^{X1}$, $R^{X2}$, $R^{X3}$, $R^{X5}$, $R^{X7}$, $R^{X8}$, $R^{X9}$, $R^{X10}$, $R^{X11}$, $R^{X14}$, $R^{X15}$, $R^{X16}$, $R^{X17}$, $R^{X18}$, $R^{X19}$, $R^{X20}$, $R^{X21}$, $R^{X22}$ and $R^{X23}$ are each independently selected from a substituent group consisting of hydrogen, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{X4}$, $R^{X6}$, $R^{X12}$, and $R^{X13}$ are each independently selected from a substituent group consisting of, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{X1}$ and $R^{X2}$, $R^{X9}$ and $R^{X10}$, $R^{X17}$ and $R^{X18}$, and $R^{X20}$ and $R^{X21}$ each may be taken together with an adjacent atom to form heterocycle, and
Z is a bond or straight or branched lower alkylene);
$R^2$ is hydrogen, halogen, hydroxy, carboxy, cyano, formyl, lower alkyl optionally substituted by substituent group A, lower alkenyl optionally substituted by substituent group A, lower alkynyl optionally substituted by substituent group A, lower alkyloxy optionally substituted by substituent group A, lower alkenyloxy optionally substituted by substituent group A, lower alkylcarbonyl optionally substituted by substituent group A, lower alkyloxycarbonyl optionally substituted by substituent group A, carbocyclic group optionally substituted by substituent group A, carbocycle lower alkyl optionally substituted by substituent group A, carbocyclecarbonyl optionally substituted by substituent group A, carbocycleoxy optionally substituted by substituent group A, carbocycleoxycarbonyl optionally substituted by substituent group A, heterocyclic group optionally substituted by substituent group A, heterocycle lower alkyl optionally substituted by substituent group A, heterocyclecarbonyl optionally substituted by substituent group A, heterocycleoxy optionally substituted by substituent group A, heterocycleoxycarbonyl optionally substituted by substituent group A,
—Z—N($R^{Y1}$)—SO$_2$—$R^{Y2}$,
—Z—N($R^{Y3}$)—C(=O)—$R^{Y4}$,
—Z—N($R^{Y5}$)—C(=O)—O—$R^{Y6}$,
—Z—C(=O)—N($R^{Y7}$)($R^{Y8}$)
—Z—N($R^{Y9}$)($R^{Y10}$), or
—Z—SO$_2$—$R^{Y11}$
(wherein $R^{Y1}$, $R^{Y3}$, $R^{Y4}$, $R^{Y5}$, $R^{Y6}$, $R^{Y7}$, $R^{Y8}$, $R^{Y9}$, and $R^{Y10}$ are each independently selected from a substituent group consisting of hydrogen, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A,
$R^{Y2}$ and $R^{Y11}$ are each independently selected from a substituent group consisting of lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A,
$R^{Y7}$ and $R^{Y8}$, and $R^{Y9}$ and $R^{Y10}$ each may be taken together with an adjacent atom to form heterocycle and
Z is a bond or straight or branched lower alkylene);
$R^3$ is hydrogen, hydroxy, carboxy, cyano, formyl, lower alkyl optionally substituted by substituent group A, lower alkenyl optionally substituted by substituent group A, lower alkynyl optionally substituted by substituent group A, lower alkyloxy optionally substituted by substituent group A, lower alkenyloxy optionally substituted by substituent group A, lower alkylcarbonyl optionally substituted by substituent group A, lower alkyloxycarbonyl optionally substituted by substituent group A, carbocyclic group optionally substituted by substituent group A, carbocycle lower alkyl optionally substituted by substituent group A, carbocycleoxy lower alkyl optionally substituted by substituent group A, carbocyclecarbonyl optionally substituted by substituent group A, carbocycleoxy optionally substituted by substituent group A, carbocycleoxycarbonyl optionally substituted by substituent group A, heterocyclic group optionally substituted by substituent group A, heterocycle lower alkyl optionally substituted by substituent group A, heterocycleoxy lower alkyl optionally substituted by substituent group A, heterocyclecarbonyl optionally substituted by substituent group A, heterocycleoxy optionally substituted by substituent group A, heterocycleoxycarbonyl optionally substituted by substituent group A, —Z—N($R^{Z1}$)—SO$_2$—$R^{Z2}$,
—Z—N($R^{Z3}$)—C(=O)—$R^{Z4}$,
—Z—N($R^{Z5}$)—C(=O)—O—$R^{Z6}$,
—Z—C(=O)—N($R^{Z7}$)($R^{Z8}$),
—Z—N($R^{Z9}$)($R^{Z10}$)
—Z—SO$_2$—$R^{Z11}$, or
—Z—N($R^{Z12}$)—O—C(=O)—$R^{Z13}$ (wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from a substituent group consisting of hydrogen, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{Z2}$ and $R^{Z11}$ are each independently selected from a substituent group consisting of lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{Z7}$ and $R^{Z8}$, and $R^{Z9}$ and $R^{Z10}$ each may be taken together with an adjacent atom to form heterocycle, and Z is a bond or straight or branched lower alkylene) and;

a) either $A^1$ or $A^2$ is CR$^5$R$^6$, and the other is NR$^7$, or $A^1$ is CR$^8$R$^9$, and $A^2$ is CR$^{10}$R$^{11}$, b) $R^5$, $R^6$, $R^7$, $R^8$, $R^9$, $R^{10}$, and $R^{11}$ are each independently selected from a substituent group consisting of hydrogen, carboxy, cyano, lower alkyl optionally substituted by substituent group A, lower alkenyl optionally substituted by substituent group A, lower alkynyl optionally substituted by substituent group A, lower alkyl carbonyl optionally substituted by substituent group A, lower alkyl oxycarbonyl optionally substituted by substituent group A, carbocyclic group optionally substituted by substituent group A, carbocycle lower alkyl optionally substituted by substituent group A, carbocycleoxy lower alkyl optionally substituted by substituent group A, carbocyclecarbonyl optionally substituted by substituent group A, carbocycleoxycarbonyl optionally substituted by substituent group A, heterocyclic group optionally substituted by substituent group A, heterocycle lower alkyl optionally substituted by substituent group A, heterocycleoxy lower alkyl optionally substituted by substituent group A, heterocyclecarbonyl optionally substituted by substituent group A, heterocycleoxycarbonyl optionally substituted by substituent group A, —Z—S—$R^{V1}$,
—Z—S(=O)—$R^{V2}$,
—Z—SO$_2$—$R^{V3}$,
—C(=O)—C(=O)—$R^{V4}$, or
—C(=O)—N($R^{V5}$)($R^{V6}$), (wherein $R^{V1}$, $R^{V4}$, $R^{V5}$, and $R^{V6}$ are each independently selected from a substituent group consisting of hydrogen, lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{V2}$ and $R^{V3}$ are each independently selected from a substituent group consisting of lower alkyl optionally substituted by substituent group A, lower alkenyl optionally substituted by substituent group A, lower alkynyl optionally substituted by substituent group A, carbocyclic group optionally substituted by substituent group A, heterocyclic group optionally substituted by substituent group A, carbocycle lower alkyl optionally substituted by substituent group A, and heterocycle lower alkyl optionally substituted by substituent group A, $R^{V5}$ and $R^{V6}$ may be taken together with an adjacent atom to form heterocycle, and Z is a bond or straight or branched lower alkylene);

1) when $A^1$ is CR$^5$R$^6$ and $A^2$ is NR$^7$,
$R^3$ and $R^7$ may be taken together with an adjacent atom to form heterocycle optionally substituted by substituent group B or may form condensed ring, 2) when $A^1$ is NR$^7$ and $A^2$ is CR$^5$R$^6$,
$R^3$ and $R^6$ may be taken together with an adjacent atom to form heterocycle optionally substituted by substituent group B or may form condensed ring, or 3) when $A^1$ is CR$^8$R$^9$ and $A^2$ is CR$^{10}$R$^{11}$,
$R^8$ and $R^{10}$ may be taken together with an adjacent atom to form a bond, and $R^8$ and $R^{10}$ may be taken together with an adjacent atom to form carbocycle or heterocycle, or $R^3$ and $R^{11}$ may be taken together with an adjacent atom to form heterocycle optionally substituted by substituent group B or may form condensed ring;

Substituent group A: halogen, cyano, hydroxy, carboxy, formyl, amino, oxo, nitro, lower alkyl, halogeno lower alkyl, lower alkyloxy, carbocyclic group, heterocyclic group, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, and lower alkylsulfonylamino;

Substituent group B: halogen, cyano, hydroxy, carboxy, formyl, amino, oxo, nitro, lower alkyl, halogeno lower alkyl, lower alkyloxy, carbocyclic group, heterocyclic group, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, lower alkylsulfonylamino, carbocyclic group optionally substituted by substituent group A, heterocyclic group optionally substituted by substituent group A, carbocycle lower alkyl optionally substituted by substituent group A, and heterocycle lower alkyl optionally substituted by substituent group A).

[Item 2]

A CAP dependent endonuclease inhibitor according to item 1, wherein $R^1$ is hydrogen, halogen, hydroxy, carboxy, cyano, formyl, lower alkyl optionally substituted by substituent group A, lower alkenyl optionally substituted by substituent group A, lower alkynyl optionally substituted by substituent group A, lower alkyloxy optionally substituted by substituent group A, lower alkenyloxy optionally substituted by substituent group A, lower alkylcarbonyl optionally substituted by substituent group A, lower alkyloxycarbonyl optionally substituted by substituent group A, carbocyclic group optionally substituted by substituent group A, carbocycle lower alkyl optionally substituted by substituent group A, carbocyclecarbonyl optionally substituted by substituent group A, carbocycleoxy optionally substituted by substituent group A, carbocycleoxycarbonyl optionally substituted by substituent group A, heterocyclic group optionally substituted by substituent group A, heterocycle lower alkyl optionally substituted by substituent group A, heterocyclecarbonyl optionally substituted by substituent group A, heterocycleoxy optionally substituted by substituent group A, heterocycleoxycarbonyl optionally substituted by substituent group A, —Z—N($R^{X1}$)($R^{X2}$),
—Z—N($R^{X3}$)—$SO_2$—($R^{X4}$),
—Z—C(=O)—N($R^{X5}$)—$SO_2$—($R^{X6}$),
—Z—N($R^{X7}$)—C(=O)—$R^{X8}$,
—Z—S—$R^{X11}$,
—Z—$SO_2$—$R^{X12}$,
—Z—S(=O)—$R^{X13}$,
—Z—N($R^{X14}$)—C(=O)—O—$R^{X15}$,
—Z—N($R^{X16}$)—C(O)—N($R^{X17}$)($R^{X18}$), or
—Z—N($R^{X22}$)—C(=O)—C(=O)—$R^{X23}$ (Substituent group A, $R^{X1}$, $R^{X2}$, $R^{X3}$, $R^{X4}$, $R^{X5}$, $R^{X6}$, $R^{X7}$, $R^{X8}$, $R^{X11}$, $R^{X12}$, $R^{X13}$, $R^{X14}$, $R^{X15}$, $R^{X16}$, $R^{X17}$, $R^{X18}$, $R^{X22}$, $R^{X23}$, and Z are same meaning as those of item 1).

[Item 3]
A CAP dependent endonuclease inhibitor according to item 1, wherein
$R^1$ is hydrogen, halogen, hydroxy, carboxy, lower alkyl optionally substituted by substituent group A, lower alkenyl optionally substituted by substituent group A, lower alkyloxy optionally substituted by substituent group A, lower alkylcarbonyl optionally substituted by substituent group A, lower alkyloxycarbonyl optionally substituted by substituent group A, heterocyclic group optionally substituted by substituent group A,
—Z—N($R^{X1}$)($R^{X2}$),
—Z—N($R^7$)—C(=O)—$R^{X8}$, or
—Z—N($R^{X14}$)—C(=O)—O—$R^{X15}$
(Substituent group A, $R^{X1}$, $R^{X2}$, $R^{X7}$, $R^{X8}$, $R^{X14}$, $R^{X15}$, and Z are same meaning as those of item 1).

[Item 4]
A CAP dependent endonuclease inhibitor according to item 1, wherein
$R^1$ is hydrogen, halogen, hydroxy, carboxy, lower alkyl optionally substituted by substituent group A, lower alkenyl optionally substituted by substituent group A, lower alkyloxy optionally substituted by substituent group A, lower alkyl carbonyl optionally substituted by substituent group A, lower alkyloxycarbonyl optionally substituted by substituent group A, heterocyclic group optionally substituted by substituent group A, or
—Z—N($R^{X1}$)($R^{X2}$)
(Substituent group A, $R^{X1}$, $R^{X2}$, and Z are same meaning as those of item 1).

[Item 5]
A CAP dependent endonuclease inhibitor according to item 1, wherein $R^1$ is hydrogen or carboxy.

[Item 6]
A CAP dependent endonuclease inhibitor according to any one of items 1 to 5, wherein
$R^2$ is hydrogen, lower alkyl optionally substituted by substituent group A, carbocycle lower alkyl optionally substituted by substituent group A, heterocycle lower alkyl optionally substituted by substituent group A, or
—Z—N($R^{Y9}$)($R^{Y10}$)
(Substituent group A, $R^{Y9}$, $R^{Y10}$, and Z are same meaning as those of item 1).

[Item 7]
A CAP dependent endonuclease inhibitor according to any one of items 1 to 5, wherein
$R^2$ is hydrogen or lower alkyl optionally substituted by substituent group A, heterocycle lower alkyl optionally substituted by substituent group A,
(Substituent group A is same meaning as that of item 1).

[Item 8]
A CAP dependent endonuclease inhibitor according to any one of items 1 to 7, wherein
$R^3$ is hydrogen, lower alkyl optionally substituted by substituent group A, lower alkenyl optionally substituted by substituent group A, lower alkynyl optionally substituted by substituent group A, carbocyclic group optionally substituted by substituent group A, carbocycle lower alkyl optionally substituted by substituent group A, carbocycleoxy lower alkyl optionally substituted by substituent group A,
—Z—N($R^{Z1}$)—$SO_2$—$R^{Z2}$,
—Z—N($R^{Z3}$)—C(=O)—$R^{Z4}$,
—Z—N($R^{Z5}$)—C(=O)—O—$R^{Z6}$,
—Z—C(=O)—N($R^{Z7}$)($R^{Z8}$), or
—Z—N($R^{Z9}$)($R^{Z10}$)
(Substituent group A, $R^{Z1}$, $R^{Z2}$, $R^{Z3}$, $R^{Z4}$, $R^{Z5}$, $R^{Z6}$, $R^{Z7}$, $R^{Z8}$, $R^{Z9}$, $R^{Z10}$, and Z are same meaning as those of item 1).

[Item 9]
A CAP dependent endonuclease inhibitor according to any one of items 1 to 8, wherein
$A^1$ is $NR^7$,
$A^2$ is $CHR^6$, and
$R^6$ and $R^7$ are each independently hydrogen, lower alkyl optionally substituted by substituent group A, carbocyclic group optionally substituted by substituent group A, carbocycle lower alkyl optionally substituted by substituent group A, carbocycleoxy lower alkyl optionally substituted by substituent group A, heterocyclic group optionally substituted by substituent group A, heterocycle lower alkyl optionally substituted by substituent group A, heterocycleoxy lower alkyl optionally substituted by substituent group A,
—Z—S—$R^{V1}$,
—Z—S(=O)—$R^{V2}$ or
—Z—$SO_2$—$R^{V3}$
(Substituent group A, $R^{V1}$, $R^{V2}$, $R^{V3}$, and Z are same meaning as those of item 1).

[Item 10]
A CAP dependent endonuclease inhibitor according to any one of items 1 to 8, wherein
$A^1$ is $CHR^9$,
$A^2$ is $CHR^{11}$, and
$R^9$ and $R^{11}$ are each independently hydrogen, lower alkyl optionally substituted by substituent group A, carbocyclic group optionally substituted by substituent group A, carbocycle lower alkyl optionally substituted by substituent group A, carbocycleoxy lower alkyl optionally substituted by substituent group A, heterocyclic group optionally substituted by substituent group A, heterocycle lower alkyl optionally substituted by substituent group A, heterocycleoxy lower alkyl optionally substituted by substituent group A,
—Z—S—$R^{V1}$,
—Z—S(=O)—$R^{V2}$, or
—Z—$SO_2$—$R^{V3}$

29

(Substituent group A, $R^{V1}$, $R^{V2}$, $R^{V3}$, and Z are same meaning as those of item 1).

[Item 11]

A CAP dependent endonuclease inhibitor according to any one of items 1 to 7, wherein
$A^1$ is $CHR^9$,
$A^2$ is $CHR^{11}$,
$R^3$ and $R^{11}$ may be taken together with an adjacent atom to form heterocycle optionally substituted by substituent group B, and $R^9$ is hydrogen, carbocyclic group optionally substituted by substituent group A, carbocycle lower alkyl optionally substituted by substituent group A, heterocyclic group optionally substituted by substituent group A, heterocycle lower alkyl optionally substituted by substituent group A, (Substituent group A and substituent group B are same meaning as those of item 1).

[Item 12]

A CAP dependent endonuclease inhibitor according to any one of items 1 to 7, wherein
$A^1$ is $CHR^6$,
A2 is $NR^7$,
$R^3$ and $R^7$ may be taken together with an adjacent atom to form heterocycle optionally substituted by substituent group B,
$R^6$ is hydrogen, carbocyclic group optionally substituted by substituent group A, carbocycle lower alkyl optionally substituted by substituent group A, heterocyclic group optionally substituted by substituent group A, heterocycle lower alkyl optionally substituted by substituent group A, (Substituent group A and substituent group B are same meaning as those of item 1).

[Item 13]

A compound represented by formula (II), or a pharmaceutically acceptable salt thereof or a solvate thereof:

[Chemical formula 9]

(II)

(wherein
$R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally

30 substituted by substituent group C, heterocycleoxy optionally substituted by substituent group C, heterocycleoxycarbonyl optionally substituted by substituent group C,
—Z—N($R^{A1}$)($R^{A2}$),
—Z—N($R^{A3}$)—SO$_2$—($R^{A4}$),
—Z—C(=O)—N($R^{A5}$)—SO$_2$—($R^{A6}$),
—Z—N($R^{A7}$)—C(=O)—$R^{A8}$,
—Z—S—$R^{A9}$,
—Z—SO$_2$—$R^{A10}$,
—Z—S(=O)—$R^{A11}$,
—Z—N($R^{A12}$)—C(=O)—O—$R^{A13}$,
—Z—N($R^{A14}$)—C(=O)—N($R^{A15}$)($R^{A16}$),
—Z—C(=O)—N($R^{A17}$)—C(=O)—N($R^{A18}$)($R^{A19}$), or
—Z—N($R^{A20}$)—C(=O)—C(=O)—$R^{A21}$
(wherein $R^{A1}$, $R^{A2}$, $R^{A3}$, $R^{A5}$, $R^{A7}$, $R^{A8}$, $R^{A9}$, $R^{A12}$, $R^{A13}$, $R^{A14}$, $R^{A15}$, $R^{A16}$, $R^{A17}$, $R^{A18}$, $R^{A19}$, $R^{A20}$, and $R^{A21}$ are each independently selected from substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C,
$R^{A4}$, $R^{A6}$, $R^{A10}$, and $R^{A11}$ are each independently selected from substituent group consisting of, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C,
$R^{A1}$ and $R^{A2}$, $R^{A15}$ and $R^{A16}$, and $R^{A18}$ and $R^{A19}$ may be taken together with an adjacent atom to form heterocycle, and
Z is a bond or straight or branched lower alkylene);
$R^{2a}$ is hydrogen, halogen, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C,
—Z—N($R^{B1}$)—SO$_2$—$R^{B2}$,
—Z—N($R^{B3}$)—C(=O)—$R^{B4}$,
—Z—N($R^{B5}$)—C(=O)—O—$R^{B6}$,
—Z—C(=O)—N($R^{B7}$)($R^{B8}$),
—Z—N($R^{B9}$)($R^{B10}$), or
—Z—SO$_2$—$R^{B11}$
(wherein $R^{B1}$, $R^{B3}$, $R^{B4}$, $R^{B5}$, $R^{B6}$, $R^{B7}$, $R^{B8}$, $R^{B9}$, and $R^{B10}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B2}$ and $R^{B11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B7}$ and $R^{B8}$, and $R^{B9}$ and $R^{B10}$ may be taken together with an adjacent atom to form heterocycle, and Z is a bond or straight or branched lower alkylene);

$R^{3a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$),
—Z—N($R^{C9}$)($R^{C10}$),
—Z—SO$_2$—$R^{C11}$, or
—Z—N($R^{C12}$)—O—C(=O)—$R^{C13}$ (wherein $R^{C1}$, $R^{C3}$, $R^{C4}$, $R^{C5}$, $R^{C6}$, $R^{C7}$, $R^{C8}$, $R^{C9}$, $R^{C10}$, $R^{C12}$ and, $R^{C13}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{C2}$ and $R^{C11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{C7}$ and $R^{C8}$, and $R^{C9}$ and $R^{C10}$ may be taken together with an adjacent atom to form heterocycle, and Z is a bond or straight or branched lower alkylene) and;

a) either $B^1$ or $B^2$ is $CR^{5a}R^{6a}$, and the other is $NR^{7a}$, or b) $B^1$ is $CR^{8a}R^{9a}$ and $B^2$ is $CR^{10a}R^{11a}$, $R^{5a}$, $R^{6a}$, $R^{7a}$, $R^{8a}$, $R^{9a}$, $R^{10a}$ and $R^{11a}$ are each independently selected from a substituent group consisting of hydrogen, carboxy, cyano, lower alkyl optionally substituted by substituent group C, lower alkenyl optionally substituted by substituent group C, lower alkynyl optionally substituted by substituent group C, lower alkyl carbonyl optionally substituted by substituent group C, lower alkyl oxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C, —Y—S—$R^{D1}$,
—Z—S(=O)—$R^{D2}$,
—Z—SO$_2$—$R^{D3}$,
—C(=O)—C(=O)—$R^{D4}$,
—C(=O)—N($R^{D5}$)($R^{D6}$),
—Z—C($R^{D7}$)($R^{D8}$)($R^{D9}$), or
—Z—CH$_2$—$R^{D10}$, (wherein $R^{D1}$, $R^{D4}$, $R^{D5}$, $R^{D6}$, and $R^{D9}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D2}$, and $R^{D3}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D7}$, $R^{D8}$, and $R^{D10}$ are each independently selected from a substituent group consisting of carbocyclic group optionally substituted by substituent group C, heterocyclic group optionally substituted by substituent group C, $R^{D5}$ and $R^{D6}$ may be taken together with an adjacent atom to form heterocycle, Y is straight or branched lower alkylene, and Z is a bond or straight or branched lower alkylene);

1) when $B^1$ is $CR^{5a}R^{6a}$ and $B^2$ is $NR^{7a}$,
$R^{3a}$ and $R^{7a}$ may be taken together with an adjacent atom to form heterocycle optionally substituted by substituent group D,
2) when $B^1$ is $NR^{7a}$ and $B^2$ is $CR^{5a}R^{6a}$,
$R^{3a}$ and $R^{6a}$ may be taken together with an adjacent atom to form heterocycle optionally substituted by substituent group D, or
3) when $B^1$ is $CR^{8a}R^{9a}$ and $B^2$ is $CR^{10a}R^{11a}$,
$R^{8a}$ and $R^{10a}$ may be taken together with an adjacent atom to form carbocycle or heterocycle optionally substituted by substituent group D, or
$R^{3a}$ and $R^{11a}$ may be taken together with an adjacent atom to form heterocycle optionally substituted by substituent group D,
wherein
when B is $CR^{8a}R^{9a}$, and $B^2$ is $CR^{10a}R^{11a}$, and $R^{9a}$ is hydrogen, and $R^{11a}$ is hydrogen,
i) either $R^{8a}$ or $R^{10a}$ is
—Z—C($R^{E1}$)($R^{E2}$)($R^{E3}$)
—Y—S—$R^{E4}$,
—Z—CH$_2$—$R^{E5}$, or
a group shown below:

[Chemical formula 10]

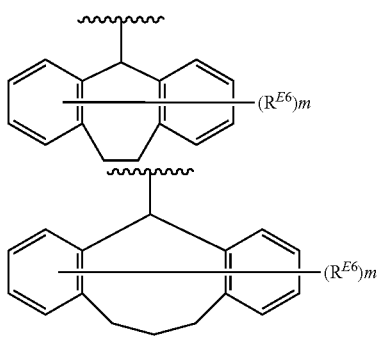

(wherein $R^{E1}$ and $R^{E2}$ are each independently, carbocyclic group optionally substituted by substituent group C, and heterocyclic group optionally substituted by substituent group C,
$R^{E3}$ is selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C,
$R^{E4}$ is selected from a substituent group consisting of carbocycle lower alkyl optionally substituted by substituent group C, and heterocycle lower alkyl optionally substituted by substituent group C,
$R^{E5}$ is aromatic heterocyclic group optionally substituted by substituent group C,
$R^{E6}$ is selected from a substituent group C,
m is an integer of 0 or more, provided that
m of $R^{E6}$s is same or different groups selected from a substituent group C
Y is straight or branched lower alkylene, and
Z is a bond or straight or branched lower alkylene); and ii) the other of $R^{8a}$ or $R^{10a}$ is,
hydrogen, carboxy, cyano, lower alkyl optionally substituted by substituent group C, lower alkenyl optionally substituted by substituent group C, lower alkynyl optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl, heterocycleoxycarbonyl optionally substituted by substituent group C,
—Y—S—$R^{F1}$,
—C(=O)—C(=O)—$R^{F2}$, or
—C(=O)—N(R$^{F3}$)(R$^{F4}$)
(wherein $R^{F1}$, $R^{F2}$, $R^{F3}$, and $R^{F4}$ are each independently, hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, and
Y is straight or branched lower alkylene);
Substituent group C: halogen, cyano, hydroxy, carboxy, formyl, amino, oxo, nitro, lower alkyl, halogeno lower alkyl, lower alkyloxy, carbocyclic group, heterocyclic group, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, and lower alkylsulfonylamino;
Substituent group D: halogen, cyano, hydroxy, carboxy, formyl, amino, oxo, nitro, lower alkyl, halogeno lower alkyl, lower alkyloxy, carbocyclic group, heterocyclic group, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, lower alkylsulfonylamino, carbocyclic group optionally substituted by substituent group C, heterocyclic group optionally substituted by substituent group C, carbocycle lower alkyl optionally substituted by substituent group C, and heterocycle lower alkyl optionally substituted by substituent group C).
[Item 14]
The compound according to item 13, or the pharmaceutically acceptable salt thereof or the solvate thereof,
wherein $R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{41}$)($R^{42}$),
—Z—N($R^{43}$)—SO$_2$—($R^{44}$),
—Z—N($R^{47}$)—C(=O)—$R^{48}$,
—Z—S—$R^{49}$,
—Z—SO$_2$—$R^{410}$,
—Z—N($R^{420}$)—C(=O)—O—$R^{413}$, or
—Z—N($R^{420}$)—C(=O)—C(=O)—$R^{421}$ (substituent group C, $R^{41}$, $R^{42}$, $R^{43}$, $R^{44}$, $R^{47}$, $R^{48}$, $R^{49}$, $R^{410}$, $R^{412}$, $R^{413}$, $R^{420}$, $R^{421}$, and Z are same meaning as those of item 13).

[Item 15]

The compound according to item 13, or the pharmaceutically acceptable salt thereof or the solvate thereof,
wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C,
—Z—N($R^{41}$)($R^{42}$),
—Z—N($R^{47}$)—C(=O)—$R^{48}$, or
—Z—N($R^{412}$)—C(=O)—O—$R^{413}$ (substituent group C, $R^{41}$, $R^{42}$, $R^{47}$, $R^{48}$, $R^{412}$, $R^{413}$, and Z are same as those of item 13).

[Item 16]

The compound according to item 13, or the pharmaceutically acceptable salt thereof or the solvate thereof,
wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkyloxycarbonyl optionally substituted by substituent group C, heterocyclic group optionally substituted by substituent group C, or
—Z—N($R^{41}$)($R^{42}$)

(substituent group C, $R^{41}$, $R^{42}$, and Z are same as those of item 13).

[Item 17]

The compound according to item 13, or the pharmaceutically acceptable salt thereof or the solvate thereof,
wherein $R^{1a}$ is hydrogen, or carboxy.

[Item 18]

The compound according to any one of items 13 to 17, or the pharmaceutically acceptable salt thereof or the solvate thereof,
wherein $R^{2a}$ is hydrogen, lower alkyl optionally substituted by substituent group C, carbocycle lower alkyl optionally substituted by substituent group C, heterocycle lower alkyl optionally substituted by substituent group C, or
—Z—N($R^{B9}$)($R^{B10}$)

(substituent group C, $R^{B9}$, $R^{B10}$, and Z are same as those of item 13).

[Item 19]

The compound according to any one of items 13 to 17, or the pharmaceutically acceptable salt thereof or the solvate thereof,
wherein $R^{2a}$ is hydrogen, lower alkyl optionally substituted by substituent group C, or heterocycle lower alkyl optionally substituted by substituent group C
(substituent group C is same as that of item 13).

[Item 20]

The compound according to any one of items 13 to 19, or the pharmaceutically acceptable salt thereof or the solvate thereof,
wherein $R^{3a}$ is hydrogen, lower alkyl optionally substituted by substituent group C, lower alkenyl optionally substituted by substituent group C, lower alkynyl optionally substituted by substituent group C, carbocyclic group optionally substituted by substituent group C, carbocycle lower alkyl optionally substituted by substituent group C, carbocycleoxy lower alkyl optionally substituted by substituent group C,
—Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$), or
—Z—N($R^{C9}$)($R^{C10}$)

(substituent group C, $R^{C1}$, $R^{C2}$, $R^{C3}$, $R^{C4}$, $R^{C5}$, $R^{C6}$, $R^{C7}$, $R^{C8}$, $R^{C9}$, $R^{C10}$, and Z are same as those of item 13).

[Item 21]

The compound according to any one of items 13 to 20, or the pharmaceutically acceptable salt thereof or the solvate thereof,
wherein $B^1$ is $NR^{7a}$, and $B^2$ is $CR^{5a}R^{6a}$, and
$R^{5a}$, $R^{6a}$ and $R^{7a}$ are each independently hydrogen, carboxy, cyano, lower alkyl optionally substituted by substituent group C, lower alkenyl optionally substituted by substituent group C, lower alkynyl optionally substituted by substituent group C, lower alkyl carbonyl optionally substituted by substituent group C, lower alkyl oxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C,
—Y—S—$R^{D1}$,
—Z—S(=O)—$R^{D2}$,
—Z—SO$_2$—$R^{D3}$,
—C(=O)—C(=O)—$R^{D4}$,
—C(=O)—N($R^{D5}$)($R^{D6}$), or
—Z—C($R^{D7}$)($R^{D8}$)($R^{D9}$)

(substituent group C, $R^{D1}$, $R^{D2}$, $R^{D3}$, $R^{D4}$, $R^{D5}$, $R^{D6}$, $R^{D7}$, $R^{D8}$, $R^{D9}$, Y, and Z are same as those of item 13).

[Item 22]

The compound according to any one of items 13 to 20, or the pharmaceutically acceptable salt thereof or the solvate thereof,
wherein $B^1$ is $NR^{7a}$, and $B^2$ is $CR^{5a}R^{6a}$,
$R^{6a}$ is hydrogen, and
$R^{5a}$ and $R^{7a}$ are each independently hydrogen, lower alkyl optionally substituted by substituent group C, carbocyclic group optionally substituted by substituent group C, carbocycleoxy lower alkyl optionally substituted by substituent group C, heterocyclic group optionally substituted by substituent group C, heterocycleoxy lower alkyl optionally substituted by substituent group C, —Z—S—R$^{D1}$, or
—Z—C(R$^{D7}$)(R$^{D8}$)(R$^{D9}$)
(substituent group C, R$^{D1}$, R$^{D7}$, R$^{D8}$, R$^{D9}$, and Z are same as item 13).

[Item 23]

The compound according to any one of items 13 to 20, or the pharmaceutically acceptable salt thereof or the solvate thereof,
wherein B$^1$ is NR$^{7a}$, and B$^2$ is CR$^{5a}$R$^{6a}$,
R$^{5a}$ is hydrogen, R$^{6a}$ is hydrogen, and
R$^{7a}$ is lower alkyl optionally substituted by substituent group C, carbocyclic group optionally substituted by substituent group C, carbocycleoxy lower alkyl optionally substituted by substituent group C, heterocyclic group optionally substituted by substituent group C, or
—Z—C(R$^{D7}$)(R$^{D8}$)(R$^{D9}$)
(substituent group C, R$^{D7}$, R$^{D8}$, R$^{D9}$, and Z are same as item 13).

[Item 24]

The compound according to any one of items 13 to 20, or the pharmaceutically acceptable salt thereof or the solvate thereof,
wherein B$^1$ is NR$^{7a}$, and B$^2$ is CR$^{5a}$R$^{6a}$,
R$^{5a}$ is hydrogen, R$^{6a}$ is hydrogen, and
R$^{7a}$ is a group shown below:

[Chemical formula 11]

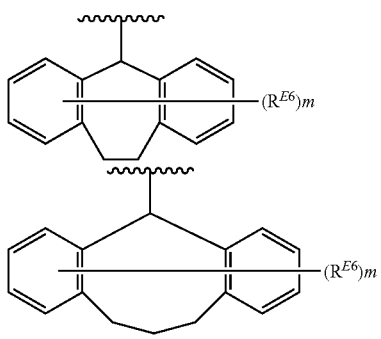

(wherein R$^{E6}$ and m are same as those of item 13).

[Item 25]

The compound according to items 13 or 20, or the pharmaceutically acceptable salt thereof or the solvate thereof,
wherein
B is CR$^{8a}$R$^{9a}$, and B$^2$ is CR$^{10a}$R$^{11a}$,
R$^{9a}$ is hydrogen, and R$^{11a}$ is hydrogen, and
i) either R$^{8a}$ or R$^{10a}$ is
—Z—C(R$^{E1}$)(R$^{E2}$)(R$^{E3}$)
—Y—S—R$^{E4}$
—Z—CH$_2$—R$^{E5}$,
or a group shown below:

[Chemical formula 12]

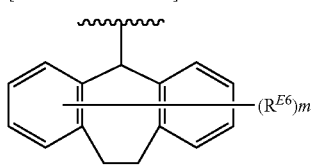

-continued

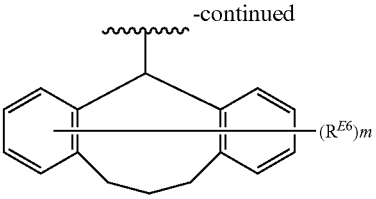

and,
ii) the other of R$^{8a}$ or R$^{10a}$ is
hydrogen, or lower alkyl optionally substituted by substituent group C, carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C, heterocycleoxy lower alkyl optionally substituted by substituent group C,
(Substituent group C is same as that of item 13).
—Z—S—R$^{F1}$,
—C(=O)—C(=O)—R$^{F2}$, or
—C(=O)—N(R$^{F3}$)(R$^{F4}$)
(substituent group C, R$^{E1}$, R$^{E2}$, R$^{E3}$, R$^{E4}$, R$^{E5}$, R$^{F1}$, R$^{F2}$, R$^{F3}$, R$^{F4}$, R$^{E6}$, m, Z, and Y are same as those of item 13).

[Item 26]

The compound according to any one of items 13 to 20, or the pharmaceutically acceptable salt thereof or the solvate thereof,
wherein B$^1$ is CR$^{8a}$R$^{9a}$, and B$^2$ is CR$^{10a}$R$^{11a}$,
R$^{9a}$ is hydrogen, R$^{10a}$ is hydrogen, and R$^{11a}$ is hydrogen,
R$^{8a}$ is —Z—CH(R$^{E1}$)(R$^{E2}$)
(R$^{E1}$, R$^{E2}$ and Z are same as those of item 13).

[Item 27]

The compound according to any one of items 13 to 20, or the pharmaceutically acceptable salt thereof or the solvate thereof,
wherein B$^1$ is CR$^{8a}$R$^{9a}$, and B$^2$ is CR$^{10a}$R$^{11a}$,
R$^{8a}$ is hydrogen, R$^{9a}$ is hydrogen, and R$^{11a}$ is hydrogen, and
R$^{10a}$ is —Z—CH(R$^{E1}$)(R$^{E2}$)
(R$^{E1}$, R$^{E2}$, and Z are same as those of item 13).

[Item 28]

The compound according to any one of items 13 to 20, or the pharmaceutically acceptable salt thereof or the solvate thereof,
wherein B$^1$ is CR$^{8a}$R$^{9a}$, and B$^2$ is CR$^{10a}$R$^{11a}$,
R$^{9a}$ is hydrogen, R$^{10a}$ is hydrogen, and R$^{11a}$ is hydrogen, and
R$^{8a}$ is a group shown below:

[Chemical formula 13]

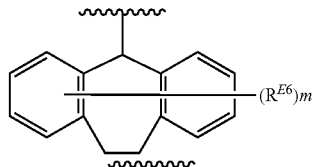

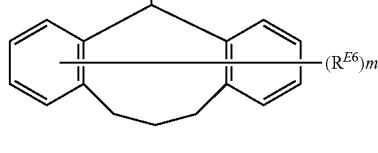

(wherein, R$^{E6}$ and m are same as those of item 13).

[Item 29]

The compound according to any one of items 13 to 20, or the pharmaceutically acceptable salt thereof or the solvate thereof,
wherein $B^1$ is $CR^{8a}R^{9a}$, and $B^2$ is $CR^{10a}R^{11a}$,
$R^{9a}$ is hydrogen, and $R^{11a}$ is hydrogen,
$R^{8a}$ and $R^{10a}$ may be taken together with an adjacent atom to form carbocycle or heterocycle optionally substituted by substituent group D,
(wherein substituent group D is same as that of item 13)

[Item 30]

The compound according to any one of items 13 to 19, or the pharmaceutically acceptable salt thereof or the solvate thereof,
wherein $B^1$ is $CR^{5a}R^{6a}$, and $B^2$ is $NR^{7a}$,
$R^{6a}$ is hydrogen,
$R^{3a}$ and $R^{7a}$ may be taken together with an adjacent atom to form heterocycle optionally substituted by substituent group D, and
$R^{5a}$ is hydrogen, lower alkyl optionally substituted by substituent group C, carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C, heterocycleoxy lower alkyl optionally substituted by substituent group C,
—Y—S—$R^{D1}$,
—C(=O)—C(=O)—$R^{D2}$, or
—C(=O)—N($R^{D3}$)($R^{D4}$)
(wherein, $R^{D1}$, $R^{D2}$, $R^{D3}$, and $R^{D4}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C,
Y is straight or branched lower alkylene, and Substituent group C and substituent group D are same as those of item 13).

[Item 31]

The compound according to item 30, or the pharmaceutically acceptable salt thereof or the solvate thereof,
wherein $B^1$ is $CR^{5a}R^{6a}$, and $B^2$ is $NR^{7a}$,
$R^{6a}$ is hydrogen,
$R^{3a}$ and $R^{7a}$ may be taken together with an adjacent atom to form heterocycle optionally substituted by substituent group D, and
$R^{5a}$ is hydrogen, carbocyclic group optionally substituted by substituent group C, carbocycle lower alkyl optionally substituted by substituent group C, carbocyclic group optionally substituted by substituent group C, or heterocycle lower alkyl optionally substituted by substituent group C (wherein substituent group C and substituent group D are same as those of item 13).

[Item 32]

The compound according to any one of items 13 to 19, or the pharmaceutically acceptable salt thereof or the solvate thereof,
wherein $B^1$ is $CR^{8a}R^{9a}$, and $B^2$ is $CR^{10a}R^{11a}$,
$R^{9a}$ is hydrogen, and $R^{10a}$ is hydrogen,
$R^{3a}$ and $R^{11a}$ may be taken together with an adjacent atom to form heterocycle optionally substituted by substituent group D, and
$R^{8a}$ is hydrogen, lower alkyl optionally substituted by substituent group C, carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C, heterocycleoxy lower alkyl optionally substituted by substituent group C,
—Y—S—$R^{D1}$,
—C(=O)—C(=O)—$R^{D2}$, or
—C(=O)—N($R^{D3}$)($R^{D4}$)
(wherein, $R^{D1}$, $R^{D2}$, $R^{D3}$, and $R^{D4}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C,
Y is straight or branched lower alkylene, and substituent group C and substituent group D are same as those of item 13).

[Item 33]

The compound according to item 32, or the pharmaceutically acceptable salt thereof or the solvate thereof,
wherein $B^1$ is $CR^{8a}R^{9a}$, and $B^2$ is $CR^{10a}R^{11a}$,
$R^{9a}$ is hydrogen, $R^{10a}$ is hydrogen,
$R^{3a}$ and $R^{11a}$ may be taken together with an adjacent atom to form heterocycle optionally substituted by substituent group D, and
$R^{8a}$ is hydrogen, carbocyclic group optionally substituted by substituent group C, carbocycle lower alkyl optionally substituted by substituent group C, carbocyclic group optionally substituted by substituent group C, or heterocycle lower alkyl optionally substituted by substituent group C)
(wherein, substituent group C and substituent group D are same as those of item 13).

[Item 34]

The compound according to any one of items 29 to 33, or the pharmaceutically acceptable salt thereof or the solvate thereof,
wherein substituent group D is carbocyclic group optionally substituted by substituent group C, heterocyclic group optionally substituted by substituent group C, carbocycle lower alkyl optionally substituted by substituent group C, or heterocycle lower alkyl optionally substituted by substituent group C

[Item 35]

A pharmaceutical composition containing a compound according to any one of items 13 to 34, or a pharmaceutically acceptable salt thereof or a solvate thereof.

[Item 36]

The pharmaceutical composition according to item 35 which exhibits CAP dependent endonuclease inhibitory activity.

[Item 37]

The pharmaceutical composition according to item 35 which exhibits anti influenza activity.

[Item 38]

A method for treating influenza infectious disease characterized in administering the compound shown by formula (II) according to above item 13, or the pharmaceutically acceptable salt thereof or the solvate thereof.

[Item 39]

Use of the compound shown by formula (II) according to above item 13, or the pharmaceutically acceptable salt thereof or the solvate thereof, for manufacturing a therapeutic agent for influenza infectious disease.

[Item 40]

The compound shown by formula (II) according to above item 13, or the pharmaceutically acceptable salt thereof or the solvate thereof, for treating influenza infectious disease.

[Item 41]

A method of producing a compound shown by formula (X4) or a salt thereof, comprising the steps of:

(Step B)

reacting a compound shown by formula (X2):

[Chemical formula 14]

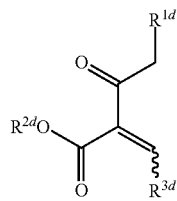

(X2)

(wherein $R^{1d}$ is hydrogen, halogen, lower alkyloxy optionally substituted by substituent E, carbocyclic group lower alkyloxy optionally substituted by substituent E, heterocycle lower alkyloxy optionally substituted by substituent E, or $-OSi(R^{1e})_3$, $R^{1e}$s are each independently lower alkyl optionally substituted by substituent E, carbocyclic group optionally substituted by substituent E, heterocyclic group optionally substituted by substituent E, carbocycle lower alkyl optionally substituted by substituent E or heterocycle lower alkyl optionally substituted by substituent E, $R^{2d}$ is hydrogen, lower alkyl optionally substituted by substituent E, carbocycle lower alkyl optionally substituted by substituent E, or heterocycle lower alkyl optionally substituted by substituent E, $R^{3d}$ is hydrogen, lower alkyl optionally substituted by substituent E, $-N(R^{3e})_2$, or $-OR^{3e}$, $R^{3e}$s are each independently lower alkyl optionally substituted by substituent E, wavy line is E form and/or Z form Substituent E: halogen, cyano, hydroxy, carboxy, formyl, amino, oxo, nitro, lower alkyl, halogeno lower alkyl, lower alkyloxy, carbocyclic group, heterocyclic group, carbocyclic group lower alkyloxy, heterocyclic group lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylamino, lower alkylaminocarbonyl, lower alkylsulfonyl, and lower alkylsulfonylamino;

with a compound shown by formula (V2):

[Chemical formula 15]

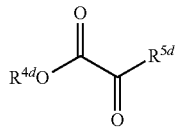

(V2)

(wherein $R^{4d}$ is lower alkyl optionally substituted by substituent E, carbocycle lower alkyl optionally substituted by substituent E, or heterocycle lower alkyl optionally substituted by substituent E, $R^{5d}$ is hydrogen, halogen, lower alkyloxy optionally substituted by substituent E, $-O-SO_2-R^{5e}$, $-O-SO_2-R^{5f}$, or $-O-SO_2-R^{5g}$, $R^{5e}$ is lower alkyl optionally substituted by substituent E, $R^{5f}$ is carbocycle lower alkyl optionally substituted by substituent E, and $R^{5g}$ is carbocycle lower alkyl optionally substituted by substituent E, and substituent E is defined above)

to obtain a compound shown by formula (X3):

[Chemical formula 16]

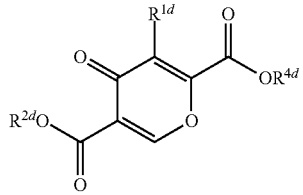

(X3)

(wherein each symbol is defined above); and (Step C)

reacting a compound shown by formula (X3) with a compound shown by formula (V3):

[Chemical formula 17]

$H_2N-R^{6d}$ (V3)

(wherein $R^{6d}$ is lower alkyl optionally substituted by substituent E, or lower alkenyl optionally substituted by substituent E, and substituent E is defined above)

to obtain a compound shown by formula (X4):

[Chemical formula 18]

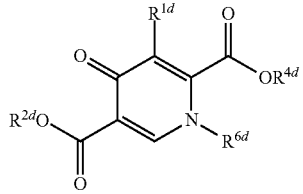

(X4)

(wherein each symbol is defined above).

[Item 42]

A method according to item 41, wherein Step B and Step C are continuously performed.

[Item 43]

A method of producing a compound shown by formula (X3), or a salt thereof:

[Chemical formula 21]

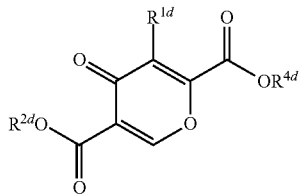

(X3)

(wherein each symbol is defined in item 41)
reacting a compound shown by formula (X2):

[Chemical formula 19]

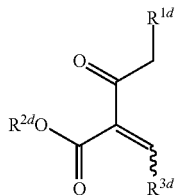

(X2)

(wherein each symbol is defined in item 41)
with a compound shown by formula (V2):

[Chemical formula 20]

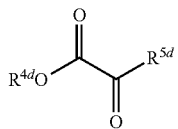

(V2)

(wherein each symbol is defined in item 41).

[Item 44]

A method of producing a compound shown by formula (X4), or a salt thereof:

[Chemical formula 24]

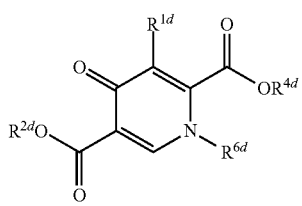

(X4)

(wherein each symbol is defined in item 41)

reacting a compound shown by formula (X3):

[Chemical formula 22]

(X3)

(wherein each symbol is defined in item 41); and with a compound shown by formula (V3):

[Chemical formula 23]

$H_2N-R^{6d}$ (V3)

(wherein symbol is defined in item 41).

[Item 45]

A method of producing a compound shown by formula (X4'), or a salt thereof:

[Chemical formula 28]

(X4')

(wherein each symbol is defined in item 41) comprising a step of:
reacting a compound shown by formula (X2):

[Chemical formula 25]

(X2)

(wherein each symbol is defined in item 41)
a compound shown by formula (V2):

[Chemical formula 26]

(V2)

(wherein each symbol is defined in item 41)

and a compound shown by formula:

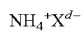
[Chemical formula 27]

(wherein $X^d$ is halogen, $CH_3COO$, or $HSO_4$)

[Item 46]

A method of producing a compound shown by formula (X4), or a salt thereof:

[Chemical formula 31]

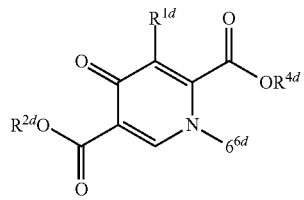
(X4)

(wherein each symbol is defined above) comprising the step of:

reacting the compound shown by formula (X4'):

[Chemical formula 29]

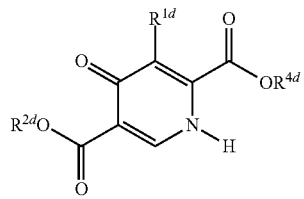
(X4')

(wherein each symbol is defined above)
obtained in the production method as defined in item 45, with a compound shown by formula (V3'):

[Chemical formula 30]

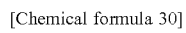
(V3')

(wherein $R^{6d}$ is defined above,
$L^d$ is halogen, $-O-SO_2-CH_3$, or $-O-SO_2-Ph-CH_3$, and Ph is a phenyl group).

[Item 47]

A method according to any one of items 41, 43, and 45, wherein the compound shown by formula (X2) is obtained by reacting a compound shown by formula (X1):

[Chemical formula 32]

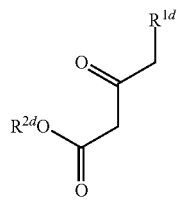
(X1)

(wherein each symbol is defined above)

with a compound shown by formula (V1):

[Chemical formula 33]

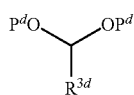
(V1)

(wherein $P^d$ is lower alkyl optionally substituted by substituent E, and substituent E is defined in item 41).

[Item 48]

A compound shown by formula (X3):

[Chemical formula 34]

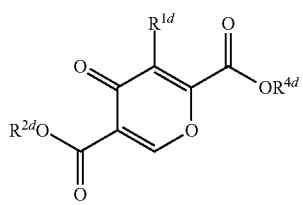
(X3)

(wherein each symbol is defined above),
or a pharmaceutically acceptable salt thereof or solvate thereof.

[Item 49]

A compound shown by formula (X4):

[Chemical formula 35]

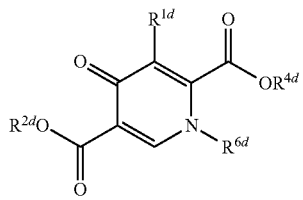
(X4)

(wherein each symbol is defined above),
or a pharmaceutically acceptable salt thereof or solvate thereof.

Effect of the Invention

The compounds of this invention, having inhibitory activities to cap-dependent endonuclease, are effective as therapeutic agents and/or preventive agents for influenza infectious disease.

BEST MODE FOR CARRYING OUT THE INVENTION

The meaning of each term used in the present description is explained below. Each term is used in a unified sense, and is used in the same sense when used alone, or when used in combination of other term.

"Optionally substituted by substituent group A" means that an arbitrary position may be substituted by one, two or more same or different substituents selected from substituent group A.

"Optionally substituted by substituent group B", "optionally substituted by substituent group C", "optionally substituted by substituent group D", and "optionally substituted by substituent group E" are also as described above.

"Halogen" includes fluorine, chlorine, bromine and iodine. Preferable is fluorine, chlorine and bromine.

"Lower alkyl" includes straight or branched alkyl of a carbon number of 1 to 15, preferably a carbon number of 1 to 10, more preferably a carbon number of 1 to 6, further preferably a carbon number of 1 to 4, and examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl etc. Examples of a preferable embodiment of "lower alkyl" include methyl, ethyl, n-propyl, isopropyl, n-butyl, isobutyl, sec-butyl, tert-butyl, and n-pentyl. Examples of a further preferable embodiment include methyl, ethyl, n-propyl, isopropyl, and tert-butyl.

"Lower alkenyl" includes straight or branched alkenyl of a carbon number of 2 to 15, preferably a carbon number of 2 to 10, more preferably a carbon number of 2 to 6, further preferably a carbon number of 2 to 4, having one or more double bonds at an arbitrary position. Specifically, lower alkenyl includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl etc. Examples of a preferable embodiment of "lower alkenyl" include vinyl, allyl, propenyl, isopropenyl, and butenyl.

"Lower alkynyl" includes straight or branched alkynyl of a carbon number of 2 to 10, preferably a carbon number of 2 to 8, further preferably a carbon number of 3 to 6, having one or more triple bonds at an arbitrary position. Specifically, lower alkynyl includes ethynyl, propynyl, butynyl, pentynyl, hexynyl, heptynyl, octynyl, nonynyl, decynyl etc. These may further have a double bond at an arbitrary position. Examples of a preferable embodiment of "lower alkynyl" include ethynyl, propynyl, butynyl, and pentynyl.

A lower alkyl part of "lower alkyloxy", "lower alkylcarbonyl", "lower alkyloxycarbonyl", "carbocycle lower alkyl", "heterocycle lower alkyl", "carbocycleoxy lower alkyl", "heterocycleoxy lower alkyl", "halogeno lower alkyl", "carbocycle lower alkyloxy", "heterocycle lower alkyloxy", "halogeno lower alkyloxy", "lower alkyloxy lower alkyl", "lower alkyloxy lower alkyloxy", "lower alkylcarbonyl", "lower alkyloxycarbonyl", "lower alkylamino", "lower alkylcarbonylamino", "lower alkylaminocarbonyl", "lower alkylsulfonyl", "lower alkylsulfonylamino", "lower alkylthio", "hydroxy lower alkyl", "carbocycle lower alkyloxy lower alkyl", "heterocycle lower alkyloxy lower alkyl", "lower alkylcarbonyloxy", "halogeno lower alkylcarbonylamino", and "lower alkylsulfinyl" is the same as the "lower alkyl" as described above.

A lower alkenyl part of "lower alkenyloxy" is the same as the "lower alkenyl" as described above.

A halogen part of "halogeno lower alkyl", "halogeno lower alkyloxy", and "halogeno lower alkylcarbonylamino" is the same as the "halogen". Herein, an arbitrary position on an alkyl group of "lower alkyl", "lower alkyloxy", and "lower alkylcarbonylamino" may be substituted by same or different one or plural halogen atoms, respectively.

"Carbocyclic group" or "carbocycle" means carbocyclic group of a carbon number of 3 to 20, preferably a carbon number of 3 to 16, more preferably a carbon number of 4 to 12, and includes cycloalkyl, cycloalkenyl, aryl and a non-aromatic condensed carbocyclic group, etc.

Specifically, "cycloalkyl" is carbocyclic group of a carbon number of 3 to 16, preferably a carbon number of 3 to 12, more preferably a carbon number of 4 to 8, and examples include cyclopropyl, cyclobutyl, cyclopentyl, cyclohexyl, cycloheptyl, cyclooctyl, cyclononyl and cyclodecyl, etc.

Specifically, "cycloalkenyl" includes cycloalkenyl having one or more double bonds at an arbitrary position in the cycloalkyl ring, and examples include cyclopropenyl, cyclobutenyl, cyclopentenyl, cyclohexenyl, cycloheptynyl, cyclooctynyl and cyclohexadienyl, etc.

Specifically, "aryl" includes phenyl, naphthyl, anthryl and phenanthryl, etc. and, particularly, phenyl is preferable.

Specifically, "non-aromatic condensed carbocyclic group" includes a group in which two or more cyclic groups selected from the "cycloalkyl", the "cycloalkenyl" and the "aryl" are condensed, and examples include indanyl, indenyl, tetrahydronaphthyl, fluorenyl, adamantyl, and a group shown below:

[Chemical formula 36]

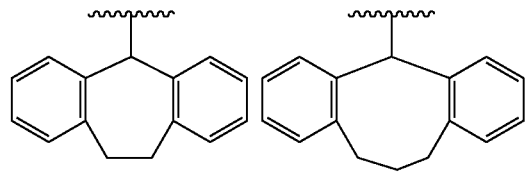

etc.

Examples of a preferable embodiment of "carbocyclic group" or "carbocycle" include cycloalkyl, aryl and a non-aromatic condensed carbocyclic group, specifically examples include cyclopropyl, cyclobutyl, cyclopentyl, cyclohexyl, cycloheptyl, phenyl, naphthyl, and a group shown below:

[Chemical formula 37]

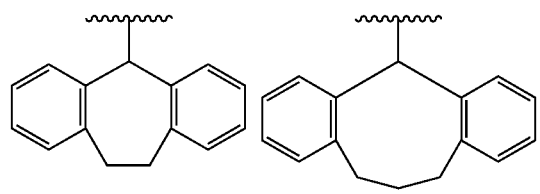

etc.

A carbocyclic part of "carbocycle lower alkyl", "carbocycle lower alkyloxy", "carbocycleoxy lower alkyl", "carbocyclecarbonyl", "carbocycleoxy", "carbocycleoxycarbonyl" and "carbocycle lower alkyloxy lower alkyl" is the same as the "carbocyclic group" or the "carbocycle" as described above.

"Heterocyclic group" or "heterocycle" includes heterocyclic group such as heteroaryl, a non-aromatic heterocyclic group, a bicyclic condensed heterocyclic group, a tricyclic condensed heterocyclic group, etc., having one or more same or different hetero atoms arbitrarily selected from O, S and N in a ring.

Specifically, "heteroaryl" includes a 5- to 6-membered aromatic cyclic group such as pyrrolyl, imidazolyl, pyrazolyl, pyridyl, pyridazinyl, pyrimidinyl, pyrazinyl, triazolyl, triazinyl, tetrazolyl, furyl, thienyl, isooxazolyl, oxazolyl, oxadiazolyl, isothiazolyl, thiazolyl, thiadiazolyl, etc.

Specifically, "non-aromatic heterocyclic group" includes a 4- to 8-membered non-aromatic heterocyclic group such as dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, etc.

Specifically, "bicyclic condensed heterocyclic group" includes a cyclic group including at least one 4- to 8-membered aromatic or non-aromatic heterocyclic group such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisooxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotrianizyl, pyridazolopyridyl, triazolopyridyl, imidazothiazolyl, pyrazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzooxezinyl, dihydrobenzodioxepinyl, dihydrothienodioxynyl, etc.

Specifically, "tricyclic condensed heterocyclic group" includes a cyclic group including at least one 4- to 8-membered aromatic or non-aromatic heterocyclic group such as carbazolyl, acridinyl, xanthenyl, phenothiazinyl, phenoxathiinyl, phenoxazinyl, dibenzofuryl, imidazoquinolyl, tetrahydrocarbazolyl, and a group shown below:

[Chemical formula 38]

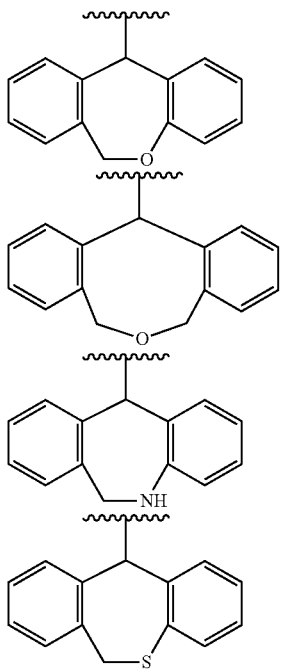

-continued

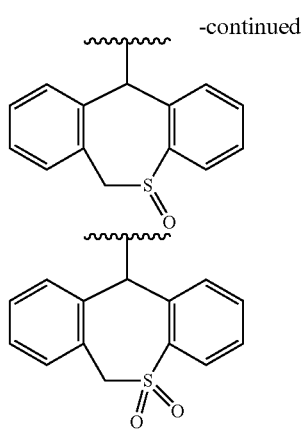

etc.

Examples of a preferable embodiment of "heterocyclic group" include 5- to 6-membered heteroaryl, a non-aromatic heterocyclic group and a tricyclic condensed heterocyclic group.

A heterocyclic part of "heterocycle lower alkyl", "heterocycle lower alkyloxy", "carbocycleoxy lower alkyl", "heterocyclecarbonyl", "heterocycleoxy", "heterocycleoxycarbonyl", and "heterocycle lower alkyloxy lower alkyl" is the same as the "heterocyclic group" or the "heterocycle" as described above.

"Heterocyclic group substituted by oxo" means the "heterocyclic group" as described above, substituted by oxo as shown below. A group shown below:

[Chemical formula 39]

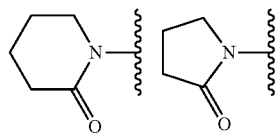

is exemplified.

"Straight or branched lower alkylene" is divalent "lower alkyl" as described above, and includes, for example, methylene, ethylene, propylene, butylene, isobutylene, pentylene, heptylene, dimethylmethylene, ethylmethylmethylene, 1,2-dimethylethylene, etc.

Examples of "lower alkyloxy" include methoxy, ethoxy, propyloxy, isopropyloxy, tert-butyloxy, isobutyloxy, sec-butyloxy, pentyloxy, isopentyloxy, hexyloxy, etc. Examples of a preferable embodiment include methoxy, ethoxy, propyloxy, isopropyloxy, and tert-butyloxy.

Examples of "lower alkylcarbonyl" include methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, hexylcarbonyl, etc. Examples of a preferable embodiment include methylcarbonyl, ethylcarbonyl, and propylcarbonyl.

Examples of "lower alkyloxycarbonyl" include methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, hexyloxycarbonyl, etc. Examples of a preferable embodiment include methyloxycarbonyl, ethyloxycarbonyl, and propyloxycarbonyl.

"Carbocycle lower alkyl" represents lower alkyl substituted by one, two or more carbocyclic groups, and examples of "carbocycle lower alkyl" include benzyl, phenethyl, phenylpropynyl, benzhydryl, trityl, cyclopropylmethyl, cyclobutylmethyl, cyclopentylmethyl, cyclohexylmethyl, naphthylmethyl, a group shown below:

[Chemical formula 40]

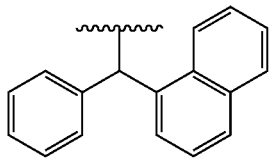

etc. Examples of a preferable embodiment include benzyl, phenethyl, and benzhydryl.

"Heterocycle lower alkyl" represents lower alkyl substituted by one, two or more heterocyclic groups, and also includes heterocycle lower alkyl in which an alkyl part is substituted by carbocyclic group. Examples of "heterocycle lower alkyl" include pyridylmethyl, tetrahydropyranylmethyl, furanylmethyl, morpholinylethyl, imidazolylmethyl, indolylmethyl, benzothiophenylmethyl, oxazolylmethyl, isooxazolylmethyl, thiazolylmethyl, isothiazolylmethyl, pyrazolylmethyl, isopyrazolylmethyl, pyrrolidinylmethyl, benzoxazolylmethyl, piperidinylmethyl, piperazinylmethyl, a group shown below:

[Chemical formula 41]

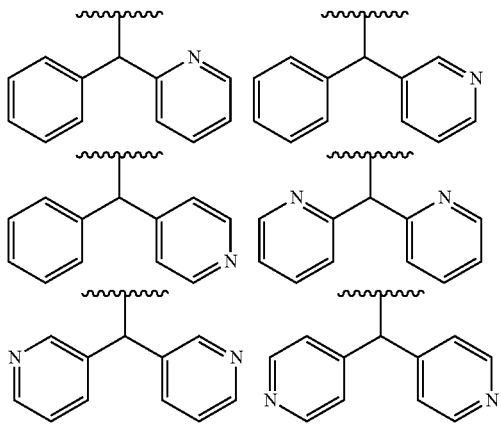

etc. Examples of a preferable embodiment include pyridylmethyl, tetrahydropyranylmethyl, furanylmethyl, and morpholinylethyl.

Examples of "carbocycleoxy lower alkyl" include phenyloxymethyl, phenyloxyethyl, cyclopropyloxymethyl, cyclopropyloxyethyl, cyclobutyloxymethyl, cyclobutyloxyethyl, cyclohexyloxymethyl, cyclohexyloxyethyl, etc. Examples of a preferable embodiment include phenyloxymethyl, and phenyloxyethyl.

Examples of "heterocycleoxy lower alkyl" include pyridyloxymethyl, pyridyloxyethyl, morpholinyloxymethyl, morpholinyloxyethyl, benzoxazolyloxymethyl, etc. Examples of a preferable embodiment include pyridyloxymethyl, morpholinyloxymethyl, etc.

"Carbocycle lower alkyloxy" represents lower alkyloxy in which an alkyl part is substituted by one, two or more carbocyclic groups, and examples of "carbocycle lower alkyloxy" include phenylmethyloxy, phenylethyloxy, cyclopropylmethyloxy, cyclobutylmethyloxy, cyclopentylmethyloxy, cyclohexylmethyloxy, etc. Examples of a preferable embodiment include phenylmethyloxy, cyclopropylmethyloxy, etc.

"Heterocycle lower alkyloxy" represents lower alkyloxy in which an alkyl part is substituted by one, two or more heterocyclic groups, and also includes heterocycle lower alkyloxy in which an alkyl part is substituted by carbocyclic group. Examples of "heterocycle lower alkyloxy" include pyridylmethyloxy, pyridylethyloxy, imidazolylmethyloxy, imidazolylethyloxy, benzoxazolylmethyloxy, benzoxazolylethyloxy, etc.

Examples of "lower alkyloxy lower alkyl" include methoxymethyl, methoxyethyl, ethoxymethyl, ethoxyethyl, methoxypropyl, methoxybutyl, ethoxypropyl, ethoxybutyl, isopropyloxymethyl, tert-butyloxymethyl, etc. Examples of a preferable embodiment include methoxymethyl, methoxyethyl, ethoxymethyl, and ethoxyethyl.

Examples of "lower alkyloxy lower alkyloxy" include methoxymethoxy, methoxyethoxy, ethoxymethoxy, ethoxyethoxy, methoxypropyloxy, methoxybutyloxy, ethoxypropyloxy, ethoxybutyloxy, isopropyloxymethyloxy, tert-butyloxymethyloxy, etc. Examples of a preferable embodiment include methoxymethoxy, methoxyethoxy, ethoxymethoxy, and ethoxyethoxy.

Examples of "lower alkylamino" include methylamino, dimethylamino, ethylamino, diethylamino, isopropylamino, N,N-diisopropylamino, N-methyl-N-ethylamino, N-isopropyl-N-ethylamino, etc. Examples of a preferable embodiment include methylamino, dimethylamino, ethylamino, and diethylamino.

Examples of "lower alkylcarbonylamino" include methylcarbonylamino, ethylcarbonylamino, propylcarbonylamino, isopropylcarbonylamino, tert-butylcarbonylamino, isobutylcarbonylamino, sec-butylcarbonylamino, etc. Examples of a preferable embodiment include methylcarbonylamino, and ethylcarbonylamino.

Examples of "lower alkylaminocarbonyl" include methylaminocarbonyl, dimethylaminocarbonyl, ethylaminocarbonyl, diethylaminocarbonyl, isopropylaminocarbonyl, N,N-diisopropylaminocarbonyl, N-methyl-N-ethylaminocarbonyl, N-isopropyl-N-ethylaminocarbonyl, etc. Examples of a preferable embodiment include methylaminocarbonyl, dimethylaminocarbonyl, ethylaminocarbonyl, and diethylaminocarbonyl.

Examples of "lower alkylsulfonyl" include methylsulfonyl, ethylsulfonyl, propylsulfonyl, isopropylsulfonyl, tert-butylsulfonyl, isobutylsulfonyl, sec-butylsulfonyl, etc. Examples of a preferable embodiment include methylsulfonyl, and ethylsulfonyl.

Examples of "lower alkylsulfonylamino" include methylsulfonylamino, ethylsulfonylamino, propylsulfonylamino, isopropylsulfonylamino, tert-butylsulfonylamino, isobutylsulfonylamino, sec-butylsulfonylamino, etc. Examples of a preferable embodiment include methylsulfonylamino, and ethylsulfonylamino.

Examples of "lower alkenyloxy" include ethylenyloxy, 1-propylenyloxy, 2-propylenyloxy, 1-butylenyloxy, 2-butylenyloxy, 3-butylenyloxy, etc.

Examples of "halogeno lower alkyl" include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl, etc. Examples of a preferable embodiment include trifluoromethyl, trichloromethyl, 1,1,1-trifluoropropan-2-yl.

Examples of "halogeno lower alkyloxy" include monofluoromethoxy, monofluoroethoxy, trifluoromethoxy, trichloromethoxy, trifluoroethoxy, trichloroethoxy, etc. Examples of a preferable embodiment include trifluoromethoxy, and trichloromethoxy.

Examples of "lower alkylthio" include methylthio, ethylthio, propylthio, etc.

Examples of "hydroxy lower alkyl" include hydroxymethyl, hydroxyethyl, hydroxypropyl, etc.

Examples of "carbocycle lower alkyloxy lower alkyl" include benzyloxymethyl, benzyloxyethyl, benzhydryloxymethyl, etc.

Examples of "heterocycle lower alkyloxy lower alkyl" include pyridylmethyloxymethyl, pyridylmethyloxyethyl, etc.

Examples of "lower alkylcarbonyloxy" include methylcarbonyloxy, ethylcarbonyloxy, etc.

Examples of "halogeno lower alkylcarbonylamino" include trifluoromethylcarbonylamino, 2,2,3,3,3-pentafluoropropylcarbonylamino, etc.

Examples of "lower alkylsulfinyl" include methylsulfinyl, ethylsulfinyl, etc.

Examples of "carbocyclecarbonyl" include phenylcarbonyl, naphthylcarbonyl, cyclopropylcarbonyl, cyclobutylcarbonyl, cyclopentylcarbonyl, cyclohexylcarbonyl, etc.

Examples of "carbocycleoxy" include phenyloxy, naphthyloxy, cyclopropyloxy, cyclobutyloxy, cyclopentyloxy, cyclohexyloxy, etc.

Examples of "carbocycleoxycarbonyl" include phenyloxycarbonyl, naphthyloxycarbonyl, cyclopropyloxycarbonyl, cyclobutyloxycarbonyl, cyclopentyloxycarbonyl, cyclohexyloxycarbonyl, etc.

Examples of "heterocyclecarbonyl" include pyridylcarbonyl, benzoxazolylcarbonyl, morpholinylcarbonyl, tetrahydropyranylcarbonyl, etc.

Examples of "heterocycleoxy" include pyridyloxy, benzoxazolyloxy, morpholinyloxy, tetrahydropyranyloxy, etc.

Examples of "heterocycleoxycarbonyl" include pyridyloxycarbonyl, benzoxazolyloxycarbonyl, morpholinyloxycarbonyl, tetrahydropyranyloxycarbonyl, etc.

"$R^{X1}$ and $R^{X2}$, $R^{X9}$ and $R^{X10}$, $R^{X17}$ and $R^{X18}$ as well as $R^{X20}$ and $R^{X21}$, each may be taken together with an adjacent atom to form a heterocycle", "$R^{Y7}$ and $R^{Y8}$, as well as $R^{Y9}$ and $R^{Y10}$, each may be taken together with an adjacent atom to form a heterocycle", "$R^{Z7}$ and $R^{Z8}$, as well as $R^{Z9}$ and $R^{Z10}$, each may be taken together with an adjacent atom to form a heterocycle", and "$R^{V5}$ and $R^{V6}$ may be taken together with an adjacent atom to form a heterocycle" in item 1' and item 1; and "$R^{A1}$ and $R^{A2}$, $R^{A15}$ and $R^{A16}$, as well as $R^{A19}$ and $R^{A20}$, each may be taken together with an adjacent atom to form a heterocycle", "$R^{B7}$ and $R^{B8}$, as well as $R^{B9}$ and $R^{B10}$, each may be taken together with an adjacent atom to form a heterocycle", "$R^{C7}$ and $R^{C8}$, as well as $R^{C9}$ and $R^{C10}$, each may be taken together with an adjacent atom to form a heterocycle", and "$R^{D5}$ and $R^{D6}$ may be taken together with an adjacent atom to form a heterocycle" in item 13' and item 13 mean a heterocycle having N atom, and include, for example, a group shown below:

[Chemical formula 42]

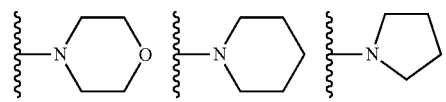

etc.

In the present description, $(R^{E6})m$ in the formula shown below:

[Chemical formula 43]

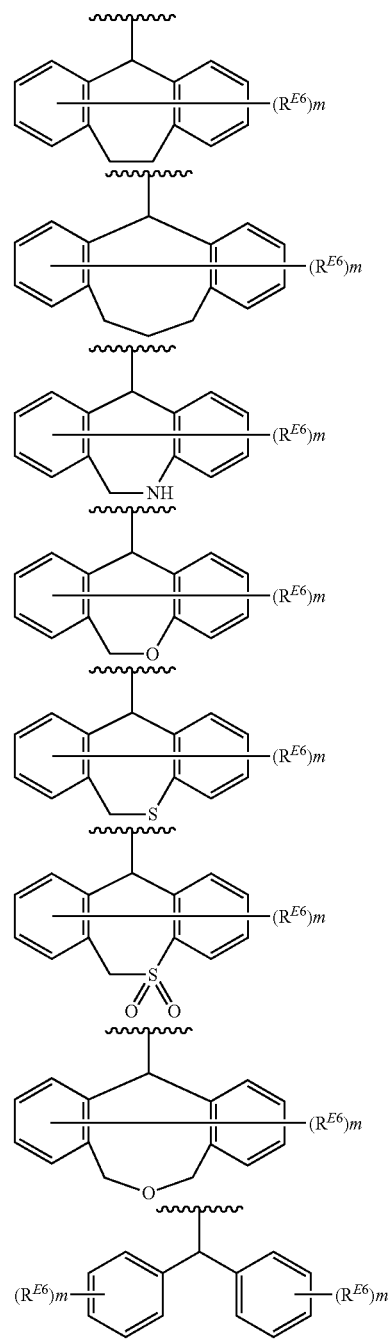

or means that an arbitrary carbon atom or nitrogen atom which can chemically have a substituent on a ring is substituted by m of $R^{E6}$s which are same or different.

For example, in the formula below:

[Chemical formula 44]

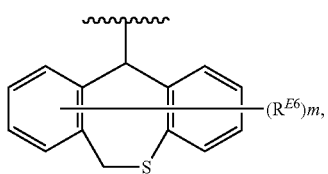

as shown by a substituent below:

[Chemical formula 45]

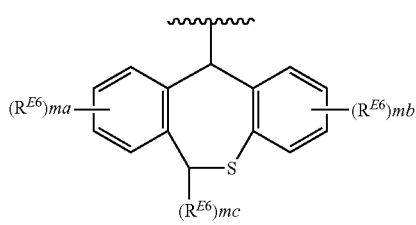

(wherein ma+mb+mc=m, and $R^{E6}$ is as defined above), it is meant that any hydrogen atom on two benzene rings and a 7-membered ring containing a sulfur atom may be substituted by $R^{E6}$, and respective $R^{E6}$s may be the same or different.

And, ma is preferably an integer of 0 to 3, mb is preferably an integer of 0 to 3, and mc is preferably an integer of 0 or 1. And, ma is more preferably an integer of 0 or 1, mb is more preferably an integer of 0 or 1, and mc is more preferably 0.

For example, in the formula below:

[Chemical formula 46]

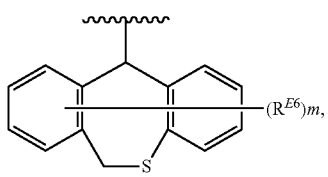

substituents shown below:

[Chemical formula 47]

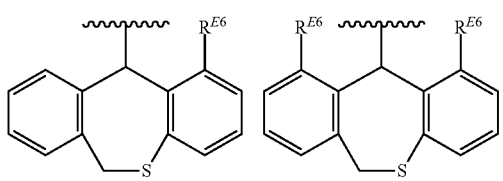

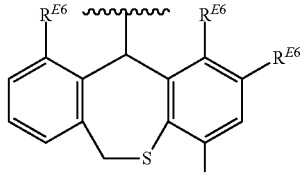
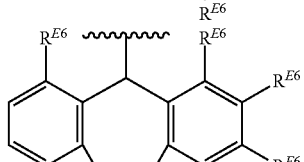
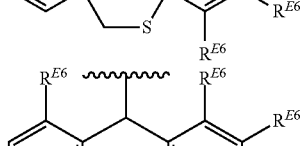
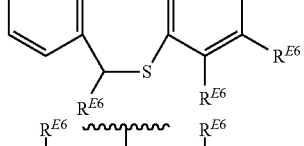
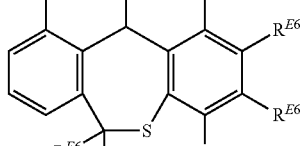
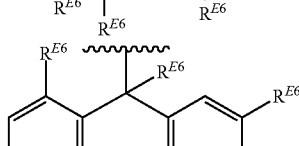
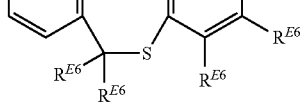

(wherein $R^{E6}$, and m are as defined in item 13')
etc. are included.

"When $A^1$ is $CR^5R^6$, and $A^2$ is $NR^7$, $R^3$ and $R^7$ may be taken together with an adjacent atom to form a heterocycle optionally substituted by substituent group B" in the formula (I) in item 1' and item 1 represents the formula (I') shown below:

[Chemical formula 48]

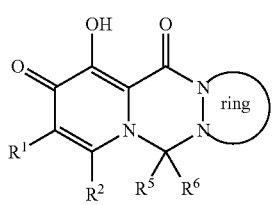

(I')

(wherein $R^1$, $R^2$, $R^5$ and $R^6$ are as defined in item 1' and item 1), and indicates that the "ring" may be substituted by one, two or more same or different substituents selected from substituent group B at an arbitrary position. The heterocycle is preferably a 5- to 7-membered ring. In addition, "the heterocycle may form a condensed ring" indicates that the ring in the formula (I') may be further condensed with a ring, and indicates that substituent group B may be bound to any of the ring in the formula (I') or the ring which is condensed with a ring. Examples of the formula (I') include compounds shown by the following formulae:

[Chemical formula 49]

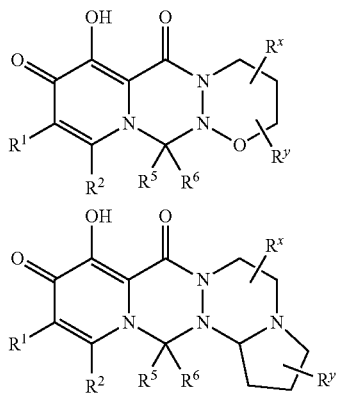

(wherein $R^x$, and $R^y$ are a substituent selected from substituent group B, and $R^1$, $R^2$, $R^5$, and $R^6$ are as defined in item 1' and item 1) etc.

"When form a heterocycle" in "when $A^1$ is $NR^7$, and $A^2$ is $CR^5R^6$, $R^3$ and $R^6$ may be taken together with an adjacent atom to form a heterocycle optionally substituted by substituent group B" in the formula (I) in item 1' and item 1 represents the formula (I'') shown below:

[Chemical formula 50]

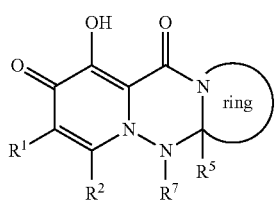

(I'')

(wherein $R^1$, $R^2$, $R^5$, and $R^6$ are as defined in item 1' and item 1), and indicates that a part of a ring may be substituted by one, two or more same or different substituents selected from substituent group B at an arbitrary position. The heterocycle is preferably a 5- to 7-membered ring. In addition, "the heterocycle may form a condensed ring" indicates that the ring in the formula (I'') may be further condensed with a ring, and indicates that one, two or more of substituent group B may be bound to any of the ring in the formula (I'') or the ring which is condensed with a ring. Examples of the formula (I'') include compounds shown in the following formula:

[Chemical formula 51]

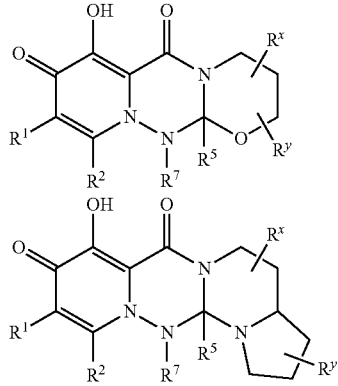

(wherein $R^x$ an $R^y$ are a substituent selected from substituent group B, and $R^1$, $R^2$, $R^5$ and $R^7$ are as defined in item 1' and item 1) etc.

"When form a bond" in "when $A^1$ is $CR^8R^9$, and $A^2$ is $CR^{10}R^{11}$, $R^8$ and $R^{10}$ may be taken together with an adjacent atom to form a bond" in the formula (I) of item 1' and item 1 represents the formula (I''') shown below:

[Chemical formula 52]

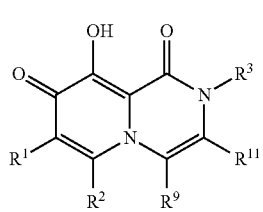

(I''')

(wherein $R^1$, $R^2$, $R^3$, $R^9$ and $R^{11}$ are as defined in item 1' and item 1).

In addition, "when form a bond" in "$R^8$ and $R^{10}$ may be taken together with an adjacent atom to form a carbocycle or a heterocycle optionally substituted by substituent group B" represents the formula (I'''') shown below:

[Chemical formula 53]

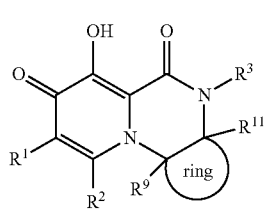

(I'''')

(wherein $R^1$, $R^2$, $R^3$, $R^9$ and $R^{11}$ are as defined in item 1' and item 1), and indicates that a part of a ring may be substituted by one, two or more same or different substituents selected from substituent group B at an arbitrary position. The carbocycle or the heterocycle is preferably a 5- to 7-membered ring. Examples of the formula (I'''') include a compound shown in the following formula:

[Chemical formula 54]

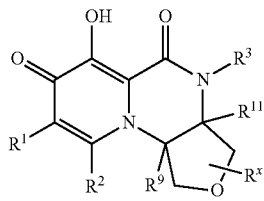

(wherein R$^x$ and R$^y$ are a substituent selected from substituent group B, and R$^1$, R$^2$, R$^3$, R$^9$ and R$^{11}$ are as defined in item 1' and item 1) etc.

Further, "R$^3$ and R$^{11}$ may be taken together with an adjacent atom to form a heterocyle optionally substituted by substituent group B, and the heterocycle may form a condensed ring" represents the formula (I'''') shown below:

[Chemical formula 55]

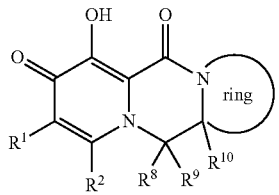

(I'''')

(wherein R$^1$, R$^2$, R$^8$, R$^9$ and R$^{10}$ are as defined in item 1' and item 1), and indicates that a part of a ring may further form a condensed ring, and the same or different substituents selected from substituent group B may be bound to any of the ring in the formula (I'''') or the ring which is condensed with a ring at an arbitrary position. The heterocycle is preferably a 5- to 7-membered ring. Examples of the formula (I'''') include compounds shown by the following formula:

[Chemical formula 56]

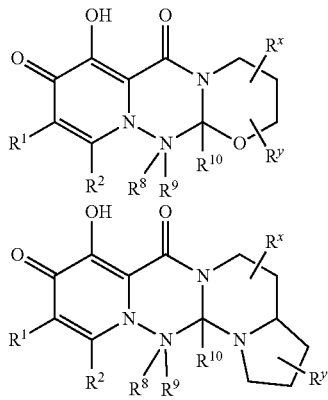

(wherein R$^x$ and R$^y$ are a substituent selected from substituent group B, and R$^1$, R$^2$, R$^8$, R$^9$ and R$^{10}$ are as defined in item 1' and item 1) etc.

"When form a heterocyle" in "when B$^1$ is CR$^{5a}$R$^{6a}$, and B$^2$ is NR$^{7a}$, R$^{3a}$ and R$^{7a}$ may be taken together with an adjacent atom to form a heterocycle optionally substituted by substituent group D" in the formula (II) in item 13 represents the formula (II') shown below:

[Chemical formula 57]

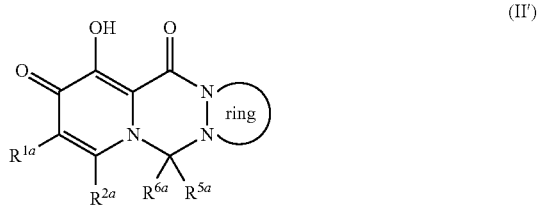

(II')

(wherein R$^{1a}$, R$^{2a}$, R$^{5a}$ and R$^{6a}$ are as defined in item 13' and item 13).

"When form a heterocycle" in "when B$^1$ is NR$^{7a}$, and B$^2$ is CR$^{5a}$R$^{6a}$, R$^{3a}$ and R$^{6a}$ may be taken together with an adjacent atom to form a heterocycle optionally substituted by substituent group D" represents the formula (II'') shown below:

[Chemical formula 58]

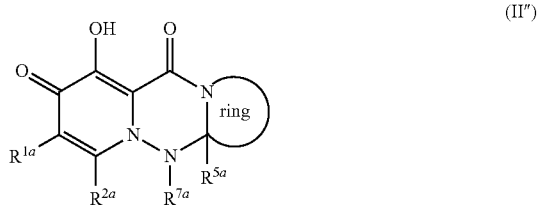

(II'')

(wherein R$^{1a}$, R$^{2a}$, R$^{5a}$ and R$^{7a}$ are as defined in item 13' and item 13). The heterocycle is preferably a 5- to 7-membered ring.

"When form a heterocycle" in "when B$^1$ is CR$^{8a}$R$^{9a}$, and B$^2$ is CR$^{10a}$R$^{11a}$, R$^{8a}$ and R$^{10a}$ may be taken together with an adjacent atom to form a carbocycle or a heterocycle optionally substituted by substituent group D" represents the formula (II''') shown below:

[Chemical formula 59]

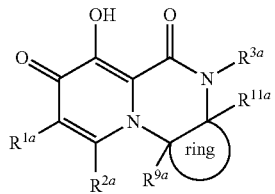

(II''')

(wherein R$^{1a}$, R$^{2a}$, R$^{3a}$, R$^{9a}$ and R$^{11a}$ are as defined in item 13' and item 13). The carbocycle or the heterocycle is preferably a 5- to 7-membered ring.

"When form a heterocycle" in "when B$^1$ is CR$^{8a}$R$^{9a}$, and B$^2$ is CR$^{10a}$R$^{11a}$, R$^{3a}$ and R$^{11a}$ may be taken together with an adjacent atom to form a heterocycle optionally substituted by substituent group D" represents the formula (II'''') shown below:

[Chemical formula 60]

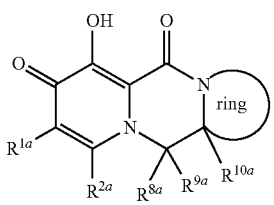

(II'''')

(wherein $R^{1a}$, $R^{2a}$, $R^{8a}$, $R^{9a}$ and $R^{10a}$ are as defined in item 13' and an item 13). The heterocycle is preferably a 5- to 7-membered ring.

"Solvate" includes, for example, a solvate with an organic solvent, a hydrate, etc. When a hydrate is formed, the compound may be coordinated with an arbitrary number of water molecules.

The compound of the present invention includes a pharmaceutically acceptable salt. Examples include salts with an alkali metal (lithium, sodium or potassium, etc.), an alkaline earth metal (magnesium or calcium, etc.), ammonium, an organic base and an amino acid, or salts with an inorganic acid (hydrochloric acid, sulfuric acid, nitric acid, hydrobromic acid, phosphoric acid or hydroiodic acid, etc.), and an organic acid (acetic acid, trifluoroacetic acid, citric acid, lactic acid, tartaric acid, oxalic acid, maleic acid, fumaric acid, mandelic acid, glutaric acid, malic acid, benzoic acid, phthalic acid, benzenesulfonic acid, p-toluenesulfonic acid, methanesulfonic acid or ethanesulfonic acid, etc.). These salts can be formed by the method which is usually performed.

In addition, the compound of the present invention is not limited to a particular isomer, but includes all possible isomers (keto-enol isomer, imine-enamine isomer, diastereoisomer, optical isomer and rotation isomer, etc.) and racemic bodies.

The formula (I) and the formula (II) in the present invention are not limited to a particular isomer, but include all possible isomers and racemic bodies. For example, they contain a tautomer and a steric isomer as follows.

[Chemical formula 61]

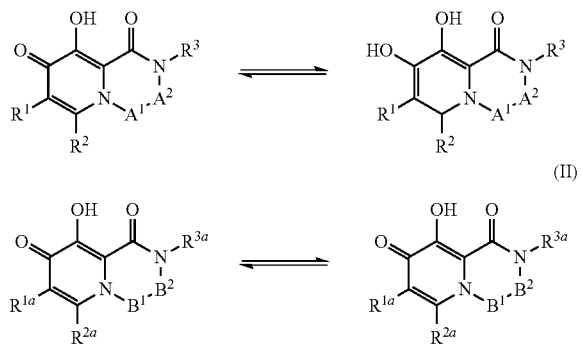

[Chemical formula 62]

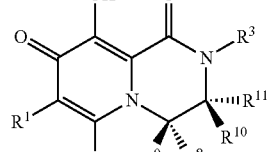

(Ia)-1

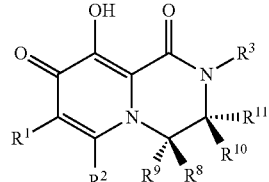

(Ia)-2

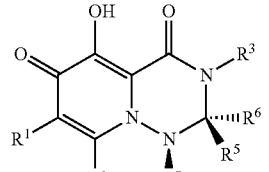

(Ib)-1

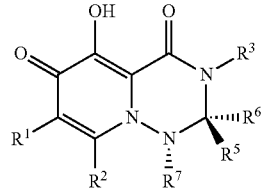

(Ib)-2

Further in the formula (I) and the formula (II) of the present invention, one or more hydrogen atoms, carbon atoms or other atoms can be substituted by an isotope of a hydrogen atom, a carbon atom or other atoms, respectively.

In addition, the compounds of the formulae (I) and (II) include all radioactive labeled bodies thereof. Such the "radioactive labeling" and "radioactive labeled form" of the compounds of the formulae (I) and (II) are included in the present invention, respectively, and are useful as a study and/or diagnostic tool in metabolized drug dynamic state study and binding assay.

Examples of an isotope which can be incorporated into the compounds of the formulae (I) and (II) of the present invention include a hydrogen atom, a carbon atom, a nitrogen atom, an oxygen atom, a phosphorus atom, a sulfur atom, a fluorine atom and a chlorine atom, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl.

A particularly preferable example of an isotope which can be incorporated into the compounds of the formulae (I) and (II) of the present invention is $^{2}$H (i.e. heavy hydrogen atom), and can be prepared by the method shown in Examples of the present description, or the method well-known in the art. In addition, a heavy hydrogen atom is expressed as "D" in Examples of the present description. Compounds of the formulae (I) and (II) of the present invention in which a hydrogen atom has been converted into a heavy hydrogen atom are excellent in respect of bioavailability, metabolism safety, drug efficacy, and toxicity as compared with unconverted forms, in some cases, and can be useful as medicaments.

"step B and step C are continuously performed" refers to execution of step C after reaction of step B without isolation operation and column chromatography purification of product generated in step B. A reaction container for step B and a reaction container for step C may be the same or different.

Examples of "lower alkyl optionally substituted by substituent group A" and "lower alkyl optionally substituted by substituent group C" include methyl, ethyl, propyl, isopropyl, butyl, tert-butyl, sec-butyl, pentan-2-yl, hydroxymethyl, hydroxyethyl, carboxymethyl, carboxyethyl, carboxypropyl, ethoxycarbonylpropyl, cyanomethyl, cyanoethyl, fluoromethyl, fluoroethyl, fluoropropyl, difluoromethyl, trifluoromethyl, chloromethyl, dichloromethyl, trichloromethyl, ethyloxycarbonylethyl, methoxymethyl, dimethoxymethyl, methoxyethyl, methoxypropyl, ethoxyethyl, 1-methyl-1-methoxymethyl, propyloxymethyl, aminopropyl, dimethylaminomethyl, aminomethyl, aminoethyl, dimethylaminoethyl, diethylaminomethyl, diethylaminoethyl, dimethylaminopropyl, cyclopropylmethyloxymethyl, methylsulfonylaminomethyl, methylaminocarbonylethyl, 1,1,1-trifluoropropan-2-yl, 1,1-difluoroethyl, 1,1,1-trifluoroethyl, 1,1,1-trifluoropropyl, trifluoromethyloxyethyl, trifluoromethylcarbonylaminomethyl, methylsulfonylethyl, methylcarbonyloxyethyl, and groups shown below:

[Chemical Formula 63]

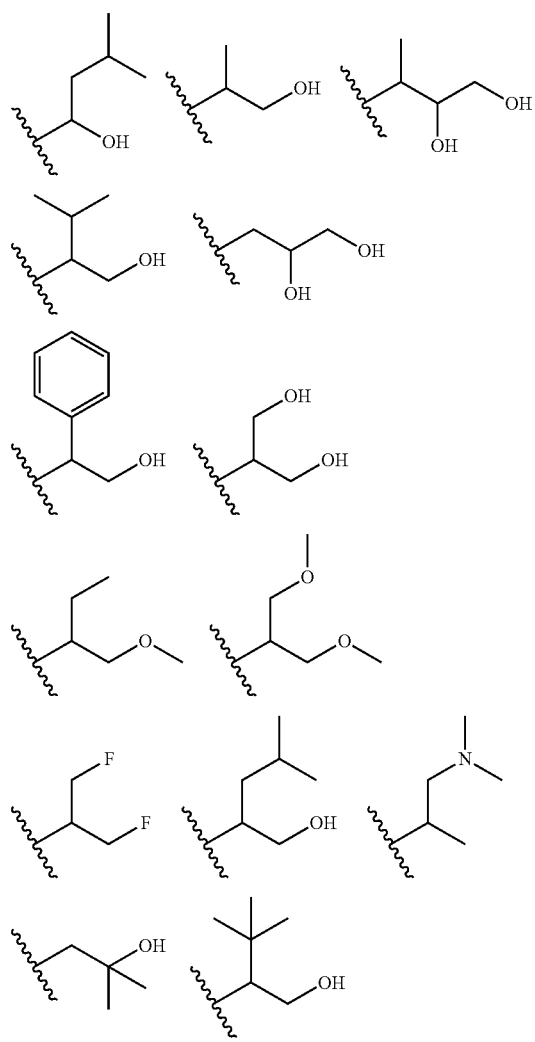

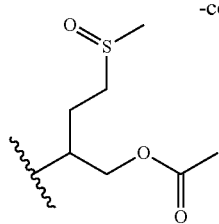

etc.

Examples of "lower alkenyl optionally substituted by substituent group A" and "lower alkenyl optionally substituted by substituent group C" include ethylenyl, 3-methyl-buten-2-yl, carboxyethylenyl, hydroxyethylenyl, difluoroethylenyl, 1-propen-2-yl, etc.

Examples of "lower alkynyl optionally substituted by substituent group A" and "lower alkynyl optionally substituted by substituent group C" include 1-propynyl, 1-butynyl, 3,3,3-trifluoromethylpropynyl, 3-hydroxy-propynyl, etc.

Examples of "lower alkyloxy optionally substituted by substituent group A" and "lower alkyloxy optionally substituted by substituent group C" include methyloxy, ethyloxy, trifluoromethyloxy, trichloromethyloxy, hydroxymethyloxy, hydroxyethyloxy, carboxymethyloxy, carboxyethyloxy, etc.

Examples of "lower alkenyloxy optionally substituted by substituent group A" and "lower alkenyloxy optionally substituted by substituent group C" include 3-fluoro-1-propenyloxy, ethylenyl, carboxyethylenyl, hydroxyethylenyloxy, difluoroethylenyloxy, etc.

Examples of "lower alkylcarbonyl optionally substituted by substituent group A" and "lower alkylcarbonyl optionally substituted by substituent group C" include methylcarbonyl, ethylcarbonyl, propylcarbonyl, isopropylcarbonyl, hydroxymethylcarbonyl, hydroxyethylcarbonyl, trifluoromethylcarbonyl, 2,2,2-trifluoromethylcarbonyl, carboxymethylcarbonyl, etc.

Examples of "lower alkyloxycarbonyl optionally substituted by substituent group A" and "lower alkyloxycarbonyl optionally substituted by substituent group C" include methyloxycarbonyl, ethyloxycarbonyl, trifluoromethyl oxycarbonyl, trichloromethyloxycarbonyl, hydroxymethyloxycarbonyl, hydroxyethyloxycarbonyl, carboxymethyloxycarbonyl, etc.

Examples of "carbocyclic group optionally substituted by substituent group A" and "carbocyclic group optionally substituted by substituent group C" include phenyl, naphthyl, anthracenyl, phenanthracenyl, adamantyl, 1-hydroxyadamantyl, 2-hydroxyadamantyl, 3-methylphenyl, 4-methylphenyl, 3-methoxyphenyl, 4-methoxyphenyl, 3-hydroxyphenyl, 4-hydroxyphenyl, 4-chlorophenyl, 4-fluorophenyl, 2-cyanophenyl, 3-cyanophenyl, 4-cyanophenyl, fluorocyclopropyl, difluorocyclobutanyl, difluorocyclohexyl, and groups shown below:

[Chemical formula 64]

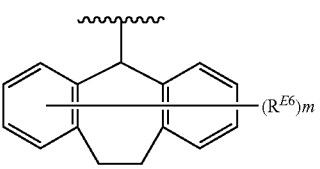

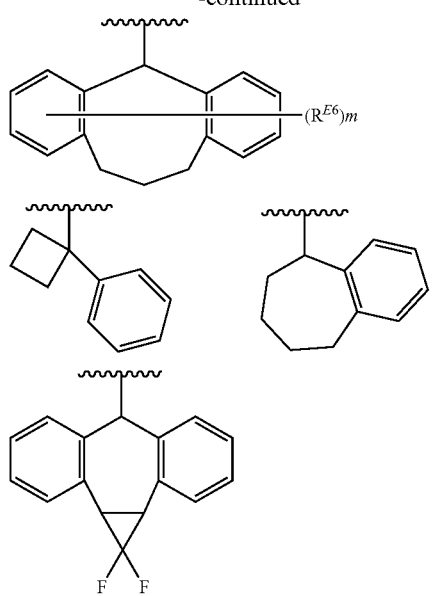

(wherein $R^{E6}$ represents a group selected from substituent group A or substituent group C, and m of $R^{E6}$s may be the same or different) etc.

Examples of "carbocycle lower alkyl optionally substituted by substituent group A" and "carbocycle lower alkyl optionally substituted by substituent group C" include cyclopropylmethyl, 4-hydroxybenzyl, cyclopentylmethyl, benzyl, 2-aminobenzyl, 2-cyanobenzyl, 2-fluorobenzyl, 4-fluorobenzyl, 2-trifluoromethylbenzyl, 1,3,5-trifluorobenzyl, 3,4,5-trifluorobenzyl, 4-methoxybenzyl, 2,4-difluorobenzyl, 2-fluoro-3-chlorobenzyl, benzhydryl, 4-phenylbenzyl, phenethyl, phenylpropyl, 4-methylcarbonylaminobenzyl, 3,4-dichlorobenzyl, 4-chloro-2-fluorobenzyl, 3,5-dihydroxybenzyl, and groups shown below:

[Chemical formula 65]

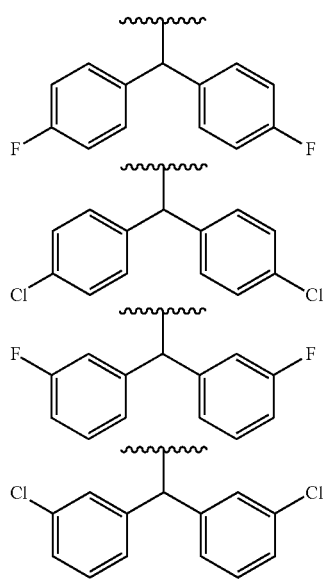

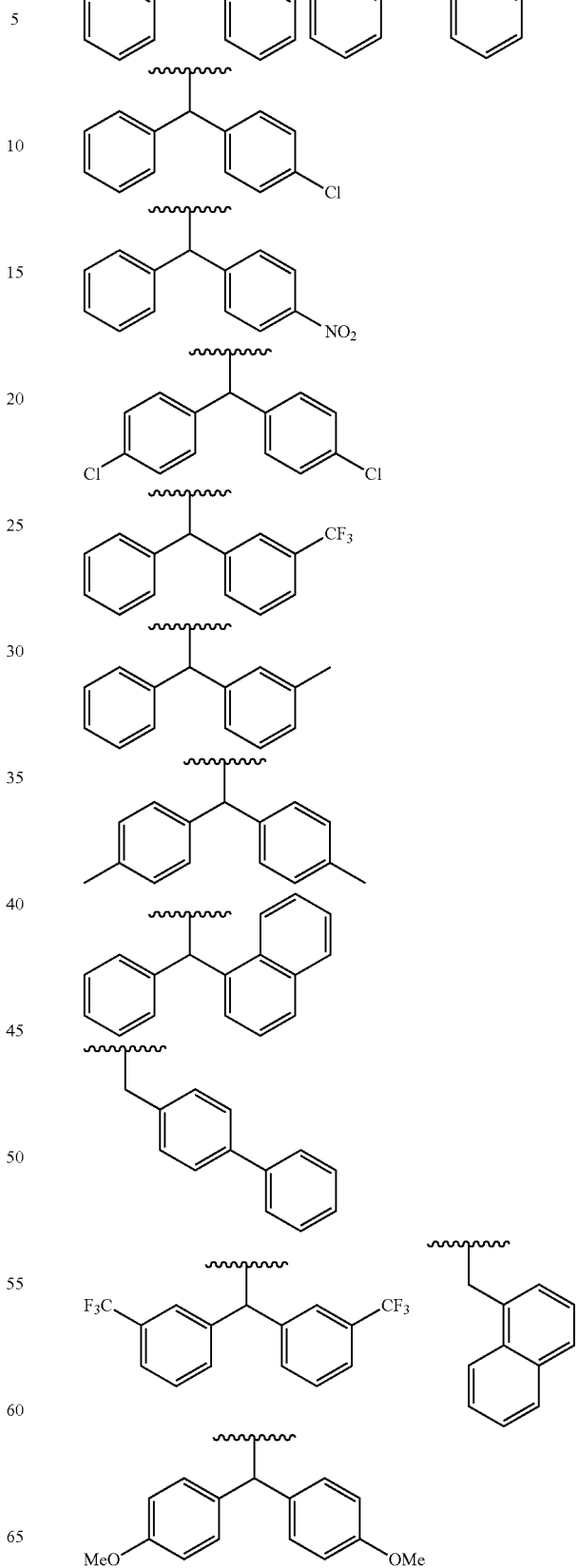

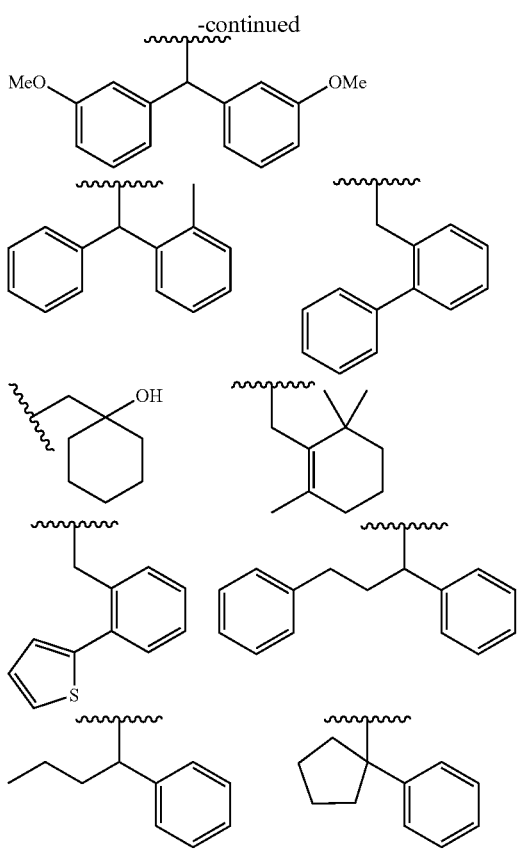

etc.

Examples of "carbocycric oxy lower alkyl optionally substituted by substituent group A" and "carbocycleoxy lower alkyl optionally substituted by substituent group C" include 4-hydroxyphenyloxymethyl, 4-hydroxyphenyloxyethyl, cyclopropyloxymethyl, cyclopentyloxymethyl, 4-fluorophenyloxymethyl, 4-fluorophenyloxyethyl, 4-trifluoromethylphenyloxymethyl, 4-trifluoromethylphenyloxyethyl, 4-methoxyphenyloxymethyl, 4-methoxyphenyloxyethyl, etc.

Examples of "carbocyclecarbonyl optionally substituted by substituent group A" and "carbocyclecarbonyl optionally substituted by substituent group C" include phenylcarbonyl, 4-fluorophenylcarbonyl, 4-trifluoromethylphenylcarbonyl, 4-methoxyphenylcarbonyl, cyclopropylcarbonyl, etc.

Examples of "carbocycleoxy optionally substituted by substituent group A" and "carbocycleoxy optionally substituted by substituent group C" include phenyloxy, cyclopropyloxy, cyclopentyloxy, 4-fluorophenyloxy, 4-trifluoromethylphenyloxy, 4-methoxyphenyloxy, etc.

Examples of "carbocycleoxycarbonyl optionally substituted by substituent group A" and "carbocycleoxycarbonyl optionally substituted by substituent group C" include phenyloxycarbonyl, cyclopropyloxycarbonyl, cyclopentyloxycarbonyl, 4-fluorophenyloxycarbonyl, 4-trifluoromethylphenyloxycarbonyl, 4-methoxyphenyloxycarbonyl, etc.

Examples of "heterocyclic group optionally substituted by substituent group A" and "heterocyclic group optionally substituted by substituent group C" include pyrimidinyl, pyridyl, benzoxazolyl, morpholinyl, tetrahydropyranyl, furyl, thiophenyl, oxazolyl, thiazolyl, pyrazolyl, methylpyrrolidinyl, isopropylpyrrolidinyl, methylsulfonylpyrrolidinyl, hydroxyethylpyrrolidinyl, methylpiperidinyl, methylpiperazinyl, tetrahydrofuryl, and groups shown below:

[Chemical formula 66]

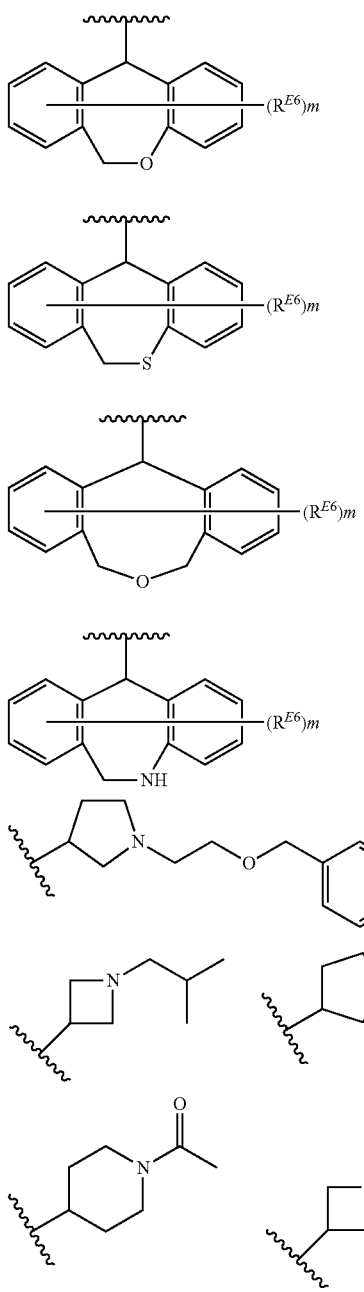

(wherein $R^{E6}$ represents a group selected from substituent group A or substituent group C, and m of $R^{E6}$s may be the same or different) etc.

Examples of "heterocycle lower alkyl optionally substituted by substituent group A" and "heterocycle lower alkyl optionally substituted by substituent group C" include tetrahydropyranylmethyl, pyridylmethyl, isoxazolylmethyl, 5-methyl-isoxazolylmethyl, 3-methyl-oxadiazolylmethyl, indolylmethyl, benzothiophenylmethyl, 5-chlorobenzothiophenylmethyl, thiazolylmethyl, 2-methylthiazolylmethyl, pyrazolylmethyl, 2-methylpyrazolylmethyl, dithiophenylmethyl, tetrazolylmethyl, quinazolylmethyl, and groups shown below:

[Chemical formula 67]

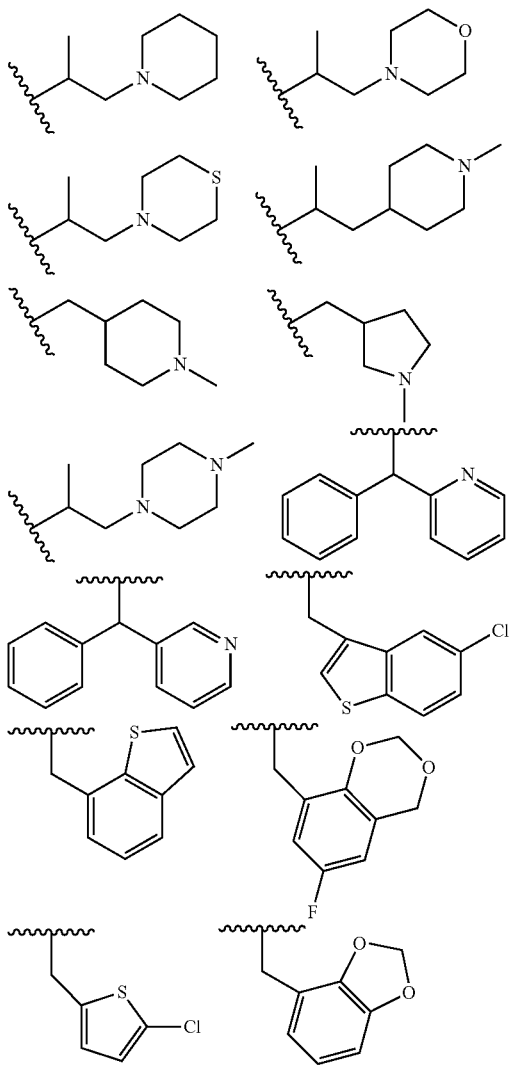

etc.

Examples of "heterocycleoxy lower alkyl optionally substituted by substituent group A" and "heterocycleoxy lower alkyl optionally substituted by a substutuent group C" include tetrahydropyranyloxymethyl, pyridyloxymethyl, isoxazolyloxymethyl, 5-methyl-isoxazolyloxymethyl, indolyloxymethyl, benzothiophenyloxymethyl, 5-chlorobenzothiophenyloxymethyl, thiazolyloxymethyl, 2-methylthiazolyloxymethyl, pyrazolyloxymethyl, 2-methylpyrazolyloxymethyl, etc.

Examples of "heterocyclecarbonyl optionally substituted by substituent group A" and "heterocyclecarbonyl optionally substituted by substituent group C" include tetrahydropyranylcarbonyl, pyridylcarbonyl, isoxazolylcarbonyl, 5-methyl-isoxazolylcarbonyl, indolylcarbonyl, benzothiophenylcarbonyl, 5-chlorobenzothiophenylcarbonyl, thiazolylcarbonyl, 2-methylthiazolylcarbonyl, pyrazolylcarbonyl, 2-methylpyrazolylcarbonyl, etc.

Examples of "heterocycleoxy optionally substituted by substituent group A", and "heterocycleoxy optionally substituted by substituent C" include tetrahydropyranyloxy, pyridyloxy, isoxazolyloxy, 5-methyl-isoxazolyloxy, indolyloxy, benzothiophenyloxy, 5-chlorobenzothiophenyloxy, thiazolyloxy, 2-methylthiazolyloxy, pyrazolyloxy, 2-methylpyrazolyloxy, etc.

Examples of "heterocycleoxycarbonyl optionally substituted by substituent group A", and "heterocycleoxycarbonyl optionally substituted by substituent group C" include tetrahydropyranyloxycarbonyl, pyridyloxycarbonyl, isoxazolyloxycarbonyl, 5-methyl-isoxazolyloxycarbonyl, indolyloxycarbonyl, benzothiophenyloxycarbonyl, 5-chlorobenzothiophenyloxycarbonyl, thiazolyloxycarbonyl, 2-methylthiazolyloxycarbonyl, pyrazolyloxycarbonyl, 2-methylpyrazolyloxycarbonyl, etc.

Examples of a preferable substituent in $R^1$ and $R^{1a}$ include hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{41}$)($R^{42}$)
—Z—N($R^{43}$)—$SO_2$—($R^{44}$)
—Z—C(=O)—N($R^{45}$)—$SO_2$—($R^{46}$),
—Z—N($R^{47}$)—C(=O)—$R^{48}$,
—Z—S—$R^{49}$,
—Z—$SO_2$—$R^{410}$,
—Z—S(=O)—$R^{411}$,
—Z—N($R^{412}$)—C(=O)—O—$R^{413}$,
—Z—N($R^{414}$)—C(=O)—N($R^{415}$)($R^{416}$),
—Z—C(=O)—N($R^{417}$)—C(=O)—N($R^{418}$)($R^{419}$), or
—Z—N($R^{42}$)—C(=O)—C(=O)—$R^{421}$,
(substituent group C, $R^{41}$, $R^{42}$, $R^{43}$, $R^{45}$, $R^{47}$, $R^{48}$, $R^{49}$, $R^{410}$, $R^{411}$, $R^{412}$, $R^{413}$, $R^{414}$, $R^{415}$, $R^{416}$, $R^{417}$, $R^{418}$, $R^{419}$, $R^{420}$, $R^{421}$, and Z are as defined in item 13' or item 13).

Examples of a more preferable substituent in $R^1$ and $R^{1a}$ include hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C,
—Z—N($R^{41}$)($R^{42}$),
—Z—N($R^{47}$)—C(=O)—$R^{48}$, or
—Z—N($R^{412}$)—C(=O)—O—$R^{413}$
(Substituent group C, $R^{41}$, $R^{42}$, $R^{47}$, $R^{48}$, $R^{412}$, $R^{413}$ and Z are as defined in item 13' or item 13)

Examples of a further preferable substituent in $R^1$ and $R^{1a}$ include hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C, or

—Z—N($R^{A1}$)($R^{A2}$)

(substituent group C, $R^{A1}$, $R^{A2}$, and Z are as defined in item 13' or item 13)

Examples of another embodiment of a preferable substituent in $R^1$ and $R^{1a}$ include hydrogen, carboxy, hydroxymethyl, methoxy, chlorine atom, bromine atom, ethoxymethyl, dimethylamino, hydroxy, —C(=O)—NH—S(=O)$_2$-Me, amino, methylamino, methylaminomethyl, —NH—C(=O)—CF$_3$, pyrazolyl, —NH—C(=O)-Me, —C(=O)N-Me$_2$, tetrazolyl, —NH—C(=O)-Ph, —C(=O)NH-Me, —C(=O)NH-Et, —C(=O)NH-cyclopropyl, methoxycarbonyl, methyl, propenyl, propyl, isopropyl, fluoromethyl
(Me represents a methyl group, Ph represents a phenyl group, and Et represents an ethyl group) etc.

Examples of another embodiment of a more preferable substituent in $R^1$ and $R^{1a}$ include hydrogen, carboxy, hydroxymethyl, methoxy, bromine atom, ethoxymethyl, dimethylamino, hydroxy, —C(=O)—NH—S(=O)$_2$-Me, amino, methylamino, methyl, propenyl
(Me represents a methyl group) etc.

Examples of another embodiment of a further preferable substituent in $R^1$ and $R^{1a}$ include hydrogen, and carboxy.

Examples of a preferable substituent in $R^2$ and $R^{2a}$ include hydrogen, halogen, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy optionally substituted by substituent group C, heterocycleoxycarbonyl optionally substituted by substituent group C, —Z—N($R^{B1}$)—SO$_2$—$R^{B2}$,
—Z—N($R^{B3}$)—C(=O)—$R^{B4}$,
—Z—N($R^{B5}$)—C(=O)—O—$R^{B6}$,
—Z—C(=O)—N($R^{B7}$)($R^{B8}$),
—Z—N($R^{B9}$)($R^{B10}$), or
—Z—SO$_2$—$R^{B11}$ (substituent group C, $R^{B1}$, $R^{B2}$, $R^{B3}$, $R^{B4}$, $R^{B5}$, $R^{B6}$, $R^{B7}$, $R^{B8}$, $R^{B9}$, $R^{B10}$, $R^{B11}$ and Z are as defined in item 13' or item 13).

Examples of a more preferable substituent in $R^2$ and $R^{2a}$ include hydrogen, lower alkyl optionally substituted by substituent group C, carbocycle lower alkyl optionally substituted by substituent group C, heterocycle lower alkyl optionally substituted by substituent group C, or

—Z—N($R^{B9}$)($R^{B10}$)

(a substituent group C, $R^{B9}$, $R^{B10}$, and Z are as defined in item 13' or item 13).

Examples of a further preferable substituent in $R^2$ and $R^{2a}$ include hydrogen, or lower alkyl optionally substituted by substituent group C, heterocycle lower alkyl optionally substituted by substituent group C (substituent group C is as defined in item 13' or item 13).

Examples of another embodiment of a preferable substituent in $R^2$ and $R^{2a}$ include hydrogen, hydroxymethyl, amino, methoxymethyl, methoxymethylcyclopropylmethyloxymethyl, cyanomethyl, aminomethyl, propyloxymethyl, —CH$_2$—NH—C(=O)-Me, methylaminomethyl, imidazolyl, dimethylaminomethyl, pyrrolidinyl, fluoromethyl, —CH$_2$—NH—C(=O)H
(Me represents a methyl group) etc.

Examples of another embodiment of a more preferable substituent in $R^2$ and $R^{2a}$ include hydrogen, hydroxymethyl, methoxymethylcyclopropylmethyloxymethyl, aminomethyl, propyloxymethyl, etc.

Examples of another embodiment of a further preferable substituent in $R^2$ and $R^{2a}$ include hydrogen.

Examples of a preferable substituent in $R^3$ and $R^{3a}$ include hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$)
—Z—N($R^{C9}$)($R^{C10}$), or
—Z—SO$_2$—$R^{C11}$ (substituent group C, $R^{C1}$, $R^{C2}$, $R^{C3}$, $R^{C4}$, $R^{C5}$, $R^{C6}$, $R^{C7}$, $R^{C8}$, $R^{C9}$, $R^{C10}$, $R^{C11}$, and Z are as defined in item 13' or item 13)

Examples of a more preferable substituent in $R^3$ and $R^{3a}$ include hydrogen, lower alkyl optionally substituted by substituent group C, lower alkenyl optionally substituted by substituent group C, lower alkynyl optionally substituted by substituent group C, carbocyclic group optionally substituted by substituent group C, carbocycle lower alkyl optionally substituted by substituent group C, carbocycleoxy lower alkyl optionally substituted by substituent group C, —Z—N($R^{C1}$)—SO$_2$—$R^{C2}$,
—Z—N($R^{C3}$)—C(=O)—$R^{C4}$,
—Z—N($R^{C5}$)—C(=O)—O—$R^{C6}$,
—Z—C(=O)—N($R^{C7}$)($R^{C8}$), or
—Z—N($R^{C9}$)($R^{C10}$)

(substituent group C, $R^{C1}$, $R^{C2}$, $R^{C3}$, $R^{C4}$, $R^{C5}$, $R^{C6}$, $R^{C7}$, $R^{C8}$, $R^{C9}$, $R^{C10}$, and Z are as defined in item 13)

Examples of a further preferable substituent in $R^3$ and $R^{3a}$ include hydrogen, lower alkyl optionally substituted by substituent group C, lower alkynyl optionally substituted by substituent group C, carbocyclic group optionally substituted by substituent group C, or carbocycle lower alkyl optionally substituted by substituent group C
(substituent group C is as defined in item 13' or item 13).

Examples of another embodiment of a preferable substituent in $R^3$ and $R^{3a}$ include hydrogen, ethoxyethyl, methyl, ethyl, propyl, 2,4-difluorobenzyl, methoxyethyl, cyanomethyl, cyanoethyl, 3-chloro-2-fluorobenzyl, 1-methoxypropyl, pyridylmethyl, isopropyl, tetrahydropyranylmethyl, cyclopropylmethyl, benzyl, methylisoxazolylmethyl, methyloxadiazolyl, isopropyloxyethyl, hydroxyethyl, 4-fluorobenzyl, cyclopropyl, ethoxycarbonylethyl, —CH(Me)CH$_2$OMe, carboxyethyl, —CH$_2$CH$_2$C(=O)—N(Me)$_2$, —CH$_2$CH$_2$N(Me)-S(=O)$_2$-Ph, —CH$_2$CH$_2$—N(Me)-S(=O)$_2$-Me, —CH$_2$CH$_2$—NHC(=O)-Ph, —CH(Me)-CH$_2$—OMe, —CH$_2$CH$_2$—NH—S(=O)$_2$-Ph, —CH$_2$CH$_2$—NH—C(=O)—O—CH(Me)$_2$, —CH$_2$CH$_2$—C(=O)—NH-Ph, —CH$_2$CH$_2$—N(Me)C(=O)-Ph, —CH$_2$CH$_2$—NH—C(=O)-Me, —CH$_2$CH$_2$—NH—S(=O)$_2$-Me, aminoethyl, —CH$_2$CH$_2$—N(Me)-C(=O)-Me, —CH$_2$CH$_2$—C(=O)—N(Me)-Ph, —CH$_2$CH$_2$—NH—C(=O)—O-tBu, piperidinylcarbonylethyl, dimethylaminoethyl, cyclopropylmethyl, methylaminoethyl, furanylmethyl, morpholinylcarbonylethyl, sec-butyl, pentan-2-yl, carboxypropyl, ethoxycarbonylpropyl, phenylpropyl, propyloxyethyl, aminopropyl, dimethylaminomethyl, dimethylaminoethyl, diethylaminomethyl, diethylaminoethyl, dimethylaminopropyl, methylaminocarbonylethyl, 1,1,1-trifluoropropan-2-yl, 1,1-difluoroethyl, 1,1,1-trifluoroethyl, 1,1,1-trifluoropropyl, trifluoromethyloxyethyl, trifluoromethylcarbonylaminomethyl, methylsulfonylethyl, methylcarbonyloxyethyl, methylcarbonyloxypropyl, 1-fluoropropyl, fluorocyclopropyl, difluorocyclopropyl, 3,3-dimethylbutan-2-yl, 1-fluoroethyl, 1-methoxypropan-2-yl, amino, thiazolylmethyl, methylsulfonylethyl, 4-fluorophenyloxyethyl, pyridyl, pentan-2-yl, butan-2-yl, 3-methylbuten-2-yl, as well as groups shown below:

[Chemical formula 68]

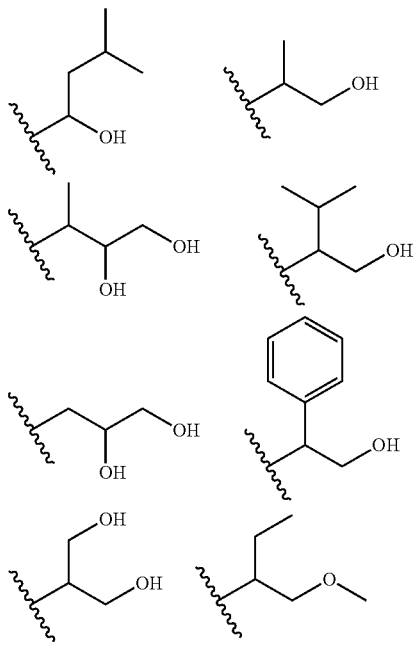

[Chemical formula 69]

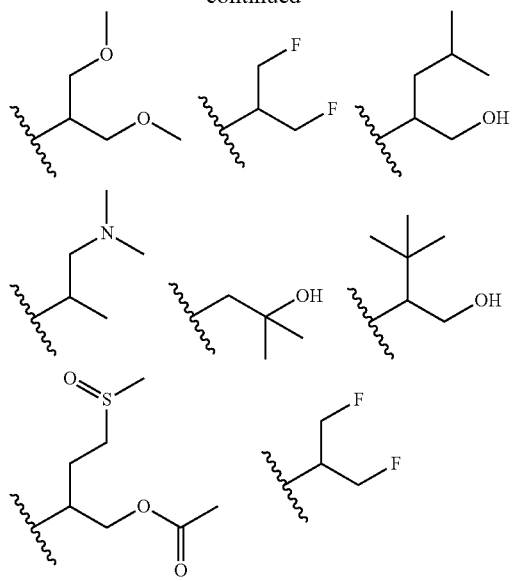

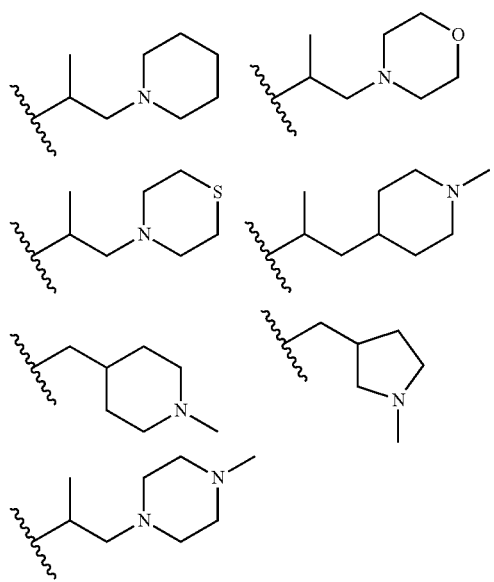

[Chemical formula 70]

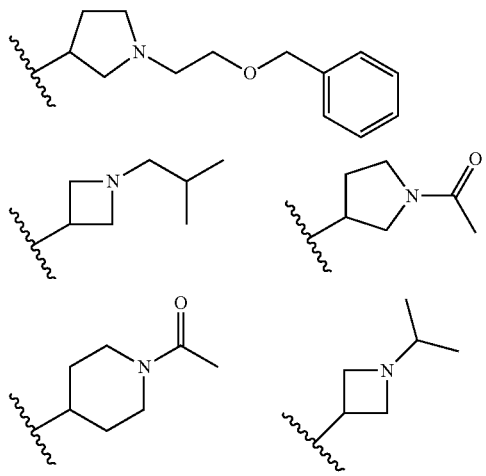

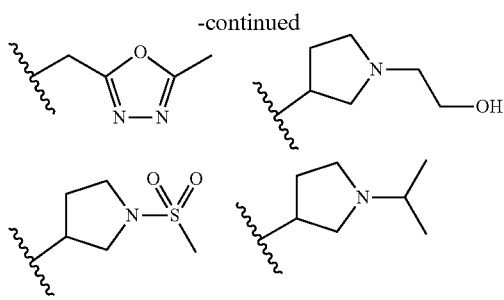

(Me represents a methyl group, Ph represents a phenyl group, and tBu represents a tert-butyl group) etc.

Examples of another embodiment of a more preferable substituent in $R^3$ and $R^{3a}$ include ethoxyethyl, methyl, ethyl, 2,4-difluorobenzyl, methoxyethyl, cyanomethyl, 3-chloro-2-fluorobenzyl, methoxypropyl, pyridylmethyl, isopropyl, tetrahydropyranylmethyl, cyclopropylmethyl, benzyl, methylisoxazolylmethyl, 4-fluorobenzyl, cyclopropyl, ethoxycarbonylethyl, —CH(Me)CH$_2$OMe, carboxyethyl, —CH$_2$CH$_2$C(=O)—N(Me)$_2$, —CH$_2$CH$_2$N(Me)-S(=O)$_2$-Ph, —CH$_2$CH$_2$—N(Me)-S(=O)$_2$-Me, —CH$_2$CH$_2$—NHC(=O)-Ph, —CH(Me)-CH$_2$—OMe, —CH$_2$CH$_2$—NH—S(=O)$_2$-Ph, —CH$_2$CH$_2$—NH—C(=O)—O—CH(Me)$_2$, —CH$_2$CH$_2$—C(=O)—NH-Ph, —CH$_2$CH$_2$—N(Me)C(=O)-Ph, —CH$_2$CH$_2$—NH—C(=O)-Me, —CH$_2$CH$_2$—NH—S(=O)$_2$-Me, aminoethyl, 1,1,1-trifluoropropan-2-yl, propyl, methylthiomethyl, hydrogen, fluorocyclopropyl, trifluoromethoxyethyl, 1-fluoropropyl, 1-fluoroethyl, methylcarbonyloxymethyl, 1,1-difluoromethyl, and groups shown below:

[Chemical formula 71]

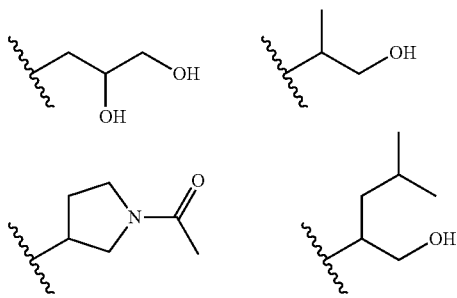

(Me represents methyl group, and Ph represents phenyl group) etc.

Examples of another embodiment of a further preferable substituent in $R^3$ and $R^{3a}$ include ethoxyethyl, methyl, ethyl, 2,4-difluorobenzyl, methoxyethyl, cyanomethyl, 3-chloro-2-fluorobenzyl, methoxypropyl, pyridylmethyl, isopropyl, tetrahydropyranylmethyl, cyclopropylmethyl, benzyl, 4-fluorobenzyl, cyclopropyl, ethoxycarbonylethyl, —CH(Me)CH$_2$OMe, carboxyethyl, 1,1,1-trifluoropropan-2-yl, hydroxyethyl, 1-fluoroethyl (Me represents methyl group) etc.

Examples of another embodiment of a most preferable substituent in $R^3$ and $R^{3a}$ include 1,1,1-trifluoropropan-2-yl.

Examples of a preferable substituent in $R^5$, $R^6$, $R^7$, $R^8$, $R^9$, $R^{10}$, and $R^{11}$ as well $R^{5a}$, $R^{6a}$, $R^{7a}$, $R^{8a}$, $R^{9a}$, $R^{10a}$, and $R^{11a}$ include hydrogen, carboxy, cyano, lower alkyl optionally substituted by substituent group C, lower alkenyl optionally substituted by substituent group C, lower alkynyl optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C,
—Y—S—R$^{D1}$,
—Z—S(=O)—R$^{D2}$,
—Z—SO$_2$—R$^{D3}$,
—C(=O)—C(=O)—R$^{D4}$,
—C(=O)—N(R$^{D5}$)(R$^{D6}$),
—Z—C(R$^{D7}$)(R$^{D8}$)(R$^{D9}$), or
—Z—CH$_2$—R$^{D10}$
(substituent group C, R$^{D1}$, R$^{D2}$, R$^{D3}$, R$^{D4}$, R$^{D5}$, R$^{D6}$, R$^{D7}$, R$^{D8}$, R$^{D9}$, R$^{D10}$ and Z are as defined in item 13' or item 13).

Examples of a more preferable substituent in $R^5$, $R^6$, $R^7$, $R^8$, $R^9$, $R^{10}$, and $R^{11}$, as well as $R^{5a}$, $R^{6a}$, $R^{7a}$, $R^{8a}$, $R^{9a}$, $R^{10a}$, and $R^{11a}$ include hydrogen, lower alkyl optionally substituted by substituent group C, carbocyclic group optionally substituted by substituent group C, carbocycleoxy lower alkyl optionally substituted by substituent group C, heterocyclic group optionally substituted by substituent group C, heterocycleoxy lower alkyl optionally substituted by substituent group C,
—Y—S—R$^{D1}$, or
—Z—C(R$^{D7}$)(R$^{D8}$)(R$^{D9}$)
(substituent group C, R$^{D1}$, R$^{D7}$, R$^{D8}$, R$^{D9}$, Y, and Z are as defined in item 13' or item 13).

Examples of another embodiment of a preferable substituent in $R^5$, $R^6$, $R^7$, $R^8$, $R^9$, $R^{10}$, and $R^{11}$, as well as $R^{5a}$, $R^{6a}$, $R^{7a}$, $R^{8a}$, $R^{9a}$, $R^{10a}$, and $R^{11a}$ include hydrogen, benzhydryl, benzyl, indolylmethyl, cyclohexylmethyl, phenethyl, benzylthiomethyl, 3,5-dimethylisoxazolyl, 5-chloro-3-ethylbenzothiophenyl, 4-fluorobenzyl, methylthiazolylmethyl, cyclopentylmethyl, 4-methoxybenzyl, 3-fluorobenzyl, naphthylmethyl, methyl, 3-trifluoromethylbenzyl, pyridylmethyl, 4-methylcarbonylaminobenzyl, pyrimidinyl, isobutyl, phenoxyethyl, methoxypropyl, phenylpropyl, as well as the following groups:

[Chemical formula 72]

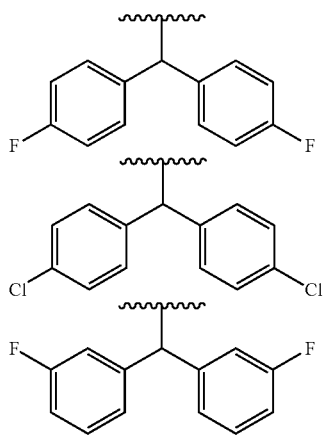

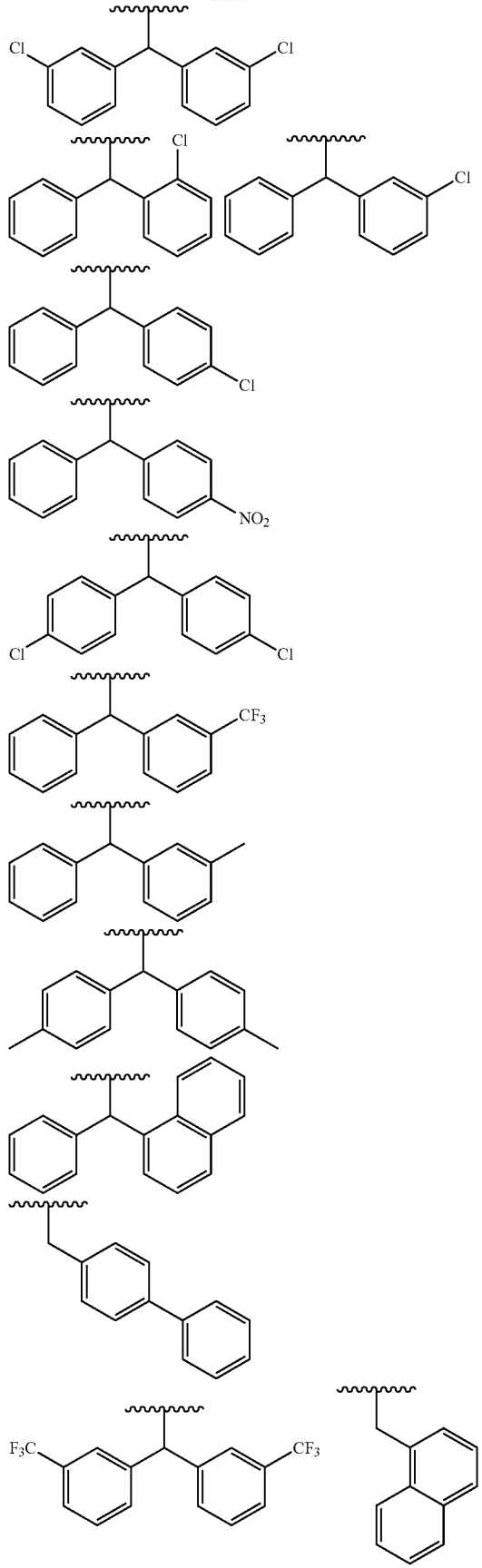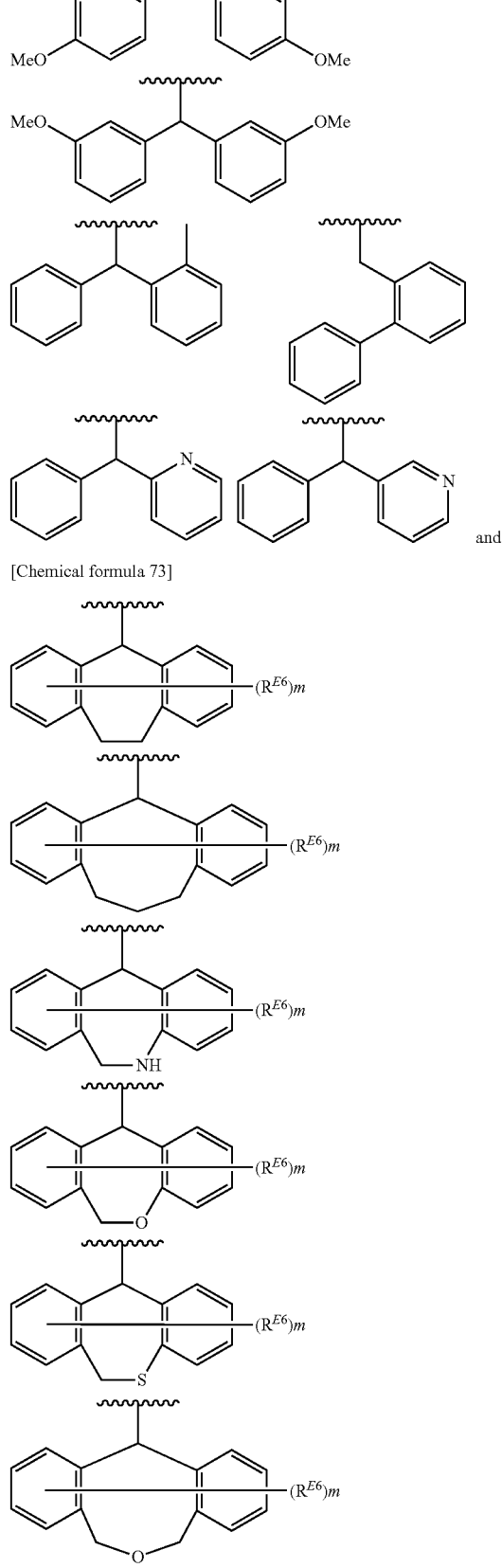

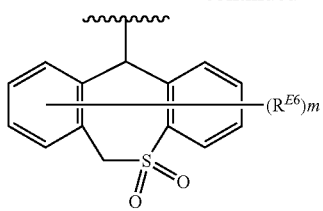

(wherein $R^{E6}$ represents a group selected from substituent group A or substituent group C, and m of $R^{E6}$s may be the same or different) etc.

Examples of another embodiment of a more preferable substituent in $R^5$, $R^6$, $R^7$, $R^8$, $R^9$, $R^{10}$, and $R^{11}$, as well as $R^{5a}$, $R^{6a}$, $R^{7a}$, $R^{8a}$, $R^{9a}$, $R^{10a}$, and $R^{11a}$ include hydrogen, benzhydryl, benzyl, indolylmethyl, cyclohexylmethyl, phenethyl, 3,5-dimethylisoxazolyl, 5-chloro-3-ethylbenzothiophenyl, biphenylmethyl, 4-fluorobenzyl, methylthiazolylmethyl, cyclopentylmethyl, 4-methoxybenzyl, 3-fluorobenzyl, naphthylmethyl, methyl, 3-trifluoromethylbenzyl, pyridylmethyl, 4-methylcarbonylaminobenzyl, pyrimidinyl, and the following groups:

[Chemical formula 74]

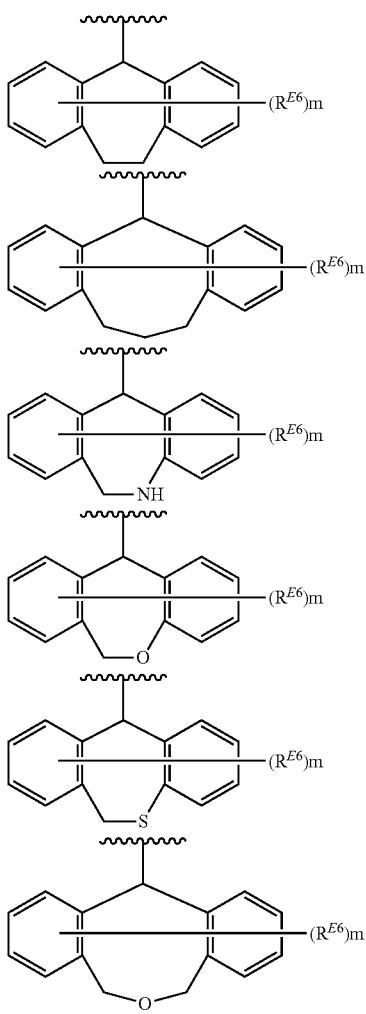

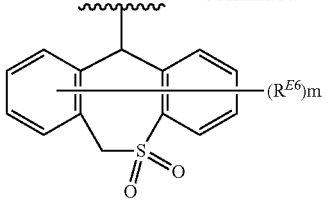

(wherein $R^{E6}$ represents a group selected from substituent group A or substituent group C, and m of $R^{E6}$s may be the same or different).
etc.

1) Examples of a preferable embodiment when $A^1$ is $CR^5R^6$, and $A^2$ is $NR^7$ include the case where $R^3$ and $R^7$ are taken together with an adjacent atom to form a heterocycle optionally substituted by substituent group B.

2) Examples of a preferable embodiment when $A^1$ is $NR^7$, and $A^2$ is $CR^5R^6$ include the case where $R^3$ and $R^6$ are taken together with an adjacent atom to form a heterocycle optionally substituted by substituent group B.

3) Examples of a preferable embodiment when $A^1$ is $CR^8R^9$, and $A^2$ is $CR^{10}R^{11}$ include the case where $R^8$ and $R^{10}$ are taken together with an adjacent atom to form a carbocycle or a heterocycle optionally substituted by substituent group B.

4) Examples of another preferable embodiment when $A^1$ is $CR^8R^9$, and $A^2$ is $CR^{10}R^{11}$ include the case where $R^3$ and $R^{11}$ are taken together with an adjacent atom to form a heterocycle optionally substituted by substituent group B.

1) Examples of a preferable embodiment when $B^1$ is $CR^{5a}R^{6a}$, and $B^2$ is $NR^{7a}$ include the case where $R^{3a}$ and $R^{7a}$ are taken together with an adjacent atom to form a heterocycle optionally substituted by substituent group D.

2) Examples of a preferable embodiment when $B^1$ is $NR^{7a}$, and $B^2$ is $CR^{5a}R^{6a}$ include the case where $R^{3a}$ and $R^{6a}$ are taken together with an adjacent atom to form a heterocycle optionally substituted by substituent group D.

3) Examples of a preferable embodiment when $B^1$ is $CR^{8a}R^{9a}$, and $B^2$ is $CR^{10a}R^{11a}$ include the case where $R^{8a}$ and $R^{10a}$ are taken together with an adjacent atom to form a carbocycle or a heterocycle optionally substituted by substituent group D.

4) Examples of another preferable embodiment when $B^1$ is $CR^{8a}R^{9a}$, and $B^2$ is $CR^{10a}R^{11a}$ include the case where $R^{3a}$ and $R^{11a}$ are taken together with an adjacent atom to form a heterocycle optionally substituted by substituent group D.

When any one of $A^1$ and $A^2$ is $CR^5R^6$, and the other is $NR^7$, the case where $A^1$ is $NR^7$, and $A^2$ is $CR^5R^6$ is more preferable.

When any one of $B^1$ and $B^2$ is $CR^{5a}R^{6a}$, and the other is $NR^{7a}$, the case where $B^1$ is $NR^{7a}$, and $B^2$ is $CR^{5a}R^{6a}$ is more preferable.

When any one of $A^1$ and $A^2$ is $CR^5R^6$, and the other is $NR^7$, it is preferable that at least any one of $R^5$ or $R^6$ is hydrogen. A more preferable embodiment is such that $R^5$ is hydrogen, and $R^6$ is hydrogen. In this case, $R^7$ is not a hydrogen atom.

When any one of $B^1$ and $B^2$ is $CR^{5a}R^{6a}$, and the other is $NR^{7a}$, it is preferable that at least any one of $R^{5a}$ or $R^{6a}$ is hydrogen. A more preferable embodiment is such that $R^{5a}$ is hydrogen, and $R^{6a}$ is hydrogen. In this case, $R^{7a}$ is not a hydrogen atom.

A preferable embodiment of $R^7$ and $R^{7a}$ is carbocyclic group optionally substituted by substituent group A, carbocycle lower alkyl optionally substituted by substituent group A, heterocyclic group optionally substituted by substituent group A, and hetereocyclic lower alkyl optionally substituted by substituent group A.

A more preferable embodiment of $R^7$ and $R^{7a}$ is cycloalkyl, cycloalkenyl, aryl, non-aromatic condensed carbocyclic group, heteroaryl, non-aromatic heterocyclic group, bicyclic condensed heterocyclic group, tricyclic condensed heterocyclic group, lower alkyl substituted by one or two carbocyclic groups, and lower alkyl substituted by one or two heterocyclic groups.

A further preferable embodiment of $R^7$ and $R^{7a}$ is benzyl, benzhydryl, 4-fluorobenzyl, p-methoxybenzyl, and the following groups:

[Chemical formula 75]

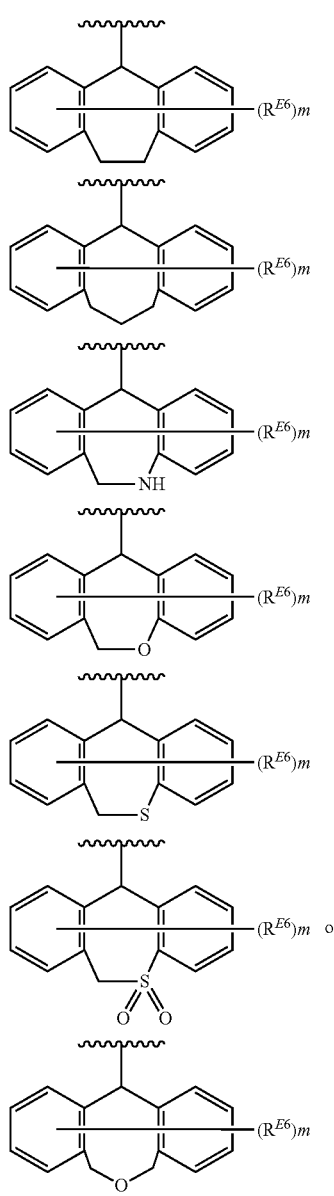

(wherein $R^{E6}$, and m are as defined in item 13').

A most preferable embodiment of $R^7$ and $R^{7a}$ is the following groups:

[Chemical formula 76]

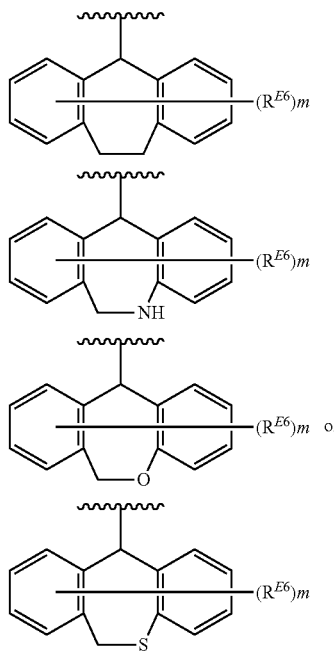

(wherein $R^{E6}$, and m are as defined in item 13').

When $A^1$ is $CR^8R^9$, and $A^2$ is $CR^{10}R^{11}$, it is preferable that $R^9$ and $R^{11}$ are hydrogen. A preferable embodiment of $R^8$ and $R^{10}$ is such that any one of them is hydrogen.

When $R^9$ and $R^{11}$ are hydrogen, and any one of $R^8$ and $R^{10}$ is hydrogen, a preferable embodiment of the other of $R^8$ and $R^{10}$ is carbocyclic group optionally substituted by substituent group A, carbocycle lower alkyl optionally substituted by substituent group A, heterocyclic group optionally substituted by substituent group A, and heterocycle lower alkyl optionally substituted by substituent group A.

When $B^1$ is $CR^{8a}R^{9a}$, and $B^2$ is $CR^{10a}R^{11a}$, it is preferable that $R^{9a}$ and $R^{11a}$ are hydrogen. A preferable embodiment of $R^{8a}$ and $R^{10a}$ is such that any one of them is hydrogen.

When $R^{9a}$ and $R^{11a}$ are hydrogen, and any one of $R^{8a}$ and $R^{10a}$ is hydrogen, a preferable embodiment of the other of $R^{8a}$ and $R^{10a}$ is the following groups

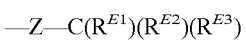

or

[Chemical formula 77]

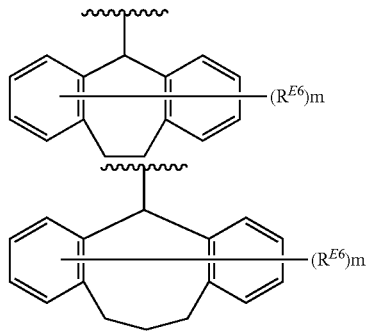

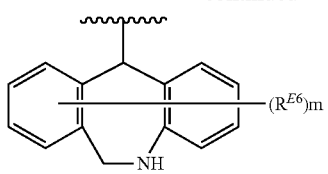

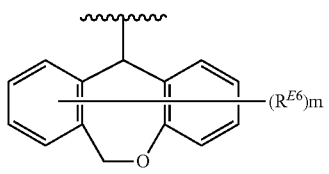

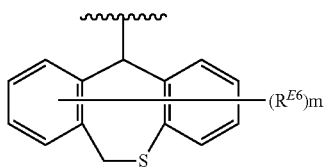

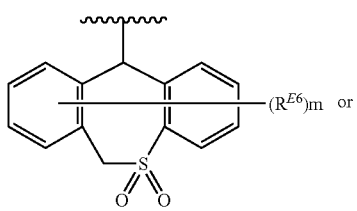

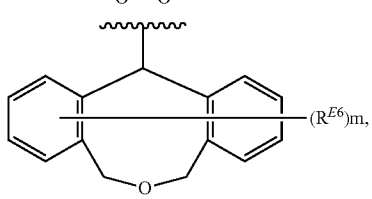

(wherein Z, $R^{E1}$, $R^{E2}$, $R^{E3}$, $R^{E6}$ and m are as defined in item 13 or item 13').

When $R^{9a}$ and $R^{11a}$ are hydrogen, and any one of $R^{8a}$ and $R^{10a}$ is hydrogen, a further preferable embodiment of the other of $R^{8a}$ and $R^{10a}$ is the following groups:

[Chemical formula 78]

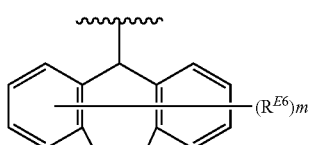

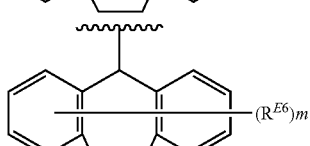

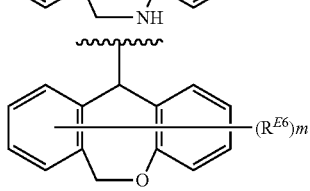

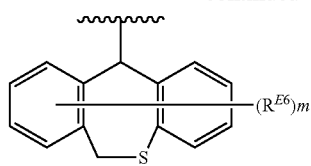

(wherein $R^{E6}$ and m are as defined in item 13 or item 13').

Examples of a preferable substituent in substituent group B and substituent group D include carbocyclic group optionally substituted by substituent group A or substituent group C, heterocyclic group optionally substituted by substituent group A or substituent group C, carbocycle lower alkyl optionally substituted by substituent group A or substituent group C, and heterocycle lower alkyl optionally substituted by substituent group A or substituent group C.

Examples of another embodiment of a preferable substituent in substituent group B and substituent group D include benzyl, benzhydryl, 4-fluorobenzyl, p-methoxybenzyl,

[Chemical formula 79]

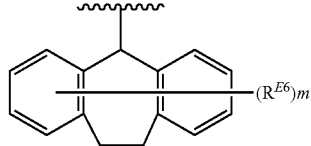

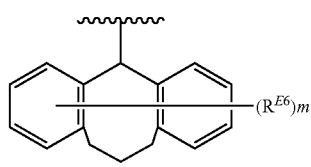

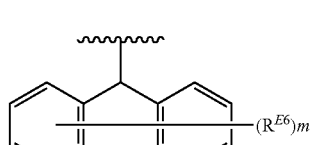


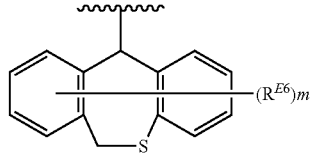

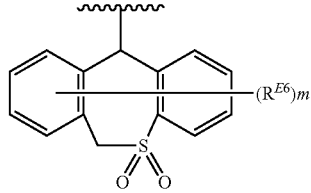

-continued

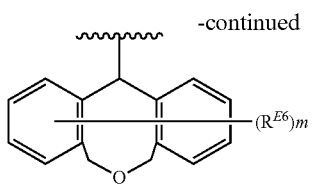

(wherein $R^{E6}$ represents a group selected from substituent group A or substituent group C, and m of $R^{E6}$s may be the same or different) etc.

Examples of a preferable substituent of $R^{E6}$ include halogen, cyano, hydroxy, carboxy, formyl, amino, oxo, nitro, lower alkyl, halogeno lower alkyl, lower alkyloxy, halogeno lower alkyloxy, etc.

Examples of a more preferable substituent of $R^{E6}$ include fluorine atom, chlorine atom, bromine atom, cyano, methyl, hydroxymethyl, isopropyl, methoxy, trifluoromethyl, oxo, carboxy, etc.

A preferable embodiment of m is an integer of 0 to 6, further preferably an integer of 0 to 3, most preferably an integer of 0 to 2.

Examples of a preferable substituent of $R^{1d}$ include hydrogen, halogen, lower alkyloxy optionally substituted by substituent group E, carbocycle lower alkyloxy optionally substituted by substituent group E, and —$OSi(R^{1e})_3$.

Examples of $R^{1e}$s each include independently lower alkyl optionally substituted by substituent group E, and carbocyclic group optionally substituted by substituent group E.

Examples of a preferable substituent of $R^{2d}$ include lower alkyl optionally substituted by substituent group E.

Examples of a preferable embodiment of $R^{3d}$ include —$N(R^{3e})_2$, or —$OR^{3e}$.

$R^{3e}$s are each independently lower alkyl optionally substituted by substituent group E.

Examples of a preferable substituent of $R^{4d}$ include lower alkyl optionally substituted by substituent group E, and carbocycle lower alkyl optionally substituted by substituent group E.

Examples of a preferable substituent of $R^{5d}$ include halogen, and lower alkyloxy optionally substituted by substituent group E.

Examples of a preferable substituent of $R^{6d}$ include lower alkyl optionally substituted by substituent group E, and lower alkenyl optionally substituted by substituent group E.

Examples of a preferable substituent of $P^d$ include lower alkyl optionally substituted by substituent group E.

Examples of another embodiment of a preferable substituent of $R^{1d}$ include hydrogen, chlorine atom, bromine atom, methoxy, ethoxy, tert-butyloxy, trifluoromethoxy, benzyloxy, p-methoxybenzyloxy, trimethylsilyloxy, triethylsilyloxy, tert-butyldimethylsilyloxy, diisopropylsilyloxy, triphenylsilyloxy, etc.

Examples of another embodiment of a preferable substituent of $R^{2d}$ include methyl, ethyl, isopropyl, tert-butyl, p-methoxybenzyl, and p-nitrobenzyl.

Examples of another embodiment of a preferable substituent of $R^{3d}$ include methoxy, ethoxy, isopropyloxy, benzyloxy, —$N(Me)_2$, —$N(Et)_2$, —$N(iPr)_2$ (Me represents methyl group, Et represents ethyl group, and $^i$Pr represents isopropyl group) etc.

Examples of another embodiment of a preferable substituent of $R^{4d}$ include methyl, ethyl, isopropyl, tert-butyl, p-methoxybenzyl, and p-nitrobenzyl, etc.

Examples of another embodiment of a preferable substituent of $R^{5d}$ include hydrogen, chlorine atom, bromine atom, methoxy, ethoxy, tert-butyloxy, trifluoromethoxy, —O—$SO_2$—$CH_3$, —O—$SO_2$-Ph-$CH_3$ (Ph represents phenyl group) etc.

Examples of another embodiment of a preferable substituent of $R^{6d}$ include methyl, ethyl, isopropyl, allyl, —$CH_2$—$CH(OMe)_2$, —$CH_2$—$CH(OEt)_2$,

[Chemical formula 80]

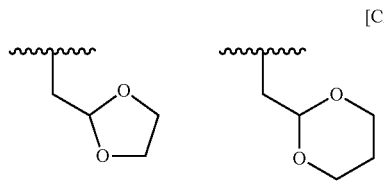

etc.

Examples of another embodiment of a preferable substituent of $P^d$ include methyl, ethyl, isopropyl, etc.

One of characteristics of the compound in the present invention is in that a polycyclic carbamoylpyridone derivative, in which two or more rings are condensed, such as shown in the formula (I) in item 1' and item 1 and/or the formula (II) in item 13' and item 13 and/or a composition including them, has high inhibitory activity on cap-dependent endonuclease.

Another characteristic of the compound in the present invention is that cap-dependent endonuclease inhibitory activity was improved, by applying a functional group as shown below to $R^1$ in the formula (I) and/or $R^{1a}$ in the formula (II). Functional group: hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C,
—Z—$N(R^{41})(R^{42})$,
—Z—$N(R^{43})$—$SO_2$—$(R^{44})$,
—Z—C(=O)—$N(R^{45})$—$SO_2$—$(R^{46})$,
—Z—$N(R^{47})$—C(=O)—$R^{48}$,
—Z—S—$R^{49}$,
—Z—$SO_2$—$R^{410}$,
—Z—S(=O)—$R^{411}$,
—Z—$N(R^{412})$—C(=O)—O—$R^{413}$,
—Z—$N(R^{414})$—C(=O)—$N(R^{415})(R^{416})$,
—Z—C(=O)—$N(R^{417})$—C(=O)—$N(R^{418})(R^{419})$, or
—Z—$N(R^{420})$—C(=O)—C(=O)—$R^{421}$
(substituent group C, $R^{41}$, $R^{42}$, $R^{43}$, $R^{45}$, $R^{47}$, $R^{48}$, $R^{49}$, $R^{412}$, $R^{413}$, $R^{414}$, $R^{415}$, $R^{416}$, $R^{417}$, $R^{418}$, $R^{419}$, $R^{420}$, and $R^{421}$ are as defined in item 13' or item 13).

The characteristic of a more preferable compound in the present invention is that cap-dependent endonuclease inhibitory activity is improved, by applying a functionl group shown below to $R^1$ in the formula (I) and/or $R^{1a}$ in the formula (II).
Functional group: hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group A,
—Z—N($R^{41}$)($R^{42}$),
—Z—N($R^{47}$)—C(=O)—$R^{48}$, or
—Z—N($R^{412}$)—C(=O)—O—$R^{413}$
(substituent group C, $R^{41}$, $R^{42}$, $R^{47}$, $R^{48}$, $R^{412}$, $R^{413}$, and Z are as defined in item 13' or item 13).

The characteristic of a further preferable compound in the present invention is that cap-dependent endonuclease inhibitory activity is improved, by applying a functional group shown below to $R^1$ in the formula (I) and/or $R^{1a}$ in the formula (II).
Functional group: hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group A, or
—Z—N($R^{41}$)($R^{42}$)
(substituent group C, $R^{41}$, $R^{42}$ and Z are as defined in item 13' or item 13).

The characteristic of a particularly preferable compound in the present invention is that cap-dependent endonuclease inhibitory activity is improved, by applying a functional group shown below to $R^1$ in the formula (I) and/or $R^{1a}$ in the formula (II).
Functional group: hydrogen, or carboxy Other characteristic of the compound in the present invention is that cap-dependent endonuclease inhibitory activity was improved, by introducing one, two or more of lipid-soluble functional groups shown below on carbon atom or on nitrogen atom of $A^1$ and/or $A^2$ in the formula (I), as well as of $B^1$ and/or $B^2$ in the formula (II).
Lipid-soluble functional group: carbocyclic group optionally substituted by substituent group C, carbocycle lower alkyl optionally substituted by substituent group C, carbocycleoxy lower alkyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocycleoxycarbonyl optionally substituted by substituent group C
(substituent group C is as defined in item 13' or item 13).

Other characteristic of a more preferable compound in the present invention is that cap-dependent endonuclease inhibitory activity is improved, by introducing one lipid-soluble functional group shown below on carbon atom or on nitrogen atom of $A^1$ and/or $A^2$ in the formula (I), as well as of $B^1$ and/or $B^2$ in the formula (II).
Lipid-soluble functional group: carbocyclic group optionally substituted by substituent group C, carbocycle lower alkyl optionally substituted by substituent group C, carbocycleoxy lower alkyl optionally substituted by substituent group C, heterocyclic group optionally substituted by substituent group C, heterocycle lower alkyl optionally substituted by substituent group C
(substituent group C is as defined in item 13' or item 13).

Other characteristic of a particularly preferable compound in the present invention is that cap-dependent endonuclease inhibitory activity was improved, by introducing one lipid-soluble functional group shown below on carbon atom or on nitrogen atom of $A^1$ and/or $A^2$ in the formula (I), as well as of $B^1$ and/or $B^2$ in the formula (II).
Lipid-soluble functional group: carbocyclic group optionally substituted by substituent group C, carbocycle lower alkyl optionally substituted by substituent group C, heterocyclic group optionally substituted by substituent group C, heterocycle lower alkyl optionally substituted by substituent group C,
(substituent group C is as defined in item 13' or item 13).

A preferable embodiment of the present invention will be exemplified below.
In the formula (III), the formula (III'), the formula (III"), the formula (III'''), the formula (III''''), the formula (III'''''):

[Chemical formula 81]

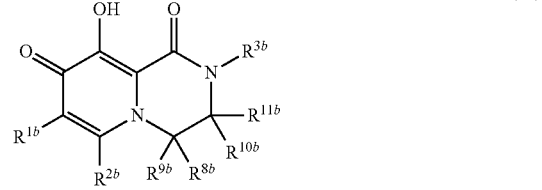
(III)

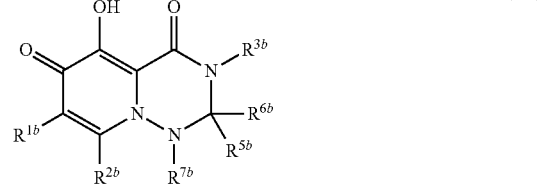
(III')

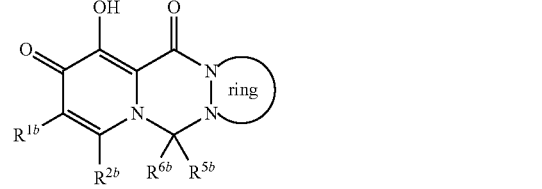
(III")

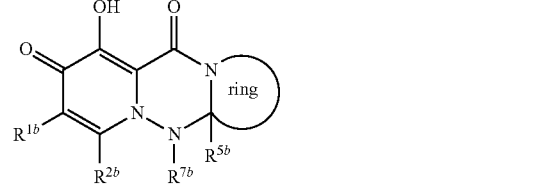
(III''')

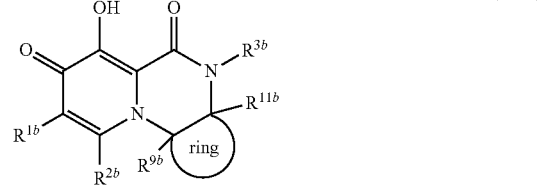
(III'''')

89
-continued (III''''')

[Chemical structure: a bicyclic ring system with OH, O, =O substituents, labeled R^{1b}, R^{2b}, R^{9b}, R^{8b}, R^{10b}, and "ring" designation]

1)
a compound in which $R^{1b}$ is hydrogen (hereinafter, $R^{1b}$ is R1-1), a compound in which $R^{1b}$ is carboxy (hereinafter, $R^b$ is R1-2) a compound in which $R^{1b}$ is halogen (hereinafter $R^{1b}$ is R1-3), a compound in which $R^{1b}$ is hydroxy (hereinafter, $R^{1b}$ is R1-4), a compound in which $R^{1b}$ is lower alkyl optionally substituted by substituent group C (hereinafter, $R^{1b}$ is R1-5),
a compound in which $R^{1b}$ is lower alkylcarbonyl optionally substituted by substituent group C (hereinafter, $R^{1b}$ is R1-6),
a compound in which $R^{1b}$ is lower alkyloxycarbonyl optionally substituted by substituent group C (hereinafter, $R^{1b}$ is R1-7),
a compound in which $R^{1b}$ is amino (hereinafter, $R^{1b}$ is R1-8),
2)
a compound in which $R^{2b}$ is hydrogen (hereinafter, $R^{2b}$ is R2-1),
a compound in which $R^{2b}$ is lower alkyl optionally substituted by substituent group C (hereinafter, $R^{2b}$ is R2-2),
3)
a compound in which $R^{3b}$ is lower alkyl optionally substituted by substituent group C (hereinafter, $R^{3b}$ is R3-1),
a compound in which $R^{3b}$ is carbocycle lower alkyl optionally substituted by substituent group C (hereinafter, $R^{3b}$ is R3-2),
a compound in which $R^{3b}$ is heterocycle lower alkyl optionally substituted by substituent group C (hereinafter, $R^{3b}$ is R3-3),
a compound in which $R^{3b}$ is carbocyclic group optionally substituted by substituent group C (hereinafter, $R^{3b}$ is R3-4),
a compound in which $R^{3b}$ is heterocyclic group optionally substituted by substituent group C (hereinafter, $R^{3b}$ is R3-5),
in the formula (III'),
1)
a compound in which $R^{7b}$ is carbocyclic group optionally substituted by substituent group C, and $R^{5b}$ and $R^{6b}$ are hydrogen (hereinafter, R7-1),
a compound in which $R^{7b}$ is heterocyclic group optionally substituted by substituent group C, and $R^{5b}$ and $R^{6b}$ are hydrogen (hereinafter, R7-2),
a compound in which $R^{7b}$ is carbocycle lower alkyl optionally substituted by substituent group C, and $R^{5b}$ and $R^{6b}$ are hydrogen (hereinafter, R7-3),
2)
a compound in which $R^{6b}$ is carbocyclic group optionally substituted by substituent group C, and $R^{5b}$ and $R^{7b}$ are hydrogen (hereinafter, R6-1),
a compound in which $R^{6b}$ is heterocyclic group optionally substituted by substituent group C, and $R^{5b}$ and $R^{7b}$ are hydrogen (hereinafter, R6-2),
a compound in which $R^{6b}$ is carbocycle lower alkyl optionally substituted by substituent group C, and $R^{5b}$ and $R^{7b}$ are hydrogen (hereinafter, R6-3),

90 in the formula (III),
a compound in which $R^{9b}$ is carbocyclic group optionally substituted by substituent group C, and $R^{8b}$, $R^{10b}$ and $R^{11b}$ are hydrogen (hereinafter, R9-1),
a compound in which $R^{9b}$ is heterocyclic group optionally substituted by substituent group C, and $R^{8b}$, $R^{10b}$ and $R^{11b}$ are hydrogen (hereinafter, R9-1),
a compound in which $R^{9b}$ is carbocycle lower alkyl optionally substituted by substituent group C, and $R^{8b}$, $R^{10b}$, and $R^{11b}$ are hydrogen (hereinafter, R9-1).

Herein, the substituent group C is at least one selected from a substituent group consisting of halogen, cyano, hydroxy, carboxy, formyl, amino, oxo, nitro, lower alkyl, halogeno lower alkyl, lower alkyloxy, carbocyclic group, heterocyclic group, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, and lower alkylsulfonylamino.

Compounds in which, in the formula (III'), a combination of $R^{1b}$, $R^{2b}$, $R^{3b}$, as well as ($R^{5b}$, $R^{6b}$, and $R^{7b}$) is as follows. (R1-1, R2-1, R3-1, R7-1), (R1-1, R2-1, R3-1, R7-2), (R1-1, R2-1, R3-1, R7-3), (R1-1, R2-1, R3-2, R7-1), (R1-1, R2-1, R3-2, R7-2), (R1-1, R2-1, R3-2, R7-3), (R1-1, R2-1, R3-3, R7-1), (R1-1, R2-1, R3-3, R7-2), (R1-1, R2-1, R3-3, R7-3), (R1-1, R2-1, R3-4, R7-1), (R1-1, R2-1, R3-4, R7-2), (R1-1, R2-1, R3-4, R7-3), (R1-1, R2-1, R3-5, R7-1), (R1-1, R2-1, R3-5, R7-2), (R1-1, R2-1, R3-5, R7-3), (R1-1, R2-2, R3-1, R7-1), (R1-1, R2-2, R3-1, R7-2), (R1-1, R2-2, R3-1, R7-3), (R1-1, R2-2, R3-2, R7-1), (R1-1, R2-2, R3-2, R7-2), (R1-1, R2-2, R3-2, R7-3), (R1-1, R2-2, R3-3, R7-1), (R1-1, R2-2, R3-3, R7-2), (R1-1, R2-2, R3-3, R7-3), (R1-1, R2-2, R3-4, R7-1), (R1-1, R2-2, R3-4, R7-2), (R1-1, R2-2, R3-4, R7-3), (R1-1, R2-2, R3-5, R7-1), (R1-1, R2-2, R3-5, R7-2), (R1-1, R2-2, R3-5, R7-3), (R1-2, R2-1, R3-1, R7-1), (R1-2, R2-1, R3-1, R7-2), (R1-2, R2-1, R3-1, R7-3), (R1-2, R2-1, R3-2, R7-1), (R1-2, R2-1, R3-2, R7-2), (R1-2, R2-1, R3-2, R7-3), (R1-2, R2-1, R3-3, R7-1), (R1-2, R2-1, R3-3, R7-2), (R1-2, R2-1, R3-3, R7-3), (R1-2, R2-1, R3-4, R7-1), (R1-2, R2-1, R3-4, R7-2), (R1-2, R2-1, R3-4, R7-3), (R1-2, R2-1, R3-5, R7-1), (R1-2, R2-1, R3-5, R7-2), (R1-2, R2-1, R3-5, R7-3), (R1-2, R2-2, R3-1, R7-1), (R1-2, R2-2, R3-1, R7-2), (R1-2, R2-2, R3-1, R7-3), (R1-2, R2-2, R3-2, R7-1), (R1-2, R2-2, R3-2, R7-2), (R1-2, R2-2, R3-2, R7-3), (R1-2, R2-2, R3-3, R7-1), (R1-2, R2-2, R3-3, R7-2), (R1-2, R2-2, R3-3, R7-3), (R1-2, R2-2, R3-4, R7-1), (R1-2, R2-2, R3-4, R7-2), (R1-2, R2-2, R3-4, R7-3), (R1-2, R2-2, R3-5, R7-1), (R1-2, R2-2, R3-5, R7-2), (R1-2, R2-2, R3-5, R7-3), (R1-3, R2-1, R3-1, R7-1), (R1-3, R2-1, R3-1, R7-2), (R1-3, R2-1, R3-1, R7-3), (R1-3, R2-1, R3-2, R7-1), (R1-3, R2-1, R3-2, R7-2), (R1-3, R2-1, R3-2, R7-3), (R1-3, R2-1, R3-3, R7-1), (R1-3, R2-1, R3-3, R7-2), (R1-3, R2-1, R3-3, R7-3), (R1-3, R2-1, R3-4, R7-1), (R1-3, R2-1, R3-4, R7-2), (R1-3, R2-1, R3-4, R7-3), (R1-3, R2-1, R3-5, R7-1), (R1-3, R2-1, R3-5, R7-2), (R1-3, R2-1, R3-5, R7-3), (R1-3, R2-2, R3-1, R7-1), (R1-3, R2-2, R3-1, R7-2), (R1-3, R2-2, R3-1, R7-3), (R1-3, R2-2, R3-2, R7-1), (R1-3, R2-2, R3-2, R7-2), (R1-3, R2-2, R3-2, R7-3), (R1-3, R2-2, R3-3, R7-1), (R1-3, R2-2, R3-3, R7-2), (R1-3, R2-2, R3-3, R7-3), (R1-3, R2-2, R3-4, R7-1), (R1-3, R2-2, R3-4, R7-2), (R1-3, R2-2, R3-4, R7-3), (R1-3, R2-2, R3-5, R7-1), (R1-3, R2-2, R3-5, R7-2), (R1-3, R2-2, R3-5, R7-3), (R1-4, R2-1, R3-1, R7-1), (R1-4, R2-1, R3-1, R7-2), (R1-4, R2-1, R3-1, R7-3), (R1-4, R2-1, R3-2, R7-1), (R1-4, R2-1, R3-2, R7-2), (R1-4, R2-1, R3-2, R7-3), (R1-4, R2-1, R3-3, R7-1), (R1-4, R2-1, R3-3, R7-2), (R1-4, R2-1, R3-3, R7-3), (R1-4, R2-1, R3-4, R7-1), (R1-4, R2-1, R3-4, R7-2), (R1-4, R2-1, R3-4, R7-3), (R1-4, R2-1, R3-5, R7-1), (R1-4, R2-1, R3-5, R7-2), (R1-4, R2-1, R3-5, R7-3), (R1-4, R2-2, R3-1, R7-1), (R1-4, R2-2, R3-1, R7-2), (R1-4, R2-2, R3-1, R7-3), (R1-4, R2-2, R3-2, R7-1), (R1-4, R2-2, R3-2, R7-2), (R1-4, R2-2, R3-2, R7-3), (R1-4, R2-2, R3-3, R7-1), (R1-4, R2-2, R3-3, R7-2), (R1-4, R2-2, R3-3, R7-3), (R1-4, R2-2, R3-4, R7-1), (R1-4, R2-2, R3-4, R7-2), (R1-4, R2-2, R3-4, R7-3), (R1-4, R2-2, R3-5, R7-1), (R1-4, R2-2, R3-5, R7-2), (R1-4, R2-2, R3-5, R7-3), (R1-5, R2-1, R3-1, R7-1), (R1-5, R2-1, R3-1, R7-2), (R1-5, R2-1, R3-1, R7-3), (R1-5, R2-1, R3-2, R7-1), (R1-5, R2-1, R3-2, R7-2), (R1-5, R2-1, R3-2, R7-3), (R1-5, R2-1, R3-3, R7-1), (R1-5, R2-1, R3-3, R7-2), (R1-5, R2-1, R3-3, R7-3), (R1-5, R2-1, R3-4, R7-1), (R1-5, R2-1, R3-4, R7-2), (R1-5, R2-1, R3-4, R7-3), (R1-5, R2-1, R3-5, R7-1), (R1-5, R2-1, R3-5, R7-2), (R1-5, R2-1, R3-5, R7-3), (R1-5, R2-2, R3-1, R7-1), (R1-5, R2-2, R3-1, R7-2), (R1-5, R2-2, R3-1, R7-3), (R1-5, R2-2, R3-2, R7-1), (R1-5, R2-2, R3-2, R7-2), (R1-5, R2-2, R3-2, R7-3), (R1-5, R2-2, R3-3, R7-1), (R1-5, R2-2, R3-3, R7-2), (R1-5, R2-2, R3-3, R7-3), (R1-5, R2-2, R3-4, R7-1), (R1-5, R2-2, R3-4, R7-2), (R1-5, R2-2, R3-4, R7-3), (R1-5, R2-2, R3-5, R7-1), (R1-5, R2-2, R3-5, R7-2), (R1-5, R2-2, R3-5, R7-3), (R1-6, R2-1, R3-1, R7-1), (R1-6, R2-1, R3-1, R7-2), (R1-6, R2-1, R3-1, R7-3), (R1-6, R2-1, R3-2, R7-1), (R1-6, R2-1, R3-2, R7-2), (R1-6, R2-1, R3-2, R7-3), (R1-6, R2-1, R3-3, R7-1), (R1-6, R2-1, R3-3, R7-2), (R1-6, R2-1, R3-3, R7-3), (R1-6, R2-1, R3-4, R7-1), (R1-6, R2-1, R3-4, R7-2), (R1-6, R2-1, R3-4, R7-3), (R1-6, R2-1, R3-5, R7-1), (R1-6, R2-1, R3-5, R7-2), (R1-6, R2-1, R3-5, R7-3), (R1-6, R2-2, R3-1, R7-1), (R1-6, R2-2, R3-1, R7-2), (R1-6, R2-2, R3-1, R7-3), (R1-6, R2-2, R3-2, R7-1), (R1-6, R2-2, R3-2, R7-2), (R1-6, R2-2, R3-2, R7-3), (R1-6, R2-2, R3-3, R7-1), (R1-6, R2-2, R3-3, R7-2), (R1-6, R2-2, R3-3, R7-3), (R1-6, R2-2, R3-4, R7-1), (R1-6, R2-2, R3-4, R7-2), (R1-6, R2-2, R3-4, R7-3), (R1-6, R2-2, R3-5, R7-1), (R1-6, R2-2, R3-5, R7-2), (R1-6, R2-2, R3-5, R7-3), (R1-7, R2-1, R3-1, R7-1), (R1-7, R2-1, R3-1, R7-2), (R1-7, R2-1, R3-1, R7-3), (R1-7, R2-1, R3-2, R7-1), (R1-7, R2-1, R3-2, R7-2), (R1-7, R2-1, R3-2, R7-3), (R1-7, R2-1, R3-3, R7-1), (R1-7, R2-1, R3-3, R7-2), (R1-7, R2-1, R3-3, R7-3), (R1-7, R2-1, R3-4, R7-1), (R1-7, R2-1, R3-4, R7-2), (R1-7, R2-1, R3-4, R7-3), (R1-7, R2-1, R3-5, R7-1), (R1-7, R2-1, R3-5, R7-2), (R1-7, R2-1, R3-5, R7-3), (R1-7, R2-2, R3-1, R7-1), (R1-7, R2-2, R3-1, R7-2), (R1-7, R2-2, R3-1, R7-3), (R1-7, R2-2, R3-2, R7-1), (R1-7, R2-2, R3-2, R7-2), (R1-7, R2-2, R3-2, R7-3), (R1-7, R2-2, R3-3, R7-1), (R1-7, R2-2, R3-3, R7-2), (R1-7, R2-2, R3-3, R7-3), (R1-7, R2-2, R3-4, R7-1), (R1-7, R2-2, R3-4, R7-2), (R1-7, R2-2, R3-4, R7-3), (R1-7, R2-2, R3-5, R7-1), (R1-7, R2-2, R3-5, R7-2), (R1-7, R2-2, R3-5, R7-3), (R1-8, R2-1, R3-1, R7-1), (R1-8, R2-1, R3-1, R7-2), (R1-8, R2-1, R3-1, R7-3), (R1-8, R2-1, R3-2, R7-1), (R1-8, R2-1, R3-2, R7-2), (R1-8, R2-1, R3-2, R7-3), (R1-8, R2-1, R3-3, R7-1), (R1-8, R2-1, R3-3, R7-2), (R1-8, R2-1, R3-3, R7-3), (R1-8, R2-1, R3-4, R7-1), (R1-8, R2-1, R3-4, R7-2), (R1-8, R2-1, R3-4, R7-3), (R1-8, R2-1, R3-5, R7-1), (R1-8, R2-1, R3-5, R7-2), (R1-8, R2-1, R3-5, R7-3), (R1-8, R2-2, R3-1, R7-1), (R1-8, R2-2, R3-1, R7-2), (R1-8, R2-2, R3-1, R7-3), (R1-8, R2-2, R3-2, R7-1), (R1-8, R2-2, R3-2, R7-2), (R1-8, R2-2, R3-2, R7-3), (R1-8, R2-2, R3-3, R7-1), (R1-8, R2-2, R3-3, R7-2), (R1-8, R2-2, R3-3, R7-3), (R1-8, R2-2, R3-4, R7-1), (R1-8, R2-2, R3-4, R7-2), (R1-8, R2-2, R3-4, R7-3), (R1-8, R2-2, R3-5, R7-1), (R1-8, R2-2, R3-5, R7-2), (R1-8, R2-2, R3-5, R7-3), (R1-1, R2-1, R3-1, R6-1), (R1-1, R2-1, R3-1, R6-2), (R1-1, R2-1, R3-1, R6-3), (R1-1, R2-1, R3-2, R6-1), (R1-1, R2-1, R3-2, R6-2), (R1-1, R2-1, R3-2, R6-3), (R1-1, R2-1, R3-3, R6-1), (R1-1, R2-1, R3-3, R6-2), (R1-1, R2-1, R3-3, R6-3), (R1-1, R2-1, R3-4, R6-1), (R1-1, R2-1, R3-4, R6-2), (R1-1, R2-1, R3-4, R6-3), (R1-1, R2-1, R3-5, R6-1), (R1-1, R2-1, R3-5, R6-2), (R1-1, R2-1, R3-5, R6-3), (R1-1, R2-2, R3-1, R6-1), (R1-1, R2-2, R3-1, R6-2), (R1-1, R2-2, R3-1, R6-3), (R1-1, R2-2, R3-2, R6-1), (R1-1, R2-2, R3-2, R6-2), (R1-1, R2-2, R3-2, R6-3), (R1-1, R2-2, R3-3, R6-1), (R1-1, R2-2, R3-3, R6-2), (R1-1, R2-2, R3-3, R6-3), (R1-1, R2-2, R3-4, R6-1), (R1-1, R2-2, R3-4, R6-2), (R1-1, R2-2, R3-4, R6-3), (R1-1, R2-2, R3-5, R6-1), (R1-1, R2-2, R3-5, R6-2), (R1-1, R2-2, R3-5, R6-3), (R1-2, R2-1, R3-1, R6-1), (R1-2, R2-1, R3-1, R6-2), (R1-2, R2-1, R3-1, R6-3), (R1-2, R2-1, R3-2, R6-1), (R1-2, R2-1, R3-2, R6-2), (R1-2, R2-1, R3-2, R6-3), (R1-2, R2-1, R3-3, R6-1), (R1-2, R2-1, R3-3, R6-2), (R1-2, R2-1, R3-3, R6-3), (R1-2, R2-1, R3-4, R6-1), (R1-2, R2-1, R3-4, R6-2), (R1-2, R2-1, R3-4, R6-3), (R1-2, R2-1, R3-5, R6-1), (R1-2, R2-1, R3-5, R6-2), (R1-2, R2-1, R3-5, R6-3), (R1-2, R2-2, R3-1, R6-1), (R1-2, R2-2, R3-1, R6-2), (R1-2, R2-2, R3-1, R6-3), (R1-2, R2-2, R3-2, R6-1), (R1-2, R2-2, R3-2, R6-2), (R1-2, R2-2, R3-2, R6-3), (R1-2, R2-2, R3-3, R6-1), (R1-2, R2-2, R3-3, R6-2), (R1-2, R2-2, R3-3, R6-3), (R1-2, R2-2, R3-4, R6-1), (R1-2, R2-2, R3-4, R6-2), (R1-2, R2-2, R3-4, R6-3), (R1-2, R2-2, R3-5, R6-1), (R1-2, R2-2, R3-5, R6-2), (R1-2, R2-2, R3-5, R6-3), (R1-3, R2-1, R3-1, R6-1), (R1-3, R2-1, R3-1, R6-2), (R1-3, R2-1, R3-1, R6-3), (R1-3, R2-1, R3-2, R6-1), (R1-3, R2-1, R3-2, R6-2), (R1-3, R2-1, R3-2, R6-3), (R1-3, R2-1, R3-3, R6-1), (R1-3, R2-1, R3-3, R6-2), (R1-3, R2-1, R3-3, R6-3), (R1-3, R2-1, R3-4, R6-1), (R1-3, R2-1, R3-4, R6-2), (R1-3, R2-1, R3-4, R6-3), (R1-3, R2-1, R3-5, R6-1), (R1-3, R2-1, R3-5, R6-2), (R1-3, R2-1, R3-5, R6-3), (R1-3, R2-2, R3-1, R6-1), (R1-3, R2-2, R3-1, R6-2), (R1-3, R2-2, R3-1, R6-3), (R1-3, R2-2, R3-2, R6-1), (R1-3, R2-2, R3-2, R6-2), (R1-3, R2-2, R3-2, R6-3), (R1-3, R2-2, R3-3, R6-1), (R1-3, R2-2, R3-3, R6-2), (R1-3, R2-2, R3-3, R6-3), (R1-3, R2-2, R3-4, R6-1), (R1-3, R2-2, R3-4, R6-2), (R1-3, R2-2, R3-4, R6-3), (R1-3, R2-2, R3-5, R6-1), (R1-3, R2-2, R3-5, R6-2), (R1-3, R2-2, R3-5, R6-3), (R1-4, R2-1, R3-1, R6-1), (R1-4, R2-1, R3-1, R6-2), (R1-4, R2-1, R3-1, R6-3), (R1-4, R2-1, R3-2, R6-1), (R1-4, R2-1, R3-2, R6-2), (R1-4, R2-1, R3-2, R6-3), (R1-4, R2-1, R3-3, R6-1), (R1-4, R2-1, R3-3, R6-2), (R1-4, R2-1, R3-3, R6-3), (R1-4, R2-1, R3-4, R6-1), (R1-4, R2-1, R3-4, R6-2), (R1-4, R2-1, R3-4, R6-3), (R1-4, R2-1, R3-5, R6-1), (R1-4, R2-1, R3-5, R6-2), (R1-4, R2-1, R3-5, R6-3), (R1-4, R2-2, R3-1, R6-1), (R1-4, R2-2, R3-1, R6-2), (R1-4, R2-2, R3-1, R6-3), (R1-4, R2-2, R3-2, R6-1), (R1-4, R2-2, R3-2, R6-2), (R1-4, R2-2, R3-2, R6-3), (R1-4, R2-2, R3-3, R6-1), (R1-4, R2-2, R3-3, R6-2), (R1-4, R2-2, R3-3, R6-3), (R1-4, R2-2, R3-4, R6-1), (R1-4, R2-2, R3-4, R6-2), (R1-4, R2-2, R3-4, R6-3), (R1-4, R2-2, R3-5, R6-1), (R1-4, R2-2, R3-5, R6-2), (R1-4, R2-2, R3-5, R6-3), (R1-5, R2-1, R3-1, R6-1), (R1-5, R2-1, R3-1, R6-2), (R1-5, R2-1, R3-1, R6-3), (R1-5, R2-1, R3-2, R6-1), (R1-5, R2-1, R3-2, R6-2), (R1-5, R2-1, R3-2, R6-3), (R1-5, R2-1, R3-3, R6-1), (R1-5, R2-1, R3-3, R6-2), (R1-5, R2-1, R3-3, R6-3), (R1-5, R2-1, R3-4, R6-1), (R1-5, R2-1, R3-4, R6-2), (R1-5, R2-1, R3-4, R6-3), (R1-5, R2-1, R3-5, R6-1), (R1-5, R2-1, R3-5, R6-2), (R1-5, R2-1, R3-5, R6-3), (R1-5, R2-2, R3-1, R6-1), (R1-5, R2-2, R3-1, R6-2), (R1-5, R2-2, R3-1, R6-3), (R1-5, R2-2, R3-2, R6-1), (R1-5, R2-2, R3-2, R6-2), (R1-5, R2-2, R3-2, R6-3), (R1-5, R2-2, R3-3, R6-1), (R1-5, R2-2, R3-3, R6-2), (R1-5, R2-2, R3-3, R6-3), (R1-5, R2-2, R3-4, R6-1), (R1-5, R2-2, R3-4, R6-2), (R1-5, R2-2, R3-4, R6-3), (R1-5, R2-2, R3-5, R6-1), (R1-5, R2-2, R3-5, R6-2), (R1-5, R2-2, R3-5, R6-3), (R1-6, R2-1, R3-1, R6-1), (R1-6, R2-1, R3-1, R6-2), (R1-6, R2-1, R3-1, R6-3), (R1-6, R2-1, R3-2, R6-1), (R1-6, R2-1, R3-2, R6-2), (R1-6, R2-1, R3-2, R6-3), (R1-6, R2-1, R3-3, R6-1), (R1-6, R2-1, R3-3, R6-2), (R1-6, R2-1, R3-3, R6-3), (R1-6, R2-1, R3-4, R6-1), (R1-6, R2-1, R3-4, R6-2), (R1-6, R2-1, R3-4, R6-3), (R1-6, R2-1, R3-5, R6-1), (R1-6, R2-1, R3-5, R6-2), (R1-6, R2-1, R3-5, R6-3), (R1-6, R2-2, R3-1, R6-1), (R1-6, R2-2, R3-1, R6-2), (R1-6, R2-2, R3-1, R6-3), (R1-6, R2-2, R3-2, R6-1), (R1-6, R2-2, R3-2, R6-2), (R1-6, R2-2, R3-2, R6-3), (R1-6, R2-2, R3-3, R6-1), (R1-6, R2-2, R3-3, R6-2), (R1-6, R2-2, R3-3, R6-3), (R1-6, R2-2, R3-4, R6-1), (R1-6, R2-2, R3-4, R6-2), (R1-6, R2-2, R3-4, R6-3), (R1-6, R2-2, R3-5, R6-1), (R1-6, R2-2, R3-5, R6-2), (R1-6, R2-2, R3-5, R6-3), (R1-7, R2-1, R3-1, R6-1), (R1-7, R2-1, R3-1, R6-2), (R1-7, R2-1, R3-1, R6-3), (R1-7, R2-1, R3-2, R6-1), (R1-7, R2-1, R3-2, R6-2), (R1-7, R2-1, R3-2, R6-3), (R1-7, R2-1, R3-3, R6-1), (R1-7, R2-1, R3-3, R6-2), (R1-7, R2-1, R3-3, R6-3), (R1-7, R2-1, R3-4, R6-1), (R1-7, R2-1, R3-4, R6-2), (R1-7, R2-1, R3-4, R6-3), (R1-7, R2-1, R3-5, R6-1), (R1-7, R2-1, R3-5, R6-2), (R1-7, R2-1, R3-5, R6-3), (R1-7, R2-2, R3-1, R6-1), (R1-7, R2-2, R3-1, R6-2), (R1-7, R2-2, R3-1, R6-3), (R1-7, R2-2, R3-2, R6-1), (R1-7, R2-2, R3-2, R6-2), (R1-7, R2-2, R3-2, R6-3), (R1-7, R2-2, R3-3, R6-1), (R1-7, R2-2, R3-3, R6-2), (R1-7, R2-2, R3-3, R6-3), (R1-7, R2-2, R3-4, R6-1), (R1-7, R2-2, R3-4, R6-2), (R1-7, R2-2, R3-4, R6-3), (R1-7, R2-2, R3-5, R6-1), (R1-7, R2-2, R3-5, R6-2), (R1-7, R2-2, R3-5, R6-3), (R1-8, R2-1, R3-1, R6-1), (R1-8, R2-1, R3-1, R6-2), (R1-8, R2-1, R3-1, R6-3), (R1-8, R2-1, R3-2, R6-1), (R1-8, R2-1, R3-2, R6-2), (R1-8, R2-1, R3-2, R6-3), (R1-8, R2-1, R3-3, R6-1), (R1-8, R2-1, R3-3, R6-2), (R1-8, R2-1, R3-3, R6-3), (R1-8, R2-1, R3-4, R6-1), (R1-8, R2-1, R3-4, R6-2), (R1-8, R2-1, R3-4, R6-3), (R1-8, R2-1, R3-5, R6-1), (R1-8, R2-1, R3-5, R6-2), (R1-8, R2-1, R3-5, R6-3), (R1-8, R2-2, R3-1, R6-1), (R1-8, R2-2, R3-1, R6-2), (R1-8, R2-2, R3-1, R6-3), (R1-8, R2-2, R3-2, R6-1), (R1-8, R2-2, R3-2, R6-2), (R1-8, R2-2, R3-2, R6-3), (R1-8, R2-2, R3-3, R6-1), (R1-8, R2-2, R3-3, R6-2), (R1-8, R2-2, R3-3, R6-3), (R1-8, R2-2, R3-4, R6-1), (R1-8, R2-2, R3-4, R6-2), (R1-8, R2-2, R3-4, R6-3), (R1-8, R2-2, R3-5, R6-1), (R1-8, R2-2, R3-5, R6-2), (R1-8, R2-2, R3-5, R6-3).

Compounds in which, in the formula (III), a combination of $R^{1b}$, $R^{2b}$, $R^{3b}$, as well as ($R^{8b}$, $R^{9b}$, $R^{10b}$, and $R^{11b}$) is as follows.

(R1-1, R2-1, R3-1, R9-1), (R1-1, R2-1, R3-1, R9-2), (R1-1, R2-1, R3-1, R9-3), (R1-1, R2-1, R3-2, R9-1), (R1-1, R2-1, R3-2, R9-2), (R1-1, R2-1, R3-2, R9-3), (R1-1, R2-1, R3-3, R9-1), (R1-1, R2-1, R3-3, R9-2), (R1-1, R2-1, R3-3, R9-3), (R1-1, R2-1, R3-4, R9-1), (R1-1, R2-1, R3-4, R9-2), (R1-1, R2-1, R3-4, R9-3), (R1-1, R2-1, R3-5, R9-1), (R1-1, R2-1, R3-5, R9-2), (R1-1, R2-1, R3-5, R9-3), (R1-1, R2-2, R3-1, R9-1), (R1-1, R2-2, R3-1, R9-2), (R1-1, R2-2, R3-1, R9-3), (R1-1, R2-2, R3-2, R9-1), (R1-1, R2-2, R3-2, R9-2), (R1-1, R2-2, R3-2, R9-3), (R1-1, R2-2, R3-3, R9-1), (R1-1, R2-2, R3-3, R9-2), (R1-1, R2-2, R3-3, R9-3), (R1-1, R2-2, R3-4, R9-1), (R1-1, R2-2, R3-4, R9-2), (R1-1, R2-2, R3-4, R9-3), (R1-1, R2-2, R3-5, R9-1), (R1-1, R2-2, R3-5, R9-2), (R1-1, R2-2, R3-5, R9-3), (R1-2, R2-1, R3-1, R9-1), (R1-2, R2-1, R3-1, R9-2), (R1-2, R2-1, R3-1, R9-3), (R1-2, R2-1, R3-2, R9-1), (R1-2, R2-1, R3-2, R9-2), (R1-2, R2-1, R3-2, R9-3), (R1-2, R2-1, R3-3, R9-1), (R1-2, R2-1, R3-3, R9-2), (R1-2, R2-1, R3-3, R9-3), (R1-2, R2-1, R3-4, R9-1), (R1-2, R2-1, R3-4, R9-2), (R1-2, R2-1, R3-4, R9-3), (R1-2, R2-1, R3-5, R9-1), (R1-2, R2-1, R3-5, R9-2), (R1-2, R2-1, R3-5, R9-3), (R1-2, R2-2, R3-1, R9-1), (R1-2, R2-2, R3-1, R9-2), (R1-2, R2-2, R3-1, R9-3), (R1-2, R2-2, R3-2, R9-1), (R1-2, R2-2, R3-2, R9-2), (R1-2, R2-2, R3-2, R9-3), (R1-2, R2-2, R3-3, R9-1), (R1-2, R2-2, R3-3, R9-2), (R1-2, R2-2, R3-3, R9-3), (R1-2, R2-2, R3-4, R9-1), (R1-2, R2-2, R3-4, R9-2), (R1-2, R2-2, R3-4, R9-3), (R1-2, R2-2, R3-5, R9-1), (R1-2, R2-2, R3-5, R9-2), (R1-2, R2-2, R3-5, R9-3), (R1-3, R2-1, R3-1, R9-1), (R1-3, R2-1, R3-1, R9-2), (R1-3, R2-1, R3-1, R9-3), (R1-3, R2-1, R3-2, R9-1), (R1-3, R2-1, R3-2, R9-2), (R1-3, R2-1, R3-2, R9-3), (R1-3, R2-1, R3-3, R9-1), (R1-3, R2-1, R3-3, R9-2), (R1-3, R2-1, R3-3, R9-3), (R1-3, R2-1, R3-4, R9-1), (R1-3, R2-1, R3-4, R9-2), (R1-3, R2-1, R3-4, R9-3), (R1-3, R2-1, R3-5, R9-1), (R1-3, R2-1, R3-5, R9-2), (R1-3, R2-1, R3-5, R9-3), (R1-3, R2-2, R3-1, R9-1), (R1-3, R2-2, R3-1, R9-2), (R1-3, R2-2, R3-1, R9-3), (R1-3, R2-2, R3-2, R9-1), (R1-3, R2-2, R3-2, R9-2), (R1-3, R2-2, R3-2, R9-3), (R1-3, R2-2, R3-3, R9-1), (R1-3, R2-2, R3-3, R9-2), (R1-3, R2-2, R3-3, R9-3), (R1-3, R2-2, R3-4, R9-1), (R1-3, R2-2, R3-4, R9-2), (R1-3, R2-2, R3-4, R9-3), (R1-3, R2-2, R3-5, R9-1), (R1-3, R2-2, R3-5, R9-2), (R1-3, R2-2, R3-5, R9-3), (R1-4, R2-1, R3-1, R9-1), (R1-4, R2-1, R3-1, R9-2), (R1-4, R2-1, R3-1, R9-3), (R1-4, R2-1, R3-2, R9-1), (R1-4, R2-1, R3-2, R9-2), (R1-4, R2-1, R3-2, R9-3), (R1-4, R2-1, R3-3, R9-1), (R1-4, R2-1, R3-3, R9-2), (R1-4, R2-1, R3-3, R9-3), (R1-4, R2-1, R3-4, R9-1), (R1-4, R2-1, R3-4, R9-2), (R1-4, R2-1, R3-4, R9-3), (R1-4, R2-1, R3-5, R9-1), (R1-4, R2-1, R3-5, R9-2), (R1-4, R2-1, R3-5, R9-3), (R1-4, R2-2, R3-1, R9-1), (R1-4, R2-2, R3-1, R9-2), (R1-4, R2-2, R3-1, R9-3), (R1-4, R2-2, R3-2, R9-1), (R1-4, R2-2, R3-2, R9-2), (R1-4, R2-2, R3-2, R9-3), (R1-4, R2-2, R3-3, R9-1), (R1-4, R2-2, R3-3, R9-2), (R1-4, R2-2, R3-3, R9-3), (R1-4, R2-2, R3-4, R9-1), (R1-4, R2-2, R3-4, R9-2), (R1-4, R2-2, R3-4, R9-3), (R1-4, R2-2, R3-5, R9-1), (R1-4, R2-2, R3-5, R9-2), (R1-4, R2-2, R3-5, R9-3),
(R1-5, R2-1, R3-1, R9-1), (R1-5, R2-1, R3-1, R9-2), (R1-5, R2-1, R3-1, R9-3), (R1-5, R2-1, R3-2, R9-1), (R1-5, R2-1, R3-2, R9-2), (R1-5, R2-1, R3-2, R9-3), (R1-5, R2-1, R3-3, R9-1), (R1-5, R2-1, R3-3, R9-2), (R1-5, R2-1, R3-3, R9-3), (R1-5, R2-1, R3-4, R9-1), (R1-5, R2-1, R3-4, R9-2), (R1-5, R2-1, R3-4, R9-3), (R1-5, R2-1, R3-5, R9-1), (R1-5, R2-1, R3-5, R9-2), (R1-5, R2-1, R3-5, R9-3), (R1-5, R2-2, R3-1, R9-1), (R1-5, R2-2, R3-1, R9-2), (R1-5, R2-2, R3-1, R9-3), (R1-5, R2-2, R3-2, R9-1), (R1-5, R2-2, R3-2, R9-2), (R1-5, R2-2, R3-2, R9-3), (R1-5, R2-2, R3-3, R9-1), (R1-5, R2-2, R3-3, R9-2), (R1-5, R2-2, R3-3, R9-3), (R1-5, R2-2, R3-4, R9-1), (R1-5, R2-2, R3-4, R9-2), (R1-5, R2-2, R3-4, R9-3), (R1-5, R2-2, R3-5, R9-1), (R1-5, R2-2, R3-5, R9-2), (R1-5, R2-2, R3-5, R9-3), (R1-6, R2-1, R3-1, R9-1), (R1-6, R2-1, R3-1, R9-2), (R1-6, R2-1, R3-1, R9-3), (R1-6, R2-1, R3-2, R9-1), (R1-6, R2-1, R3-2, R9-2), (R1-6, R2-1, R3-2, R9-3), (R1-6, R2-1, R3-3, R9-1), (R1-6, R2-1, R3-3, R9-2), (R1-6, R2-1, R3-3, R9-3), (R1-6, R2-1, R3-4, R9-1), (R1-6, R2-1, R3-4, R9-2), (R1-6, R2-1, R3-4, R9-3), (R1-6, R2-1, R3-5, R9-1), (R1-6, R2-1, R3-5, R9-2), (R1-6, R2-1, R3-5, R9-3), (R1-6, R2-2, R3-1, R9-1), (R1-6, R2-2, R3-1, R9-2), (R1-6, R2-2, R3-1, R9-3), (R1-6, R2-2, R3-2, R9-1), (R1-6, R2-2, R3-2, R9-2), (R1-6, R2-2, R3-2, R9-3), (R1-6, R2-2, R3-3, R9-1), (R1-6, R2-2, R3-3, R9-2), (R1-6, R2-2, R3-3, R9-3), (R1-6, R2-2, R3-4, R9-1), (R1-6, R2-2, R3-4, R9-2), (R1-6, R2-2, R3-4, R9-3), (R1-6, R2-2, R3-5, R9-1), (R1-6, R2-2, R3-5, R9-2), (R1-6, R2-2, R3-5, R9-3), (R1-7, R2-1, R3-1, R9-1), (R1-7, R2-1, R3-1, R9-2), (R1-7, R2-1, R3-1, R9-3), (R1-7, R2-1, R3-2, R9-1), (R1-7, R2-1, R3-2, R9-2), (R1-7, R2-1, R3-2, R9-3), (R1-7, R2-1, R3-3, R9-1), (R1-7, R2-1, R3-3, R9-2), (R1-7, R2-1, R3-3, R9-3), (R1-7, R2-1, R3-4, R9-1), (R1-7, R2-1, R3-4, R9-2), (R1-7, R2-1, R3-4, R9-3), (R1-7, R2-1, R3-5, R9-1), (R1-7, R2-1, R3-5, R9-2), (R1-7, R2-1, R3-5, R9-3), (R1-7, R2-2, R3-1, R9-1), (R1-7, R2-2, R3-1, R9-2), (R1-7, R2-2, R3-1, R9-3), (R1-7, R2-2, R3-2, R9-1), (R1-7, R2-2, R3-2, R9-2), (R1-7, R2-2, R3-2, R9-3), (R1-7, R2-2, R3-3, R9-1), (R1-7, R2-2, R3-3, R9-2), (R1-7, R2-2, R3-3, R9-3), (R1-7, R2-2, R3-4, R9-1), (R1-7, R2-2, R3-4, R9-2), (R1-7, R2-2, R3-4, R9-3), (R1-7, R2-2, R3-5, R9-1), (R1-7, R2-2, R3-5, R9-2), (R1-7, R2-2, R3-5, R9-3), (R1-8, R2-1, R3-1, R9-1), (R1-8, R2-1, R3-1, R9-2), (R1-8,

R2-1, R3-1, R9-3), (R1-8, R2-1, R3-2, R9-1), (R1-8, R2-1, R3-2, R9-2), (R1-8, R2-1, R3-2, R9-3), (R1-8, R2-1, R3-3, R9-1), (R1-8, R2-1, R3-3, R9-2), (R1-8, R2-1, R3-3, R9-3), (R1-8, R2-1, R3-4, R9-1), (R1-8, R2-1, R3-4, R9-2), (R1-8, R2-1, R3-4, R9-3), (R1-8, R2-1, R3-5, R9-1), (R1-8, R2-1, R3-5, R9-2), (R1-8, R2-1, R3-5, R9-3), (R1-8, R2-2, R3-1, R9-1), (R1-8, R2-2, R3-1, R9-2), (R1-8, R2-2, R3-1, R9-3), (R1-8, R2-2, R3-2, R9-1), (R1-8, R2-2, R3-2, R9-2), (R1-8, R2-2, R3-2, R9-3), (R1-8, R2-2, R3-3, R9-1), (R1-8, R2-2, R3-3, R9-2), (R1-8, R2-2, R3-3, R9-3), (R1-8, R2-2, R3-4, R9-1), (R1-8, R2-2, R3-4, R9-2), (R1-8, R2-2, R3-4, R9-3), (R1-8, R2-2, R3-5, R9-1), (R1-8, R2-2, R3-5, R9-2), (R1-8, R2-2, R3-5, R9-3).

(Method for Producing Compound of the Present Invention)

A general method for producing the compound of the present invention will be exemplified below. And, as extraction and purification, treatment which is performed in a normal experiment of organic chemistry may be conducted.

Synthesis of the compound of the present invention can be carried out referring to the procedures known in the art.

As a raw material compound, commercially available compounds, compounds described in the present description, compounds described in the references cited in the present description, and other known compounds can be utilized.

Among the compounds of the present invention, there are compounds in which a tautomer can be present, and the present invention includes all possible isomers and a mixture thereof, including them.

When one wants to obtain a salt of the compound of the present invention, in the case where the compound of the present invention is obtained in a form of a salt, it may be purified as it is and, in the case where the compound of the present invention is obtained in a free form, a salt may be formed by a normal method by dissolving or suspending the compound in a suitable organic solvent, and adding an acid or a base.

In addition, the compound of the present invention and a pharmaceutically acceptable salt thereof are present in a form of adducts with water or various solvents (hydrate or solvate) in some cases, and these adducts are included in the present invention.

In a general synthesis method as well as Examples and Reference Examples, the meaning of each abbreviation is as follows.
DMF: N,N-dimethylformamide
DMA: N,N-dimethylacetamide,
NMP: N-methylpyrrolidone
DMI: dimethylimidazolidinone
THF: tetrahydrofuran
Ms: methanesulfonyl
Ts: paratoluenesulfonyl
Boc: tert-butoxycarbonyl
DIBALH: diisobutylaluminum hydride
WSC or EDCI: N-ethyl-N'-(3-dimethylaminopropyl)carbodiimide
HOBt: 1-hydroxybenzotriazole
HATU: O-(7-azabenzotriazol-1-yl)-N,N,N',N'-tetramethyluronium hexafluorophosphate
NBS: N-bromosuccinimide
NCS: N-chlorosuccinimide
TEMPO: 2,2,6,6-tetramethylpiperidine-1-oxyl radical
PDC: pyridinium dichloromate
DEAD: diethyl azodicarboxylate
DIAD: diisopropyl azodicarboxylate
DMAP: 4-dimethylaminopyridine
mCPBA: m-chloroperbenzoic acid
DBU: 1,8-diazabicyclo[5.4.0]-7-undecene
DIPEA: diisopropylethylamine
TBAF: tetrabutylammonium fluoride
IBX: 2-iodoxybenzoic acid
DMSO: dimethyl sulfoxide
NaHMDS: sodium hexamethyldisilazide
TFA: trifluoroacetic acid Synthesis of Objective Compound aj (See: Example 1)

[Chemical formula 82]

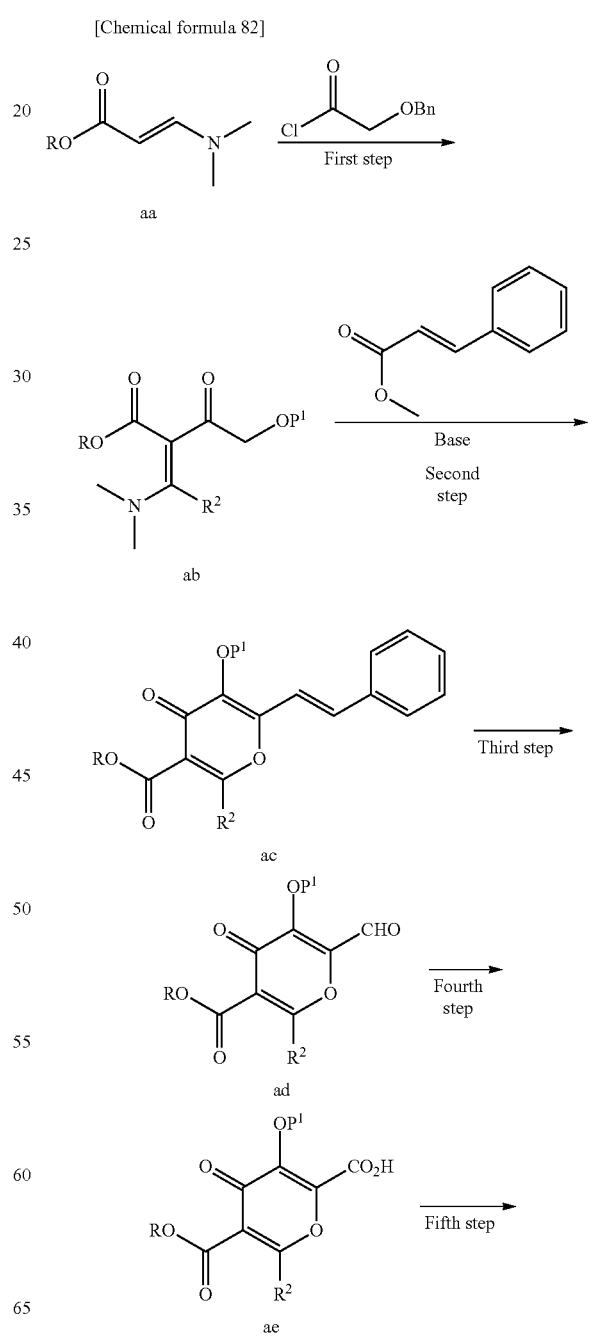

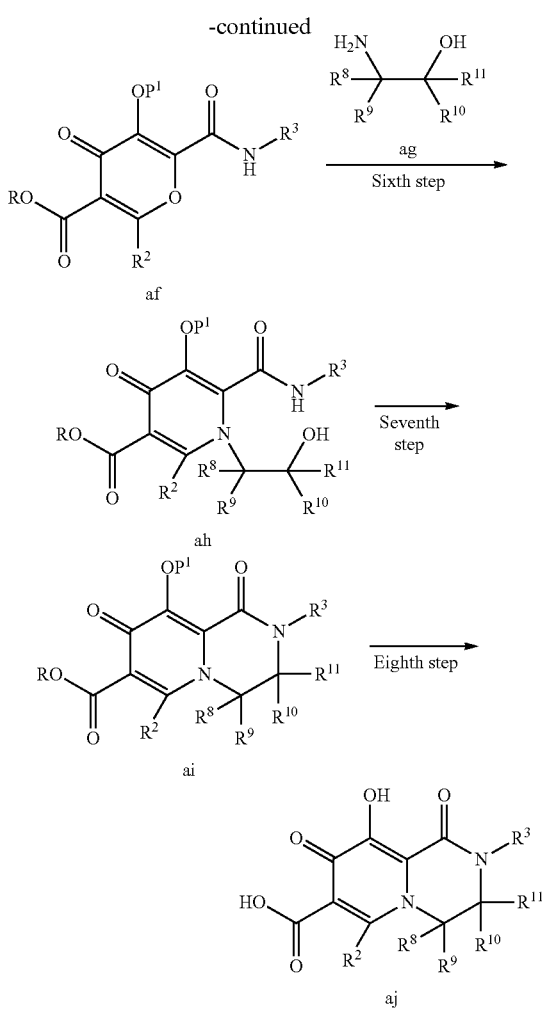

(wherein R is carboxy protective group, $P^1$ is hydroxyl protective group, $R^2$, $R^3$, $R^8$, $R^9$, R and $R^{11}$ are as defined in item 1' or item 1, R and $P^1$ may be a group which can be protected and/or deprotected by the method described in Protective Groups in Organic Synthesis, Theodora W Green (John Wiley & Sons) etc. and, for example, R is lower alkyl etc., and $P^1$ is arylalkyl etc.)

First Step

A compound ab can be obtained by reacting a compound aa which is commercially available or can be prepared by the known method at −20° C. to 30° C., preferably 0° C. to 20° C. for 0.1 hour to 24 hours, preferably 0.5 hour to 12 hours in a solvent such as dichloromethane, toluene, THF etc. or a mixed solvent thereof, by adding dropwise tertiary amine such as pyridine, trimethylamine, N-methylmorpholine, 4-dimethylaminopyridine etc. and benzyloxyacetyl chloride.

Second Step

A compound ac can be obtained by adding an organometallic base such as lithium hexamethyldisilazane, lithium diisopropylamide, butyllithium, tert-butyllithium etc. to the compound ab in a solvent such as ether, dichloromethane, THF etc. or a mixed solvent thereof, in the presence of cinnamoyl chloride, and performing a reaction at −80° C. to 0° C., preferably −80° C. to −40° C. for 1 minute to 2 hours, preferably 10 minutes to 1 hour.

Third Step

A compound ad can be obtained by adding a catalytic amount of an oxidizing agent such as ruthenium chloride and sodium periodate, TEMPO, manganese dioxide, as well as PDC etc. to the compound ac in a solvent such as ether, dichloromethane, THF, acetonitrile etc. or a mixed solvent thereof, and performing a reaction at −40° C. to 80° C., preferably 0° C. to 40° C. for 0.1 hour to 24 hours, preferably 0.2 hour to 3 hours.

Fourth Step

Concentrated sulfuric acid and an aqeuous solution of amidosuluflic acid are added to the compound ad at 0° C. to 60° C., preferably 10° C. to 40° C. in the presence of a solvent such as ether, dichloromethane, THF, acetonitrile, acetone, water etc. or in a mixed solvent thereof. An aqueous sodium chlorite solution is added dropwise thereto at the same temperature to perform a reaction for 1 minute to 3 hours, preferably 5 minutes to 1 hour, thereby, a compound ae can be obtained.

Fifth Step

A compound af can be obtained by adding a compound $R^3$—$NH_2$ having a substituent corresponding to an objective compound to the compound ae in a solvent such as DMF, THF, dichloromethane, acetonitrile etc. in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5,-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU etc., and performing a reaction at −20° C. to 60° C., preferably −10° C. to 40° C. for 0.1 hour to 24 hours, preferably 1 hour to 12 hours.

Sixth Step

A compound ah can be obtained by adding a compound ag to the compound af in the presence of a solvent such as toluene, xylene, THF, dioxane etc. or in a mixed solvent thereof, and performing a reaction for 0.1 hour to 12 hours, preferably 0.2 hour to 6 hours under the heat-refluxing condition.

Seventh Step

A compound ai can be obtained by adding triphenylphosphine and a condensation agent such as DEAD, DIAD etc. to the compound ah in the presence of a solvent such as THF, dioxane, ethyl acetate, acetonitrile etc. or in a mixed solvent thereof, and performing a reaction at 0° C. to 60° C., preferably 10° C. to 40° C. for 0.1 hour to 12 hours, preferably 0.2 hour to 6 hours.

Eighth Step

By subjecting the compound ai to the known general deprotecting reaction of a carboxyl protective group and a hydroxyl protective group, a compound aj can be obtained.

Synthesis of Compound bk (See: Example 12)

[Chemical formula 83]

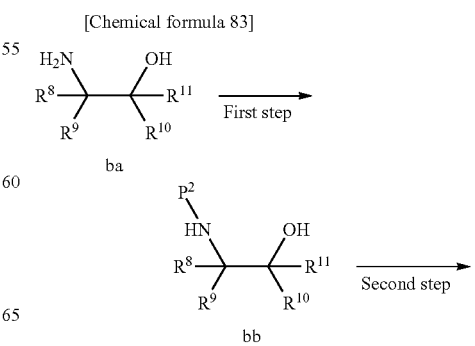

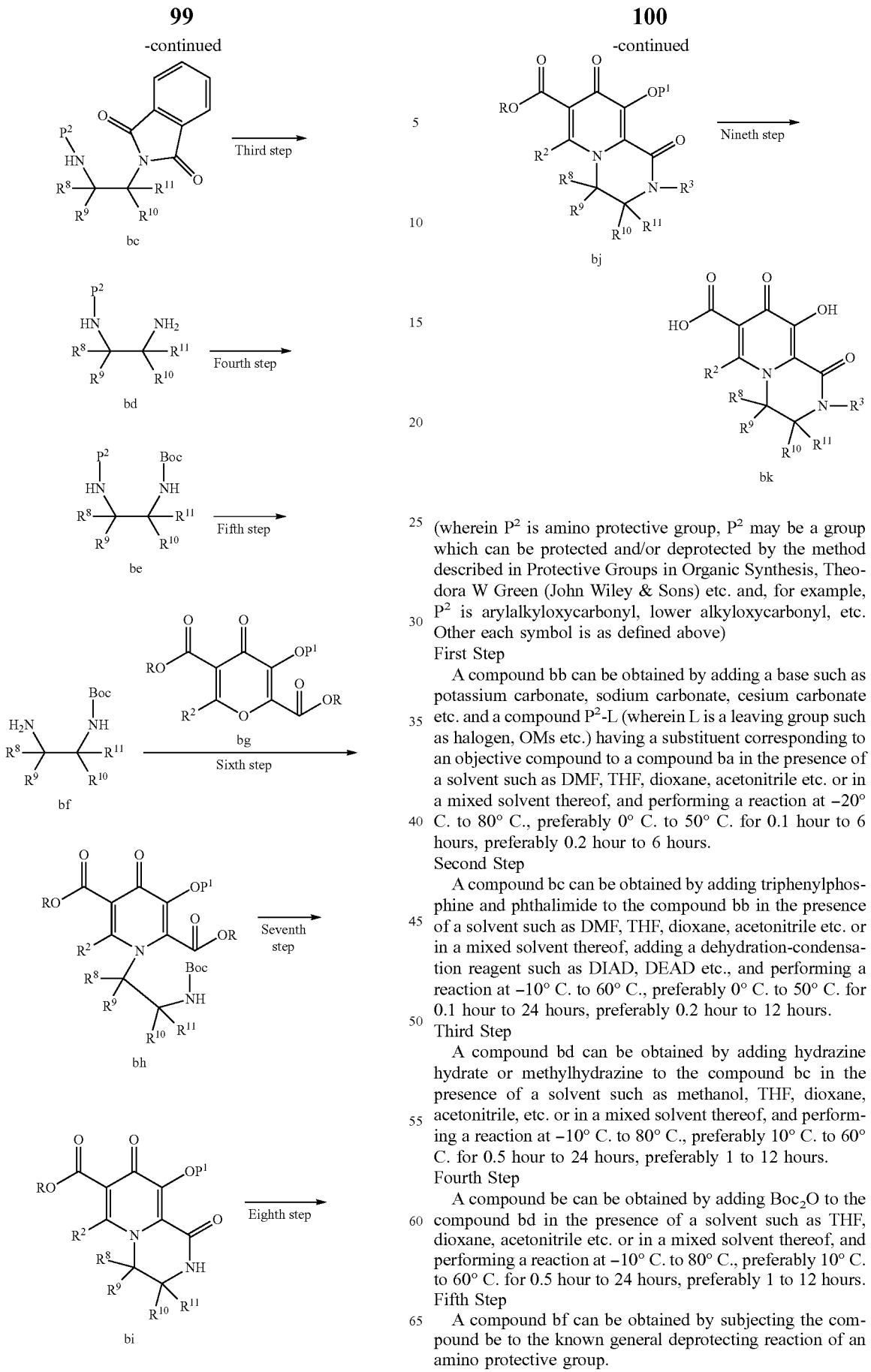

(wherein $P^2$ is amino protective group, $P^2$ may be a group which can be protected and/or deprotected by the method described in Protective Groups in Organic Synthesis, Theodora W Green (John Wiley & Sons) etc. and, for example, $P^2$ is arylalkyloxycarbonyl, lower alkyloxycarbonyl, etc. Other each symbol is as defined above)

First Step

A compound bb can be obtained by adding a base such as potassium carbonate, sodium carbonate, cesium carbonate etc. and a compound $P^2$-L (wherein L is a leaving group such as halogen, OMs etc.) having a substituent corresponding to an objective compound to a compound ba in the presence of a solvent such as DMF, THF, dioxane, acetonitrile etc. or in a mixed solvent thereof, and performing a reaction at −20° C. to 80° C., preferably 0° C. to 50° C. for 0.1 hour to 6 hours, preferably 0.2 hour to 6 hours.

Second Step

A compound bc can be obtained by adding triphenylphosphine and phthalimide to the compound bb in the presence of a solvent such as DMF, THF, dioxane, acetonitrile etc. or in a mixed solvent thereof, adding a dehydration-condensation reagent such as DIAD, DEAD etc., and performing a reaction at −10° C. to 60° C., preferably 0° C. to 50° C. for 0.1 hour to 24 hours, preferably 0.2 hour to 12 hours.

Third Step

A compound bd can be obtained by adding hydrazine hydrate or methylhydrazine to the compound bc in the presence of a solvent such as methanol, THF, dioxane, acetonitrile, etc. or in a mixed solvent thereof, and performing a reaction at −10° C. to 80° C., preferably 10° C. to 60° C. for 0.5 hour to 24 hours, preferably 1 to 12 hours.

Fourth Step

A compound be can be obtained by adding Boc₂O to the compound bd in the presence of a solvent such as THF, dioxane, acetonitrile etc. or in a mixed solvent thereof, and performing a reaction at −10° C. to 80° C., preferably 10° C. to 60° C. for 0.5 hour to 24 hours, preferably 1 to 12 hours.

Fifth Step

A compound bf can be obtained by subjecting the compound be to the known general deprotecting reaction of an amino protective group.

Sixth Step

A compound bh can be obtained by adding a compound bg to the compound bf in the presence of a solvent such as toluene, THF, dioxane, acetonitrile etc. or in a mixed solvent thereof, and performing a reaction at 20° C. to 110° C., preferably 40° C. to under heat-refluxing for 0.5 hour to 24 hours, preferably 1 hour to 12 hours.

Seventh Step

HCl-ethyl acetate, HCl-dioxane, formic acid etc. is added to the compound bh, and they are reacted at 0° C. to 40° C., preferably 0° C. to 20° C. for 0.5 hour to 12 hours, preferably 1 hour to 6 hours. After the solvent is distilled off under reduced pressure, an aqueous saturated sodium bicarbonate solution is added, and the mixture is stirred, thereby, a compound bi can be obtained.

Eighth Step

A compound bj can be obtained by adding a base such as potassium carbonate, sodium carbonate, lithium carbonate, cesium carbonate etc. and a compound $R^3$-L (L is a leaving group such as halogen, OMs etc.) to the compound bi in the presence of a solvent such as DMF, THF, DMA, NMP etc. or in a mixed solvent thereof, and performing a reaction at 0° C. to 60° C., preferably 10° C. to 30° C. for 0.5 hour to 12 hours, preferably 1 hour to 6 hours.

Ninth Step

A compound bk can be obtained by subjecting the compound bj to the known general deprotecting reaction of a carboxyl protective group and a hydroxyl protective group.

Synthesis of Compound cd (See: Examples 28 and 43)

[Chemical formula 84]

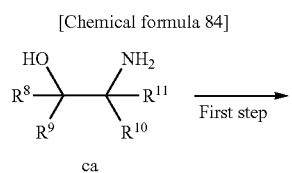

ca

[Chemical formula 85]

(wherein each symbol is as defined above)

First Step

A compound cb can be obtained by adding tertiary amine such as triethylamine, DMAP, morpholine etc. or a base such as sodium carbonate, sodium bicarbonate etc. to a compound ca in the presence of a solvent such as THF, dioxane, acetonitrile, water etc. or in a mixed solvent thereof, adding $Boc_2O$, and performing a reaction at −10° C. to 80° C., preferably 10° C. to 60° C. for 0.5 hour to 24 hours, preferably 1 to 12 hours.

Second Step

A compound cc can be obtained by adding triphenylphosphine and phthalimide to the compound cb in the presence of a solvent such as DMF, THF, dioxane, acetonitrile etc. or in a mixed solvent thereof, adding a dehydration-condensation reagent such as DIAD, DEAD etc., and performing a reaction at −10° C. to 60° C., preferably 0° C. to 50° C. for 0.1 hour to 24 hours, preferably 0.2 hour to 12 hours.

Third Step

A compound cd can be obtained by adding hydrazine hydrate to the compound cc in the presence of a solvent such as methanol, THF, dioxane, acetonitrile etc. or in a mixed solvent thereof, and performing a reaction at −10° C. to 80° C., preferably 10° C. to 60° C. for 0.5 hour to 24 hours, preferably 1 to 12 hours.

Synthesis of Compound dg (See: Examples 36, 41 and 46)

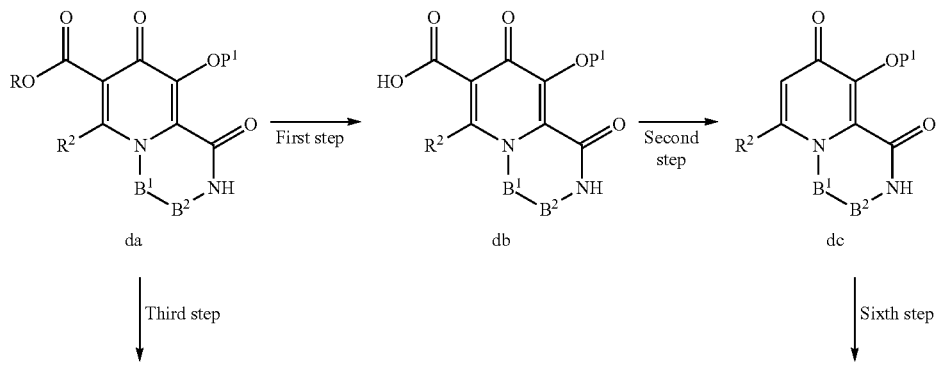

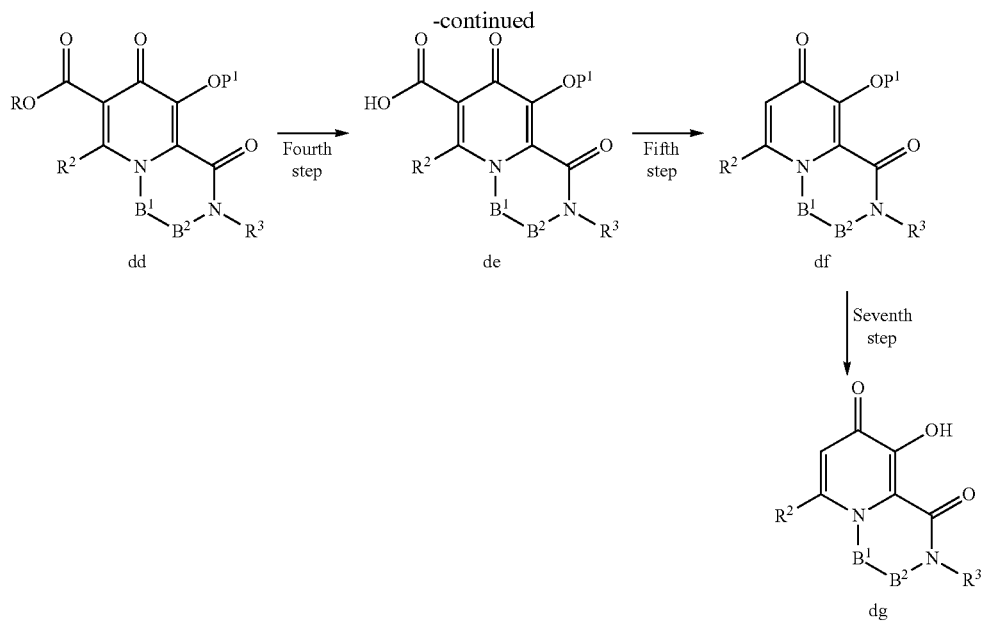

(wherein B¹ and B² are as defined in item 13' or item 13, and other each symbol is as defined above).

First Step

A compound db can be obtained by subjecting the compound da obtained by the same method as the synthesis method of bi to the known general carboxyl deprotecting reaction.

Second Step

A decarbonized compound dc can be obtained by reacting the compound db for 1 minute to 2 hours under microwave irradiation in a solvent such as diphenyl ether etc. And, a decarbonized compound dc can be obtained by adding copper in a quinoline solvent, and performing a reaction at 180° C. for 2 to 48 hours.

Third Step

A compound dd can be obtained by adding a base such as potassium carbonate, sodium carbonate, lithium carbonate, cesium carbonate etc. and a compound R³-L (L is a leaving group such as halogen, OMs etc.) to the compound da obtained by the method described in Example 12 in the presence of a solvent such as DMF, THF, DMA, NMP etc. or in a mixed solvent thereof, and performing a reaction at 0° C. to 60° C., preferably 10° C. to 30° C. for 0.5 hour to 12 hours, preferably 1 hour to 6 hours.

Fourth Step

A compound de can be obtained by the same method as that of the first step.

Fifth Step

A compound df can be obtained by the same method as that of the second step.

Sixth Step

A compound df can be obtained by the same method as that of the third step.

Seventh Step

A compound dg can be obtained by subjecting the compound df to the known general hydroxyl group deprotecting reaction.

Synthesis of Compound ec (See: Example 48)

[Chemical formula 86]

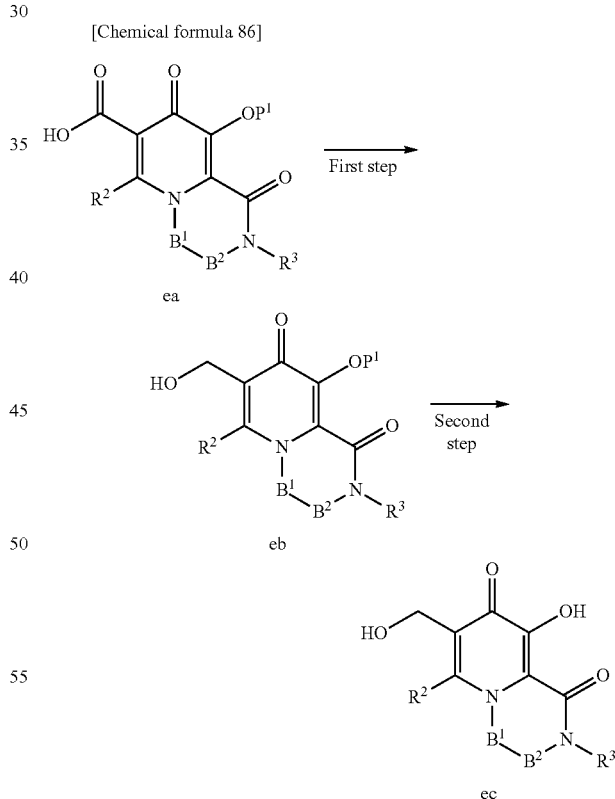

(wherein each symbol is as defined above)

First Step

A base such as triethylamine, N-methylmorpholine, diisopropylethylamine etc. and ethyl chloroformate are added to a compound ea in the presence of a solvent such as THF, dioxane, dichloromethane, toluene etc. or in a mixed solvent thereof. A reducing agent having a low reducing power such as sodium borohydride etc. is added thereto, and a reaction is performed at −20° C. to 60° C., preferably −10° C. to 20° C. for 0.2 hour to 12 hours, preferably 0.5 hour to 6 hours, thereby, a compound eb can be obtained.

Second Step

A compound ec can be obtained by subjecting the compound eb to the known general hydroxyl group deprotecting reaction.

Synthesis of Compound fh (See: Example 50)

[Chemical formula 87]

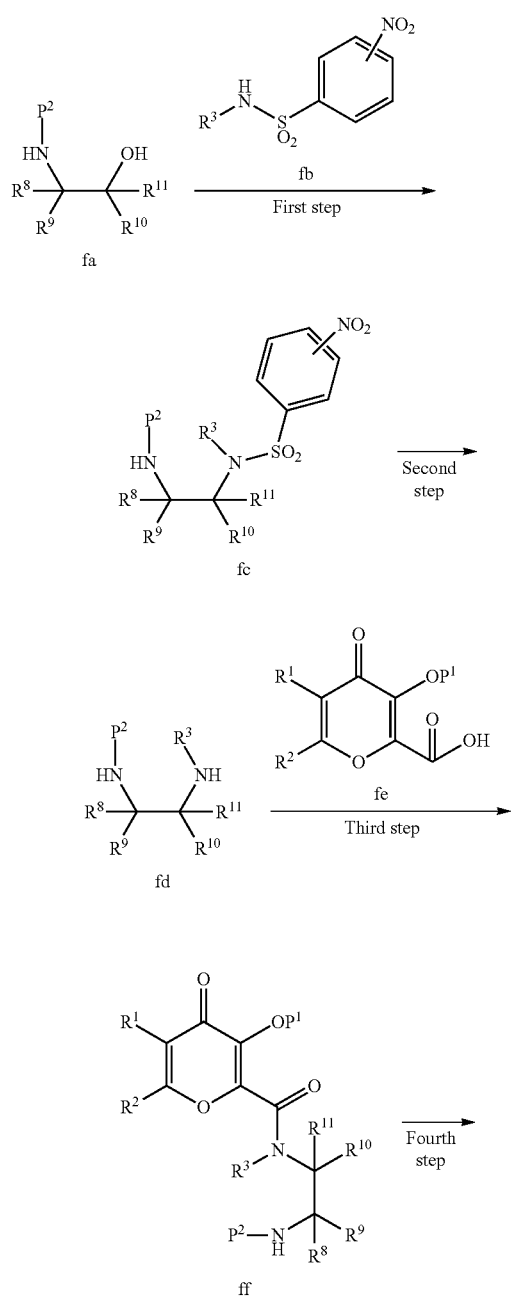

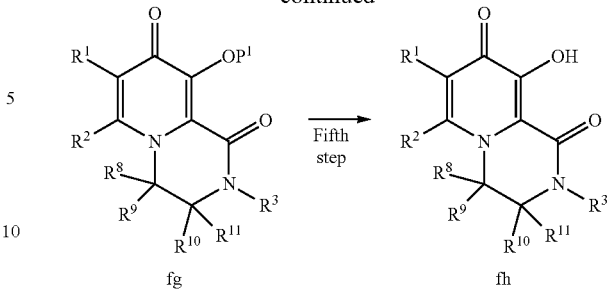

(wherein each symbol is as defined above)

First Step

A compound fb and triphenylphosphine are added to a compound fa in the presence of a solvent such as THF, dichloromethane, dioxane, acetonitrile etc. or in a mixed solvent thereof. DIAD is added thereto, and a reaction is performed at 0° C. to 60° C., preferably 10° C. to 30° C. for 0.5 hour to 12 hours, preferably 1 hour to 12 hours, thereby, a compound fc can be obtained.

Second Step

A compound fd can be obtained by adding a base such as potassium carbonate, sodium carbonate, lithium carbonate, cesium carbonate etc. and thiol such as benzenethiol etc. to the compound fc in the presence of a solvent such as THF, dioxane, acetonitrile etc. or in a mixed solvent thereof, and performing a reaction at 0° C. to 60° C., preferably 10° C. to 30° C. for 0.5 hour to 12 hours, preferably 1 hour to 12 hours.

Third Step

A compound ff can be obtained by adding a compound fe having a substituent corresponding to an objective compound to the compound fd in a solvent such as DMF, THF, dichloromethane, acetonitrile etc. in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl etc., and performing a reaction at 0° C. to 60° C., preferably 10° C. to 40° C. for 1 hour to 48 hours, preferably 2 hours to 24 hours.

Fourth Step

A compound fg can be obtained by subjecting the compound ff to the known general deprotecting reaction concerning a $P^2$ group on an amino group, subsequently, adding a base such as an aqueous sodium carbonate solution, an aqueous potassium carbonate solution etc. in a solvent such as water, ethanol, methanol, acetonitrile etc. or in a mixed solvent thereof, and performing a reaction at 20° C. to 80° C., preferably 20° C. to 70° C. for 0.5 hour to 24 hours, preferably 1 hour to 6 hours.

Fifth Step

A compound fh can be obtained by subjecting the compound fd to the known general hydroxyl group deprotecting reaction.

Synthesis of Compound ga (See: Example 51)

[Chemical formula 88]

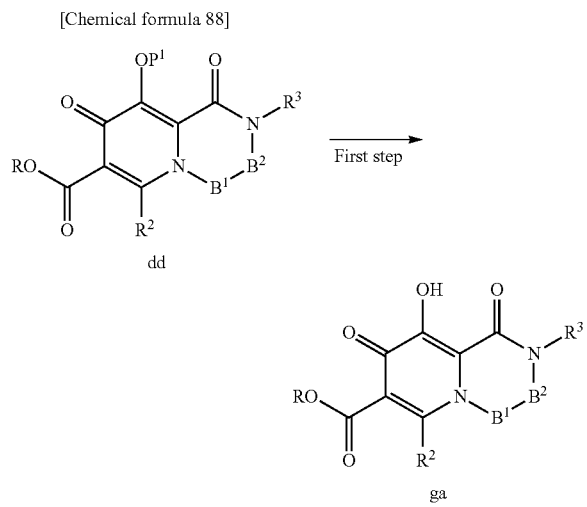

(wherein each symbol is as defined above)

First Step

A compound ga can be obtained by subjecting a compound dd to the known general hydroxyl group deprotecting reaction.

Synthesis of Compound hh (See: Example 52)

[Chemical formula 89]

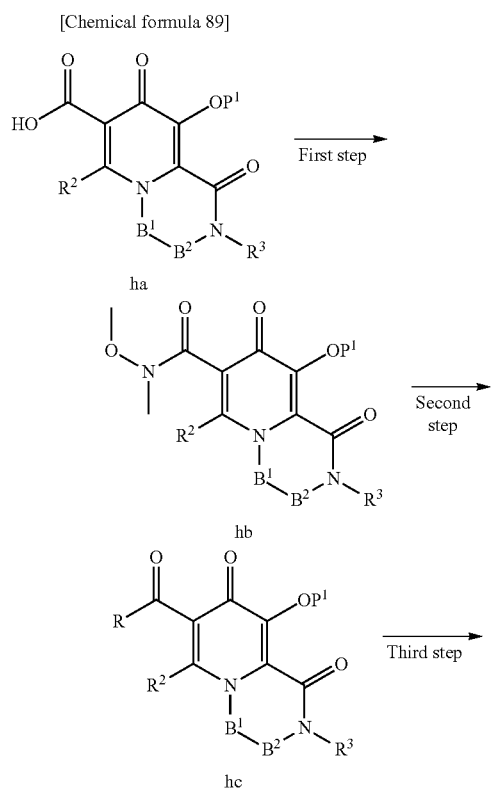

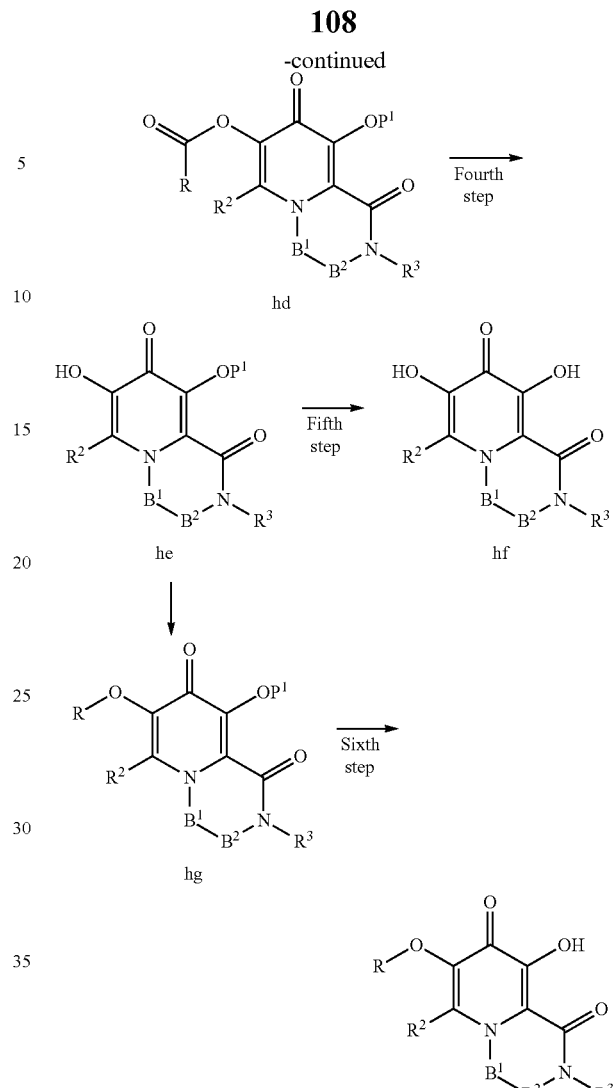

(wherein each symbol is as defined above)

First Step

A compound hb can be obtained by adding O,N-dimethylhydroxylamine hydrochloride to a compound ha in a solvent such as DMF, THF, dichloromethane, acetonitrile etc. in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU etc., adding a tertiary base such as triethylamine, diisopropylethylamine, N-methylmorpholine etc., and performing a reaction at 0° C. to 60° C., preferably 10° C. to 40° C. for 1 hour to 24 hours, preferably 1 hour to 12 hours.

Second Step

A compound hc can be obtained by adding a Grignard reagent (R—MgBr) to the compound hb at −80° C. to −40° C. in the presence of a solvent such as THF, ether, dichloromethane, dioxane etc. or in a mixed solvent thereof, and performing a reaction at −80° C. to 0° C., preferably −60° C. to −20° C. for 0.5 hour to 24 hours, preferably 0.5 hour to 6 hours.

Third Step

A compound hd can be obtained by adding mCPBA to the compound hc in the presence of a solvent such as chloroform and dichloromethane, and performing a reaction at −20° C. to 30° C., preferably 10° C. to 30° C. for 0.1 hour to 12 hours, preferably 0.5 hour to 6 hours.

Fourth Step

A compound he can be obtained by adding an aqueous sodium hydroxide solution to the compound hd in the presence of a solvent such as ethanol etc., and performing a reaction at 0° C. to 120° C., preferably 30° C. to 90° C. for 1 minute to 10 hours, preferably 30 minutes to 120 minutes.

Fifth Step

A compound hf can be obtained by subjecting the compound he to the known general hydroxyl group deprotecting reaction.

Sixth Step

A compound hg can be obtained by adding a compound R—Br etc. corresponding to an objective compound to a compound he in the presence of a solvent such as chloroform, dichloromethane, THF, toluene etc. or in a mixed solvent thereof, adding a metal base such as sodium hydride, sodium methylate, n-butyllithium etc., and performing a reaction at −20° C. to 120° C., preferably 0° C. to 30° C. for 0.5 hour to 12 hours, preferably 1 hour to 6 hours.

Seventh Step

A compound hh can be obtained by subjecting the compound hg to the known general hydroxyl group deprotecting reaction.

Synthesis of Compound ic (See: Example 53)

First Step

Tertiary amine such as triethylamine, diisopropylethylamine, N-methylmorpholine etc., and a chlorinating reagent such as ethyl chlorocarbonate, and ethyl chloroformate are added to a compound ia in the presence of a solvent such as DMF, DMA, NMP, THF etc. or in a mixed solvent thereof, and the mixture is stirred at 0° C. to 30° C. for 0.1 hour to 1 hour. A compound R—SO$_2$—NH$_2$ (e.g.: methanesulfonylamide) corresponding to an objective substance and DMAP are added thereto, and a reaction is performed at 40° C. to 100° C., preferably 40° C. to 80° C. for 0.5 hour to 12 hours, preferably 1 hour to 6 hours, thereby, a compound ib can be obtained.

Second Step

A compound ic can be obtained by subjecting the compound ib to the known general hydroxyl group deprotecting reaction.

Synthesis of Compound je (See: Example 54)

[Chemical formula 90]

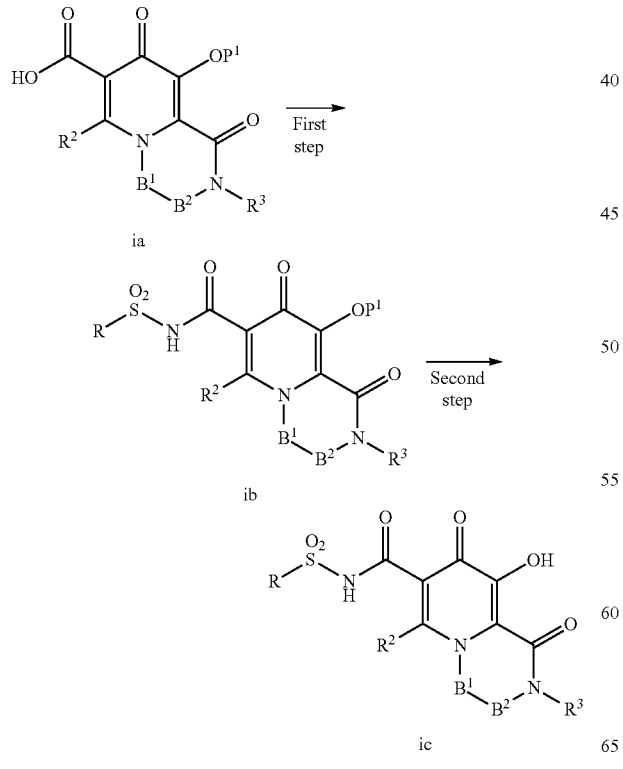

[Chemical formula 91]

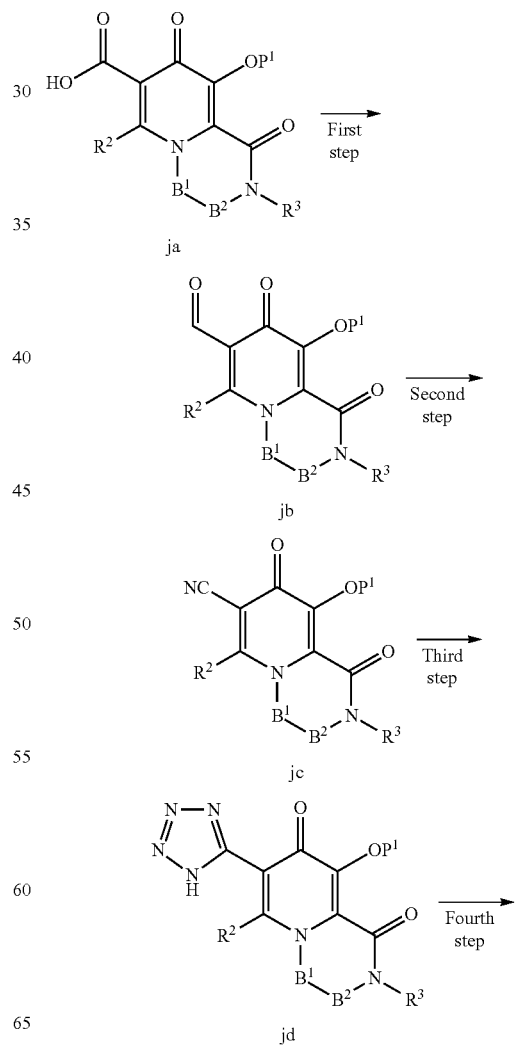

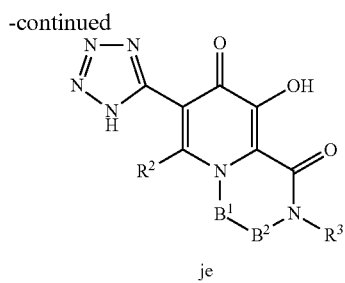

Third Step

A compound jd can be obtained by adding sodium azide, and tertiary amine such as triethylamine, diisopropylethylamine, N-methylmorpholine etc. to the compound jc in the presence of a solvent such as toluene, xylene, THF, dioxane etc. or in a mixed solvent thereof, and performing a reaction at 0° C. to 60° C., preferably 10° C. to 40° C. for 0.5 hour to 24 hours, preferably 1 hour to 12 hours.

Fourth Step

A compound je can be obtained by subjecting the compound jd to the known general hydroxyl group deprotecting reaction.

(wherein each symbol is as defined above)

Synthesis of Compounds kd and kf (See: Example 56 and Derivative Thereof)

[Chemical formula 92]

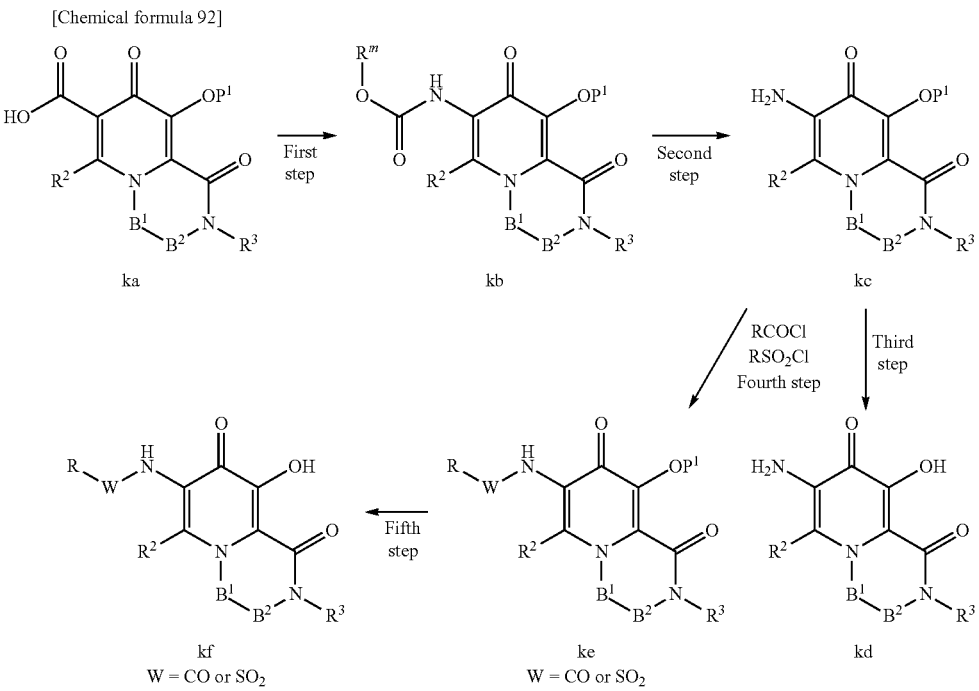

(wherein $R^m$ is lower alkyl, R is a substituent corresponding to an objective compound, W is —C(=O)— or —SO$_2$—, and other each symbol is as defined above)

First Step

Tertiary amine such as triethylamine, N-methylmorpholine, diisopropylethylamine etc. and ethyl chloroformate or ethyl chlorocarbonate are added to a compound ja in the presence of a solvent such as THF, dioxane, dichloromethane, toluene, DMF etc. or in a mixed solvent thereof. A reducing agent having low reactivity such as sodium borohydride etc. is added thereto, and a reaction is performed at −20° C. to 40° C., preferably −10° C. to 20° C. for 0.2 hour to 12 hours, preferably 0.5 hour to 6 hours to obtain an alcohol intermediate. This intermediate is dissolved in dichloromethane, chloroform, etc., an oxidizing agent such as TEMPO, manganese dioxide, PDC etc. is added, and a reaction is performed at −40° C. to 30° C., preferably 0° C. to 30° C. for 0.1 hour to 24 hours, preferably 0.5 hour to 12 hours, thereby, a compound jb can be obtained.

Second Step

A compound jc can be obtained by adding 28% aqueous ammonia and iodine to the compound jb in the presence of a solvent such as THF, dioxane, dichloromethane etc., and performing a reaction at 0° C. to 40° C., preferably 10° C. to 30° C. for 0.5 hour to 24 hours, preferably 1 hour to 6 hours.

First Step

Tertiary amine such as triethylamine, N-methylmorpholine, diisopropylethylamine etc. and ethyl chloroformate or ethyl chlorocarbonate are added to a compound ka in the presence of a solvent such as THF, dioxane, dichloromethane, toluene, DMF etc. or in a mixed solvent thereof. Sodium azide is added thereto to perform a reaction at 0° C. to 40° C., preferably 10° C. to 30° C. for 0.5 hour to 24 hours, preferably 1 hour to 12 hours. Thereafter, an alcohol ($R^m$—OH) is added, and a reaction is performed at 20° C. to 60° C., preferably 20° C. to 50° C. for 0.5 hour to 24 hours, preferably 1 hour to 12 hours, thereby, a compound kb can be obtained.

Second Step

A compound kc can be obtained by adding a base such as an aqueous sodium hydroxide solution, an aqueous potassium hydroxide solution etc. to the compound kb in a solvent such as ethanol, methanol, water etc. or in a mixed solvent thereof, and performing a reaction at 20° C. to 80° C., preferably 40° C. to 60° C. for 0.5 hour to 24 hours, preferably 1 hour to 12 hours.

Third Step

A compound kd can be obtained by subjecting the compound kc to the known general hydroxyl group deprotecting reaction.

Fourth Step

A compound ke can be obtained by adding acid chloride (R—CO—Cl) or sulfonyl chloride (R—SO$_2$—Cl) corresponding to an objective substance to a compound kc in a solvent such as THF, dioxane, toluene, dichloromethane etc., adding tertiary amine such as pyridine, triethylamine, N-methylmorpholine etc. as necessary, and performing a reaction at −20° C. to 40° C., preferably 0° C. to 30° C. for 0.1 hour to 12 hours, preferably 0.2 hour to 6 hours.

Fifth Step

A compound kf can be obtained by subjecting the compound ke to the known general hydroxyl group deprotecting reaction.

Synthesis of Compound lc (See: Example 60)

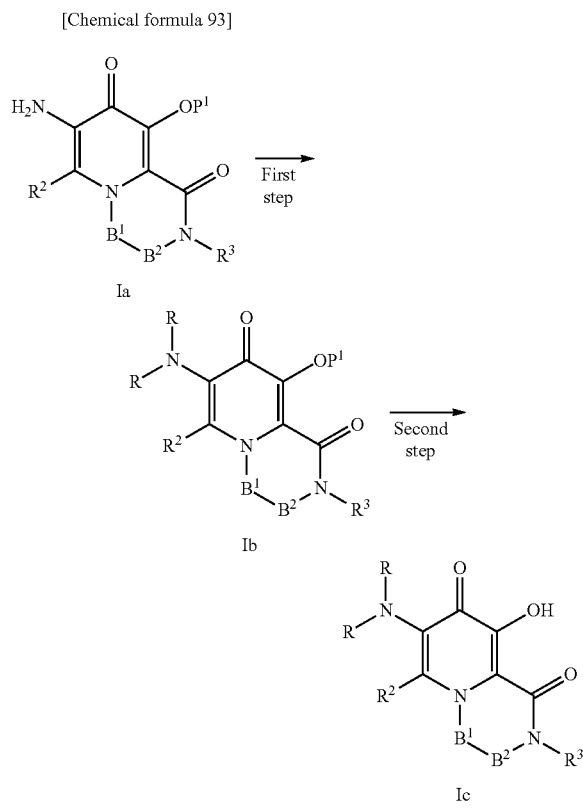

(wherein R is a substituent corresponding to an objective compound, and other each symbol is as defined above)

First Step

Sodium hydride is added to a compound la in a solvent such as THF, dichloromethane, DMF etc. R-L (L is a leaving group such as halogen, OMs etc.) corresponding to an objective substance is added thereto, and a reaction is performed at −20° C. to 40° C., preferably 0° C. to 30° C. for 0.1 hour to 12 hours, preferably 0.2 hour to 6 hours, thereby, a compound lb can be obtained.

Alternatively, a compound lb can be obtained by adding formaldehyde to a compound la in a solvent of formic acid, and performing a reaction at 70° C. to 110° C. for 0.5 hour to 24 hours, preferably 1 hour to 12 hours.

Second Step

A compound lc can be obtained by subjecting the compound lb to the known general hydroxyl group deprotecting reaction.

Synthesis of Compound md (See: Example 61)

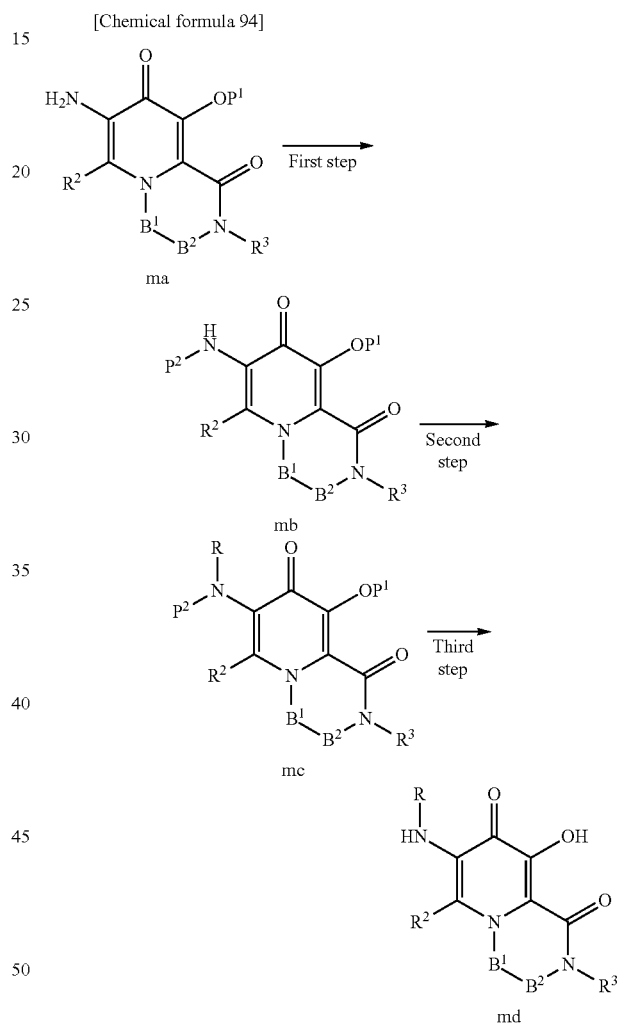

(wherein R is a substituent corresponding to an objective compound, and other each symbol is as defined above)

First Step

An amino-protected body mb can be obtained by adding Boc$_2$O etc. to a compound ma in a solvent such as THF, dioxane, acetonitrile, water etc. or in a mixed solvent thereof, and subjecting this to an amine protecting reaction.

Second Step

Sodium hydride is added to a compound mb in a solvent such as THF, dichloromethane, DMF etc. R-L (L is a leaving group such as halogen, OMs etc.) corresponding to an objective substance is added thereto, and a reaction is performed at −20° C. to 40° C., preferably 0° C. to 30° C.

for 0.1 hour to 12 hours, preferably 0.2 hour to 6 hours, thereby, a compound mc can be obtained.
Third Step
A compound md can be obtained by subjecting the compound mc to the known general amino group and hydroxyl group deprotecting reaction.

Synthesis of Compound nc and Compound ne (See: Examples 63 and 64)

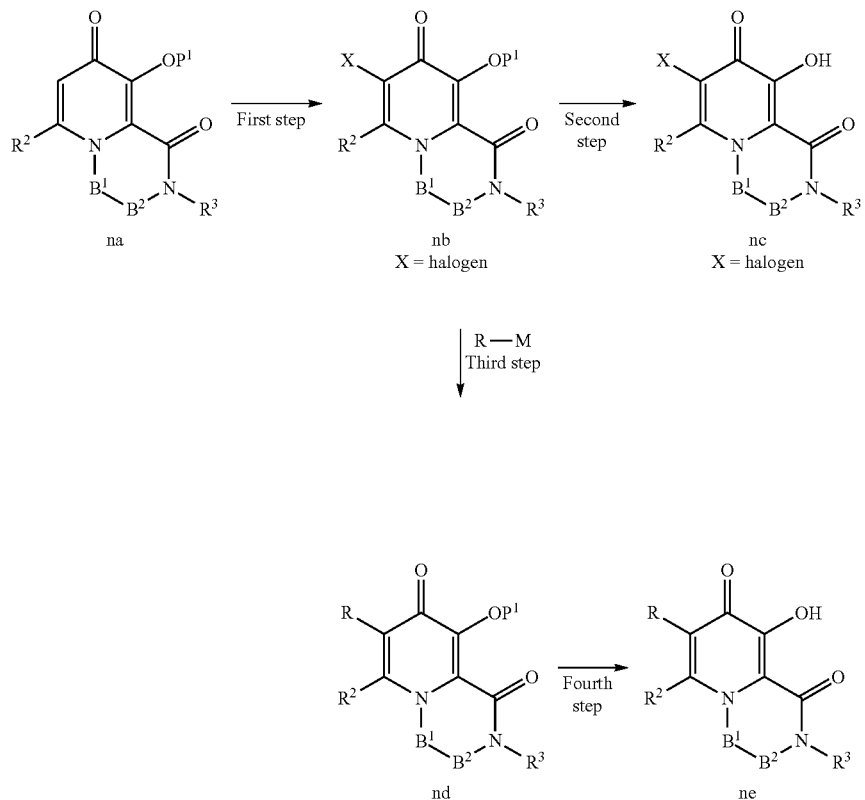

(wherein X is halogen, M is boronic acid ester such as B(O-phenyl)$_3$ etc., and other each symbol is as defined above)
First Step
A compound nb can be obtained by adding a halogenating reagent (e.g. NBS, NCS, bromine etc.) to a compound na in a solvent such as dichloromethane, toluene, THF, dioxane etc., and performing a reaction for 0.1 hour to 12 hours, preferably 0.2 hour to 6 hours under the overheating refluxing condition.
Second Step
A compound nc can be obtained by subjecting the compound nb to the known general hydroxyl group deprotecting reaction.
Third Step
Boronic acid ester (R-M) corresponding to an objective substance is added to a compound nb in a solvent such as toluene, THF, DMF etc. or in a mixed solvent thereof, and a base such as potassium carbonate, sodium carbonate, sodium hydroxide etc. is added. A 0-valent palladium catalyst (e.g.: Pd(PPh$_3$)$_4$) is added thereto under nitrogen stream, and a reaction is performed at 60° C. to 120° C., preferably 80° C. to 110° C. for 1 hour to 48 hours, preferably 2 hours to 24 hours, thereby, a compound nd can be obtained.
Fourth Step
A compound ne can be obtained by subjecting the compound nd to the known general hydroxyl group deprotecting reaction.

Synthesis of Compound oh (See: Example 65)

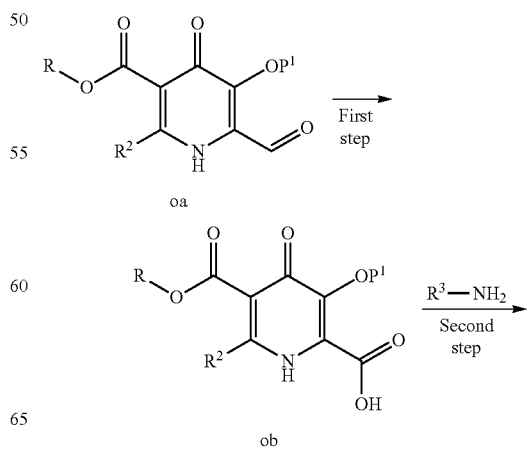

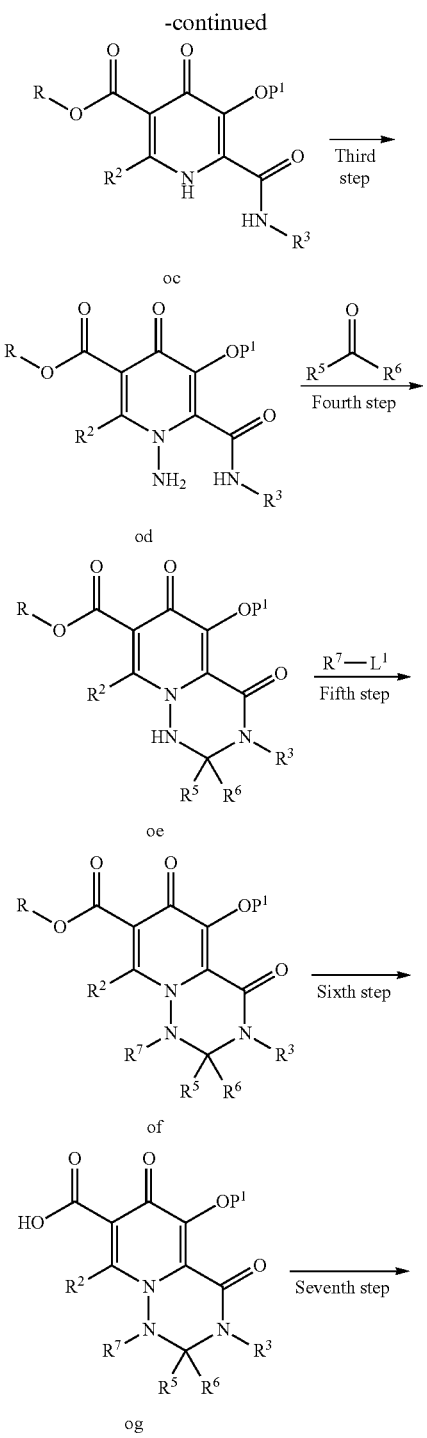

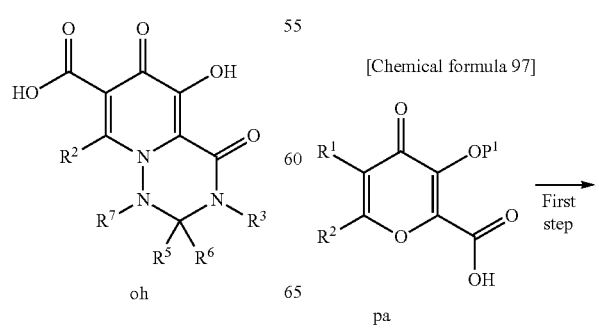

(wherein R is a carboxyl protective group such as lower alkyl etc., $R^7$ is as defined in item 1' or item 1, $L^1$ is a leaving group such as halogen, OMs, OTs etc., and other symbol is as defined above)

First Step

A compound ob can be obtained by adding sodium chlorite and amidosulfuric acid to a compound oa in the presence of a solvent such as THF, dioxane, dichloromethane, acetonitrile etc., and performing a reaction at 0° C. to 40° C., preferably 0° C. to 30° C. for 0.1 hour to 24 hours, preferably 1 hour to 12 hours.

Second Step

A compound oc can be obtained by adding a condensation agent such as HATU, WSC.HCl etc. to the compound ob in the presence of a solvent such as DMF, DMA, NMP, THF etc., adding amine ($R^3$—$NH_2$) corresponding to an objective substance, and tertiary amine such as triethylamine, N-methylmorpholine, pyridine etc., and performing a reaction at 10° C. to 60° C., preferably 20° C. to 40° C. for 0.1 hour to 24 hours, preferably 1 hour to 12 hours.

Third Step

A compound od can be obtained by adding potassium carbonate, sodium carbonate, and O-(2,4-dinitrophenyl)hydroxylamine to the compound oc in the presence of a solvent such as DMF, DMA, NMP, THF etc., and performing a reaction at 10° C. to 60° C., preferably 20° C. to 40° C. for 0.1 hour to 24 hours, preferably 1 hour to 12 hours.

Fourth Step

A compound oe can be obtained by adding $R^5$—C(=O)—$R^6$ and acetic acid to the compound od in the presence of a solvent such as toluene, DMF, DMA, NMP, THF etc., and performing a reaction at 60° C. to 120° C., preferably 80° C. to 110° C. for 0.1 hour to 24 hours, preferably 1 hour to 12 hours.

Fifth Step

A compound of can be obtained by adding a compound $R^7$-$L^1$ corresponding to an objective substance, and a base such as sodium carbonate, potassium carbonate, cesium carbonate etc. to the compound oe in the presence of a solvent such as DMF, DMA, NMP, THF etc., and performing a reaction at 0° C. to 60° C., preferably 10° C. to 40° C. for 0.1 hour to 24 hours, preferably 1 hour to 12 hours.

Sixth Step

A compound og can be obtained by subjecting the compound of to the known general carboxyl group deprotecting reaction.

Seventh Step

A compound oh can be obtained by subjecting the compound og to the known general hydroxyl group deprotecting reaction.

Synthesis of Compound pg (See: Example 95)

[Chemical formula 97]

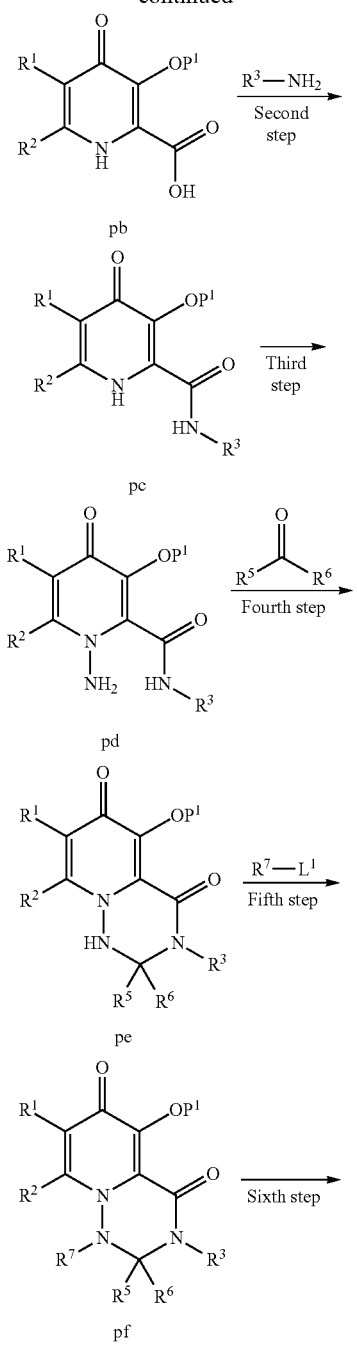

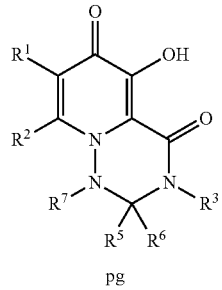

(wherein each symbol is as defined above)

First Step

A compound pb can be obtained by adding aqueous ammonia to a compound pa, and performing a reaction at 0° C. to 30° C., preferably 10° C. to 30° C. for 0.5 hour to 48 hours, preferably 1 hour to 24 hours.

Second Step

A compound pc can be obtained by adding a condensation agent such as HATU, WSC.HCl etc. to the compound pb in the presence of a solvent such as DMF, DMA, NMP, THF etc. or in a mixed solvent thereof, adding amine ($R^3$—$NH_2$) corresponding to an objective substance and, if necessary, tertiary amine such as triethylamine, N-methylmorpholine etc., and performing a reaction at 10° C. to 60° C., preferably 20° C. to 40° C. for 0.1 hour to 24 hours, preferably 1 hour to 12 hours.

Third Step

A compound pd can be obtained by adding potassium carbonate, sodium carbonate, and O-(2,4-dinitrophenyl)hydroxylamine to the compound pc in the presence of a solvent such as DMF, DMA, NMP, THF etc., and performing a reaction at 10° C. to 60° C., preferably 20° C. to 40° C. for 0.1 hour to 24 hours, preferably 1 hour to 12 hours.

Fourth Step

A compound pe can be obtained by adding $R^5$—C(=O)—$R^6$ and acetic acid to the compound pd in the presence of a solvent such as toluene, DMF, DMA, NMP, THF etc., and performing a reaction at 60° C. to 120° C., preferably 80° C. to 110° C. for 0.1 hour to 12 hours, preferably 0.2 hour to 6 hours.

Fifth Step

A compound pf can be obtained by adding a compound $R^7$-$L^1$ corresponding to an objective substance, and a base such as sodium carbonate, potassium carbonate, cesium carbonate etc. to the compound pe in the presence of a solvent such as DMF, DMA, NMP, THF etc., and performing a reaction at 0° C. to 60° C., preferably 10° C. to 40° C. for 0.1 hour to 24 hours, preferably 1 hour to 12 hours.

Sixth Step

A compound pg can be obtained by subjecting the compound pf to the known general hydroxyl group deprotecting reaction.

Synthesis of Compound qg, Compound qi, and Compound qk (See: Example 128)

[Chemical formula 98]

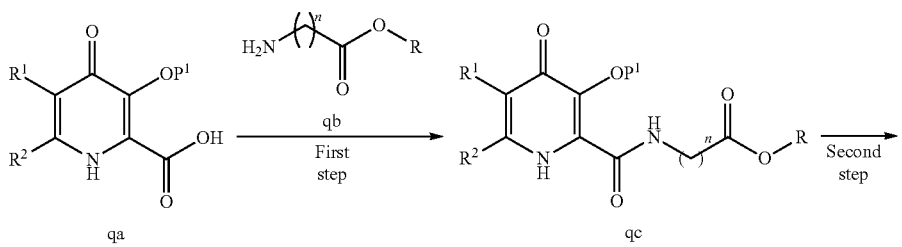

-continued

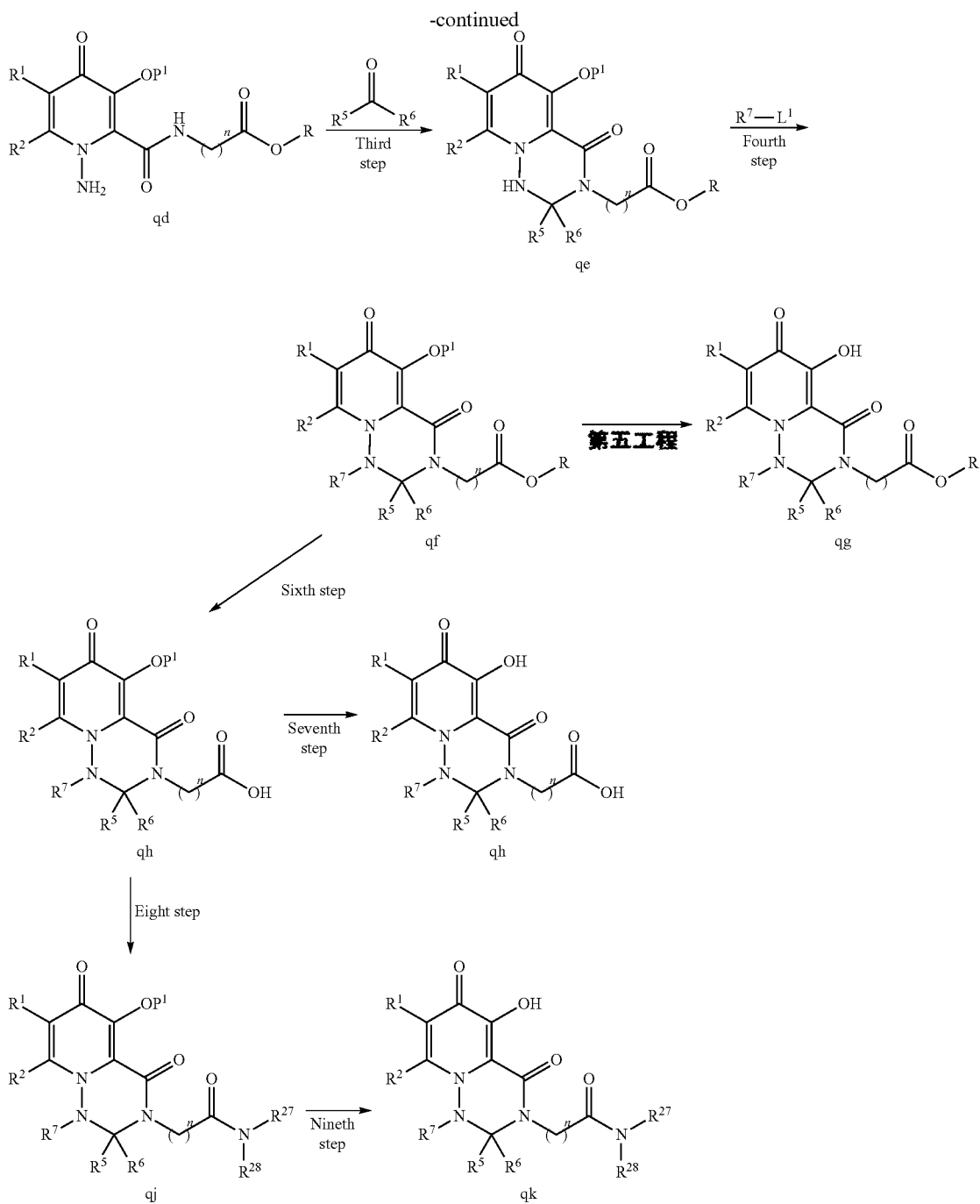

(wherein R represents a carboxyl protective group, n represents an integer of 0 to 6, $R^{27}$ and $R^{28}$ are as defined in item 1' or item 1, and other each symbol is as defined above)

First Step

A compound qc can be obtained by adding a condensation agent such as HATU, WSC.HCl etc. to a compound qa in the presence of a solvent such as pyridine, DMF, DMA, NMP, THF etc. or in a mixed solvent thereof, adding a compound qb and, if necessary, tertiary amine such as triethylamine, N-methylmorpholine etc., and performing a reaction at 10° C. to 60° C., preferably 20° C. to 40° C. for 0.1 hour to 24 hours, preferably 1 hour to 12 hours.

Second Step

A compound qd can be obtained by adding potassium carbonate, sodium carbonate, and O-(2,4-dinitrophenyl)hydroxylamine to the compound qc in the presence of a solvent such as DMF, DMA, NMP, THF etc. or in a mixed solvent thereof, and performing a reaction at 10° C. to 60° C., preferably 20° C. to 40° C. for 0.1 hour to 48 hours, preferably 1 hour to 24 hours.

Third Step

A compound pe can be obtained by adding $R^5$—C(=O)—$R^6$ and acetic acid to the compound qd in the presence of a solvent such as toluene, DMF, DMA, NMP, THF etc. or in a mixed solvent thereof, and performing a reaction at 60° C. to 120° C., preferably 80° C. to 110° C. for 0.1 hour to 12 hours, preferably 0.2 hour to 6 hours.

Alternatively, a compound qe can be obtained by performing a reaction at 100° C. to 200° C. for 5 minutes to 1 hour under microwave irradiation condition in a solvent such as ethanol, isopropyl alcohol etc.

Fourth Step

A compound qf can be obtained by adding a compound $R^7$-$L^1$ corresponding to an objective substance, and a base such as sodium carbonate, potassium carbonate, cesium carbonate etc. to the compound qe in the presence of a solvent such as DMF, DMA, NMP etc. or in a mixed solvent thereof, and performing a reaction at 0° C. to 60° C., preferably 10° C. to 40° C. for 0.1 hour to 48 hours, preferably 1 hour to 24 hours.

Fifth Step

A compound qg can be obtained by subjecting the compound qf to the known general hydroxyl group deprotecting reaction.

Sixth Step

A compound qh can be obtained by subjecting the compound qf to the known general carboxyl group deprotecting reaction.

Seventh Step

A compound qi can be obtained by subjecting the compound qh to the known general hydroxyl group deprotecting reaction.

Eighth Step

A compound qj can be obtained by adding a condensation agent such as HATU, WSC.HCl etc. to a compound qh in the presence of a solvent such as pyridine, DMF, DMA, NMP, THF etc. or in a mixed solvent thereof, adding a compound $HNR^{Z7}R^{Z8}$ and, if necessary, tertiary amine such as triethylamine, diisopropylethylamine, N-methylmorpholine etc., and performing a reaction at 10° C. to 60° C., preferably 20° C. to 40° C. for 0.1 hour to 24 hours, preferably 1 hour to 12 hours.

Ninth Step

A compound qk can be obtained by subjecting the compound qj to the known general hydroxyl group deprotecting reaction.

Synthesis of Compound qq, Compound qs, Compound qu, and Compound qw (See: Example 128)

[Chemical formula 99]

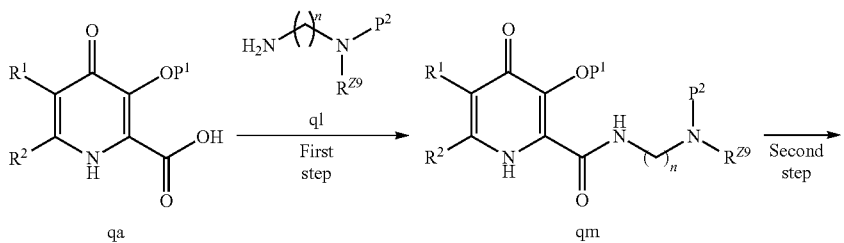

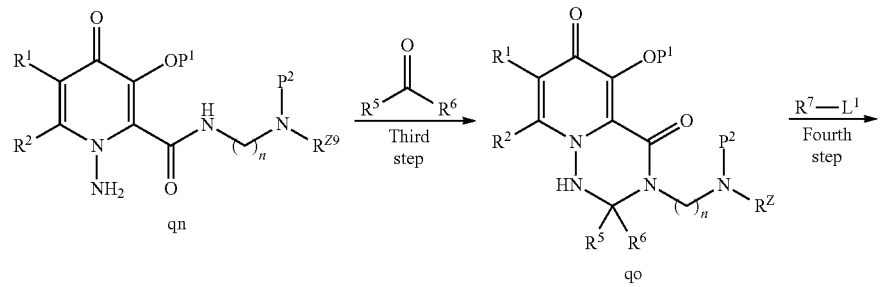

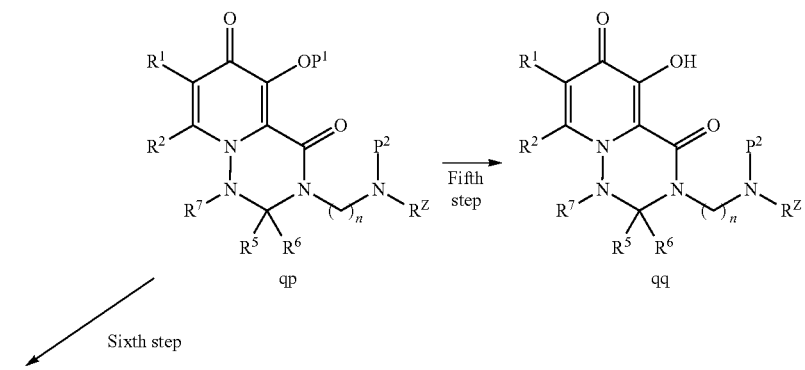

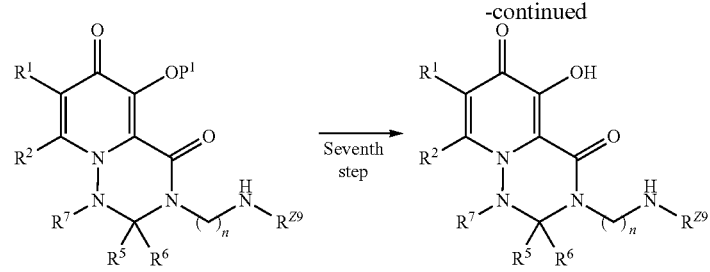

(wherein $R^{Z2}$, $R^{Z4}$, $R^{Z9}$, $R^{Z10}$, and $R^{Z13}$ are as defined in item 1' or item 1, and other each symbol is as defined above)

Step 1

A compound qm can be obtained by adding a condensation agent such as HATU, WSC.HCl, etc. to a compound qa in the presence of a solvent such as pyridine, DMF, DMA, NMP etc. or in a mixed solvent thereof, adding a compound ql and, if necessary, tertiary amine such as triethylamine, diisopropylethylamine, N-methylmorpholine, etc., and performing a reaction at 10° C. to 60° C., preferably 20° C. to 40° C. for 0.1 hour to 24 hours, preferably 1 hour to 12 hours.

Second Step

A compound qn can be obtained by adding potassium carbonate, sodium carbonate, and O-(2,4-dinitrophenyl)hydroxylamine to the compound qm in the presence of a solvent such as DMF, DMA, NMP, THF etc., and performing a reaction at 10° C. to 60° C., preferably 20° C. to 40° C. for 0.1 hour to 48 hours, preferably 1 hour to 24 hours.

Third Step

A compound pe can be obtained by adding $R^5$—C(=O)—$R^6$ and acetic acid to the compound qn in the presence of a solvent such as toluene, DMF, DMA, NMP, THF etc. or in a mixed solvent thereof, and performing a reaction at 60° C. to 120° C., preferably 80° C. to 110° C. for 0.1 hour to 12 hours, preferably 0.2 hour to 6 hours.

Alternatively, a compound qo can be obtained by performing a reaction at 100° C. to 200° C. for 5 minutes to 1 hour under microwave irradiation condition in a solvent such as ethanol etc.

Fourth Step

A compound qp can be obtained by adding a compound $R^7$-$L^1$ corresponding to an objective substance, and a base such as sodium carbonate, potassium carbonate, cesium carbonate, etc. to the compound qo in the presence of a solvent such as DMF, DMA, NMP, THF, etc. or in a mixed solvent thereof, and performing a reaction at 0° C. to 60° C., preferably 10° C. to 40° C. for 0.1 hour to 48 hours, preferably 1 hour to 24 hours.

Fifth Step

A compound qq can be obtained by subjecting the compound qp to the known general hydroxyl group deprotecting reaction.

Sixth Step

A compound qr can be obtained by subjecting the compound qp to the known general amino group deprotecting reaction.

Seventh Step

A compound qs can be obtained by subjecting the compound qr to the known general hydroxyl group deprotecting reaction.

Eighth Step

A compound qt can be obtained by adding a compound $R^{Z10}\text{-}L^1$ corresponding to an objective substance, and a base such as sodium carbonate, potassium carbonate, cesium carbonate, etc. to the compound qr in the presence of a solvent such as DMF, DMA, NMP, THF, etc. or in a solvent thereof, and performing a reaction at 0° C. to 60° C., preferably 10° C. to 40° C. for 0.1 hour to 48 hours, preferably 1 hour to 24 hours.

Ninth Step

A compound qu can be obtained by subjecting the compound qt to the known general hydroxyl group deprotecting reaction.

Tenth Step

A base such as sodium carbonate, potassium carbonate, cesium carbonate etc. is added to the compound qr in the presence of a solvent such as THF, dioxane, dichloromethane, acetonitrile, etc. A compound ($R^{Z4}COCl$, $R^{Z2}SO_2Cl$, or $R^{Z13}OCOCl$) corresponding to an objective substance is added thereto, and a reaction is performed at −20° C. to 60° C., preferably 0° C. to 30° C. for 0.1 hour to 48 hours, preferably 1 hour to 24 hours, thereby, a compound qv can be obtained.

Eleventh Step

A compound qw can be obtained by subjecting the compound qv to the known general hydroxyl group deprotecting reaction.

Synthesis of Compound rb (See: Example 155)

[Chemical formula 100]

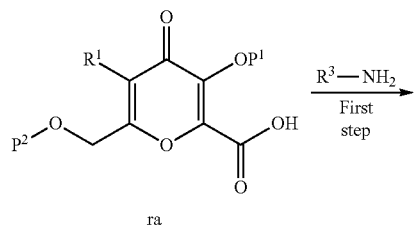

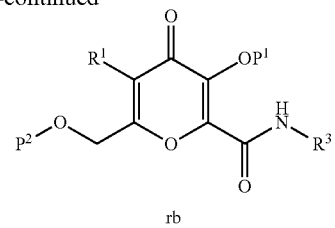

(wherein each symbol is as defined above)

A compound rb can be obtained by adding a compound $R^3NH_2$ having a substituent corresponding to an objective compound to a compound ra in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU, etc. in a solvent such as DMF, THF, dichloromethane, acetonitrile, etc. or in a mixed solvent thereof, and performing a reaction at −20° C. to 60° C., preferably −10° C. to 40° C. for 0.1 hour to 24 hours, preferably 1 hour to 12 hours.

Alternatively, a compound rb can be obtained by adding an acylating reagent such as diphenylchlorophosphate, thionyl chloride, oxalyl chloride, etc. to a compound ra in the presence or absence of a base such as pyridine, triethylamine, diisopropylethylamine, 1-methylimidazole, etc. in the presence of a solent such as THF, dioxane, dichloromethane, DMF, etc. to generate acid chloride, adding a compound $R^3$—$NH_2$ having a substituent corresponding to an objective compound, and performing a reaction at −20° C. to 60° C., preferably −10° C. to 40° C. for 0.1 hour to 24 hours, preferably 0.5 hour to 12 hours.

Synthesis of Compound sl (See: Example 49)

[Chemical formula 101]

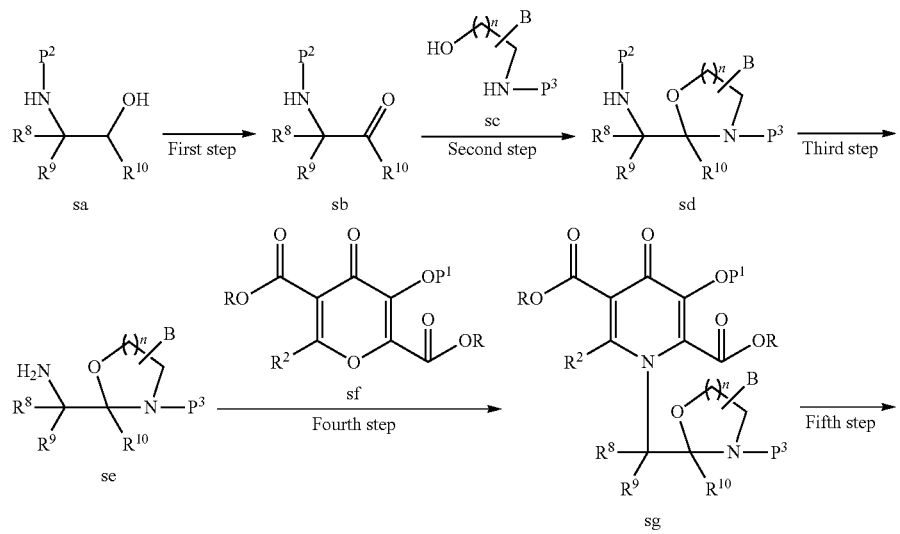

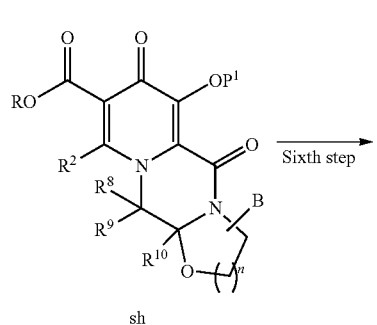 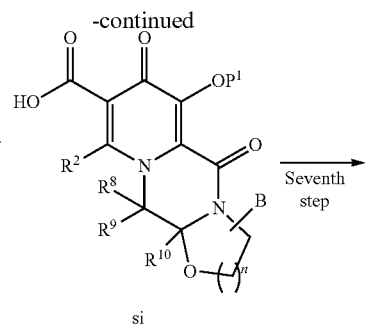 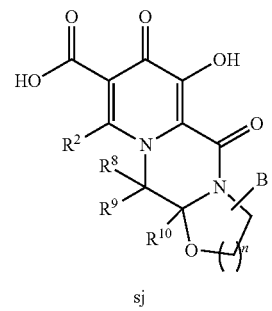

-continued

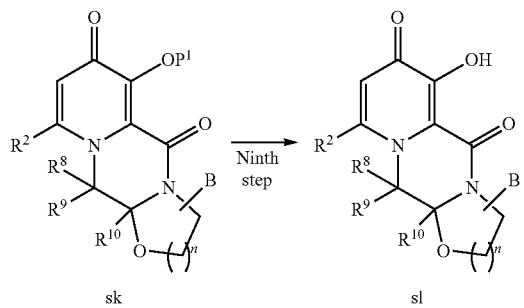

(wherein P³ is an amino protective group, and may be a group which can be protected and/or deprotected by the method described in Protective Groups in Organic Synthesis, Theodora W Green (John Wiley & Sons) etc. and, for example, P³ is aryl lower alkyloxycarbonyl, lower alkylcarbonyl, etc. B is as defined in item 1' or item 1, and other each symbol is as defined above.)

First Step

A compound sb can be obtained by adding an oxidizing reagent such as Dess Martin Periodinane, manganese dioxide, PDC, etc, to a compound sa in the presence of a solvent such as dichloromethane, THF, dioxane, toluene etc., and performing a reaction at −20° C. to 60° C., preferably 0° C. to 40° C. for 0.1 hour to 24 hours, preferably 0.5 hour to 12 hours.

Second Step

A compound sd can be obtained by adding sodium sulfate and an aminoalcohol sc corresponding to an objective substance to the compound sb in the presence or absence of a solvent such as toluene, THF etc., and performing a reaction at 0° C. to 80° C., preferably 20° C. to 60° C. for 0.1 hour to 24 hours, preferably 0.5 hour to 12 hours.

Third Step

A compound se can be obtained by subjecting the compound sd to the known general amino group deprotecting reaction.

Fourth Step

A compound sg can be obtained by adding a compound sf to the compound se in the presence of a solvent such as toluene, THF, dioxane etc., and performing a reaction at 40° C. to 110° C., preferably 60° C. to 100° C. for 0.5 hour to 24 hours, preferably 1 hour to 12 hours.

Fifth Step

A compound sh can be obtained by subjecting the compound sg to the known general amino group deprotecting reaction and, thereafter, performing a reaction at 40° C. to 110° C., preferably 60° C. to 100° C. for 0.1 hour to 12 hours, preferably 0.2 hour to 6 hours in the presence of a solvent such as toluene, THF, dioxane, etc.

Sixth Step

A compound si can be obtained by subjecting the compound sh to the known general carboxyl group deprotecting reaction.

Seventh Step

A compound sj can be obtained by subjecting the compound si to the known general hydroxyl group deprotecting reaction.

Eighth Step

A decarbonized compound sk can be obtained by reacting the compound si for 1 minute to 2 hours under microwave irradiation in a solvent such as diphenyl ether etc.

Ninth Step

A compound sl can be obtained by subjecting the compound sk to the known general hydroxyl group deprotecting reaction.

Synthesis of Compound un (See: Example 177)

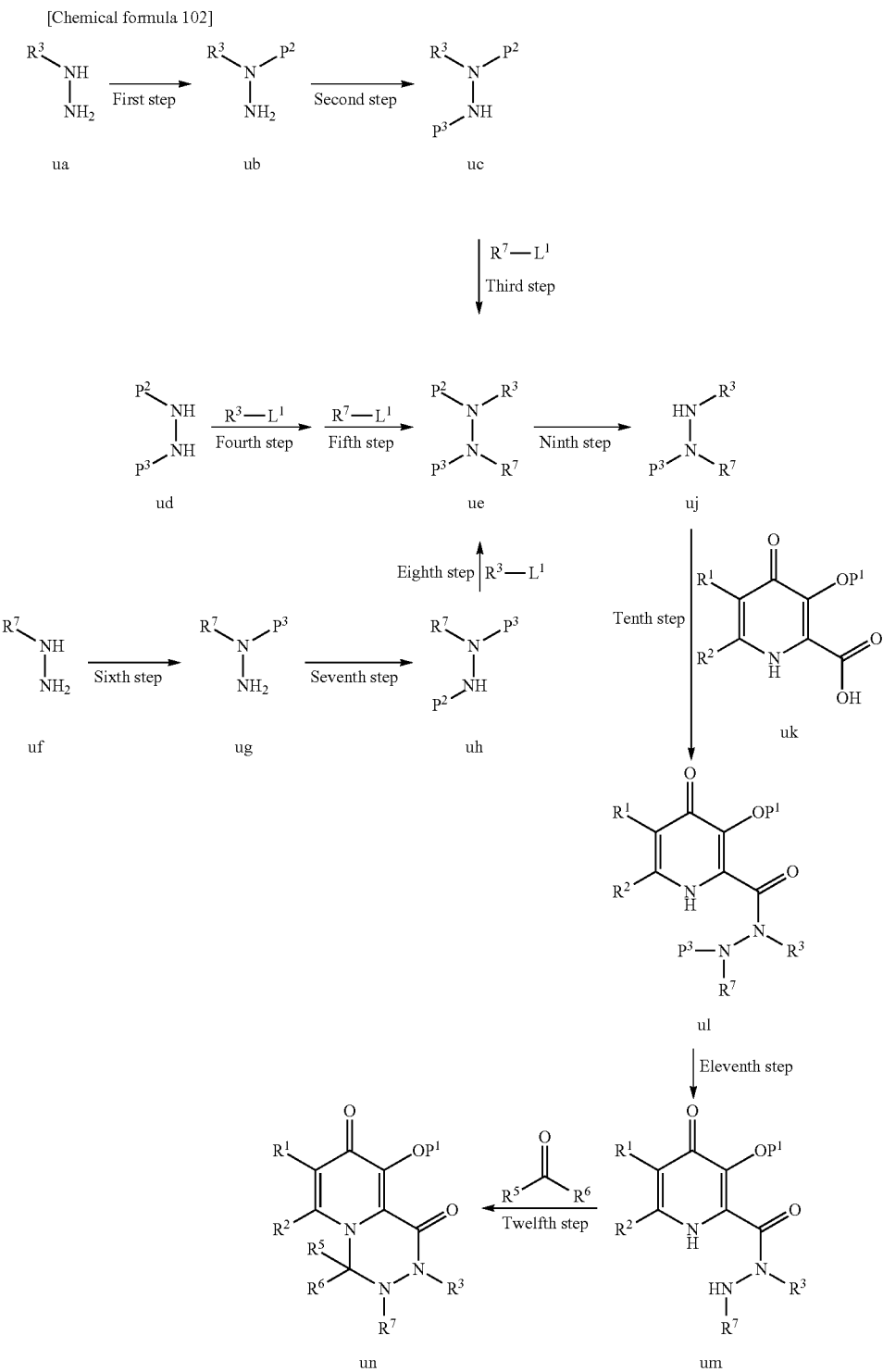

(wherein L¹ represents a leaving group such as halogen, OMs, OTs etc., and other each symbol is as defined above)

First Step

A compound ub can be obtained by subjecting a compound ua to a secondary amino group protecting reaction.

Second Step

A compound uc can be obtained by subjecting the compound ub to a general amino group protecting reaction.

Third Step

A compound ue can be obtained by adding a compound $R^7$-$L^1$ corresponding to an objective compound to the compound uc in the presence of a solvent such as DMF, DMA, NMP, etc. and a base such as NaH etc., and performing a reaction at 0° C. to 80° C., preferably 20° C. to 60° C. for 0.5 hour to 12 hours, preferably 1 hour to 6 hours.

Fourth Step, Fifth step (wherein $R^3$ and $R^7$ may be bound adjacently and, in this case, a fourth step and a fifth step are performed simultaneously).

A compound ue can be obtained by reacting a compound ud sequentially with compounds corresponding to an objective compound, $R^3$-$L^1$ and $R^7$-$L^1$ in the presence of a solvent such as DMF, DMA, NMP etc. and a base such as NaH etc.

Sixth Step

A compound ug can be obtained by subjecting a compound uf to a secondary amino group protecting reaction.

Seventh Step

A compound uh can be obtained by subjecting the compound ug to a secondary amino group protecting reaction.

Eighth Step

A compound ue can be obtained by adding a base such as NaH etc. to the compound uh in the presence of a solvent such as DMF, DMA, NMP, acetonitrile etc. or in a mixed solvent thereof, and performing a reaction with a compound $R^3$-$L^1$ corresponding to an objective compound.

Ninth Step

A compound uj can be obtained by subjecting the compound ue to a general secondary amine deprotecting reaction.

Tenth Step

A compound ul can be obtained by adding a condensation agent such as HATU, WSC.HCl etc. to a compound uk in the presence of a solvent such as DMF, DMA, THF, etc., adding amine uj corresponding to an objective substance, and tertiary amine such as pyridine, triethylamine, N-methylmorpholine etc., and performing a reaction at 10° C. to 60° C., preferably 20° C. to 40° C. for 0.1 hour to 24 hours, preferably 1 hour to 12 hours.

Eleventh Step

A compound um can be obtained by subjecting the compound ul to a general amino group protecting reaction.

Twelfth Step

A compound un can be obtained by adding $R^5$—C(=O)—$R^6$, tertiary amine such as, triethylamine, diisopropylethylamine, N-methylmorpholine, etc. to the compound um in the presence of a solvent such as toluene, DMF, DMA, NMP etc., and performing a reaction at 60° C. to 120° C., preferably 80° C. to 100° C. for 0.1 hour to 24 hours, preferably 1 hour to 12 hours.

Synthesis of Compound te

[Chemical formula 103]

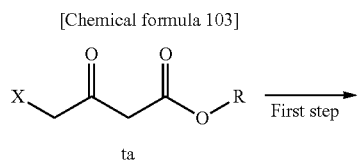

ta

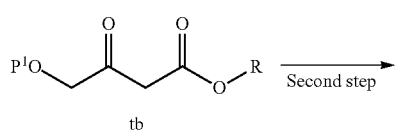

tb

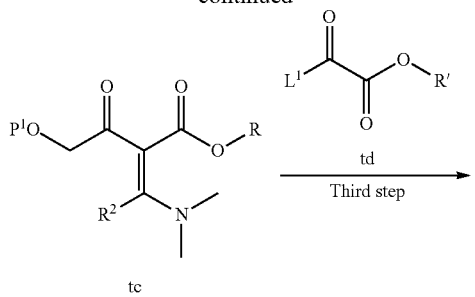

tc

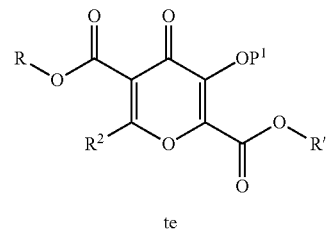

te (wherein R' may be a group which can be protected and/or deprotected by the method described in Protective Groups in Organic Synthesis, Theodora W Green (John Wiley & Sons) etc. and, for example, R' is lower alkyl etc. X is halogen, and other each symbol is as defined above.)

First Step

An alcohol ($P^1$—OH) corresponding to an objective substance is added to an organometallic base such as sodium tert-pentoxide, n-butyllithium, tert-butyllithium etc. in a solvent such as THF, ether, dichloromethane, DMI, DMF, DMA, etc. or in a mixed solution thereof. A solution of a compound ta is added dropwise thereto, and a reaction is performed at −20° C. to 40° C., preferably 0° C. to 30° C. for 0.1 hour to 12 hours, preferably 0.5 hour to 6 hours, thereby, a compound tb can be obtained.

Second Step

A compound tc can be obtained by adding N,N-dimethylformamidodimethylacetal to the compound tb in a solvent such as THF, dioxane, toluene, ethyl acetate etc. or in a mixed solvent thereof, or without a solvent, and performing a reaction at 0° C. to 80° C., preferably 20° C. to 40° C. for 0.5 hour to 24 hours, preferably 1 hour to 12 hours.

Third Step

A compound td corresponding to an objective substance is added to an organometallic base such as sodium tert-pentoxide, n-butyllithium, tert-butyllithium, sodium methoxide, sodium ethoxide, sodium tert-butoxide, potassium tert-butoxide etc. in a solvent such as THF, ether, DMI, methanol, ethanol, etc. or in a mixed solvent thereof. A solution of the compound tc is added dropwise thereto, a reaction is performed at −20° C. to 60° C., preferably 0° C. to 30° C. for 0.5 hour to 24 hours, preferably 1 hour to 12 hours and, thereafter, an acid such as hydrochloric acid, sulfuric acid etc. is added to perform a reaction at −20° C. to 60° C., preferably 0° C. to 30° C. for 0.5 hour to 24 hours, preferably 1 hour to 12 hours, thereby, a compound te can be obtained.

Synthesis of Compound tm and Compound tp (See: Examples 165, and 169)

[Chemical formula 104]

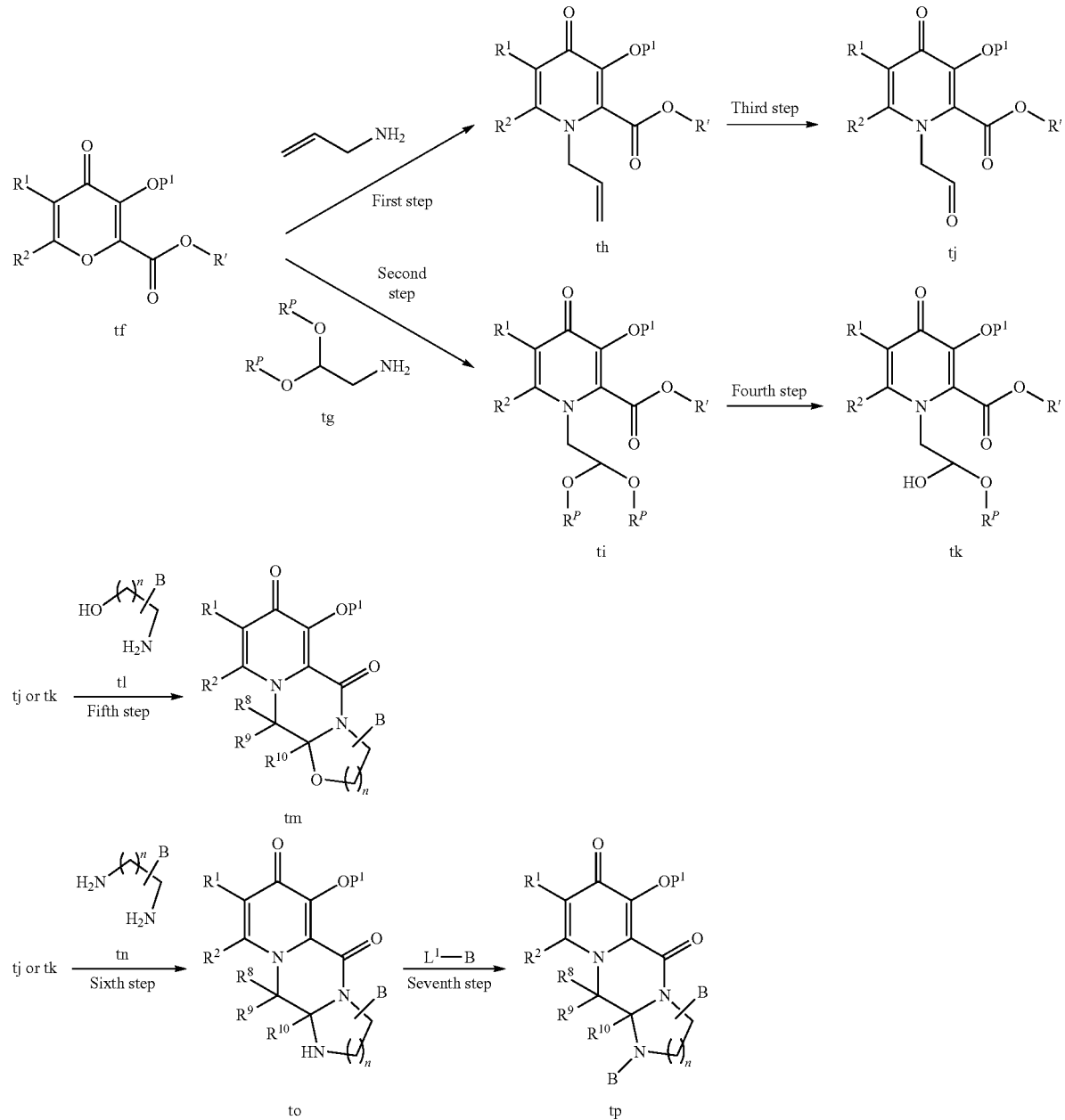

(wherein $R^P$ may be an acetal protective group which can protect and/or can be deprotected by the method described in Protective Groups in Organic Synthesis, Theodora W Green (John Wiley & Sons) etc. and, for example, $R^P$ is lower alkyl etc. Other each symbol is as defined above.)

First Step

A compound th can be obtained by adding allylamine to a compound tf which can be synthesized by the same method as that of a compound te in the presence of a solvent such as ethanol, THF, dioxane, acetonitrile, etc. or in a mixed solvent thereof, and performing a reaction at 0° C. to 80° C., preferably 20° C. to 60° C. for 0.5 hour to 48 hours, preferably 1 hour to 24 hours.

Second Step

A compound ti can be obtained by adding a compound tg to a compound tf in the presence of a solvent such as ethanol, THF, dioxane, acetonitrile etc. or in a mixed solvent thereof, and performing a reaction at 0° C. to 80° C., preferably 20° C. to 60° C. for 0.5 hour to 48 hours, preferably 1 hour to 24 hours.

Third Step

A compound tj can be obtained by adding potassium osmate dihydrate, sodium periodate, and water to the compound th in the presence of a solvent such as THF, ethyl acetate, dioxane, etc. or in a mixed solvent thereof, and performing a reaction at 0° C. to 60° C., preferably 10° C. to 40° C. for 0.5 hour to 24 hours, preferably 1 hour to 12 hours.

Alternatively, a compound tj can be obtained by introducing ozone into the compound th at −10° C. to 20° C. in the presence of a solvent such as THF, ethyl acetate, dioxane etc. or in a mixed solvent thereof and, subsequent to completion of the reaction, adding zinc-acetic acid, (EtO)$_3$P, or dimethyl sulfide.

Fourth Step

A compound tk can be obtained by adding an acid such as formic acid, trifluoroacetic acid, paratoluenesulfonic acid, etc. to the compound ti in a solvent such as acetone, acetonitrile, ethanol, water, etc. or in a mixed solvent thereof, or adding sulfuric acid in a formic acid solvent, and performing a reaction at 0° C. to 90° C., preferably 20° C. to 80° C. for 0.5 hour to 24 hours, preferably 1 hour to 12 hours.

Fifth Step

A compound tm can be obtained by adding a compound tl and acetic acid to the compound tj or the compound tk in the presence of a solvent such as chloroform, dichloromethane, THF, etc., and performing a reaction at 0° C. to 40° C., preferably 10° C. to 30° C. for 0.5 hour to 24 hours, preferably 1 hour to 12 hours.

Sixth Step

A compound to can be obtained by adding a compound tn and acetic acid to the compound tj or the compound tk in the presence of a solvent such as chloroform, dichloromethane, THF, etc., and performing a reaction at 0° C. to 40° C., preferably 10° C. to 30° C. for 0.5 hour to 24 hours, preferably 1 hour to 12 hours.

Seventh Step

A compound tp can be obtained by adding a compound B-L$^1$ corresponding to an objective compound to the compound to in the presence of a solvent such as DMF, DMA, NMP, THF, etc. or in a mixed solvent thereof, and performing a reaction at 0° C. to 80° C., preferably 20° C. to 60° C. for 0.5 hour to 12 hours, preferably 1 hour to 6 hours.

Synthesis of Compound vf (See: Examples 583 and 584)

[Chemical formula 105]

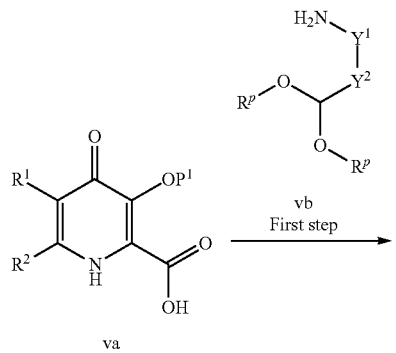

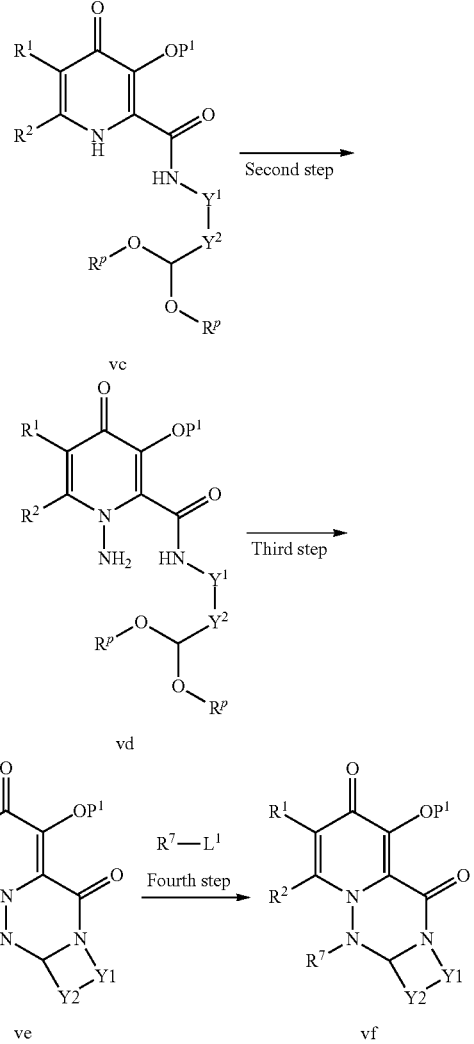

(wherein Y1 is a substituent corresponding to R$^3$ or R$^{3a}$, and Y2 is a substituent corresponding to R$^{11}$ or R$^{11a}$. Other each symbol is as defined above.)

First Step

A compound vc can be obtained by adding a compound vb having a substituent corresponding to an objective compound to a compound va in the presence of a dehydration-condensation agent such as dicyclohexylcarbodiimide, carbonyldiimidazole, dicyclohexylcarbodiimido-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU, etc. in a solvent such as DMF, THF, dichloromethane, acetonitrile etc. or in a mixed solvent thereof, and performing a reaction at −20° C. to 60° C., preferably −10° C. to 40° C. for 0.1 hour to 24 hours, preferably 1 hour to 12 hours.

Alternatively, a compound vc can be obtained by adding an acylating reagent such as diphenylchlorophosphate, thionyl chloride, oxalyl chloride etc. to a compound va in the presence or absence of a base such as pyridine, triethylamine, diisopropylethylamine, 1-methylimidazole, etc. in the presence of a solvent such as THF, dioxane, dichloromethane, DMF etc., thereby, generating acid chloride, and adding a compound vb having a substituent corresponding to an objective compound, and performing a reaction at −20° C. to 60° C., preferably −10° C. to 40° C. for 0.1 hour to 24 hours, preferably 0.5 hour to 12 hours.

Second Step

A compound vd can be obtained by adding potassium carbonate, sodium carbonate, and O-(2,4-dinitrophenyl)hydroxylamine to the compound vc in the presence of a solvent such as DMF, DMA, NMP, THF, etc., and performing a reaction at 10° C. to 60° C., preferably 20° C. to 40° C. for 0.1 hour to 48 hours, preferably 1 hour to 24 hours.

Third Step

A deprotecting reaction of an acetal protective group of the compound vd can be performed by the general method described in Protective Groups in Organic Synthesis, Theodora W Green (John Wiley & Sons) etc. Thereafter, a generated aldehyde group is subjected to an intramolecular reaction, thereby, a compound ve can be obtained.

For example, a compound ve can be obtained by adding acetic acid and/or paratoluenesulfonic acid to the compound vd in the presence of a solvent such as DMF, toluene, THF, etc., and performing a reaction at 10° C. to 80° C., preferably 30° C. to 60° C. for 0.5 hour to 12 hours, preferably 1 hour to 6 hours.

Fourth Step

A compound vf can be obtained by adding a compound $R^7$-$L^1$ corresponding to an objective substance, and a base such as sodium carbonate, potassium carbonate, cesium carbonate, etc. to the compound ve in the presence of a solvent such as DMF, DMA, NMP, THF, etc. or in a mixed solvent thereof, and performing a reaction at 0° C. to 60° C., preferably 10° C. to 400° C. for 0.1 hour to 48 hours, preferably 1 hour to 24 hours.

The present invention will be explained in more detail below by way of Examples and Reference Examples, as well as Test Examples of the present invention, but the present invention is not limited by them.

Example 1

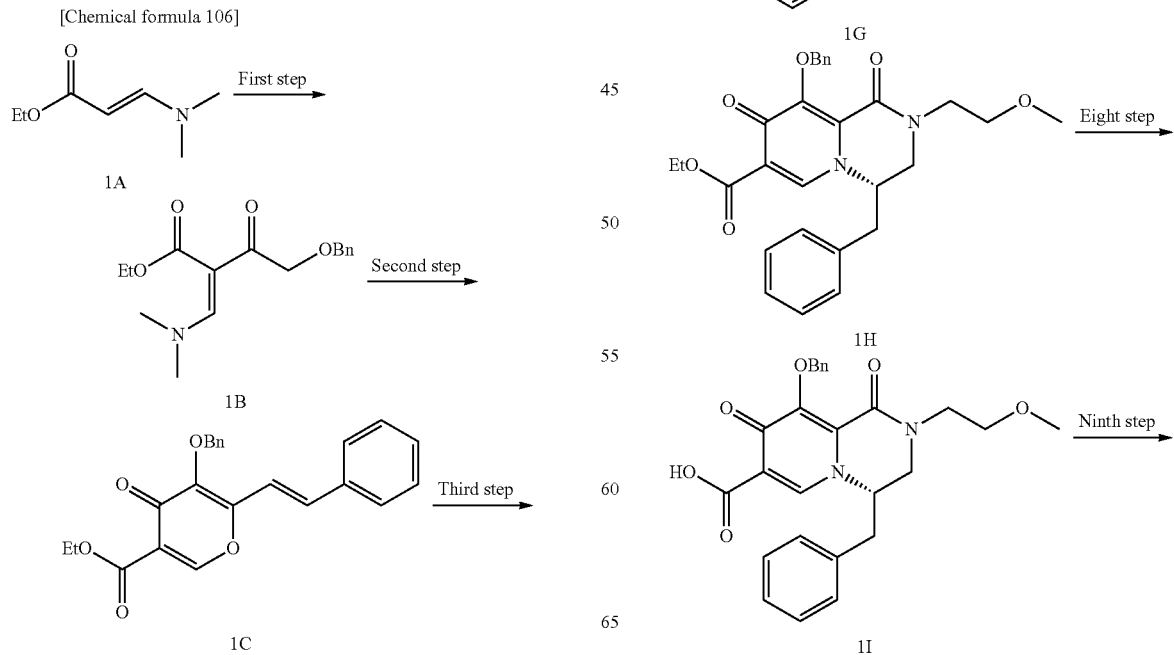

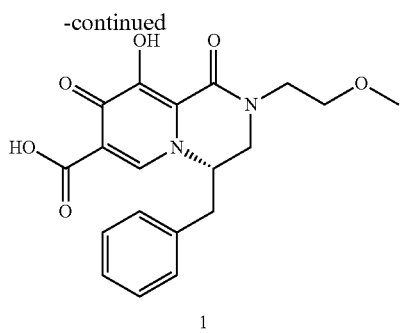

1

First Step

A dichloromethane (90 mL) solution of compound 1A (12.8 g, 89.4 mmol) and pyridine (8.50 g, 107 mmol) was cooled to 1 to 3° C., and a dichloromethane (90 mL) solution of benzyloxyacetyl chloride (19.8 g, 107 mmol) was added dropwise over 50 minutes while the same temperature was retained. After the reaction solution was stirred at the same temperature for 30 minutes, temperature was gradually raised to 15° C. over 60 minutes, and ice water was added. The dichloromethane layer was separated, and the aqueous layer was extracted with dichloromethane once. The combined extracts were washed with water three times, washed with an aqueous saturated sodium chloride solution, and dried. The solvent was distilled off, and the resulting oil was purified by silica gel column chromatography. The materials were eluted firstly with n-hexane and, then, with n-hexane-ethyl acetate (1:1, v/v). Concentration of objective fraction afforded 22.2 g of compound 1B as an oil.

$^1$H-NMR (CDCl$_3$) δ: 1.25 (3H, t, J=7.2 Hz), 2.90 (3H, brs), 3.24 (3H, brs), 4.15 (2H, q, J=7.2 Hz), 4.45 (2H, s), 4.58 (2H, s), 7.25-7.38 (5H, m), 7.72 (1H, s).

Second Step

A 1N lithiumhexamethyldisilazane THF solution (4.29 ml, 4.29 mmol) was cooled to −78° C., and a THF solution (4 ml) of compound 1B (500 mg, 1.72 mmol) and cinnamoyl chloride (343.2 mg, 2.06 mmol) were added dropwise thereto over 3 minutes while the same temperature was retained. After the reaction solution was stirred at the same temperature for 25 minutes, 2N hydrochloric acid (10 ml) was added, and the mixture was further stirred at room temperature for 10 minutes. To the reaction solution was added ethyl acetate, the organic layer was separated, and the aqueous layer was extracted with ethyl acetate three times. The combined extracts were dried with sodium sulfate. The solvent was distilled off, and the resulting oil was purified by silica gel column chromatography. From fraction eluted with n-hexane-ethyl acetate (1:1, v/v), 364.3 mg (yield 56%) of compound 1C was obtained as a solid.

$^1$H-NMR (CDCl$_3$) δ: 1.40 (3H, t, J=7.2 Hz), 4.39 (2H, q, J=7.2 Hz), 5.27 (2H, s), 6.99 (1H, d, J=16.2 Hz), 7.23 (1H, d, J=16.2), 7.26-7.48 (10H, m), 8.45 (1H, s).

Third Step

To a MeCN (5 ml) solution of compound 1C and ruthenium chloride (2.76 mg, 0.0133 mmol) was added dropwise an aqueous solution (8 ml) of sodium periodate (625.8 mg, 2.93 mmol) and 96% sulfuric acid (287.4 mg, 2.93 mmol) over 10 minutes at room temperature under nitrogen stream. After the reaction solution was stirred at the same temperature for 5 minutes, ethyl acetate was added, the organic layer was separated, and the aqueous layer was extracted with ethyl acetate two times. The combined extracts were dried with sodium sulfate. The solvent was distilled off, and the resulting oil was purified by silica gel column chromatography. From fraction eluted with n-hexane-ethyl acetate (1:1, v/v), 303.2 mg (yield 75%) of compound 1D was obtained as an oil.

$^1$H-NMR (CDCl$_3$) δ: 1.39 (3H, t, J=6.9 Hz), 4.40 (2H, q, J=6.9 Hz), 5.54 (2H, s), 7.37 (5H, s), 8.48 (1H, s), 9.85 (1H, s).

Fourth Step

To a MeCN (15 ml) solution of compound 1D (1.00 g, 3.31 mmol) was added an aqueous solution (10 ml) of 96% sulfuric acid (421.7 mg, 4.30 mmol) and amidosululic acid (642.7 mg, 6.62 mmol) at room temperature, the mixture was stirred, and an aqueous solution (10 ml) of sodium chlorite (388.9 mg, 4.30 mmol) was added dropwise over 5 minutes while the same temperature was retained. After the reaction solution was stirred at the same temperature for 5 minutes, an aqueous saturated sodium chloride solution was added, and the mixture was extracted with ethyl acetate three times. The combined extracts were dried with sodium sulfate. The solvent was distilled off, and the resulting oil was purified by silica gel column chromatography. The materials were eluted firstly with chloroform and, then, with chloroform-MeOH (7:3, v/v). Concentration of objective fraction afforded 748.8 mg (yield 71%) of compound 1E as an oil.

$^1$H-NMR (CDCl$_3$) δ: 1.40 (3H, t, J=7.2 Hz), 3.93 (1H, br s), 4.40 (2H, q, J=7.2 Hz), 5.61 (2H, s), 7.38-7.44 (10H, m), 8.52 (1H, s).

Fifth Step

To a DMF (10 ml) solution of compound 1E (1.00 g, 3.14 mmol) were added WSC HCl (1.20 g, 6.28 mmol) and HOBt (551.6 mg, 4.08 mmol) at room temperature, and the mixture was stirred at the same temperature for 90 minutes. The reaction solution was cooled to 0° C., and a DMF (2 ml) solution of 2-methoxyethanamine (236.0 mg, 3.14 mmol) was added dropwise over 3 minutes. The reaction solution was stirred at the same temperature for 1 hour, water was added, and the mixture was extracted with ethyl acetate three times. The extract was washed with water three times, and dried with sodium sulfate. The solvent was distilled off, and the resulting oil was purified by silica gel chromatography. The materials were eluted firstly with n-hexane-ethyl acetate (1:1, v/v) and, then, with n-hexane-ethyl acetate (1:9, v/v). Concentration of objective fraction afforded 928.5 mg (yield 79%) of compound 1F as an oil.

$^1$H-NMR (CDCl$_3$) δ: 1.39 (3H, t, J=7.2 Hz), 3.29 (3H, s), 3.41 (2H, t, J=5.4 Hz), 3.47-3.53 (2H, m), 4.39 (2H, q, J=7.2 Hz), 5.44 (2H, s), 7.36 (3H, m), 7.44-7.47 (2H, m), 8.07 (1H, br s), 8.54 (1H, s).

Sixth Step

A xylene (2 ml) solution of compound 1F (500 mg, 1.33 mmol) and (S)-2-amino-3-phenylpropan-1-ol (604.2 mg, 4.0 mmol) was heated to 120° C., and stirred for 30 minutes. After the reaction solution was cooled to room temperature, and the solvent was distilled off, the resulting oil was purified by silica gel chromatography. The materials were eluted firstly with chloroform and, then, with chloroform-MeOH (9:1, v/v). Concentration of objective fraction afforded 487 mg (yield 72%) of compound 1G as an oil.

$^1$H-NMR (CDCl$_3$) δ: 1.41 (3H, t, J=6.9 Hz), 2.24-2.34 (1H, m), 2.24-3.00 (1H, m), 3.03-3.16 (1H, m), 3.05 (3H, m), 3.25-3.32 (2H, m), 4.13-4.19 (1H, m), 4.17-4.30 (1H, m), 4.36-4.47 (1H, m), 4.51-4.54 (1H, m), 4.55 (1H, d, J=10.5 Hz), 5.78 (1H, t, J=6.9 Hz), 7.17-7.26 (4H, m), 7.28-7.35 (5H, m), 7.49 (1H, t, J=5.4 Hz), 6.32 (1H, s).

Seventh Step

To a THF (6 ml) solution of compound 1G (2.86 g, 5.63 mmol) and triphenylphosphine (2.21 g, 8.45 mmol) was added dropwise a DEAD 40 wt % toluene solution (3.68 g, 8.45 mmol) at room temperature over 3 minutes. The reaction solution was stirred at the same temperature for 30 minutes, the solvent was distilled off, and the resulting oil was purified by silica gel chromatography. From a fraction eluted with ethyl acetate-MeOH (9:1, v/v), 1.37 g (yield 50%) of compound 1H was obtained as an oil.

$^1$H-NMR (CDCl$_3$) δ: 1.31 (3H, t, J=7.2 Hz), 3.07 (2H, d, J=6.9 Hz), 3.33 (3H, s), 3.57-3.80 (4H, m), 3.95 (1H, dd, J=3.0 Hz, 6.6 Hz), 4.01-4.14 (1H, m), 4.16-4.34 (2H, m), 5.24 (1H, d, J=9.9 Hz), 5.51 (1H, d, J=9.9 Hz), 7.01-7.03 (2H, m), 7.21-7.37 (5H, m), 7.41-7.58 (1H, m), 7.64-7.69 (2H, m).

Eighth Step

To an EtOH (6 ml) solution of compound 1H (1.0 g, 2.04 mmol) was added a 2N aqueous sodium hydroxide solution (6 ml), and the mixture was stirred at room temperature for 30 minutes. The reaction solution was neutralized with 2N hydrochloric acid, and the precipitated solid was filtered, and dried to obtain 754 mg (yield 80%) of compound 1I.

$^1$H-NMR (CDCl$_3$) δ: 3.10 (2H, d, J=7.8 Hz), 3.33 (3H, s), 3.57-3.69 (4H, m), 3.82-3.90 (1H, m), 3.95 (1H, dd, J=3.3 Hz, 13.8 Hz), 4.36 (1H, dd, J=6.3 Hz, 7.5 Hz), 5.36 (1H, d, J=10.2 Hz), 5.45 (1H, d, J=10.2 Hz), 6.98-7.01 (2H, m), 7.28-7.39 (6H, m), 7.59 (2H, dd, J=1.8 Hz, 8.1 Hz), 7.87 (1H, s).

Ninth Step

Compound 1I (1.0 g, 2.16 mmol) was dissolved in THF (10 ml), 10% Pd—C(200 mg) was added, and the mixture was subjected to a catalytic reduction under hydrogen stream. The catalyst was removed by filtration, and the filtrate was concentrated. The resulting residue was washed with ether to obtain 512 mg (yield 64%) of compound 1.

$^1$H-NMR (CDCl$_3$) δ: 6.24 (2H, d, J=6.3 Hz), 3.36 (3H, s), 3.60-3.86 (5H, m), 4.14 (1H, d, J=12.9 Hz), 4.47 (1H, s), 7.03-7.05 (2H, m), 7.30-7.35 (3H, m), 7.88 (1H, s), 12.68 (1H, s), 14.83 (1H, s).

Example 2

[Chemical formula 107]

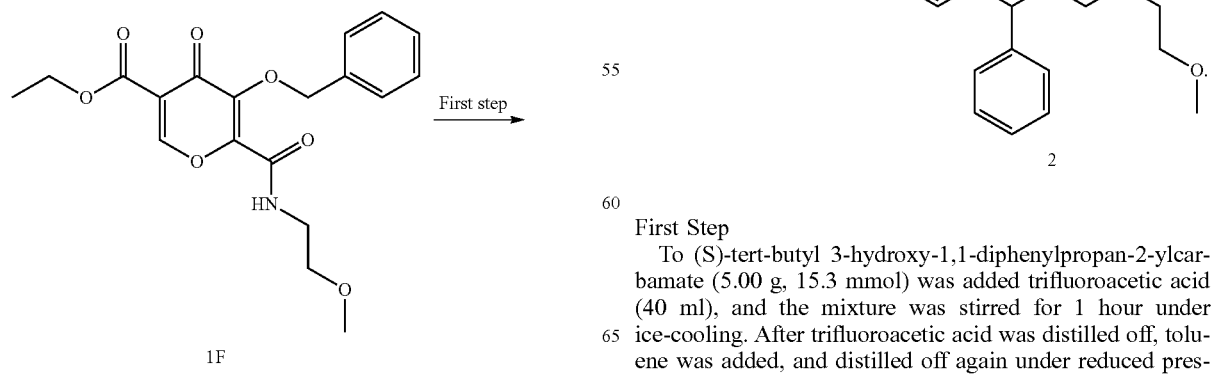

First Step

To (S)-tert-butyl 3-hydroxy-1,1-diphenylpropan-2-ylcarbamate (5.00 g, 15.3 mmol) was added trifluoroacetic acid (40 ml), and the mixture was stirred for 1 hour under ice-cooling. After trifluoroacetic acid was distilled off, toluene was added, and distilled off again under reduced pressure to obtain crude (S)-2-amino-3,3-diphenylpropan-1-ol.

To the resulting (S)-2-amino-3,3-diphenylpropan-1-ol were added compound 1F (5.73 g, 15.3 mmol), toluene (50 ml), and triethylamine (6.4 ml, 45.8 mmol), the mixture was stirred at 90° C. for 1 hour, and cooled to room temperature and, thereafter, the solvent was distilled off. To the resulting residue was added dichloromethane, and the mixture was washed with 2N hydrochloric acid, an aqueous saturated sodium bicarbonate solution, and an aqueous saturated sodium chloride solution. After separation of the organic layer, after magnesium sulfate was added, the mixture was filtered with celite, and the filtrate was distilled off to obtain candy-like compound 2A (9.12 g)

MS: m/z=585.2 [M+H]$^+$.

Second Step

The compound 2A (8.60 g, 14.7 mmol) and triphenylphosphine (7.72 g, 29.4 mmol) were dissolved in tetrahydrofuran (90 ml), and a 2.2M toluene solution of diethyl azodicarboxylate (10.0 ml, 22.0 mmol) was added dropwise under ice-cooling. After the mixture was stirred for 2 hours under ice-cooling, and for 18 hours under room temperature, the solvent was distilled off. The resulting residue was purified by silica gel column chromatography to obtain foamy compound 2B (3.88 g, 6.85 mmol).

$^1$H-NMR (DMSO-d$_6$) δ: 1.18 (3H, m), 3.11 (3H, s), 3.16 (1H, m), 3.28 (1H, m), 3.76 (1H, m), 3.97-4.13 (3H, m), 4.31 (1H, d, J=11.3 Hz), 5.08 (2H, s), 5.52 (1H, d, J=12.0 Hz), 7.18-7.25 (6H, m), 7.25-7.45 (6H, m), 7.55-7.66 (6H, m).

MS: m/z=567.7 [M+H]$^+$.

Third Step

To compound 2B (3.4 g, 6.0 mmol) were added ethanol (36 ml), water (12 ml), and a 2N aqueous sodium hydroxide solution (4.5 ml, 9.0 mmol), and the mixture was stirred at room temperature for 40 minutes, thereafter, ethanol (10 ml) and water (10 ml) were added, and the mixture was further stirred for 30 minutes. Ethanol was distilled off, ethyl acetate and water were added, and the mixture was stirred vigorously and, thereafter, layers were separated. The ethyl acetate layer was washed with 2N sodium hydroxide three times, and the aqueous layers were combined into one aqueous layer. To the aqueous layer was added ethyl acetate, the mixture was neutralized using 2N hydrochloric acid, then the mixture was stirred vigorously and, thereafter, the ethyl acetate layer was separated. To the ethyl acetate layer was added magnesium sulfate, the mixture was filtered with celite, and the filtrate was distilled off. The resulting residue was dissolved in MeOH, and the solvent was distilled off to obtain a solid of compound 2C (3.0 g, 5.64 mmol).

$^1$H-NMR (DMSO-d$_6$) δ: 3.11 (3H, s), 3.16 (1H, m), 3.25 (1H, m), 3.75 (1H, m), 4.11 (1H, m), 4.36 (1H, d, J=11.6 Hz), 5.18 (2H, dd, J=15.7 Hz, 10.4 Hz), 5.71 (1H, d, J=11.6 Hz), 7.08-7.20 (5H, m), 7.29-7.45 (6H, m), 7.55 (2H, d, J=6.7 Hz), 7.61 (2H, d, J=7.5 Hz), 7.98 (1H, s).

MS: m/z=539.4 [M+H]$^+$.

Fourth Step

To compound 2C (1.50 g, 2.79 mmol) were added methanol (22 ml), and 10% palladium carbon-50% wet (150 mg), and the mixture was stirred for 1 hour under hydrogen atmosphere. Ethyl acetate (44 ml) was added, the mixture was filtered with celite, and the filtrate was distilled off. The resulting residue was dissolved in methanol (20 ml), water (10 ml) was added, and methanol was distilled off. The precipitate was filtered, and dried to obtain compound 2 (1.15 g, 2.56 mmol).

$^1$H-NMR (DMSO-d$_6$) δ: 3.15 (3H, s), 3.50-3.70 (5H, m), 4.19 (1H, dd, J=13.8 Hz, 3.1 Hz), 4.49 (1H, d, J=11.6 Hz), 5.78 (1H, d, J=9.6 Hz), 7.10-7.27 (6H, m), 7.34 (1H, m), 7.46 (2H, t, J=7.5 Hz), 7.63 (2H, t, J=7.7 Hz), 7.94 (1H, s), 12.94 (1H, s), 15.08 (1H, s).

MS: m/z=449.4 [M+H]$^+$.

Example 3

[Chemical formula 108]

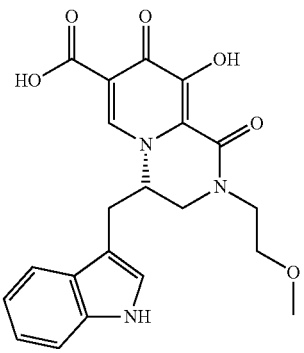

3

According to Example 2, compound 3 was synthesized by the same procedure.

$^1$H-NMR (DMSO-d$_6$) δ: 3.15 (1H, m), 3.26 (3H, s), 3.52-3.70 (4H, m), 3.70-3.80 (2H, m), 4.10 (1H, d, J=12.9 Hz), 4.92 (1H, brs), 6.98 (1H, t, J=7.4 Hz), 7.03 (1H, brs), 7.08 (1H, t, 7.6 Hz), 7.34 (1H, d, J=7.8 Hz), 7.47 (1H, d, J=7.3 Hz), 7.80 (1H, s), 10.94 (1H, brs), 15.38 (1H, brs).

MS: m/z=412.4 [M+H]$^+$.

Example 4

[Chemical formula 109]

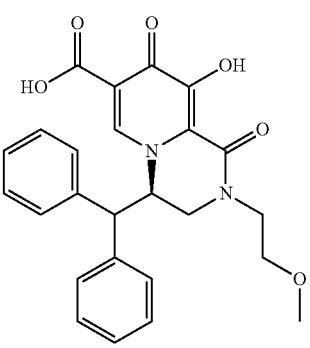

4

According to Example 2, compound 4 was synthesized by the same procedure.

$^1$H-NMR (DMSO-d$_6$) δ: 3.13 (3H, s), 3.46-3.72 (5H, m), 4.16 (1H, d, J=12.6 Hz), 4.48 (1H, d, J=10.9 Hz), 5.77 (1H, d, J=11.6 Hz), 7.10-7.27 (6H, m), 7.32 (1H, m), 7.44 (2H, m), 7.61 (2H, m), 7.93 (1H, s), 15.04 (1H, s).

MS: m/z=449.3 [M+H]$^+$.

Example 5

[Chemical formula 110]

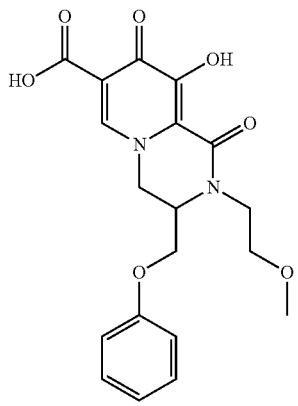

According to Example 2, compound 5 was synthesized by the same procedure.

$^1$H-NMR (DMSO-$d_6$) δ: 3.28 (3H, s), 3.52-3.68 (4H, m), 4.06 (1H, m), 4.25 (2H, m), 4.41 (1H, brs), 4.56 (1H, d, J=13.6 Hz), 4.82 (1H, d, J=13.9 Hz), 6.74 (2H, d, J=7.6 Hz), 6.92 (1H, t, J=7.20 Hz), 7.25 (2H, t, J=7.8 Hz), 8.58 (1H, s), 12.48 (1H, brs), 15.55 (1H, brs).

MS: m/z=389.4 [M+H]$^+$.

Example 6

[Chemical formula 111]

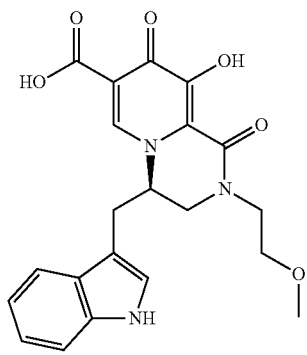

According to Example 2, compound 6 was synthesized by the same procedure.

$^1$H-NMR (DMSO-$d_6$) δ: 3.16 (1H, m), 3.26 (3H, s), 3.50-3.70 (4H, m), 3.70-3.80 (2H, m), 4.10 (1H, d, J=13.4 Hz), 4.92 (1H, brs), 6.98 (1H, t, J=7.1 Hz), 7.03 (1H, brs), 7.08 (1H, t, J=7.3 Hz), 7.34 (1H, d, J=7.8 Hz), 7.48 (1H, d, J=7.3 Hz), 7.81 (1H, s), 12.91 (1H, s), 15.36 (1H, s).

MS: m/z=412.4 [M+H]$^+$.

Example 7

[Chemical formula 112]

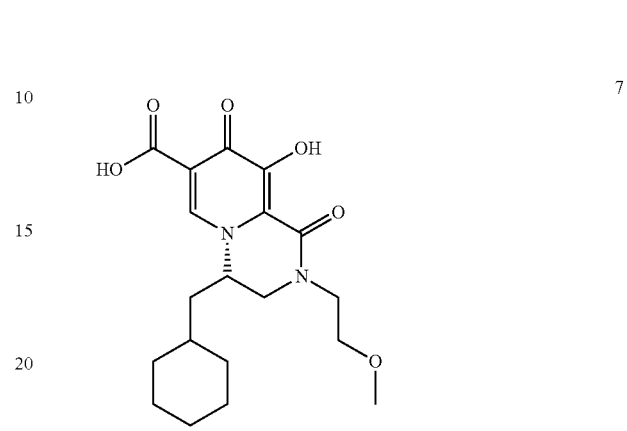

According to Example 2, compound 7 was synthesized by the same method.

$^1$H-NMR (DMSO-$d_6$) δ: 0.85-0.95 (2H, m), 1.05-1.25 (5H, m), 1.45-1.80 (8H, m), 3.28 (3H, s), 3.46 (1H, m), 3.58 (1H, m), 3.72 (1H, d, J=13.9 Hz), 3.93 (1H, m), 4.04 (1H, d, J=13.1 Hz), 4.88 (1H, s), 8.56 (1H, s), 12.80 (1H, s), 15.51 (1H, s).

MS: m/z=379.3 [M+H]$^+$.

Example 8

[Chemical formula 113]

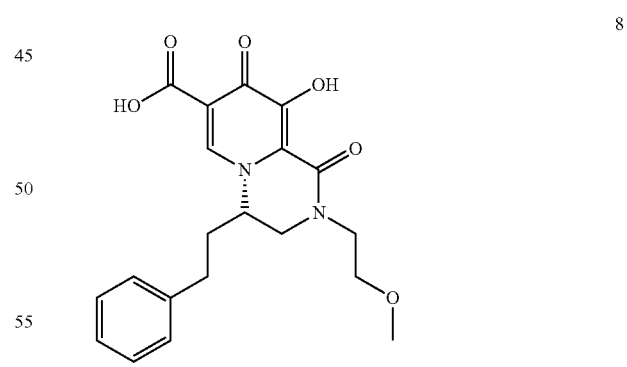

According to Example 2, compound 8 was synthesized by the same procedure.

$^1$H-NMR (DMSO-$d_6$) δ: 2.07 (2H, m), 2.55 (1H, m), 2.74 (1H, m), 3.17 (1H, s), 3.23 (3H, s), 3.48-3.65 (4H, m), 3.79 (1H, d, J=13.6 Hz), 3.87 (1H, m), 4.09 (1H, d, J=13.6 Hz), 4.80 (1H, s), 7.10-7.29 (5H, m), 8.59 (1H, s), 12.77 (1H, s), 15.49 (1H, s).

MS: m/z=387.3 [M+H]$^+$.

Example 9

[Chemical formula 114]

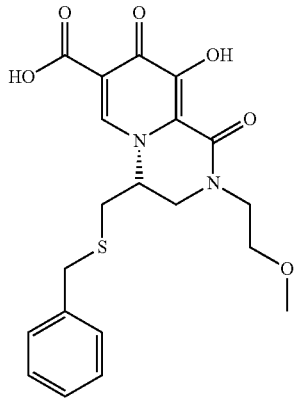

According to Example 2, compound 9 was synthesized by the same procedure.

$^1$H-NMR (DMSO-$d_6$) δ: 2.80 (1H, dd, J=14.5 Hz, J2=8.5 Hz), 2.93 (1H, dd, J=14.4 Hz, 5.6 Hz), 3.21 (3H, s), 3.40-3.55 (4H, m), 3.77 (2H, s), 3.82 (1H, d, J=13.1 Hz), 3.88 (1H, m), 4.13 (1H, d, J=13.6 Hz), 4.85 (1H, s), 7.20-7.35 (5H, m), 8.61 (1H, s), 12.79 (1H, s), 15.43 (1H, s).

MS: m/z=419.3 [M+H]$^+$.

Example 10

[Chemical formula 115]

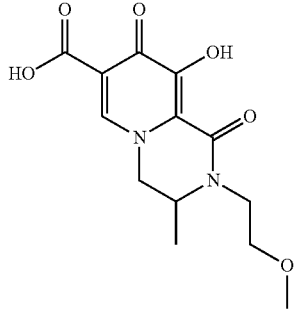

According to Example 2, compound 10 was synthesized by the same procedure.

$^1$H-NMR (DMSO-$d_6$) δ: 1.22 (3H, d, J=6.2 Hz), 3.29 (3H, s), 3.43 (1H, m), 3.58 (2H, m), 3.94 (1H, m), 4.12 (1H, brs), 4.41 (1H, d, J=13.6 Hz), 4.49 (1H, d, J=13.1 Hz), 8.59 (1H, s), 12.65 (1H, s), 15.53 (1H, s).

MS: m/z=297.2 [M+H]$^+$.

Example 11

[Chemical formula 116]

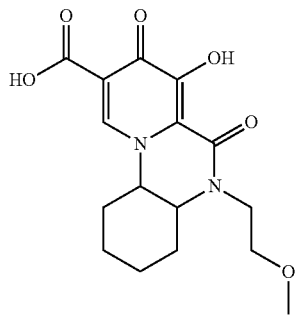

According to Example 2, compound 11 was synthesized by the same procedure.

$^1$H-NMR (DMSO-$d_6$) δ: 1.46 (4H, brs), 1.76-1.90 (2H, m), 2.22 (1H, brs), 3.27 (3H, s), 3.57 (1H, d, J=5.3 Hz), 4.07 (1H, m), 4.69 (1H, m), 8.47 (1H, s), 13.04 (1H, s), 15.52 (1H, s).

MS: m/z=337.2 [M+H]$^+$.

Example 12

[Chemical formula 117]

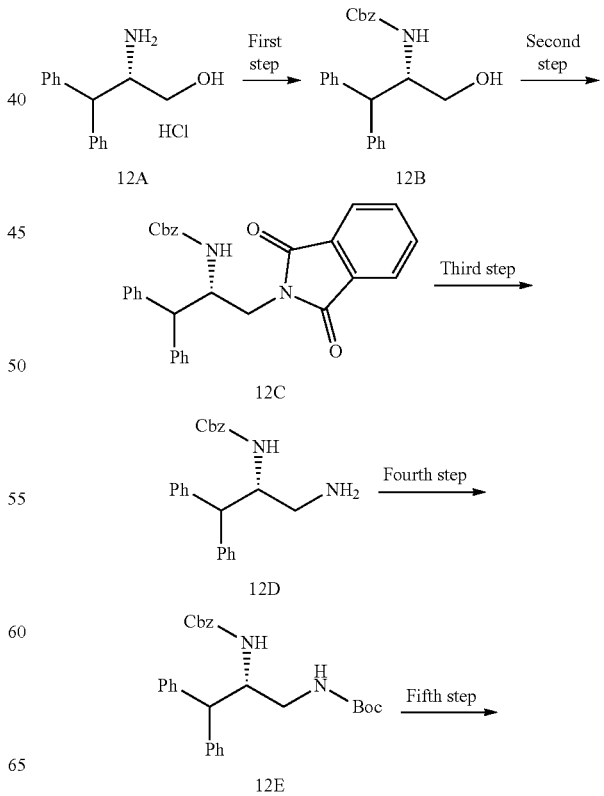

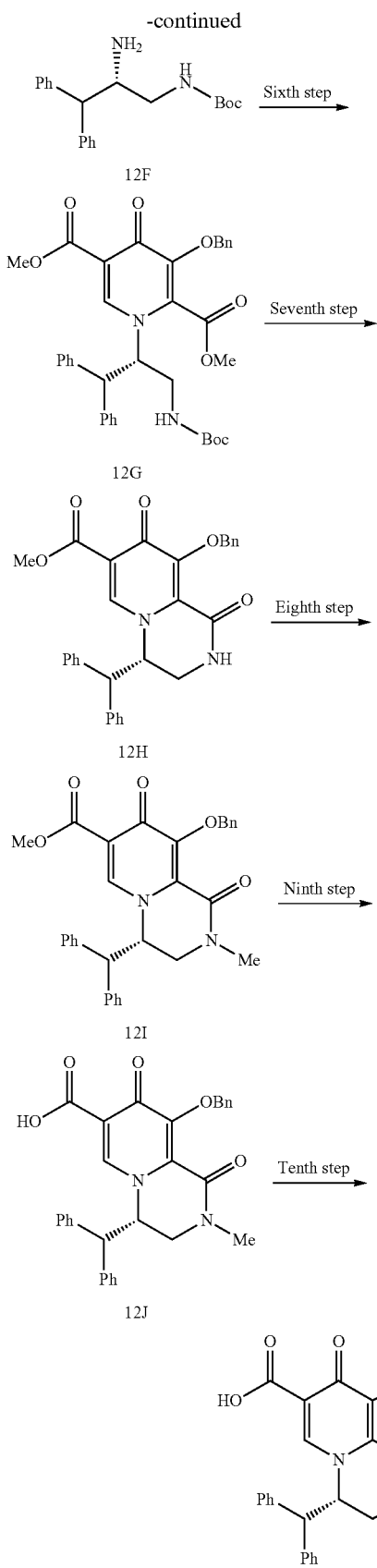

First Step

Compound 12A (1.53 g, 5.80 mmol) were dissolved in THF (6 ml) and water (6 ml), potassium carbonate (2.41 g, 17.4 mmol) was added, the mixture was stirred, and benzyl chloroformate (1.09 g, 6.38 mmol) was added dropwise at 0° C. After stirring at 0° C. for 10 minutes, the mixture was stirred at room temperature for 2 hours. The reaction solution was poured into sodium bicarbonate water, and the mixture was extracted with ethyl acetate. The extract was washed with 1N hydrochloric acid and an aqueous saturated sodium chloride solution, and dried with sodium sulfate. The solvent was distilled off to obtain 2.32 g of compound 12B as a colorless gummy solid.

$^1$H-NMR (CDCl$_3$) δ: 1.98 (1H, brs), 3.55 (1H, m), 3.75 (1H, m), 4.20 (1H, d, J=10.5 Hz), 4.58 (1H, m), 4.83 (1H, brs), 5.07 (2H, s), 7.16-7.39 (15H, m).

Second Step

The compound 12B (1.94 g, 5.37 mmol), triphenylphosphine (2.11 g, 8.05 mmol) and phthalimide (948 mg, 6.44 mmol) were added to THF (20 ml), and diisopropyl azodicarboxylate (2.2M in toluene, 3.66 ml, 8.05 mmol) was added dropwise at room temperature. After stirring at room temperature for 4 hours, the solvent was distilled off under reduced pressure. The resulting crude product was purified by silica gel column chromatography (n-hexane-ethyl acetate, 1:1, v/v) to obtain 2.39 g of compound 12C as a colorless solid.

$^1$H-NMR (CDCl$_3$) δ: 3.73 (2H, m), 4.05 (1H, d, J=10.1 Hz), 4.70 (1H, d, J=9.6 Hz), 4.77 (2H, d, J=7.2 Hz) 5.02 (1H, m), 7.03-7.42 (15H, m), 7.68 (2H, dd, J=5.7, 2.1 Hz), 7.78 (2H, dd, J=5.7, 2.1 Hz).

Third Step

The compound 12C (2.39 g, 4.87 mmol) was added to THF (20 ml) and methanol (20 ml), hydrazine hydrate (4.88 g, 97.4 mmol) was added, and the mixture was stirred at 50° C. for 4 hours. The white precipitate was removed by filtration, and washed with methanol. After the filtrate was distilled off under reduced pressure, the resulting crude product was purified by amino column chromatography (chloroform-methanol, 99:1, v/v) to obtain 1.41 g of compound 12D as a colorless solid.

$^1$H-NMR (CDCl$_3$) δ: 2.63 (1H, dd, J=13.2, 5.8 Hz), 2.86 (1H, d, J=9.9 Hz), 4.07 (1H, d, J=10.4 Hz), 4.53 (1H, m), 4.81 (1H, m), 5.00 (2H, d, 8.4 Hz), 7.20-7.36 (10H, m).

Fourth Step

Compound 12D (1.41 g, 3.91 mmol) was dissolved in THF (15 ml), and Boc$_2$O (896 mg, 4.11 mmol) was added at room temperature. After stirring for 1.5 hours, the solvent was concentrated under reduced pressure. The resulting crude product was purified by silica gel column chromatography (n-hexane-ethyl acetate, 1:1, v/v) to obtain 1.77 g of compound 12E as a colorless solid.

$^1$H-NMR (CDCl$_3$) δ: 1.41 (9H, s), 3.23 (2H, brm), 3.97 (1H, d, J=9.8 Hz), 4.58-4.80 (3H, m), 5.00 (2H, d, J=9.8 Hz), 7.15-7.29 (10H, m).

Fifth Step

Compound 12E (1.73 g, 3.76 mmol) and palladium-active carbon (10%, wet, 200 mg) were added to methanol (20 ml), and the mixture was stirred at room temperature for 1 hour under hydrogen atmosphere. After filtration with celite, the solvent was concentrated under reduced pressure to obtain 1.01 g of a colorless oily substance 12F.

$^1$H-NMR (CDCl$_3$) δ: 1.44 (9H, s), 2.82 (1H, m), 3.31 (1H, m), 3.73 (2H, d, J=6.9 Hz), 4.98 (1H, s), 7.18-7.39 (10H, m).

Sixth Step

Dimethyl 3-(benzyloxy)-4-oxo-4H-pyran-2,5-dicarboxylate (974 mg, 3.06 mmol) obtained by the method shown in Reference Example 1, and 12F (999 mg, 3.06 mmol) were added to toluene (10 ml), and the mixture was stirred at 110° C. for 5 hours. After the solvent was distilled off under reduced pressure, the resulting crude product was purified by silica gel column chromatography (chloroform-methanol, 98:2, v/v) to obtain 1.51 g of compound 12G as a pale yellow solid.

$^1$H-NMR (CDCl$_3$) δ: 1.36 (9H, s), 3.40 (1H, m), 3.53 (1H, m), 3.82 (3H, s), 3.91 (3H, s), 4.29 (1H, d, J=11.3 Hz), 4.78 (1H, m), 4.82 (1H, m), 5.11 (1.9H, d, J=7.5 Hz), 7.10-7.38 (10H, m), 8.27 (1H, s).

Seventh Step

To compound 12G (1.45 g, 2.31 mmol) was added 4N HCl (ethyl acetate solution, 20 ml), and the mixture was stirred at room temperature for 1.5 hours. After the solvent was distilled off under reduced pressure, sodium bicarbonate water was added, and the mixture was stirred at room temperature for 1.5 hours. This was extracted with chloroform, and dried with sodium sulfate. After the solvent was distilled off under reduced pressure, the resulting crude product was purified by silica gel column chromatography (chloroform-methanol, 95:5, v/v) to obtain 1.01 g of compound 12H as a colorless solid.

$^1$H-NMR (CDCl$_3$) δ: 3.40 (1H, dd, J=13.6, 6.6 Hz), 3.78 (3H, s), 3.80 (1H, m), 4.37 (1H, d, J=11.6 Hz), 4.59 (1H, d, J=11.0 Hz), 5.43 (2H, d, J=10.2 Hz), 5.93 (1H, d, J=5.8 Hz), 7.03-7.21 (5H, m), 7.37 (9H, m), 7.63 (2H, m).

Eighth Step

Compound 12H (50 mg, 0.10 mmol) was dissolved in DMF (1 ml), and cesium carbonate (165 mg, 0.50 mmol) was added. After stirring at room temperature for 30 minutes, iodomethane (0.032 ml, 0.50 mmol) was added, and the mixture was stirred at room temperature for 3.5 hours. The reaction solution was poured into water, and the mixture was extracted with ethyl acetate, and dried with sodium sulfate. After the solvent was distilled off under reduced pressure, the resulting crude product was purified by silica gel column chromatography (chloroform-methanol, 95:5, v/v) to obtain 49 mg of compound 12I as a colorless solid.

Ninth Step

Compound 12I (49 mg, 0.096 mmol) was dissolved in THF (0.5 ml) and methanol (0.5 ml), a 2N aqueous sodium hydroxide solution (0.24 ml, 0.48 mmol) was added at room temperature, and the mixture was stirred for 1.5 hours. After 1N hydrochloric acid was added, and the mixture was extracted with ethyl acetate, the extract was dried with sodium sulfate. After the solvent was distilled off under reduced pressure, 54 mg of compound 12J was obtained as a colorless solid.

MS: m/z=481 [M+H]$^+$.

Tenth Step

To compound 12J obtained in the ninth step was added trifluoroacetic acid (1 ml), and the mixture was stirred at room temperature for 1 hour. After concentration under reduced pressure, pH was adjusted to 3 with sodium bicarbonate water and 2N hydrochloric acid, and the mixture was extracted with chloroform, and dried with sodium sulfate. After the solvent was distilled off under reduced pressure, chloroform-methanol-ethyl ether were added, and the precipitated solid was filtered to obtain 26 mg of compound 12 as a colorless solid.

$^1$H-NMR (DMSO-d$_6$) δ: 3.01 (3H, s), 3.26 (1H, t, J=14.4 Hz), 4.23 (1H, dd, J=13.5, 3.8 Hz), 4.57 (1H, d, J=11.6 Hz), 5.78 (1H, d, J=11.3 Hz), 7.16-7.70 (10H, m), 8.00 (1H, s), 13.00 (1H, s), 15.10 (1H, s).

MS: m/z=405 [M+H]$^+$.

Example 13

[Chemical formula 118]

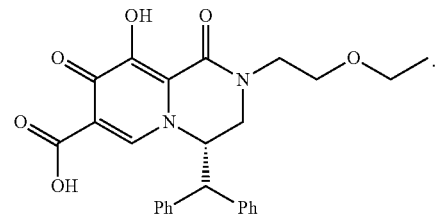

13

According to Example 12, compound 13 was synthesized by the same procedure.

$^1$H-NMR (DMSO-d$_6$) δ: 1.05 (3H, t, J=6.9 Hz), 3.43-3.65 (3H, m), 4.22 (1H, d, J=10.6 Hz), 4.55 (1H, d, J=11.6 Hz), 5.81 (1H, d, J=10.1 Hz), 7.15-7.68 (10H, m), 7.97 (1H, s), 12.96 (1H, s), 15.07 (1H, s).

MS: m/z=463 [M+H]$^+$.

Example 14

[Chemical formula 119]

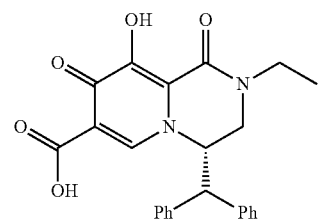

14

According to Example 12, compound 14 was synthesized by the same procedure.

$^1$H-NMR (DMSO-d$_6$) δ: 0.98 (3H, t, J=7.17 Hz), 3.44-3.64 (3H, m), 4.15 (1H, dd, J=13.7, 3.5 Hz), 4.45 (1H, d, J=11.6 Hz), 5.79 (1H, d, J=12.2 Hz), 7.08-7.63 (10H, m), 7.89 (1H, s), 13.01 (1H, s), 15.06 (1H, s).

MS: m/z=419 [M+H]$^+$.

Example 15

[Chemical formula 120]

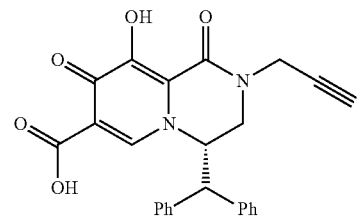

15

According to Example 12, compound 15 was synthesized by the same procedure.

¹H-NMR (DMSO-d₆) δ: 3.22 (1H, s), 3.47 (1H, d, J=13.3 Hz), 4.17 (2H, m), 4.44 (2H, dd, J=16.7, 3.0 Hz), 5.79 (1H, d, J=12.2 Hz), 7.10-7.64 (10H, m), 7.98 (1H, s), 12.56 (1H, s), 15.05 (1H, brs).

Example 16

[Chemical formula 121]

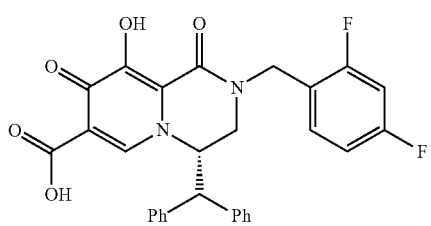

16

According to Example 12, compound 16 was synthesized by the same procedure.

¹H-NMR (DMSO-d₆) δ: 3.24 (1H, d, J=13.2 Hz), 4.23 (1H, m), 4.25 (1H, d, J=14.7 Hz), 4.40 (1H, d, J=14.8 Hz), 4.92 (1H, d, J=15.4 Hz), 5.79 (1H, m), 7.03-7.48 (10H, m), 7.93 (1H, s), 12.82 (1H, s), 15.06 (1H, s).

Example 17

[Chemical formula 122]

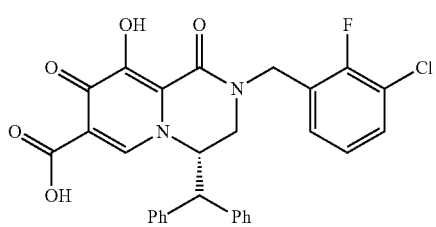

17

According to Example 12, compound 17 was synthesized by the same procedure.

¹H-NMR (DMSO-d₆) δ: 3.23 (1H, d, J=13.4 Hz), 4.22 (1H, m), 4.25 (1H, d, J=12.0 Hz), 4.45 (1H, d, J=14.9 Hz), 4.93 (1H, d, J=15.3 Hz), 5.77 (1H, d, J=11.6 Hz), 7.09-7.56 (10H, m), 7.92 (1H, s), 12.74 (1H, s), 15.06 (1H, s).

Example 18

[Chemical formula 123]

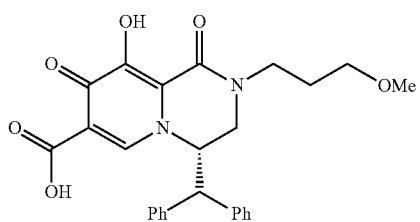

18

According to Example 12, compound 18 was synthesized by the same procedure.

¹H-NMR (DMSO-d₆) δ: 1.63 (2H, m), 3.20 (3H, s), 3.44 (5H, m), 4.19 (1H, d, J=10.2 Hz), 4.51 (1H, d, J=11.8 Hz), 5.80 (1H, d, J=11.0 Hz), 7.13-7.65 (10H, m), 7.93 (1H, s), 13.02 (1H, s).

MS: m/z=463 [M+H]⁺.

Example 19

[Chemical formula 124]

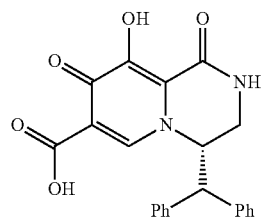

19

According to Example 12, compound 19 was synthesized by the same procedure.

¹H-NMR (DMSO-d₆) δ: 3.15 (1H, d, J=9.5 Hz), 3.95 (1H, dd, J=13.5, 3.4 Hz), 4.51 (1H, d, J=11.6 Hz), 5.74 (1H, d, J=11.1 Hz), 7.11-7.62 (10H, m), 7.93 (1H, s), 9.34 (1H, s), 12.97 (1H, s), 15.07 (1H, brs).

MS: m/z=391 [M+H]⁺.

Example 20

[Chemical formula 125]

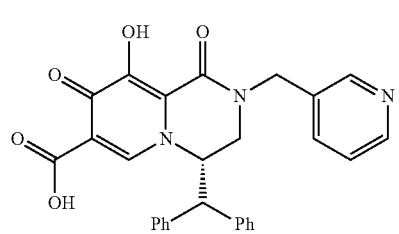

20

According to Example 12, compound 20 was synthesized by the same procedure.

¹H-NMR (DMSO-d₆) δ: 3.26 (1H, m), 4.24 (1H, m), 4.27 (1H, d, J=12.0 Hz), 4.41 (1H, d, J=14.8 Hz), 4.87 (1H, d, J=14.9 Hz), 5.75 (1H, d, J=7.6 Hz), 7.09-7.77 (12H, m), 7.93 (1H, s), 8.52 (2H, m), 12.79 (1H, s), 15.07 (1H, brs).

MS: m/z=482 [M+H]⁺.

Example 21

[Chemical formula 126]

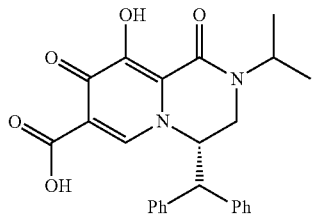

According to Example 12, compound 21 was synthesized by the same procedure.

$^{1}$H-NMR (DMSO-d$_{6}$) δ: 0.62 (3H, d, J=6.9 Hz), 0.82 (3H, d, J=6.6 Hz), 3.18 (1H, m), 3.75 (1H, d, J=10.2 Hz), 4.25 (1H, d, J=11.8 Hz), 4.58 (1H, m), 5.65 (1H, d, J=11.3 Hz), 6.89-7.43 (10H, m), 7.67 (1H, s), 12.94 (1H, s).

MS: m/z=433 [M+H]$^{+}$.

Example 22

[Chemical formula 127]

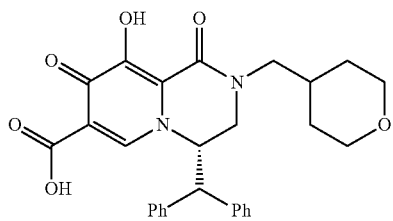

According to Example 12, compound 22 was synthesized by the same procedure.

$^{1}$H-NMR (DMSO-d$_{6}$) δ: 1.07-1.70 (5H, m), 3.04-3.34 (5H, m), 3.82 (2H, dm), 4.18 (1H, d, J=10.2 Hz), 4.42 (1H, d, J=12.0 Hz), 5.81 (1H, d, J=11.7 Hz), 7.11-7.59 (10H, m), 7.86 (1H, s), 12.96 (1H, s), 15.07 (1H, brs).

MS: m/z=489 [M+H]$^{+}$.

Example 23

[Chemical formula 128]

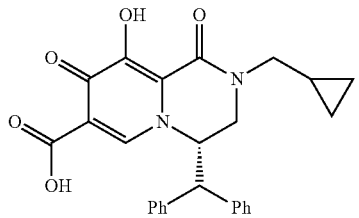

According to Example 12, compound 23 was synthesized by the same procedure.

$^{1}$H-NMR (DMSO-d$_{6}$) δ: 0.01-0.79 (5H, m), 3.05 (1H, dd, J=14.1, 7.5 Hz), 3.49-3.59 (2H, m), 4.16 (1H, dd, J=14.0, 3.3 Hz), 4.50 (1H, d, J=11.9 Hz), 5.82 (1H, d, J=11.1 Hz), 7.11-7.62 (10H, m), 7.89 (1H, s), 12.99 (1H, s), 15.07 (1H, brs).

MS: m/z=445 [M+H]$^{+}$.

Example 24

[Chemical formula 129]

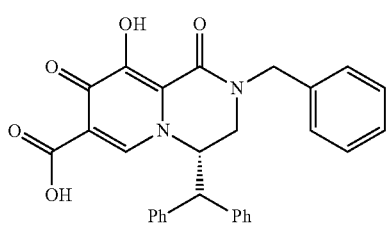

According to Example 12, compound 24 was synthesized by the same procedure.

$^{1}$H-NMR (DMSO-d$_{6}$) δ: 3.23 (1H, d, J=13.7 Hz), 4.16 (1H, dd, J=13.2, 3.3 Hz), 4.19 (2H, d, J=12.0 Hz), 4.38 (1H, d, J=14.6 Hz), 4.84 (1H, d, J=14.6 Hz), 5.72 (1H, d, J=11.4 Hz), 7.08-7.33 (15H, m), 7.98 (1H, s), 12.88 (1H, s), 15.07 (1H, s).

MS: m/z=481 [M+H]$^{+}$.

Example 25

[Chemical formula 130]

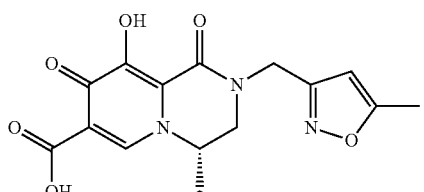

According to Example 12, compound 25 was synthesized by the same procedure.

$^{1}$H-NMR (DMSO-d$_{6}$) δ: 2.39 (3H, s), 3.37 (1H, m), 4.21 (1H, dd, J=14.4, 3.9 Hz), 4.40 (1H, dd, J=11.7 Hz), 4.45 (1H, d, J=15.3 Hz), 4.81 (1H, d, J=15.4 Hz), 5.78 (1H, d, J=12.0 Hz), 6.30 (1H, s), 7.09-7.42 (10H, m), 7.95 (1H, s), 12.65 (1H, s), 15.07 (1H, s).

MS: m/z=486 [M+H]$^{+}$.

Example 26

[Chemical formula 131]

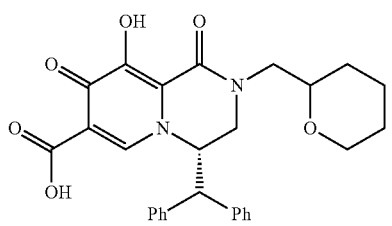

26

According to Example 12, compound 26 was synthesized by the same procedure.

$^1$H-NMR (DMSO-$d_6$) δ: 1.20-1.77 (6H, m), 3.11-3.61 (6H, m), 4.21 (1H, d, J=9.9 Hz), 4.53 (1H, d, J=11.7 Hz), 5.80 (1H, d, J=11.8 Hz), 7.14-7.65 (10H, m), 7.95 (1H, s), 12.95 (1H, brs), 15.06 (1H, brs).

MS: m/z=489 [M+H]$^+$.

Example 27

[Chemical formula 132]

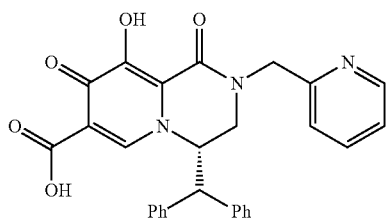

27

According to Example 12, compound 27 was synthesized by the same procedure.

$^1$H-NMR (DMSO-$d_6$) δ: 3.36 (1H, m), 4.28 (1H, d, J=12.0 Hz), 4.54 (1H, d, J=11.4 Hz), 4.62 (1H, d, J=15.3 Hz), 4.79 (1H, d, J=15.4 Hz), 5.77 (1H, d, J=9.9 Hz), 7.09-7.79 (13H, m), 7.98 (1H, s), 8.46 (1H, d, J=4.6 Hz), 12.82 (1H, brs), 15.06 (1H, brs).

MS: m/z=482 [M+H]$^+$.

Example 28

[Chemical formula 133]

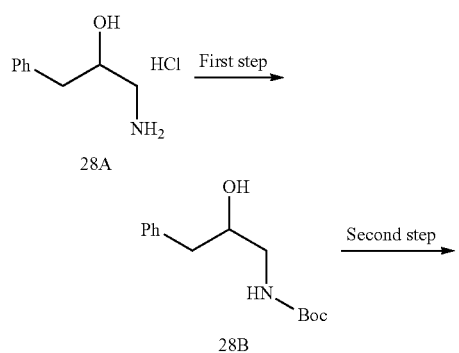

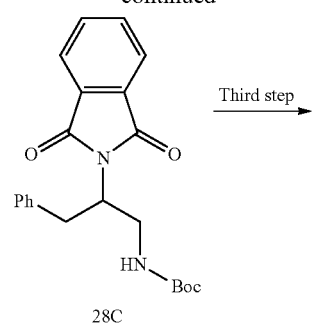

28C

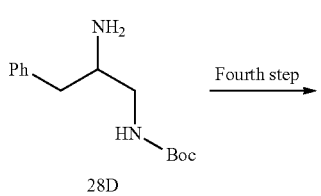

28D

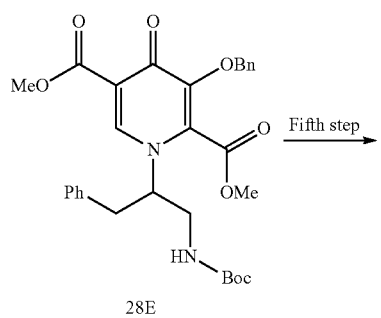

28E

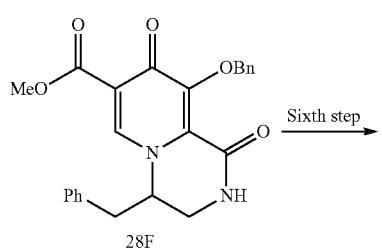

28F

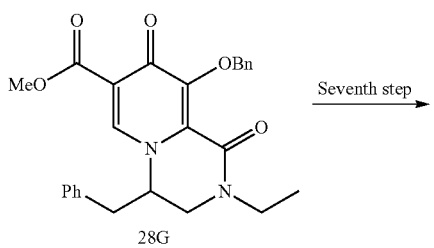

28G

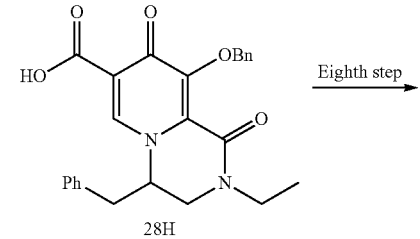

28H

-continued

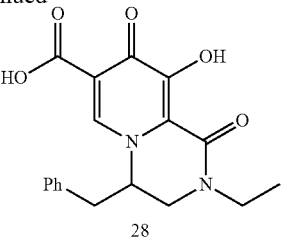

28

First Step

Compound 28A (3.20 g, 17.1 mmol) was added to THF (20 ml), triethylamine (2.60 ml, 18.8 mmol) was added, and the mixture was stirred at room temperature for 10 minutes. After Boc$_2$O (4.09 g, 18.8 mmol) was added at room temperature, the mixture was stirred for 2 hours. The solvent was distilled off under reduced pressure, water was added, and the mixture was extracted with ethyl acetate. The organic layer was washed with an aqueous saturated sodium chloride solution, and dried with sodium sulfate. The solvent was distilled off under reduced pressure to obtain 5.17 g of compound 28B as a colorless solid.

$^1$H-NMR (CDCl$_3$) δ: 1.52 (9H, s), 2.77 (2H, m), 3.03-3.12 (1H, m), 3.38 (1H, m), 3.90-3.98 (1H, m), 4.93 (1H, brs), 7.20-7.35 (5H, m).

Second Step

Compound 28B (4.29 g, 17.1 mmol), triphenylphosphine (5.37 g, 20.5 mmol) and phthalimide (2.76 g, 18.8 mmol) were added to THF (60 ml), and diethyl azodicarboxylate (2.2M in toluene, 11.6 ml, 25.6 mmol) was added dropwise at room temperature. After the mixture was stirred at room temperature for 1 hour, the solvent was distilled off under reduced pressure. The resulting crude product was purified by silica gel column chromatography (n-hexane-ethyl acetate, 2:1, v/v) to obtain 6.13 g of compound 28C as a colorless solid.

$^1$H-NMR (CDCl$_3$) δ: 1.30 (9H, s), 3.14 (1H, dd, J=13.8, 6.2 Hz), 3.39 (2H, m), 3.87 (1H, m), 4.67 (1H, m), 4.81 (1H, brs), 7.16-7.19 (5H, m), 7.66 (2H, dd, J=5.3, 3.1 Hz), 7.75 (2H, dd, J=5.7, 3.0 Hz).

Third Step

Compound 28C (1.00 g, 2.63 mmol) was added to THF (7 ml) and methanol (7 ml), hydrazine hydrate (2.63 g, 52.6 mmol) was added, and the mixture was stirred at 50° C. for 2 hours. The white precipitate was removed by filtration, and washed with methanol. After the filtrate was distilled off under reduced pressure, the resulting crude product was purified by amino column chromatography (chloroform-methanol, 99:1, v/v) to obtain 249 mg of compound 28D as a colorless solid.

$^1$H-NMR (CDCl$_3$) δ: 1.44 (9H, s), 1.95 (2H, brs), 2.55-3.31 (5H, m), 5.06 (1H, brs), 7.18-7.33 (5H, m).

Fourth Step

Dimethyl 3-(benzyloxy)-4-oxo-4H-pyran-2,5-dicarboxylate (313 mg, 0.983 mmol) and 28D (246 mg, 0.983 mmol) were added to toluene (3 ml), and the mixture was stirred at 100° C. for 2.5 hours. After the solvent was distilled off under reduced pressure, the resulting crude product was purified by silica gel column chromatography (chloroform-methanol, 98:2, v/v) to obtain 320 mg of compound 28E as a pale yellow gummy substance.

$^1$H-NMR (CDCl$_3$) δ: 1.42 (9H, s), 3.07 (2H, m), 3.56 (2H, m), 3.68 (3H, s), 3.95 (3H, s), 4.26 (1H, s), 4.86 (1H, s), 5.18 (1H, d, J=10.8 Hz), 5.22 (1H, d, J=10.8 Hz), 7.01 (2H, m), 7.24-7.38 (8H, m), 8.22 (1H, s).

MS: m/z=551 [M+H]$^+$.

Fifth Step

To compound 28E (315 mg, 0.572 mmol) was added 4N HCl (ethyl acetate solution, 5 ml), and the mixture was stirred at room temperature for 30 minutes. After the solvent was distilled off under reduced pressure, aqueous sodium bicarbonate water was added, and the mixture was extracted with chloroform, and dried with sodium sulfate. After the solvent was distilled off under reduced pressure, the resulting crude product was purified by silica gel column chromatography (chloroform-methanol, 95:5, v/v) to obtain 210 mg of compound 28F as a colorless solid.

$^1$H-NMR (CDCl$_3$) δ: 3.07-3.15 (2H, m), 3.34 (1H, dd, J=13.2, 6.0 Hz), 3.74 (2H, m), 3.86 (3H, s), 4.12 (1H, m), 5.27 (1H, d, J=10.1 Hz), 5.47 (1H, d, J=10.1 Hz), 6.76 (1H, d, J=6.4 Hz), 7.04 (2H, m), 7.32 (6H, m), 7.62 (2H, dd, J=7.7, 1.4 Hz), 7.70 (1H, s).

MS: m/z=419 [M+H]$^+$.

Sixth Step

Compound 28F (50 mg, 0.12 mmol) was dissolved in DMF (1 ml), and cesium carbonate (195 mg, 0.597 mmol) was added. After the mixture was stirred at room temperature for 30 minutes, iodoethane (0.048 ml, 0.60 mmol) was added, and the mixture was stirred at room temperature for 3.5 hours. The reaction solution was poured into water, and the mixture was extracted with ethyl acetate, and dried with sodium sulfate. After the solvent was distilled off under reduced pressure, the resulting crude product was purified by silica gel column chromatography (chloroform-methanol, 95:5, v/v) to obtain 47 mg of compound 28G as a colorless solid.

$^1$H-NMR (CDCl$_3$) δ: 1.22 (3H, t, J=7.2 Hz), 3.00-3.15 (2H, m), 3.28 (1H, dd, J=13.6, 1.6 Hz), 3.48 (1H, m), 3.75 (1H, m), 3.85 (3H, s), 3.88 (1H, dd, J=13.3, 3.2 Hz), 4.15 (1H, m), 5.25 (1H, d, J=9.9 Hz), 5.50 (1H, d, J=9.9 Hz), 7.04 (2H, m), 7.29-7.38 (6H, m), 7.60 (1H, s), 7.68 (2H, m).

MS: m/z=447 [M+H]$^+$.

Seventh Step

Compound 28G (47 mg, 0.11 mmol) was dissolved in THF (0.5 ml) and methanol (0.5 ml), a 2N aqueous sodium hydroxide solution (0.26 ml, 0.53 mmol) was added at room temperature, and the mixture was stirred for 1 hour. After 1N hydrochloric acid was added, and the mixture was extracted with ethyl acetate, the extract was dried with sodium sulfate. After the solvent was distilled off under reduced pressure, 40 mg of compound 28H was obtained as a colorless solid.

MS: m/z=433 [M+H]$^+$.

Eighth Step

To compound 28H obtained in the seventh step was added trifluoroacteic acid (1 ml), and the mixture was stirred at room temperature for 1 hour. After concentration under reduced pressure, pH was adjusted to 3 with sodium bicarbonate water and 2N hydrochloric acid, the mixture was extracted with chloroform, and the extract was dried with sodium sulfate. After the solvent was distilled off under reduced pressure, chloroform-methanol-ethyl ether were added, and the precipitated solid was filtered to obtain 17 mg of compound 28 as a colorless solid.

$^1$H-NMR (DMSO-d$_6$) δ: 1.17 (3H, t, J=7.2 Hz), 3.08 (2H, m), 3.51-3.63 (3H, m), 4.08 (1H, dd, J=13.6, 3.9 Hz), 5.03 (1H, brs), 7.21 (5H, m), 8.07 (1H, s), 12.98 (1H, s), 15.07 (1H, brs).

MS: m/z=343 [M+H]$^+$.

Example 29

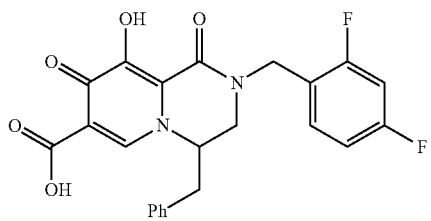

29

According to Example 28, compound 29 was synthesized by the same procedure.

$^1$H-NMR (DMSO-$d_6$) δ: 2.96 (2H, d, J=7.6 Hz), 3.46 (1H, d, J=13.3 Hz), 4.06 (1H, dd, J=13.6, 3.8 Hz), 4.64 (1H, d, J=14.9 Hz), 4.89 (1H, d, J=14.6 Hz), 4.98 (1H, m), 6.97 (2H, m), 7.10-7.37 (5H, m), 7.57 (1H, m), 8.12 (1H, s), 12.75 (1H, s), 15.07 (1H, brs).

Example 30

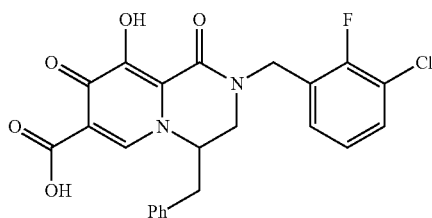

30

According to Example 28, compound 30 was synthesized by the same procedure.

$^1$H-NMR (DMSO-$d_6$) δ: 2.99 (2H, dd, J=7.5, 3.6 Hz), 3.48 (1H, d, J=13.4 Hz), 4.09 (1H, dd, J=13.4, 4.0 Hz), 4.73 (1H, d, J=15.1 Hz), 4.92 (1H, d, J=15.1 Hz), 4.99 (1H, m), 6.97 (2H, m), 7.18-7.29 (4H, m), 7.49 (1H, m), 7.61 (1H, m), 8.15 (1H, s), 12.69 (1H, s), 15.06 (1H, brs).

Example 31

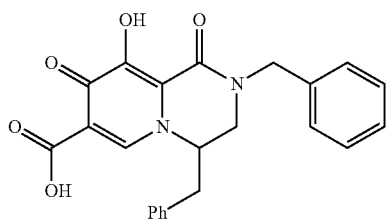

31

According to Example 28, compound 31 was synthesized by the same procedure.

$^1$H-NMR (DMSO-$d_6$) δ: 2.91 (2H, m), 3.45 (1H, d, J=13.1 Hz), 4.02 (1H, dd, J=13.6, 4.0 Hz), 4.57 (1H, d, J=14.6 Hz), 4.91 (1H, d, J=14.6 Hz), 4.93 (1H, m), 6.89 (2H, m), 7.18 (3H, m), 7.40 (5H, m), 8.16 (1H, s), 12.86 (1H, brs), 15.06 (1H, brs).

MS: m/z=405 [M+H]$^+$.

Example 32

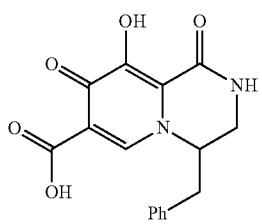

32

According to Example 28, compound 32 was synthesized by the same procedure.

$^1$H-NMR (DMSO-$d_6$) δ: 3.10 (2H, m), 3.39 (1H, d, J=13.6 Hz), 3.84 (1H, dd, J=13.6, 4.0 Hz), 4.94 (1H, m), 7.23 (5H, m), 8.19 (1H, s), 9.44 (1H, brs), 12.97 (1H, s), 15.06 (1H, brs).

MS: m/z=315 [M+H]$^+$.

Example 33

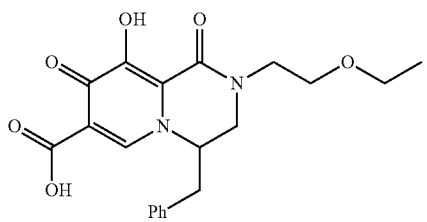

33

According to Example 28, compound 33 was synthesized by the same procedure.

$^1$H-NMR (DMSO-$d_6$) δ: 1.09 (3H, t, J=6.9 Hz), 3.10 (2H, m), 3.42-3.50 (2H, m), 3.71 (5H, m), 4.11 (1H, dd, J=13.6, 3.8 Hz), 4.99 (1H, brs), 7.11-7.29 (5H, m), 7.99 (1H, s), 12.88 (1H, s), 15.06 (1H, brs).

MS: m/z=387 [M+H]$^+$.

Example 34

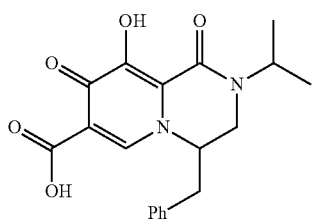

34

According to Example 28, compound 34 was synthesized by the same procedure.

$^1$H-NMR (DMSO-$d_6$) δ: 1.16 (3H, d, J=6.9 Hz), 1.21 (3H, d, J=6.9 Hz), 2.98 (1H, dd, J=13.6, 9.8 Hz), 3.13 (1H, dd, J=13.7, 5.8 Hz), 3.68 (1H, d, J=12.8 Hz), 3.87 (1H, dd, J=13.6, 3.7 Hz), 4.83 (1H, quin, J=6.8 Hz), 5.07 (1H, brs), 7.19 (5H, m), 7.90 (1H, s), 13.09 (1H, s), 15.08 (1H, brs).

MS: m/z=357 [M+H]$^+$.

Example 35

[Chemical formula 140]

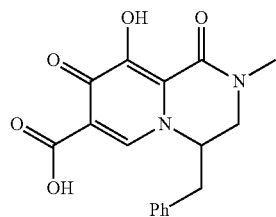

According to Example 28, compound 35 was synthesized by the same procedure.

$^1$H-NMR (DMSO-$d_6$) δ: 3.07 (3H, s), 3.14 (2H, m), 3.49 (1H, d, J=13.3 Hz), 4.08 (1H, dd, J=13.7, 4.0 Hz), 4.99 (1H, m), 7.13-7.31 (5H, m), 8.18 (1H, s), 12.95 (1H, s), 15.06 (1H, brs).

MS: m/z=329 [M+H]$^+$.

Example 36

[Chemical formula 141]

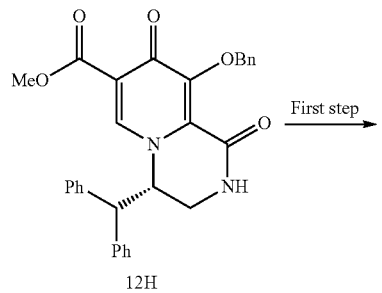

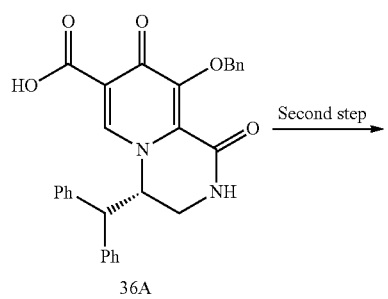

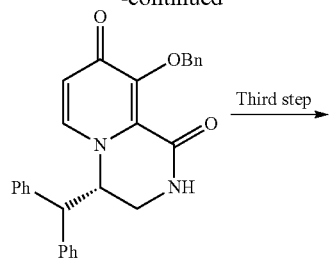

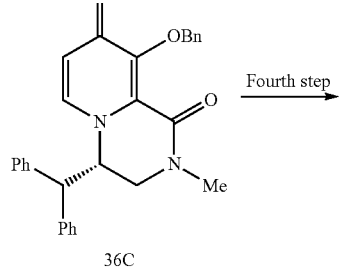

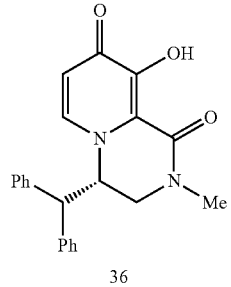

First Step

Compound 12H (460 mg, 0.930 mmol) was dissolved in THF (2.5 ml) and methanol (2.5 ml), a 2N aqueous sodium hydroxide solution (2.33 ml, 4.65 mmol) was added at room temperature, and the mixture was stirred for 1.5 hours. After 1N hydrochloric acid was added, and the mixture was extracted with ethyl acetate, the extract was dried with sodium sulfate. After the solvent was distilled off under reduced pressure, 405 mg of compound 36A was obtained as a colorless solid.

$^1$H-NMR (CDCl$_3$) δ: 3.45 (1H, ddd, J=13.8, 6.9, 1.3 Hz), 3.80 (1H, dd, J=13.5, 2.1 Hz), 4.35 (1H, d, J=11.6 Hz), 4.77 (1H, d, J=11.3 Hz), 5.46 (1H, d, J=10.5 Hz), 5.52 (1H, d, J=10.5 Hz), 6.11 (1H, d, J=5.8 Hz), 6.94-6.98 (2H, m), 7.17 (3H, m), 7.31-7.46 (8H, m), 7.58 (3H, m).

Second Step

Compound 36A (402 mg, 0.837 mmol) was added to diphenyl ether (5 ml), and the mixture was stirred at 245° C. for 1 hour under microwave irradiation. The reaction solution was poured into n-hexane, and the precipitated solid was filtered. The resulting crude product was purified by amino column chromatography (chloroform-methanol, 99:1, v/v) to obtain 164 mg of compound 36B as a colorless solid.

$^1$H-NMR (CDCl$_3$) δ: 3.36 (1H, dd, J=13.0, 7.0 Hz), 3.72 (1H, d, J=11.1 Hz), 4.35 (1H, d, J=11.4 Hz), 4.49 (18, d, J=10.2 Hz), 5.38 (1H, d, J=10.5 Hz), 5.43 (1H, d, J=10.4 Hz), 5.94 (1H, d, J=7.2 Hz), 6.29 (1H, d, J=6.6 Hz), 6.38 (1H, d, J=7.5 Hz), 6.99 (2H, m), 7.17 (3H, m), 7.36 (8H, m), 7.60 (2H, m).

Third Step

Compound 36B (40 mg, 0.092 mmol) was dissolved in DMF (1 ml), and cesium carbonate (179 mg, 0.55 mmol) was added. After stirring at room temperature for 30 minutes, iodomethane (0.029 ml, 0.46 mmol) was added, and the mixture was stirred at room temperature for 3.5 hours. After the reaction solution was poured into water, and the mixture was extracted with ethyl acetate, the extract was dried with sodium sulfate. After the solvent was distilled off under reduced pressure, the resulting crude product was purified by silica gel column chromatography (chloroform-methanol, 95:5, v/v) to obtain 44 mg of compound 36C as a colorless gummy substance.

Fourth Step

To compound 36C obtained in the third step was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, chloroform-ethyl ether were added, and the precipitated solid was filtered to obtain 24 mg of compound 36 as a colorless solid.

$^1$H-NMR (DMSO-$d_6$) δ: 2.93 (3H, s), 3.17 (1H, d, J=13.0 Hz), 4.13 (1H, dd, J=13.6, 3.4 Hz), 4.47 (1H, d, J=11.4 Hz), 5.52 (1H, dd, J=9.3, 3.4 Hz), 5.99 (1H, d, J=7.3 Hz), 7.18 (4H, m), 7.30 (3H, m), 7.41 (2H, t, J=7.5 Hz), 7.60 (2H, d, J=7.2 Hz).

MS: m/z=361 [M+H]$^+$.

Example 37

[Chemical formula 142]

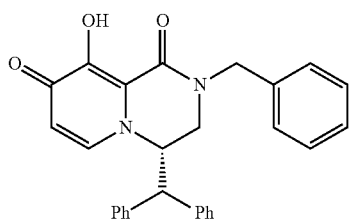

37

According to Example 36, compound 37 was synthesized by the same procedure.

$^1$H-NMR (DMSO-$d_6$) δ: 3.16 (2H, d, J=13.3 Hz), 4.05 (1H, d, J=10.5 Hz), 4.15 (1H, d, J=11.7 Hz), 4.38 (1H, d, J=14.9 Hz), 4.74 (1H, d, J=14.5 Hz), 5.35 (1H, d, J=11.4 Hz), 5.65 (1H, d, J=7.3 Hz), 6.99 (1H, d, J=7.5 Hz), 7.21 (15H, m).

MS: m/z=437 [M+H]$^+$.

Example 38

[Chemical formula 143]

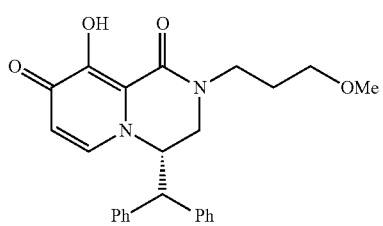

38

According to Example 36, compound 38 was synthesized by the same procedure.

$^1$H-NMR (DMSO-$d_6$) δ: 1.57 (2H, m), 3.17 (3H, s), 3.21-3.31 (5H, m), 4.07 (1H, dd, J=13.5, 3.7 Hz), 4.36 (1H, d, J=11.6 Hz), 5.42 (1H, d, J=9.2 Hz), 5.61 (1H, d, J=7.3 Hz), 6.89 (1H, d, J=7.5 Hz), 7.13-7.31 (6H, m), 7.40 (2H, t, J=6.3 Hz), 7.57 (2H, d, J=7.3 Hz), 12.31 (1H, brs).

MS: m/z=419 [M+H]$^+$.

Example 39

[Chemical formula 144]

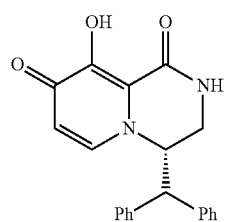

39

According to Example 36, compound 39 was synthesized by the same procedure.

$^1$H-NMR (DMSO-$d_6$) δ: 3.12 (1H, dd, J=13.6, 5.5 Hz), 3.87 (1H, d, J=9.5 Hz), 4.44 (1H, d, J=11.7 Hz), 5.45 (1H, d, J=10.4 Hz), 5.83 (1H, d, J=7.5 Hz), 7.04 (1H, d, J=7.2 Hz), 7.14-7.31 (6H, m), 7.40 (2H, t, J=7.5 Hz), 7.58 (2H, d, J=7.5 Hz), 9.09 (1H, d, J=5.2 Hz).

MS: m/z=347 [M+H]$^+$.

Example 40

[Chemical formula 145]

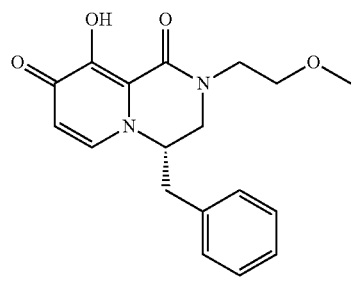

40

According to Example 36, compound 40 was synthesized by the same procedure.

$^1$H-NMR (DMSO-$d_6$) δ: 2.88-3.15 (2H, m), 3.27 (3H, s), 3.53-3.73 (5H, m), 3.99 (1H, dd, J=13.27, 3.97 Hz), 4.56-4.60 (1H, m), 5.89 (1H, d, J=7.32 Hz), 7.08-7.30 (6H, m).

Example 41

[Chemical formula 146]

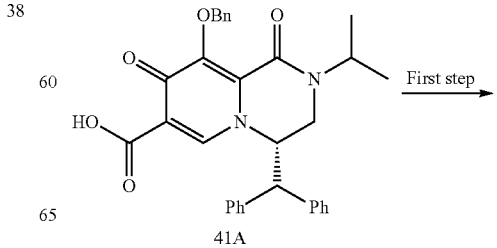

41A

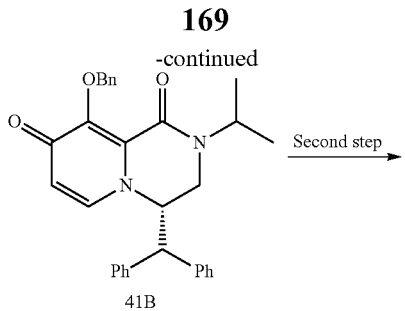

41B

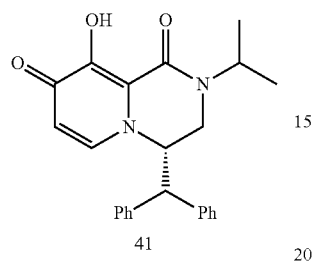

41

First Step

Compound 41A (290 mg, 0.555 mmol) synthesized according to Example 12 was added to diphenyl ether (5 ml), and the mixture was stirred at 245° C. for 1 hour under microwave irradiation. The reaction solution was poured into n-hexane, and the precipitated solid was filtered. The resulting crude product was purified by amino column chromatography (chloroform-methanol, 99:1→97:3, v/v) to obtain 86 mg of compound 41B as a colorless solid.

$^1$H-NMR (CDCl$_3$) δ: 0.76 (3H, d, J=6.7 Hz), 0.98 (3H, d, J=6.9 Hz), 3.43-3.52 (2H, m), 3.62 (1H, dd, J=13.6, 3.5 Hz), 4.22 (1H, d, J=11.6 Hz), 4.52 (1H, d, J=11.6 Hz), 4.86-4.95 (1H, m), 5.37 (1H, d, J=10.2 Hz), 5.45 (1H, d, J=10.2 Hz), 5.90 (1H, d, J=7.5 Hz), 6.22 (1H, d, J=7.5 Hz), 6.89 (2H, m), 7.15 (3H, m), 7.36 (8H, m), 7.67 (2H, m).

Second Step

To compound 41B obtained in the first step was added trifluoroacetic acid (2 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 45 mg of compound 41 as a colorless solid.

$^1$H-NMR (DMSO-d$_6$) δ: 0.82 (3H, d, J=6.7 Hz), 1.05 (3H, d, J=6.7 Hz), 3.90 (1H, dd, J=13.6, 3.4 Hz), 4.39 (1H, d, J=11.9 Hz), 4.77-4.86 (1H, m), 5.50 (1H, d, J=8.6 Hz), 5.69 (1H, d, J=7.4 Hz), 6.92 (1H, d, J=7.4 Hz), 7.15-7.48 (8H, m), 7.63 (2H, d, J=7.7 Hz) 12.51 (1H, Brs).

MS: m/z=389 [M+H]$^+$.

Example 42

[Chemical formula 147]

42

According to Example 41, compound 42 was synthesized by the same procedure.

$^1$H-NMR (DMSO-d$_6$) δ: 3.12 (3H, s), 3.51 (5H, m), 4.05 (1H, dd, J=13.9, 3.5 Hz), 4.37 (1H, d, J=11.4 Hz), 5.38 (1H, d, J=11.6 Hz), 5.60 (1H, d, J=7.3 Hz), 6.90 (1H, d, J=7.5 Hz), 7.22 (6H, m), 7.40 (2H, t, J=7.5 Hz), 7.56 (2H, d, J=7.2 Hz).

MS: m/z=405 [M+H]$^+$.

Example 43

[Chemical formula 148]

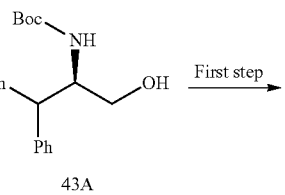

43A

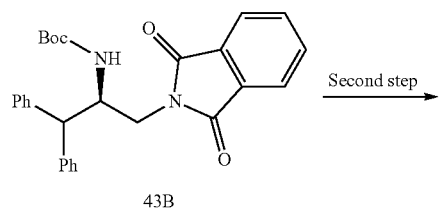

43B

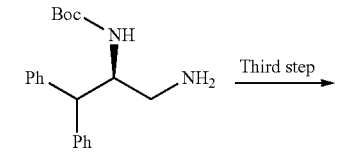

43C

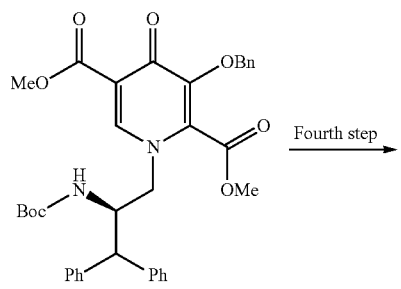

43D

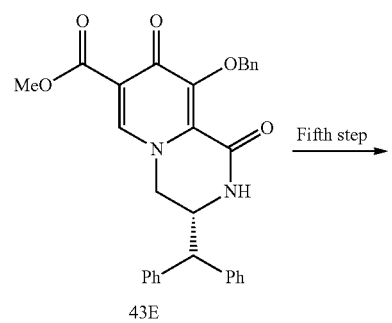

43E

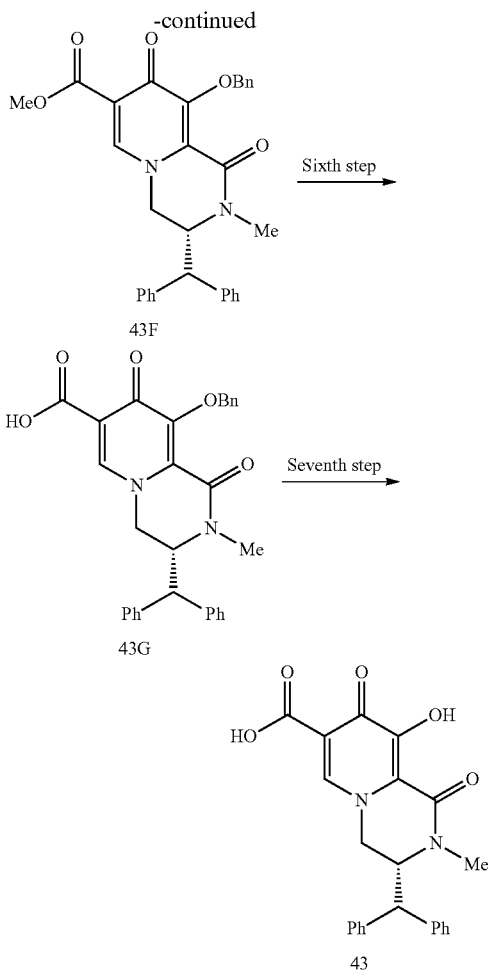

First Step

Compound 43A (2.00 g, 6.11 mmol), triphenylphosphine (2.40 g, 9.16 mmol) and phthalimide (1.08 g, 7.33 mmol) were added to THF (20 ml), and diethyl azodicarboxylate (2.2M in toluene, 4.16 ml, 9.16 mmol) was added dropwise at room temperature. After stirring at room temperature for 3 hours, the solvent was distilled off under reduced pressure. The resulting crude product was purified by silica gel column chromatography (n-hexane-ethyl acetate, 1:1, v/v) to obtain 2.39 g of compound 43B as a colorless solid.

$^1$H-NMR (DMSO-d$_6$) δ: 1.00 (9H, s), 3.30 (1H, m), 3.61 (1H, dd, J=13.4, 10.2 Hz), 4.15 (1H, d, J=12.2 Hz), 4.75 (1H, m), 6.79 (1H, d, J=9.5 Hz), 7.25 (15H, m), 7.76-7.89 (4H, m).

Second Step

Compound 43B (2.06 g, 4.51 mmol) was added to THF (20 ml) and methanol (20 ml), hydrazine hydrate (4.52 g, 90.2 mmol) was added, and the mixture was stirred at 60° C. for 5 hours. The white precipitate was removed by filtration, and washed with methanol. After the filtrate was distilled off under reduced pressure, the resulting crude product was purified by amino column chromatography (chloroform-methanol, 99:1, v/v), n-hexane was added, and the precipitated solid was filtered to obtain 1.25 g of compound 43C as a colorless solid.

$^1$H-NMR (CDCl$_3$) δ: 1.32 (9H, s), 2.55 (1H, dd, J=13.3, 6.0 Hz), 2.80 (1H, dd, J=13.3, 3.5 Hz), 3.99 (1H, d, J=10.1 Hz), 4.47 (2H, m), 7.13-7.33 (10H, m).

Third Step

Dimethyl 3-(benzyloxy)-4-oxo-4H-pyran-2,5-dicarboxylate (488 mg, 1.53 mmol) and 43C (500 mg, 1.53 mmol) were added to toluene (8 ml), and the mixture was stirred at 110° C. for 1 hour. After the solvent was distilled off under reduced pressure, the resulting crude product was purified by silica gel column chromatography (chloroform-methanol, 97:3→96:4→94:6, v/v) to obtain 667 mg of compound 43D as a pale yellow gummy substance.

$^1$H-NMR (CDCl$_3$) δ: 1.28 (9H, s), 3.63 (3H, s), 3.80 (1H, m), 3.87 (3H, s), 4.02 (1H, dd, J=14.5, 10.1 Hz), 4.21 (1H, d, J=10.4 Hz), 4.47 (2H, m), 5.20 (1H, d, J=10.8 Hz), 5.26 (1H, d, J=10.7 Hz), 7.30 (15H, m), 8.05 (1H, s).

MS: m/z=627 [M+H]$^+$.

Fourth Step

To compound 43D (664 mg, 1.06 mmol) was added 4N HCl (ethyl acetate solution, 10 ml), and the mixture was stirred at room temperature for 1 hour. After the solvent was distilled off under reduced pressure, THF and saturated sodium bicarbonate water were added, and the mixture was stirred for 2.5 hours. This was extracted with chloroform, and the extract was dried with sodium sulfate. After the solvent was distilled off under reduced pressure, methylene chloride-ethyl ether were added, and the precipitated solid was filtered to obtain 458 mg of compound 43E as a colorless solid.

$^1$H-NMR (CDCl$_3$) δ: 3.86 (3H, m), 3.92 (3H, s), 4.41-4.48 (1H, m), 5.32 (1H, d, J=10.8 Hz), 5.42 (1H, d, J=10.1 Hz), 5.92 (1H, s), 7.21-7.39 (13H, m), 7.59 (2H, m), 7.89 (1H, s).

MS: m/z=495 [M+H]$^+$.

Fifth Step

Compound 43E (50 mg, 0.10 mmol) was dissolved in DMF (1 ml), and cesium carbonate (165 mg, 0.51 mmol) was added. After the mixture was stirred at room temperature for 30 minutes, iodomethane (0.025 ml, 0.40 mmol) was added, and the mixture was stirred at room temperature for 1 hour. After the reaction solution was poured into water, and the mixture was extracted with ethyl acetate, the extract was dried with sodium sulfate. After the solvent was distilled off under reduced pressure, the resulting crude product was purified by silica gel column chromatography (chloroform-methanol, 97:3→95:5, v/v) to obtain 60 mg of compound 43F as a colorless solid.

$^1$H-NMR (CDCl$_3$) δ: 2.57 (3H, s), 3.75 (2H, d, J=11.3 Hz), 3.93 (3H, s), 4.20-4.29 (2H, m), 5.25 (1H, d, J=9.9 Hz), 5.57 (1H, d, J=9.9 Hz), 7.15-7.41 (13H, m), 7.63 (1H, s), 7.72-7.76 (2H, m).

Sixth Step

Compound 43F obtained in the fifth step was dissolved in THF (0.5 ml) and methanol (0.5 ml), a 2N aqueous sodium hydroxide solution (0.25 ml, 0.50 mmol) was added at room temperature, and the mixture was stirred for 1 hour. After 1N hydrochloric acid was added, and the mixture was extracted with ethyl acetate, the extract was dried with sodium sulfate. After the solvent was distilled off under reduced pressure, a colorless gummy compound 43G was obtained.

Seventh Step

To compound 43G obtained in the sixth step was added trifluoroacetic acid (2 ml), and the mixture was stirred at room temperature for 1 hour. After concentration under reduced pressure, pH was adjusted to 3 with sodium bicarbonate water and 2N hydrochloric acid, the mixture was extracted with chloroform, and the extract was dried with sodium sulfate. After the solvent was distilled off under reduced pressure, chloroform-ethyl ether were added, and the precipitated solid was filtered to obtain 27 mg of compound 43 as a colorless solid.

¹H-NMR (DMSO-d₆) δ: 2.53 (3H, s), 4.26 (1H, d, J=10.9 Hz), 4.35 (1H, d, J=13.3 Hz), 4.58 (1H, dd, J=13.8, 3.5 Hz), 5.06 (1H, d, J=10.9 Hz), 7.36 (10H, m), 8.36 (1H, s), 12.58 (1H, s), 15.62 (1H, s).
MS: m/z=405 [M+H]⁺.

Example 44

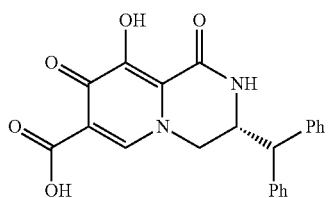

44

According to Example 43, compound 44 was synthesized by the same procedure.
¹H-NMR (DMSO-d₆) δ: 4.19 (2H, m), 4.42 (1H, dd, J=13.3, 3.8 Hz), 4.90 (1H, d, J=9.2 Hz), 7.17-7.41 (10H, m), 8.40 (1H, s), 9.66 (1H, s), 12.70 (1H, s), 15.60 (1H, s).
MS: m/z=391 [M+H]⁺.

Example 45

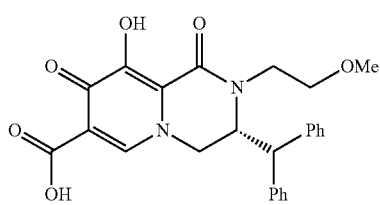

45

According to Example 43, compound 45 was synthesized by the same procedure.
¹H-NMR (DMSO-d₆) δ: 2.17-2.26 (1H, m), 3.22 (3H, s), 3.39 (2H, m), 3.58-3.67 (1H, m), 4.19 (1H, d, J=10.7 Hz), 4.38 (2H, m), 4.95 (1H, d, J=10.8 Hz), 7.20-7.44 (10H, m), 8.28 (1H, s), 12.40 (1H, s), 15.60 (1H, s).
MS: m/z=449 [M+H]⁺.

Example 46

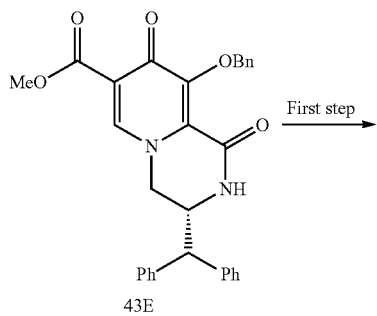

43E

First step

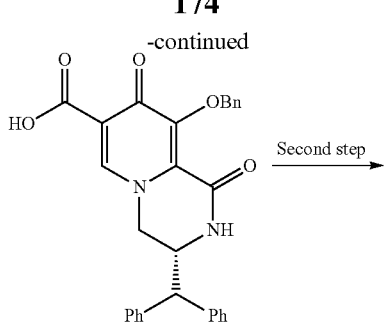

46A

Second step

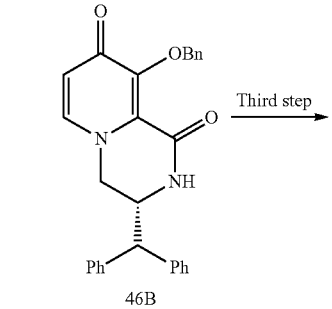

46B

Third step

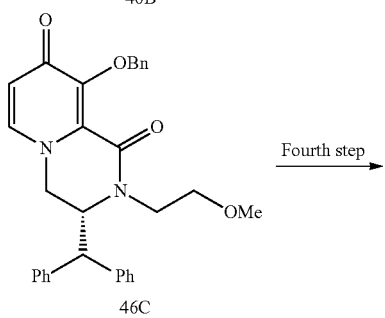

46C

Fourth step

46

First Step

Compound 43E (289 mg, 0.584 mmol) obtained in Example 35 was dissolved in THF (3 ml) and methanol (3 ml), a 2N aqueous sodium hydroxide solution (1.46 ml, 2.92 mmol) was added at room temperature, and the mixture was stirred for 1.5 hours. After 1N hydrochloric acid was added, and the mixture was extracted with ethyl acetate, the extract was dried with sodium sulfate. After the solvent was distilled off, 342 mg of compound 46A was obtained as a colorless solid.
¹H-NMR (CDCl₃) δ: 3.72-4.04 (3H, m), 4.46 (1H, m), 5.39 (1H, d, J=10.4 Hz), 5.44 (1H, d, J=10.4 Hz), 6.04 (1H, brs), 7.19-7.60 (15H, m), 8.10 (1H, s).

Second Step

Compound 46A (402 mg, 0.837 mmol) was added to diphenyl ether (5 ml), and the mixture was stirred at 245° C. for 1 hour under microwave irradiation. The reaction solution was poured into n-hexane, and the precipitated solid was filtered. The resulting crude product was purified by silica gel column chromatography (chloroform-methanol, 97:3→95:5→92:8, v/v) to obtain 85 mg of compound 46B as a colorless solid.

$^1$H-NMR (CDCl$_3$) δ: 3.86 (3H, m), 4.45 (1H, m), 5.35 (1H, d, J=10.5 Hz), 5.41 (1H, d, J=10.4 Hz), 5.94 (1H, brs), 6.48 (1H, d, J=7.4 Hz), 7.00 (1H, d, J=7.4 Hz), 7.25-7.44 (13H, m), 7.62 (2H, m).

Third Step

Compound 46B (39 mg, 0.089 mmol) was dissolved in DMF (1 ml), and cesium carbonate (145 mg, 0.445 mmol) was added. After stirring at room temperature for 30 minutes, 1-bromo-2-methoxyethane (0.033 ml, 0.36 mmol) was added, and the mixture was stirred at room temperature for 3.5 hours. After the reaction solution was poured into water, and the mixture was extracted with ethyl acetate, the extract was dried with sodium sulfate. After the solvent was distilled off under reduced pressure, the resulting crude product was purified by silica gel column chromatography (chloroform-methanol, 97:3→95:5→92:8, v/v) to obtain 66 mg of compound 46C as a colorless gummy substance.

Fourth Step

To compound 46C obtained in the third step was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 21 mg of compound 46 as a colorless solid.

$^1$H-NMR (DMSO-d$_6$) δ: 2.12-2.21 (1H, m), 3.20 (3H, s), 3.55-3.64 (3H, m), 3.81 (1H, d, J=13.0 Hz), 3.99 (1H, d, J=11.0 Hz), 4.22 (1H, dd, J=13.3, 3.1 Hz), 4.86 (1H, d, J=11.0 Hz), 6.11 (1H, d, J=7.2 Hz), 7.18-7.45 (11H, m).

MS: m/z=405 [M+H]$^+$.

Example 47

[Chemical formula 152]

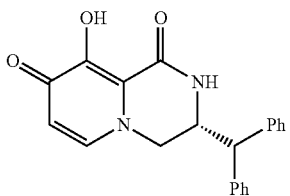

47

According to Example 46, compound 47 was synthesized by the same procedure.

$^1$H-NMR (DMSO-d$_6$) δ: 3.70 (1H, d, J=12.2 Hz), 4.02 (1H, d, J 10.7 Hz), 4.17 (1H, dd, J=13.2, 3.6 Hz), 4.79 (1H, t, J=3.4 Hz), 6.11 (1H, d, J=7.3 Hz), 7.18-7.44 (11H, m), 9.23 (1H, d, J=4.3 Hz).

MS: m/z=347 [M+H]$^+$.

Example 48

[Chemical formula 153]

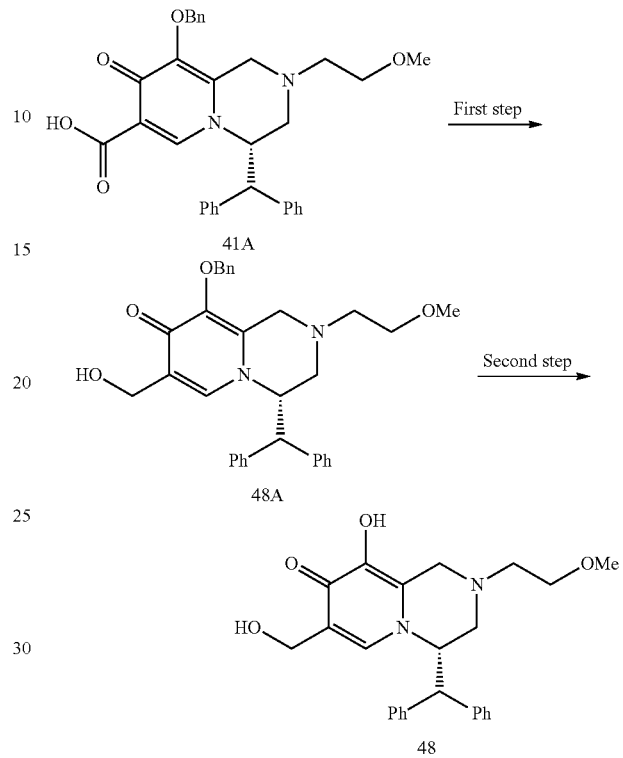

First Step

Compound 41A (400 mg, 0.743 mmol) was dissolved in DMF (5 ml), triethylamine (0.21 ml, 1.5 mmol) and ethyl chloroformate (0.143 ml, 1.49 mmol) were added at 0° C., and the mixture was stirred for 20 minutes. Sodium borohydride (70.2 mg, 1.86 mmol) was added at 0° C., and the mixture was stirred at room temperature for 30 minutes. Sodium borohydride (70.2 mg, 1.86 mmol) was further added at 0° C., and the mixture was stirred at room temperature for 2 hours. The reaction solution was poured into water, the mixture was extracted with ethyl acetate, and the extract was dried with sodium sulfate. After the solvent was distilled off under reduced pressure, the resulting crude product was purified by silica gel column chromatography (chloroform-methanol, 97.3, v/v) to obtain 160 mg of compound 48A as a colorless solid.

$^1$H-NMR (CDCl$_3$) δ: 3.19 (3H, s), 3.37-3.54 (3H, m), 3.65-3.73 (1H, m), 3.87 (1H, m), 4.06 (2H, d, J=13.9 Hz), 4.31 (1H, d, J=11.2 Hz), 4.39 (1H, d, J=13.8 Hz), 4.77 (1H, d, J=11.2 Hz), 5.36 (1H, d, J=10.1 Hz), 5.41 (1H, d, J=10.1 Hz), 6.65 (1H, brs), 7.00 (2H, m), 7.19 (3H, m), 7.33-7.49 (8H, m), 7.70 (2H, m).

Second Step

To compound 48A (50 mg, 0.095 mmol) was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. The solvent was distilled off under reduced pressure, chroloform-ethyl ether were added, and the precipitated solid was filtered to obtain 3.5 mg of compound 48 as a colorless solid.

$^1$H-NMR (DMSO-d$_6$) δ: 3.12 (3H, s), 3.51 (5H, m), 3.71 (1H, d, J=13.7 Hz), 4.02 (1H, d, J=9.9 Hz), 4.09 (1H, d, J=12.0 Hz), 4.36 (1H, d, J=11.6 Hz), 4.73 (1H, brs), 5.45 (1H, d, J=12.5 Hz), 7.00 (1H, s), 7.15 (5H, m), 7.28 (1H, t, J=7.2 Hz), 7.40 (2H, t, J=7.5 Hz), 7.59 (2H, d, J=7.6 Hz).

MS: m/z=435 [M+H]$^+$.

Example 49

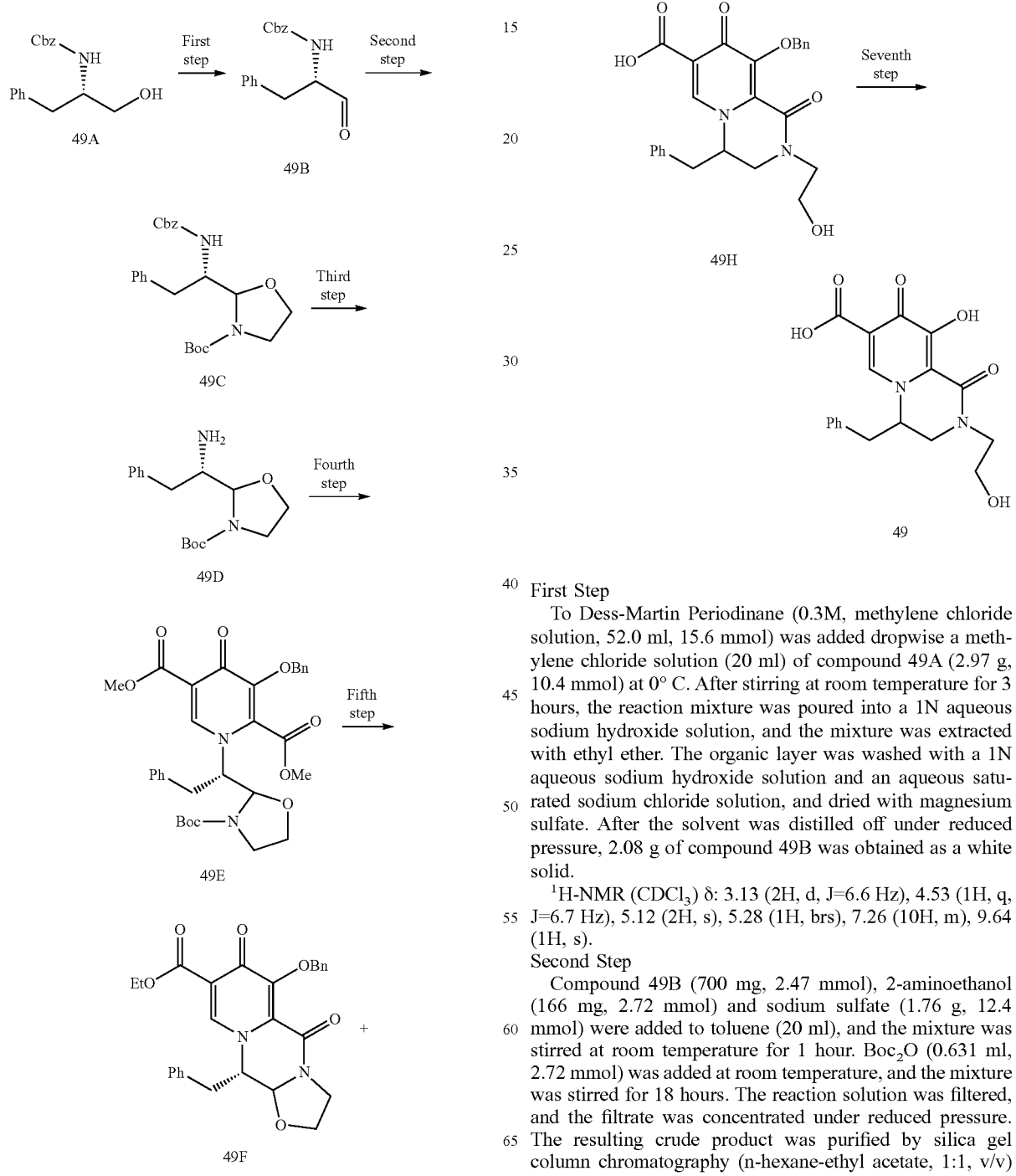

First Step

To Dess-Martin Periodinane (0.3M, methylene chloride solution, 52.0 ml, 15.6 mmol) was added dropwise a methylene chloride solution (20 ml) of compound 49A (2.97 g, 10.4 mmol) at 0° C. After stirring at room temperature for 3 hours, the reaction mixture was poured into a 1N aqueous sodium hydroxide solution, and the mixture was extracted with ethyl ether. The organic layer was washed with a 1N aqueous sodium hydroxide solution and an aqueous saturated sodium chloride solution, and dried with magnesium sulfate. After the solvent was distilled off under reduced pressure, 2.08 g of compound 49B was obtained as a white solid.

$^1$H-NMR (CDCl$_3$) δ: 3.13 (2H, d, J=6.6 Hz), 4.53 (1H, q, J=6.7 Hz), 5.12 (2H, s), 5.28 (1H, brs), 7.26 (10H, m), 9.64 (1H, s).

Second Step

Compound 49B (700 mg, 2.47 mmol), 2-aminoethanol (166 mg, 2.72 mmol) and sodium sulfate (1.76 g, 12.4 mmol) were added to toluene (20 ml), and the mixture was stirred at room temperature for 1 hour. Boc$_2$O (0.631 ml, 2.72 mmol) was added at room temperature, and the mixture was stirred for 18 hours. The reaction solution was filtered, and the filtrate was concentrated under reduced pressure. The resulting crude product was purified by silica gel column chromatography (n-hexane-ethyl acetate, 1:1, v/v) to obtain 893 mg of 49C as a colorless gummy substance.

Third Step

Compound 49C (890 mg, 2.09 mmol) and palladium-active carbon (10% wet, 200 mg) were added to ethanol (20 ml), and the mixture was stirred at room temperature for 2 hours under hydrogen atmosphere. After filtration with celite, the solvent was concentrated under reduced pressure to obtain 656 mg of a colorless oily substance 49D.

$^1$H-NMR (CDCl$_3$) δ: 1.40 (9H, s), 2.65-2.86 (2H, m), 3.32 (2H, m), 3.80 (2H, m), 4.03-4.12 (1H, m), 4.86 (1H, brs), 7.22 (5H, m).

Fourth Step

Dimethyl 3-(benzyloxy)-4-oxo-4H-pyran-2,5-dicarboxylate (610 mg, 2.09 mmol) and 49D (664 mg, 2.09 mmol) were added to toluene (6 ml), and the mixture was stirred at 100° C. for 4 hours. After the solvent was distilled off under reduced pressure, the resulting crude product was purified by silica gel column chromatography (n-hexane-ethyl acetate, 1:1, v/v) to obtain 884 mg of compound 49E as a pale yellow gummy substance.

MS: m/z=593 [M+H]$^+$.

Fifth Step

To compound 49E (860 mg, 1.45 mmol) was added 4N HCl (ethyl acetate solution, 10 ml). After stirring at room temperature for 30 minutes, the solvent was distilled off under reduced pressure. Subsequently, toluene (10 ml) and 2-aminoethanol (0.175 ml, 2.90 mmol) were added, and the mixture was stirred at 80° C. for 30 minutes. After the solvent was distilled off under reduced pressure, the resulting crude product was purified by silica gel column chromatography (chloroform-methanol, 99:1→95:5→90:0, v/v) to obtain 157 mg of compound 49F as a colorless gummy substance and 217 mg of compound 49G as a yellow solid.

49F: $^1$H-NMR (CDCl$_3$) δ: 2.48 (1H, dd, J=14.0, 11.4 Hz), 3.22 (1H, dd, J=14.1, 3.3 Hz), 3.69 (1H, m), 3.77 (3H, s), 3.83-3.95 (1H, m), 4.08 (1H, m), 4.29 (1H, m), 4.41 (1H, m), 5.34 (2H, m), 5.48 (1H, d, J=10.1 Hz), 6.86 (2H, m), 7.20-7.39 (7H, m), 7.64 (2H, m)

49G: $^1$H-NMR (DMSO-d$_6$) δ: 3.70 (2H, t, J=5.3 Hz), 3.73 (3H, s), 3.86 (2H, t, J=5.3 Hz), 4.14 (2H, s), 4.98 (1H, t, J=5.0 Hz), 5.06 (2H, s), 6.98 (1H, s), 7.35 (8H, m), 7.62 (2H, d, J=7.1 Hz), 8.34 (1H, d, J=0.8 Hz).

Sixth Step

The compound 49G (214 mg, 0.465 mmol) was dissolved in THF (4 ml), ethanol (2 ml) and methylene chloride (2 ml), a 2N aqueous sodium hydroxide solution (1.16 ml, 2.32 mmol) was added at room temperature, and the mixture was stirred for 2.5 hours. After 1N hydrochloric acid was added, and the mixture was extracted with chloroform, the extract was dried with sodium sulfate. After the solvent was distilled off under reduced pressure, 158 mg of compound 49H was obtained as a yellow solid.

$^1$H-NMR (DMSO-d$_6$) δ: 3.70 (2H, q, J=5.2 Hz), 3.89 (2H, t, J=5.3 Hz), 4.22 (2H, s), 4.97 (1H, t, J=5.6 Hz), 5.12 (2H, s), 7.23-7.41 (9H, m), 7.60 (2H, m), 8.54 (1H, s).

Seventh Step

Compound 49H (50.0 mg, 0.112 mmol) and palladium-active carbon (10%, wet, 12 mg) were added to methanol (1 ml) and DMF (3 ml), and the mixture was stirred at room temperature for 5 hours under hydrogen atmosphere. After filtration with celite, the solvent was concentrated under reduced pressure, chloroform-methanol-ethyl ether were added, and the precipitated solid was filtered to obtain 9.0 mg of compound 49 as a colorless solid.

$^1$H-NMR (DMSO-d$_6$) δ: 3.10 (2H, m), 3.51-3.69 (4H, m), 4.10 (1H, d, J=10.7 Hz), 4.94 (2H, m), 7.11-7.26 (5H, m), 8.03 (1H, s), 12.94 (1H, brs), 15.30 (1H, brs).

MS: m/z=359 [M+H]$^+$.

Example 50

[Chemical formula 155]

First Step

Compound 50A (1.00 g, 3.98 mmol), triphenylphosphine (1.15 g, 4.48 mmol) and N-methyl-2-nitrobenzenesulfonamide (860 mg, 3.98 mmol) were added to THF (10 ml), diethyl azodicarboxylate (2.2M in toluene, 1.99 ml, 4.38 mmol) was added dropwise at room temperature. After stirring at room temperature for 3 hours, and the solvent was distilled off under reduced pressure. The resulting crude product was purified by silica gel column chromatography (n-hexane-ethyl acetate, 1;1, v/v) to obtain 710 mg of compound 50B as a colorless gummy substance.

Second Step

Compound 50B (458 mg, 1.02 mmol) was dissolved in acetonitrile, potassium carbonate (422 mg, 3.06 mmol) and benzenethiol (0.126 ml, 1.22 mmol) were added, and the mixture was stirred at room temperature for 5 hours. The reaction solution was poured into a 1N aqueous sodium hydroxide solution, the mixture was extracted with methylene chloride, and the extract was dried with sodium sulfate. The resulting crude product was purified by amino column chromatography (chloroform-methanol, 95:5, v/v) to obtain 147 mg of compound 50C as a colorless oily substance.

$^1$H-NMR (CDCl$_3$) δ: 1.36 (9H, s), 2.40 (3H, s), 2.51-2.89 (4H, m), 3.90 (1H, s), 4.69 (1H, s), 7.17-7.31 (5H, m).

Third Step

Compound 50C (140 mg, 0.530 mmol) and 3-(benzyloxy)-4-oxo-4H-pyran-2-carboxylic acid (WO 2006/116764, 119 mg, 0.482 mmol) were added to THF (3 ml), 1-(3-dimethylaminopropyl)-3-ethylcarbodiimide hydrochloride (111 mg, 0.578 mmol) and 1-hydroxybenzotriazole (65.1 mg, 0.482 mmol) were added, and the mixture was stirred at room temperature for 18 hours. The reaction solution was poured into sodium bicarbonate water, the mixture was extracted with ethyl acetate, and the extract was dried with sodium sulfate. The resulting crude product was purified by silica gel column chromatography (chloroform-methanol, 97;3, v/v) to obtain 219 mg of compound 50D as a colorless solid.

MS: m/z=493 [M+H]$^+$.

Fourth Step

To compound 50D (216 mg, 0.439 mmol) was added 4N HCl (ethyl acetate solution, 3 ml). After the mixture was stirred at room temperature for 1 hour, the solvent was distilled off under reduced pressure. Subsequently, ethanol (4 ml) and an aqueous saturated sodium carbonate solution (3 ml) were added, and the mixture was stirred at 60° C. for 2 hours. After water was added, and the mixture was extracted with ethyl acetate, the extract was dried with sodium sulfate. The resulting crude product was purified by amino column chromatography (chloroform-methanol, 95;5, v/v) to obtain 108 mg of compound 50E as a pale yellow gummy substance.

$^1$H-NMR (CDCl$_3$) δ: 3.00 (2H, m), 3.13 (3H, s), 3.18 (1H, m), 3.88 (1H, dd, J=13.5, 3.4 Hz), 4.00-4.07 (1H, m), 5.26 (1H, d, J=10.2 Hz), 5.46 (1H, d, J=10.1 Hz), 6.25 (1H, d, J=7.5 Hz), 6.73 (1H, d, J=7.5 Hz), 6.99-7.02 (2H, m), 7.28-7.37 (6H, m), 7.63-7.67 (2H, m).

Fifth Step

To compound 50E (105 mg, 0.280 mmol) was added trifluoroacetic acid (2 ml), and the mixture was stirred at room temperature for 30 minutes. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-methanol-ethyl ether were added, and the precipitated solid was filtered to obtain 29 mg of compound 50 as a colorless solid.

$^1$H-NMR (DMSO-d$_6$) δ: 2.99 (3H, s), 3.26-3.47 (3H, m), 4.07 (1H, d, J=11.1 Hz), 4.80 (1H, m), 6.43 (1H, d, J=6.9 Hz), 7.11-7.29 (5H, m), 7.50 (1H, d, J=6.9 Hz).

MS: m/z=285 [M+H]$^+$.

Example 51

[Chemical formula 156]

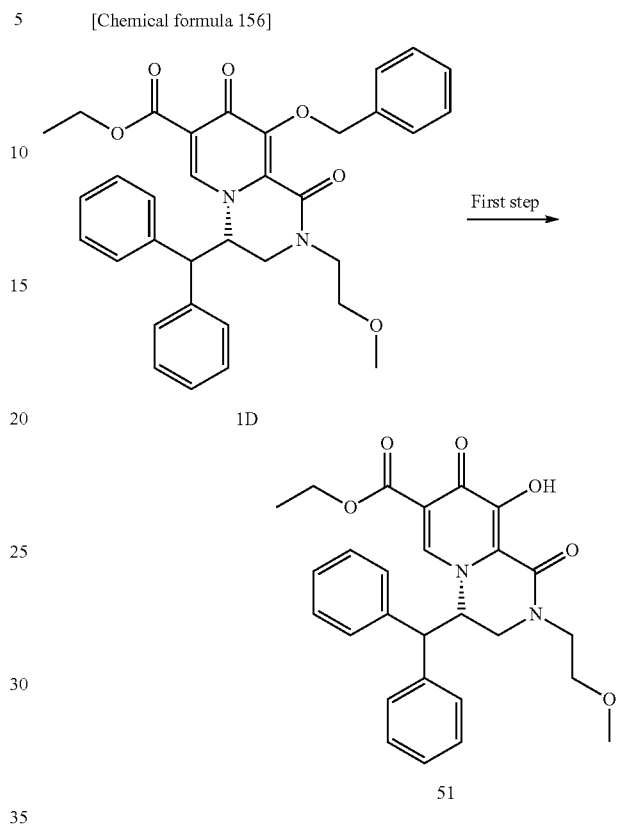

First Step

Compound 1D (60 mg, 0.11 mmol) was dissolved in trifluoroacetic acid (1 ml), and the mixture was stirred at room temperature for 1 hour. The reaction solution was distilled off, and the resulting residue was purified by LC/MS to obtain compound 51 (43 mg, 0.09 mmol).

$^1$H-NMR (DMSO-d$_6$) δ: 1.17 (3H, t, J=6.9 Hz), 3.11 (3H, s), 3.48-3.58 (2H, m), 3.95-4.12 (3H, m), 4.40 (1H, d, J=11.4 Hz), 5.59 (1H, d, J=11.4 Hz), 7.11 (1H, d, J=7.3 Hz), 7.17 (2H, t, J=7.2 Hz), 7.26 (2H, d, J=7.1 Hz), 7.30 (1H, t, J=7.3 Hz), 7.42 (2H, t, J=7.2 Hz), 7.60 (3H, m), 12.55 (1H, brs).

MS: m/z=477.2 [M+H]$^+$.

Example 52

[Chemical formula 157]

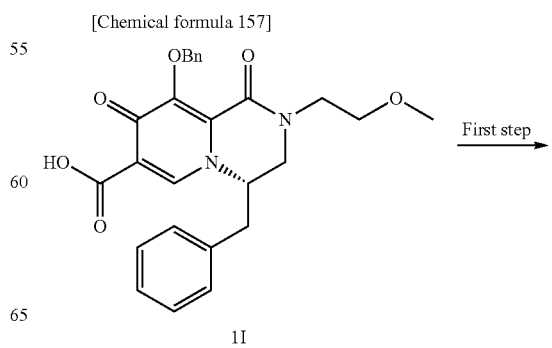

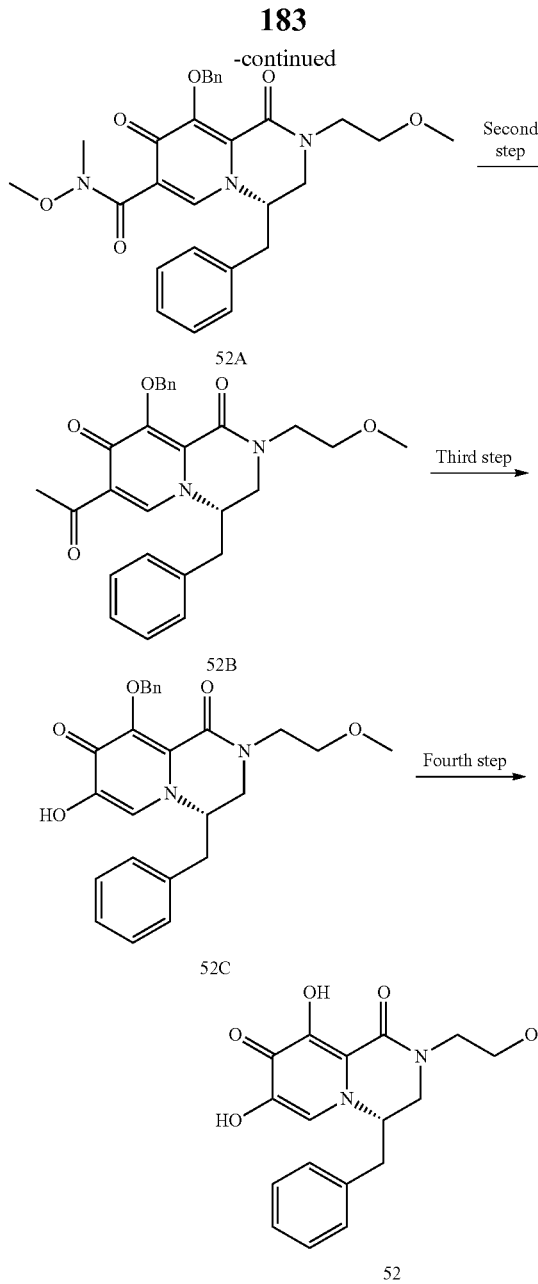

First Step

To a DMF (10 ml) solution of compound 1I (2.0 g, 4.32 mmol) were added WSC HCl (1.24 g, 6.49 mmol) and HOBt (876.9 mg, 6.49 mmol) at room temperature, and the mixture was stirred at the same temperature for 1 hour. To the reaction solution were added O,N-dimethylhydroxylamine hydrochloride (842.7 mg, 8.64 mmol) and triethylamine (2.19 g, 21.6 mmol), the mixture was stirred at the same temperature for 3 hours, thereafter, water was added, and the mixture was extracted with ethyl acetate three times. After the extract was washed with water three times, and dried with sodium sulfate, the solvent was distilled off, and the resulting oil was purified by silica gel chromatography. The materials were eluted firstly with n-hexane-ethyl acetate (7:3, v/v) and, then, with only ethyl acetate. Concentration of an objective fraction afforded 543 mg (yield 25%) of compound 52A as an oil.

MS: m/z=506 [M+H]$^+$.

Second Step

A THF (5 ml) solution of compound 52A (543 mg, 1.07 mmol) was cooled to −78° C., a methylmagnesium bromide 0.97M THF solution (1.66 ml, 1.61 mmol) was added, and temperature was raised up to −20° C. over 2 hours. To the reaction solution was added 1N hydrochloric acid, and the mixture was extracted with ethyl acetate three times. After the extract was dried with sodium sulfate, the solvent was distilled off, and the resulting oil was purified by silica gel chromatography. The materials were eluted firstly with n-hexane-ethyl acetate (7:3, v/v) and, then, with only ethyl acetate. Concentration of an objective fraction afforded 256.8 mg (yield 52%) of compound 52B as an oil.

$^1$H-NMR (CDCl$_3$) δ: 2.65 (3H, s), 3.08 (2H, d, J=7.5 Hz), 3.12 (3H, s), 3.53-3.68 (4H, m), 3.79-3.95 (1H, m), 3.92 (1H, dd, J=3.3 Hz, 13.5 Hz), 4.10-4.16 (1H, m), 5.30 (1H, d, J=10.2 Hz), 5.45 (1H, d, J=10.2 Hz), 6.99-7.02 (2H, m), 7.25-7.38 (6H, m), 7.49 (1H, s), 7.63-7.66 (2H, m).

Third Step

To a dichloromethane (4 ml) solution of compound 52B (256 mg, 0.558 mmol) was added mCPBA (144.3 mg, 0.836 mmol) under ice-cooling, and the mixture was stirred at room temperature for 2 hours. To the reaction solution was added an aqueous sodium thiosulfate solution, and the mixture was extracted with ethyl acetate three times. After the extract was washed with saturated sodium bicarbonate water two times, and dried with sodium sulfate, the solvent was distilled off, the resulting oil was dissolved in ethanol (4 ml), and a 2N-aqueous sodium hydroxide solution (1 ml) was added, followed by refluxing for 1 hour. After the solvent was distilled off, the precipitated solid was washed with diisopropyl ether to obtain 242 mg (yield 100%) of compound 52C.

$^1$H-NMR (CDCl$_3$) δ: 3.09 (2H, d, J=6.9 Hz), 3.32 (3H, s), 3.54 (1H, d, J=14.1 Hz), 3.59-3.71 (2H, m), 3.76-3.85 (1H, m), 3.92 (1H, dd, J=3.6 Hz, 13.5 Hz), 4.03 (1H, brt), 5.28 (1H, d, J=10.2 Hz), 5.47 (1H, d, J=10.2 Hz), 6.68 (1H, s), 7.00-7.04 (2H, m), 7.23-7.37 (6H, m), 7.64 (2H, d, J=6.3 Hz).

Fourth Step

To a THF (3 ml) solution of compound 52C (242 mg, 0.558 mmol) was added 10% Pd—C (50 mg), and the mixture was subjected to a catalytic reduction under hydrogen stream. The catalyst was removed by filtration, and the filtrate was concentrated. To the resulting residue was added diisopropyl ether, and the precipitated solid was filtered to obtain 60 mg (yield 31%) of compound 52.

$^1$H-NMR (CDCl$_3$) δ: 3.05 (2H, brs), 3.36 (3H, s), 3.58 (1H, d, J=12 Hz), 3.66-3.68 (2H, m), 3.74-3.75 (2H, m), 4.11-4.19 (2H, m), 6.80 (1H, brs), 6.90-7.04 (2H, m), 7.30 (3H, brs).

Example 53

[Chemical formula 158]

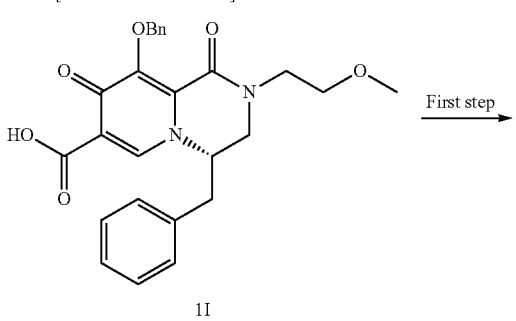

185
-continued

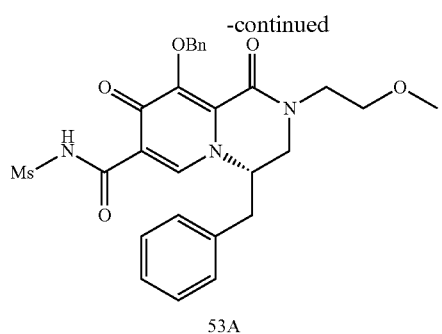

53A

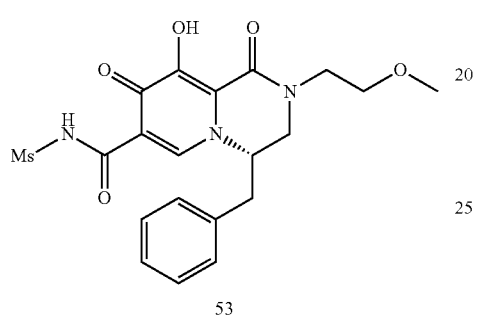

53

First Step

To a DMF (10 ml) solution of compound 1I (1.0 mg, 2.23 mmol) were added triethylamine (677 mg, 6.69 mmol) and ethyl chlorocarbonate (729 mg, 6.69 mmol) under ice-cooling, and the mixture was stirred at room temperature for 10 minutes. To the reaction solution were added methanesulfonamide (1.06 g, 11.15 mmol) and DMAP (272.4 mg, 2.23 mmol), and the mixture was heated to stir at 80° C. for 2 hours. To the reaction solution was added water, and the mixture was extracted with ethyl acetate three times. After the extract was washed with water three times, and dried with sodium sulfate, the solvent was distilled off, and the resulting oil was purified by silica gel chromatography. The materials were eluted firstly with only chloroform and, then, with chloroform-MeOH (9;1, v/v). Concentration of an objective fraction afforded 535 mg (yield 46%) of compound 53A as an oil.

MS: m/z=463 [M+H]⁺.

Second Step

To a THF (5 ml) solution of compound 53A (535 mg, 0.991 mmol) was added 10% Pd—C (218 mg), and the mixture was subjected to a catalytic reduction under hydrogen stream. The catalyst was removed by filtration, and the filtrate was concentrated. To the resulting residue was added diisopropyl ether, and the precipitated solid was filtered to obtain 235 mg (yield 53%) of compound 53.

¹H-NMR (DMSO-d₆) δ: 2.99-3.17 (2H, m), 3.27 (3H, s), 3.33 (3H, s), 3.53-3.76 (5H, m), 4.06 (1H, dd, J=3.6 Hz, 13.8 Hz), 4.98 (1H, brs), 7.14 (2H, d, J=6.6 Hz), 7.19-7.30 (3H, m), 8.07 (1H, s), 12.84 (1H, s), 13.24 (1H, s).

186

Example 54

[Chemical formula 159]

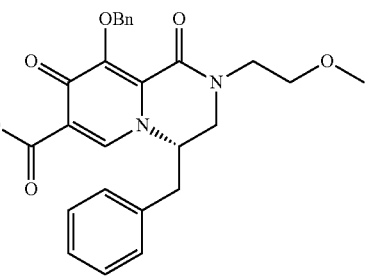

1I

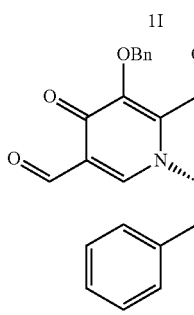

54A

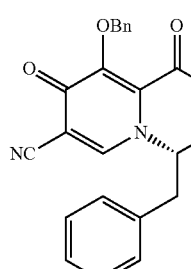

54B

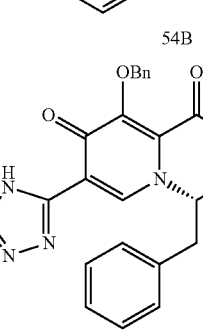

54C

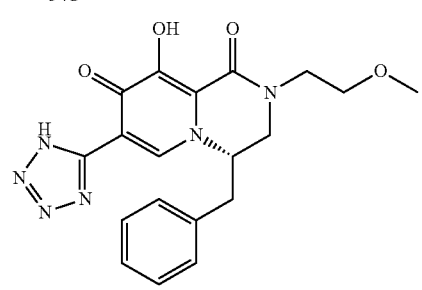

54

First Step

To a DMF (10 ml) solution of compound 1I (1.0 mg, 2.23 mmol) were added triethylamine (677 mg, 6.69 mmol) and ethyl chlorocarbonate (729 mg, 6.69 mmol) under ice-cooling, and the mixture was stirred at the same temperature for 10 minutes. The reaction solution was added dropwise to an ice-cooled solution of sodium borohydride (441 mg, 11.7 mmol) in water (5 ml), and the mixture was stirred at the same temperature for 2 hours. To the reaction solution was added 2N hydrochloric acid to stop the reaction, and the mixture was neutralized with a 2N aqueous sodium hydroxide solution, and extracted with ethyl acetate three times. After the extract was washed with water three times, and dried with sodium sulfate, the solvent was distilled off, and the resulting crude product was dissolved in dichloromethane (5 ml).

To the dichloromethane solution was added manganese dioxide (2.1 g, 24.15 mmol), and the mixture was stirred at room temperature for 6 hours. After the reaction solution was filtered, and the solvent was distilled off, the resulting oil was purified by silica gel chromatography. Elution with ethyl acetate-MeOH (9;1, v/v) and concentration of an objective fraction afforded 188 mg (yield 19%) of compound 54A.

MS: m/z=447 [M+H]$^+$.

Second Step

Compound 54A (188 mg, 0.422 mmol) was dissolved in THF (6 ml), 28% aqueous ammonia and iodine (117.7 mg, 0.464 mmol) were added at room temperature, and the mixture was stirred at the same temperature for 2 hours. To the reaction solution was added an aqueous sodium thiosulfate solution, and the mixture was extracted with ethyl acetate three times. After the extract was dried with sodium sulfate, the solvent was distilled off, and the resulting oil was purified by silica gel chromatography. Elution with ethyl acetate-MeOH (9:1, v/v) and concentration of an objective fraction afforded 54.7 mg (yield 29%) of compound 54B.

$^1$H-NMR (CDCl$_3$) δ: 3.05 (2H, d, J=7.5 Hz), 3.33 (3H, s), 3.56-3.79 (5H, m), 3.99 (1H, dd, J=3.6 Hz, 13.8 Hz), 4.08 (1H, brt), 5.33 (1H, d, J=10.2 Hz), 5.46 (1H, d, J=10.2 Hz), 6.83 (1H, s), 6.93-6.97 (2H, m), 7.25-7.37 (5H, m), 7.58-7.62 (2H, m).

Third Step

To a toluene (2 ml) solution of compound 54B (216 mg, 0.487 mmol) were added sodium azide (95 mg, 1.46 mmol) and triethylamine (201 mg, 1.46 mmol), and the mixture was stirred at room temperature for 6 hours. The reaction solution was extracted with a 2N aqueous sodium hydroxide solution two times, and the extract was neutralized with 2N hydrochloric acid, and extracted with ethyl acetate three times. After drying of the organic layer with sodium sulfate, the solvent was distilled off to obtain 65 mg (yield 27%) of compound 54C.

$^1$H-NMR (CDCl$_3$) δ: 3.08-3.21 (2H, m), 3.33 (3H, s), 3.55-3.70 (4H, m), 3.81-3.90 (1H, m), 3.96-4, 01 (1H, m), 4.51 (1H, brt), 5.31 (1H, d, J=10.2 Hz), 5.42 (1H, d, J=10.2 Hz), 7.03-7.05 (2H, m), 7.18-7.37 (6H, m), 7.58-7.61 (2H, m), 8.33 (1H, s).

Fourth Step

To a THF (2 ml)-MeOH (2 ml) solution of compound 54C (500 mg, 1.03 mmol) was added 10% Pd—C (100 mg), and the mixture was subjected to a catalytic reduction under hydrogen stream. The catalyst was removed by filtration, and the filtrate was concentrated. The resulting residue was dissolved in dichloromethane (10 ml), and the solution was extracted with a 2N aqueous sodium hydroxide solution two times. After the extract was neutralized with 2N hydrochloric acid, the mixture was extracted with ethyl acetate three times. The organic layer was dried with sodium sulfate, the solvent was distilled off, and the resulting solid was washed with diisopropyl ether, and filtered to obtain 55 mg (yield 14%) of compound 54.

$^1$H-NMR (DMSO-d$_6$) δ: 3.01-3.19 (2H, m), 3.28 (3H, s), 3.51-3.79 (5H, m), 4.09 (1H, dd, J=3.9 Hz, 13.5 Hz), 4.95 (1H, brs), 7.13-7.26 (5H, m), 8.20 (1H, s), 12.23 (1H, s).

Example 55

[Chemical formula 160]

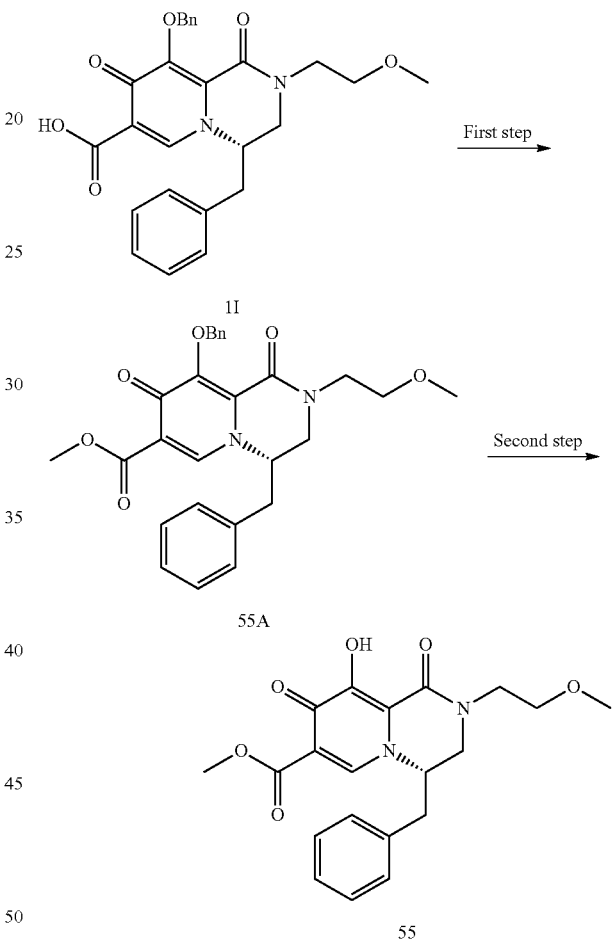

First Step

To a THF (5 ml) solution of compound 1I (500 mg, 1.08 mmol) was added a trimethylsilyldiazomethane 2M hexane solution (1 ml, 2.0 mmol) at room temperature, and the mixture was heated to 50° C., and stirred. After the solvent was distilled off, the resulting oil was purified by silica gel chromatography. Elution with n-hexane-ethyl acetate (1;1, v/v) and concentration of objective fraction afforded 115 mg (yield 22%) of compound 55A.

$^1$H-NMR (CDCl$_3$) δ: 3.06 (2H, d, J=7.5 Hz), 3.31 (3H, s), 3.51-3.72 (5H, m), 3.81 (3H, s), 3.98 (1H, dd, J=3.6 Hz), 13.5 Hz), 4.11 (1H, brt), 5.22 (1H, d, J=9.6 Hz), 5.46 (1H, d, J=9.6 Hz), 6.99-7.02 (2H, m), 7.26-7.37 (6H, m), 7.46 (1H, s), 7.65-7.69 (2H, m).

Second Step

Compound 55A (210 mg, 0.441 mmol) was dissolved in THF (2 ml), 10% Pd—C (85.7 mg) was added, and the mixture was subjected to a catalytic reduction under hydrogen stream. The catalyst was removed by filtration, and the filtrate was concentrated. The resulting residue was washed with diisopropyl ether to obtain 50 mg (yield 23%) of compound 55.

$^1$H-NMR (CDCl$_3$) δ: 1.55 (2H, d, J=7.5 Hz), 3.37 (3H, s), 3.59-3.84 (5H, m), 4.23-4.32 (2H, m), 7.00 (2H, dd, J=1.5 Hz, 6.9 Hz), 7.23-7.32 (3H, m), 7.39 (1H, s), 12.31 (1H, brs).

Example 56

[Chemical formula 161]

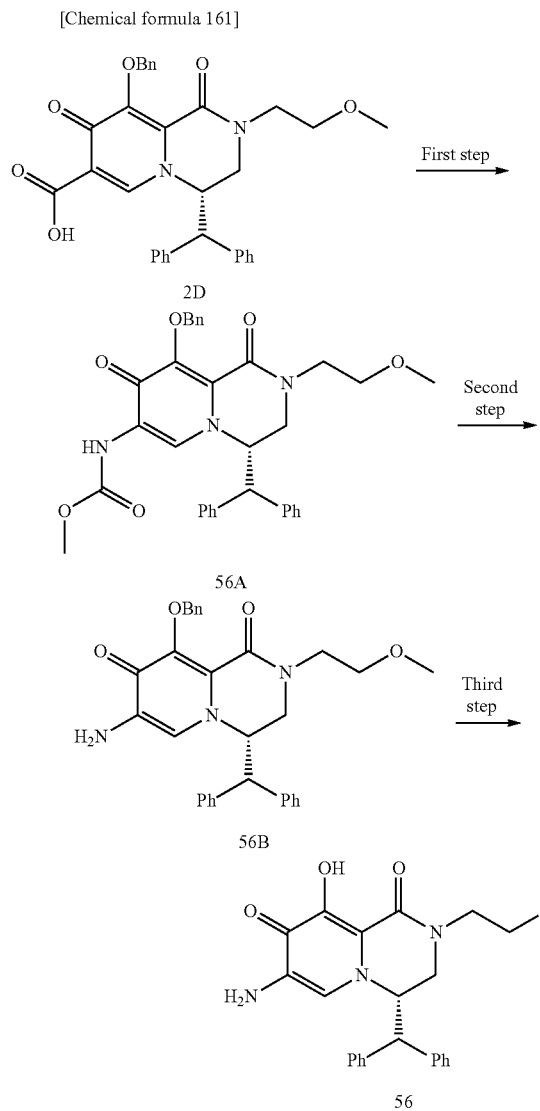

First Step

A DMF (5 ml) solution of compound 2D (424 mg, 0.787 mmol) was ice-cooled, and triethylamine (327 ul, 2.36 mmol) and, subsequently, ethyl chloroformate (150 ul, 1.57 mmol) were added. After the reaction solution was stirred at room temperature for 10 minutes, it was ice-cooled again, sodium azide (154 mg, 2.36 mmol) was added, and the mixture was stirred for 1 hour. To the reaction solution were added dichloromethane, water and a small amount of methanol, the dichloromethane layer was separated, and the aqueous layer was extracted with dichloromethane once. The combined extracts were concentrated, methanol (8 ml) was added to the resulting residue, the mixture was stirred at 50° C. for 3 hours, and the solvent was distilled off. The resulting oil was purified by silica gel column chromatography. The materials were eluted firstly with n-hexane-ethyl acetate (1:1, v/v) and, then, with only ethyl acetate. Concentration of objective fraction afforded 160 mg of compound 56A as a white solid.

$^1$H-NMR (CDCl$_3$) δ: 3.08-3.18 (4H, m), 3.35-3.49 (3H, m), 3.68 (3H, s), 3.98 (2H, dt, J=23.1, 5.6 Hz), 4.32 (1H, d, J=11.3 Hz), 4.59 (1H, d, J=11.3 Hz), 5.37 (2H, dd, J=12.0, 10.4 Hz), 6.98-7.70 (15H, m).

MS: m/z=568.25 [M+H]$^+$.

Second Step

Compound 56A (160 mg, 0.102 mmol) was dissolved in EtOH (10 mL), a 2N aqueous sodium hydroxide solution (14 ml) was added, and the mixture was stirred at 60° C. for 2 hours. After the reaction solution was concentrated under reduced pressure, the residue was distributed between dichloromethane and water. The dichloromethane layer was separated, and the aqueous layer was extracted with dichloromethane three times. The solvent was distilled off to obtain compound 56B.

$^1$H-NMR (CDCl$_3$) δ: 2.97-3.06 (1H, m), 3.15 (3H, s), 3.38-3.44 (3H, m), 3.71 (2H, s), 3.93-3.99 (2H, m), 4.35 (2H, dd, J=19.3, 11.1 Hz), 5.37 (2H, dd, J=31.6, 10.1 Hz), 6.04 (1H, s), 6.98 (2H, dd, J=6.4, 2.9 Hz), 7.17 (4H, t, J=3.3 Hz), 7.28-7.69 (12H, m).

MS: m/z=509.23 [M+H]$^+$.

Third Step

Compound 56B (56 mg, 0.11 mmol) was dissolved in TFA (3 mL), and the mixture was stirred at room temperature for 1 hour. The reaction mixture was subjected to toluene azeotropy, and the resulting residue was purified using a LCMS fractionation device. The eluted solvent was distilled off, isopropyl ether was added to the residue, and the precipitated solid was filtered. Washing with isopropyl ether and drying afforded 7 mg of compound 56.

MS: m/z=420.07 [M+H]$^+$.

Example 57

[Chemical formula 162]

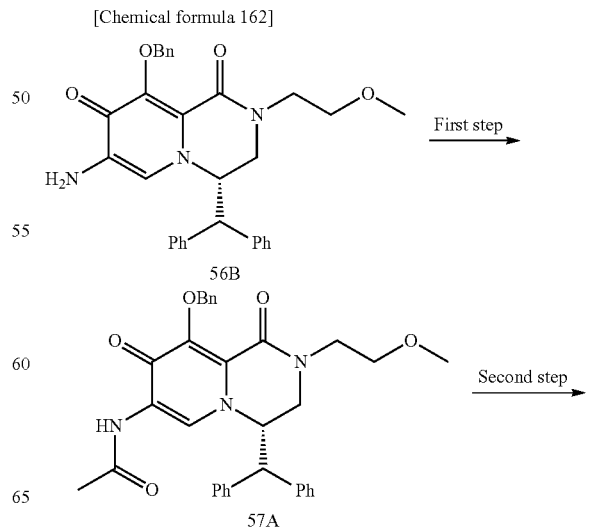

191

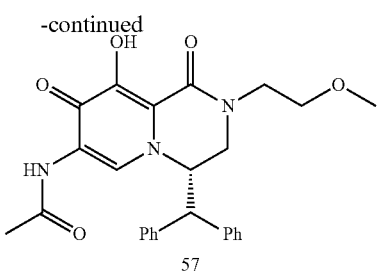

57

First Step

To a THF (1 mL) solution of compound 56B (25 mg, 0.049 mmol) were added triethylamine (20 ul, 0.015 mmol) and, subsequently, acetic acid anhydride (7.0 ul, 0.074 mmol) under ice-cooling, and the mixture was stirred at room temperature for 15 minutes. Then, 4-fluorobenzyl amine (330 mg, 1.75 mmol) was added, and the mixture was stirred for 7 hours. Further, triethylamine (20 uL, 0.15 mmol) and, subsequently, acetic acid anhydride (7.0 ul, 0.074 mmol) were added, and the mixture was stirred overnight. To the reaction solution were added water, ethyl acetate, and brine, the ethyl acetate layer was separated, and the aqueous layer was extracted with ethyl acetate. To the combined extracts was added sodium sulfate, and filtration and concentration afforded 18 mg of compound 57A as a white solid.

$^1$H-NMR (CDCl$_3$) δ: 2.05 (3H, s), 3.09-3.14 (4H, m), 3.41-3.45 (3H, m), 3.95-4.02 (2H, m), 4.31 (1H, d, J=11.4 Hz), 4.59 (1H, d, J=12.4 Hz), 5.36 (2H, s), 7.00 (2H, d, J=4.0 Hz), 7.11-7.16 (3H, m), 7.36 (7H, tt, J=14.5, 5.1 Hz), 7.62 (2H, t, J=7.3 Hz), 8.02 (1H, s), 8.18 (1H, s).

MS: m/z=552.20 [M+H]$^+$.

Second Step

Compound 57A (21 mg, 0.038 mmol) was dissolved in TFA (3 mL), and the mixture was stirred at room temperature for 3.5 hours. The reaction mixture was subjected to toluene azeotropy, isopropyl ether was added to the resulting residue, and the precipitated solid was filtered. Washing with isopropyl ether, and drying afforded 10 mg of compound 57.

$^1$H-NMR (CDCl$_3$) δ: 2.12 (3H, s), 3.20 (3H, s), 3.39-3.60 (4H, m), 3.76-3.86 (1H, m), 4.08 (1H, dd, J=13.7, 3.7 Hz), 4.31 (1H, d, J=11.5 Hz), 4.68 (1H, dd, J=8.5, 4.3 Hz), 6.96-7.19 (4H, m), 7.30-7.44 (6H, m), 8.11 (1H, s).

MS: m/z=462.20 [M+H]$^+$.

Example 58

[Chemical formula 163]

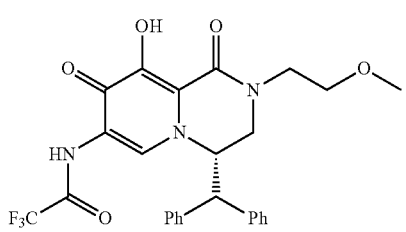

58

According to Example 57, compound 58 was synthesized by the same procedure.

$^1$H-NMR (CDCl$_3$) δ: 3.20 (3H, s), 3.41-3.54 (3H, m), 3.60-3.68 (2H, m), 3.73-3.85 (1H, m), 4.12 (1H, dt, J=14.0,

192

3.5 Hz), 4.31 (1H, d, J=11.4 Hz), 4.68 (1H, dd, J=11.4, 2.6 Hz), 6.95-7.21 (5H, m), 7.39 (5H, dt, J=26.9, 7.6 Hz), 7.94 (1H, s), 8.88 (1H, s).

MS: m/z=516.10 [M+H]$^+$.

Example 59

[Chemical formula 164]

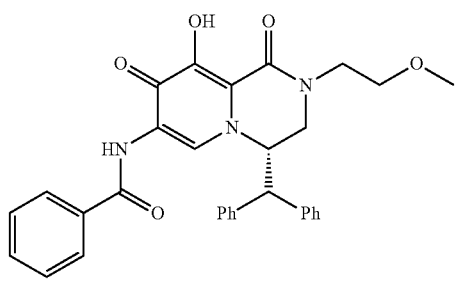

59

According to Example 57, compound 59 was synthesized by the same procedure.

$^1$H-NMR (CDCl$_3$) δ: 3.21 (3H, s), 3.43-3.63 (4H, m), 3.82 (1H, d, J=14.0 Hz), 4.12 (1H, dd, J=8.3, 4.2 Hz), 4.35 (1H, d, J=11.2 Hz), 4.74 (1H, d, J=8.3 Hz), 6.90-7.18 (5H, m), 7.34-7.60 (8H, m), 7.82 (2H, d, J=6.8 Hz), 8.34 (1H, s), 8.89 (1H, s).

MS: m/z=523.21 [M+H]$^+$.

Example 60

[Chemical formula 165]

56B

60

To compound 56B (30 mg, 0.059 mmol) were added formic acid (1.0 mL, 26 mmol) and, subsequently, a 37% formaldehyde solution (0.5 mL, 6.7 mmol), and the mixture was stirred at 100° C. for 7 hours. The reaction solution was subjected to toluene azeotropy, DMSO was added, insolubles were filtered and, thereafter, purification was performed using a LCMS fractionating device. The eluted solvent was distilled off, isopropyl ether was added to the residue, and the precipitated solid was filtered. Washing with isopropyl ether, and drying afforded 3 mg of compound 60.

$^1$H-NMR (CDCl$_3$) δ: 2.37 (6H, s), 3.18 (3H, s), 3.29-3.66 (4H, m), 3.82 (1H, d, J=12.5 Hz), 4.06-4.15 (1H, m), 4.31 (1H, d, J=11.7 Hz), 4.54 (1H, d, J=8.1 Hz), 5.97 (1H, s), 7.01 (2H, dd, J=6.4, 2.8 Hz), 7.17 (3H, t, J=2.9 Hz), 7.32-7.45 (6H, m).

MS: m/z=448.15 [M+H]$^+$.

Example 61

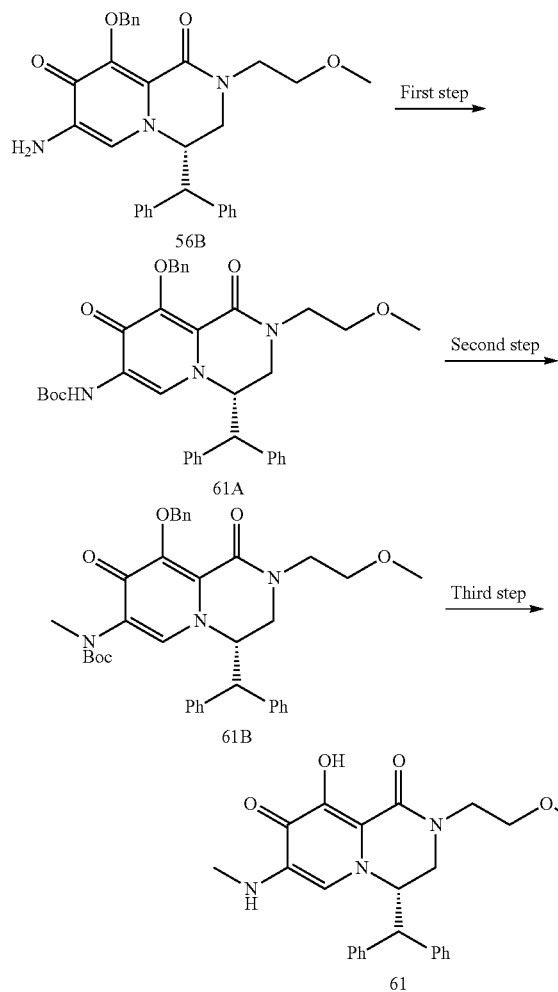

First Step

Compound 56B (50 mg, 0.098 mmol) was dissolved in THF (1 mL), Boc$_2$O (0.068 mL, 0.29 mmol) and, subsequently, DMAP (6.0 mg, 0.049 mmol) were added, and the mixture was stirred at room temperature for 5 hours. To the reaction solution were added water and ethyl acetate, the ethyl acetate layer was separated, and the aqueous layer was extracted with ethyl acetate. To the combined extracts was added sodium sulfate, the mixture was filtered, and the solvent was distilled off. The resulting residue was purified by silica gel column chromatography. Concentration of an objective fraction afforded 20 mg of compound 61A as a colorless transparent oil.

MS: m/z=610.50 [M+H]$^+$.

Second Step

Compound 61A (20 mg, 0.033 mmol) was dissolved in DMF (1 mL), sodium hydride (2.6 mg, 0.066 mmol) was added under ice-cooling, the mixture was stirred for 10 minutes, methyl iodide (4.1 uL, 0.066 mmol) was added, and the mixture was stirred at room temperature for 1.5 hours. Ice water, ethyl acetate and brine were added, the ethyl acetate layer was separated, and the aqueous layer was extracted with ethyl acetate. To the combined extracts was added sodium sulfate, the mixture was filtered, and the solvent was distilled off. The resulting residue was purified by silica gel column chromatography. Concentration of an objective fraction afforded 13 mg of compound 61B as a white solid.

MS: m/z=624.25 [M+H]$^+$.

Third Step

Compound 61B (13 mg, 0.021 mmol) was dissolved in TFA (3 mL), and the mixture was stirred at room temperature for 3 hours. The reaction mixture was subjected to toluene azeotropy, and the resulting residue was purified using a LCMS fractionating device. The eluted solvent was distilled off, isopropyl ether-hexane were added to the residue, and the precipitated solid was filtered. Washing with isopropyl ether, and drying afforded 7.5 mg of compound 61.

$^1$H-NMR (CDCl$_3$) δ: 2.19 (3H, s), 3.26 (3H, s), 3.46-3.70 (4H, m), 4.23 (1H, d, J=11.0 Hz), 4.58-4.60 (1H, br m), 5.41-5.44 (1H, br m), 6.28 (1H, br s), 6.99 (2H, br s), 7.13 (3H, br s), 7.31-7.46 (6H, m).

MS: m/z=434.10 [M+H]$^+$.

Example 62

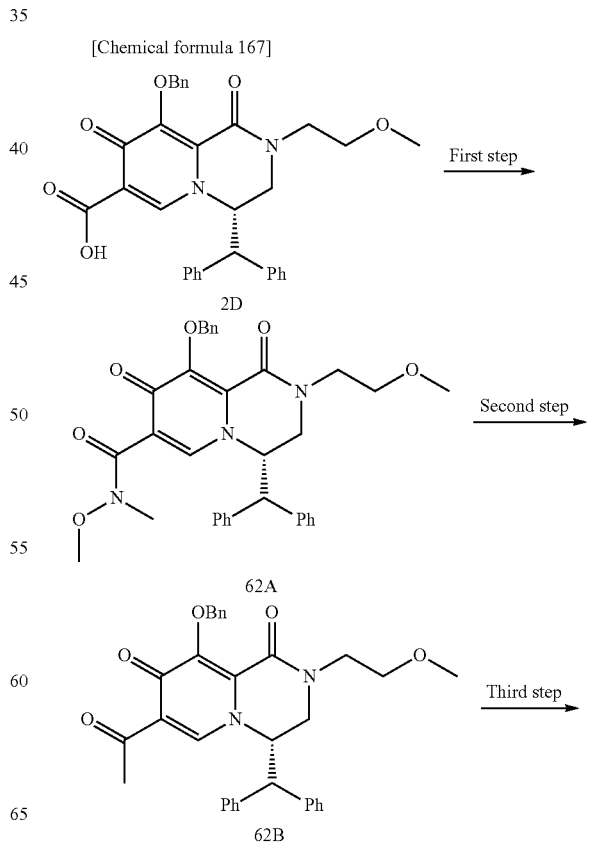

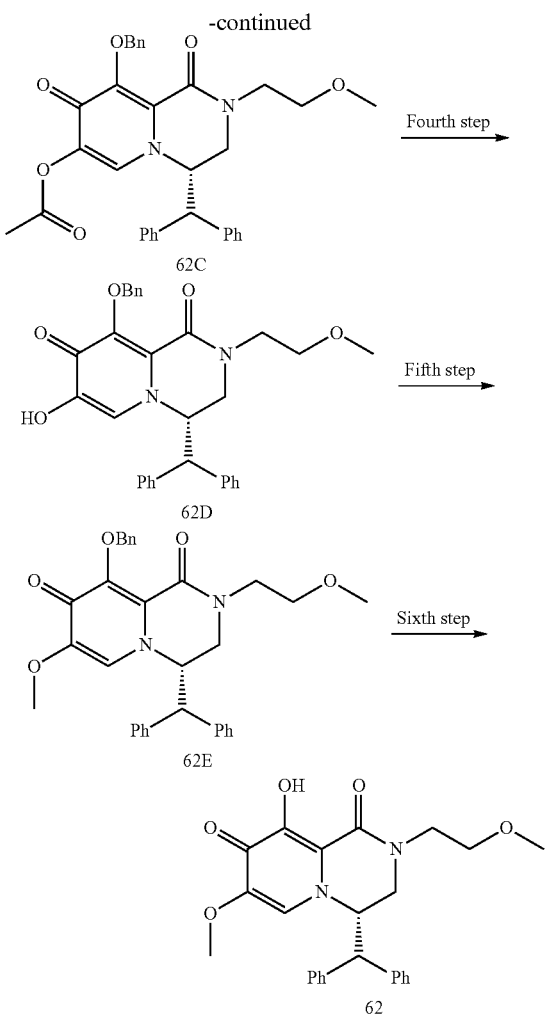

First Step

Compound 2D (112 mg, 0.208 mmol) was dissolved in DMF (2 mL), triethylamine (0.144 ml, 1.04 mmol) and, subsequently, ethyl chloroformate (0.040 mL, 0.42 mmol) were added under ice-cooling, the mixture was stirred at room temperature for 10 minutes, thereafter, N,O-dimethylhydroxyamine hydrochloride (41 mg, 0.42 mmol) and, subsequently, DMAP (3 mg, 0.02 mmol) were added, and the mixture was stirred at room temperature for 1 hour. To the reaction solution were added water, and ethyl acetate, the ethyl acetate layer was separated, and the aqueous layer was extracted with ethyl acetate. To the combined extracts was added sodium sulfate, the mixture was filtered, and the solvent was distilled off. The resulting residue was purified by silica gel column chromatography. Concentration of an objective fraction afforded 127 mg of crude purified product 62A as a yellow oil.

MS: m/z=582.20 [M+H]$^+$.

Second Step

Compound 62A (137 mg, 0.236 mmol) was dissolved in THF (8 mL), a 2M THF solution of methylmagnesium bromide (0.444 ml, 0.471 mmol) was added at −78° C. under nitrogen stream, and the mixture was stirred for 30 minutes while temperature was raised to −50° C. To the reaction solution was added IM hydrochloric acid (4 ml), the mixture was stirred at 0° C. for 20 minutes, ethyl acetate was added, the ethyl acetate layer was separated, and the aqueous layer was extracted with ethyl acetate. The combined extracts were neutralized with an aqueous saturated sodium bicarbonate solution, sodium sulfate was added to the organic layer, the mixture was filtered, and the solvent was distilled off. The resulting residue was purified by silica gel column chromatography. Concentration of an objective fraction afforded 67 mg of compound 62B as a yellow oil.

$^1$H-NMR (CDCl$_3$) δ: 2.55 (3H, s), 3.01-3.14 (1H, m), 3.16 (3H, s), 3.37-3.54 (3H, m), 3.91-4.07 (2H, m), 4.28 (1H, d, J=11.3 Hz), 4.50-4.60 (1H, m), 5.42 (2H, d, J=1.2 Hz), 6.97-6.99 (2H, m), 7.14-7.17 (4H, m), 7.31-7.45 (8H, m), 7.65 (2H, d, J=6.5 Hz).

MS: m/z=537.20 [M+H]$^+$.

Third Step

Compound 62B (67 mg, 0.13 mmol) was dissolved in dichloromethane (4 mL), mCPBA (32 mg, 0.19 mmol) was added at 0° C. under nitrogen stream, and the mixture was stirred at room temperature for 3 hours. The reaction solution was ice-cooled, an aqueous sodium thiosulfate solution, and ethyl acetate were added, the ethyl acetate layer was separated, and the aqueous layer was extracted with ethyl acetate. The combined extracts were neutralized with an aqueous saturated sodium bicarbonate solution, sodium sulfate was added to the organic layer, the mixture was filtered, and the solvent was distilled off to obtain 64 mg of compound 62C.

MS: m/z=553.23 [M+H]$^+$.

Fourth Step

Compound 62C (64 mg, 0.12 mmol) was dissolved in ethanol (8 mL), and the solution was heated to reflux for 4 hours. The reaction solution was concentrated, and the resulting residue was purified by silica gel column chromatography. Concentration of an objective fraction afforded 42 mg of compound 62D.

$^1$H-NMR (CDCl$_3$) δ: 2.93-3.09 (1H, m), 3.16 (3H, s), 3.33-3.53 (4H, m), 3.90-4.07 (2H, m), 4.29-4.47 (2H, m), 5.41 (2H, q, J=10.4 Hz), 6.34 (1H, s), 6.95-6.99 (2H, m), 7.12-7.21 (4H, m), 7.33-7.42 (8H, m), 7.64 (2H, d, J=6.9 Hz).

MS: m/z=511.21 [M+H]$^+$.

Fifth Step

Compound 62D (41 mg, 0.080 mmol) was dissolved in DMF (1 mL), sodium hydride (6.4 mg, 0.16 mmol) was added under ice-cooling, the mixture was stirred for 10 minutes, methyl iodide (0.010 ml, 0.16 mmol) was added, and the mixture was stirred at room temperature for 1.5 hours. To the reaction solution were added ice water and ethyl acetate, the ethyl acetate layer was separated, and the aqueous layer was extracted with ethyl acetate. To the combined extracts was added sodium sulfate, the mixture was filtered, and the solvent was distilled off. The resulting residue was purified by silica gel column chromatography. Concentration of an objective fraction afforded 41 mg of compound 62E as a white solid.

$^1$H-NMR (CDCl$_3$) δ: 2.99-3.09 (1H, m), 3.16 (3H, s), 3.25 (3H, s), 3.32-3.38 (1H, m), 3.42-3.50 (2H, m), 3.94-4.03 (2H, m), 4.28 (1H, d, J=11.3 Hz), 4.43 (1H, br s), 5.40 (2H, dd, J=28.3, 10.2 Hz), 6.01 (1H, s), 6.90-7.19 (5H, m), 7.28-7.44 (8H, m), 7.66 (2H, d, J=6.4 Hz).

MS: m/z=525.21 [M+H]$^+$.

Sixth Step

Compound 62E (40 mg, 0.076 mmol) was dissolved in TFA (3 mL), and the mixture was stirred at room temperature for 30 minutes. The reaction mixture was subjected to toluene azeotropy, and the resulting residue was purified using a LCMS fractionating device. The eluted solvent was distilled off, ethyl acetate-isopropyl ether-hexane were added to the residue, and the precipitated solid was filtered. Washing with isopropyl ether, and drying afforded 7.1 mg of compound 62 as a pink solid.

¹H-NMR (CDCl₃) δ: 3.17 (3H, s), 3.22 (3H, s), 3.40-3.53 (4H, m), 3.63-3.71 (1H, m), 4.24 (1H, d, J=11.5 Hz), 4.45 (1H, d, J=13.3 Hz), 4.60 (1H, d, J=11.2 Hz), 6.08 (1H, d, J=11.7 Hz), 6.96-6.99 (2H, br m), 7.13-7.17 (3H, m), 7.30-7.43 (5H, m).

MS: m/z=435.15 [M+H]⁺.

Example 63

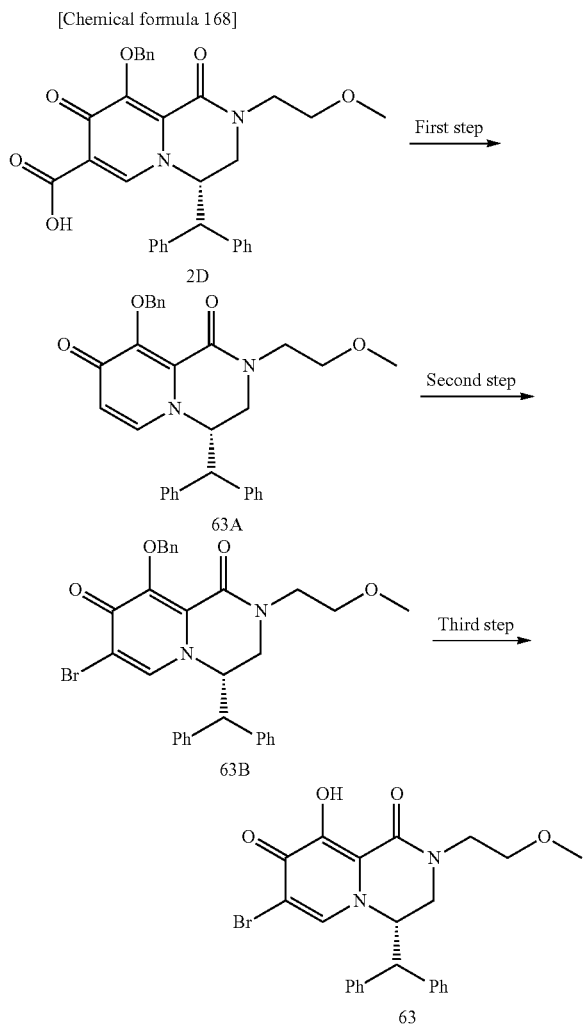

Second Step

To a dichloromethane (4 mL) solution of compound 63A (21 mg, 0.042 mmol) was added NBS (11 mg, 0.062 mmol), and the mixture was heated to reflux for 1 hour. The reaction solution was allowed to cool, and purified by silica gel column chromatography. Concentration of an objective fraction afforded 26 mg of compound 63B as a white solid.

¹H-NMR (CDCl₃) δ: 3.01-3.09 (1H, m), 3.16 (3H, s), 3.35-3.53 (3H, m), 3.92-4.47 (4H, m), 5.41 (2H, dd, J=32.6, 10.0 Hz), 6.72 (1H, s), 6.97-7.00 (2H, br m), 7.20-7.22 (3H, m), 7.30-7.46 (8H, m), 7.66-7.70 (2H, m).

MS: m/z=573.20 [M+H]⁺.

Third Step

Compound 63B (10 mg, 0.017 mmol) was dissolved in TFA (3 mL), and the mixture was stirred at room temperature for 50 minutes. The reaction mixture was subjected to toluene azeotropy, isopropyl ether was added to the resulting residue, and the precipitated solid was filtered. Washing with isopropyl ether, and drying afforded 1.4 mg of compound 63 as an orange solid.

MS: m/z=483.15 [M+H]⁺.

Example 64

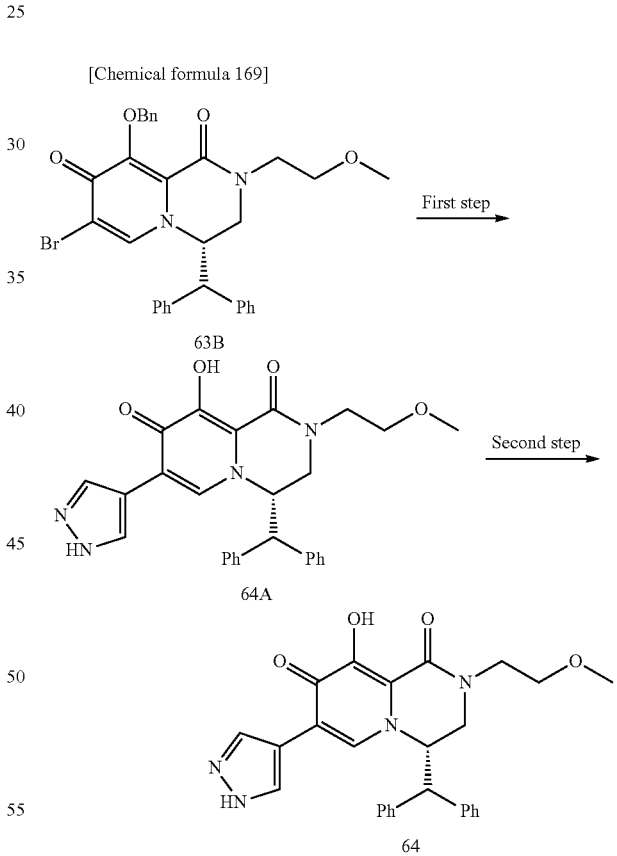

First Step

Compound 2D (164 mg, 0.304 mmol) was dissolved in diphenyl ether (1 mL), the mixture was stirred at 245° C. for 1 hour using a microwave apparatus and, thereafter, the reaction solution was purified by silica gel column chromatography. Concentration of an objective fraction afforded 72 mg of compound 63A as a brown solid.

¹H-NMR (CDCl₃) δ: 2.92-3.01 (1H, m), 3.16 (3H, s), 3.32-3.50 (3H, m), 3.90-4.46 (4H, m), 5.42 (2H, dd, J=26.1, 10.3 Hz), 5.94 (1H, d, J=7.4 Hz), 6.28 (1H, d, J=7.5 Hz), 6.96-6.99 (2H, m), 7.15-7.19 (3H, m), 7.28-7.44 (8H, m), 7.62-7.65 (2H, m).

MS: m/z=495.21 [M+H]⁺.

First Step

To a DMF solution (2 mL) of compound 63B (20 mg, 0.035 mmol) were added pyrazole-4-boronic acid pinacol ester (36 mg, 0.19 mmol) and, subsequently, potassium carbonate (29 mg, 0.21 mmol) and, thereafter, tetrakistriphenylphosphinepalladium (24 mg, 0.021 mmol) was added under nitrogen atmosphere, and the mixture was stirred at 110° C. for 8.5 hours. After the reaction solution was concentrated, ethyl acetate and methanol were added, and insolubles were removed. The filtrate was concentrated, and the resulting residue was purified by silica gel column chromatography. Concentration of an objective fraction afforded 18 mg of compound 64A as a white solid.

MS: m/z=561.30 [M+H]$^+$.

Second Step

Compound 64A (14 mg, 0.025 mmol) was dissolved in TFA (2 mL), and the mixture was stirred at room temperature for 30 minutes. The reaction mixture was subjected to toluene azeotropy, and the resulting residue was purified using a LCMS fractionating device. The eluted solvent was distilled off, isopropyl ether was added to the residue, and the precipitated solid was filtered. Washing with isopropyl ether, and drying afforded 1.1 mg of compound 64 as an orange solid.

MS: m/z=471.20 [M+H]$^+$.

Example 65

[Chemical formula 170]

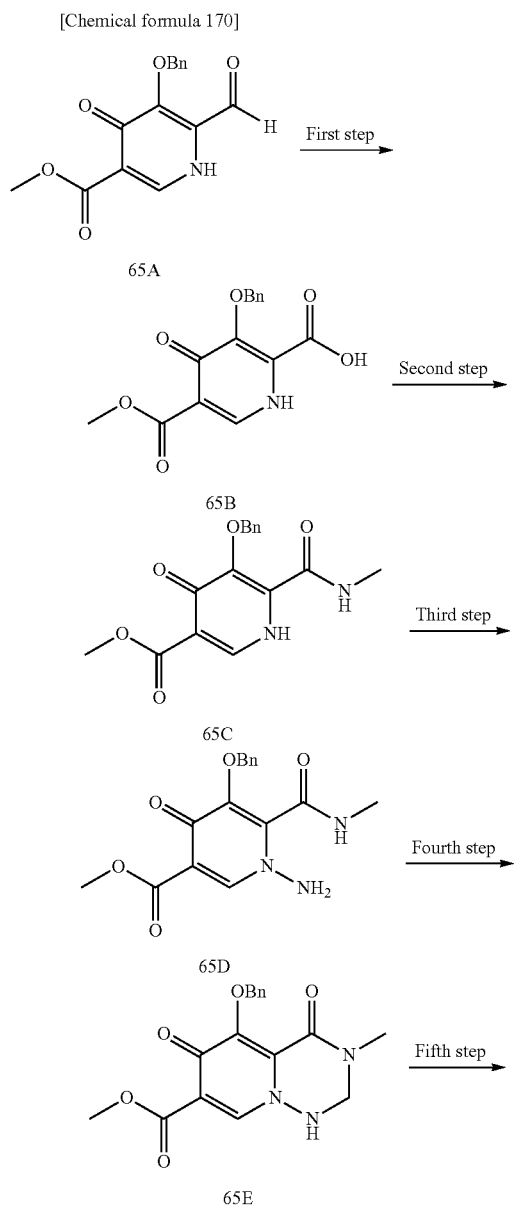

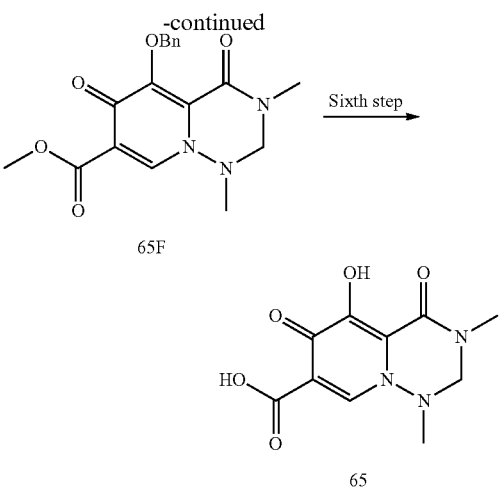

First Step

A THF (1.1 L) solution of compound 65A (WO 2006/088173, 20.0 g, 69.6 mmol) was retained at 25° C. on a water bath, an aqueous (378 mL) solution of sodium chlorite (25.2 g, 278 mmol) and amidosulfuric acid (27.0 g, 278 mmol) was added dropwise over 30 minutes. The reaction solution was stirred at the same temperature for 1 hour, and concentrated under reduced pressure. To the residue were added ice water (100 mL) and diethyl ether (100 mL), and the precipitated solid was filtered. The resulting crude purified product was washed with water and diethyl ether to obtain 20.3 g of compound 65B as a white solid.

$^1$H-NMR (DMSO-d$_6$) δ: 3.74 (3H, s), 5.11 (2H, s), 7.31-7.38 (3H, m), 7.48 (2H, d, J=7.2 Hz), 8.11 (1H, s), 12.07 (1H, brs).

Second Step

Compound 65B (2.0 g, 6.59 mmol) was dissolved in DMF (340 mL), HATU (2.76 g, 7.25 mmol), methylamine (2 mol/L, THF solution, 3.63 mL, 7.25 mmol) and triethylamine (9.89 mmol) were added, and the mixture was stirred at room temperature for 5 hours. The reaction solution was distributed between ethyl acetate and water, the ethyl acetate layer was separated. and the aqueous layer was extracted with ethyl acetate once. The combined extracts were washed with water and an aqueous saturated sodium chloride solution, and dried. The solvent was distilled off to obtain 1.66 g of a crude purified product of compound 65C as a white solid.

$^1$H-NMR (DMSO-d$_6$) δ: 3.38 (3H, brs), 3.75 (3H, s), 5.37 (2H, s), 7.34-7.44 (5H, m), 8.10 (1H, s), 8.38 (1H, s), 11.84 (1H, brs).

Third Step

To a DMF (20 mL) solution of compound 65C (1.2 g, 3.79 mmol) were added potassium carbonate (1.04 g, 7.59 mmol) and O-(2,4-dinitrophenyl)hydroxylamine (831 mg, 4.17 mmol), and the mixture was stirred at room temperature for 3 hours. To the reaction solution was added water, and the precipitated solid was filtered, and washed with water to obtain 1.0 g of a crude purified product of compound 65D.

$^1$H-NMR (DMSO-d$_6$) δ: 3.74 (3H, s), 3.83 (3H, brs), 5.05 (2H, s), 6.46 (2H, brs), 7.31-7.38 (5H, m), 8.20 (1H, s), 8.52 (1H, brs).

Fourth Step

To a DMF (10 mL) solution of compound 65D (1.0 g, 3.02 mmol) were added paraformaldehyde (109 mg, 3.62 mmol) and acetic acid (0.017 ml, 0.302 mmol) at room temperature, and the mixture was stirred at 105° C. for 2 hours. The reaction solution was cooled to 0° C., cesium carbonate (3.44 g, 10.6 mmol) was added, and the mixture was stirred at room temperature for 1 hour. To the reaction solution was added water, and the mixture was distributed between ethyl acetate and water. The organic layer was washed with an aqueous saturated sodium chloride solution, and dried. The solvent was distilled off to obtain 120 mg of compound 65E.

MS: m/z=344 [M+H]$^+$.

Fifth Step

To a DMF (1 mL) solution of compound 65E (17.0 mg, 0.05 mmol) were added cesium carbonate (81.4 mg, 0.25 mmol) and methylamine (2 mol/L THF solution, 0.125 ml, 0.25 mmol), and the mixture was stirred at room temperature for 5 hours. The reaction solution was filtered, and the filtrate was fractionated and purified by LCMS to obtain compound 65F.

MS: m/z=358 [M+H]$^+$.

Sixth Step

To a DMF (0.5 mL) solution of compound 65F was added a 2N aqueous sodium hydroxide solution (0.2 mL), and the mixture was stirred at room temperature for 2 hours. To the reaction solution was added ion-exchange resin DOWEX (50W-X8), and the mixture was filtered, and washed with DMF. After concentration of the filtrate, trifluoroacetic acid (0.5 mL) was added, and the mixture was stirred at 80° C. for 4 hours. After concentration of the reaction solution, water and chloroform were added, and the organic layer was separated. The organic layer was concentrated, and fractionation-purified by LCMS to obtain 6.47 mg of compound 65.

MS: m/z=254 [M+H]$^+$.

According to Example 65, the following compounds were synthesized by the same procedure.

TABLE 1

| Example | Structure | MS |
|---|---|---|
| Example 66 | 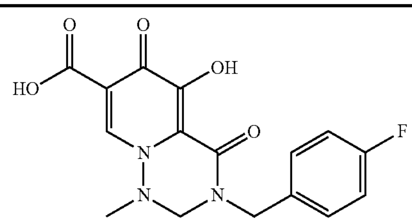 | 348 |
| Example 67 | 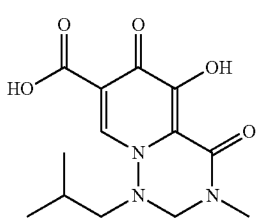 [SMILES: CC(C)CN1CN(C)C(=O)c2c(O)c(=O)c(C(=O)O)cn21] | 296 |
| Example 68 | 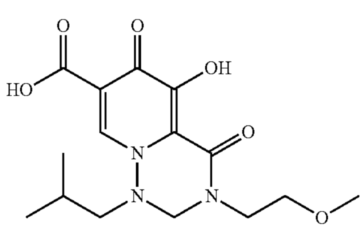 [SMILES: COCCN1CN(CC(C)C)n2cc(C(=O)O)c(=O)c(O)c2C1=O] | 340 |

TABLE 1-continued

| Example | Structure | MS |
|---|---|---|
| Example 69 | 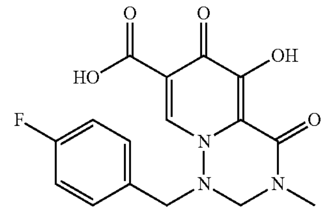 [SMILES: CN1CN(Cc2ccc(F)cc2)n2cc(C(=O)O)c(=O)c(O)c2C1=O] | 348 |
| Example 70 | 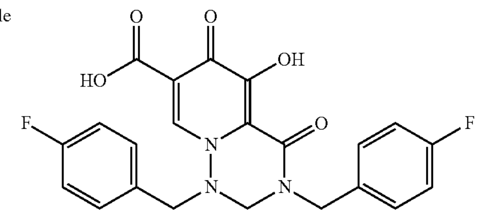 | 442 |
| Example 71 | 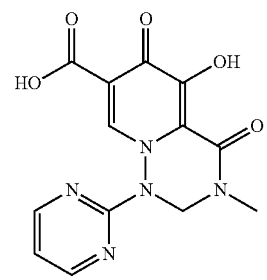 [SMILES: CN1CN(c2ncccn2)n2cc(C(=O)O)c(=O)c(O)c2C1=O] | 318 |

TABLE 2

| Example | Structure | MS |
|---|---|---|
| Example 72 | 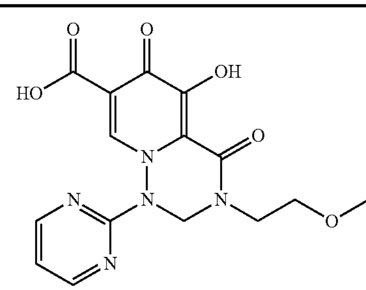 | 362 |
| Example 73 | 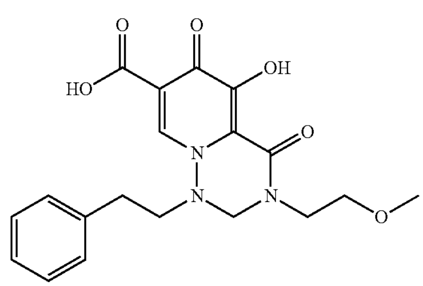 [SMILES: COCCN1CN(CCc2ccccc2)n2cc(C(=O)O)c(=O)c(O)c2C1=O] | 388 |

TABLE 2-continued

| Example | Structure | MS |
|---|---|---|
| Example 74 | 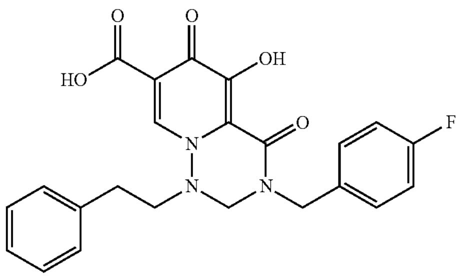 [SMILES: O=C(O)c1cn2c(c(O)c1=O)C(=O)N(Cc1ccc(F)cc1)CN2CCc1ccccc1] | 438 |
| Example 75 | 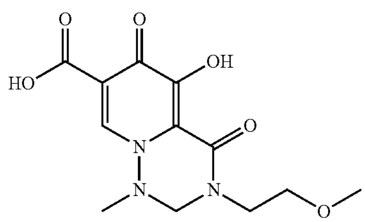 [SMILES: COCCN1CN(C)n2cc(C(=O)O)c(=O)c(O)c2C1=O] | 298 |
| Example 76 | 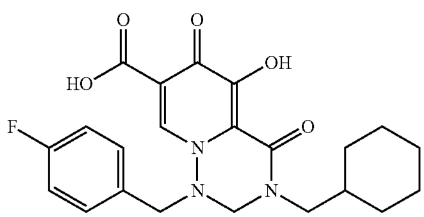 [SMILES: O=C(O)c1cn2c(c(O)c1=O)C(=O)N(CC1CCCCC1)CN2Cc1ccc(F)cc1] | 430 |
| Example 77 | 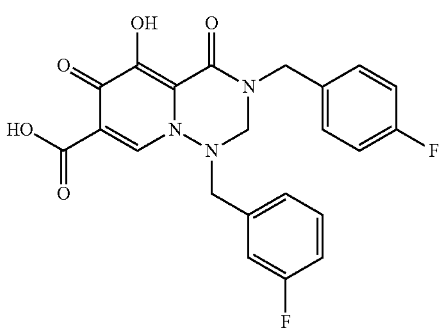 [SMILES: O=C(O)c1cn2c(c(O)c1=O)C(=O)N(Cc1ccc(F)cc1)CN2Cc1cccc(F)c1] | 442 |

TABLE 3

| Example | Structure | MS |
|---|---|---|
| Example 78 | | 442 |
| Example 79 | 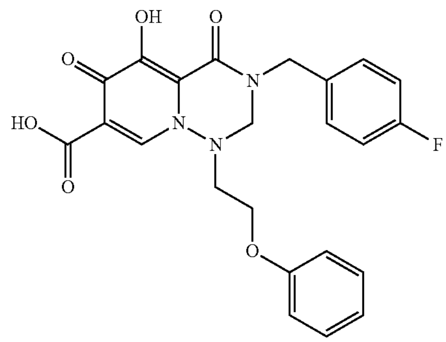 [SMILES: O=C(O)c1cn2c(c(O)c1=O)C(=O)N(Cc1ccc(F)cc1)CN2CCOc1ccccc1] | 454 |
| Example 80 | 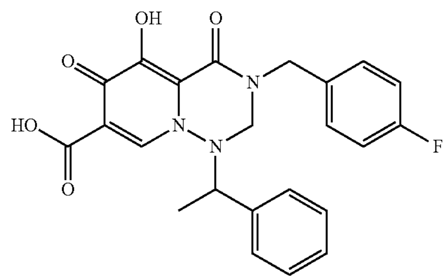 [SMILES: CC(c1ccccc1)N1CN(Cc2ccc(F)cc2)C(=O)c2c(O)c(=O)c(C(=O)O)cn21] | 438 |
| Example 81 | 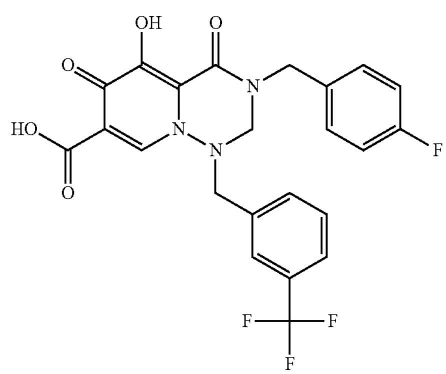 [SMILES: O=C(O)c1cn2c(c(O)c1=O)C(=O)N(Cc1ccc(F)cc1)CN2Cc1cccc(C(F)(F)F)c1] | 492 |
| Example 82 | 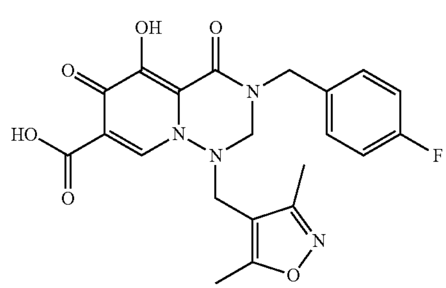 [SMILES: Cc1noc(C)c1CN1CN(Cc2ccc(F)cc2)C(=O)c2c(O)c(=O)c(C(=O)O)cn21] | 443 |

TABLE 4
| Example | Structure | MS |
|---|---|---|
| Example 83 | 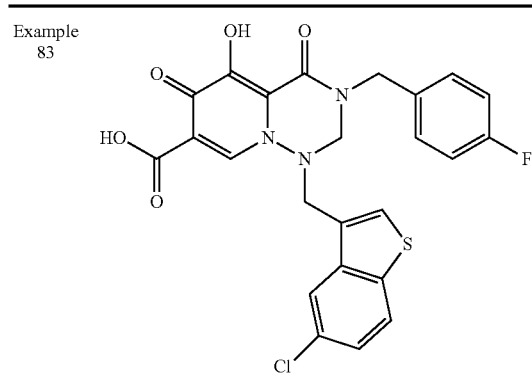 | 513 |
| Example 84 | 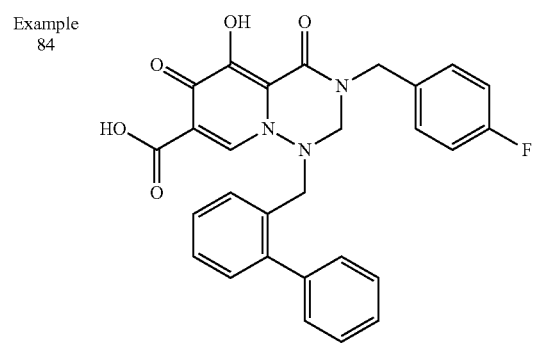 | 500 |
| Example 85 | 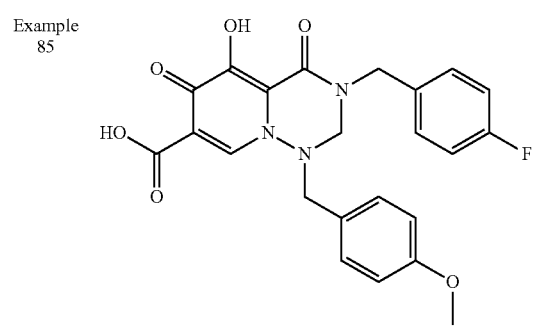 | 454 |
| Example 86 | 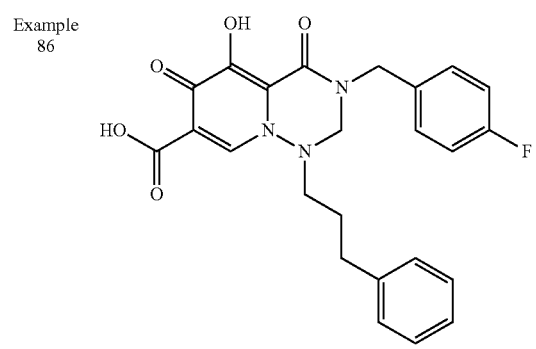 | 452 |
TABLE 4-continued
| Example | Structure | MS |
|---|---|---|
| Example 87 | 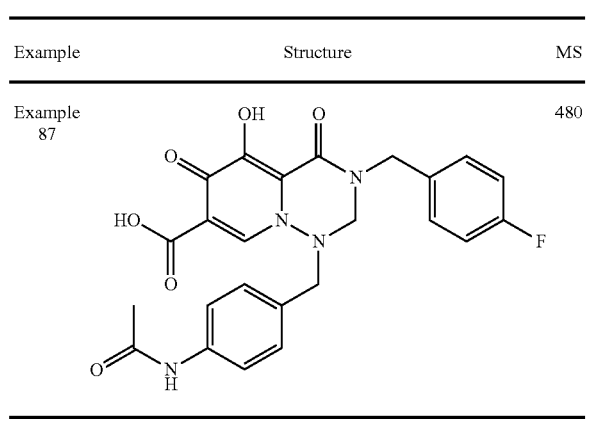 | 480 |
TABLE 5
| Example | Structure | MS |
|---|---|---|
| Example 88 | 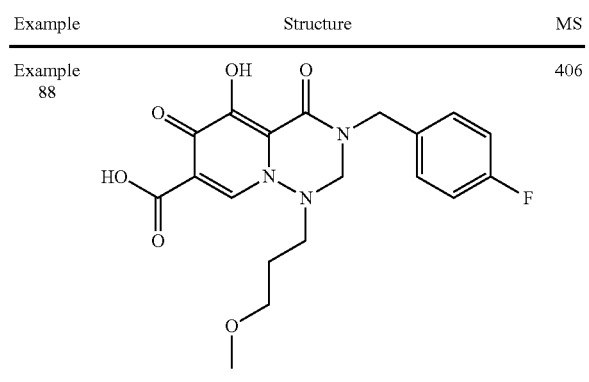 | 406 |
| Example 89 | 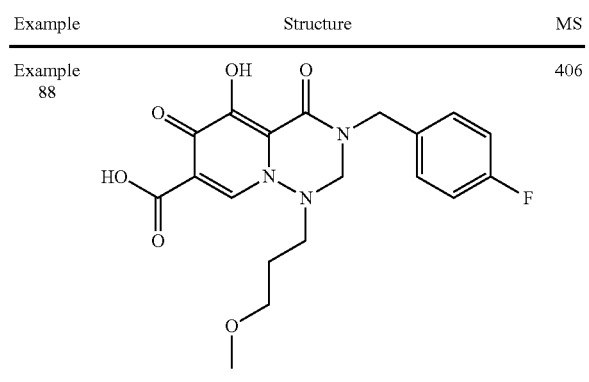 | 445 |
| Example 90 | 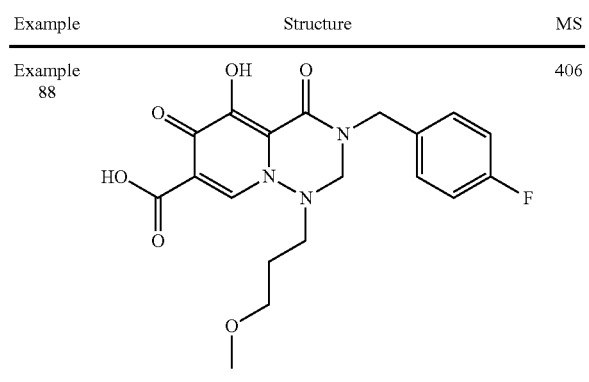 | 500 |

TABLE 5-continued

| Example | Structure | MS |
|---------|-----------|-----|
| Example 91 | 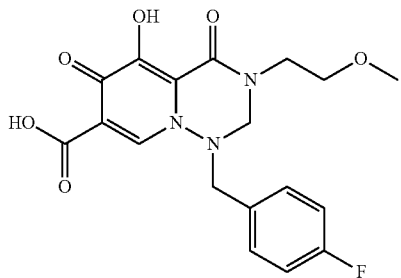 | 416 |
| Example 92 | 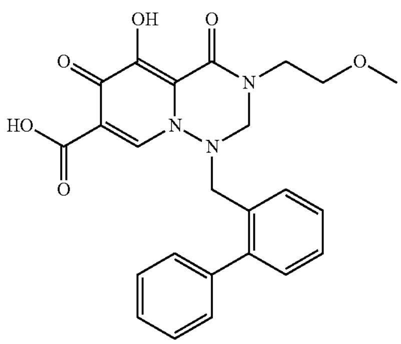 [SMILES: COCCN1CN(Cc2ccccc2-c2ccccc2)n2cc(C(=O)O)c(=O)c(O)c2C1=O] | 450 |

[Chemical formula 171]

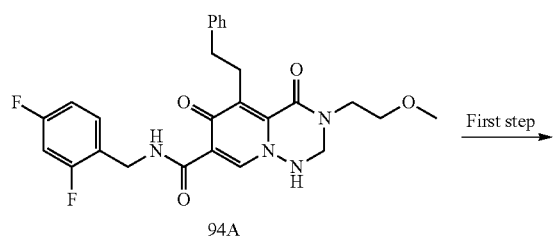

93

According to Example 65, compound 93 was synthesized by the same procedure.

$^1$H-NMR (CDCl$_3$) δ: 3.34 (3H, s), 3.57-3.68 (2H, m), 3.73 (2H, br s), 4.18 (2H, s), 4.75 (2H, br s), 7.06-7.12 (2H, m), 7.21-7.24 (2H, m), 8.10 (1H, s), 11.96 (1H, br s), 14.52 (1H, brs).

Example 94

[Chemical formula 172]

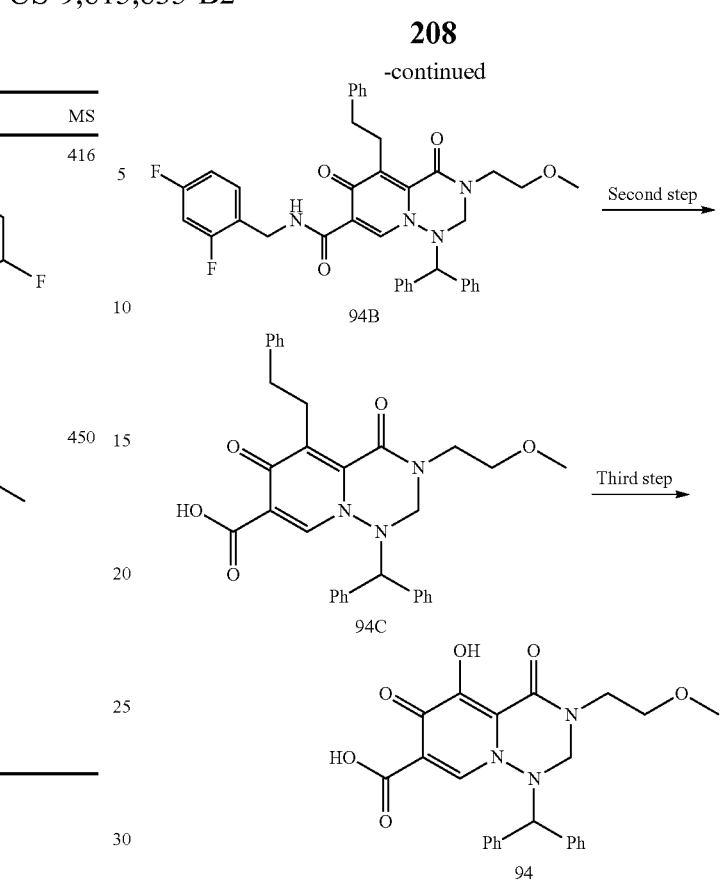

First Step

Using compound 94A (WO 2007/049675), and according to the same procedure as that of the fifth step of Example 65, compound 94B was synthesized.

$^1$H-NMR (CDCl$_3$) δ: 3.00-3.09 (1H, m), 3.18 (3H, s), 3.44 (2H, dd, J=7.55, 2.82 Hz), 4.02-4.08 (1H, m), 4.44-4.59 (3H, m), 4.86 (1H, d, J=13.57 Hz), 5.25 (1H, s), 5.36 (2H, dd, J=14.87, 9.99 Hz), 6.74-6.84 (2H, m), 7.09-7.60 (16H, m), 7.90 (1H, s), 10.07 (1H, t, J=5.87 Hz).

Second Step

To a MeCN (20 ml) solution of compound 94B (1.1 g, 1.655 mmol) were added DMAP (202 mg, 1.655 mmol) and Boc$_2$O (20 ml, 86 mmol) at room temperature under nitrogen stream, and the mixture was heated to reflux for 5 hours. Further, Boc$_2$O (20 ml, 86 mmol) was added, and the mixture was heated to reflux for 5 hours. After concentration under reduced pressure, to the residue were added ethanol (20.00 ml) and an aqueous sodium hydroxide solution (40%, 25 ml), and the mixture was stirred at room temperature for 5 hours. To the reaction mixture were added ethyl acetate-water to make the aqueous layer acidic. After extraction with ethyl acetate (2×200 mL), the organic layer was washed with an aqueous saturated sodium chloride solution. After drying with magnesium sulfate, the solvent was distilled off under reduced pressure. The crude product was purified by silica gel column chromatography (CHCl$_3$/MeOH 20:1) to obtain compound 94C. (750 mg, 63%)

$^1$H-NMR (DMSO-d$_6$) δ: 3.13 (3H, s), 3.25-3.34 (3H, m), 3.79 (1H, d, J=13.73 Hz), 4.42 (1H, d, J=14.03 Hz), 5.11-5.27 (3H, m), 5.48 (1H, s), 7.18-7.21 (5H, m), 7.33-7.49 (6H, m), 7.56-7.58 (2H, m), 7.74 (2H, d, J=7.32 Hz), 8.01 (1H, s).

Third Step

Using compound 94C, and according to the same procedure as that of the tenth step of Example 12, compound 94 was synthesized.

$^1$H-NMR (DMSO-$d_6$) δ: 3.13 (3H, s), 3.41-3.56 (4H, m), 4.50 (1H, d, J=13.57 Hz), 5.21 (1H, d, J=13.42 Hz), 5.58 (1H, s), 7.16-7.50 (8H, m), 7.72 (2H, d, J=7.32 Hz), 7.93 (1H, s), 12.12 (1H, s).

Example 95

[Chemical formula 173]

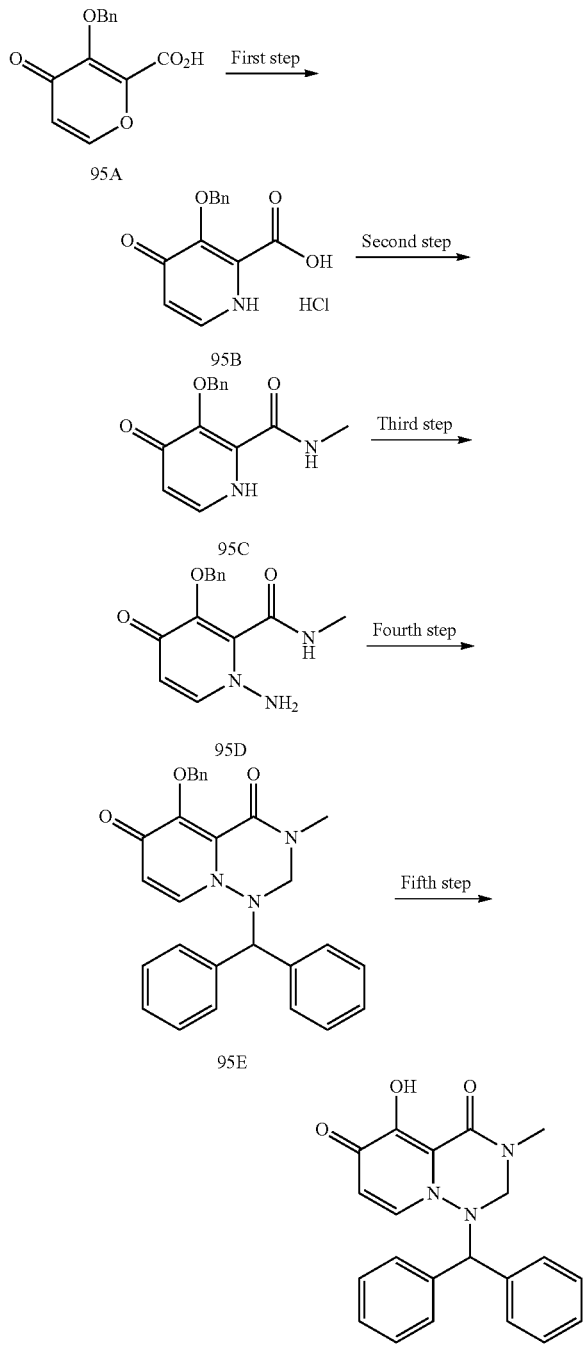

First Step

Compound 95A (WO 2006/116764, 1 g, 4.06 mmol) was dissolved in 28% aqueous ammonia, and the solution was stirred at room temperature for 12 hours. After concentration of the reaction solution, the resulting residue was neutralized with 2N hydrochloric acid, and the precipitated solid was suspended in ethyl acetate, filtered, and dried to obtain 1.14 g (yield 100%) of compound 95B.

$^1$H-NMR (DMSO-$d_6$) δ: 5.14 (2H, s), 7.31 (1H, d, J=6.6 Hz), 7.34-7.41 (3H, m), 7.45-7.51 (2H, m), 8.17 (1H, d, J=6.6 Hz).

Second Step

To a DMF (10 ml) solution of compound 95B (3.00 g, 10.65 mmol) were added WSC HCl (3.06 g, 15.98 mmol) and HOBt (1.58 g, 11.7 mmol) at room temperature, the mixture was stirred for 10 minutes, and a methylamine 33 wt % ethanol solution (1.50 g, 15.98 mmol) was added dropwise. After the reaction solution was stirred at the same temperature for 2 hours, water was added, and the mixture was extracted with chloroform five times. The extract was dried with sodium sulfate, the solvent was distilled off, and the resulting oil was purified by silica gel chromatography. From a fraction eluted with ethyl acetate-MeOH (6:4, v/v), 2.62 g (yield 95%) of compound 95C was obtained as a solid.

$^1$H-NMR (CDCl$_3$) δ: 2.77 (3H, d, J=4.8 Hz), 5.49 (2H, s), 6.57 (1H, d, J=6.9 Hz), 7.25-7.43 (5H, m), 7.48 (1H, t, J=6.0 Hz), 8.23 (1H, brs), 9.77 (1H, brs).

Third Step

Into a DMF (10 ml) solution of compound 95C (2.62 g, 10.14 mmol) was suspended potassium carbonate (4.20 g, 30.42 mmol) at room temperature, the suspension was stirred for 5 minutes, O-(2,4-dinitrophenyl)hydroxylamine (3.03 g, 15.21 mmol) was added, and the mixture was stirred at the same temperature for 3 hours. To the reaction solution was added water, the mixture was extracted with chloroform five times, and the extract was dried with sodium sulfate. After the solvent was distilled off, the resulting oil was purified by silica gel chromatography. From a fraction eluted with ethyl acetate-MeOH (6:4, v/v), 1.41 g (yield 51%) of compound 95D was obtained as a solid.

$^1$H-NMR (CDCl$_3$) δ: 2.62 (3H, d, J=5.1 Hz), 5.06 (2H, s), 5.22 (2H, s), 6.18 (1H, d, J=7.8 Hz), 7.25-7.36 (5H, m), 5.89 (1H, d, J=7.8 Hz), 7.57 (1H, q, J=5.1 Hz).

Fourth Step

A toluene (10 ml) solution of compound 95D (1.0 g, 3.66 mmol) were added paraformaldehyde (109.9 mg, 3.66 mmol) and acetic acid (22 mg, 0.37 mmol), and the mixture was heated to stir at 100° C. for 40 minutes. After cooling, the solvent was distilled off, the residue was dissolved in DMF (10 ml) without purification, cesium carbonate (3.58 g, 10.98 mmol) was added under ice-cooling, and the mixture was stirred for 10 minutes. To the reaction solution was added benzohydryl bromide (1.36 g, 5.49 mmol), the mixture was stirred at room temperature for 3 hours, water was added, and the mixture was extracted with ethyl acetate three times. The extract was washed with water three times, and dried with sodium sulfate. The solvent was distilled off, and the resulting oil was purified by silica gel chromatography. From a fraction eluted with ethyl acetate-MeOH (9:1, v/v), 1.26 g (yield 71%) of compound 95E was obtained as a solid.

$^1$H-NMR (CDCl$_3$) δ: 2.91 (3H, s), 4.26 (1H, d, J=13.2 Hz), 4.77 (1H, d, J=13.2 Hz), 5.12 (1H, s), 5.42 (1H, J=13.2 Hz), 5.45 (1H, d, J=13.2 Hz), 5.82 (1H, J=7.5 Hz), 6.71 (1H, d, J=7.5 Hz), 7.10-7.23 (5H, m), 7.27-7.46 (6H, m), 7.52 (2H, d, J=6.9 Hz), 7.60-7.64 (2H, m).

Fifth Step

Compound 95E (100 mg, 0.221 mmol) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 50 mg (yield 63%) of compound 95.

$^1$H-NMR (CDCl$_3$) δ: 2.95 (3H, s), 4.36 (1H, d, J=13.2 Hz), 4.95 (1H, d, J=13.2 Hz), 5.22 (1H, s), 5.71 (1H, d, J=7.8 Hz), 6.75 (1H, d, J=7.8 Hz), 7.21 (5H, br s), 7.33-7.47 (4H, m), 7.55 (2H, d, J=6.6 Hz).

According to Example 95, the following compounds were synthesized by the same procedure.

Example 96

[Chemical formula 174]

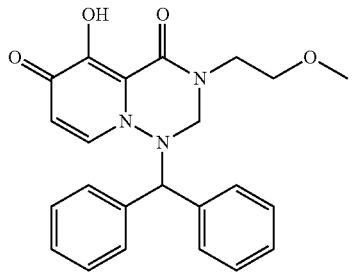

96

$^1$H-NMR (CDCl$_3$) δ: 3.12-3.18 (1H, m), 3.21 (3H, s), 3.38-3.52 (2H, m), 3.81 (1H, ddd, J=3.3 Hz, 4.2 Hz, 14.1 Hz), 4.52 (1H, d, J=13.2 Hz), 5.00 (1H, d, J=13.2 Hz), 5.28 (1H, s), 5.71 (1H, d, J=7.8 Hz), 6.74 (1H, d, J=7.8 Hz), 7.14-7.21 (5H, m), 7.32-7.46 (3H, m), 7.53 (2H, d, J=7.5 Hz).

Example 97

[Chemical formula 175]

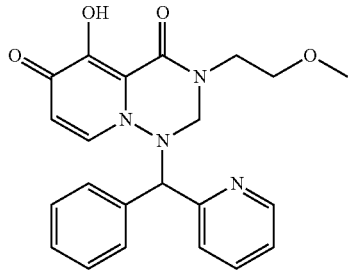

97

$^1$H-NMR (CDCl$_3$) δ: 2.99-3.06 (0.54H, m), 3.18-3.23 (3.9H, m), 3.42-3.54 (2.5H, m), 3.86-3.91 (0.42H, m), 4.03-4.08 (0.58H, m), 4.37 (0.58H, d, J=13.5 Hz), 4.54 (0.42H, d, J=13.8 Hz), 4.98 (0.58H, d, J=13.5 Hz), 5.08 (0.42H, d, J=13.8 Hz), 5.36 (0.58H, s), 5.43 (0.42H, s), 5.70-5.77 (1H, m), 6.77 (0.42H, d, J=7.5 Hz), 6.94 (0.58H, d, J=7.8 Hz), 7.08-7.53 (6H, m), 7.60-7.78 (2H, m), 8.55 (0.58H, d, J=4.2 Hz), 8.72 (0.42H, d, J=3.9 Hz).

Example 98

[Chemical formula 176]

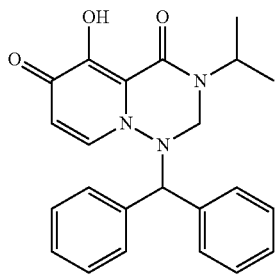

98

$^1$H-NMR (CDCl$_3$) δ: 0.930 (3H, d, J=6.9 Hz), 1.09 (3H, d, J=6.9 Hz), 4.58 (1H, d, J=12.6 Hz), 4.79 (1H, d, J=12.6 Hz), 4.83-4.90 (1H, m), 5.20 (1H, s), 5.67 (1H, d, J=7.5 Hz), 6.66 (1H, d, J=7.5 Hz), 7.07-7.09 (2H, m), 7.13-7.19 (3H, m), 7.34-7.46 (3H, m), 7.52 (1H, d, J=7.5 Hz).

Example 99

[Chemical formula 177]

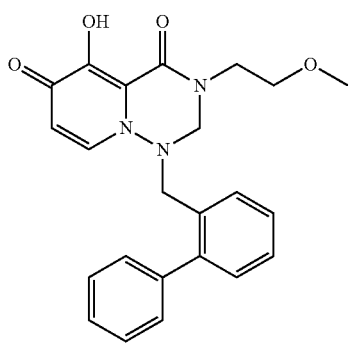

99

$^1$H-NMR (CDCl$_3$) δ: 3.30 (3H, s), 3.49 (1H, brs), 3.54-3.56 (2H, m), 3.73 (1H, brs), 4.11 (2H, brs), 4.25 (1H, brs), 4.78 (1H, brs), 6.00 (1H, d, J=7.5 Hz), 8.33 (1H, d, J=7.5 Hz), 7.19-7.24 (3H, m), 7.34-7.37 (2H, m), 7.38-7.48 (4H, m).

Example 100

[Chemical formula 178]

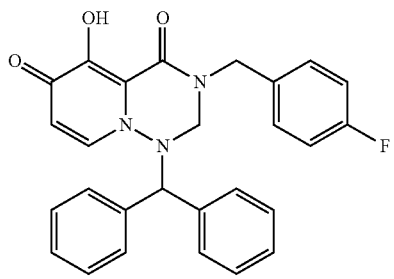

¹H-NMR (CDCl₃) δ: 4.32 (1H, d, J=14.7 Hz), 4.41 (1H, d, J=12.9 Hz), 4.69 (1H, d, J=14.7 Hz), 4.88 (1H, d, J=12.9 Hz), 4.97 (1H, s), 5.68 (1H, d, J=7.5 Hz), 6.70 (1H, d, J=7.5 Hz), 6.91-6.98 (2H, m), 7.05-7.08 (2H, m), 7.12-7.20 (7H, m), 7.30-7.32 (4H, m).

Example 101

[Chemical formula 179]

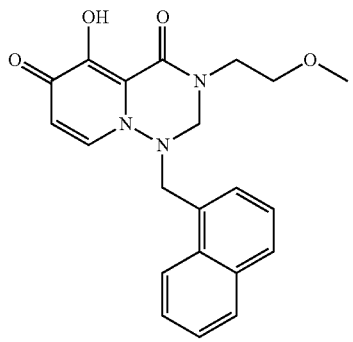

¹H-NMR (CDCl₃) δ: 3.35 (3H, s), 3.66-3.69 (3H, m), 3.89 (1H, brs), 4.51 (1H, brs), 4.64 (2H, brs), 5.05 (1H, brs), 5.89 (1H, d, J=7.5 Hz), 6.58 (1H, d, J=7.5H), 7.11 (1H, d, J=7.2 Hz), 7.26-7.40 (1H, m), 7.54-7.62 (2H, m), 7.86-7.93 (2H, m), 8.13 (1H, d, J=8.4 Hz).

[Chemical formula 180]

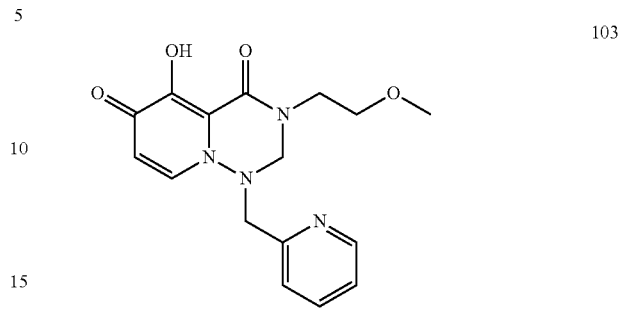

¹H-NMR (CDCl₃) δ: 4.54 (1H, d, J=12.9 Hz), 4.56 (2H, s), 4.94 (1H, d, J=12.9 Hz), 5.14 (1H, s), 5.68 (1H, d, J=7.8 Hz), 6.20 (1H, d, J=3.0 Hz), 6.25-6.27 (1H, m), 6.72 (1H, d, J=7.8 Hz), 7.10-7.37 (11H, m).

Example 103

[Chemical formula 181]

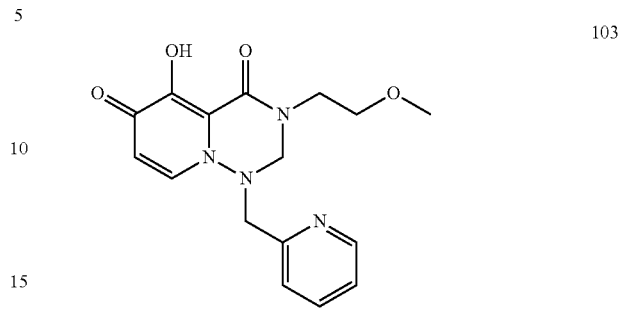

¹H-NMR (CDCl₃) δ: 3.33 (3H, s), 3.63-3.66 (2H, m), 3.75 (2H, brs), 4.27 (2H, brs), 4.67 (1H, brs), 5.00 (1H, brs), 6.09 (1H, d, J=7.8 Hz), 6.99 (1H, d, J=7.8 Hz), 7.18 (1H, d, J=7.8 Hz), 7.27-7.32 (1H, m), 7.66-7.71 (1H, m), 8.63-8.65 (1H, m).

Example 104

[Chemical formula 182]

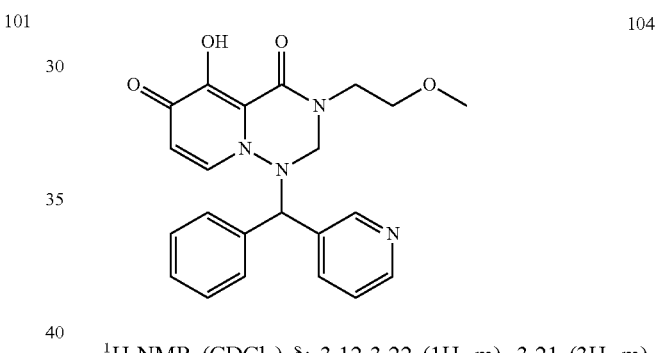

¹H-NMR (CDCl₃) δ: 3.12-3.22 (1H, m), 3.21 (3H, m), 3.38-3.55 (3H, m), 3.74-3.80 (0.55H, m), 3.87-3.94 (0.44H, m), 4.46-4.54 (1H, m), 5.00-5.07 (1H, m), 5.30-5.39 (1H, m), 5.70 (0.55H, d, J=7.5 Hz), 5.77 (0.45H, d, J=7.5 Hz), 6.74 (0.55H, d, J=7.8 Hz), 6.81 (0.45H, d, J=7.8 Hz), 7.11-7.54 (7.45H, m), 7.90 (0.55H, d, J=7.8 Hz), 8.459-8.783 (2H, m).

Example 105

[Chemical formula 183]

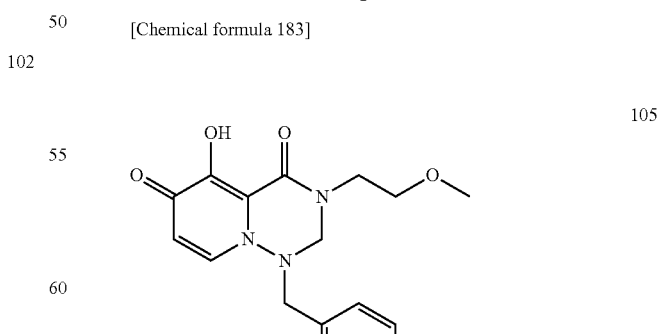

¹H-NMR (CDCl₃) δ: 3.34 (3H, s), 3.65-3.70 (4H, m), 4.18 (1H, brs), 4.21 (1H, brs), 4.48 (1H, brs), 4.98 (1H, brs), 6.12 (1H, d, J=7.8 Hz), 6.97 (1H, d, J=7.8 Hz), 7.36 (1H, d, J=7.5 Hz), 7.49 (1H, t, J=7.8 Hz), 7.61-7.66 (2H, m).

Example 106

[Chemical formula 184]

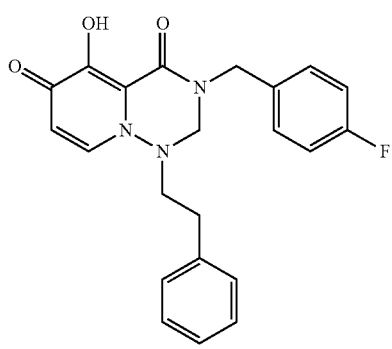

106

¹H-NMR (CDCl₃) δ: 2.54 (2H, t, J=7.5 Hz), 3.01 (2H, t, J=7, 5 Hz), 4.38 (2H, brs), 4.77 (2H, brs), 6.27 (1H, d, J=7.5 Hz), 6.96-7.00 (2H, m), 7.04-7.09 (3H, m), 7.19-7.33 (5H, m).

Example 107

[Chemical formula 185]

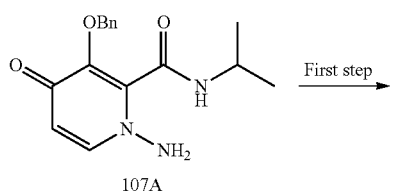

107A

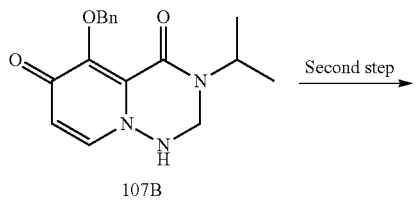

107B

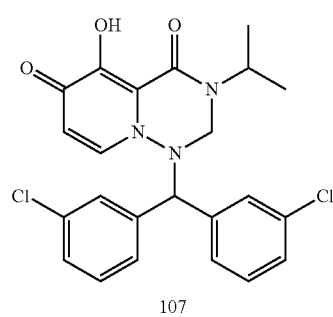

107

First Step

To a DMF (30 ml) solution of compound 107A (3.0 g, 9.96 mmol) synthesized according to the method of synthesizing compound 95D were added paraformaldehyde (299 mg, 9.96 mmol) and acetic acid (1 ml), and the mixture was heated to stir at 120° C. for 4 hours. After the solvent was distilled off, to the residue were added ethyl acetate-diisopropyl ether, and the precipitated solid was filtered to obtain 2.85 g (yield 91%) of compound 107B.

¹H-NMR (CDCl₃) δ: 1.19 (6H, J=6.6 Hz), 4.34 (2H, J=7.5 Hz), 4.72-4.86 (1H, m), 5.30 (2H, s), 5.49 (1H, t, J=7.5 Hz), 6.36 (1H, d, J=7.8 Hz), 7.26-7.35 (4H, m), 7.37 (1H, d, J=7.8 Hz), 7.55-7.58 (2H, m).

Second Step

To an acetic acid (2 ml) solution of compound 107B (100 mg, 0.319 mmol) were added 96% sulfuric acid (0.5 ml) and bis(3-chlorophenyl)methanol (242.3 mg, 0.957 mmol) at room temperature, and the mixture was stirred at 80° C. for 2 hours. After the reaction solution was cooled to room temperature, water was added, and the mixture was extracted with ethyl acetate three times. The organic layer was washed with water once, and dried with sodium sulfate. After the solvent was distilled off, to the residue was added diisopropyl ether, and the precipitated solid was filtered to obtain 42 mg (yield 29%) of compound 107.

¹H-NMR (CDCl₃) δ: 0.953 (3H, d, J=3.9 Hz), 1.12 (3H, d, J=4.2 Hz), 4.51 (1H, 13.5 Hz), 4.83 (1H, d, J=13.5 Hz), 4.83-4.92 (1H, m), 5.18 (1H, s), 5.74 (1H, d, J=7.8 Hz), 6.73 (1H, d, J=7.8 Hz), 6.90 (1H, d, J=7.5 Hz), 7.12 (2H, dd, J=7.2 Hz, 8.1 Hz), 7.19-7.22 (1H, m), 7.37-7.41 (3H, m), 7.55 (1H, s).

According to Example 107, the following compounds were synthesized by the same procedure.

Example 108

[Chemical formula 186]

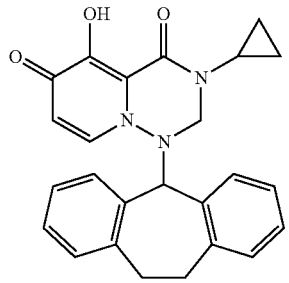

108

¹H-NMR (CDCl₃) δ: 0.465-0.549 (1H, m), 0.642-0.738 (1H, m), 0.754-0.907 (2H, m), 2.71-2.79 (1H, m), 2.86 (1H, ddd, J=4.8 Hz, 5.7 Hz, 14.7 Hz), 3.01 (2H, ddd, J=4.2 Hz, 16.0 Hz, 16.8 Hz), 3.88 (1H, ddd, J=4.8 Hz, 5.1 Hz, 16.8 Hz), 4.08-4.14 (1H, m), 4.16 (1H, d, J=12.9 Hz), 4.70 (1H, d, J=12.9 Hz), 4.96 (1H, s), 5.75 (1H, d, J=7.8 Hz), 6.58 (1H, d, J=7.8 Hz), 6.61 (1H, d, J=7.5 Hz), 6.92 (1H, dd, J=6.0 Hz, 7.5 Hz), 7.11-7.80 (6H, m).

Example 109

[Chemical formula 187]

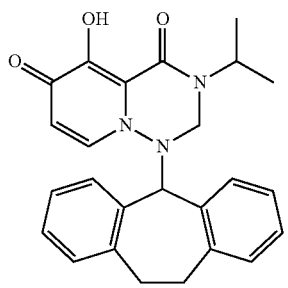

109

¹H-NMR (CDCl₃) δ: 1.14 (3H, d, J=6.9 Hz), 1.18 (3H, d, J=6.9 Hz), 2.82 (1H, ddd, J=4.5 Hz, 4.8 Hz, 14.1 Hz), 3.08 (1H, ddd, J=4.2 Hz, 13.2 Hz, 17.7 Hz), 3.53 (1H, ddd, J=4.2 Hz, 4.5 Hz, 17.7 Hz), 4.27 (1H, d, J=12.9 Hz), 4.26-4.37 (1H, m), 4.62-4.71 (1H, m), 4.68 (1H, d, J=12.9 Hz), 5.05 (1H, s), 5.71 (1H, d, J=7.5 Hz), 6.63 (2H, d, J=7.2 Hz), 6.90 (1H, t, J=7.5 Hz), 7.08-7.63 (6H, m).

Example 110

[Chemical formula 188]

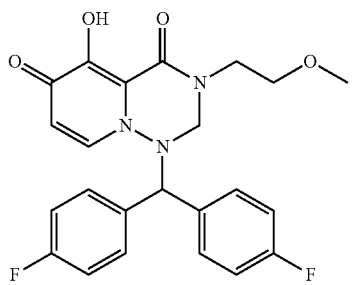

110

¹H-NMR (CDCl₃) δ: 3.16-3.28 (1H, m), 3.22 (3H, s), 3.46-3.50 (2H, m), 3.86 (1H, ddd, J=3.6 Hz, 3.6 Hz, 14.4 Hz), 4.47 (1H, d, J=13.2 Hz), 5.01 (1H, d, J=13.2 Hz), 5.30 (1H, s), 5.76 (1H, d, J=7.5 Hz), 6.72 (1H, d, J=7.5 Hz), 6.90 (2H, t, J=8.4 Hz), 7.06-7.18 (4H, m), 7.51 (2H, dd, J=5.4 Hz, 8.7 Hz).

Example 111

[Chemical formula 189]

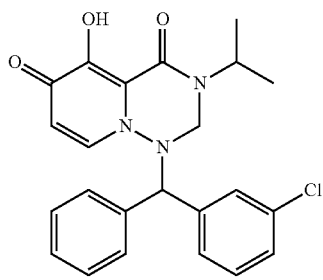

111

¹H-NMR (CDCl₃) δ: 0.903 (1.3H, d, J=6.9 Hz), 0.982 (1.5H, d, J=6.6 Hz), 1.08-1.14 (3.2H, m), 4.55 (1H, dd, J=13.2 Hz, 16.5 Hz), 4.78-4.93 (2H, m), 5, 20 (1H, s), 5.66 (0.58H, d, J=7.5 Hz), 5.75 (0.42H, d, J=7.5 Hz), 6.67 (0.55H, d, J=7.5 Hz), 6.73 (0.45H, d, J=7.5 Hz), 6.92 (0.45H, d, J=7.2 Hz), 7.04-7.59 (8.6H, m).

Example 112

[Chemical formula 190]

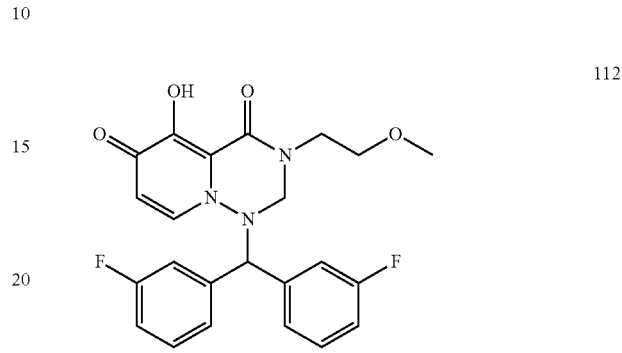

112

¹H-NMR (CDCl₃) δ: 3.22 (3H, s), 3.24-3.32 (1H, m), 3.47-3.50 (2H, m), 3.84 (1H, ddd, J=3.3 Hz, 3.9 Hz, 14.4 Hz), 4.51 (1H, d, J=13.5 Hz), 5.03 (1H, d, J=13.5 Hz), 5.32 (1H, s), 5.77 (1H, d, J=7.8 Hz), 6.80 (1H, d, J=7.8 Hz), 6.84 (1H, d, J=7.8 Hz), 6.93 (2H, t, J=8.4 Hz), 7.06-7.20 (2H, m), 7.25-7.29 (2H, m), 7.39-7.47 (1H, m).

Example 113

[Chemical formula 191]

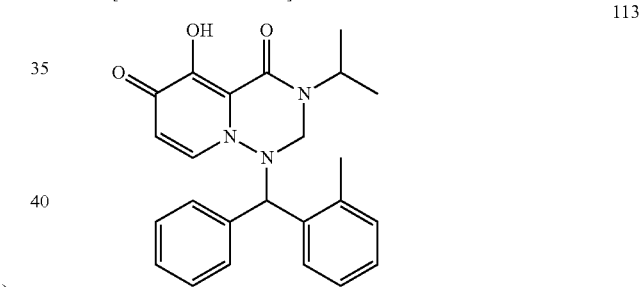

113

¹H-NMR (CDCl₃) δ: 0.88 (3H, d, J=6.9 Hz), 1.10 (3H, d, J=6.6 Hz), 2.10 (3H, s), 4.62-4.69 (1H, m), 4.79-4.92 (2H, m), 5.32 (1H, s), 5.64 (0.74H, 7.5 Hz), 5.72 (0.26H, d, J=7.5 Hz), 6.61 (0.74H, d, J=7.8 Hz), 6.82 (0.26H, d, J=7.8 Hz), 6.96-7.52 (8.26H, m), 7.48 (0.74H, d, J=7.5 Hz).

Example 114

[Chemical formula 192]

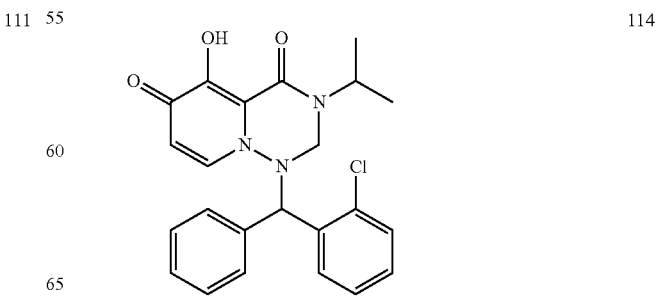

114

¹H-NMR (CDCl₃) δ: 0.976 (2H, d, J=6.9 Hz), 1.09-1.14 (3H, m), 5.63 (0.74H, d, J=7.8 Hz), 5.65 (0.74H, s), 5.73 (0.26H, d, J=7.8 Hz), 6.20 (0.26H, s), 6.65 (0.74H, d, J=7.8 Hz), 6.79 (0.26H, d, J=7.8 Hz), 7.05-7.24 (4.26H, m), 7.31-7.56 (4H, m), 8.02 (0.74H, d, J=6.3 Hz).

Example 115

[Chemical formula 193]

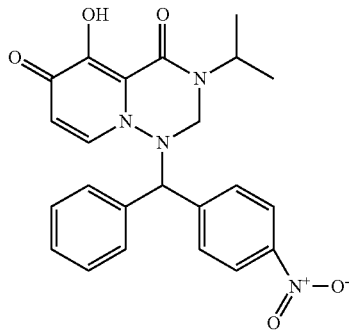

115

¹H-NMR (CDCl₃) δ: 0.893 (1.2H, d, J=6.6 Hz), 0.958 (1.8H, d, J=6.9 Hz), 1.09-1.13 (3H, m), 4.44 (0.56H, d, J=13.2 Hz), 4.63 (0.44H, d, J=13.5 Hz), 4.81-4.93 (2H, m), 5.35 (1H, m), 5.67 (0.56H, d, J=7.8 Hz), 5.72 (0.44H, d, J=7.8 Hz), 6.67-6.73 (1H, m), 7.03 (1H, d, J=6.6 Hz), 7.20-7.51 (5H, m), 7.75 (1H, d, 0.8.4 Hz), 8.06 (0.88H, d, J=8.7 Hz), 8.33 (1.1H, d, J=8.7 Hz).

Example 116

[Chemical formula 194]

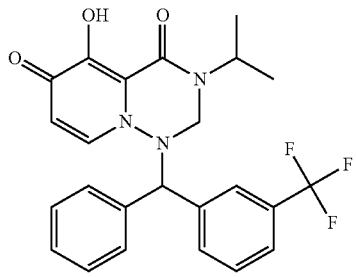

116

¹H-NMR (CDCl₃) δ: 0.91-0.0.948 (3H, m), 1.10-1.14 (3H, m), 3.61-3.68 (1H, m), 4.44 (0.56H, d, J=12.9 Hz), 4.59 (0.44H, d, J=12.9 Hz), 4.79-4.91 (2H, m), 5.29 (1H, s), 5.67-5.69 (1H, m), 6.63-6.70 (2H, m), 6.90-7.81 (8H, m).

Example 117

[Chemical formula 195]

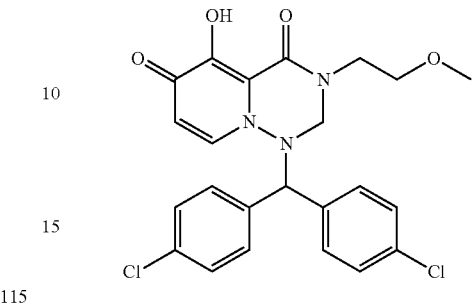

117

¹H-NMR (CDCl₃) δ: 3.19-3.28 (1H, m), 3.22 (3H, s), 3.46-3.50 (2H, m), 3.85 (1H, ddd, J=3 Hz, 4.2 Hz, 14.4 Hz), 4.47 (1H, d, J=13.2 Hz), 5.01 (1H, d, J=13.2 Hz), 5.28 (1H, s), 5.78 (1H, d, J=7.8 Hz), 6.73 (1H, d, J=7.8 Hz), 7.04 (2H, d, J=8.4 Hz), 7.19 (2H, d, 8.4 Hz), 7.36-7.50 (4H, m).

Example 118

[Chemical formula 196]

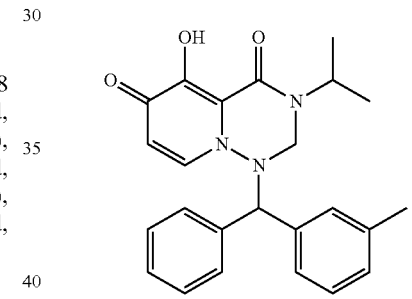

118

¹H-NMR (CDCl₃) δ: 0.914-0.957 (3H, m), 1.08-1.14 (3H, m), 2.20 (1.4H, s), 2.39 (1.6H, s), 4.56 (0.48H, d, J=4.5 Hz), 4.60 (0.52H, d, J=4.2 Hz), 4.77-4.89 (2H, m), 5.16 (1H, s), 5.66-5.70 (1H, m), 6.65-6.69 (1H, m), 6.85-6.91 (1H, m), 6.98-7.10 (2H, m), 7.14-7.19 (2H, m), 7.30-7.39 (2H, m), 7.44 (1H, t, J=6.9 Hz), 7.51 (1H, d, J=6.9 Hz).

Example 119

[Chemical formula 197]

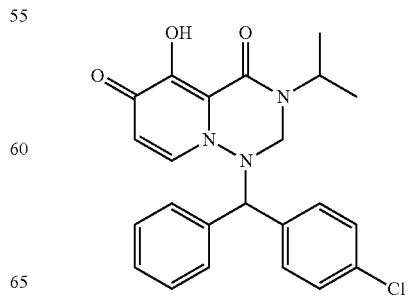

119

¹H-NMR (CDCl₃) δ: 0.893-0.982 (3H, m), 1.08-1.14 (3H, m), 4.49-4.60 (1H, m), 4.78-4.90 (2H, m), 5.20 (1H, s), 5.65 (0.57H, J=7.5 Hz), 5.76 (0.43H, d, J=7.8 Hz), 6.64-6.70 (1H, m), 7.03 (2H, d, J=8.1 Hz), 7.10-7.20 (3H, m), 7.28-7.51 (4H, m).

Example 120

[Chemical formula 198]

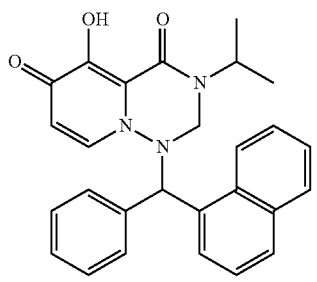

120

¹H-NMR (CDCl₃) δ: 0.526 (3H, d, J=6.9 Hz), 1.01 (3H, d, J=6.6 Hz), 4.69 (1H, d, J=13.8 Hz), 4.75-4,83 (1H, m), 4.86 (1H, d, J=13.8 Hz), 5.69 (1H, d, J=7.8 Hz), 6.03 (1H, s), 0.6.70 (1H, d, J=7.8 Hz), 7.16 (5H, s), 7.40-7.48 (2H, m), 7.67 (1H, t, J=7.8 Hz), 7.81-7.91 (3H, m), 8.16 (1H, d, J=7.2 Hz).

Example 121

[Chemical formula 199]

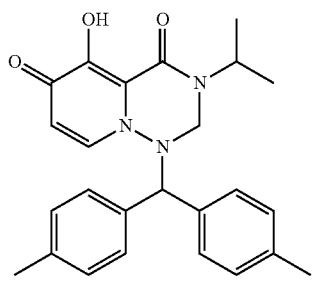

121

¹H-NMR (CDCl₃) δ: 0.947 (3H, d, J=6.9 Hz), 1.09 (3H, d, J=7.2 Hz), 2.22 (3H, s), 2.37 (3H, s), 4.58 (1H, d, J=12.9 Ha), 4.76 (1H, d, J=12.9 Hz), 4.78-4.88 (1H, m), 5.13 (1H, s), 5.72 (1H, d, J=7.8 Hz), 6.67 (1H, d, J=7.8 Hz), 6.72 (1H, s), 6.90-6.98 (4H, m), 7.22 (2H, d, J=7.8 Hz), 7.38 (2H, d, J=7.8 Hz).

Example 122

[Chemical formula 200]

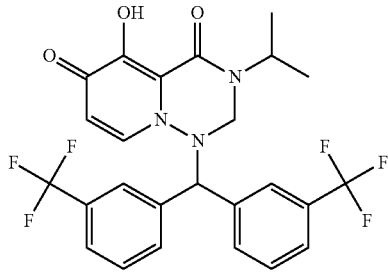

122

¹H-NMR (CDCl₃) δ: 0.932 (3H, d, J=6.6 Hz), 1.12 (3H, d, J=6.9 Hz), 4.44 (1H, d, J=13.2 Hz), 4.86 (1H, d, J=13.2 Hz), 4.87-4.93 (1H, m), 5.38 (1H, s), 5.67 (1H, d, J=7.8 Hz), 6.67 (1H, d, J=7.8 Hz), 7.21-7.24 (1H, m), 7.32-7.40 (2H, m), 7.52 (1H, d, J=7.5 Hz), 7.60-7.72 (2H, m), 7.77-7.79 (2H, m).

Example 123

[Chemical formula 201]

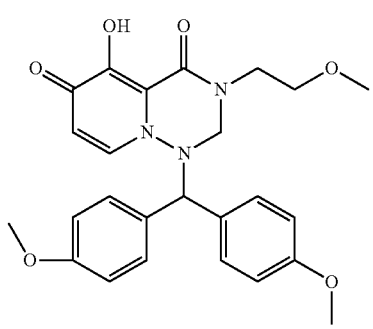

123

¹H-NMR (CDCl₃) δ: 3.08-3.17 (1H, m), 3.23 (3H, s), 3.40-3.54 (2H, m), 3.71 (3H, s), 3.82 (3H, s), 3.95 (1H, ddd, J=3.3 Hz, 3.9 Hz, 14.4 Hz), 4.48 (1H, d, J=13.5 Hz), 4.96 (1H, d, J=13.5 Hz), 5.16 (1H, s), 5.76 (1H, d, J=7.5 Hz), 6.70 (2H, d, J=9.0 Hz), 6.73 (1H, d, J=7.5 Hz), 6.94 (2H, d, J=8.7 Hz), 7.03 (2H, d, J=8.7 Hz), 7.42 (2H, d, J=8.7 Hz).

Example 124

[Chemical formula 202]

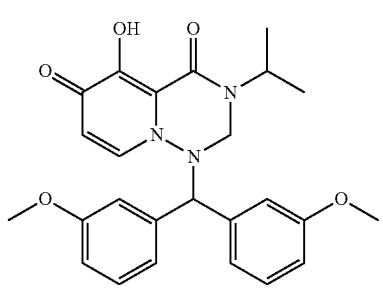

124

¹H-NMR (CDCl₃) δ: 0.966 (3H, d, J=6.9 Hz), 1.10 (3H, d, J=6.9 Hz), 3.67 (3H, s), 3.83 (3H, s), 4.60 (1H, d, J=12.9 Hz), 4.78 (1H, d, J=12.9 Hz), 4.80-4.90 (1H, m), 5.13 (1H, m), 5.23 (1H, d, J=7.8 Hz), 6.66 (2H, d, J=7.2 Hz), 6.72-6.87 (2H, m), 6.87-6.90 (1H, m), 7.06-7.11 (3H, m), 7.34 (1H, t, J=8.1 Hz).

Example 125

[Chemical formula 203]

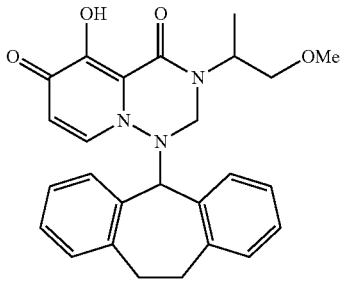

¹H-NMR (DMSO-d₆) δ: 1.05 (2H, d, J=7.0 Hz), 1.15 (1H, d, J=7.5 Hz), 2.73-3.63 (8H, m), 4.20-4.93 (4H, m), 5.25 (0.4H, s), 5.30 (0.6H, s), 5.46 (1H, d, J=7.8 Hz), 6.68-7.46 (11H, m).

MS: m/z=446 [M+H]⁺.

Example 126

[Chemical formula 204]

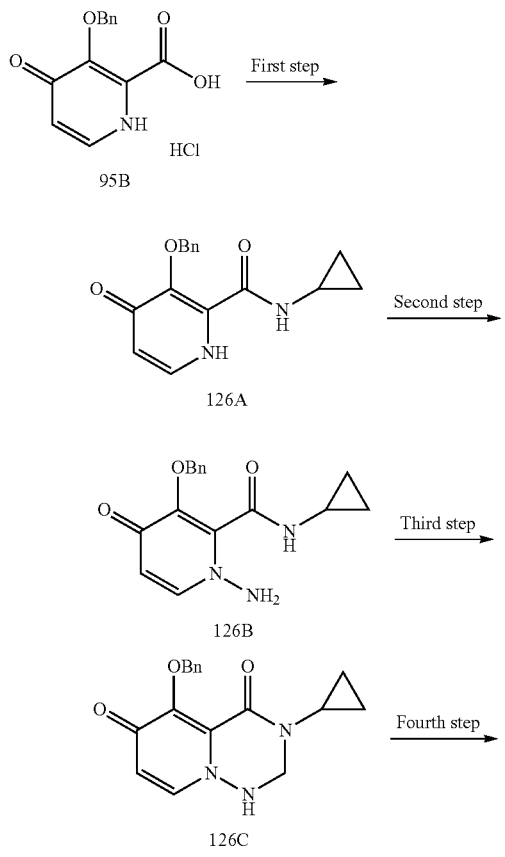

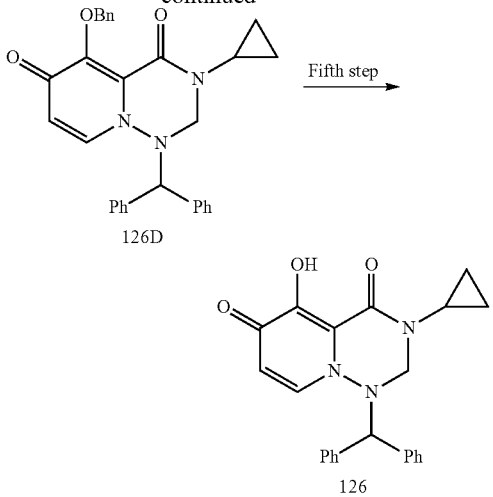

First Step

Compound 95B (1.00 g, 3.55 mmol) and cyclopropanamine (0.492 ml, 7.10 mmol) were added to pyridine (20 ml), 1-hydroxybenzotriazole (544 mg, 3.55 mmol) and 1-(3-dimethylaminopropyl)-3-ethylcarbodiimide hydrochloride (1.36 g, 7.10 mmol) were sequentially added, and the mixture was stirred at room temperature for 18 hours. After the solvent was distilled off under reduced pressure, the resulting crude product was purified by silica gel column chromatography (chloroform-methanol, 95:5, v/v) and, subsequently, amino column chromatography (chloroform-methanol, 99:1, v/v) to obtain 1.19 g of compound 126A as a colorless solid.

¹H-NMR (CDCl₃) δ: 0.22 (1H, m), 0.70 (2H, m), 2.76-2.83 (1H, m), 5.50 (2H, s), 6.59 (1H, dd, J=7.0, 1.9 Hz), 7.44 (5H, d, J=0.7 Hz), 7.53 (1H, dd, J=6.9, 6.2 Hz), 8.30 (1H, brs), 9.71 (1H, brs).

Second Step

Compound 126A (1.19 g, 4.19 mmol) was dissolved in DMF (15 ml), potassium carbonate (2.90 g, 20.1 mmol) was added, and the mixture was stirred at room temperature for 30 minutes. O-(2,4-dinitrophenyl)hydroxylamine (1.67 g, 8.38 mmol) was added, and the mixture was stirred at room temperature for 18 hours. To the reaction solution was added chloroform, the precipitated yellow precipitate was removed by filtration, and the filtrate was concentrated under reduced pressure. The resulting crude product was purified by amino column chromatography (chloroform-methanol, 97:3→95:5, v/v) to obtain 851 mg of compound 126B as a yellow solid.

¹H-NMR (CDCl₃) δ: 0.41-0.46 (2H, m), 0.76 (2H, m), 2.73-2.81 (1H, m), 5.19 (2H, s), 5.61 (2H, s), 6.26 (1H, d, J=7.2 Hz), 7.38 (5H, s), 7.44 (1H, d, J=7.8 Hz), 7.70 (1H, s).

Third Step

Compound 126B (847 mg, 2.83 mmol) and paraformaldehyde (255 mg, 8.49 mmol) were added to ethanol (12 ml), and the mixture was stirred at 140° C. for 30 minutes under microwave irradiation. The reaction solution was concentrated under reduced pressure, the resulting crude product was purified by silica gel column chromatography (chloroform-methanol, 97:3→95:5→90:10, v/v) and, subsequently, amino column chromatography (chloroform-methanol, 97:3, v/v), methylene chloride-ethyl ether were added, and the precipitated solid was filtered to obtain 665 mg of compound 126C as a colorless solid.

¹H-NMR (CDCl₃) δ: 0.61-0.66 (2H, m), 0.87 (2H, m), 2.68-2.76 (1H, m), 4.32 (2H, d, J=7.9 Hz), 5.28 (2H, s), 6.33 (1H, d, J=7.7 Hz), 6.45 (1H, t, J=7.7 Hz), 7.33 (3H, m), 7.38 (1H, d, J=7.7 Hz), 7.52 (2H, m).

Fourth Step

Compound 126C (100 mg, 0.321 mmol) was dissolved in DMF (0.5 ml), cesium carbonate (314 mg, 0.964 mmol) and (bromomethylene)dibenzene (119 mg, 0.482 mmol) were added at 0° C., and the mixture was stirred at room temperature for 2 hours. The reaction solution was poured into water, the mixture was extracted with ethyl acetate, and the organic layer was washed with water, and dried with sodium sulfate. The solvent was distilled off under reduced pressure, and the resulting crude product was purified by silica gel column chromatography (chloroform-methanol, 97:3→95:5, v/v) to obtain 124 mg of compound 126D as a colorless gummy substance.

¹H-NMR (CDCl₃) δ: 0.37-0.47 (2H, m), 0.74 (2H, m), 2.63-2.68 (1H, m), 4.35 (1H, d, J=13.4 Hz), 4.65 (1H, d, J=13.4 Hz), 5.07 (1H, s), 5.40 (1H, d, J=10.7 Hz), 5.47 (1H, d, J=10.5 Hz), 5.79 (1H, d, J=7.6 Hz), 6.67 (1H, d, J=7.8 Hz), 7.04-7.62 (15H, m).

Fifth Step

To compound 126D obtained in the fourth step was added trifluoroacetic acid (2 ml), and the mixture was stirred at room temperature for 1.5 hours. After concentration under reduced pressure, pH was adjusted to 6 with sodium bicarbonate water and 2N hydrochloric acid, and the mixture was extracted with chloroform, and dried with sodium sulfate. After the solvent was distilled off under reduced pressure, methylene chloride-ethyl ether were added, and the precipitated solid was filtered to obtain 52 mg of compound 126 as a colorless solid.

¹H-NMR (DMSO-d₆) δ: −0.19-0.06 (1H, m), 0.44-0.54 (1H, m), 0.82 (2H, m), 2.62-2.69 (1H, m), 4.21 (1H, d, J=13.3 Hz), 5.11 (1H, d, J=13.1 Hz), 5.32 (1H, s), 5.47 (1H, t, J=11.1 Hz), 7.13 (1H, d, J=7.6 Hz), 7.23 (3H, m), 7.28-7.47 (8H, m), 7.69 (2H, t, J=8.5 Hz).

MS: m/z=388 [M+H]⁺.

Example 127

[Chemical formula 205]

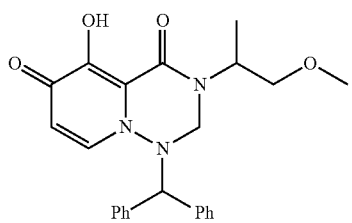

127

According to Example 126, compound 127 was synthesized by the same procedure.

¹H-NMR (DMSO-d₆) δ: 0.86 (1.5H, d, J=7.0 Hz), 1.04 (1.5H, d, J=7.2 Hz), 3.08 (1.5H, s), 3.16 (1.5H, s), 4.52-5.05 (3H, m), 5.48 (2H, m), 7.31-7.47 (9H, m), 7.66 (2H, t, J=8.4 Hz).

MS: m/z=420 [M+H]⁺.

Example 128

[Chemical formula 206]

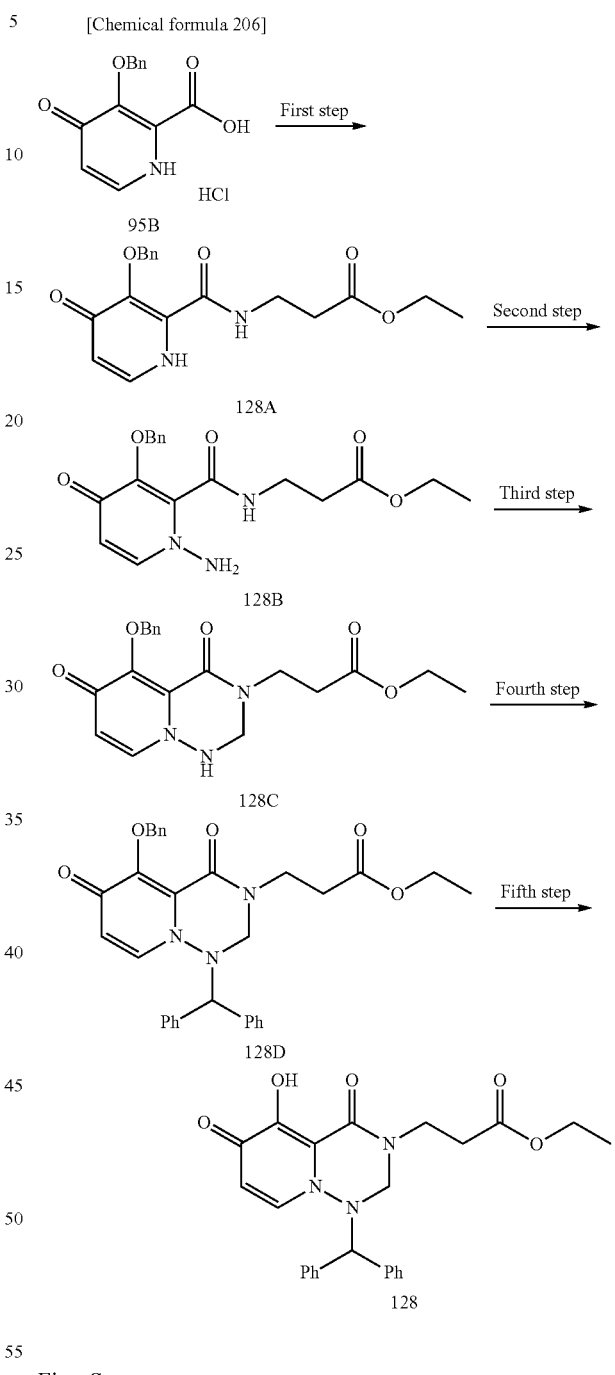

First Step

Compound 95B (2.40 g, 8.52 mmol) and ethyl 3-aminopropanoate hydrochloride (2.62 g, 17.0 mmol) were added to pyridine (30 ml), 1-hydroxybenzotriazole (1.31 g, 8.52 mmol) and 1-(3-dimethylaminopropyl)-3-ethylcarbodiimide hydrochloride (3.27 g, 17.0 mmol) were sequentially added, and the mixture was stirred at room temperature for 2 hours. The solvent was distilled off under reduced pressure, and the resulting crude product was purified by amino column chromatography (chloroform-methanol, 95:5, v/v) to obtain 1.90 g of compound 128A as a colorless solid.

¹H-NMR (CDCl₃) δ: 1.29 (3H, t, J=7.1 Hz), 2.48 (2H, t, J=6.4 Hz), 3.58 (2H, q, J=6.3 Hz), 4.17 (2H, q, J=7.1 Hz), 5.59 (2H, s), 6.57 (1H, dd, J=7.1, 1.6 Hz), 7.37-7.52 (6H, m), 8.73 (1H, brs), 9.72 (1H, brs).

Second Step

Compound 128A (2.58 g, 7.49 mmol) was dissolved in DMF (30 ml), potassium carbonate (5.18 g, 37.5 mmol) was added, and the mixture was stirred at room temperature for 30 minutes. O-(2,4-dinitrophenyl)hydroxylamine (2.98 g, 15.0 mmol) was added, and the mixture was stirred at room temperature for 20 hours. To the reaction solution was added chloroform, the precipitated yellow precipitate was removed by filtration, and the filtrate was concentrated under reduced pressure. The resulting crude product was purified by amino column chromatography (chloroform-methanol, 97:3→95:5, v/v) and, subsequently, silica gel column chromatography (chloroform-methanol, 95:5→92:8, v/v) to obtain 1.67 g of compound 128B as a yellow solid.

¹H-NMR (CDCl₃) δ: 1.26 (3H, t, J=7.2 Hz), 2.42 (2H, t, J=6.6 Hz), 3.43 (2H, q, J=6.4 Hz), 4.12 (2H, q, J=7.1 Hz), 5.13 (2H, s), 5.53 (2H, s), 6.21 (1H, d, J=7.6 Hz), 7.33 (5H, s), 7.39 (1H, d, J=7.6 Hz), 7.85 (1H, t, J=5.6 Hz).

Third Step

Compound 128B (1.66 g, 4.62 mmol) and paraformaldehyde (416 mg, 13.9 mmol) were added to ethanol (20 ml), and the mixture was stirred at 140° C. for 30 minutes under microwave irradiation. The reaction solution was concentrated under reduced pressure, the resulting crude product was purified by amino column chromatography (chloroform-methanol, 99:1→95:5, v/v) to obtain 1.57 g of compound 128C as a colorless solid.

¹H-NMR (CDCl₃) δ: 1.27 (3H, t, J=7.2 Hz), 2.70 (2H, t, J=5.7 Hz), 3.57 (2H, t, J=5.8 Hz), 4.13 (2H, q, J=7.1 Hz), 4.50 (2H, d, J=7.9 Hz), 5.27 (2H, s), 5.87 (1H, t, J=7.8 Hz), 6.32 (1H, d, J=7.6 Hz), 7.31 (4H, m), 7.54 (2H, m).

Fourth Step

Compound 128C (1.00 g, 2.69 mmol) was dissolved in DMF (10 ml), cesium carbonate (2.63 g, 8.08 mmol) and (bromomethylene)dibenzene (998 mg, 4.04 mmol) were added at 0° C., and the mixture was stirred at room temperature for 18 hours. The reaction solution was poured into water, the mixture was extracted with ethyl acetate, and the organic layer was washed with water, and dried with sodium sulfate. The solvent was distilled off under reduced pressure, and the resulting crude product was purified by silica gel column chromatography (chloroform/methanol, 98:2, v/v) to obtain 500 mg of compound 128D as a colorless gummy substance.

¹H-NMR (CDCl₃) δ: 1.25 (3H, t, J=7.3 Hz), 2.46 (1H, m), 2.70-2.80 (1H, m), 2.87-2.96 (1H, m), 4.11 (2H, q, J=7.3 Hz), 4.12 (1H, m), 4.48 (1H, d, J=13.7 Hz), 4.85 (1H, d, J=13.7 Hz), 5.10 (1H, s), 5.47 (2H, s), 5.83 (1H, d, J=8.0 Hz), 6.73 (1H, d, J=8.0 Hz), 7.37 (15H, m).

Fifth Step

To compound 128D (40 mg, 0.074 mmol) was added trifluoroacetic acid (1 ml), and the mixture was stirred at room temperature for 1 hour. After concentration under reduced pressure, pH was adjusted to 6 with sodium bicarbonate water and 2N hydrochloric acid, and the mixture was extracted with chloroform, and dried with sodium sulfate. After the solvent was distilled off under reduced pressure, methylene chloride-ethyl ether were added, and the precipitated solid was filtered to obtain 20 mg of compound 128 as a colorless solid.

¹H-NMR (DMSO-d₆) δ: 1.16 (3H, t, J=7.1 Hz), 2.45-2.58 (3H, m), 3.70 (1H, m), 4.02 (2H, q, J=7.1 Hz), 4.39 (1H, d, J=13.4 Hz), 5.09 (1H, d, J=13.3 Hz), 5.48 (1H, d, J=3.2 Hz), 5.51 (1H, s), 7.19-7.38 (7H, m), 7.45 (2H, t, J=7.3 Hz), 7.69 (2H, d, J=7.2 Hz).

MS: m/z=448 [M+H]⁺.

Example 129

[Chemical formula 207]

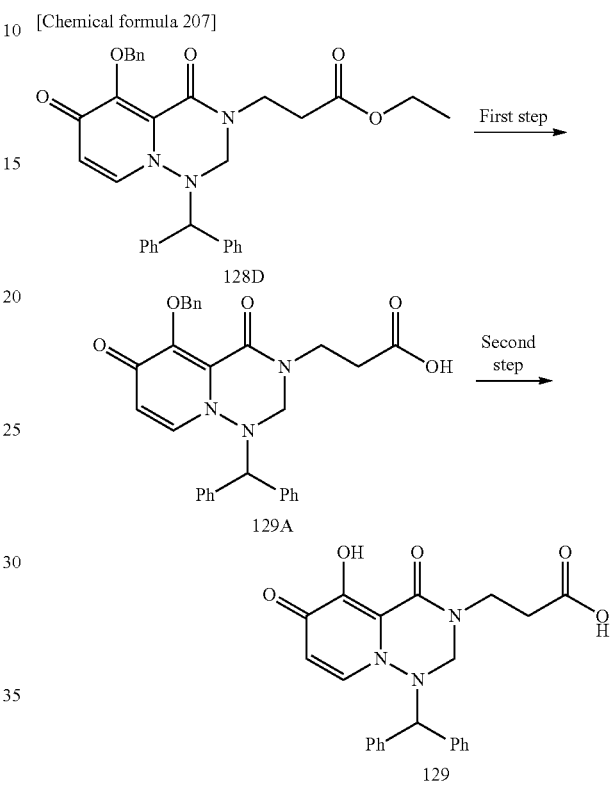

First Step

Compound 128D (426 mg, 0.792 mmol) was dissolved in ethanol (3 ml) and THF (3 ml), a 2N aqueous sodium hydroxide solution (1.19 ml, 2.38 mmol) was added, and the mixture was stirred at room temperature for 1.5 hours. To the reaction solution was added 2N hydrochloric acid, and the mixture was extracted with chloroform, and dried with sodium sulfate. To the resulting crude product were added methylene chloride-ethyl ether, and the precipitated solid was filtered to obtain 359 mg of compound 129A as a colorless solid.

Second Step

To compound 129A (40 mg, 0.079 mmol) was added trifluoroacetic acid (1 ml), and the mixture was stirred at room temperature for 1 hour. After concentration under reduced pressure, pH was adjusted to 3 with sodium bicarbonate water and 2N hydrochloric acid, and the mixture was extracted with chloroform, and dried with sodium sulfate. After the solvent was distilled off under reduced pressure, chloroform-methanol-ethyl ether were added, and the precipitated solid was filtered to obtain 25 mg of compound 129 as a colorless solid.

¹H-NMR (DMSO-d₆) δ: 2.31-2.41 (1H, m), 2.57 (1H, m), 3.63-3.72 (1H, m), 4.37 (1H, d, J=13.3 Hz), 5.09 (1H, d, J=13.3 Hz), 5.47 (1H, s), 5.50 (1H, d, J=7.8 Hz), 7.28 (7H, m), 7.44 (2H, t, J=7.5 Hz), 7.69 (2H, d, J=7.2 Hz), 12.40 (1H, brs).

MS: m/z=420 [M+H]⁺.

Examples 130

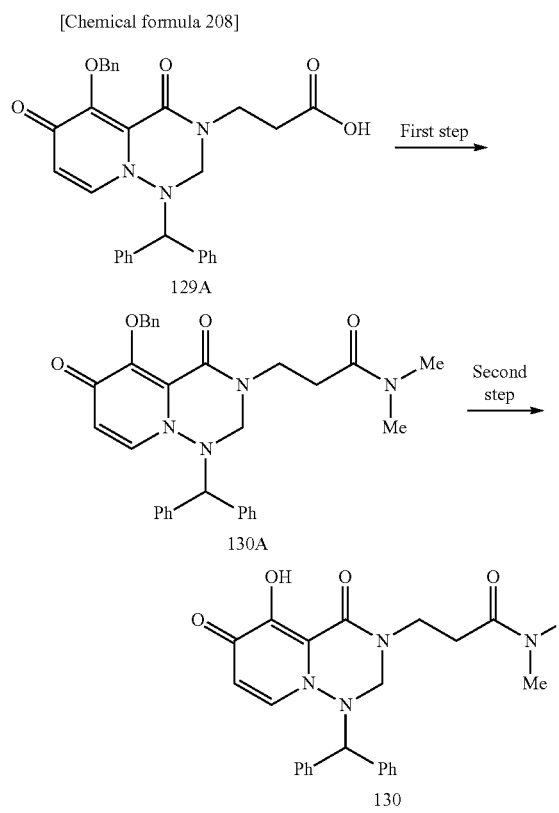

First Step

Compound 129A (50 mg, 0.098 mmol) was added to DMF (1 ml), 1-hydroxybenzotriazole (14 mg, 0.098 mmol), dimethylamine hydrochloride (24 mg, 0.29 mmol), triethylamine (0.048 ml, 0.34 mmol), and 1-(3-dimethylaminopropyl)-3-ethylcarbodiimide hydrochloride (28 mg, 0.15 mmol) were added, and the mixture was stirred at room temperature for 1.5 hours. The reaction solution was poured into water, and the mixture was extracted with ethyl acetate, washed with sodium bicarbonate water, and dried with sodium sulfate. The solvent was distilled off under reduced pressure to obtain compound 130A as a colorless gummy substance.

Second Step

To compound 130A obtained in the first step was added trifluoroacetic acid (1 ml), and the mixture was stirred at room temperature for 2 hours. After concentration under reduced pressure, pH was adjusted to 6 with sodium bicarbonate water and an aqueous ammonium chloride solution, and the mixture was extracted with chloroform, and dried with sodium sulfate. The solvent was distilled off under reduced pressure, chloroform-ethyl ether were added, and the precipitated solid was filtered to obtain 25 mg of compound 130 as a colorless solid.

$^1$H-NMR (DMSO-$d_6$) δ: 2.33-2.43 (1H, m), 2.66 (1H, m), 2.78 (3H, s), 2.89 (3H, s), 3.56 (2H, m), 4.45 (1H, d, J=13.6 Hz), 5.05 (1H, d, J=13.6 Hz), 5.47 (s, 1H), 5.49 (1H, d, J=7.5 Hz), 7.27 (7H, m), 7.44 (2H, t, J=7.3 Hz), 7.69 (2H, d, J=7.3 Hz).

Example 131

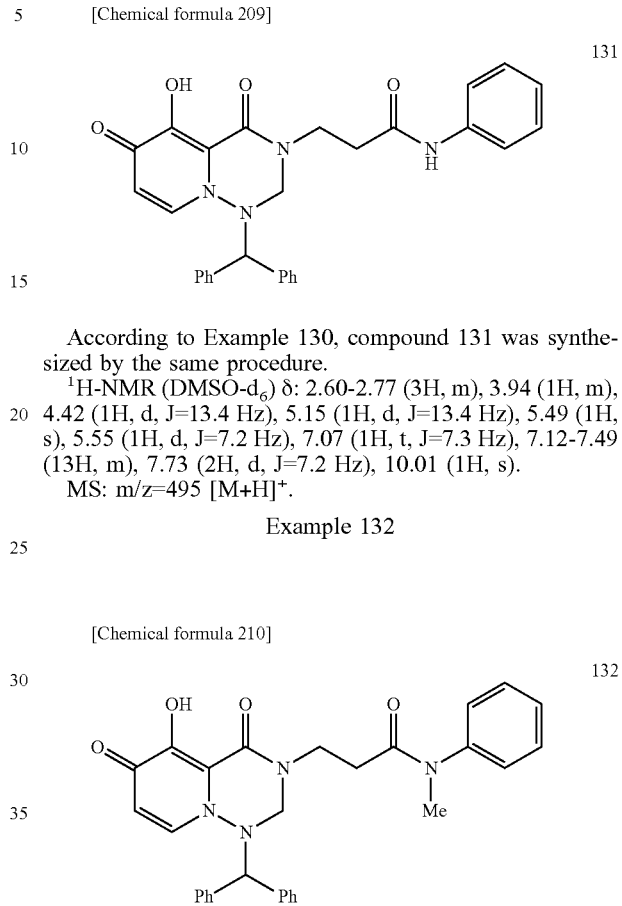

According to Example 130, compound 131 was synthesized by the same procedure.

$^1$H-NMR (DMSO-$d_6$) δ: 2.60-2.77 (3H, m), 3.94 (1H, m), 4.42 (1H, d, J=13.4 Hz), 5.15 (1H, d, J=13.4 Hz), 5.49 (1H, s), 5.55 (1H, d, J=7.2 Hz), 7.07 (1H, t, J=7.3 Hz), 7.12-7.49 (13H, m), 7.73 (2H, d, J=7.2 Hz), 10.01 (1H, s).

MS: m/z=495 [M+H]$^+$.

Example 132

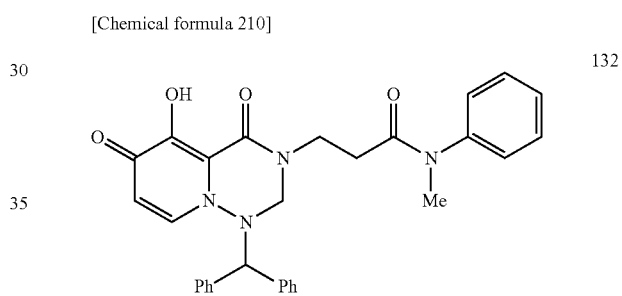

According to Example 130, compound 132 was synthesized by the same procedure.

$^1$H-NMR (DMSO-$d_6$) δ: 3.14 (3H, s), 3.65 (4H, m), 4.34 (1H, d, J=13.6 Hz), 5.06 (1H, d, J=13.6 Hz), 5.42 (1H, s), 5.53 (1H, d, J=7.5 Hz), 7.42-7.58 (16H, m).

MS: m/z=509 [M+H]$^+$.

Example 133

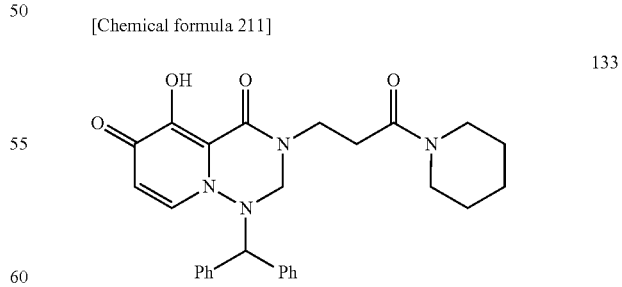

According to Example 130, compound 133 was synthesized by the same procedure.

$^1$H-NMR (DMSO-$d_6$) δ: 1.08-1.55 (8H, m), 2.33 (1H, m), 2.68 (1H, m), 4.45 (1H, d, J=13.6 Hz), 5.05 (1H, d, J=13.6 Hz), 5.50 (2H, brs), 7.46-7.68 (11H, m).

MS: m/z=487 [M+H]$^+$.

Example 134

[Chemical formula 212]

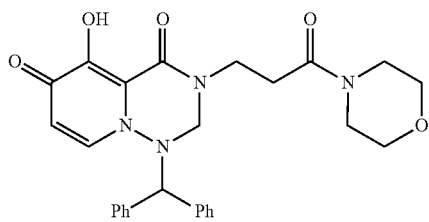

134

According to Example 130, compound 134 was synthesized by the same procedure.

$^1$H-NMR (DMSO-d$_6$) δ: 2.34-2.40 (1H, m), 2.61-2.77 (1H, m), 3.51-3.69 (10H, m), 4.44 (1H, d, J=13.4 Hz), 5.03-5.11 (1H, d, J=13.4 Hz), 5.51 (2H, s), 7.18-7.52 (9H, m), 7.69-7.75 (2H, m).

Example 135

[Chemical formula 213]

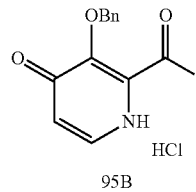
95B

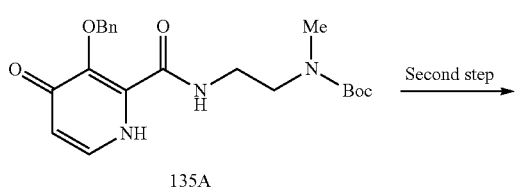
135A

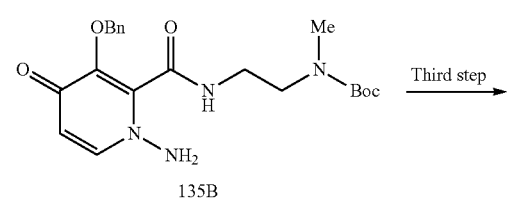
135B

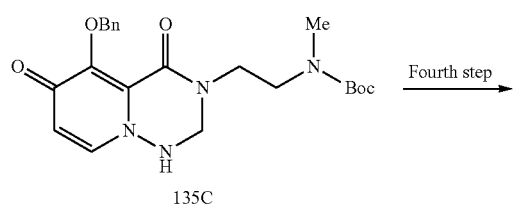
135C

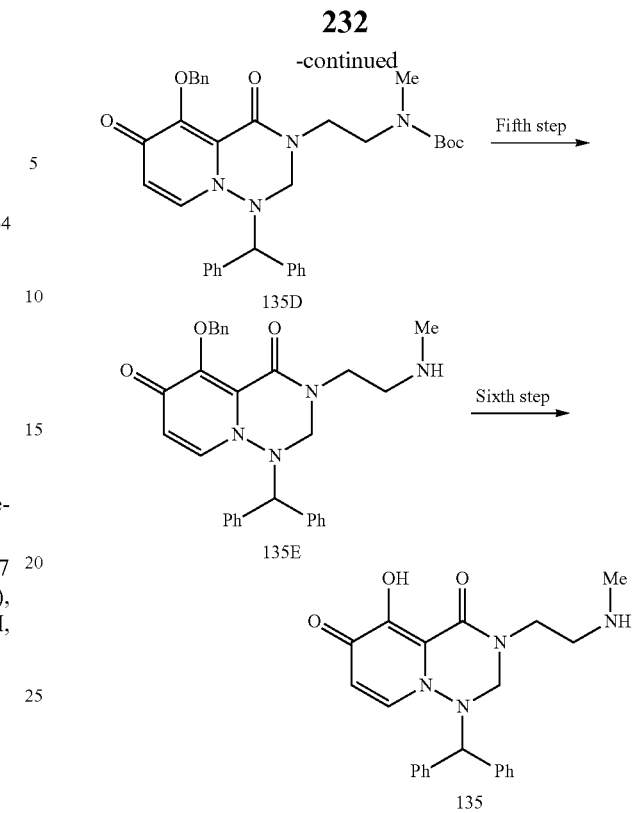

First Step

Compound 95B (1.50 g, 5.32 mmol) and tert-butyl 2-aminoethyl(methyl)carbamate (1.86 g, 10.7 mmol) were added to pyridine (20 ml), 1-hydroxybenzotriazole (815 mg, 5.32 mmol) and 1-(3-dimethylaminopropyl)-3-ethylcarbodiimide hydrochloride (2.04 g, 10.7 mmol) were sequentially added, and the mixture was stirred at room temperature for 2 hours. The reaction solution was poured into 1N hydrochloric acid, and the mixture was extracted with ethyl acetate, and dried with sodium sulfate. The solvent was distilled off under reduced pressure, and the resulting crude product was purified by amino column chromatography (chloroform-methanol, 95:5, v/v) and, subsequently, silica gel column chromatography (chloroform-methanol, 95:5, v/v) to obtain 1.63 g of compound 135A as a colorless gummy substance.

$^1$H-NMR (CDCl$_3$) δ: 1.44 (9H, s), 2.82 (3H, s), 3.28 (4H, m), 5.59 (2H, s), 6.57 (1H, d, J=6.0 Hz), 7.46 (6H, m), 8.46 (1H, m), 9.68 (1H, brs).

Second Step

Compound 135A (1.05 g, 2.62 mmol) was dissolved in DMF (15 ml), potassium carbonate (1.81 g, 13.1 mmol) was added, and the mixture was stirred at room temperature for 30 minutes. O-(2,4-dinitrophenyl)hydroxylamine (1.04 g, 5.23 mmol) was added, and the mixture was stirred at room temperature for 18 hours. To the reaction solution was added chloroform, the precipitated yellow precipitate was removed by filtration, and the filtrate was concentrated under reduced pressure. The resulting crude product was purified by amino column chromatography (chloroform-methanol, 97:3→95:5, v/v) to obtain 887 mg of compound 135B as a pale yellow solid.

$^1$H-NMR (CDCl$_3$) δ: 1.44 (9H, s), 2.84 (3H, s), 3.38 (4H, m), 5.33 (2H, s), 5.68 (1H, brs), 5.80 (1H, brs), 6.35 (1H, d, J=7.6 Hz), 6.74 (1H, brs), 7.39 (5H, brm), 7.52 (1H, t, J=9.5 Hz).

Third Step

Compound 135B (880 mg, 2.11 mmol) and paraformaldehyde (190 mg, 6.34 mmol) were added to ethanol (18 ml), and the mixture was stirred at 140° C. for 30 minutes under microwave irradiation. The reaction solution was concentrated under reduced pressure, and the resulting crude product was purified by silica gel column chromatography (chloroform-methanol, 97:3→95:5→90:10 v/v) and, subsequently, amino column chromatography (chloroform-methanol, 97:3, v/v) to obtain 721 mg of compound 135C as a colorless solid.

$^1$H-NMR (CDCl$_3$) δ: 1.29 (9H, s), 2.95 (3H, s), 4.38 (2H, brs), 5.33 (2H, brs), 6.36 (1H, d, J=7.6 Hz), 6.85 (1H, t, J=7.4 Hz), 7.33 (4H, m), 7.55 (2H, m).

MS: m/z=429 [M+H]$^+$.

Fourth Step

Compound 135C (720 mg, 1.68 mmol) was dissolved in DMF (3.5 ml), cesium carbonate (1.64 g, 5.04 mmol) and (bromomethylene)dibenzene (623 mg, 2.52 mmol) were added at 0° C., and the mixture was stirred at room temperature for 18 hours. The reaction solution was poured into water, the mixture was extracted with ethyl acetate, and the organic layer was washed with water, and dried with sodium sulfate. The solvent was distilled off under reduced pressure, and the resulting crude product was purified by silica gel column chromatography (chloroform-methanol, 97:3→95:5 v/v) to obtain 732 mg of compound 135D.

Fifth Step

To compound 135D (727 mg, 1.22 mmol) was added 4N HCl (ethyl acetate solution, 10 ml). After stirring at room temperature for 1 hour, the solvent was distilled off under reduced pressure. Saturated sodium bicarbonate water was added, the mixture was extracted with chloroform, and the extract was dried with sodium sulfate. The solvent was distilled off under reduced pressure, to the resulting crude product were added methylene chloride-ethyl ether, and the precipitated solid was filtered to obtain 575 mg of compound 135E as a colorless solid.

Sixth Step

To compound 135E (50 mg, 0.10 mmol) was added trifluoroacetic acid (2 ml), and the mixture was stirred at room temperature for 1.5 hours. After concentration under reduced pressure, pH was adjusted to 6 with sodium bicarbonate water and an aqueous ammonium chloride solution, the mixture was extracted with chloroform, and the extract was dried with sodium sulfate. After the solvent was distilled off under reduced pressure, ethylene chloride-ethyl ether were added, and the precipitated solid was filtered to obtain 15 mg of compound 135 as a colorless solid.

$^1$H-NMR (DMSO-d$_6$) δ: 2.40 (3H, s), 2.80 (1H, s), 3.12 (3H, m), 3.87 (1H, m), 4.37 (1H, d, J=13.6 Hz), 5.10 (1H, d, J=13.4 Hz), 5.52 (1H, s), 5.53 (1H, d, J=5.5 Hz), 7.15-7.70 (11H, m).

MS: m/z=405 [M+H]$^+$.

Example 136

[Chemical formula 214]

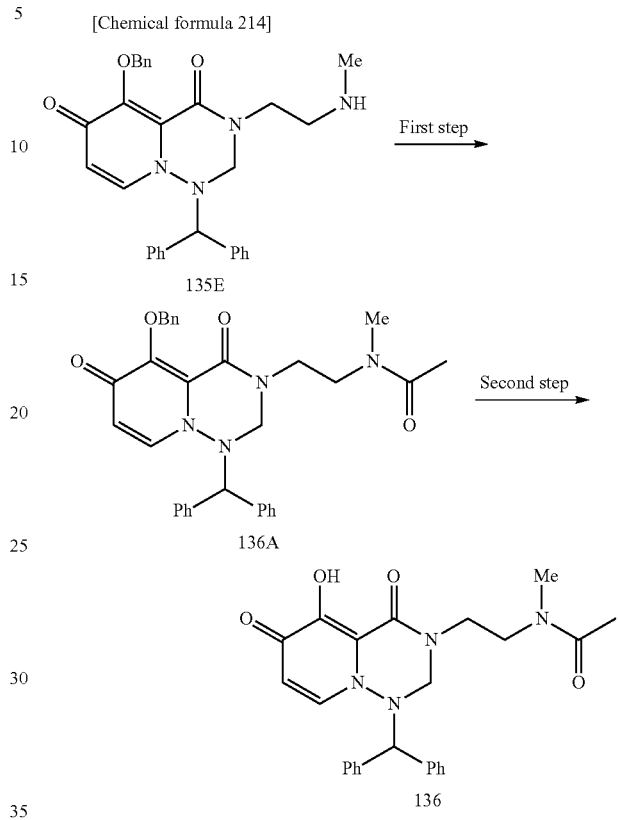

First Step

Compound 135E (50 mg, 0.10 mmol) was dissolved in methylene chloride (1 ml), triethylamine (0.042 ml, 0.30 mmol) and acetyl chloride (0.011 ml, 0.15 mmol) were added, and the mixture was stirred at room temperature for 1 hour. The solvent was distilled off under reduced pressure, and the resulting crude product was purified by silica gel column chromatography (chloroform-methanol, 97:3→95: 5, v/v) and, subsequently, amino column chromatography (chloroform-methanol, 97:3, v/v) to obtain 72 mg of compound 136A as a colorless solid.

Second Step

To compound 136A obtained in the first step was added trifluoroacetic acid (2 ml), and the mixture was stirred at room temperature for 1.5 hours. After concentration under reduced pressure, pH was adjusted to 6 with sodium bicarbonate water and an aqueous ammonium chloride solution, the mixture was extracted with chloroform, and the extract was dried with sodium sulfate. After the solvent was distilled off under reduced pressure, methylene chloride-ethyl ether were added, and the precipitated solid was filtered to obtain 23 mg of compound 136 as a colorless solid.

$^1$H-NMR (DMSO-d$_6$) δ: 1.89 (2H, s), 1.92 (1H, s), 2.73 (1H, s), 2.95 (2H, s), 3.00-3.06 (1H, m), 3.43 (2H, m), 3.80 (1H, m), 4.34 (0.7H, d, J=13.3 Hz), 4.45 (0.3H, d, J=13.1 Hz), 5.11 (1H, m), 5.49 (2H, m), 7.20-7.73 (11H, m).

Example 137

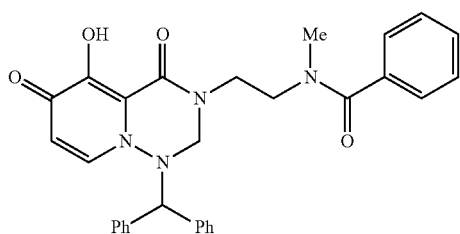

137

According to Example 136, compound 137 was synthesized by the same procedure.

$^1$H-NMR (DMSO-d$_6$) δ: 2.95 (3H, s), 3.13-4.07 (4H, m), 4.46 (1H, d, J=13.2 Hz), 5.16 (1H, d, J=13.0 Hz), 5.51 (1H, d, J=7.3 Hz), 5.62 (1H, s), 7.17-7.78 (16H, m).

MS: m/z=509 [M+H]$^+$.

Example 138

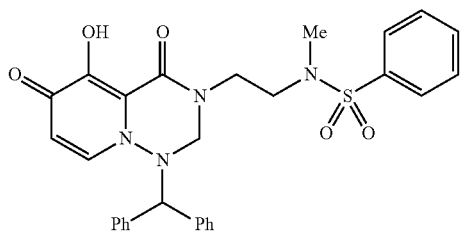

138

According to Example 136, compound 138 was synthesized by the same procedure.

$^1$H-NMR (DMSO-d$_6$) δ: 2.62 (3H, s), 3.03-3.22 (4H, m), 3.72 (2H, d, J=13.3 Hz), 4.39 (1H, d, J=13.3 Hz), 5.08 (1H, d, J=13.3 Hz), 5.53 (1H, d, J=7.8 Hz), 5.55 (1H, s), 7.19-7.79 (16H, m).

MS: m/z=545 [M+H]$^+$.

Example 139

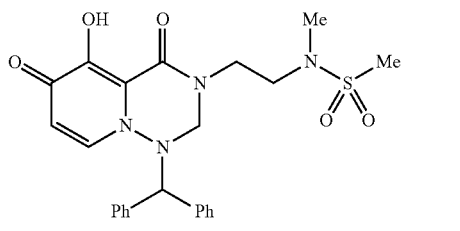

139

According to Example 136, compound 139 was synthesized by the same procedure.

$^1$H-NMR (DMSO-d$_6$) δ: 2.72 (3H, s), 2.88 (3H, s), 3.12-3.24 (3H, m), 3.75-3.80 (1H, m), 4.37 (1H, d, J=13.0 Hz), 5.10 (1H, d, J=13.4 Hz), 5.51 (1H, d, J=7.6 Hz), 5.54 (1H, s), 7.19-7.46 (19H, m), 7.72 (2H, d, J=7.0 Hz).

MS: m/z=483 [M+H]$^+$.

Example 140

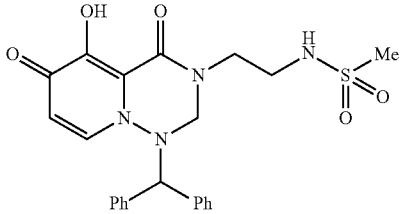

140

According to Example 136, compound 140 was synthesized by the same procedure.

$^1$H-NMR (DMSO-d$_6$) δ: 2.88 (3H, s), 2.98-3.12 (3H, m), 3.77 (1H, m), 4.31 (1H, d, J=13.3 Hz), 5.13 (1H, d, J=13.3 Hz), 5.51 (1H, s), 5.52 (1H, d, J=7.6 Hz), 7.13-7.46 (9H, m), 7.71 (2H, d, J=7.2 Hz).

MS: m/z=469 [M+H]$^+$.

Example 141

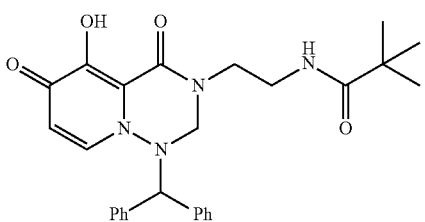

141

According to Example 136, compound 141 was synthesized by the same procedure.

$^1$H-NMR (DMSO-d$_6$) δ: 1.07 (9H, s), 2.84 (1H, m), 3.19 (2H, d, J=3.9 Hz), 3.96 (1H, d, m), 4.28 (1H, d, J=13.1 Hz), 5.21 (1H, d, J=13.1 Hz), 5.52 (1H, s), 5.56 (1H, t, J=4.2 Hz), 7.25-7.59 (10H, m), 7.75 (2H, d, J=7.7 Hz).

MS: m/z=475 [M+H]$^+$.

Example 142

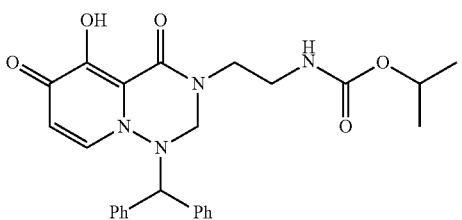

142

According to Example 136, compound 142 was synthesized by the same procedure.

¹H-NMR (DMSO-d₆) δ: 1.10 (6H, m), 2.98 (3H, m), 3.78 (1H, m), 4.27 (1H, d, J=13.6 Hz), 4.68 (1H, m), 5.11 (1H, d, J=12.8 Hz), 5.51 (2H, m), 7.07-7.46 (10H, m), 7.70 (2H, d, J=7.2 Hz).

MS: m/z=477 [M+H]⁺.

Example 143

[Chemical formula 221]

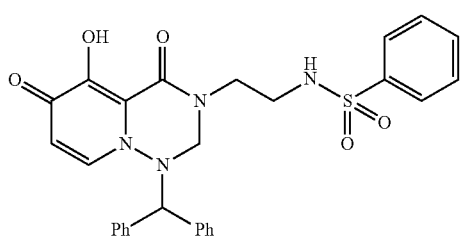

143

According to Example 136, compound 143 was synthesized by the same procedure.

¹H-NMR (DMSO-d₆) δ: 2.89 (3H, m), 3.62 (1H, m), 4.17 (1H, d, J=13.1 Hz), 4.99 (1H, d, J=13.1 Hz), 5.45 (1H, s), 5.51 (1H, d, J=7.8 Hz), 7.18-7.77 (17H, m).

MS: m/z=531 [M+H]⁺.

Example 144

[Chemical formula 222]

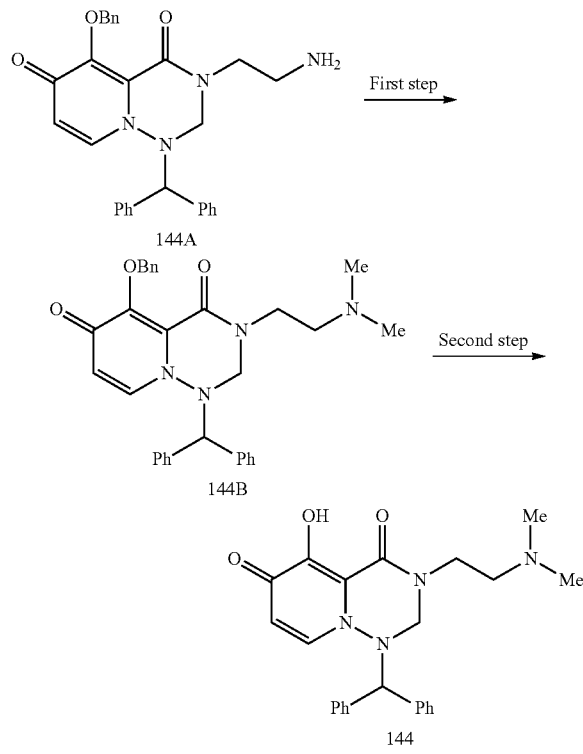

First Step

To compound 144A synthesized according to the first to fifth steps of Example 135 were added formic acid and formalin, and the mixture was stirred at 80 degree for 1.5 hours. The solvent was distilled off under reduced pressure, saturated sodium bicarbonate water was added, then the mixture was extracted with chloroform, and the extract was dried with sodium sulfate. The solvent was concentrated under reduced pressure, and the resulting crude product was purified by silica gel column chromatography (chloroform-methanol, 95:5→92:8, v/v) to obtain 26 mg of compound 144B.

¹H-NMR (CDCl₃) δ: 2.06 (6H, s), 2.18-2.26 (1H, m), 2.36-2.45 (1H, m), 2.89-2.98 (1H, m), 3.91 (1H, dt, J=14.1, 5.9 Hz), 4.43 (1H, d, J=13.6 Hz), 4.82 (1H, d, J=13.4 Hz), 5.20 (1H, s), 5.41 (1H, d, J=10.8 Hz), 5.46 (1H, d, J=10.7 Hz), 5.80 (1H, d, J=7.8 Hz), 6.69 (1H, d, J=7.8 Hz), 7.05-7.64 (15H, m).

Second Step

To compound 144B obtained in the first step was added trifluoroacetic acid (1 ml), and the mixture was stirred at room temperature for 1 hour. After concentration under reduced pressure, pH was adjusted to 6 with sodium bicarbonate water and an aqueous ammonium chloride solution, then the mixture was extracted with chloroform, and the extract was dried with sodium sulfate. After the solvent was distilled off under reduced pressure, methylene chloride-ethyl ether were added, and the precipitated solid was filtered to obtain 13 mg of compound 144 as a colorless solid.

¹H-NMR (DMSO-d₆) δ: 2.17 (6H, s), 2.38-2.46 (3H, m), 3.59 (1H, m), 4.41 (1H, d, J=13.1 Hz), 5.09 (1H, d, J=13.3 Hz), 5.50 (1H, d, J=6.4 Hz), 5.51 (1H, s), 7.19-7.47 (9H, m), 7.66 (2H, d, J=7.3 Hz).

MS: m/z=419 [M+H]⁺.

Example 145

[Chemical formula 223]

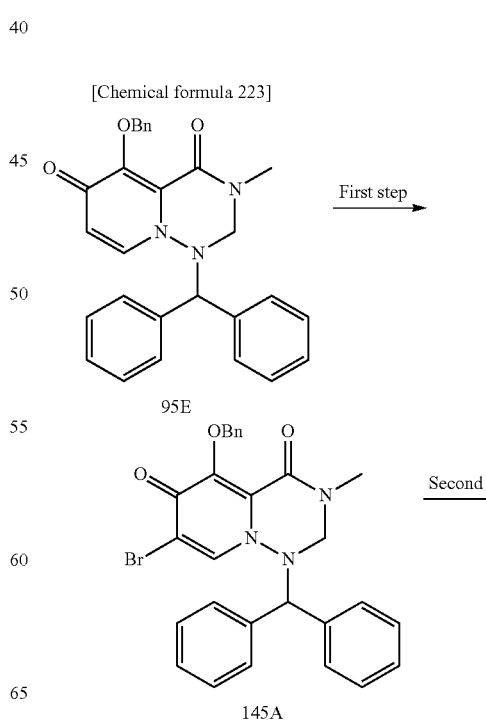

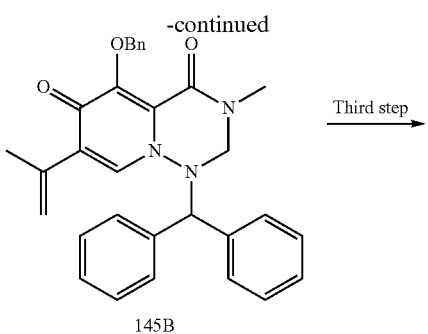

145B

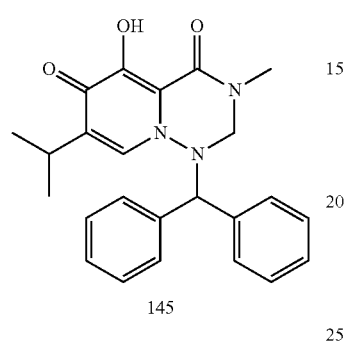

145

First Step

To a dichloromethane (5 ml) solution of compound 95E (300 mg, 0.664 mmol) was added NBS (130 mg, 0.731 mmol) under ice-cooling, temperature was raised to room temperature and, thereafter, the mixture was refluxed for 1 hour. After the solvent was distilled off, the resulting residue was purified by silica gel chromatography. The materials were eluted firstly with n-hexane-ethyl acetate (1:1, v/v) and, then, with ethyl acetate. Concentration of an objective fraction afforded 326.7 mg (yield 93%) of compound 145A as a solid.

$^1$H-NMR (CDCl$_3$) δ: 2.93 (3H, s), 4.27 (1H, d, J=13.5 Hz), 4.82 (1H, d, J=13.5 Hz), 5.13 (1H, s), 5.41 (2H, s), 5.41-7.12 (2H, m), 7.15 (1H, s), 7.17-7.28 (3H, m), 7.31-7.47 (6H, m), 7.52 (2H, d, J=6.6 Hz), 7.63-7.67 (2H, m).

Second Step

To a DMF (3 ml) solution of compound 145A (100 mg, 0.189 mmol) were added a solution of potassium carbonate (78.4 mg, 0.567 mmol) in water (0.5 ml), 4,4,5,5-tetramethyl-2-(prop-1-en-2-yl)-1,3,2-dioxaborolane (47.6 mg, 0.284 mmol) and tetakistriphenylphosphinepalladium (21.8 mg, 0.189 mmol), and the mixture was heated to stir at 80° C. for 4 hours. After the reaction solution was cooled to room temperature, water was added, and the mixture was extracted with ethyl acetate three times. The extract was washed with water three times, and dried with sodium sulfate and, thereafter, the resulting oil was purified by silica gel chromatography. Elution with only ethyl acetate, and concentration of an objective fraction afforded 42.0 mg (yield 45%) of compound 145B as an oil.

$^1$H-NMR (CDCl$_3$) δ: 1.73 (3H, s), 2.92 (3H, s), 4.29 (1H, d, J=13.5 Hz), 4.83 (1H, d, J=13.5 Hz), 4.96-4.97 (1H, m), 5.15 (1H, s), 5.21-5.21 (1H, m), 5.37 (1H, d, J=10.8 Hz), 5.40 (1H, d, J=10.8 Hz), 6.82 (1H, s), 7.15-7.21 (5H, m), 7.27-7.47 (6H, m), 7.54 (2H, d, J=6.9 Hz), 7.64-7.69 (2H, m).

Third Step

To a THF (2 ml) solution of compound 145B (40 mg, 0.081 mmol) was added 10% Pd—C (8 mg), and the mixture was subjected to a catalytic reduction under hydrogen stream. The catalyst was removed by filtration, and the filtrate was concentrated. The resulting residue was washed with ether to obtain 6.8 mg (yield 21%) of compound 145.

$^1$H-NMR (CDCl$_3$) δ: 0.629 (3H, d, J=6.9 Hz), 0.900 (3H, d, J=6.9 Hz), 2.87-3.00 (1H, m), 2.94 (3H, s), 4.37 (1H, d, J=13.2 Hz), 4.93 (1H, d, J=13.2 Hz), 5.21 (1H, s), 6.69 (1H, s), 7.21 (5H, s), 7.35-7.47 (3H, m), 7.57 (2H, d, J=7.5 Hz).

Example 146

[Chemical formula 224]

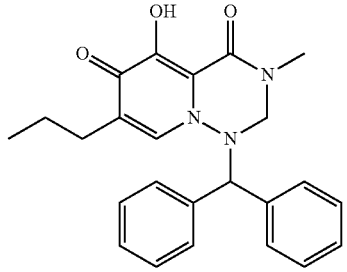

146

According to Example 145, compound 146 was synthesized by the same procedure.

$^1$H-NMR (CDCl$_3$) δ: 0.738 (3H, t, J=7.2 Hz), 1.05-1.18 (2H, m), 2.01-2.18 (2H, m), 2.94 (3H, s), 4.35 (1H, d, J=13.2 Hz), 4.95 (1H, d, J=13.2 Hz), 5.22 (1H, s), 6.71 (1H, s), 7.20 (5H, s), 7.35-7.47 (3H, m), 7.55 (2H, d, J=6.9 Hz).

Example 147

[Chemical formula 225]

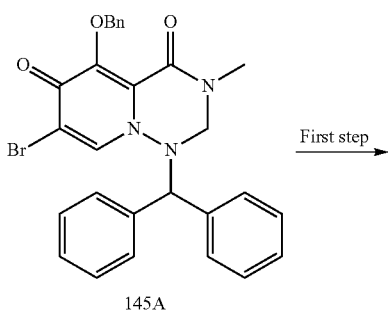

145A

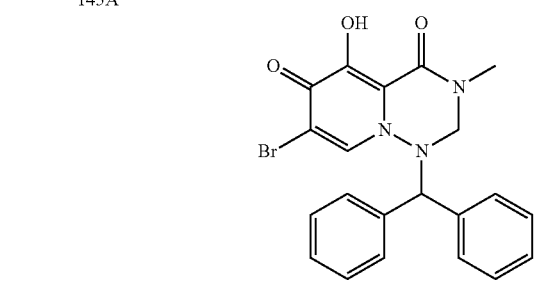

147

First Step

Compound 145A (60 mg, 0.113 mg) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 30 mg (yield 60%) of compound 147.

$^1$H-NMR (CDCl$_3$) δ: 2.97 (3H, s), 4.36 (1H, d, J=13.2 Hz), 5.01 (1H, d, J=13.2 Hz), 5.21 (1H, s), 7.14 (1H, s), 7.17-7.25 (5H, m), 7.36-7.48 (3H, m), 7.54 (2H, d, J=7.2 Hz).

Example 148

[Chemical formula 226]

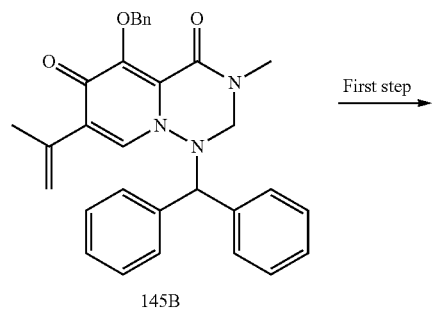

145B

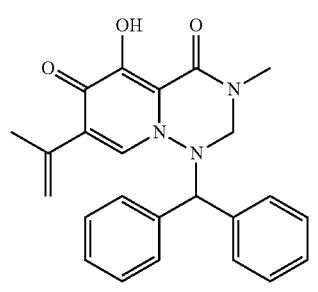

148

Compound 145B (41 mg, 0.083 mg) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 12 mg (yield 36%) of compound 148.

$^1$H-NMR (CDCl$_3$) δ: 1.70 (3H, s), 2.95 (3H, s), 4.36 (1H, d, J=12.9 Hz), 4.95 (1H, d, J=12.9 Hz), 4.96-4.98 (1H, m), 5.23 (1H, s), 5.32-5.33 (1H, m), 6.86 (1H, s), 7.21 (5H, s), 7.35-7.48 (3H, m), 7.56 (2H, d, J=7.2 Hz).

Example 149

[Chemical formula 227]

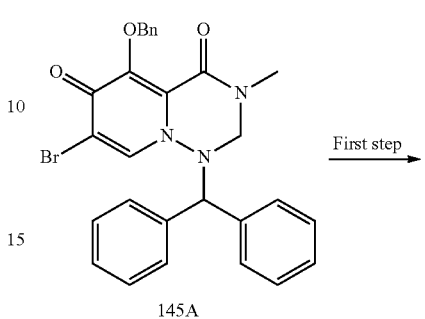

145A

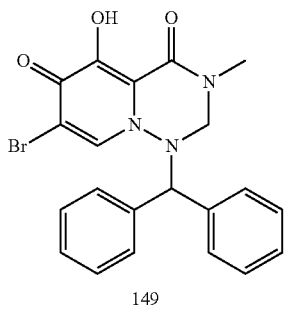

149

To a THF (2 ml) solution of compound 145A (100 mg, 0.189 mg) were added a 2N methylzinc chloride THF solution (0.377 ml, 0.754 mmol) and tetrakistriphenylphosphinepalladium (10.9 mg, 0.0945 mmol) at room temperature, and the mixture was heated to stir at 60° C. for 4 hours. After the reaction solution was cooled to room temperature, water was added, and the mixture was extracted with chloroform three times. After the extract was dried with sodium sulfate, the solvent was distilled off, and the resulting oil was purified by a MS trigger reverse layer column to obtain 9.6 mg (yield 14%) of compound 149.

$^1$H-NMR (CDCl$_3$) δ: 1.63 (3H, s), 2.95 (3H, s), 4.34 (1H, d, J=12.9 Hz), 4.68 (1H, d, J=12.9 Hz), 5.21 (1H, s), 6.70 (1H, s), 7.18 (5H, s), 7.37-7.47 (3H, m), 7.54 (2H, d, J=6.9 Hz).

Example 150

[Chemical formula 228]

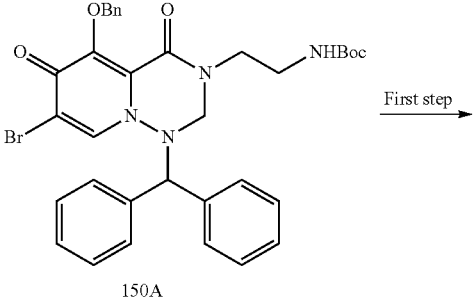

150A

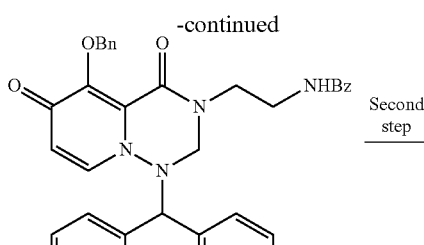

150B

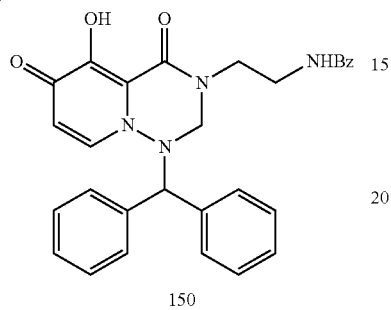

150

First Step

Compound 150A (465 mg, 0.801 mmol) synthesized according to the first to fourth step of Example 135 was dissolved in a 4N hydrochloric acid dioxane solution (5 ml), and the mixture was stirred at room temperature for 2 hours. The reaction solution was neutralized with saturated sodium bicarbonate water, and was extracted with dichloromethane three times. After the extract was dried with sodium sulfate, the solvent was distilled off, and 100 mg of the resulting oil was dissolved in dichloromethane (2 ml). To the dichloromethane solution were added triethylamine (63.2 mg, 0.624 mmol) and benzoyl chloride (31.9 mg, 0.312 mmol) under ice-cooling, and the mixture was stirred at room temperature for 1 hour. To the reaction solution was added water, and the mixture was extracted with dichloromethane three times. After the extract was dried with sodium sulfate, the solvent was distilled off, and the resulting residue was washed with diethyl ether to obtain 68 mg (yield 56%) of compound 150B.

$^1$H-NMR (CDCl$_3$) δ: 3.05-3.12 (1H, m), 3, 38-3.45 (1H, m), 3.64-3.70 (1H, m), 3.93-3.99 (1H, m), 4.22 (1H, d, J=13.2 Hz), 5.04 (1H, s), 5.07 (1H, d, J=13.2 Hz), 5.22 (1H, d, J=10.2 Hz), 5.31 (1H, d, J=10.2 Hz), 5.70 (1H, d, J=7.8 Hz), 6.55 (1H, d, J=7.8 Hz), 6.98 (2H, d, J=6.6 Hz), 7.08-7.19 (4H, m), 7.29-7.46 (5H, m), 7.49-7.53 (2H, m), 7.87 (2H, d, J=7.2 Hz), 8.06 (1H, brs).

Second Step

Compound 150B (30 mg, 0.051 mg) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 15 mg (yield 59%) of compound 150.

$^1$H-NMR (CDCl$_3$) δ: 2.91-2.98 (1H, m), 3.54-3.66 (1H, m), 3.76-3.84 (1H, m), 4.13-4.18 (1H, m), 4.28 (1H, d, J=12.9 Hz), 5.11 (1H, s), 5.43 (1H, d, J=12.9 Hz), 5.45 (1H, d, J=7.5 Hz), 6.68 (1H, d, J=7.5 Hz), 7.10-7.18 (4H, m), 7.35-7.47 (8H, m), 7.89 (2H, d, J=7.2 Hz), 8.41 (1H, s).

Example 151

[Chemical formula 229]

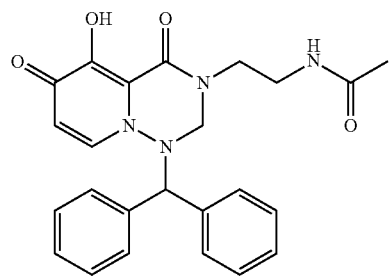

151

According to Example 150, compound 151 was synthesized by the same procedure.

$^1$H-NMR (CDCl$_3$) δ: 2.02 (3H, s), 2.69 (1H, br t, J=10.8 Hz), 3.40-3.49 (1H, m), 3.06-3.74 (1H, m), 4.12-4.22 (1H, m), 4.20 (1H, d, J=12.9 Hz), 5.08 (1H, s), 5.47 (1H, d, J=7.8 Hz), 5.50 (1H, d, J=12.9 Hz), 6.67 (1H, d, J=7.8 Hz), 7.12-7.21 (5H, m), 7.28-7.46 (5H, m), 8.31 (1H, brs).

Example 152

[Chemical formula 230]

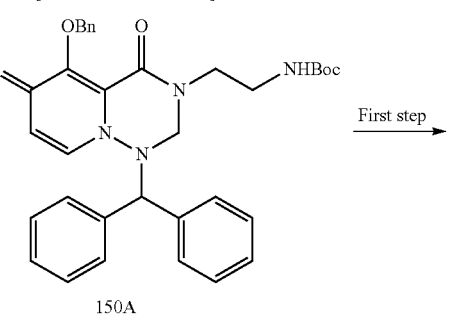

150A

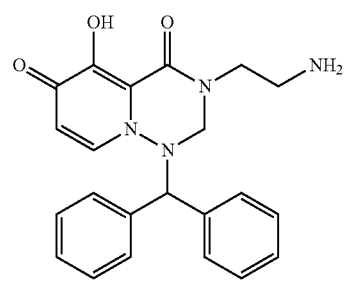

152

First Step

Compound 150A (50 mg, 0.801 mmol) was dissolved in a 4N hydrochloric acid dioxane solution (5 ml), and the mixture was stirred at room temperature for 2 hours. The reaction solution was neutralized with saturated sodium bicarbonate water, and was extracted with dichloromethane three times. After the extract was dried with sodium sulfate, the solvent was distilled off, and 50 mg of the resulting oil was dissolved in methanol (2 ml). To the methanol solution was added 10% Pd—C (10 mg), and the mixture was subjected to a catalytic reduction under hydrogen stream. The catalyst was removed by filtration, and the filtrate was concentrated. To the resulting residue was added diisopropyl ether, and the precipitated solid was filtered to obtain 10 mg (yield 25%) of compound 152.

$^1$H-NMR (DMSO-d$_6$) δ: 2.74-2.78 (2H, m), 3.00-3.07 (1H, m), 3.78-3.85 (1H, m), 4.34 (1H, d, J=13.5 Hz), 5.13 (1H, d, J=13.5 Hz), 5.48-5.54 (1H, m), 5.10 (1H, s), 7.20-7.47 (9H, m), 7.63-7.71 (2H, m).

Example 153

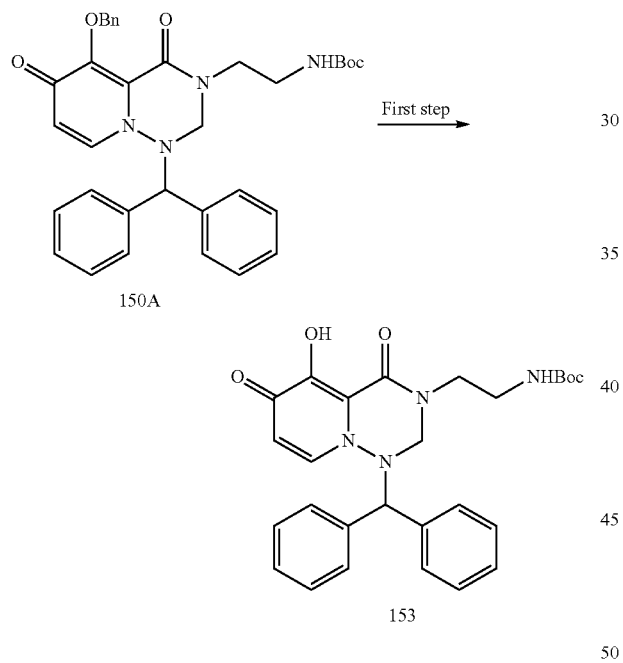

First Step

To a THF (3 ml) solution of compound 150A (30 mg, 0.052 mmol) was added 10% Pd—C (10 mg), and the mixture was subjected to a catalytic reduction under hydrogen stream. The catalyst was removed by filtration, and the filtrate was concentrated. To the resulting residue was added diisopropyl ether, and the precipitated solid was filtered to obtain 20 mg (yield 79%) of compound 153.

$^1$H-NMR (CDCl$_3$) δ: 1.34 (9H, s), 2.84-2.91 (1H, m), 3.18-3.25 (2H, m), 4.03-4.11 (1H, m), 4.35 (1H, d, J-=13.2 Hz), 5.20 (1H, s), 5.24 (1H, d, J=13.2 Hz), 5.49 (1H, brs), 5.70 (1H, d, J=7.8 Hz), 6.73 (1H, d, J=7.8 Hz), 7.16-7.20 (5H, m), 7.32-7.46 (3H, m), 7.53 (2H, d, J=7.2 Hz).

Example 154

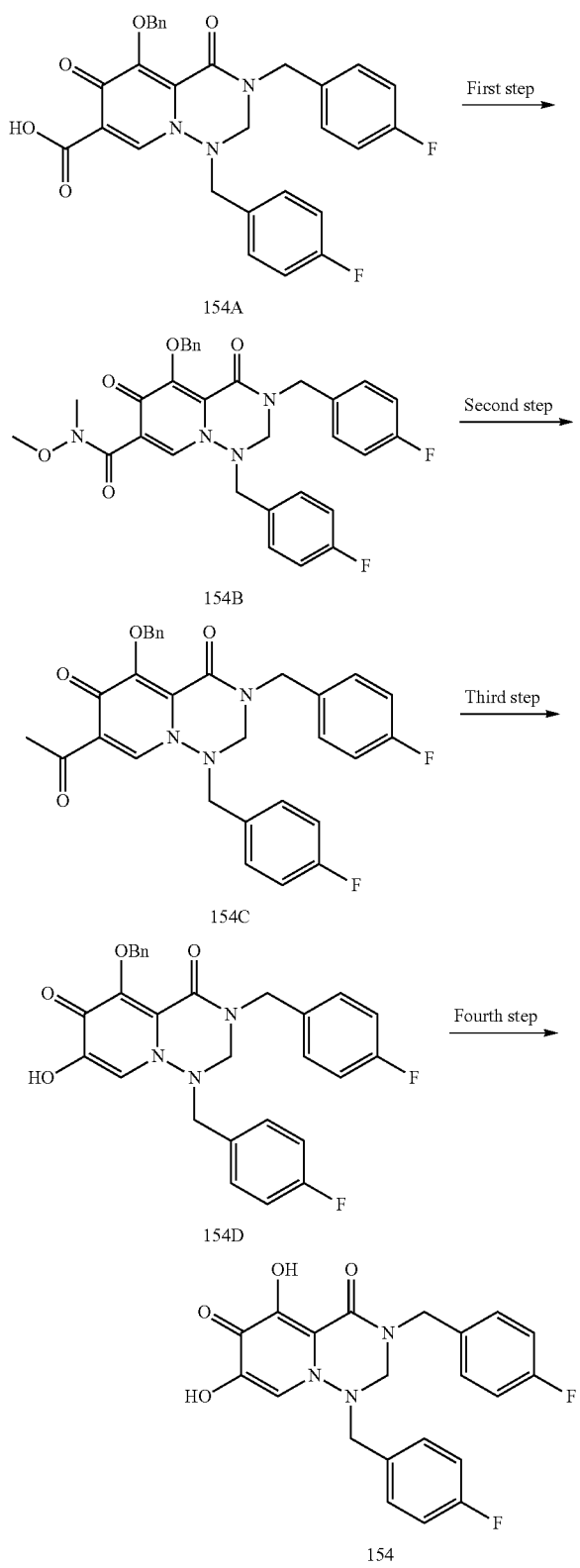

247

First Step

To a DMF (10 ml) solution of compound 154A (539 mg, 1.01 mmol) synthesized according to the synthesis method of Example 65 were added triethylamine (615.7 mg, 6.08 mmol) and ethyl chlorocarbonate (328.8 mg, 3.03 mmol) under ice-cooling, and the mixture was stirred at room temperature for 10 minutes. To the reaction solution were added O,N-dimethylhydroxylamine hydrochloride (295.0 mg, 3.03 mmol) and DMAP (12.3 mg, 0.101 mmol), the mixture was stirred at the same temperature for 2 hours, water was added, and was extracted with ethyl acetate three times. After the extract was washed with water three times, and dried with sodium sulfate, the solvent was distilled off, and the resulting oil was purified by silica gel chromatography. The materials were eluted firstly with n-hexane-ethyl acetate (7:3, v/v) and, then, with only ethyl acetate. Concentration of an objective fraction afforded 445.4 mg (yield 76%) of compound 154B as an oil.

$^1$H-NMR (DMSO-$d_6$) δ: 3.09 (3H, s), 3.52 (3H, s), 3.94 (2H, s), 4.40 (1H, brs), 4.64 (2H, s), 4.96 (1H, brs), 5.15 (2H, s), 7.06-7.15 (4H, m), 7.21 (2H, t, J=8.7 Hz), 7.28-7.38 (3H, m), 7.43 (2H, dd, J=5.7 Hz, 8.4 Hz), 7.52-7.54 (2H, m), 7.66 (1H, s).

Second Step

A THF (5 ml) solution of compound 154B (250 mg, 0.435 mmol) was cooled to −78° C., a methylmagnesium bromide 0.97M THF solution (0.673 ml, 0.653 mmol) was added, and temperature was raised to −20° C. over 2 hours. To the reaction solution was added 1N hydrochloric acid, and the mixture was extracted with ethyl acetate three times. After the extract was dried with sodium sulfate, the solvent was distilled off, and the resulting oil was purified by silica gel chromatography. The materials were eluted firstly with only chloroform and, then, with chloroform-methanol (7:3, v/v). Concentration of an objective fraction afforded 117.0 mg (yield 51%) of compound 154C as an oil.

$^1$H-NMR (CDCl$_3$) δ: 2.68 (3H, s), 3.80 (2H, brs), 4.29 (2H, brs), 4.71 (2H, brs), 5.45 (2H, brs), 6.83 (2H, m), 6.92-6.98 (2H, m), 7.03-7.10 (2H, m), 7.28-7.39 (5H, m), 7.90 (1H, s).

Third Step

To a dichloromethane (2 ml) solution of compound 154C (117 mg, 0.221 mmol) was added mCPBA (52.7 mg, 0.332 mmol) under ice-cooling, and the mixture was stirred at room temperature for 2 hours. To the reaction solution was added an aqueous sodium thiosulfate solution, and the mixture was extracted with ethyl acetate three times. After the extract was washed with saturated sodium bicarbonate water two times, and dried with sodium sulfate, the solvent was distilled off, the resulting oil was dissolved in ethanol (2 ml), and the solution was refluxed for 1 hour. After the solvent was distilled off, the precipitated solid was washed with diisopropyl ether to obtain 54 mg (yield 49%) of compound 154D.

$^1$H-NMR (CDCl$_3$) δ: 3.74 (1H, brs), 3.85 (1H, brs), 4.20 (2H, brs), 4.61 (1H, brs), 4.93 (1H, brs), 5, 41 (2H, brs), 6.79-6.86 (2H, m), 6.91-6.96 (2H, m), 7.02-7.09 (2H, m), 7.15-7.16 (1H, m), 7.26-7.34 (5H, m), 7.56-7.65 (2H, m).

Fourth Step

248

To a THF (3 ml) solution of compound 154D (54 mg, 0.107 mmol) was added 10% Pd—C (20 mg), and the mixture was subjected to a catalytic reduction under hydrogen stream. The catalyst was removed by filtration, and the filtrate was concentrated. To the resulting residue was added diisopropyl ether, and the precipitated solid was filtered to obtain 21 mg (yield 47%) of compound 154.

$^1$H-NMR (DMSO-$d_6$) δ: 3.90 (2H, brs), 3.95 (2H, s), 4, 66 (2H, brs), 7.07-7.12 (4H, m), 7.22 (2H, t, J=8.7 Hz), 7.29 (1H, s), 7.43-7.47 (2H, m).

Example 155

[Chemical formula 233]

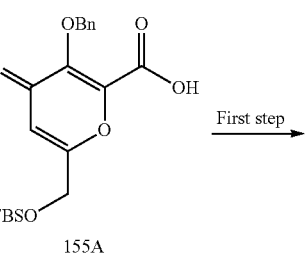

155A

First step →

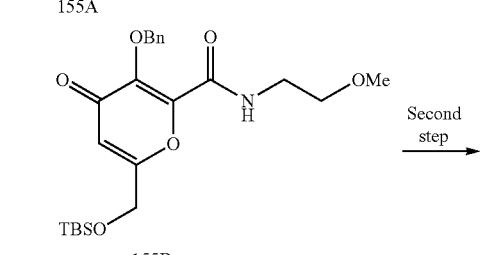

155B

Second step →

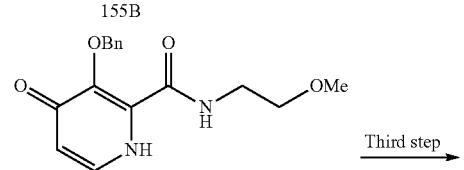

155C

Third step →

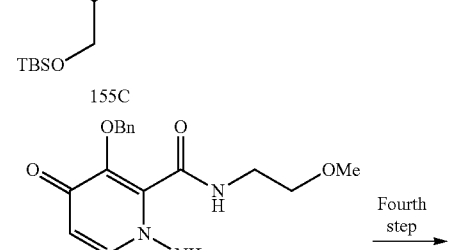

155D

Fourth step →

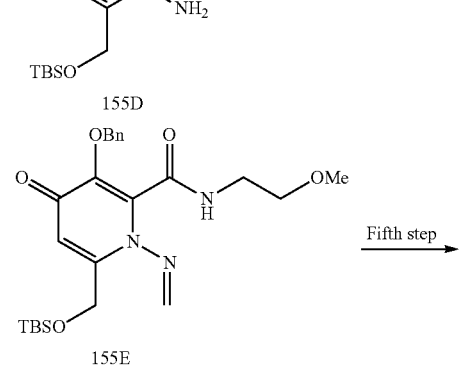

155E

Fifth step →

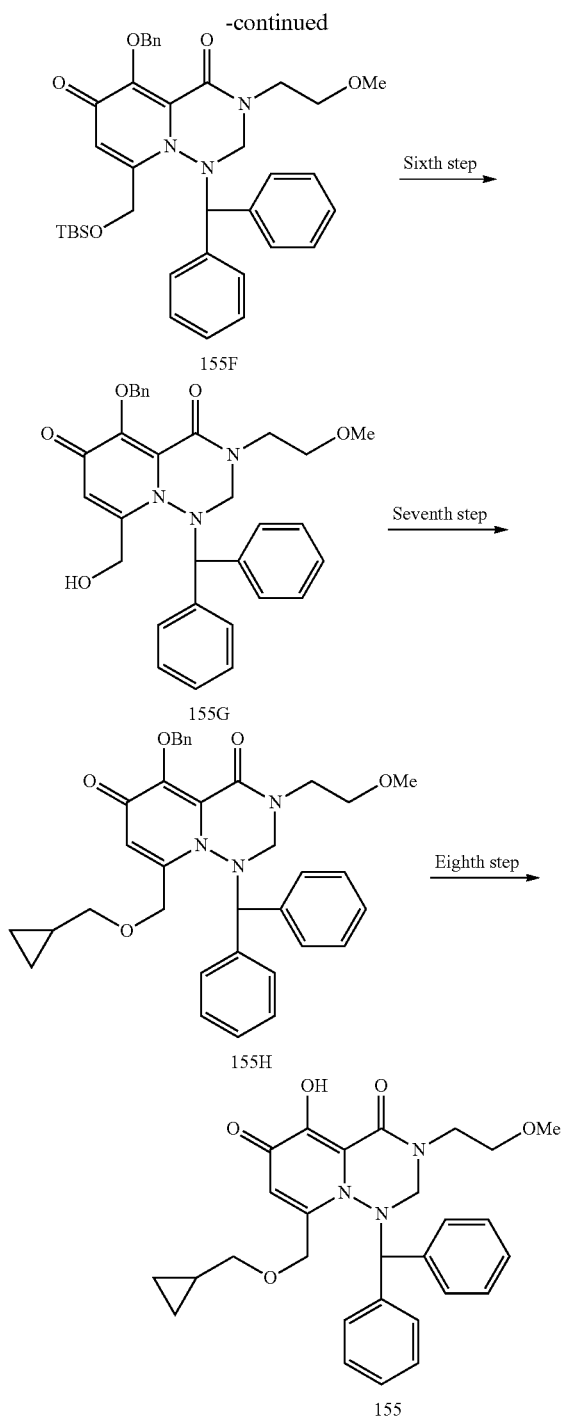

after, the mixture was extracted with ethyl acetate. The extract was sequentially washed with water (100 mL), saturated sodium bicarbonate water (150 mL) and an aqueous saturated sodium chloride solution (100 ml) and, thereafter, dried with sodium sulfate. The solvent was distilled off under reduced pressure, and the resulting residue was purified by silica gel column chromatography (ethyl acetate/n-hexane=25%→50%) to obtain compound 155B (7.86 g, 46%) as a colorless oil.

$^1$H-NMR (CDCl$_3$) δ: 0.10 (6H, s), 0.93 (9H, s), 3.29 (3H, s), 3.39 (2H, m), 3.47 (2H, m), 4.56 (2H, d, J=1.2 Hz), 5.41 (2H, s), 6.60 (1H, s), 7.35-7.42 (5H, m), 8.11 (1H, brt).

Second Step

To an ethanol (80 mL) solution of compound 155B (7.70 g, 17.2 mmol) was added aqueous ammonia (40 mL) at room temperature, and the mixture was stirred for 18 hours. The solvent was distilled off under reduced pressure, and the resulting residue was purified by silica gel column chromatography (ethyl acetate/n-hexane=75%→100%) to obtain compound 155C (7.15 g, 93%) as a colorless oil.

$^1$H-NMR (CDCl$_3$) δ: 0.14 (6H, s), 0.97 (9H, s), 3.28 (3H, s), 3.38 (2H, m), 3.49 (2H, m), 4.64 (2H, s), 5.53 (2H, s), 6.31 (1H, s), 7.34-7.49 (5H, m), 8.61 (1H, brs), 9.94 (1H, brs).

Third Step

To a DMF (125 mL) solution of compound 155C (7.15 g, 16.0 mmol) and potassium carbonate (6.64 g, 48.0 mmol) was added O-(2,4-dinitrophenyl)hydroxylamine (7.97 g, 40.0 mmol) at room temperature, and the mixture was stirred for 2 days. To the reaction solution was added water (250 mL) under ice-cooling and, thereafter, the mixture was extracted with ethyl acetate (300 mL×2). After the extract was sequentially washed with water (300 mL), saturated sodium bicarbonate water (300 mL×2) and an aqueous saturated sodium chloride solution (150 mL), the mixture was dried with sodium sulfate. The solvent was distilled off under reduced pressure, and the resulting residue was purified by silica gel column chromatography (methanol/chloroform=0%→10%) to obtain compound 155D (6.47 g, 88%) as a pale yellow solid.

$^1$H-NMR (CDCl$_3$) δ: 0.11 (6H, s), 0.94 (9H, s), 3.26 (3H, s), 3.35 (4H, m), 4.66 (2H, s), 5.16 (2H, s), 5.24 (2H, s), 6.43 (1H, s), 7.31-7.40 (5H, m), 7.59 (1H, brs).

Fourth Step

To a toluene (100 mL) solution of compound 155D (6.47 g, 14.0 mmol) and acetic acid (0.080 mL, 1.4 mmol) was added paraformaldehyde (0.422 g, 14.1 mmol) at room temperature, and the mixture was stirred at 80° C. for 2 hours. The solvent was distilled off under reduced pressure, and the resulting crude product of compound 155E was utilized in a next step without purification.

Fifth Step

To a DMF (100 mL) solution of the crude product of compound 155E obtained in the fourth step was added cesium carbonate (22.7 g, 69.8 mmol) under ice-cooling, and the mixture was stirred for 1 hour. Under ice-cooling, bromodiphenylmethane (5.20 g, 21.0 mmol) was added, and the mixture was stirred at room temperature for 19 hours. To the reaction solution was added water (200 mL) under ice-cooling and, thereafter, the mixture was extracted with ethyl acetate (200 mL×3). The extract was sequentially washed with water (200 mL×2) and an aqueous saturated sodium chloride solution (100 mL), and dried with sodium sulfate. The solvent was distilled off under reduced pressure, and the resulting crude product of compound 155F was utilized in a next step without purification.

MS: m/z=640 [M+H]$^+$.

First Step

To a toluene (150 ml) solution of compound 155A (WO 2006/066414, 15.0 g, 38.4 mmol) were sequentially added N,N-diisopropylethylamine (16.1 mL, 92.0 mmol), 1-methylimidazole (3.70 mL, 46.4 mmol) and 2-methoxyethylamine (4.05 mL, 46.4 mmol) under ice-cooling and, thereafter, diphenyl chlorophosphate (9.60 mL, 46.1 mmol) was further added dropwise over 10 minutes. After the reaction solution was stirred for 20 minutes under ice-cooling, acetonitrile (50 mL) was added, and the mixture was further stirred for 2 hours. To the reaction solution was added an aqueous acetic acid solution (10%, 100 mL) under ice-cooling and, there- Sixth Step To a methanol (100 mL) solution of the crude product of compound 155F obtained in the fifth step was added hydrogen chloride (4N ethyl acetate solution, 40 mL) at room temperature, and the mixture was stirred for 2.5 hours. To the reaction solution was added an aqueous sodium hydroxide solution (2N, 75 mL) to perform neutralization (pH=6) under ice-cooling, and the mixture was extracted with chloroform (200 mL×3). The extract was dried with sodium sulfate, the solvent was distilled off under reduced pressure, and the resulting residue was purified by silica gel column chromatography (methanol/chloroform=5%→40%) to obtain compound 155G (5.18 g, 3 step 70%) as an orange oil.

$^1$H-NMR (CDCl$_3$) δ: 3.16 (3H, s), 3.18-3.43 (3H, m), 3.60-3.74 (2H, m), 4.06 (1H, d, J=13.5 Hz), 4.19 (1H, brs), 4.58 (1H, d, J=14.7 Hz), 5.00 (1H, d, J=13.5 Hz), 5.24 (1H, s), 5.27 (2H, s), 5.96 (1H, s), 6.78 (2H, m), 6.98-7.10 (3H, m), 7.30-7.42 (8H, m), 7.72 (2H, m).

Seventh Step

To a THF (2 mL) solution of compound 155G (100 mg, 0.190 mmol), (bromomethyl)cyclopropane (0.110 mL, 1.12 mmol) and sodium iodide (5.0 mg, 0.033 mmol) was added potassium tert-butoxide (78.0 mg, 0.695 mmol) at room temperature, the mixture was stirred at room temperature for 22 hours and, thereafter, the mixture was stirred at 100° C. for 10 minutes under microwave irradiation. To the reaction solution were added water and hydrochloric acid (2N) (pH=1), the mixture was extracted with chloroform, and the extract was dried with sodium sulfate. The solvent was distilled off under reduced pressure, and the resulting crude product of compound 155H was utilized in a next step without purification.

MS: m/z=580 [M+H]$^+$.

Eighth Step

To a DMF (2 mL) solution of the crude product of compound 155H obtained in the seventh step was added lithium chloride (35.0 mg, 0.826 mmol) at room temperature, and the mixture was stirred at 150° C. for 15 minutes under microwave irradiation. The reaction solution was purified by preparative LCMS to obtain compound 155 (4.3 mg, 2 step 5%) as a white solid.

$^1$H-NMR (CDCl$_3$) δ: 0.16 (2H, m), 0.52 (2H, m), 0.98 (1H, m), 3.08 (3H, m), 3.20 (3H, s), 3.46 (2H, m), 3.68 (1H, dd, J=0.6, 14.1 Hz), 3.90 (1H, m), 4.52 (1H, d, J=13.2 Hz), 4.58 (1H, d, J=14.1 Hz), 4.93 (1H, d, J=13.2 Hz), 5.38 (1H, s), 6.01 (1H, s), 6.98 (2H, m), 7.11-7.48 (8H, m).

MS: m/z=490 [M+H]$^+$.

Example 156

[Chemical formula 234]

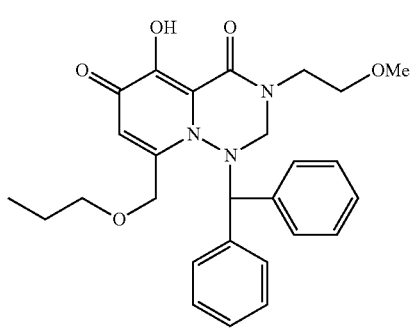

156

According to Example 155, compound 156 was synthesized by the same procedure.

$^1$H-NMR (CDCl$_3$) δ: 0.88 (3H, t, J=7.4 Hz), 1.51 (2H, m), 3.15-3.23 (6H, m), 3.46 (2H, m), 3.69 (1H, dd, J=0.6, 14.1 Hz), 3.88 (1H, m), 4.54 (2H, d, J=14.1 Hz), 4.58 (1H, d, J=14.1 Hz), 4.93 (1H, d, J=13.5 Hz), 5.39 (1H, s), 6.12 (1H, s), 6.97 (2H, m), 7.12-7.47 (8H, m).

MS: m/z=478 [M+H]$^+$.

Example 157

[Chemical formula 235]

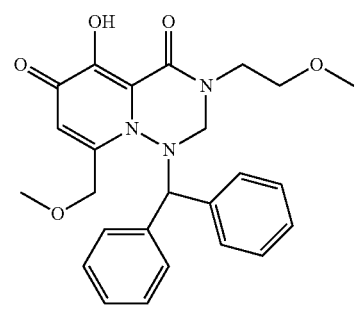

157

According to Example 155, compound 157 was synthesized by the same procedure.

$^1$H-NMR (CDCl$_3$) δ: 3.13-3.22 (1H, m), 3.18 (3H, s), 3.20 (3H, s), 3.41-3.51 (2H, m), 3.60 (1H, d, J=13.8 Hz), 3.89 (1H, ddd, J=3.3 Hz, 4.2 Hz, 14.4 Hz), 4.52 (1H, d, J=13.2 Hz), 4.53 (1H, d, J=13.8 Hz), 4.92 (1H, d, J=13.2 Hz), 5.38 (1H, s), 5.98 (1H, s), 6.98 (2H, d, J=8.4 Hz), 7.11-7.22 (3H, m), 7.36-7.48 (5H, m).

Example 158

[Chemical formula 236]

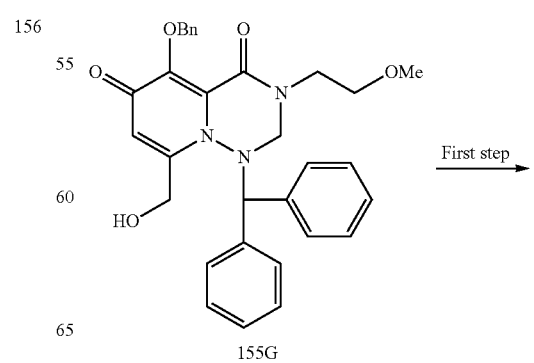

155G

First step →

253

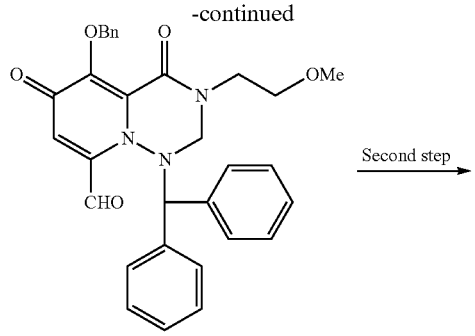

158A

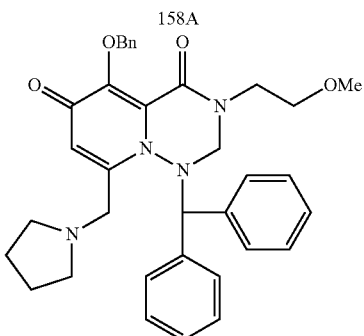

158B

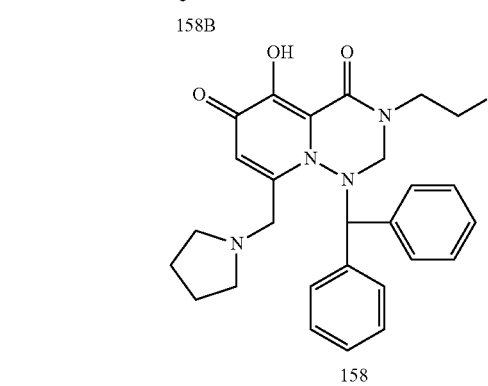

158

First Step

To a THF (100 mL) solution of compound 155G (960 mg, 1.83 mmol) was added manganese dioxide (2.06 g, 92.0 mmol) at room temperature, and the mixture was stirred for 2 days. After the reaction solution was filtered, the filtrate was distilled off under reduced pressure, and the resulting residue was purified by silica gel column chromatography (ethyl acetate/n-hexane=60%→100%) to obtain compound 158A (554 mg, 58%) as a pale yellow foam.

$^1$H-NMR (CDCl$_3$) δ: 2.96 (1H, m), 3.18 (3H, s), 3.44 (2H, m), 4.18 (1H, m), 4.56 (1H, d, J'=13.8 Hz), 4.98 (1H, d, J=13.8 Hz), 5.28 (1H, s), 5.54 (1H, d, J=10.5 Hz), 5.64 (1H, d, J=10.5 Hz), 6.35 (1H, s), 6.85 (2H, m), 7.03 (2H, m), 7.18 (1H, m), 7.26-7.48 (8H, m), 7.64 (2H, m), 10.10 (1H, s).

Second Step

To a methylene chloride (4 mL) solution of compound 158A (83.0 mg, 0.159 mmol), pyrrolidine (0.0400 mL, 0.484 mmol) and acetic acid (0.100 ml) was added sodium triacetoxyborohydride (136 mg, 0.642 mmol) at room temperature, and the mixture was stirred for 28 hours. To the reaction solution was added water, the mixture was extracted with chloroform, and the extract was dried with sodium sulfate. The solvent was distilled off under reduced pressure, and the resulting crude product of compound 158B was utilized in a next step without purification.

MS: m/z=579 [M+H]$^+$.

254

Third Step

To a DMF (2 mL) solution of the crude product of compound 158B obtained in the second step was added lithium chloride (39.2 mg, 0.925 mmol) at room temperature, and the mixture was stirred at 150° C. for 15 minutes under microwave irradiation. The reaction solution was distilled off under reduced pressure, and the resulting residue was purified by preparative LCMS to obtain compound 158 (8.8 mg, 2 step 11%) as a yellow oil.

$^1$H-NMR (CDCl$_3$) δ: 1.84 (4H, m), 2.70-2.85 (5H, m), 3.19 (3H, s), 3.20-3.47 (3H, m), 3.80 (1H, m), 4.25 (1H, d, J=14.7 Hz), 4.57 (1H, d, J=13.5 Hz), 5.07 (1H, d, J=13.5 Hz), 5.39 (1H, s), 6.06 (1H, s), 6.97 (2H, m), 7.12-7.54 (8H, m), 8.29 (1H, s).

MS: m/z=489 [M+H]$^+$.

Example 159

[Chemical formula 237]

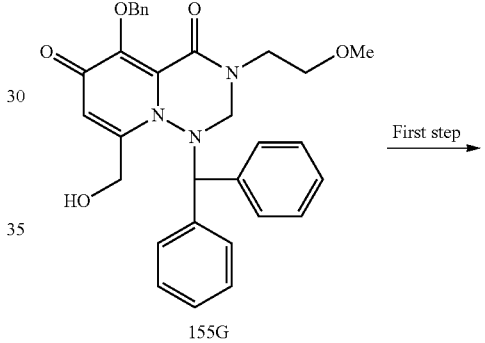

155G

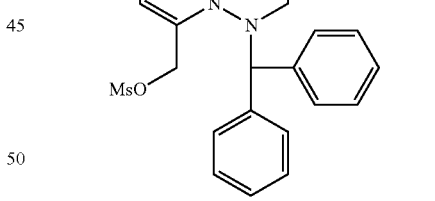

159A

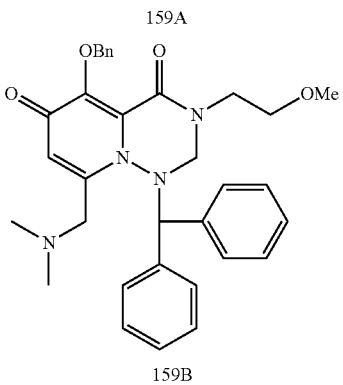

159B

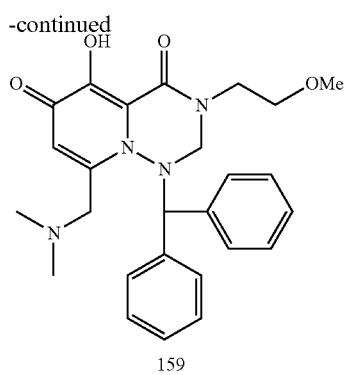

159

First Step

To a methylene chloride (20 mL) solution of compound 155G (950 mg, 1.81 mmol) and N,N-diisopropylethylamine (0.380 mL, 2.18 mmol) was added dropwise methanesulfonyl chloride (0.148 mL, 1.90 mmol) under ice-cooling, and the mixture was stirred for 90 minutes. To the reaction solution was added water (20 mL), the mixture was extracted with chloroform (50 mL), and the extract was dried with sodium sulfate. The solvent was distilled off under reduced pressure, and the resulting crude product (1.06 g) of compound 159A was utilized in a next step without purification.

MS: m/z=604 [M+H]$^+$.

Second Step

To the crude product (161 mg) of compound 159A obtained in the first step was added dimethylamine (2M THF solution, 2.00 mL, 4.00 mmol) at room temperature, and the mixture was stirred for 3 days. To the reaction solution was added an aqueous saturated sodium chloride solution (2 mL), the mixture was extracted with ethyl acetate, and the extract was dried with sodium sulfate. The solvent was distilled off under reduced pressure, and the resulting crude-product of compound 159B was utilized in a next step without purification.

MS: m/z=553 [M+H]$^+$.

Third Step

To a DMF (2 mL) solution of the crude product of compound 159B obtained in the second step was added lithium chloride (56.0 mg, 1.32 mmol) at room temperature, and the mixture was stirred at 150° C. for 30 minutes under microwave irradiation. The reaction solution was distilled off under reduced pressure, and the resulting residue was purified by preparative LCMS to obtain compound 159 (33.6 mg, 3 step 27%) as a white solid.

$^1$H-NMR (CDCl$_3$) δ: 2.37 (6H, s), 2.69 (1H, d, J=14.4 Hz), 3.19 (3H, s), 3.30-3.46 (3H, m), 3.76 (1H, m), 4.00 (1H, d, J=14.4 Hz), 4.60 (1H, d, J=13.5 Hz), 5.20 (1H, d, J=13.5 Hz), 5.40 (1H, s), 6.01 (1H, s), 6.97 (2H, m), 7.11-7.42 (8H, m).

MS: m/z=463 [M+H]$^+$.

Example 160

[Chemical formula 238]

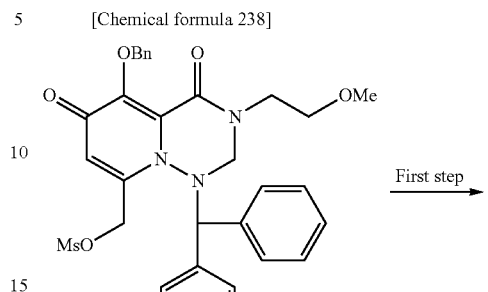
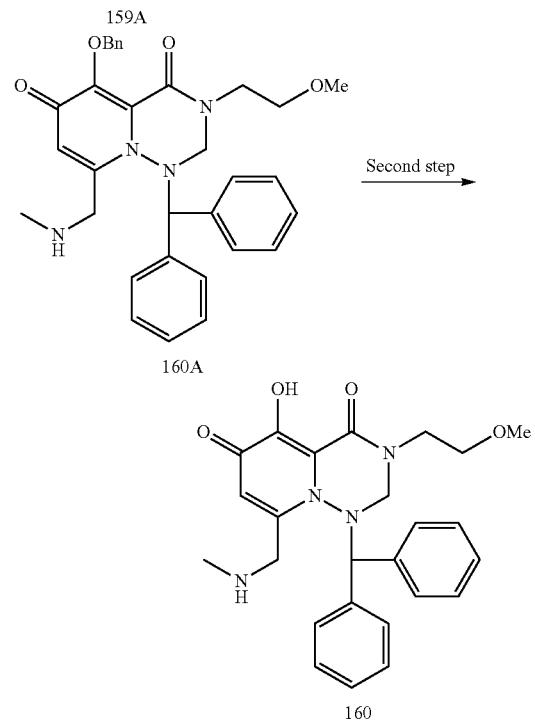

First Step

To a crude product (95.8 mg) of compound 159A was added methylamine (2M THF solution, 2.00 mL, 4.00 mmol) at room temperature, and the mixture was stirred for 3 days. The reaction solution was filtered, the solvent was distilled off under reduced pressure, and the resulting crude product of compound 160A was utilized in a next step without purification.

MS: m/z=539 [M+H]$^+$.

Second Step

To an acetonitrile (3 mL) suspension of the crude product of compound 160A and sodium iodide (100 mg, 0.667 mmol) was added chlorotrimethylsilane (0.0850 mL, 0.665 mmol) at room temperature, and the mixture was stirred for 5 hours. To the reaction solution was added water (1 mL), the solvent was distilled off under reduced pressure, and the resulting residue was purified by preparative LCMS to obtain compound 160 (59.8 mg, 3 step 84%) as a white solid.

$^1$H-NMR (CDCl$_3$) δ: 2.75 (3H, s), 3.08 (1H, d, J=13.5 Hz), 3.24 (3H, s), 3.30-3.40 (3H, m), 3.75 (1H, m), 4.32 (1H, d, J=13.8 Hz), 4.66 (1H, d, J=13.8 Hz), 5.33 (1H, s), 5.58 (1H, d, J=13.5 Hz), 6.40 (1H, s), 6.98 (2H, m), 7.12-7.25 (3H, m), 7.40-7.51 (2H, m), 7.60 (2H, m).

MS: m/z=449 [M+H]+.

Example 161

[Chemical formula 239]

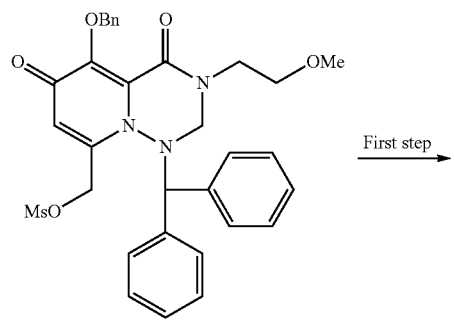

159A

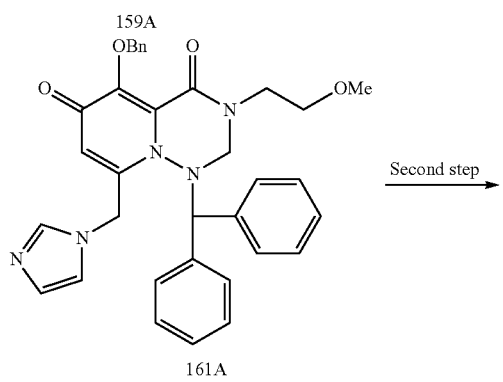

161A

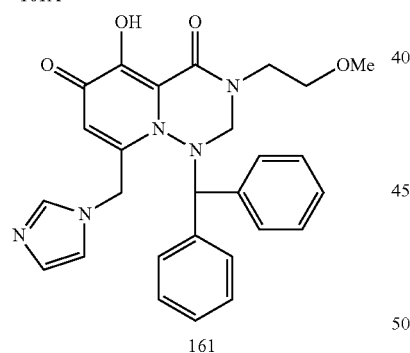

161

First Step

After a DMF (2 mL) suspension of a crude product (156 mg) of compound 159A, imidazole (19.5 mg, 0.286 mmol) and potassium carbonate (37.7 mg, 0.273 mmol) was stirred at room temperature for 4 hours, sodium hydride (60%, 11.7 mg, 0.293 mmol) was added, and the mixture was stirred for 3 days. To the reaction solution was added an aqueous acetic acid solution (10%), the mixture was extracted with chloroform, and the extract was dried with sodium sulfate. The solvent was distilled off under reduced pressure, and the resulting crude product of compound 161A was utilized in a next step without purification.

MS: m/z=576 [M+H]+.

Second Step

To the crude product of compound 161A was added trifluoroacetic acid (1 mL) at room temperature, and the mixture was stirred for 18 hours and, thereafter, the mixture was stirred at 60° C. for 3 hours. The reaction solution was distilled off under reduced pressure, and the resulting residue was purified by preparative LCMS to obtain compound 161 (19.8 mg, 3 step 16%) as a pale orange amorphous substance.

1H-NMR (CDCl3) δ: 3.17-3.25 (1H, m), 3.21 (3H, s), 3.38-3.47 (2H, m), 3.82 (1H, m), 4.40 (1H, d, J=16.5 Hz), 4.54 (1H, d, J=13.5 Hz), 5.02 (1H, d, J=13.5 Hz), 5.09 (1H, s), 5.32 (1H, d, J=16.5 Hz), 5.40 (1H, s), 6.65 (1H, brs), 7.03 (2H, m), 7.15-7.49 (8H, m), 8.08 (1H, brs).

MS: m/z=486 [M+H]+.

Example 162

[Chemical formula 240]

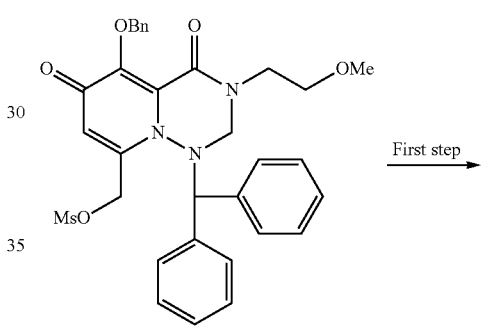

159A

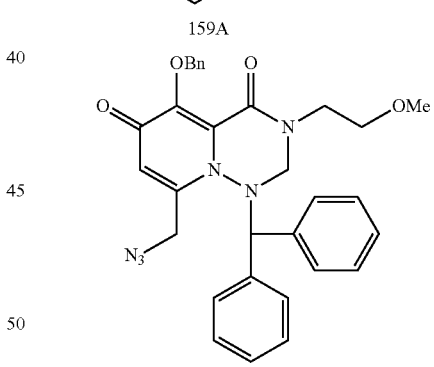

162A

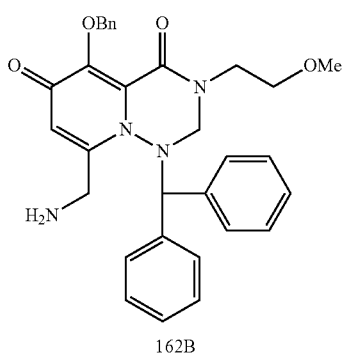

162B

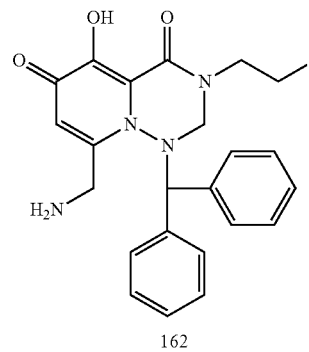

162

First Step

To a DMF (2 mL) solution of a crude product (192 mg) of compound 159A was added sodium azide (24.2 mg, 0.372 mmol) at room temperature, and the mixture was stirred at 60° C. for 2 hours. The reaction solution was distilled off under reduced pressure, and the resulting crude product of compound 162A was utilized in a next step without purification.

MS: m/z=551 [M+H]$^+$.

Second Step

To a THF (4 mL) solution of the crude product of compound 162A were sequentially added water (0.200 mL) and triphenylphosphine (83.0 mg, 0.316 mmol) at room temperature, and the mixture was stirred at 60° C. for 1 hour. The reaction solution was distilled off under reduced pressure, and the resulting residue was purified by preparative LCMS to obtain compound 162B (110 mg, 3 step 66%) as a colorless oil.

MS: m/z=525 [M+H]$^+$.

Third Step

To an acetonitrile (1 mL) suspension of compound 162B (50.0 mg, 0.0950 mmol) and sodium iodide (56.2 mg, 0.375 mmol) was added chlorotrimethylsilane (0.0490 mL, 0.381 mmol) at room temperature, and the mixture was stirred for 6 hours. To the reaction solution was added water (0.5 mL), the solvent was distilled off under reduced pressure, and the resulting residue was purified by preparative LCMS to obtain compound 162 (25.9 mg, 63%) as a pale orange solid.

$^1$H-NMR (CDCl$_3$) δ: 3.12 (1H, d, J=14.7 Hz), 3.27 (3H, s), 3.35-3.48 (3H, m), 3.81 (1H, m), 4.65 (1H, d, J=13.5 Hz), 5.31 (1H, s), 5.59 (1H, d, J=13.5 Hz), 6.40 (1H, s), 6.98 (2H, m), 7.19 (3H, m), 7.40 (1H, m), 7.50 (2H, m), 7.62 (2H, m), 8.11 (1H, s).

MS: m/z=435 [M+H]$^+$.

Example 163

[Chemical formula 241]

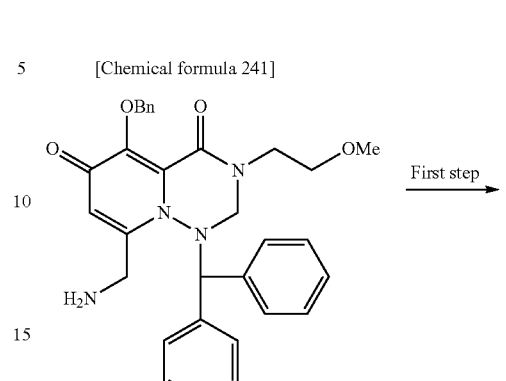

162B

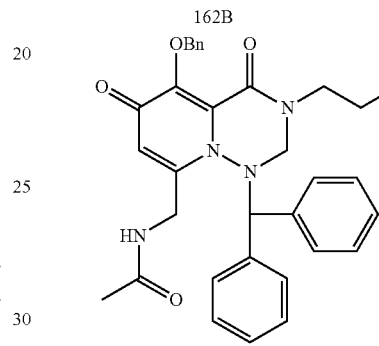

163A

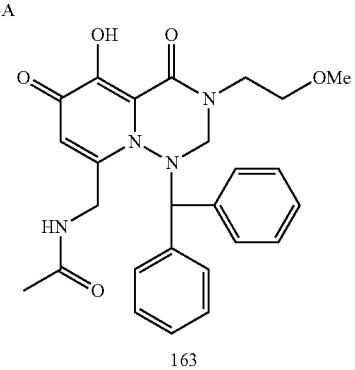

163

First Step

To an acetonitrile (3 mL) solution of compound 162B (50.0 mg, 0.0950 mmol) and N,N-diisopropylethylamine (0.0366 mL, 0.210 mmol) was added acetic anhydride (0.0100 mL, 0.106 mmol) at room temperature, and the mixture was stirred for 6 hours. The reaction solution was distilled off under reduced pressure, and the resulting crude product of compound 163A was utilized in a next step without purification.

MS: m/z=567 [M+H]$^+$.

Second Step

To an acetonitrile (5 mL) suspension of the crude product of compound 163A and sodium iodide (59.2 mg, 0.395 mmol) was added chlorotrimethylsilane (0.0487 mL, 0.381 mmol) at room temperature, and the mixture was stirred for 16 hours. To the reaction solution was added water (0.5 mL), the solvent was distilled off under reduced pressure, and the resulting residue was purified by preparative LCMS to obtain compound 163 (28.1 mg, 2 step 62%) as a pale orange foam.

¹H-NMR (CDCl₃) δ: 2.07 (3H, s), 3.24 (3H, s), 3.27-3.52 (4H, m), 3.67 (1H, m), 4.54 (1H, d, J=13.5 Hz), 4.78 (1H, dd, J=6.5, 14.9 Hz), 5.17 (1H, d, J=13.5 Hz), 5.28 (1H, s), 5.61 (1H, s), 7.01 (2H, m), 7.01-7.58 (9H, m).

MS: m/z=477 [M+H]⁺.

Example 164

[Chemical formula 242]

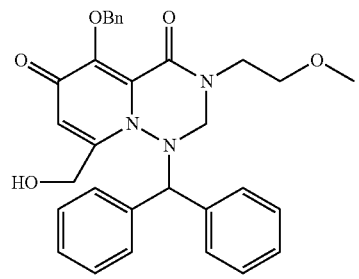

155G

First step →

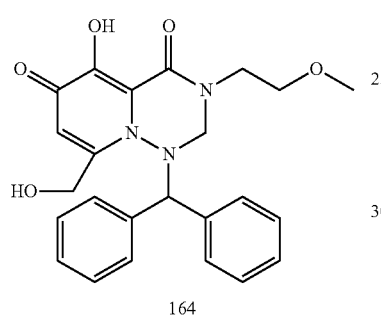

164

First Step

Compound 155G (43.3 mg, 0.221 mmol) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 22 mg (yield 61%) of compound 164.

¹H-NMR (CDCl₃) δ: 1.13 (6H, d, J=6.0 Hz), 3.18-3.77 (7H, m), 3.26 (3H, s), 4.49 (1H, d, J=12.3 Hz), 4.76 (1H, d, J=12.3 Hz), 5.27 (2H, brs), 5.89 (1H, s), 6.90 (2H, d, J=7.2 Hz), 6.98-7.14 (3H, m), 7.315-7.50 (5H, m).

Example 165

[Chemical formula 243]

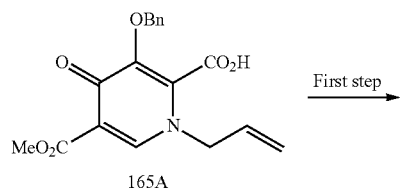

165A

First step →

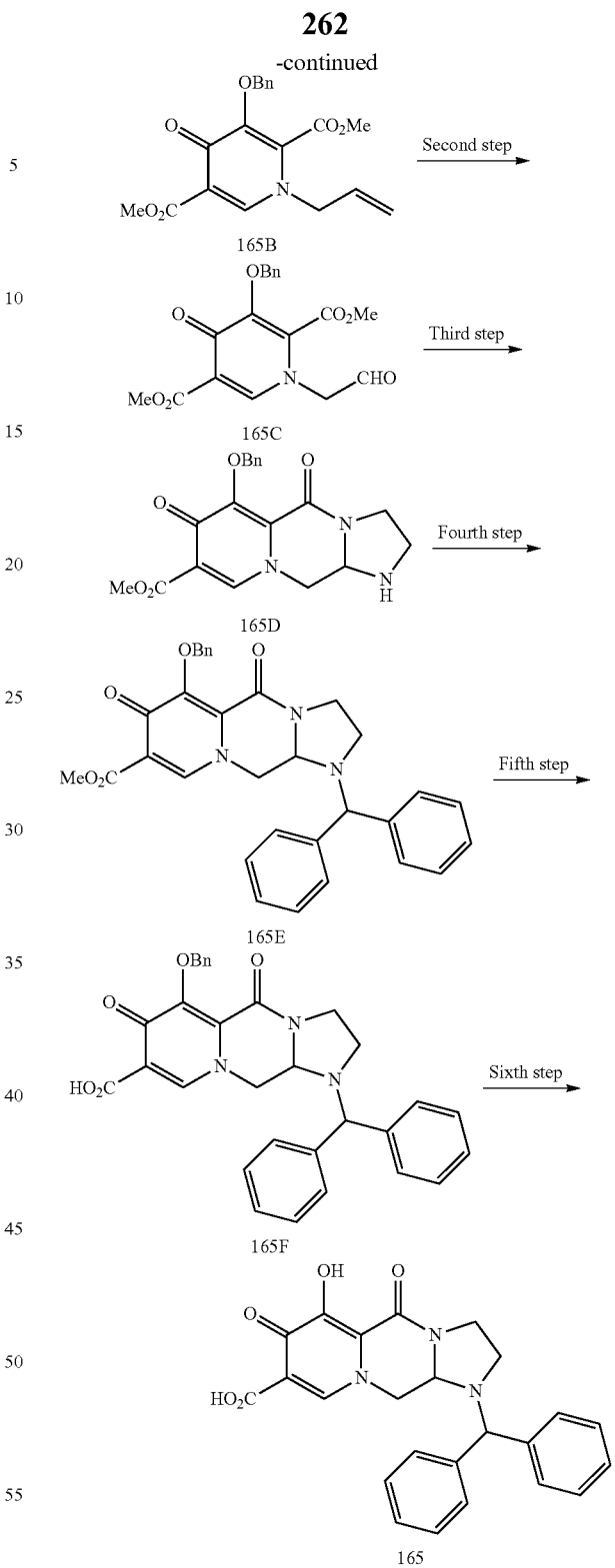

First Step

To a DMF (370 mL) solution of compound 165A (WO 2006/088173, 37.0 g, 108 mmol) were sequentially added potassium carbonate (17.9 mg, 129 mmol) and methyl iodide (8.03 mL, 129 mmol) at room temperature, and the mixture was stirred for 1.5 hours. The reaction solution was added to a solution of ammonium chloride (20.8 g, 390 mmol) in water (1110 mL) under ice-cooling, and the precipitated solid was filtered, and washed with water to obtain a crude product (33 g). In addition, the aqueous layer was salted out with sodium chloride, and the mixture was extracted with ethyl acetate, and dried with sodium sulfate. The solvent was distilled off under reduced pressure, and a crude product (9 g) was obtained from the resulting residue. The crude products were combined and purified by silica gel column chromatography (ethyl acetate/n-hexane=50%→100%) to obtain compound 165B (36.5 g, 95%) as a white solid.

Second Step

To a 1,4-dioxane (548 mL) solution of compound 165B (36.5 g, 102 mmol) were sequentially added potassium osmate dihydrate (1.13 g, 3.06 mmol), sodium periodate (87.3 g, 408 mmol) and water (365 mmol) at room temperature, and the mixture was stirred for 6 hours. The reaction solution was extracted with methylene chloride, and the extract was dried with sodium sulfate. The solvent was distilled off under reduced pressure, and the resulting residue was purified by silica gel column chromatography (ethyl acetate/n-hexane=50%→100%) to obtain compound 165C (33.0 g, 90%) as a bronzed foam.

Third Step

To a toluene (25 mL) suspension of compound 165C (1.38 g, 3.66 mmol) were sequentially added ethylenediamine (0.247 mL, 3.66 mmol) and acetic acid (0.0210 mL, 0.366 mmol) at room temperature and, thereafter, the mixture was stirred for 1 hour, and further stirred at 50° C. for 17 hours. The precipitated solid was filtered, and washed with ether to obtain compound 165D (1.11 g, 100%) as a pale yellow solid.

$^1$HNMR (DMSO-$d_6$) δ: 3.05 (2H, m), 3.26 (1H, m), 3.63 (2H, m), 3.75 (3H, s), 3.87 (1H, m), 4.52 (1H, dd, J=3.3, 12.6 Hz), 4.69 (1H, m), 4.99 (1H, d, J=10.4 Hz), 5.15 (1H, d, J=10.4 Hz), 7.35 (3H, m), 7.54 (2H, m), 8.41 (1H, s).

Fourth Step

To an acetonitrile (30 mL) suspension of compound 165D (2.77 g, 7.50 mmol), potassium carbonate. (2.23 g, 16.1 mmol) and sodium iodide (102 mg, 0.680 mmol) was added bromodiphenylmethane (2.26 g, 9.14 mmol) at room temperature, and the mixture was stirred at 90° C. for 7 hours. The reaction solution was poured into hydrochloric acid (2N, 10 mL) and an ice (20 g), the mixture was extracted with chloroform (100 mL×2), and the extract was dried with sodium sulfate. The solvent was distilled off under reduced pressure, and the residue was purified by silica gel column chromatography (chloroform/methanol=0%→5%) to obtain compound 165E (2.72 g, 68%) as a pale yellow solid.

Fifth Step

To an ethanol (30 mL) solution of compound 165E (2.72 g, 5.08 mmol) was added an aqueous sodium hydroxide solution (2N, 10 mL) at room temperature, and the mixture was stirred for 3 days. To the reaction solution was added hydrochloric acid (1N, 20 mL) (pH=1) at room temperature, the mixture was extracted with chloroform (100 mL×2), and the extract was dried with sodium sulfate. The solvent was distilled off under reduced pressure, and the resulting residue was purified by silica gel column chromatography (chloroform/methanol=0%→10%) to obtain compound 165F (1.77 g, 67%) as a pale yellow solid.

$^1$HNMR (DMSO-$d_6$) δ: 2.63 (1H, m), 3.16 (1H, m), 3.49 (1H, m), 3.73 (1H, m), 4.12 (2H, m), 4.56 (1H, m), 5.04 (1H, s), 5.09 (1H, d, J=10.7 Hz), 5.19 (1H, d, J=10.7 Hz), 7.28-7.53 (15H, m), 8.32 (1H, s), 8.39 (1H, s).

Sixth Step

A N,N'-dimethylimidazolidinone (20 mL) solution of compound 165F (1.77 g, 3.39 mmol) and lithium chloride (0.515 g, 12.2 mmol) was stirred at 90° C. for 1 hour. To the reaction solution were sequentially added water (10 mL), hydrochloric acid (2N, 10 mL) and water (10 mL) at room temperature. The precipitated solid was filtered, and washed with ether, DMF-water were added, and the precipitated solid was filtered to obtain compound 165 (599 mg, 41%) as a white solid.

$^1$HNMR (DMSO-$d_6$) δ: 2.60 (1H, m), 3.20 (1H, m), 3.64 (2H, m), 4.00 (2H, m), 4.55 (1H, m), 5.01 (1H, s), 7.28-7.47 (10H, m), 8.16 (1H, s), 11.97 (1H, brs).

MS: m/z=432 [M+H]$^+$.

Example 166

[Chemical formula 244]

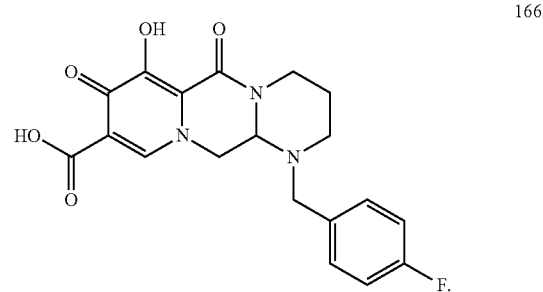

According to Example 165, following compound 166 was synthesized by the same procedure.

$^1$HNMR (DMSO-$d_6$) δ: 1.54 (1H, d, J=12.6H), 1.66-1.78 (1H, m), 2.60 (1H, t, J=9.9 Hz), 2.83 (1H, d, J=11.7 Hz), 3.01 (1H, t, J=11.7 Hz), 3.34-3.38 (1H, m), 3.94 (1H, d, J=13.8 Hz), 4.44-4.59 (3H, m), 4.82 (1H, d, J=14.7 Hz), 7.06 (2H, t, J=8.7 Hz), 7.18-7.23 (2H, m), 8.27 (1H, s), 12.84 (1H, brs).

Example 167

[Chemical formula 245]

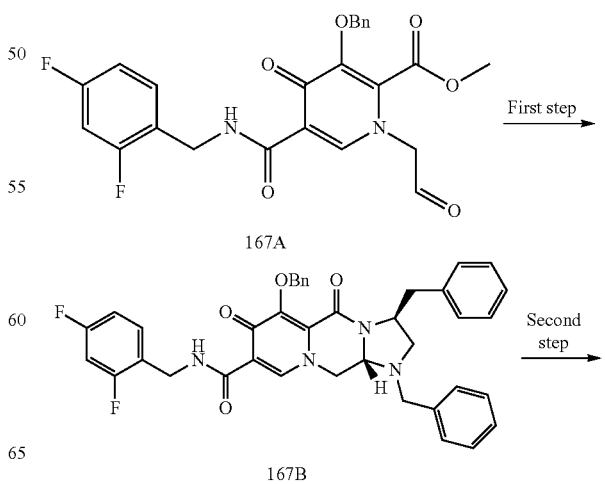

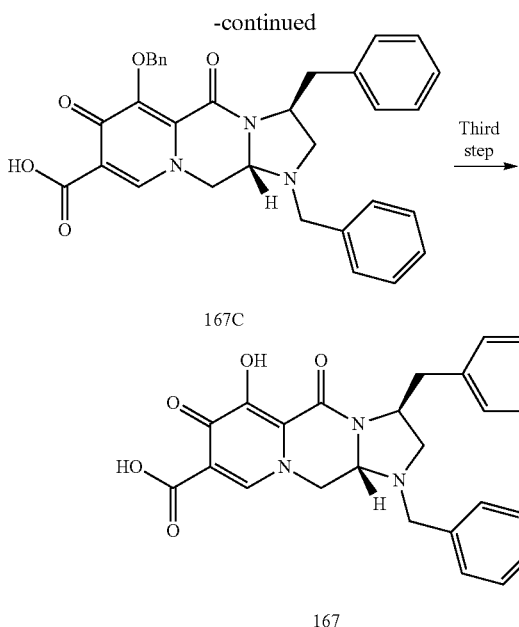

167C

167

First Step

To a xylene (30 ml) solution of compound 167A (WO 2006/11674, 3.58 g, 7.61 mmol) were added (S)—N1-benzyl-3-phenylpropane-1,2-diamine (Journal of the American Chemical Society; English; 127; 30; 2005; 10504, 1.83 g, 7.61 mmol) and acetic acid (0.5 ml), and the mixture was refluxed for 2 hours. After cooling to room temperature, the solvent was distilled off, and the resulting oil was purified by silica gel chromatography. The materials were eluted firstly with n-hexane-ethyl acetate (9:1, v/v) and, then, with n-hexane-ethyl acetate (1:1, v/v). Concentration of an objective fraction afforded 349 mg (yield 7%) of compound 167B as an oil.

$^1$HNMR (CDCl$_3$) δ: 2.54 (1H, t, J=9.6 Hz), 2.77 (1H, dd, J=9.0 Hz, 13.2 Hz), 3.31 (1H, dd, J=6.9 Hz, 9.6 Hz), 3.43-3.78 (5H, m), 4.04-4.15 (1H, m), 4.42-4.48 (1H, m), 4.62 (2H, d, J=6.0 Hz), 5.29 (1H, d, J=10.5 Hz), 5.43 (1H, d, J=10.5 Hz), 6.77-6.85 (2H, m), 7.19-7.39 (14H, m), 7.60 (2H, d, J=6.3 Hz), 8.05 (1H, s).

Second Step

To a MeCN (10 ml) solution of compound 167B (968 mg, 1.47 mmol) were added Boc$_2$O (3 ml) and DMAP (180 mg, 1.47 mmol), and the mixture was heated to reflux for 5 hours. To the reaction solution was added a 2N aqueous sodium hydroxide solution to stop the reaction, the reaction solution was neutralized using 2N hydrochloric acid and, thereafter, the mixture was extracted with ethyl acetate three times. After the extract was washed with an aqueous saturated sodium chloride solution, the solvent was distilled off, and the resulting oil was purified by silica gel chromatography. The materials were eluted firstly with n-hexane-ethyl acetate (6:4, v/v) and, then, only with ethyl acetate. Concentration of an objective fraction afforded 349 mg (yield 45%) of compound 167C.

$^1$HNMR (CDCl$_3$) δ: 2.54 (1H, t=9.0 Hz), 2.76 (1H, dd, J=9.3 Hz, 16.5 Hz), 3.31 (1H, dd, J=6.9 Hz, 9.6 Hz), 3.45 (1H, dd, J=3.3 Hz, 12.6 Hz), 3.51-3.78 (4H, m), 4.04-4.13 (1H, m), 4.42-4.52 (1H, m), 4.61 (2H, d, J=6.0 Hz), 2.79 (1H, d, J=10.2 Hz), 5.29 (1H, d, J=10.2 Hz), 5.43 (1H, d, J=10.2 Hz), 6.76-7.39 (11H, m), 7.60 (2H, d, J=6.6 Hz), 8.05 (1H, s), 10.42 (1H, t, J=5.7 Hz).

Third Step

Compound 167C (150 mg, 0.280 mmol) was dissolved in trifluoroacetic acid (2 ml), and the mixture was stirred at room temperature for 1 hour. The solvent was distilled off, the residue was dissolved in dichloromethane (2 ml), and the solution was neutralized with saturated sodium bicarbonate water. The resulting solution was made acidic with an aqueous citric acid solution, and the organic layer was separated. The aqueous layer was extracted with dichloromethane once, and the combined organic layers were washed with water, and dried with sodium sulfate. After the solvent was distilled off, the resulting solid was washed with diisopropyl ether to obtain 71 mg (yield 57%) of compound 167.

$^1$HNMR (CDCl$_3$) δ: 2.65 (1H, dd, J=8.4 Hz, 9.6 Hz), 2.97 (1H, dd, J=9 Hz, 13.5 Hz), 3.43 (1J, dd, J=7.2 Hz, 9.6 Hz), 3.55 (1H, dd, J=3.0 Hz, 13.2 Hz), 3.61-3.80 (4H, m), 4.15 (1H, dd, J=4.2 Hz, 9.9 Hz), 4.51-4.60 (1H, m), 7.15-7.18 (2H, m), 7.28-7.38 (8H, m), 8.02 (1H, s), 12.04 (1H, s).

Example 168

[Chemical formula 246]

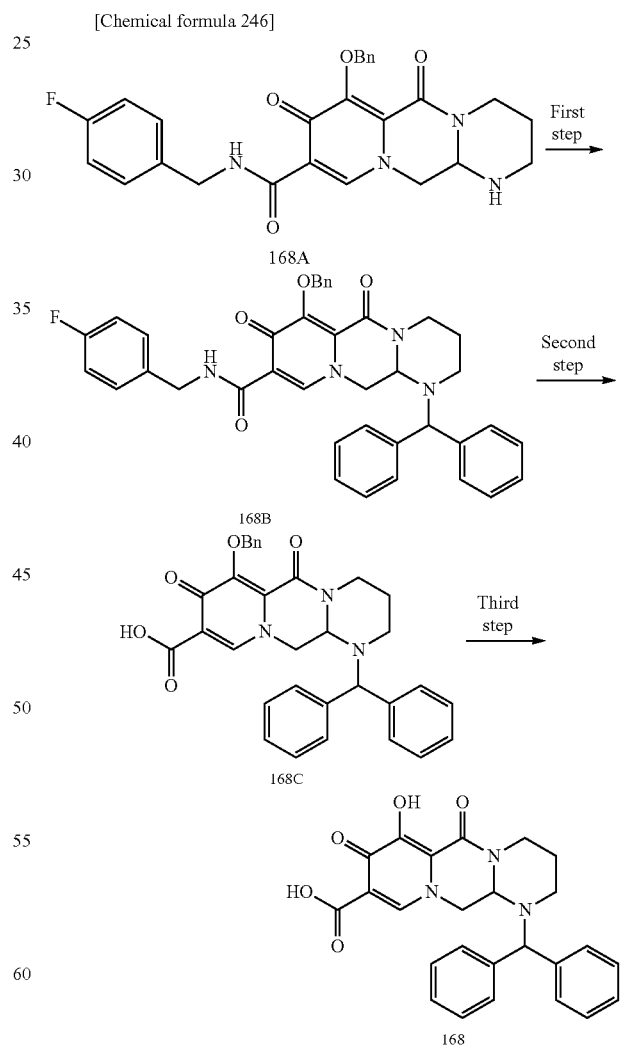

168

First Step

To a DMF (3 mL) solution of compound 168A (WO 2006/116764, 400 mg, 0.840 mmol) were added cesium carbonate (821 mg, 2.52 mmol) and, subsequently, bromomethylenedibenzene (311 mg, 1.26 mmol), and the mixture was stirred at 100° C. for 5 hours. To the reaction solution were added 2N hydrochloric acid, water and ethyl acetate, the ethyl acetate layer was separated, and the aqueous layer was extracted with ethyl acetate once. The combined extracts were washed with an aqueous saturated sodium bicarbonate solution and brine, dried with magnesium sulfate, filtered and concentrated. The resulting residue was purified by silica gel column chromatography. Concentration of an objective fraction afforded 100 mg of compound 168B as a yellow oil.

$^1$H-NMR (CDCl$_3$) δ: 1.79-1.84 (2H, m), 2.67-2.77 (1H, m), 2.84-3.05 (2H, m), 4.03 (1H, dd, J=13.0, 4.2 Hz), 4.28 (1H, dd, J=13.6, 6.5 Hz), 4.49 (1H, dd, J=6.4, 3.8 Hz), 4.57 (2H, d, J=5.7 Hz), 4.78 (1H, dd, J=13.4, 5.7 Hz), 4.93 (1H, s), 5.27 (2H, s), 7.00 (2H, t, J=8.8 Hz), 7.15-7.37 (14H, m), 7.57-7.63 (2H, m), 7.76 (1H, s), 10.44 (1H, t, J=5.9 Hz).

MS: m/z=643.20 [M+H]$^+$.

Second Step

Compound 168B (100 mg, 0.156 mmol) was dissolved in acetonitrile (3 mL), Boc$_2$O (4.0 mL, 17.3 mmol) and, subsequently, DMAP (84 mg, 0.69 mmol) were added, and the mixture was stirred at 80° C. for 6 hours. The reaction solution was allowed to cool, a 2N aqueous sodium hydroxide solution (8 mL) and, subsequently, ethanol (3 mL) were added, and the mixture was stirred at 60° C. for 2 hours. To the reaction solution were added 2N hydrochloric acid and ethyl acetate, the ethyl acetate layer was separated, and the aqueous layer was extracted with ethyl acetate. The solvent was distilled off, and the resulting residue was purified by silica gel chromatography. Elution with ethyl acetate-methanol, and concentration of an objective fraction afforded 84 mg of compound 168C.

MS: m/z=536.25 [M+H]$^+$.

Third Step

To a DMI (2 mL) solution of compound 168C (80 mg, 0.15 mmol) was added lithium chloride (19 mg, 0.45 mmol), and the mixture was stirred at 90° C. for 2 hours. To the reaction mixture were added water and 2N hydrochloric acid, the precipitated solid was filtered, and the resulting solid was purified using a LCMS fractionating device. The eluted solvent was distilled off, to the residue was added isopropyl ether, and the precipitated solid was filtered. Washing with isopropyl ether and drying afforded 12 mg of compound 168.

MS: m/z=446.05 [M+H]$^+$.

Example 169

[Chemical formula 247]

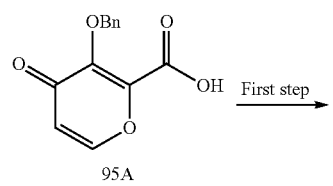

95A

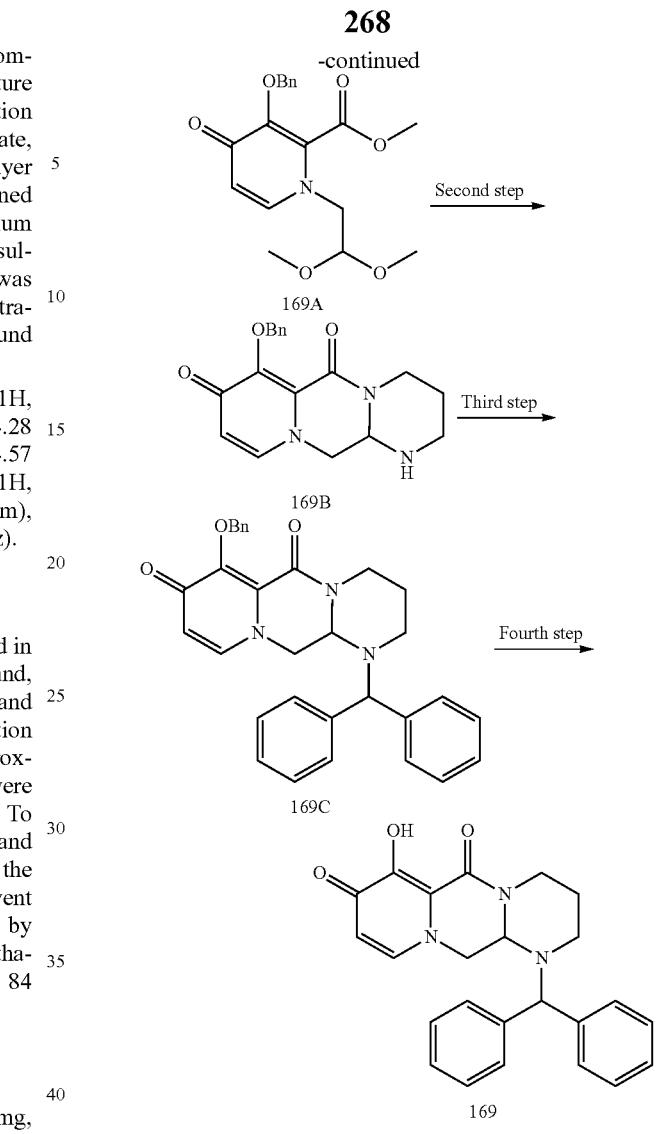

First Step

To an ethanol (5 mL) solution of compound 95A (WO 2006/116764, 500 mg, 2.03 mmol) was added 2,2-dimethoxyethanamine (0.49 ml, 4.47 mmol), and the mixture was stirred at 80° C. for 3 hours. After the reaction solution was allowed to cool, acetic acid (0.27 ml, 4.69 mmol) was added at room temperature, and the mixture was concentrated under reduced pressure. The resulting residue was dissolved in DMF (5 mL), DBU (0.66 mL, 4.4 mmol) and, subsequently, methyl iodide (1.02 mL, 16.2 mmol) were added under nitrogen atmosphere, and the mixture was stirred at room temperature for 3 hours. To the reaction solution were added an aqueous saturated sodium bicarbonate solution and ethyl acetate, the ethyl acetate layer was separated, and the aqueous layer was extracted with ethyl acetate. To the combined extracts was added sodium sulfate, the mixture was filtered and concentrated, and the resulting residue was purified by silica gel chromatography. Elution with chloroform-methanol (9:1) and concentration of an objective fraction afforded 258 mg of compound 169A as a brown oil.

$^1$H-NMR (CDCl$_3$) δ: 3.37 (6H, s), 3.80 (3H, s), 3.87 (2H, d, J=4.8 Hz), 4.46 (1H, t, J=4.8 Hz), 5.30 (2H, s), 6.75 (1H, d, J=6.0 Hz), 7.30-7.41 (6H, m).

269

Second Step

To compound 169A (1.00 g, 2.88 mmol) were added formic acid (31 mL) and, subsequently, water (5 mL), and the mixture was stirred at 70° C. for 6.5 hours. To the reaction mixture were added water and ethyl acetate, the ethyl acetate layer was separated, and the aqueous layer was extracted with ethyl acetate. After the combined extracts were washed with an aqueous saturated sodium bicarbonate solution, and sodium sulfate was added, then the mixture was filtered and concentrated, and the resulting residue was purified by silica gel chromatography. Elution with ethyl acetate-methanol, and concentration of an objective fraction afforded a mixture of aldehyde hydride and methylacetal as a colorless transparent oil. The resulting oil was dissolved in dichloromethane (5 mL), 1,3-diaminopropane dihydrochloride (354 mg, 2.41 mmol) and, subsequently, acetic acid (0.069 ml, 1.2 mmol) were added, and the mixture was stirred at room temperature for 6 hours. The reaction solution was diluted with dichloromethane, insolubles were filtered and, thereafter, the mixture was concentrated under reduced pressure to obtain a crude purified product of compound 169B.

MS: m/z=326.20 [M+H]$^+$.

Third Step

To an acetonitrile (4 mL) solution of compound 168B (391 mg, 1.20 mmol) were added potassium carbonate (498 mg, 3.61 mmol) and, subsequently, bromomethylenedibenzene (890 mg, 3.61 mmol). After the reaction solution was stirred at 90° C. for 2 hours, to the reaction solution were added water, ethyl acetate and brine, the ethyl acetate layer was separated, and the aqueous layer was extracted with ethyl acetate once. After the combined extracts were dried with magnesium sulfate, then the mixture was filtered and concentrated. The resulting residue was purified by silica gel column chromatography. Elution with ethyl acetate-methanol, and concentration of an objective fraction afforded 106 mg of compound 169C as an orange solid.

MS: m/z=492.15 [M+H]$^+$.

Fourth Step

To a DMI (2 mL) solution of compound 169C (105 mg, 0.214 mmol) was added lithium chloride (27.2 mg, 0.641 mmol), and the mixture was stirred at 900° C. for 3 hours. Further, lithium chloride (27.2 mg, 0.641 mmol) was added, and the mixture was stirred at 90° C. for 1 hour. The reaction solution was concentrated under reduced pressure, and the resulting residue was purified using a LCMS fractionating device. The eluted solvent was distilled off, to the residue was added diethyl ether, and the precipitated solid was filtered. Washing with diethyl ether, and drying afforded 27 mg of compound 169.

$^1$H-NMR (CD$_3$OD) δ: 1.63 (1H, dd, J=13.4, 2.8 Hz), 1.84 (1H, br s), 2.55-2.64 (1H, m), 2.90-3.10 (2H, m), 4.30 (1H, dd, J=14.5, 4.0 Hz), 4.52 (4H, dd, J=14.5, 3.8 Hz), 4.63-4.75 (4H, m), 5.16 (1H, s), 6.16 (1H, d, J=7.2 Hz), 6.78 (1H, d, J=7.2 Hz), 7.16-7.32 (10H, m).

MS: m/z=402.10 [M+H]$^+$.

270

Example 170

[Chemical formula 248]

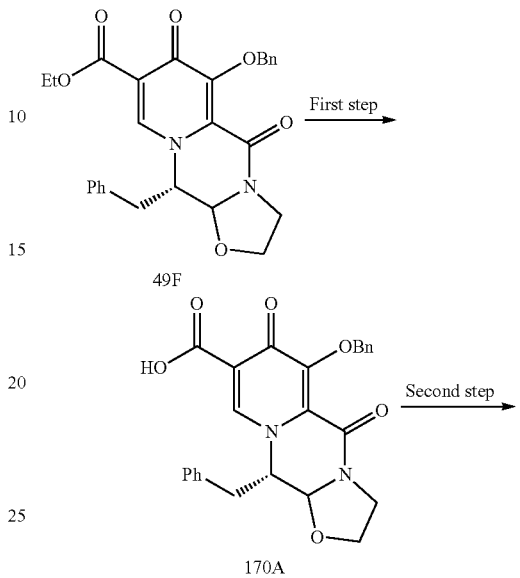

First Step

Compound 49F (87 mg, 0.19 mmol) was dissolved in ethanol (1 ml) and THF (1 ml), a 2N aqueous sodium hydroxide solution (0.47 ml, 0.95 mmol) was added, and the mixture was stirred at room temperature for 1.5 hours. To the reaction solution was added 2N hydrochloric acid, the mixture was extracted with ethyl acetate, and the extract was dried with sodium sulfate. The resulting crude product was purified by silica gel column chromatography (chloroform-methanol 95:5→90:10, v/v) to obtain 60 mg of compound 170A.

$^1$H-NMR (CDCl$_3$) δ: 2.48 (1H, dd, J=13.8, 11.8 Hz), 3.27 (1H, dd, J=14.2, 3.4 Hz), 3.73-3.80 (1H, m), 3.92 (1H, m), 4.16 (1H, m), 4.45 (2H, m), 5.34 (1H, d, J=3.5 Hz), 5.47 (1H, d, J=10.4 Hz), 5.52 (1H, d, J=10.7 Hz), 6.73 (2H, d, J=6.9 Hz), 7.18-7.42 (7H, m), 7.60 (2H, d, J=6.9 Hz), 14.63 (1H, s).

Second Step

To compound 170A (57 mg, 0.13 mmol) was added trifluoroacetic acid (1 ml), and the mixture was stirred at room temperature for 1 hour. After concentration under reduced pressure, pH was adjusted to 3 with sodium bicarbonate water and 2N hydrochloric acid, then the mixture was extracted with chloroform, and the extract was dried with sodium sulfate. After the solvent was distilled off under reduced pressure, chloroform-ethyl ether were added, and the precipitated solid was filtered to obtain 19 mg of compound 170 as a colorless solid.

$^1$H-NMR (DMSO-d$_6$) δ: 2.74 (1H, t, J=12.1 Hz), 3.10-3.22 (1H, m), 3.76 (2H, m), 4.12 (1H, q, J=8.0 Hz), 4.44 (1H, m), 5.35 (1H, m), 5.49 (1H, d, J=3.4 Hz), 7.05 (5H, m), 7.77 (1H, s), 12.05 (1H, brs).

Example 171

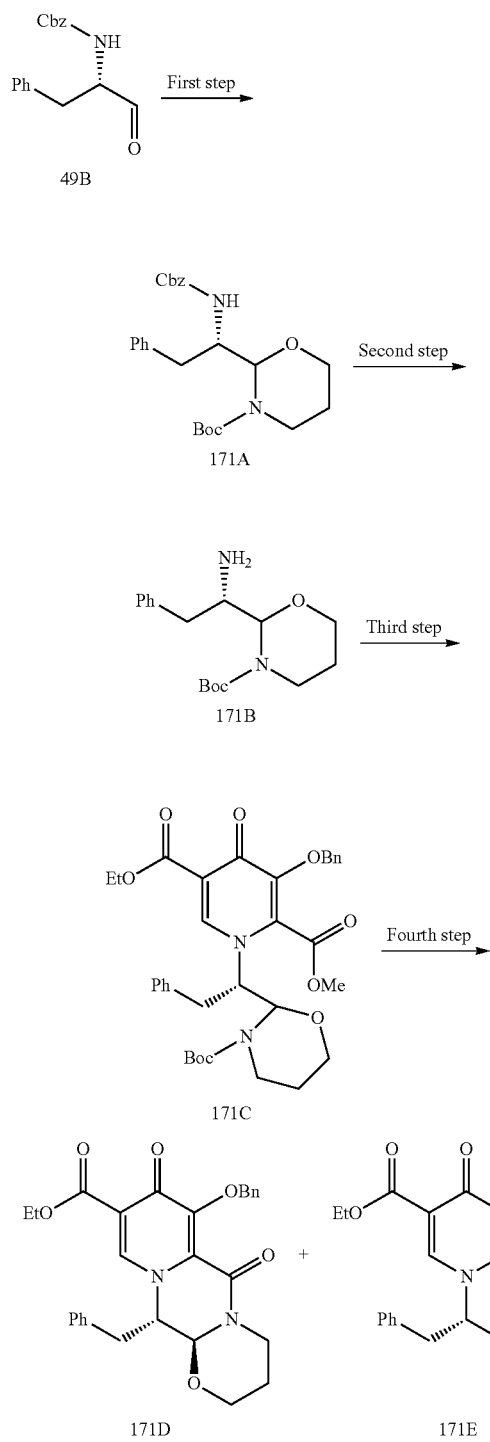

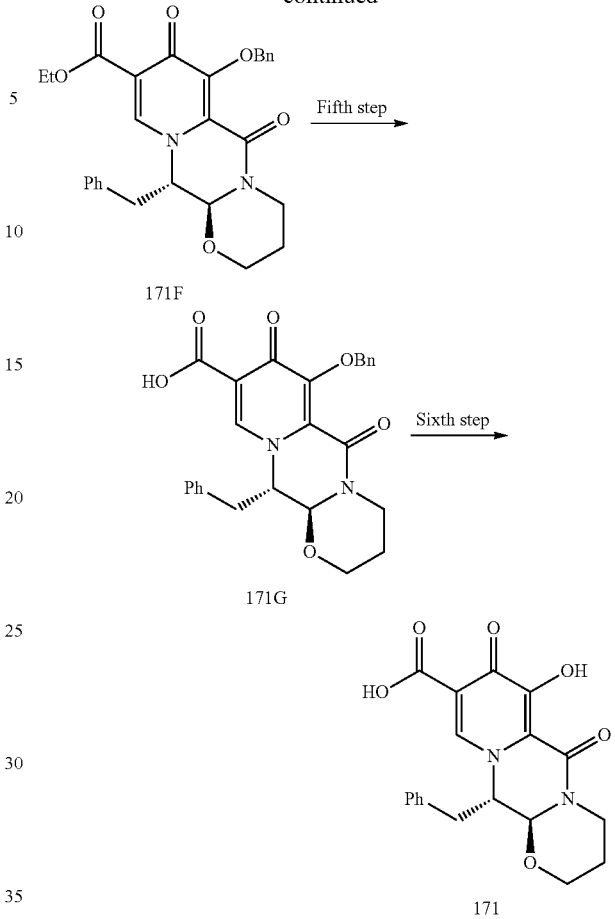

First Step

Compound 49B (950 mg, 3.35 mmol), 3-aminopropan-1-ol (277 mg, 3.69 mmol) and sodium sulfate (1.91 g, 13.4 mmol) were added to toluene (25 ml), and the mixture was stirred at room temperature for 1 hour. Boc$_2$O (0.856 ml, 3.69 mmol) was added at room temperature, and the mixture was stirred for 18 hours. Further, Boc$_2$O (0.400 ml, 1.72 mmol) was added at room temperature, and the mixture was stirred for 60 hours. The reaction solution was filtered, and the filtrate was concentrated under reduced pressure. The resulting crude product was purified by silica gel column chromatography (n-hexane-ethyl acetate, 1:1, v/v) to obtain 1.02 g of compound 171A as a colorless gummy substance.

Second Step

Compound 171A (1.01 g, 2.29 mmol) and palladium-active carbon (10%, wet, 200 mg) were added to ethanol (20 ml), and the mixture was stirred at room temperature for 1.5 hours under hydrogen atmosphere. After filtration with celite, the solvent was concentrated under reduced pressure to obtain 755 mg of a colorless oily substance 171B.

$^1$H-NMR (CDCl$_3$) δ: 1.42 (5H, s), 1.49 (4H, s), 1.56-1.92 (2H, m), 2.49 (0.4H, dd, J=13.6, 9.8 Hz), 2.62 (0.6H, dd, J=13.6, 8.5 Hz), 2.81 (0.4H, dd, J=13.5, 3.6 Hz), 3.16 (1.6H, m), 3.60-4.14 (4H, m), 5.13 (0.6H, d, J=8.8 Hz), 5.19 (0.4H, d, J=8.5 Hz), 7.22-7.37 (5H, m).

Third Step

Dimethyl 3-(benzyloxy)-4-oxo-4H-pyran-2,5-dicarboxylate (660 mg, 1.99 mmol) and compound 171B (609 mg, 1.99 mmol) were added to toluene (8 ml), and the mixture was stirred at 100° C. for 1.5 hours. After the solvent was distilled off under reduced pressure, the resulting crude product was purified by silica gel column chromatography (chloroform-methanol, 99:1, v/v) to obtain 1.02 g of compound 171C as a pale yellow gummy substance.

Fourth Step

To compound 171C (991 mg, 1.60 mmol) was added 4N HCl (ethyl acetate solution, 12 ml). After the mixture was stirred at room temperature for 1 hour, the solvent was distilled off under reduced pressure. Subsequently, toluene (12 ml) and 3-aminopropan-1-ol (0.244 ml, 3.19 mmol) were added, the mixture was stirred at 80° C. for 10 minutes. After the solvent was distilled off under reduced pressure, the resulting crude product was purified by silica gel column chromatography (chloroform-methanol, 99:1→95:5→90:10, v/v) to obtain 341 mg of compound 171D as a yellow gummy substance and 338 mg of compound 171E as a colorless solid.

171D: $^1$H-NMR (CDCl$_3$) δ: 1.29 (3H, t, J=7.1 Hz), 1.51 (1H, d, J=13.7 Hz), 1.97 (1H, m), 2.91 (1H, dd, J=13.8, 9.8 Hz), 2.99-3.10 (2H, m), 3.90 (1H, td, J=12.1, 2.5 Hz), 4.12 (2H, m), 4.25 (2H, m), 4.83 (2H, m), 5.33 (1H, d, J=10.1 Hz), 5.51 (1H, d, J=10.1 Hz), 6.88 (2H, m), 7.23-7.40 (7H, m), 7.68 (2H, m)

171E: $^1$H-NMR (CDCl$_3$) δ: 1.19 (3H, t, J=7.2 Hz), 1.82-1.99 (2H, m), 2.73 (1H, dd, J=14.0, 11.3 Hz), 3.13 (1H, m), 3.35 (1H, dd, J=14.0, 3.4 Hz), 3.63 (1H, m), 3.90-4.26 (4H, m), 4.43 (1H, d, J=13.6 Hz), 5.27 (1H, t, J=3.5 Hz), 5.31 (2H, s), 6.78 (2H, dd, J=6.3, 3.2 Hz), 7.01 (1H, d, J=7.0 Hz), 7.18 (3H, t, J=3.1 Hz), 7.28-7.39 (3H, m), 7.67 (2H, m).

Fifth Step

Compound 171D (329 mg, 0.673 mmol) was dissolved in ethanol (2 ml) and THF (4 ml), a 2N aqueous sodium hydroxide solution (1.69 ml, 3.38 mmol) was added, and the mixture was stirred at room temperature for 1 hour. To the reaction solution was added 2N hydrochloric acid, the mixture was extracted with ethyl acetate, and the extract was dried with sodium sulfate. The solvent was concentrated under reduced pressure to obtain 215 mg of compound 171F as a colorless solid.

MS: m/z=461 [M+H]$^+$.

Sixth Step

To compound 171F (50 mg, 0.11 mmol) was added trifluoroacetic acid (2 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, chloroform-methanol-ethyl ether were added, and the precipitated solid was filtered to obtain 24 mg of compound 171 as a colorless solid.

$^1$H-NMR (DMSO-d$_6$) δ: 1.63 (1H, d, J=12.6 Hz), 1.83 (1H, m), 2.96-3.29 (3H, m), 4.05 (2H, m), 4.55 (1H, dd, J=13.2, 4.4 Hz), 5.08 (1H, dd, J=9.2, 5.4 Hz), 5.30 (1H, s), 7.19 (5H, m), 8.09 (1H, s), 12.84 (1H, brs).

MS: m/z=371 [M+H]$^+$.

Example 172

[Chemical formula 250]

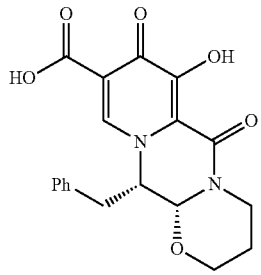

172

According to Example 171, using compound 171E, compound 172 was synthesized by the same procedure.

$^1$H-NMR (DMSO-d$_6$) δ: 1.91 (2H, m), 2.94 (1H, dd, J=14.0, 10.8 Hz), 3.11-3.21 (3H, m), 3.71 (1H, m), 4.19 (1H, m), 4.29-4.35 (1H, m), 5.08-5.14 (1H, m), 5.47 (1H, d, J=4.0 Hz), 6.92-7.22 (5H, m), 7.71 (1H, s), 12.80 (1H, brs), 15.06 (1H, brs).

MS: m/z=371 [M+H]$^+$.

Example 173

[Chemical formula 251]

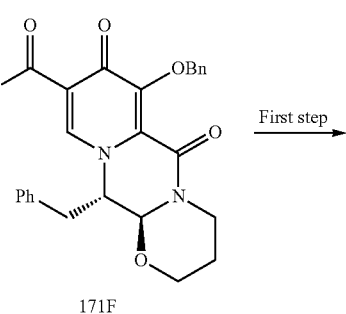

171F

First step →

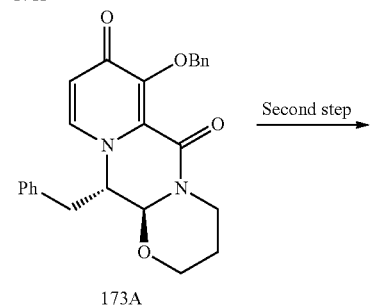

173A

Second step →

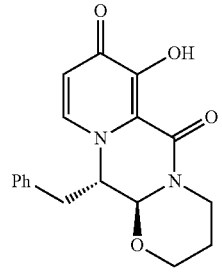

173

First Step

Compound 171F (159 mg, 0.345 mmol) was added to diphenyl ether (2.5 ml), and the mixture was stirred at 245° C. for 1 hour under microwave irradiation. The reaction solution was poured into n-hexane, and the precipitated solid was filtered. The resulting crude product was purified by silica gel column chromatography (chloroform-methanol, 95:5→90:10, v/v) to obtain compound 173A.

Second Step

To compound 173A obtained in the first step was added trifluoroacetic acid (1 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 10 mg of compound 173 as a colorless solid.

$^1$H-NMR (DMSO-d$_6$) δ: 1.55-1.86 (2H, m), 2.84-3.26 (3H, m), 3.92-4.09 (2H, m), 4.55 (2H, m), 5.15 (1H, s), 5.89 (1H, d, J=7.5 Hz), 7.17 (6H, m), 12.11 (1H, brs)

MS: m/z=327 [M+H]$^+$.

Example 174

[Chemical formula 252]

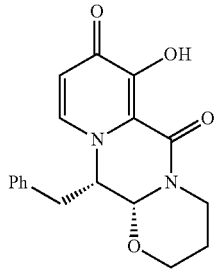

174

According to Example 173, compound 174 was synthesized by the same procedure.

$^1$H-NMR (DMSO-d$_6$) δ: 1.86 (2H, m), 2.87 (1H, t, J=12.3 Hz), 3.18 (2H, m), 3.68 (1H, t, J=10.4 Hz), 4.16 (1H, d, J=10.1 Hz), 4.29 (1H, d, J=12.4 Hz), 4.71 (1H, d, J=9.2 Hz), 5.37 (1H, d, J=3.5 Hz), 5.75 (1H, d, J=7.5 Hz), 7.00 (6H, m), 12.51 (1H, brs).

MS: m/z=327 [M+H]$^+$.

Example 175

[Chemical formula 253]

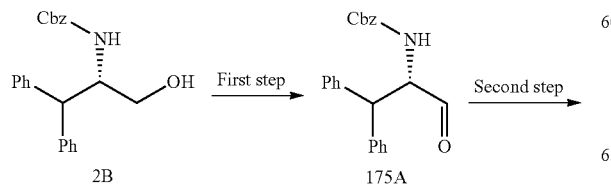

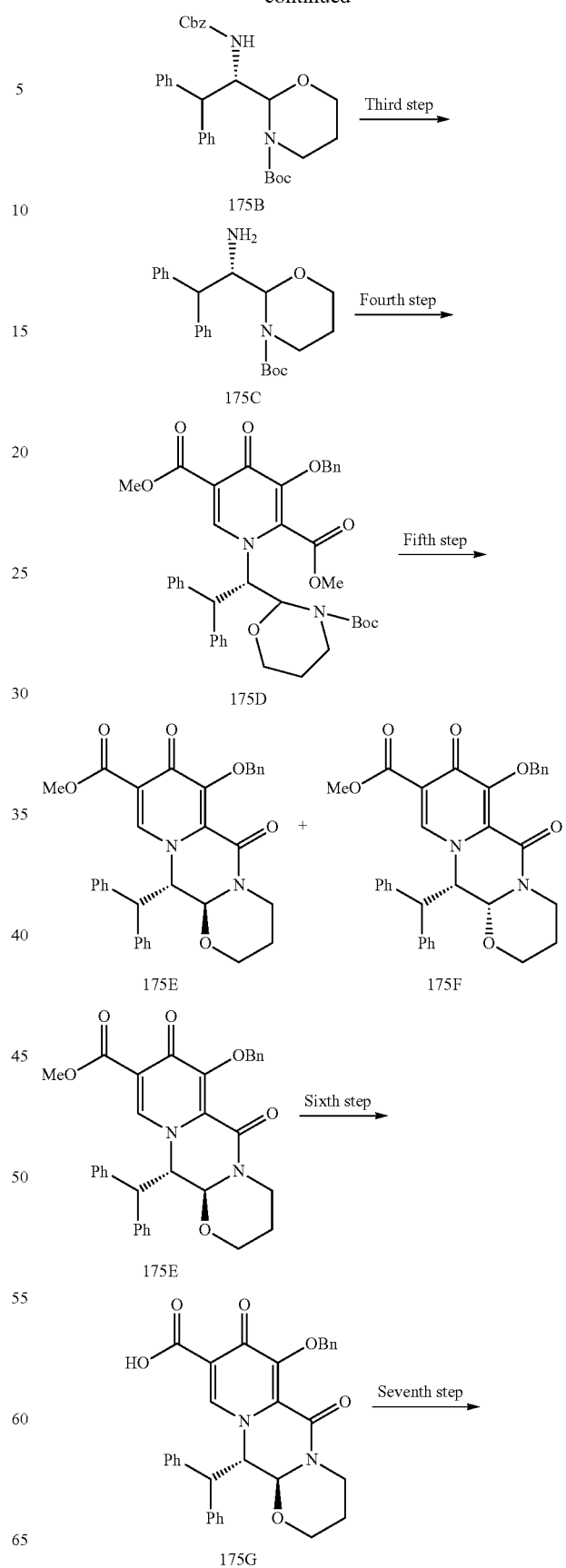

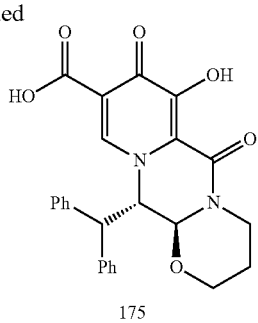

175

First Step

To Dess-Martin Periodinane (0.3M, methylene chloride solution, 25.0 ml, 7.50 mmol) was added dropwise a methylene chloride solution (10 ml) of compound 2B (1.98 g, 5.48 mmol) at 0° C. After the mixture was stirred at room temperature for 3 hours, the mixture was poured into a 1N aqueous sodium hydroxide solution, and extracted with ethyl ether. The organic layer was washed with a 1N aqueous sodium hydroxide solution and an aqueous saturated sodium chloride solution, and dried with magnesium sulfate. After the solvent was distilled off under reduced pressure, purification was performed by silica gel column chromatography (n-hexane-ethyl acetate, 2:1, v/v) to obtain 1.73 g of compound 175A as a white solid.

$^1$H-NMR (CDCl$_3$) δ: 4.55 (1H, d, J=7.3 Hz), 5.09 (2H, s), 5.14 (2H, m), 7.22-7.35 (15H, m), 9.62 (1H, s).

Second Step

Compound 175A (1.30 g, 4.59 mmol), 3-aminopropan-1-ol (379 mg, 5.05 mmol) and sodium sulfate (3.26 g, 22.4 mmol) were added to toluene (40 ml), and the mixture was stirred at room temperature for 1 hour. Boc$_2$O (1.17 ml, 5.05 mmol) was added at room temperature, and the mixture was stirred for 18 hours. Boc$_2$O (1.17 ml, 5.05 mmol) and sodium sulfate (3.26 g, 22.4 mmol) were added, and the mixture was stirred for 60 hours. The reaction solution was filtered, and the filtrate was concentrated under reduced pressure. The resulting crude product was purified by silica gel column chromatography (n-hexane-ethyl acetate, 1:1, v/v) to obtain 635 mg of compound 175B as a colorless solid.

Third Step

Compound 175B (632 mg, 1.22 mmol) and palladium-active carbon (10%, wet, 100 mg) were added to ethanol (10 ml) and THF (5 ml), and the mixture was stirred at room temperature for 3 hours under hydrogen atmosphere. After filtration with celite, the solvent was concentrated under reduced pressure to obtain 502 mg of a colorless oily substance 175C.

$^1$H-NMR (CDCl$_3$) δ: 1.45 (9H, s), 1.77 (2H, m), 3.18-3.27 (1H, m), 3.43-3.51 (1H, m), 4.04 (4H, m), 4.92 (1H, d, J=4.7 Hz), 7.28 (10H, m).

Fourth Step

Dimethyl 3-(benzyloxy)-4-oxo-4H-pyran-2,5-dicarboxylate (390 mg, 1.22 mmol) and compound 175C (468 mg, 1.22 mmol) were added to toluene (5 ml), and the mixture was stirred at 100° C. for 2 hours. After the solvent was distilled off under reduced pressure, the resulting crude product was purified by silica gel column chromatography (n-hexane-ethyl acetate, 1:1, v/v) to obtain 391 mg of compound 175D as a pale yellow gummy substance.

Fifth Step

To compound 175D (388 mg, 0.568 mmol) was added 4N HCl (ethyl acetate solution, 4 ml). After the mixture was stirred at room temperature for 1 hour, the solvent was distilled off under reduced pressure. Subsequently, toluene (4 ml) and 3-aminopropan-1-ol (0.0870 ml, 1.14 mmol) were added, and the mixture was stirred at 80° C. for 5 hours. After the solvent was distilled off under reduced pressure, the resulting crude product was purified by silica gel column chromatography (chloroform-methanol, 98:2, v/v) to obtain 57 mg of compound 175E as a yellow gummy substance and 44 mg of compound 175F as a brown gummy substance.

175E: $^1$H-NMR (CDCl$_3$) δ: 1.91-2.00 (2H, m), 2.87 (1H, m), 3.78 (3H, s), 3.87-4.15 (3H, m), 4.61 (1H, d, J=12.1 Hz), 4.78 (2H, m), 5.33 (1H, d, J=10.2 Hz), 5.63 (1H, d, J=10.2 Hz), 6.95 (2H, m), 7.13-7.53 (12H, m), 7.76 (2H, m)

175F: $^1$H-NMR (CDCl$_3$) δ: 1.83-1.97 (2H, m), 3.12-3.22 (1H, m), 3.50 (1H, m), 3.85 (3H, s), 3.90 (1H, m), 4.34-4.40 (1H, m), 4.74 (1H, d, J=8.6 Hz), 4.84-4.89 (1H, m), 5.09 (1H, d, J=3.3 Hz), 5.15 (1H, d, J=9.9 Hz), 5.26 (1H, d, J=9.6 Hz), 7.08-7.50 (13H, m), 7.65-7.77 (3H, m).

Sixth Step

Compound 175E (57 mg, 0.10 mmol) was dissolved in THF (0.5 ml) and ethanol (0.5 ml), a 2N aqueous sodium hydroxide solution (0.25 ml, 0.50 mmol) was added at room temperature, and the mixture was stirred for 1 hour. After 1N hydrochloric acid was added, and the mixture was extracted with chloroform, the extract was dried with sodium sulfate. The solvent was distilled off under reduced pressure, the resulting crude product was purified by silica gel column chromatography (chloroform-methanol, 98:2, v/v) to obtain compound 175G.

Seventh Step

To compound 175G obtained in the sixth step was added trifluoroacetic acid (1 ml), and the mixture was stirred at room temperature for 1 hour. After concentration under reduced pressure, pH was adjusted to 3 with sodium bicarbonate water and 2N hydrochloric acid, then the mixture was extracted with chloroform, and the extract was dried with sodium sulfate. After the solvent was distilled off under reduced pressure, chloroform-methanol-ethyl ether were added, and the precipitated solid was filtered to obtain 11 mg of compound 175 as a colorless solid.

$^1$H-NMR (DMSO-d$_6$) δ: 1.50 (1H, d, J=13.1 Hz), 1.79 (1H, m), 3.17 (1H, m), 3.86 (1H, t, J=11.0 Hz), 4.03 (1H, dd, J=10.8, 4.1 Hz), 4.46 (1H, d, J=12.0 Hz), 4.53 (1H, dd, J=12.7, 4.2 Hz), 4.84 (1H, s), 5.85 (1H, d, J=11.7 Hz), 7.22 (7H, m), 7.44 (2H, t, J=7.6 Hz), 7.65 (2H, d, J=7.3 Hz), 8.14 (1H, s), 12.75 (1H, s), 15.33 (1H, brs).

MS: m/z=447 [M+H]$^+$.

Example 176

[Chemical formula 254]

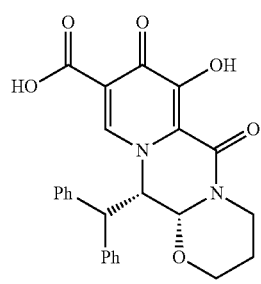

176

According to Example 175, using compound 175F, compound 176 was synthesized by the same procedure.

$^1$H-NMR (DMSO-$d_6$) δ: 1.75 (2H, m), 3.17 (2H, m), 3.43 (1H, m), 3.60 (1H, d, J=10.7 Hz), 4.31 (1H, d, J=12.7 Hz), 4.73 (1H, d, J=9.8 Hz), 5.52 (1H, d, J=3.4 Hz), 5.87 (1H, dd, J=9.9, 3.4 Hz), 7.10 (7H, m), 7.29 (2H, t, J=7.5 Hz), 7.58 (2H, d, J=7.3 Hz), 8.37 (1H, s), 12.65 (1H, brs).

MS: m/z=447 [M+H]$^+$.

Example 177

[Chemical formula 255]

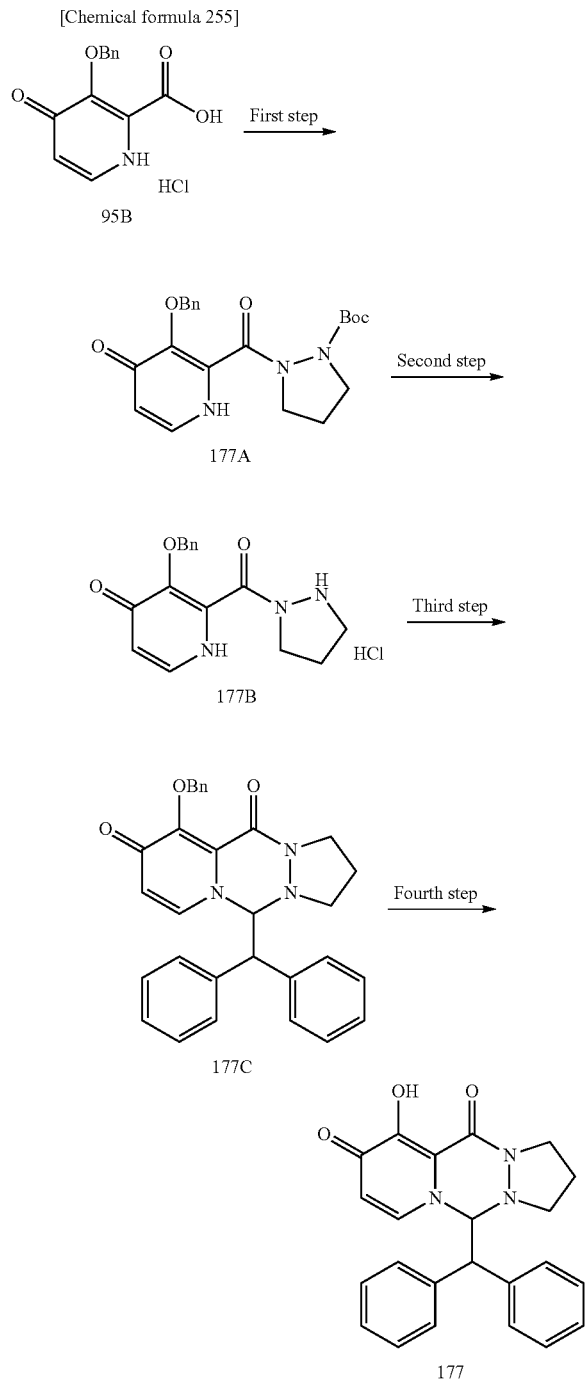

First Step

Tert-butyl pyrazolidine-1-carboxylate (275 mg, 1.60 mmol) synthesized according to the method of the reference (Journal of the Chemical Society, Perkin Transactions 1: Organic and Bio-Organic Chemistry (1972-1999), 1975, p. 1712), and compound 95B (409 mg, 1.45 mmol) were dissolved in pyridine (5 ml), HATU (607 mg, 1.60 mmol) was added at room temperature, and the mixture was stirred for 18 hours. The reaction solution was poured into 1N hydrochloric acid, then the mixture was extracted with ethyl acetate, and the extract was dried with sodium sulfate The solvent was distilled off under reduced pressure, and the resulting crude product was purified by silica gel column chromatography (chloroform-methanol, 97:3→95:5, v/v) to obtain 529 mg of compound 177A as a yellow solid.

$^1$H-NMR (CDCl$_3$) δ: 1.35 (9H, s), 1.88-2.10 (2H, m), 3.04 (1H, s), 3.31 (1H, s), 3.86 (2H, m), 4.96 (1H, d, J=9.3 Hz), 5.45 (1H, d, J=11.0 Hz), 6.56 (1H, d, J=6.7 Hz), 7.29-7.43 (6H, m).

Second Step

To compound 177A (525 mg, 1.31 mmol) was added 4N HCl (dioxane solution, 6 ml). After the mixture was stirred at room temperature for 1.5 hours, the solvent was distilled off under reduced pressure to obtain 413 mg of compound 177B as a colorless solid.

$^1$H-NMR (DMSO-$d_6$) δ: 1.95-2.05 (2H, m), 2.78 (2H, t, J=6.6 Hz), 3.41-3.54 (2H, m), 5.11 (2H, s), 7.38 (5H, m), 7.46 (1H, d, J=6.6 Hz), 8.36 (1H, d, J=6.7 Hz).

Third Step

Compound 177B (100 mg, 0.298 mmol) was added to ethanol (2 ml), 2,2-diphenylacetaldehyde (58 mg, 0.30 mmol), triethylamine (0.083 ml, 0.596 mmol) and acetic acid (0.051 ml, 0.89 mmol) were added, and the mixture was stirred at 80° C. for 3 hours. The reaction solution was poured into water, the mixture was extracted with chloroform, and the extract was dried with sodium sulfate. The solvent was distilled off under reduced pressure, and the resulting crude product was purified by silica gel column chromatography (chloroform-methanol, 97:3→95:5→93:7-90:10, v/v) to obtain 106 mg of compound 177C as a yellow gummy substance.

MS: m/z=478 [M+H]$^+$.

Fourth Step

To compound 177C obtained in the third step was added trifluoroacetic acid (2 ml), and the mixture was stirred at room temperature for 1 hour. After concentration under reduced pressure, pH was adjusted to 6 with sodium bicarbonate water and 2N hydrochloric acid, the mixture was extracted with chloroform, and the extract was dried with sodium sulfate. After the solvent was distilled off under reduced pressure, methylene chloride-ethyl ether were added, and the precipitated solid was filtered to obtain 7 mg of compound 177 as a colorless solid.

$^1$H-NMR (DMSO-$d_6$) δ: 1.95 (2H, m), 2.76 (1H, m), 2.96-3.17 (2H, m), 4.04 (1H, m), 4.68 (1H, d, J=10.4 Hz), 5.66 (1H, d, J=7.3 Hz), 6.56 (1H, d, J=10.5 Hz), 7.03 (1H, d, J=7.2 Hz), 7.17 (6H, m), 7.34 (2H, t, J=7.3 Hz), 7.55 (2H, d, J=7.5 Hz).

MS: m/z=388 [M+H]$^+$.

Example 178

[Chemical formula 256]

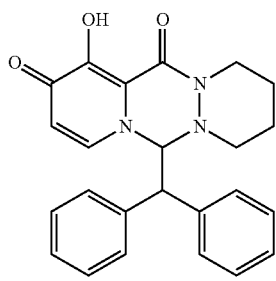

According to Example 177, compound 178 was synthesized by the same procedure.

¹H-NMR (DMSO-d$_6$) δ: 1.55 (4H, m), 2.35-7.49 (1H, m), 2.39 (1H, t, J=12.6 Hz), 2.77 (1H, t, J=10.0 Hz), 3.09 (1H, d, J=11.4 Hz), 4.34 (1H, d, J=12.8 Hz), 4.55 (1H, d, J=10.8 Hz), 5.71 (1H, d, J=7.0 Hz), 6.17 (1H, d, J=10.8 Hz), 6.82 (1H, d, J=7.3 Hz), 7.13-7.40 (8H, m), 7.48 (2H, d, J=7.3 Hz).

MS: m/z=402 [M+H]⁺.

Example 179

[Chemical formula 257]

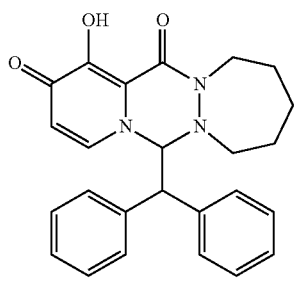

According to Example 177, compound 179 was synthesized by the same procedure.

¹H-NMR (DMSO-d$_6$) δ: 1.31 (6H, m), 2.68 (2H, m), 3.21 (1H, m), 4.04 (1H, m), 4.40 (1H, d, J=10.8 Hz), 5.77 (1H, t, J=5.2 Hz), 6.26 (1H, d, J=10.8 Hz), 6.78 (1H, d, J=7.3 Hz), 7.27 (8H, m), 7.53 (2H, d, J=7.2 Hz).

MS: m/z=416 [M+H]⁺.

Example 180

[Chemical formula 258]

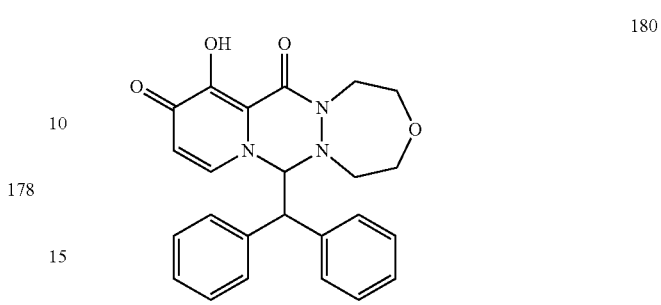

According to Example 177, compound 180 was synthesized by the same procedure.

¹H-NMR (DMSO-d$_6$) δ: 2.78-3.74 (7H, m), 4.17 (1H, m), 4.49 (1H, d, J=10.8 Hz), 5.79 (1H, d, J=7.2 Hz), 6.32 (1H, d, J=10.8 Hz), 6.79 (1H, d, J=7.2 Hz), 7.28 (8H, m), 7.55 (2H, d, J=7.6 Hz).

MS: m/z=418 [M+H]⁺.

Using amines which are commercially available or known in the references and halides which are commercially available or known in the references, and according to the method of Example 12, Examples 181 to 187 were synthesized.

Example 181

[Chemical formula 259]

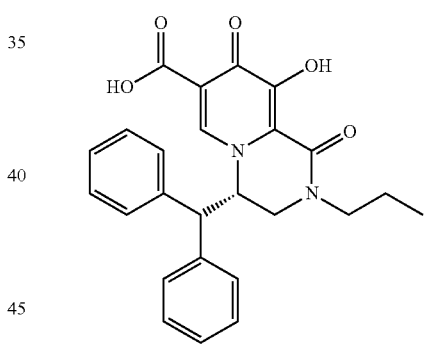

MS: m/z=433 [M+H]⁺.

Example 182

[Chemical formula 260]

MS: m/z=459 [M+H]⁺.

Example 183

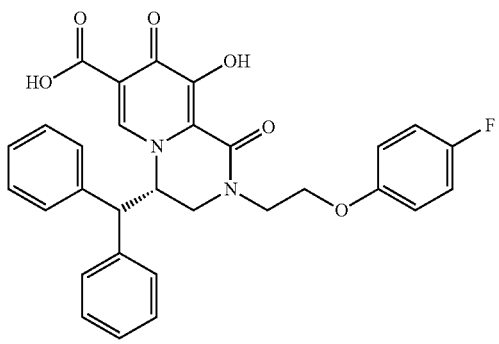
[Chemical formula 261]

MS: m/z=529 [M+H]+.

Example 184

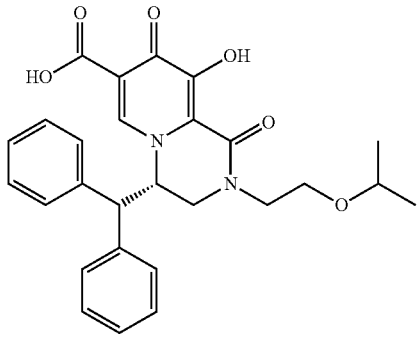
[Chemical formula 262]

MS: m/z=477 [M+H]+.

Example 185

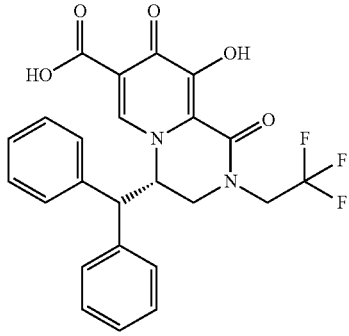
[Chemical formula 263]

MS: m/z=473 [M+H]+.

Example 186

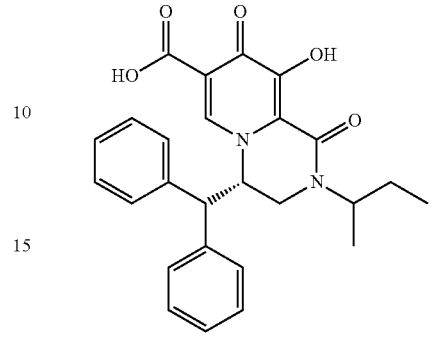
[Chemical formula 264]

MS: m/z=447 [M+H]+.

Example 187

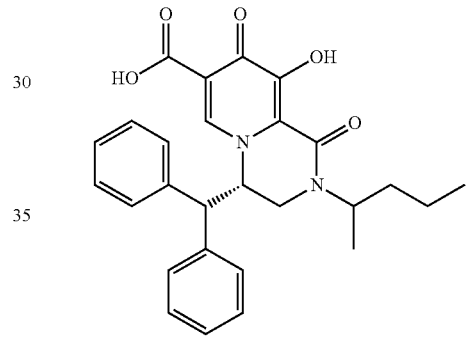
[Chemical formula 265]

MS: m/z=461 [M+H]+

Example 188

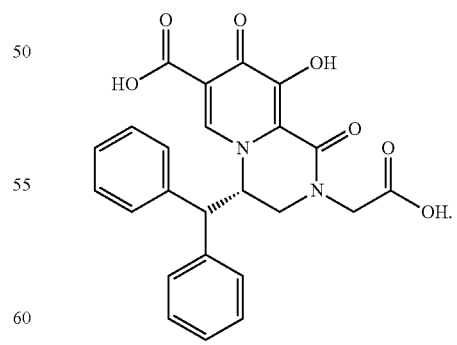
[Chemical formula 266]

According to Example 12 and Example 129, compound 188 was synthesized by the same procedure.
MS: m/z=449 [M+H]+.
Using amines which are commercially available or known in the references and halides which are commercially available or known in the references, and according to the method of Example 95, Examples 189 to 229 were synthesized.
Example 189
[Chemical formula 267]
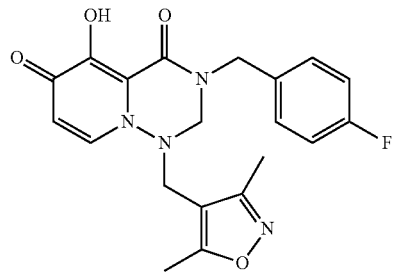
MS: m/z=399 [M+H]+.
Example 190
[Chemical formula 268]
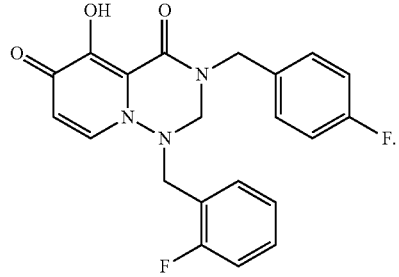
MS: m/z=488 [M+H]+
Example 191
[Chemical formula 269]
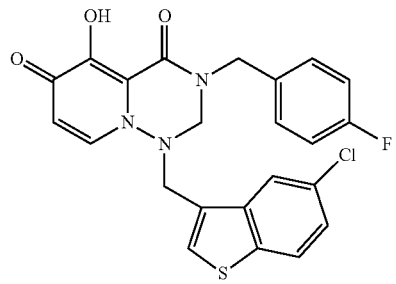
MS: m/z=470 [M+H]+
Example 192
[Chemical formula 270]
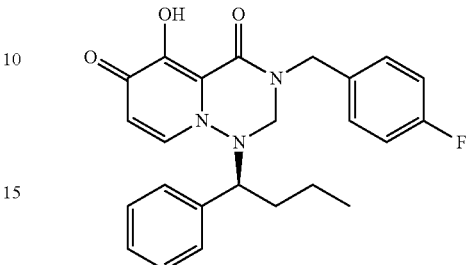
MS: m/z=422 [M+H]+.
Example 193
[Chemical formula 271]
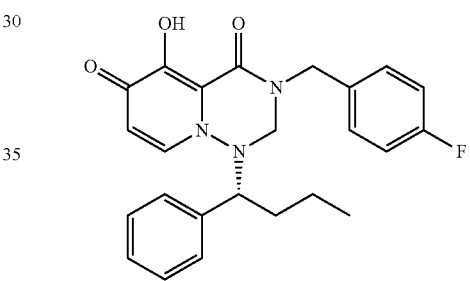
MS: m/z=422 [M+H]+
Example 194
[Chemical formula 272]
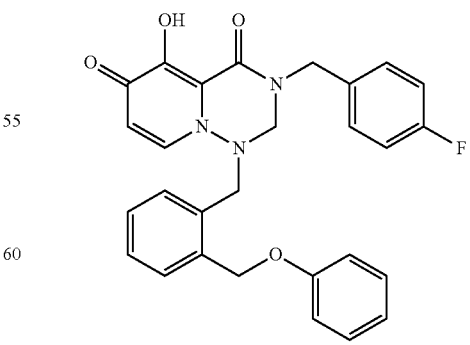
MS: m/z=486 [M+H]+

Example 195
[Chemical formula 273]
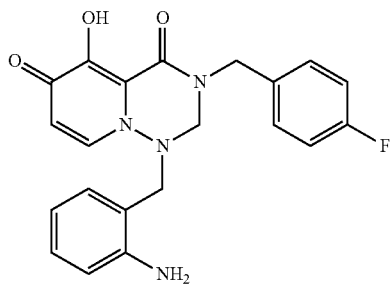
MS: m/z=365 [M+H]+
Example 196
[Chemical formula 274]
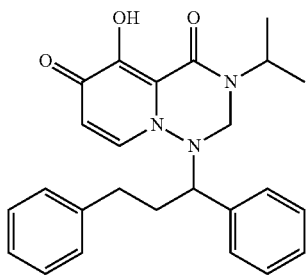
MS: m/z=418 [M+H]+
Example 197
[Chemical formula 275]
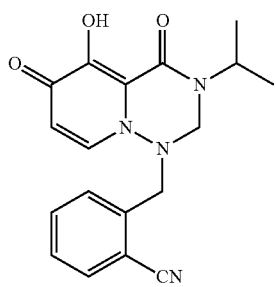
MS: m/z=339 [M+H]+
Example 198
[Chemical formula 276]
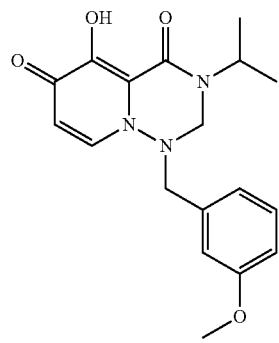
MS: m/z=344 [M+H]+
Example 199
[Chemical formula 277]
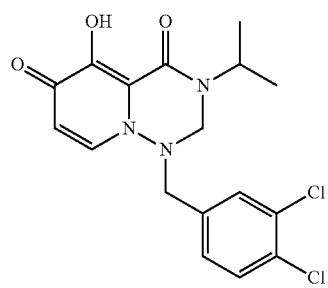
MS: m/z=383 [M+H]+
Example 200
[Chemical formula 278]
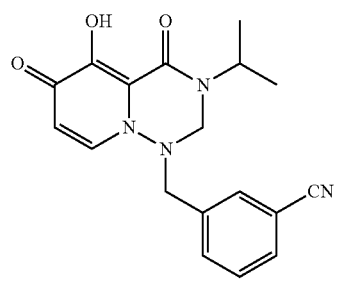
MS: m/z=339 [M+H]+

Example 201
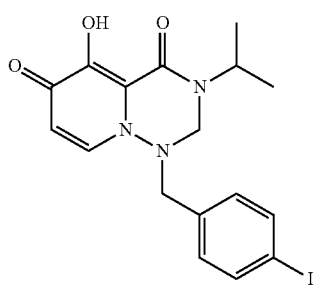
MS: m/z=440 [M+H]+
Example 202
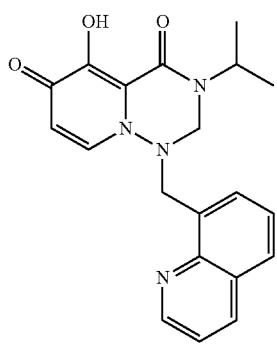
MS: m/z=365 [M+H]+
Example 203
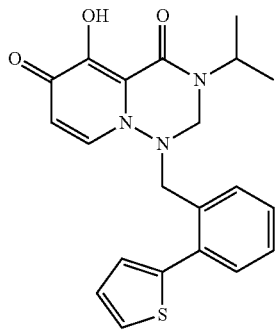
MS: m/z=396 [M+H]+
Example 204
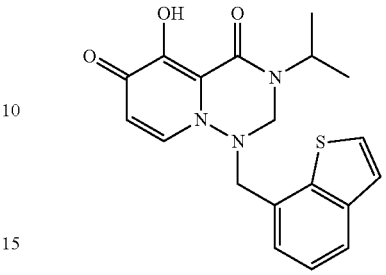
MS: m/z=370 [M+H]+
Example 205
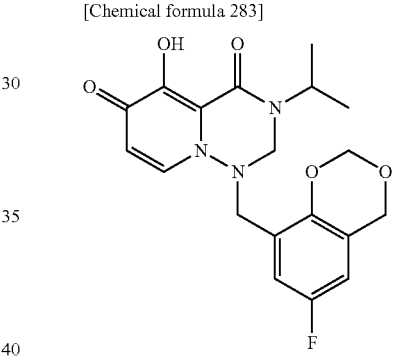
MS: m/z=390 [M+H]+
Example 206
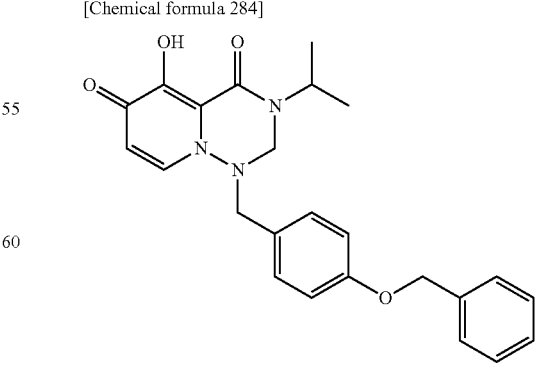
MS: m/z=420 [M+H]+

Example 207
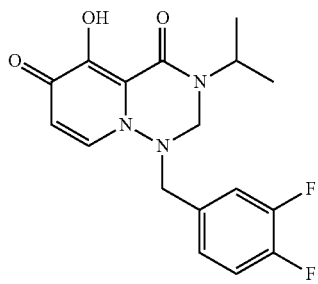
MS: m/z=350 [M+H]$^+$
Example 208
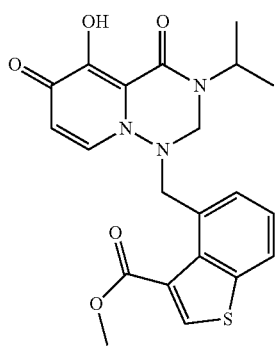
MS: m/z=428 [M+H]$^+$
Example 209
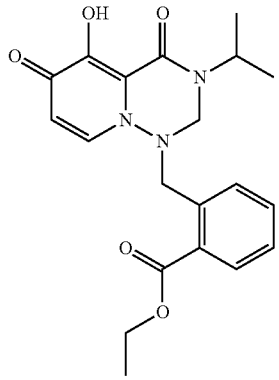
MS: m/z=386 [M+H]$^+$
Example 210
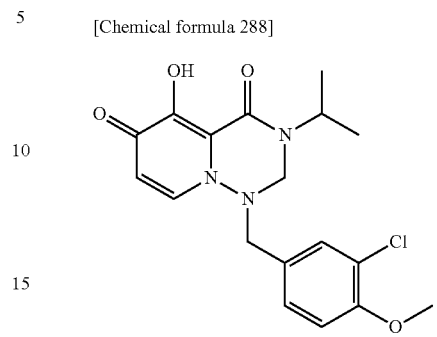
MS: m/z=378 [M+H]$^+$
Example 211
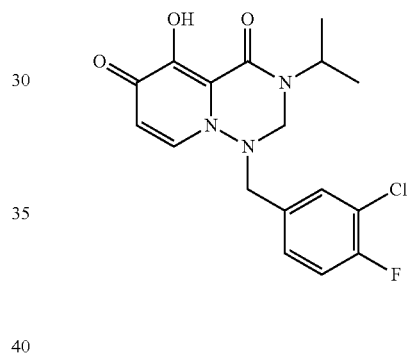
MS: m/z=366 [M+H]$^+$
Example 212
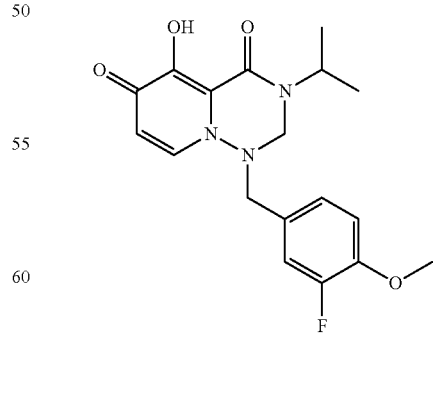
MS: m/z=362 [M+H]$^+$

Example 213
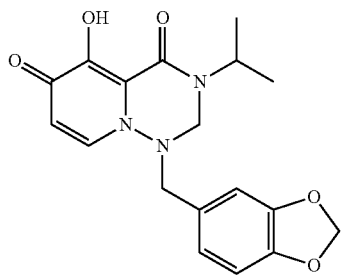
MS: m/z=358 [M+H]⁺
Example 214
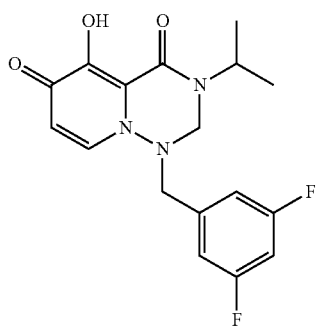
MS: m/z=350 [M+H]⁺
Example 215
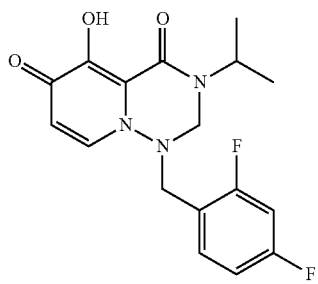
MS: m/z=350 [M+H]⁺
Example 216
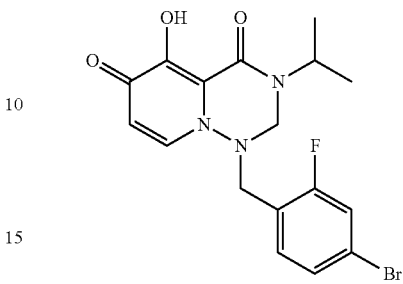
MS: m/z=411 [M+H]⁺
Example 217
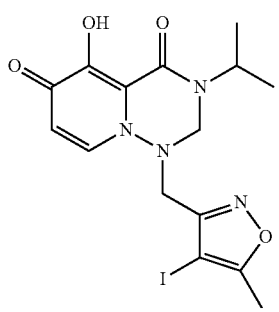
MS: m/z=445 [M+H]⁺
Example 218
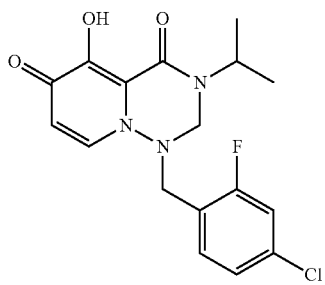
MS: m/z=366 [M+H]⁺

Example 219
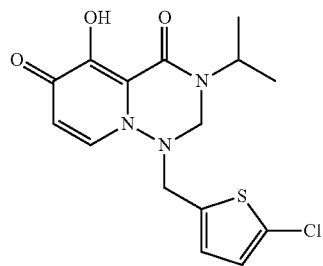
MS: m/z=354 [M+H]+
Example 220
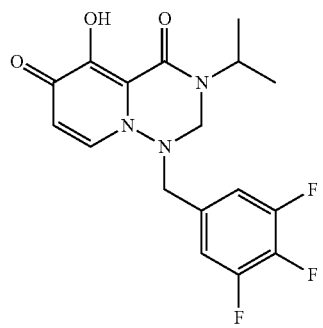
MS: m/z=368 [M+H]+
Example 221
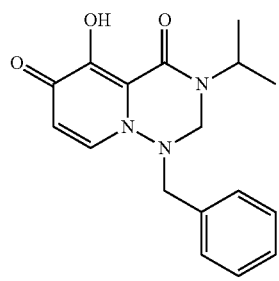
MS: m/z=314 [M+H]+
Example 222
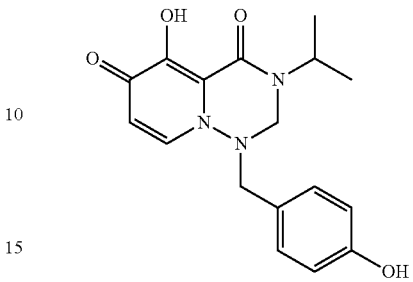
MS: m/z=330 [M+H]+
Example 223
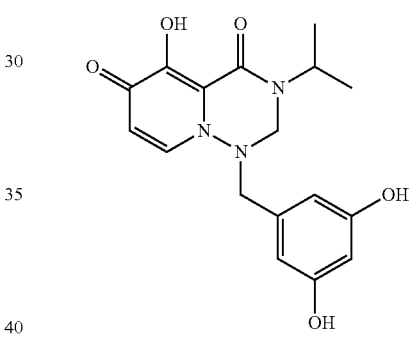
MS: m/z=346 [M+H]+
Example 224
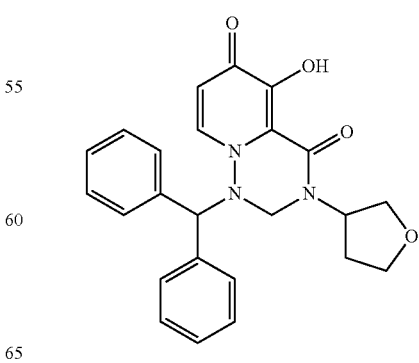
MS: m/z=418 [M+H]+.

Example 225
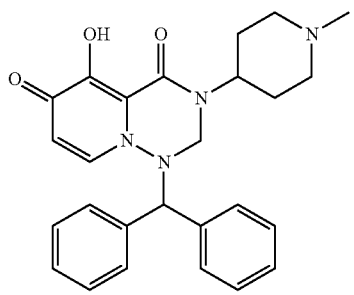
MS: m/z=445 [M+H]⁺.
Example 226
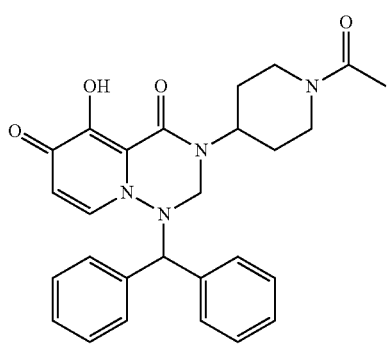
MS: m/z=473 [M+H]⁺.
Example 227
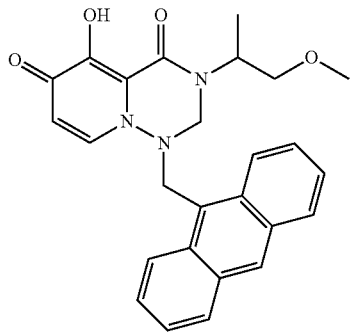
MS: m/z=444 [M+H]⁺.
Example 228
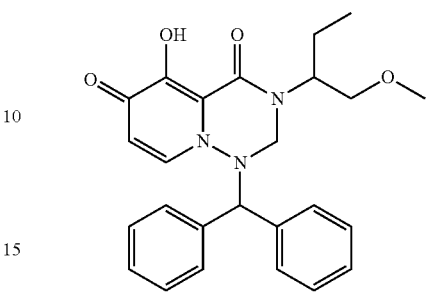
MS: m/z=434 [M+H]⁺.
Example 229
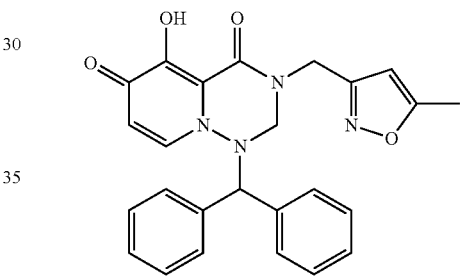
MS: m/z=443 [M+H]⁺.
Example 230
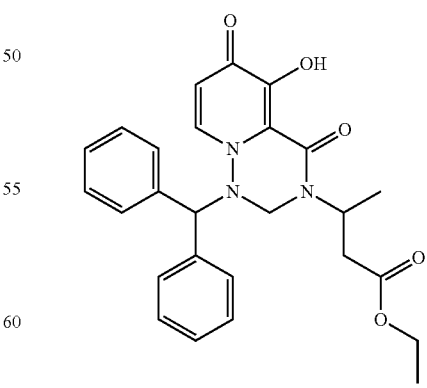
According to Example 128, compound 230 was synthesized by the same procedure.
MS: m/z=461 [M+H]⁺.

Example 231

[Chemical formula 309]

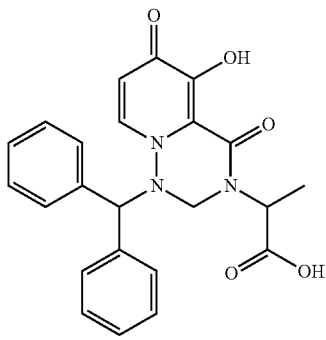

According to Example 129, compound 231 was synthesized by the same procedure.
MS: m/z=420 [M+H]⁺.

Example 232

[Chemical formula 310]

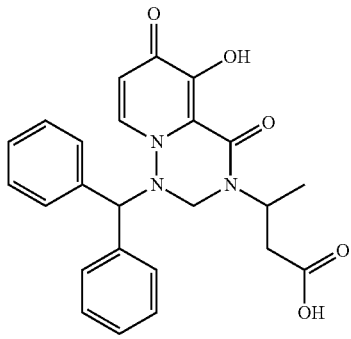

According to Example 129, compound 232 was synthesized by the same procedure.
MS: m/z=434 [M+H]⁺.

Example 233

[Chemical formula 311]

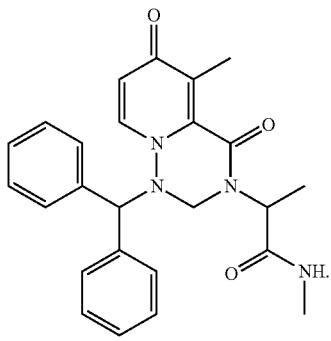

According to Example 130, compound 233 was synthesized by the same procedure.
MS: m/z=433 [M+H]⁺.

Example 234

[Chemical formula 312]

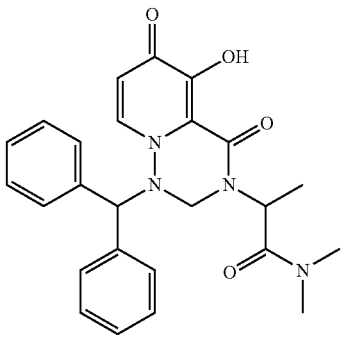

According to Example 130, compound 234 was synthesized by the same procedure.
MS: m/z=447 [M+H]⁺.

Example 235

[Chemical formula 313]

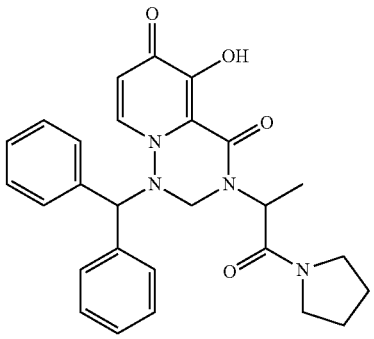

According to Example 130, compound 235 was synthesized by the same procedure

MS: m/z=473 [M+H]⁺.

Example 236

[Chemical formula 314]

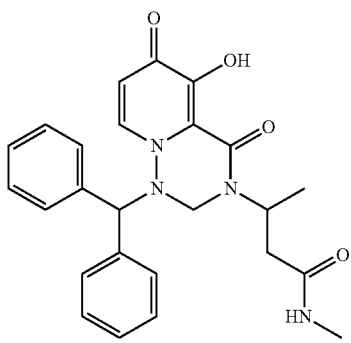

According to Example 130, compound 236 was synthesized by the same procedure.
MS: m/z=447 [M+H]⁺.

Example 237

[Chemical formula 315]

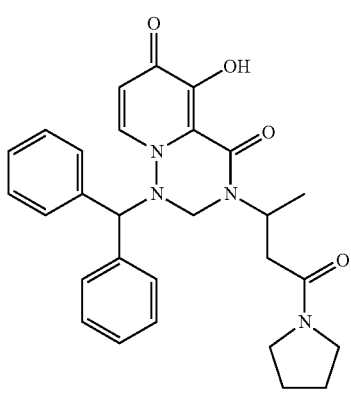

According to Example 130, compound 237 was synthesized by the same procedure.
MS: m/z=487 [M+H]⁺.

Example 238

[Chemical formula 316]

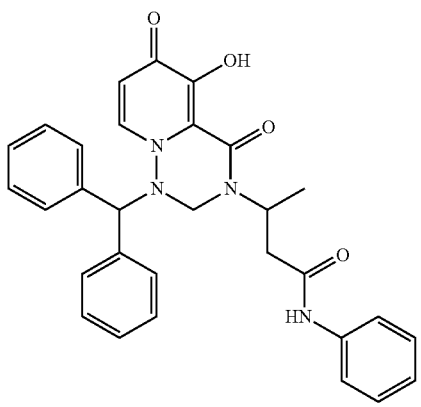

According to Example 130, compound 238 was synthesized by the same procedure.
MS: m/z=509 [M+H]⁺.

Example 239

[Chemical formula 317]

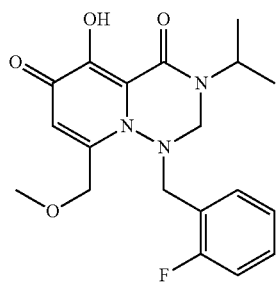

MS: m/z=376 [M+H]⁺.

According to Example 157, compound 239 was synthesized by the same procedure.

Using amines which are commercially available or known in the references and alcohols which are commercially available or known in the references, and according to the method of Example 107, Examples 240 to 245 were synthesized.

Example 240

[Chemical formula 318]

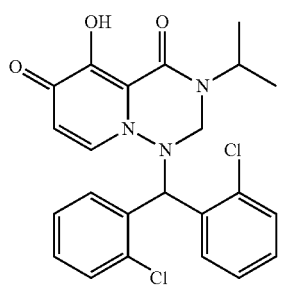

$^1$H-NMR (CDCl$_3$) δ: 1.05 (3H, d, J=6.9 Hz), 1.04-1.14 (4H, m), 4.49 (1H, d, J=13.2 Hz), 4.83 (1H, d, J=13.2 Hz), 4.91-4.99 (1H, m), 5.73 (1H, d, J=7.8 Hz), 6.50 (1H, s), 6.70 (1H, d, J=7.8 Hz), 7.12-7.30 (4H, m), 7.33-7.43 (2H, m), 7.46-7.54 (1H, m), 8.06 (1H, d, J=7.5 Hz).

Example 241
[Chemical formula 319]
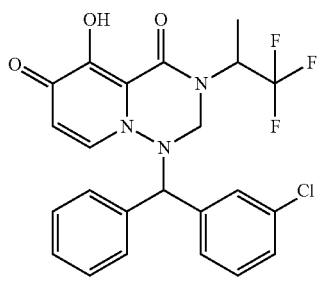
MS: m/z=478 [M+H]+.
Example 242
[Chemical formula 320]
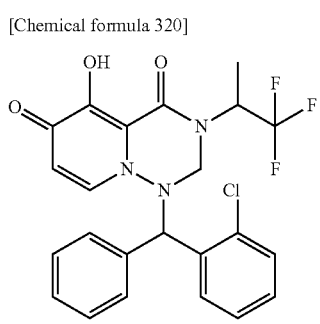 [SMILES: CC(N1CN(C(c2ccccc2)c2ccccc2Cl)n2ccc(=O)c(O)c2C1=O)C(F)(F)F]
MS: m/z=478 [M+H]+.
Example 243
[Chemical formula 321]
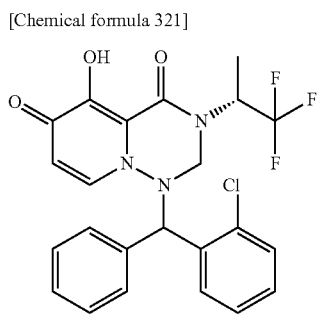 [SMILES: C[C@@H](N1CN(C(c2ccccc2)c2ccccc2Cl)n2ccc(=O)c(O)c2C1=O)C(F)(F)F]
MS: m/z=478 [M+H]+.
Example 244
[Chemical formula 322]
$^1$H-NMR (CDCl$_3$) δ: 1.14 (6H, d, J=6.9 Hz), 4.59 (1H, d, J=12.6 Hz), 4.77 (1H, d, J=12.6 Hz), 4.81-4.91 (1H, m), 5.82 (1H, d, J=7.5 Hz), 5.82 (1H, s), 6.71 (1H, brs), 6.78 (1H, brs), 6.87 (1H, d, J=7.5 Hz), 7.05 (1H, brs), 7.16 (1H, brs), 7.25 (1H, brs), 7.41 (1H, brs).
Example 245
[Chemical formula 323]
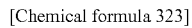
MS: m/z=490 [M+H]+.
Example 246
[Chemical formula 324]
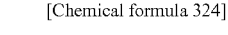
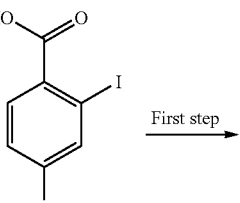
246A

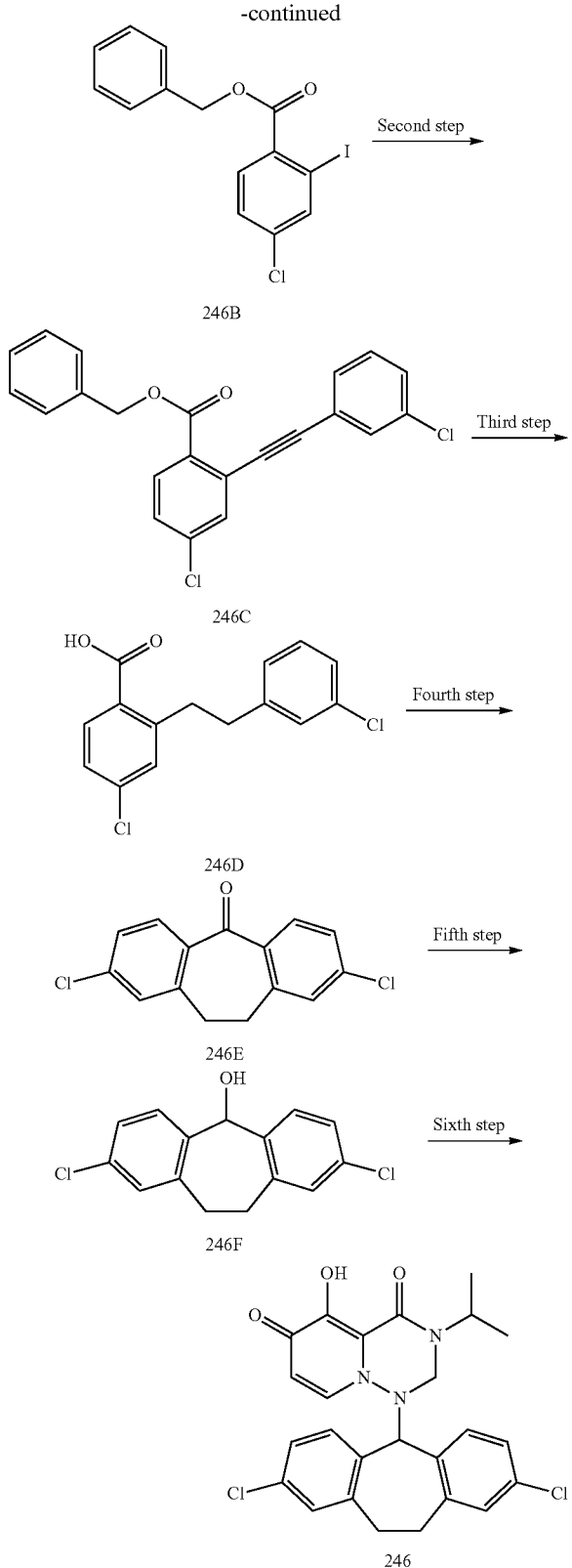

1 hour. To the reaction solution was added ethyl acetate (80 ml), insolubles were filtered off, and 1N hydrochloric acid was added. The organic layer was separated, and the aqueous layer was extracted with ethyl acetate two times. The combined organic layers were washed with water once and, further, washed with sodium bicarbonate water once, and with an aqueous saturated sodium chloride solution once. The resulting solution was dried with sodium sulfate, and the solvent was distilled off to obtain 6.98 g of compound 246B as an oil.

$^1$H-NMR (CDCl$_3$) δ: 5.36 (2H, s), 7.35-7.47 (6H, m), 7.78 (1H, d, J=8.4 Hz), 8.01 (1H, d, J=2.1 Hz).

Second Step

To a dimethylformamide (15 ml) solution of compound 246B (3 g, 8.05 mmol) and 1-chloro-3-ethynylbenzene (1.32 g, 9.66 mmol) and triethylamine (4.07 g, 40.25 mmol) were added copper chloride (76.6 mg, 0.403 mmol) and dichlorobis(triphenylphosphine)palladium (282.5 mg, 0.403 mmol) under nitrogen atmosphere, and the mixture was stirred at room temperature for 5 hours. The reaction solution was diluted with water, and the mixture was extracted with ethyl acetate three times. The combined extracts were washed with water three times, and dried with sodium sulfate, then the solvent was distilled off. The resulting oil was purified by silica gel column chromatography. The material were eluted firstly with hexane and, then, with hexane-ethyl acetate (7:3, v/v). Concentration of an objective fraction afforded 3.10 g of compound 246C as an oil.

$^1$H-NMR (CDCl$_3$) δ: 5.39 (2H, s), 7.21-7.46 (9H, m), 7.62 (1H, d, J=2.1 Hz), 7.98 (1H, d, J=8.4 Hz).

Third Step

To a methanol (30 ml) solution of compound 246C (3.10 g, 8.05 mmol) was added 10% palladium carbon (620 mg, 20 wt %), and the mixture was stirred at room temperature under 1 atm hydrogen atmosphere. The reaction solution was filtered with celite, the solvent was distilled off, to the resulting crude product were added ethyl acetate-diisopropyl ether, and the precipitated residue was filtered to obtain 618 mg of compound 246D as a solid.

$^1$H-NMR (CDCl$_3$) δ: 2.90 (2H, dd, J=7.8 Hz, 10.8 Hz), 3.29 (2H, dd, J=7.5 Hz, 10.5 Hz), 7.06-7.09 (1H, m), 7.18-7.25 (4H, m), 7.31 (1H, dd, J=2.1 Hz, 8.7 Hz), 8.05 (1H, d, J=8.4 Hz).

Fourth Step

To compound 246D (2.20 g, 7.45 mmol) was added polyphosphoric acid (20 g), and the mixture was stirred at 200° C. for 1 hour. After cooled to room temperature, water was added, and the mixture was extracted with ethyl acetate three times. The combined extracts were washed with saturated sodium bicarbonate water, and dried with sodium sulfate and, thereafter, the solvent was distilled off. The resulting oil was purified by silica gel column chromatography. The materials were eluted firstly with hexane and, then, with hexane-ethyl acetate (7:3, v/v). Concentration of an objective fraction afforded 1.05 g of compound 246E as an oil.

$^1$H-NMR (CDCl$_3$) δ: 3.17 (4H, s), 7.24 (2H, d, J=2.1 Hz), 7.32 (2H, dd, J=2.1 Hz, 8.4 Hz), 8.00 (2H, d, J=8.4 Hz).

Fifth Step

A methanol (10 ml) suspension of sodium borohydride (409 mg, 10.82 mmol) was cooled to 1 to 3° C., and compound 246E (1.0 g, 3.61 mmol) was added while the same temperature was retained. After the reaction solution was stirred at the same temperature for 30 minutes, water was added. The precipitated solid was filtered to obtain 968 mg of compound 246F.

First Step

To a dimethylformamide (20 ml) solution of compound 246A (5.30 g, 18.76 mmol) and potassium carbonate (5.19 g, 27.53 mmol) was added benzyl bromide (3.21 g, 18.76 mmol), and the mixture was stirred at room temperature for ¹H-NMR (CDCl₃) δ: 2.25 (1H, d, J=3.0 Hz), 3.05-3.16 (2H, m), 3.27-3.38 (2H, m), 5.95 (1H, d, J=3.0 Hz), 7.14-7.17 (4H, m), 7.39 (2H, d, J=8.1 Hz).

Sixth Step

According to Example 107, compound 246 was synthesized by the same procedure.

¹H-NMR (CDCl₃) δ: 1.14 (3H, d, J=6.9 Hz), 1.20 (3H, d, J=6.9 Hz), 2.79 (1H, ddd, J=4.5 Hz, 4.5 Hz, 14.4 Hz), 2.99-3.11 (1H, m), 3.50 (1H, ddd, J=4.8 Hz, 4.8 Hz, 17.7 Hz), 4.21-4.33 (1H, m), 4.23 (1H, d, J=12.9 Hz), 4.62-4.74 (2H, m), 5.04 (1H, s), 5.84 (1H, d, J=7.8 Hz), 6.57 (1H, d, J=8.1 Hz), 6.65-6.72 (2H, m), 6.89-6.92 (1H, m), 7.11-7.30 (4H, m).

Using amines which are commercially available or known in the references and intermediates corresponding to compound 246A to compound 246F which are commercially available or known in the references, and according to the method of Example 246, compounds 247 to 284 were synthesized.

Example 247

[Chemical formula 325]

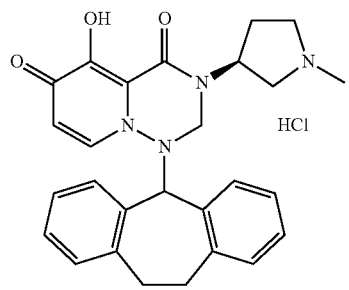

MS: m/z=457 [M+H]⁺.

Example 248

[Chemical formula 326]

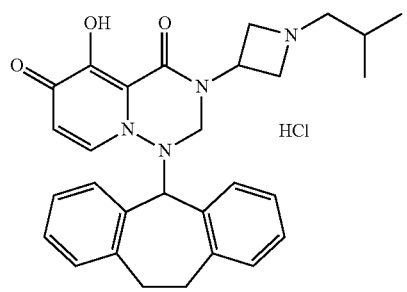

MS: m/z=485 [M+H]⁺.

Example 249

[Chemical formula 327]

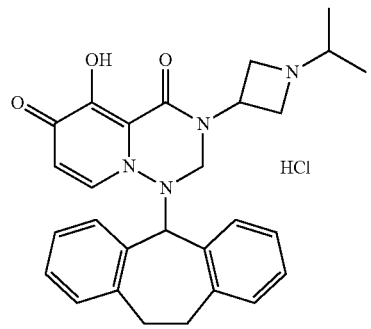

MS: m/z=471 [M+H]⁺.

Example 250

[Chemical formula 328]

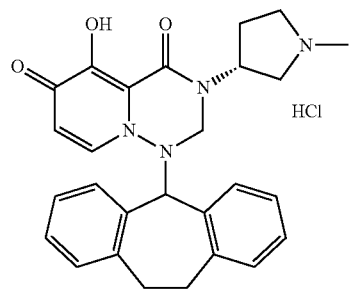

MS: m/z=457 [M+H]⁺.

Example 251

[Chemical formula 329]

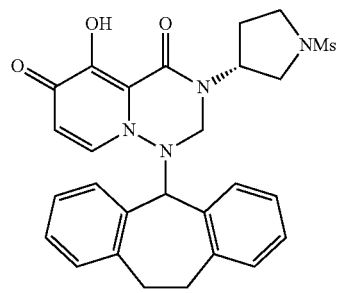

MS: m/z=521 [M+H]⁺.

Example 252
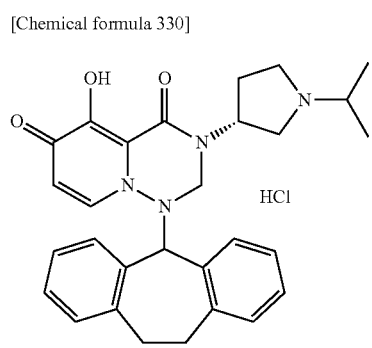
MS: m/z=485 [M+H]⁺.
Example 253
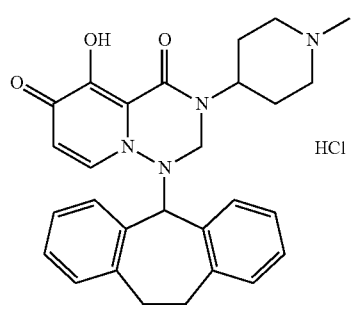
MS: m/z=471 [M+H]⁺.
Example 254
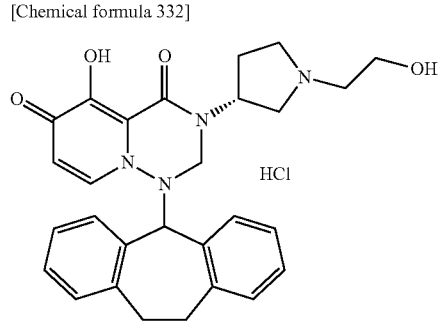
MS: m/z=487 [M+H]⁺.
Example 255
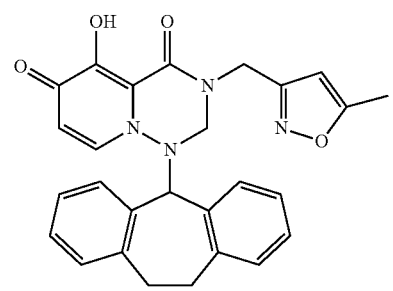
MS: m/z=469 [M+H]⁺.
Example 256
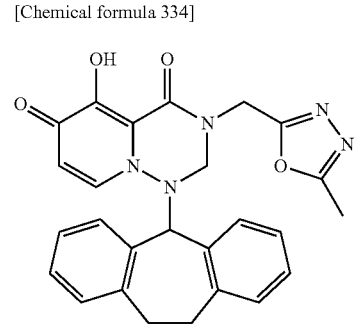
MS: m/z=470 [M+H]⁺.
Example 257
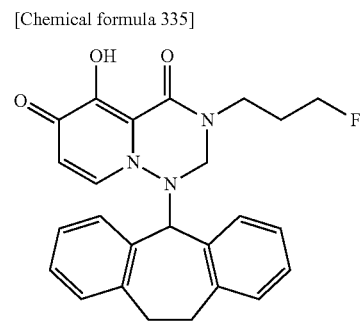
MS: m/z=434 [M+H]⁺.

Example 258

[Chemical formula 336]

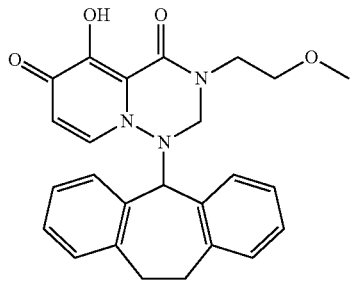

$^1$H-NMR (DMSO-$d_6$) δ: 2.88 (3H, m), 3.43 (2H, m), 3.69 (1H, dt, J=16.9, 5.1 Hz), 4.01 (1H, d, J=13.4 Hz), 4.07-4.17 (2H, m), 4.97 (1H, d, J=13.4 Hz), 5.24 (1H, s), 5.50 (1H, d, J=7.6 Hz), 6.73 (1H, d, J=7.2 Hz), 6.85-6.94 (2H, m), 7.14-7.41 (6H, m), 11.73 (1H, s).
MS: m/z=432 [M+H]$^+$.

Example 259

[Chemical formula 337]

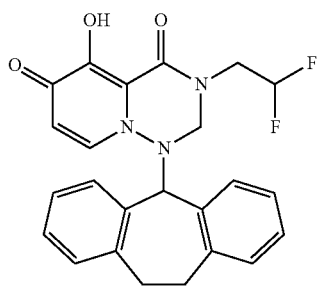

$^1$H-NMR (DMSO-$d_6$) δ: 2.80 (1H, td, J=9.6, 4.5 Hz), 2.86-2.99 (1H, m), 3.00-3.18 (1H, m), 3.67 (1H, dt, J=17.1, 5.0 Hz), 4.03-4.19 (2H, m), 4.32-4.52 (1H, m), 5.05 (1H, d, J=13.3 Hz), 5.26 (1H, s), 5.53 (1H, d, J=7.6 Hz), 6.17 (1H, tt, J=55.0, 3.5 Hz), 6.72 (1H, d, J=7.5 Hz), 6.87-6.94 (2H, m), 7.12-7.27 (3H, m), 7.30-7.43 (3H, m).
MS: m/z=438 [M+H]$^+$.

Example 260

[Chemical formula 338]

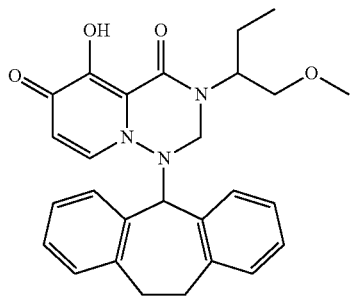

MS: m/z=460 [M+H]$^+$.

Example 261

[Chemical formula 339]

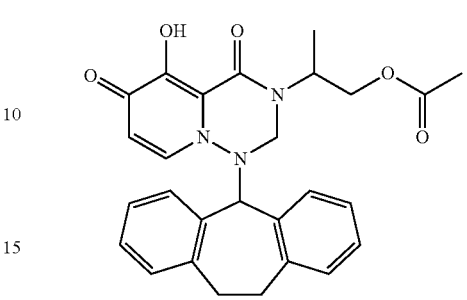

MS: m/z=474 [M+H]$^+$.

Example 262

[Chemical formula 340]

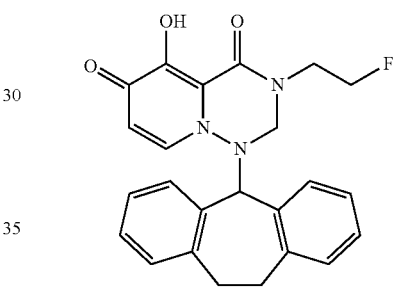

$^1$H-NMR (DMSO-$d_6$) δ: 2.80 (1H, dt, J=14.2, 5.1 Hz), 2.86-2.99 (1H, m), 3.00-3.18 (1H, m), 3.68 (1H, dt, J=16.9, 5.3 Hz), 4.05 (1H, d, J=13.3 Hz), 4.07-4.32 (2H, m), 4.37-4.52 (1H, m), 4.53-4.67 (1H, m), 5.02 (1H, d, J=13.0 Hz), 5.26 (1H, s), 5.50 (1H, d, J=7.8 Hz), 6.73 (1H, d, J=7.6 Hz), 6.85-6.94 (2H, m), 7.12-7.27 (3H, m), 7.30-7.43 (3H, m).
MS: m/z=420 [M+H]$^+$.

Example 263

[Chemical formula 341]

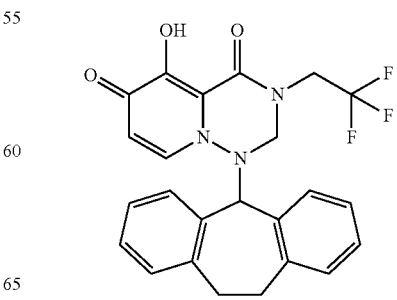

$^1$H-NMR (DMSO-$d_6$) δ: 2.76-3.00 (2H, m), 3.46-3.73 (2H, m), 4.06-4.22 (2H, m), 4.77-4.91 (1H, m), 5.15 (1H, d, J=12.9 Hz), 5.24 (1H, s), 5.56 (1H, d, J=7.7 Hz), 6.72 (1H, d, J=7.1 Hz), 6.88-6.95 (1H, m), 6.96 (1H, d, J=7.7 Hz), 7.09-7.41 (7H, m).

MS: m/z=456 [M+H]$^+$.

Example 264

[Chemical formula 342]

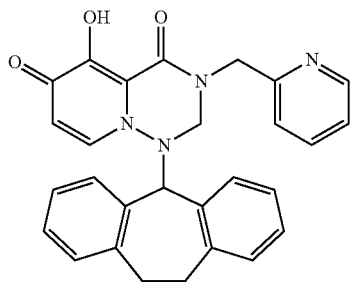

$^1$H-NMR (DMSO-$d_6$) δ: 2.74-2.99 (2H, m), 3.62-3.73 (1H, m), 4.01-4.20 (3H, m), 5.12 (1H, d, J=13.2 Hz), 5.15 (1H, d, J=15.7 Hz), 5.34 (1H, s), 5.52 (1H, d, J=7.7 Hz), 6.78 (1H, d, J=8.0 Hz), 6.89-6.96 (2H, m), 7.10-7.23 (5H, m), 7.27-7.35 (3H, m), 7.43 (1H, d, J=7.7 Hz), 7.79 (1H, td, J=7.6, 1.8 Hz), 8.45-8.50 (1H, m).

MS: m/z=465 [M+H]$^+$.

Example 265

[Chemical formula 343]

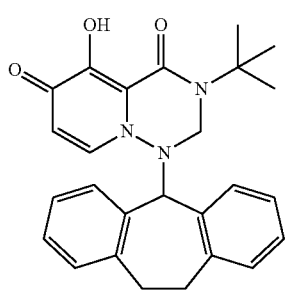

$^1$H-NMR (DMSO-$d_6$) δ: 1.32 (9H, s), 2.76-2.86 (1H, m), 2.87-3.01 (1H, m), 3.59-3.70 (1H, m), 4.12-4.25 (1H, m), 4.29 (1H, d, J=13.5 Hz), 4.90 (1H, d, J=13.2 Hz), 5.20 (1H, s), 5.49 (1H, d, J=7.4 Hz), 6.75 (1H, d, J=8.0 Hz), 6.81 (1H, d, J=7.4 Hz), 6.91 (1H, t, J=6.6 Hz), 7.12-7.21 (2H, m), 7.22-7.30 (1H, m), 7.33-7.38 (2H, m), 7.46 (1H, d, J=7.4 Hz).

MS: m/z=430 [M+H]$^+$.

Example 266

[Chemical formula 344]

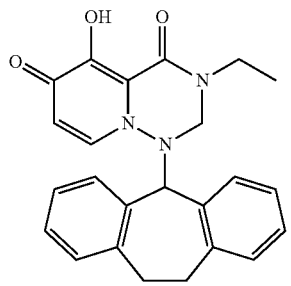

$^1$H-NMR (DMSO-$d_6$) δ: 1.05 (3H, t, J=7.2 Hz), 2.80 (1H, dt, J=14.4, 5.1 Hz), 2.85-2.99 (2H, m), 3.68 (1H, dt, J=16.8, 5.0 Hz), 3.74-3.87 (1H, m), 4.02 (1H, d, J=13.3 Hz), 4.06-4.19 (1H, m), 4.98 (1H, d, J=13.1 Hz), 5.22 (1H, s), 5.48 (1H, d, J=7.6 Hz), 6.73 (1H, d, J=7.5 Hz), 6.83-6.94 (2H, m), 7.12-7.40 (6H, m).

MS: m/z=402 [M+H]$^+$.

Example 267

[Chemical formula 345]

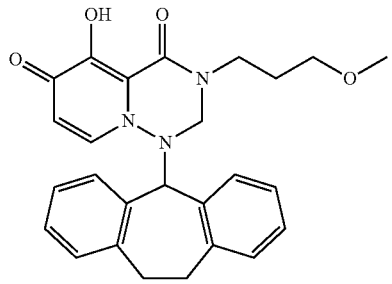

$^1$H-NMR (CDCl$_3$) δ: 1.74-1.86 (2H, m), 2.71-2.82 (1H, m), 2.83-2.93 (1H, m), 2.98-3.11 (1H, m), 3.25 (3H, s), 3.39 (2H, t, J=5.4 Hz), 3.62-3.74 (1H, m), 4.02-4.14 (2H, m), 4.16-4.28 (1H, m), 4.82 (1H, d, J=13.2 Hz), 5.03 (1H, s), 5.76 (1H, d, J=7.7 Hz), 6.58 (1H, d, J=7.7 Hz), 6.64 (1H, d, J=7.4 Hz), 6.89-6.97 (1H, m), 7.12-7.39 (6H, m).

MS: m/z=446 [M+H]$^+$.

Example 268

Chemical formula 346]

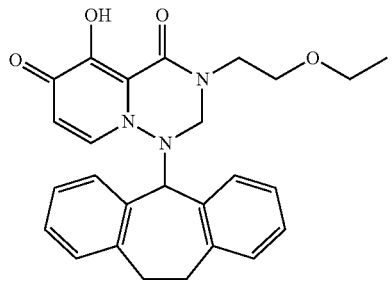

¹H-NMR (CDCl₃) δ: 1.09 (3H, t, J=7.0 Hz), 2.65-2.77 (1H, m), 2.83-2.94 (1H, m), 2.97-3.10 (1H, m), 3.40 (2H, q, J=7.0 Hz), 3.45-3.52 (1H, m), 3.55-3.64 (1H, m), 3.65-3.76 (1H, m), 4.00-4.15 (2H, m), 4.36-4.45 (1H, m), 4.90 (1H, d, J=13.5 Hz), 5.02 (1H, s), 5.79 (1H, d, J=7.7 Hz), 6.59 (1H, d, J=7.7 Hz), 6.63 (1H, d, J=7.4 Hz), 6.90-6.97 (1H, m), 7.13-7.39 (6H, m).
MS: m/z=446 [M+H]⁺.

Example 269

[Chemical formula 347]

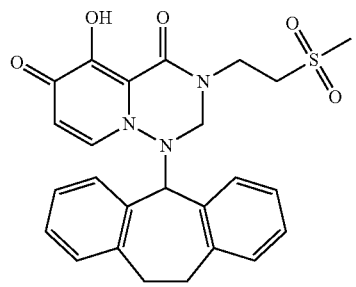

MS: m/z=480 [M+H]⁺.

Example 270

[Chemical formua 348]

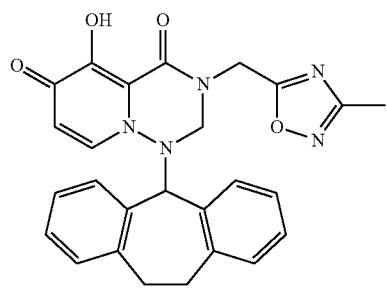

¹H-NMR (DMSO-d₆) δ: 2.33 (3H, s), 2.85 (2H, m), 3.68 (1H, m), 4.16 (1H, m), 4.29 (1H, d, J=13.3 Hz), 4.45 (1H, d, J=17.1 Hz), 5.12 (1H, d, J=13.1 Hz), 5.26 (1H, d, J=17.4 Hz), 5.36 (1H, s), 5.55 (1H, d, J=7.6 Hz), 6.74 (1H, d, J=7.6 Hz), 6.89-7.38 (8H, m).
MS: m/z=470 [M+H]⁺.

Example 271

[Chemical formula 349]

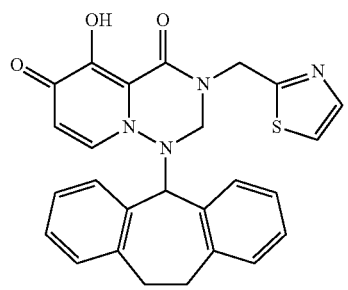

¹H-NMR (DMSO-d₆) δ: 2.87 (2H, m), 3.61-3.69 (1H, m), 4.15 (1H, m), 4.18 (1H, d, J=13.2 Hz), 4.51 (1H, d, J=15.9 Hz), 5.08 (1H, d, J=13.1 Hz), 5.21 (1H, s), 5.22 (1H, d, J=15.6 Hz), 5.52 (1H, d, J=7.6 Hz), 6.72 (1H, d, J=7.5 Hz), 6.89-7.32 (8H, m), 7.76 (2H, s).
MS: m/z=471 [M+H]⁺.

Example 272

[Chemical formula 350]

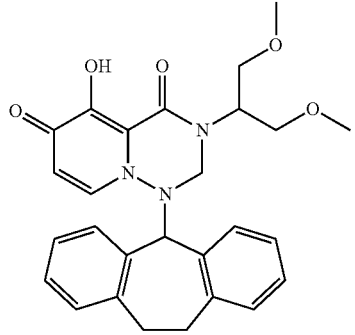

MS: m/z=476 [M+H]⁺.

Example 273

[Chemical formula 351]

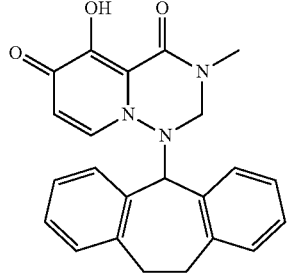

¹H-NMR (CDCl₃) δ: 2.84-2.93 (1H, m), 2.98 (3H, s), 2.98-3.09 (1H, m), 3.66-3.75 (1H, m), 3.99-4.15 (1H, m), 4.06 (1H, d, J=12.9 Hz), 4.80 (1H, d, J=13.2 Hz), 5.03 (1H, s), 5.74 (1H, d, J=7.5 Hz), 6.56 (1H, d, J=7.5 Hz), 6.63 (1H, d, J=6.6 Hz), 6.90-6.96 (1H, m), 7.14-7.37 (6H, m).

Example 274

[Chemical formula 352]

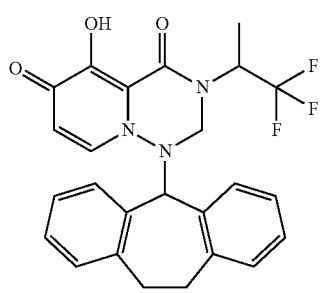

MS: m/z=470 [M+H]⁺.

Example 275

[Chemical formula 353]

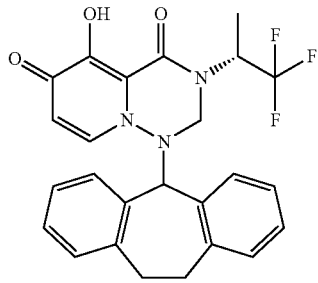

MS: m/z=470 [M+H]+

Example 276

[Chemical formula 354]

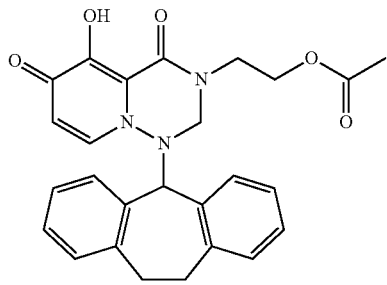

MS: m/z=460 [M+H]+

Example 277

[Chemical formula 355]

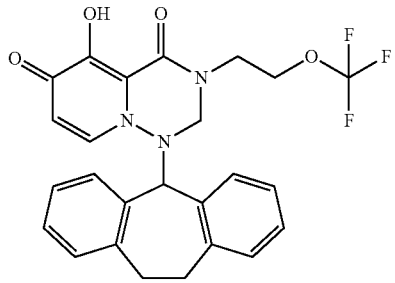

MS: m/z=486 [M+H]+.

Example 278

[Chemical formula 356]

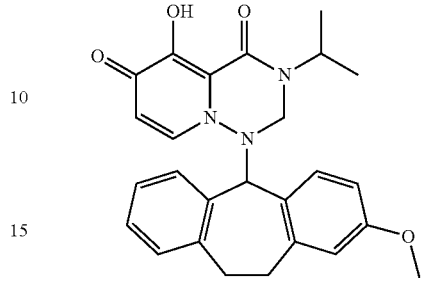

MS: m/z=446 [M+H]+

Example 279

[Chemical formula 357]

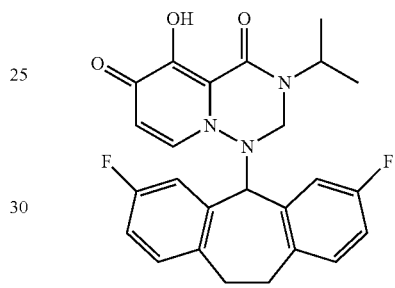

$^1$H-NMR (CDCl$_3$) δ: 1.08-1.21 (6H, m), 2.84 (1H, ddd, J=4.8 Hz, 4.8 Hz, 14.4 Hz), 2.97-3.08 (1H, m), 3.54 (1H, ddd, J=4.8 Hz, 6.6 Hz, 17.1 Hz), 4.09-4.26 (1H, m), 4.24 (1H, d, J=13.2 Hz), 4.64-4.74 (m, 1H), 4.70 (1H, d, J=13.2 Hz), 4.94 (1H, s), 5.81 (1H, d, J=7.8 Hz), 6.42 (1H, dd, J=2.7 Hz, 9.0 Hz), 6.67 (1H, d, J=7.8 Hz), 6.89-7.12 (4H, m), 7.19-7.36 (1H, m).

Example 280

[Chemical formula 358]

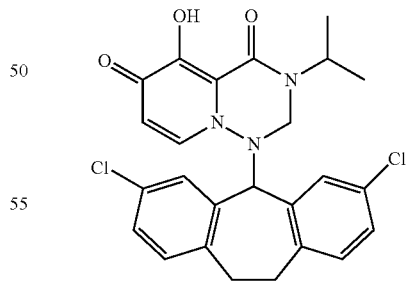

$^1$H-NMR (CDCl$_3$) δ: 1.15 (3H, d, J=6.9 Hz), 1.20 (3H, d, J=6.9 Hz), 2.84 (1H, ddd, J=4.8 Hz, 5.1 Hz, 14.4 Hz), 2.96-3.07 (1H, m), 3.55 (1H, ddd, J=4.8 Hz, 5.1 Hz, 17.4 Hz), 4.11-4.23 (1H, m), 4.21 (1H, d, J=12.9 Hz), 4.65-4.74 (1H, m), 4.70 (1H, d, J=12.9 Hz), 4.95 (1H, s), 5.78 (1H, d, J=7.8 Hz), 6.63 (1H, d, J=7.8 Hz), 6.69 (1H, d, J=2.1 Hz), 7.06 (1H, d, J=8.4 Hz), 7.18 (1H, dd, J=2.1 Hz, 8.4 Hz), 7.23-7.26 (2H, m), 7.24 (1H, dd, J=2.1 Hz, 8.1 Hz).

Example 281

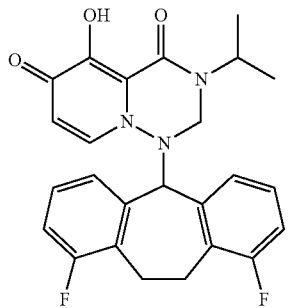
[Chemical formula 359]

$^1$H-NMR (CDCl$_3$) δ: 1.13 (3H, d, J=6.6 Hz), 1.20 (3H, d, J=6.9 Hz), 2.90-3.32 (1H, m), 3.36 (1H, ddd, J=4.5 Hz, 4.5 Hz, 9.6 Hz), 3.42-3.51 (1H, m), 3.95-4.02 (1H, m), 4.28 (1H, d, J=12.9 Hz), 4.64-4.75 (1H, m), 1.89 (1H, d, J=12.9 Hz), 5.15 (1H, s), 5.80 (1H, d, J=7.5 Hz), 6.46-6.49 (1H, m), 6.70 (1H, d, J=7.8 Hz), 6.88-7.00 (2H, m), 7.03-7.06 (1H, m), 7.11-7.22 (2H, m).

Example 282

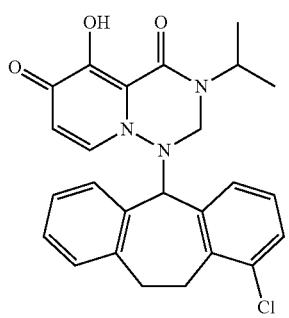
[Chemical formula 360]

$^1$H-NMR (CDCl$_3$) δ: 1.09-1.19 (6H, m), 2.80-3.10 (2H, m), 3.40-3.60 (1H, m), 4.16-4.41 (2H, m), 4.61-4.47 (2H, m), 5.06-5.10 (1H, m), 5.71 (0.45H, d, J=7.5 Hz), 5.74 (0.55H, d, J=7.8 Hz), 6.60-6.72 (2H, m), 6.86-6.94 (1H, m), 7.10-7.46 (6H, m).

Example 283

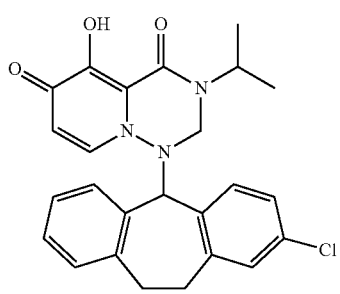
[Chemical formula 361]

$^1$H-NMR (CDCl$_3$) δ: 1.10-1.21 (6H, m), 2.75-2,86 (1H, m), 2.99-3.14 (1H, m), 4.23-4.37 (2H, m), 4,59-4.74 (2H, m), 5.04 (1H, s), 5.67-5.80 (1H, m), 6.58-6.67 (2H, m), 6.88-7.08 (1H, m), 7.11-7.38 (5H, m).

Example 284

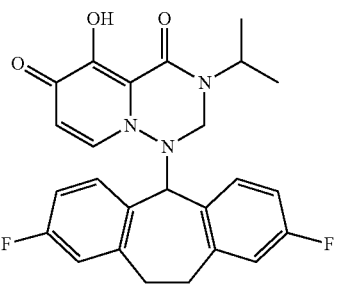
[Chemical formula 362]

$^1$H-NMR (CDCl$_3$) δ: 1.15 (3H, d, J=6.9 Hz), 1.20 (3H, d, J=6.9 Hz), 2.80 (1H, ddd, J=4.5 Hz, 4.5 Hz, 9.9 Hz), 3.07 (1H, t, J=3.9 Hz, 13.2 Hz, 13.2 Hz), 3.50 (1H, ddd, J=4.2 Hz, 4.2 Hz, 18.0 Hz), 4.24 (1H, 6.9 Hz), 4.34 (1H, ddd, J=4.2 Hz, 13.5 Hz, 13.5 Hz), 4.63-4.74 (2H, m), 5.06 (1H, s), 5.81 (1H, d, J=7.8 Hz), 6.57-6.64 (2H, m), 6.65 (1H, d, J=7.5 Hz), 6.82 (1H, d, J=9.3 Hz), 6.90 (1H, ddd, J=2.7 Hz, 8.4 Hz, 8.4 Hz), 7.02 (1H, dd, J=2.7 Hz, 9.0 Hz), 7.19-7.26 (2H, m).

Example 285

[Chemical formula 363]

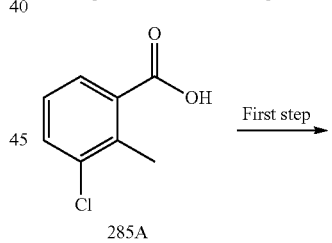 First step

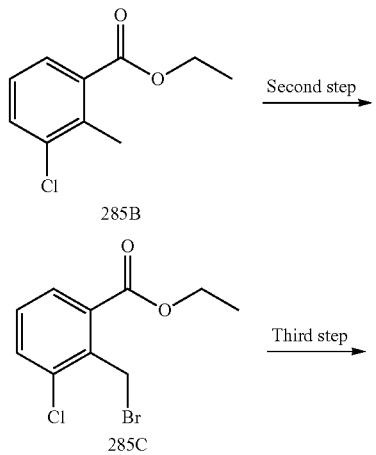 Second step

Third step

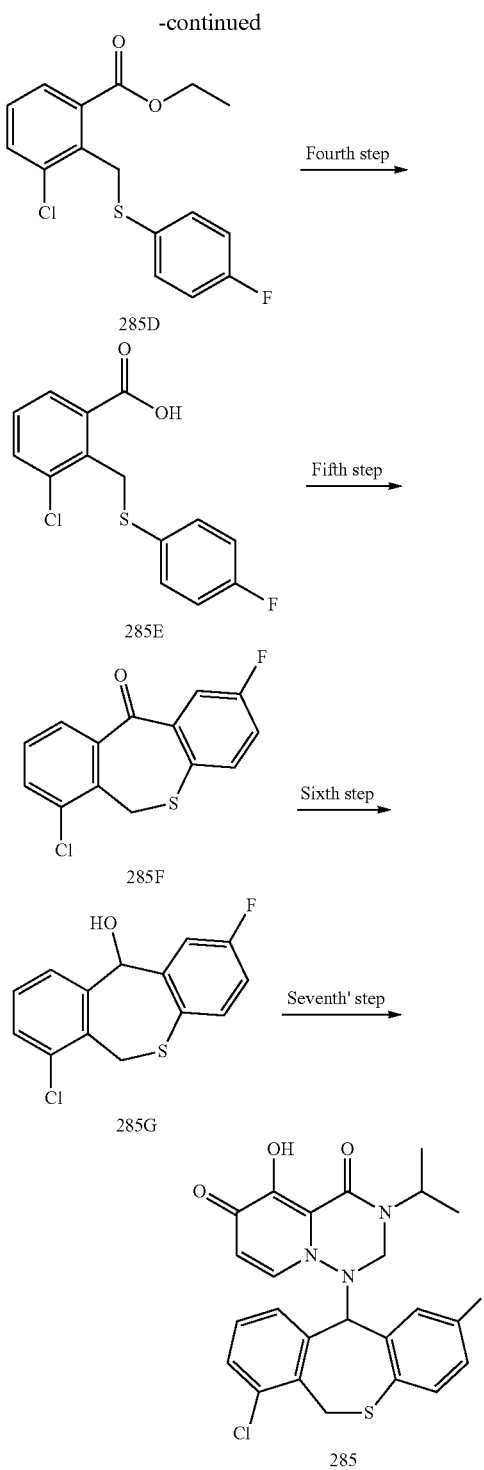

¹H-NMR (CDCl₃) δ: 1.40 (3H, t, J=7.2 Hz), 2.60 (3H, s), 4.37 (2H, q, J=7.1 Hz), 7.17 (1H, td, J=7.9, 0.6 Hz), 7.49 (1H, ddd, J=8.0, 1.4, 0.4 Hz), 7.68 (1H, ddd, J=7.8, 1.4, 0.3 Hz).

Second Step

Compound 285B (5.63 g, 28.3 mmol) obtained in the first step was dissolved in carbon tetrachloride (150 ml), N-bromosuccinimide (5.55 g, 31.2 mmol) was added, and the mixture was stirred at 100° C. for 18 hours. The reaction solution was cooled to room temperature, and washed with water and an aqueous saturated sodium chloride solution. The organic layer was dried with sodium sulfate, and the solvent was distilled off under reduced pressure to obtain 8.08 g of an orange oily substance 285C.

¹H-NMR (CDCl₃) δ: 1.43 (3H, t, J=7.6 Hz), 4.42 (2H, q, J=7.1 Hz), 5.10 (2H, s), 7.31 (1H, t, J=8.6 Hz), 7.57 (1H, d, J=8.1 Hz), 7.84 (1H, d, J=8.1 Hz).

Third Step

Compound 285C (2.17 g, 7.8 mmol) obtained in the second step was dissolved in acetone (25 ml), 4-fluorobenzenethiol (1.00 g, 7.80 mmol) and potassium carbonate (1.62 g, 11.7 mmol) were added, and the mixture was stirred at 80° C. for 18 hours. After cooled to room temperature, the reaction solution was poured into water, the mixture was extracted with ethyl acetate, the extract was washed with an aqueous saturated sodium chloride solution, and the organic layer was dried with sodium sulfate. The solvent was distilled off under reduced pressure, and the resulting crude product was purified by silica gel column chromatography and eluted with n-hexane-ethyl acetate (4:1, v/v) to obtain 2.20 g of a colorless oily substance 285D.

¹H-NMR (CDCl₃) δ: 1.35 (3H, t, J=7.2 Hz), 4.25 (2H, d, J=7.5 Hz), 4.65 (2H, s), 6.91 (2H, t, J=8.8 Hz), 7.19-7.31 (3H, m), 7.48 (1H, dd, J=8.2, 1.4 Hz), 7.70 (1H, dd, J=7.6, 1.5 Hz).

Fourth Step

Compound 285D (2.20 g, 6.77 mmol) obtained in the third step was dissolved in ethanol (20 ml), a 2N aqueous sodium hydroxide solution (16.9 ml, 33.8 mmol) was added, and the mixture was stirred at room temperature for 3 hours. To the reaction solution was added water, the mixture was made acidic with dilute hydrochloric acid, and extracted with ethyl acetate. The organic layer was washed with an aqueous saturated sodium chloride solution, and dried with sodium sulfate, and the solvent was distilled off under reduced pressure. To the resulting compound was added n-hexane, and the precipitated residue was filtered to obtain 1.81 g of a white solid 285E.

¹H-NMR (CDCl₃) δ: 4.74 (2H, s), 6.95 (2H, t, J=8.8 Hz), 7.34 (3H, m), 7.59 (1H, dd, J=7.9, 1.5 Hz), 7.92 (1H, dd, J=7.9, 1.3 Hz).

Fifth Step

To compound 285E (1.81 g, 6.10 mmol) obtained in the fourth step was added polyphosphoric acid (10.0 g), and the mixture was stirred at 120° C. for 5 hours. After cooled to room temperature, water was added, and the mixture was extracted with ethyl acetate. The organic layer was dried with sodium sulfate, the solvent was concentrated under reduced pressure, to the resulting compound were added n-hexane-ethyl acetate, and the precipitated residue was filtered to obtain 1.18 g of a white solid 285F.

¹H-NMR (CDCl₃) δ: 4.28 (2H, s), 7.18 (1H, ddd, J=9.3, 6.6, 2.3 Hz), 7.33 (2H, m), 7.46 (1H, dd, J=7.7, 1.5 Hz), 7.59 (1H, dd, J=7.9, 1.3 Hz), 7.91 (1H, dd, J=10.1, 2.9 Hz).

Sixth Step

To compound 285F (1.17 g, 4.20 mmol) was added methanol (15 ml), sodium borohydride (191 mg, 5.04 mmol)

First Step

Compound 285A (5.00 g, 29.3 mmol) was dissolved in dimethylformamide (150 ml), potassium carbonate (14.2 mmol) and iodoethane (7.11 ml, 88.0 mmol) were added, and the mixture was stirred at room temperature for 2 hours. To the reaction solution was added hexane, and the mixture was washed with water and an aqueous saturated sodium chloride solution. The organic layer was dried with sodium sulfate, and the solvent was distilled off under reduced pressure to obtain a colorless oily substance 285B.

was added at 0° C., and the mixture was stirred at room temperature for 2 hours. The reaction solution was poured into water, the mixture was extracted with dichloromethane, the organic layer was dried with sodium sulfate, and the solvent was distilled off. To the resulting compound were added n-hexane-dichloromethane, and the precipitated residue was filtered to obtain 945 mg of a white solid 285G.

$^1$H-NMR (CDCl$_3$) δ: 2.58 (1H, d, J=3.2 Hz), 4.46 (1H, d, J=14.3 Hz), 4.58 (1H, d, J=14.6 Hz), 6.33 (1H, d, J=3.7 Hz), 6.82 (1H, td, J=8.3, 2.9 Hz), 7.07 (1H, dd, J=8.5, 5.4 Hz), 7.20 (1H, t, J=7.9 Hz), 7.33 (2H, m), 7.44 (1H, d, J=6.9 Hz).

Seventh Step

According to the same procedure as that of Example 107, compound 285 was synthesized.

MS: m/z=486 [M+H]$^+$.

Using amines which are commercially available or known in the references and intermediates corresponding to compound 285A to compound 285G which are commercially available or known in the references. Then according to the method of Example 285, compounds 286 to compound 359 were synthesized.

Example 286

[Cheemical formula 364]

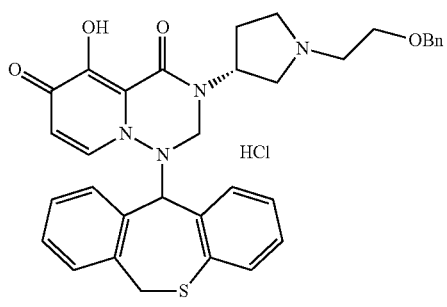

MS: m/z=595 [M+H]$^+$.

Example 287

[Chemical formula 365]

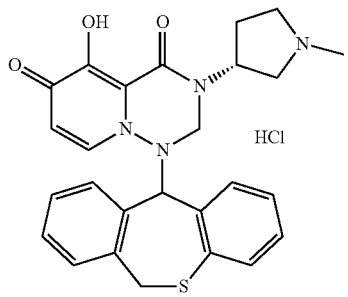

MS: m/z=475 [M+H]$^+$.

Example 288

[Chemical formula 366]

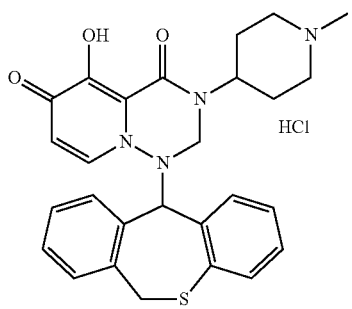

$^1$H-NMR (DMSO-d$_6$) δ: 1.57 (1H, brs), 1.84-1.99 (2H, m), 2.68 (3H, d, J=4.6 Hz), 3.08-3.17 (2H, m), 3.39 (3H, brs), 3.89 (1H, d, J=13.4 Hz), 4.16 (1H, d, J=13.3 Hz), 4.54 (1H, brs), 5.10 (1H, d, J=12.7 Hz), 5.50 (1H, s), 5.63 (1H, d, J=13.4 Hz), 5.73 (1H, d, J=7.8 Hz), 6.82-7.94 (9H, m).

MS: m/z=489 [M+H]$^+$.

Example 289

[Chemical formula 367]

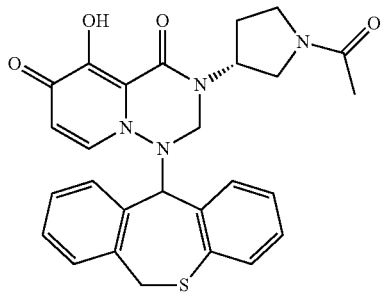

MS: m/z=503 [M+H]$^+$.

Example 290

[Chemical formula 368]

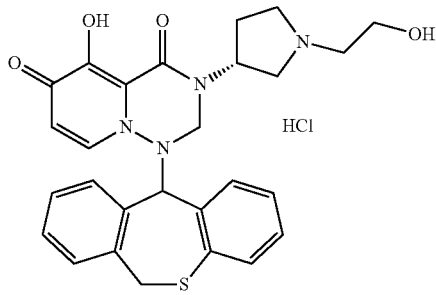

MS: m/z=505 [M+H]$^+$.

325
Example 291
[Chemical formula 369]
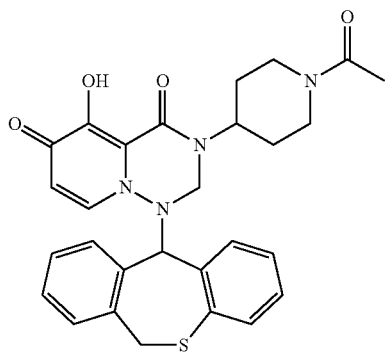
MS: m/z=517 [M+H]+.
Example 292
[Chemical formula 370]
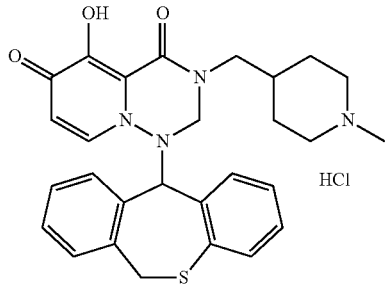
MS: m/z=503 [M+H]+.
Example 293
[Chemical formula 371]
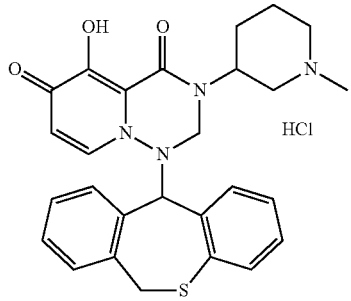
MS: m/z=489 [M+H]+.
326
Example 294
[Chemical formula 372]
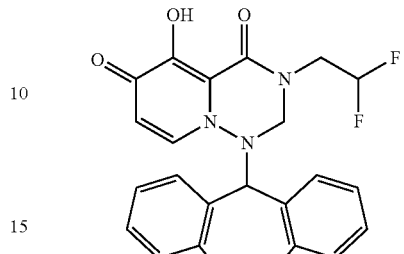
MS: m/z=456 [M+H]+.
Example 295
[Chemical formula 373]
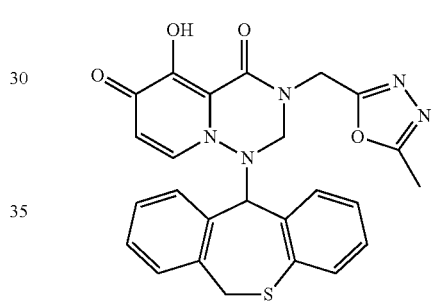
MS: m/z=488 [M+H]+.
Example 296
[Chemical formula 374]
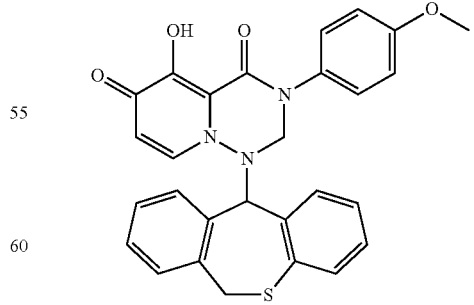
MS: m/z=498 [M+H]+.

Example 297

[Chemical formula 375]

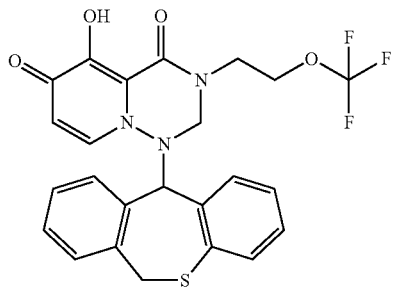

¹H-NMR (DMSO-d₆) δ: 3.21 (1H, m), 3.85 (1H, d, J=13.4 Hz), 4.08-4.18 (3H, m), 4.28 (1H, d, J=13.4 Hz), 5.10 (1H, d, J=13.7 Hz), 5.45 (1H, s), 5.57-5.64 (2H, m), 6.82-7.50 (10H, m).
MS: m/z=504 [M+H]⁺.

Example 298

[Chemical formula 376]

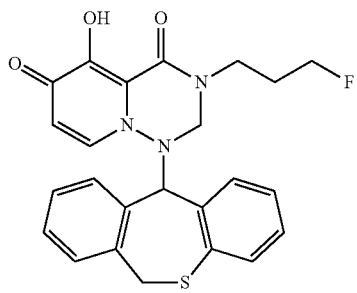

According to Example 107, compound 298 was synthesized by the same procedure.
MS: m/z=452 [M+H]⁺.

Example 299

[Chemical formula 377]

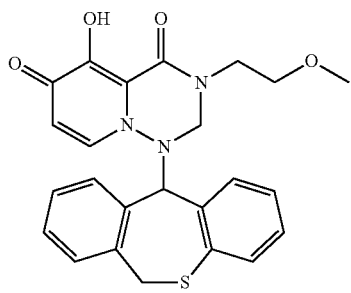

MS: m/z=450 [M+H]⁺.

Example 300

[Chemical formula 378]

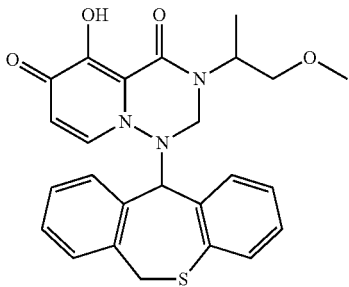

MS: m/z=464 [M+H]⁺.

Example 301

[Chemical formula 379]

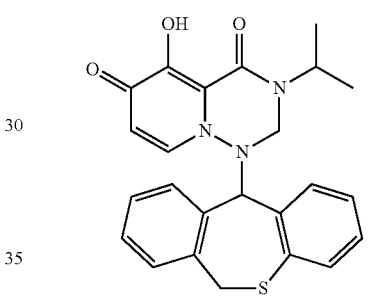

¹H-NMR (DMSO-d₆) δ: 1.00 (3H, d, J=6.9 Hz), 1.06 (3H, d, J=6.9 Hz), 3.88 (1H, d, J=13.4 Hz), 4.32 (1H, d, J=13.3 Hz), 4.67 (1H, m), 4.97 (1H, d, J=13.4 Hz), 5.43 (1H, s), 5.59 (2H, m), 6.84-7.45 (9H, m), 11.90 (1H, brs).
MS: m/z=434 [M+H]⁺.

Example 302

[Chemical formula 380]

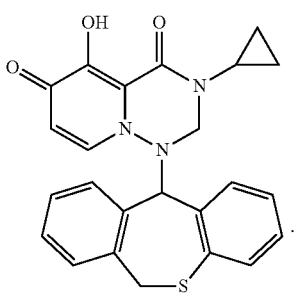

¹H-NMR (DMSO-d₆) δ: 0.11 (1H, m), 0.54-0.92 (3H, m), 2.71 (1H, m), 3.85 (1H, d, J=13.7 Hz), 4.06 (1H, d, J=13.1 Hz), 5.06 (1H, d, J=13.1 Hz), 5.35 (1H, s), 5.57 (2H, m), 7.15 (9H, m), 11.66 (1H, brs).
MS: m/z=432 [M+H]⁺.

Example 303

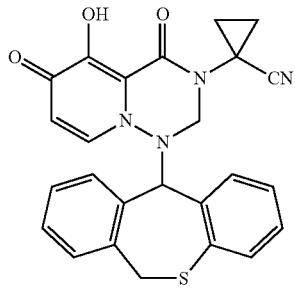

[Chemical formula 381]

¹HNMR (CDCl₃) δ: 1.14 (1H, m), 1.54 (2H, m), 1.67 (1H, m), 3.60 (1H, d, J=13.5 Hz), 4.39 (1H, d, J=12.6 Hz), 5.02 (1H, s), 5.07 (1H, d, J=12.6 Hz), 5.60 (1H, d. J=13.5 Hz), 5.77 (1H, d, J=7.7 Hz), 6.69 (1H, d, J=7.7 Hz), 7.07-7.13 (3H, m), 7.25-7.44 (4H, m).
MS: m/z=457.10 [M+H]⁺.

Example 304

[Chemical formula 382]

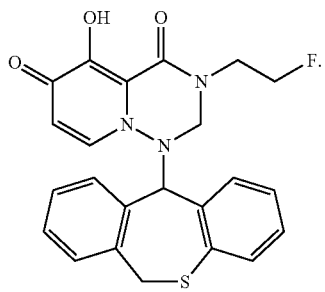

¹H-NMR (DMSO-d₆) δ: 3.33-3.42 (1H, m), 3.84 (1H, d, J=13.1 Hz), 3.90-4.10 (1H, m), 4.24 (1H, d, J=13.4 Hz), 4.35-4.66 (2H, m), 5.13 (1H, d, J=13.4 Hz), 5.43 (1H, s), 5.54-5.64 (2H, m), 6.80-6.95 (2H, m), 7.04-7.50 (8H, m).
MS: m/z=438 [M+H]⁺.

Example 305

[Chemical formula 383]

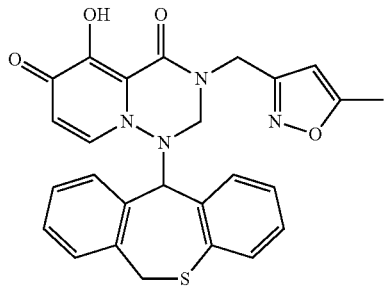

MS: m/z=487 [M+H]⁺.

Example 306

[Chemical formula 384]

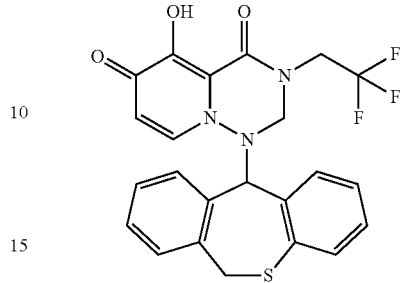

¹H-NMR (DMSO-d₆) δ: 3.69-3.82 (1H, m), 3.89 (1H, d, J=13.6 Hz), 4.40 (1H, d, J=12.9 Hz), 4.60-4.77 (1H, m), 5.27 (1H, d, J=13.3 Hz), 5.43 (1H, s), 5.60 (1H, d, J=13.6 Hz), 5.70 (1H, d, J=7.7 Hz), 6.84-6.95 (1H, m), 7.08-7.55 (9H, m).
MS: m/z=474 [M+H]⁺.

Example 307

[Chemical formula 385]

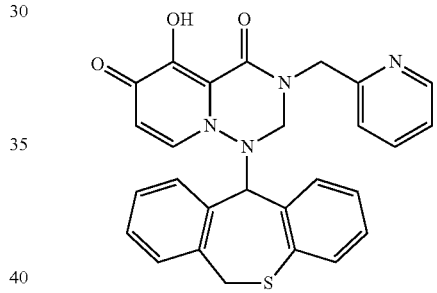

¹H-NMR (DMSO-d₆) δ: 3.81 (1H, d, J=13.5 Hz), 4.29 (1H, d, J=13.5 Hz), 4.33 (1H, d, J=16.2 Hz), 4.96 (1H, d, J=16.2 Hz), 5.23 (1H, d, J=13.5 Hz), 5.49 (1H, s), 5.59 (1H, d, J=13.2 Hz), 5.64 (1H, d, J=7.7 Hz), 6.82-6.97 (2H, m), 7.05-7.41 (10H, m), 7.80 (1H, td, J=7.6, 1.7 Hz), 8.47 (1H, d, J=4.9 Hz).
MS: m/z=483 [M+H]⁺.

Example 308

[Chemical formula 386]

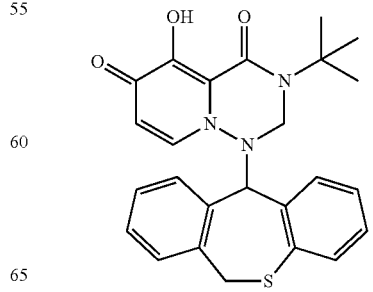

¹H-NMR (DMSO-d₆) δ: 1.28 (9H, s), 3.86 (1H, d, J=13.6 Hz), 4.42 (1H, d, J=13.3 Hz), 4.99 (1H, d, J=13.4 Hz), 5.32 (1H, s), 5.53 (1H, d, J=13.3 Hz), 5.60 (1H, d, J=7.6 Hz), 6.81-7.63 (10H, m).
MS: m/z=448 [M+H]⁺.

Example 309

[Chemical formula 387]

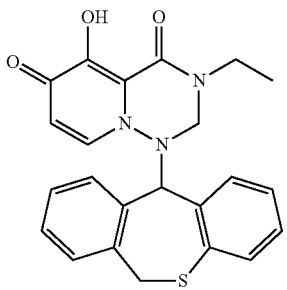

¹H-NMR (DMSO-d₆) δ: 1.03 (3H, t, J=7.4 Hz), 3.12-3.26 (1H, m), 3.43-3.58 (1H, m), 3.85 (1H, d, J=13.6 Hz), 4.21 (1H, d, J=13.4 Hz), 5.07 (1H, d, J=13.4 Hz), 5.40 (1H, s), 5.57 (1H, d, J=13.1 Hz), 5.59 (1H, d, J=7.3 Hz), 6.80-6.88 (1H, m), 6.91 (1H, d, J=7.9 Hz), 7.03-7.55 (8H, m).
MS: m/z=420 [M+H]⁺.

Example 310

[Chemical formula 388]

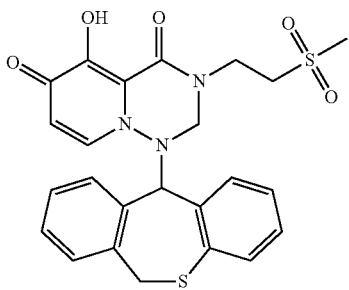

MS: m/z=498 [M+H]⁺.

Example 311

[Chemical formula 389]

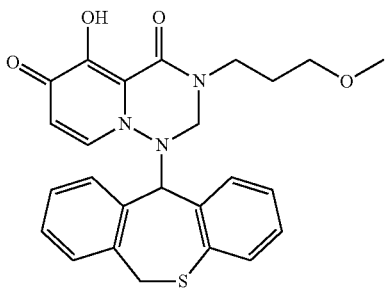

¹H-NMR (CDCl₃) δ: 1.73-1.85 (2H, m), 2.96-3.07 (1H, m), 3.27 (3H, s), 3.42 (2H, t, J=5.6 Hz), 3.56 (1H, d, J=13.5 Hz), 3.93-4.04 (1H, m), 4.25 (1H, d, J=13.2 Hz), 4.95 (1H, d, J=12.9 Hz), 5.13 (1H, s), 5.65 (1H, d, J=13.2 Hz), 5.82 (1H, d, J=7.7 Hz), 6.69 (1H, d, J=7.7 Hz), 6.78-6.86 (1H, m), 7.03-7.15 (3H, m), 7.17-7.47 (5H, m).
MS: m/z=464 [M+H]⁺.

Example 312

[Chemical formula 390]

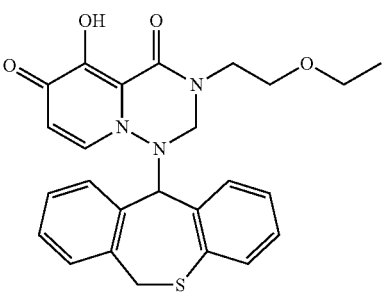

¹H-NMR (CDCl₃) δ: 1.10 (3H, t, J=6.9 Hz), 2.79-2.91 (1H, m), 3.41 (2H, q, J=7.1 Hz), 3.46-3.69 (3H, m), 4.30 (1H, d, J=13.5 Hz), 5.01 (1H, d, J=13.5 Hz), 5.12 (1H, s), 5.65 (1H, d, J=13.5 Hz), 5.83 (1H, d, J=7.7 Hz), 6.68 (1H, d, J=7.7 Hz), 6.77-6.86 (1H, m), 7.03-7.12 (3H, m), 7.16-7.46 (5H, m).
MS: m/z=464 [M+H]⁺.

Example 313

[Chemical formula 391]

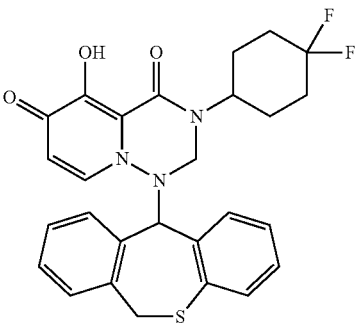

¹H-NMR (CDCl₃) δ: 1.30-1.47 (1H, m), 1.49-1.67 (1H, m), 1.73-2.02 (4H, m), 2.09-2.23 (2H, m), 3.60 (1H, d, J=13.5 Hz), 4.39 (1H, d, J=12.9 Hz), 4.45-4.64 (1H, m), 4.93 (1H, d, J=12.6 Hz), 5.10 (1H, s), 5.65 (1H, d, J=13.5 Hz), 5.87 (1H, d, J=7.4 Hz), 6.67 (1H, d, J=8.0 Hz), 6.76-6.85 (1H, m), 7.08 (2H, d, J=3.8 Hz), 7.16 (2H, d, J=7.7 Hz), 7.23-7.31 (1H, m), 7.34-7.48 (2H, m).
MS: m/z=510 [M+H]⁺.

Example 314

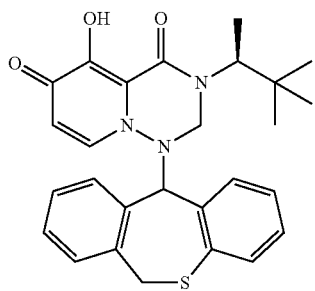
[Chemical formula 392]

MS: m/z=476 [M+H]+.

Example 315

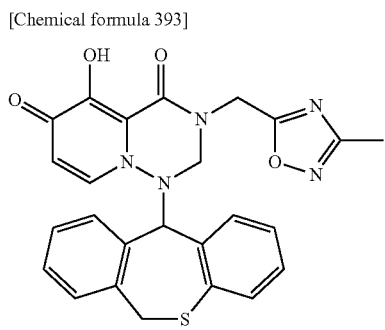
[Chemical formula 393]

MS: m/z=488 [M+H]+.

Example 316

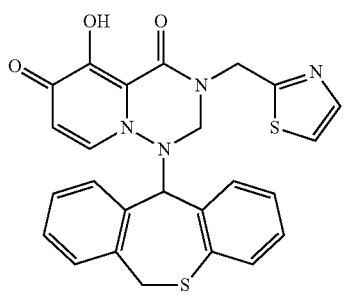
[Chemical formula 394]

1H-NMR (DMSO-d6) δ: 3.83 (1H, d, J=13.4 Hz), 4.34 (1H, d, J=13.1 Hz), 4.67 (1H, d, J=15.9 Hz), 5.05 (1H, d, J=15.9 Hz), 5.20 (1H, d, J=13.4 Hz), 5.33 (1H, s), 5.60 (1H, d, J=13.8 Hz), 5.64 (1H, d, J=7.8 Hz), 6.87 (3H, m), 7.05-7.19 (4H, m), 7.35-7.44 (2H, m), 7.74 (1H, d, 3.3 Hz), 7.77 (1H, d, 3.3 Hz).

Example 317

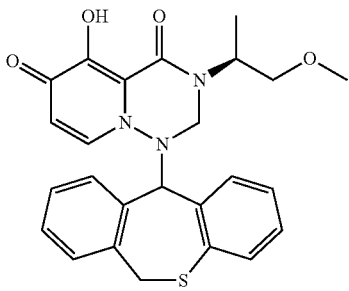
[Chemical formula 395]

MS: m/z=464 [M+H]+.

Example 318

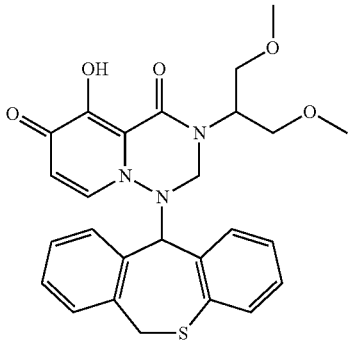
[Chemical formula 396]

MS: m/z=494 [M+H]+.

Example 319

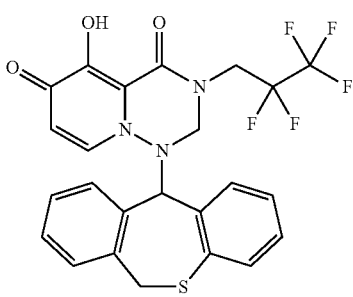
[Chemical formula 397]

1H-NMR (CDCl3) δ: 3.18-3.35 (1H, m), 3.60 (1H, d, J=13.7 Hz), 4.37 (1H, d, J=13.2 Hz), 4.75-4.95 (1H, m), 5.07-5.15 (2H, m), 5.60 (1H, d, J=13.7 Hz), 5.85 (1H, d, J=7.7 Hz), 6.68 (1H, d, J=7.7 Hz), 6.79-6.88 (1H, m), 7.09-7.14 (3H, m), 7.16 (1H, d, J=7.7 Hz), 7.29-7.36 (1H, m), 7.36-7.41 (1H, m), 7.42-7.50 (1H, m).
MS: m/z=524 [M+H]+.

Example 320

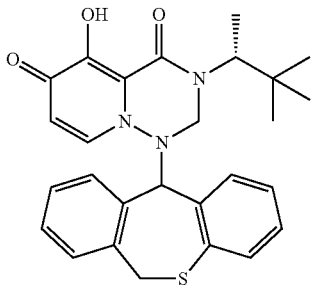

[Chemical formula 398]

¹H-NMR (CDCl₃) δ: 0.89 (9H, s), 0.97 (3H, d, J=7.1 Hz), 3.61 (1H, d, J=13.2 Hz), 4.43 (1H, d, J=13.2 Hz), 4.84-4.92 (2H, m), 5.11 (1H, s), 5.70 (1H, d, J=13.2 Hz), 5.83 (1H, d, J=7.7 Hz), 6.72 (1H, d, J=7.4 Hz), 6.79-6.85 (1H, m), 7.03-7.09 (2H, m), 7.16-7.24 (3H, m), 7.29-7.44 (2H, m).
MS: m/z=476 [M+H]⁺.

Example 321

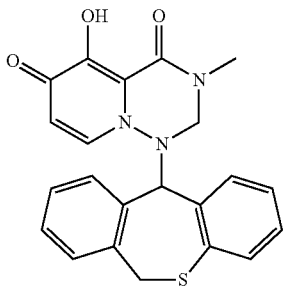

[Chemical formula 399]

¹H-NMR (CDCl₃) δ: 2.87 (0.75H, s), 3.01 (2.25H, s), 3.55 (1.5H, d, J=10.2 Hz), 3.62 (0.5H, 13.5 Hz), 4.17 (0.5H, d, J=13.2 Hz), 4.22 (1.5 Hz, J=12.9 Hz), 4.97 (1H, d, J=12.9 Hz), 5.02 (0.25H, s), 5.11 (0.75H, s), 5.63 (0.75H, d, J=13.5 Hz), 5.77-5.83 (1.25H, m), 6.64-6.68 (1H, m), 6.76-6.85 (1H, m), 7.01 (1H, d, J=7.5 Hz), 7.05-7.13 (2H, m), 7.17-7.45 (3H, m).

Example 322

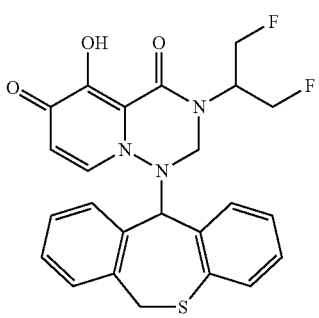

[Chemical formula 400]

¹H-NMR (CDCl₃) δ: 3.63 (1H, d, J=13.4 Hz), 4.51-4.59 (2H, m), 4.68-4.98 (4H, m), 5.13 (1H, d, J=12.9 Hz), 5.28 (1H, s), 5.71 (1H, d, J=13.3 Hz), 5.85 (1H, d, J=7.7 Hz), 6.77 (1H, d, J=7.4 Hz), 6.82-6.89 (1H, m), 7.12 (2H, d, J=3.5 Hz), 7.24 (1H, d, J=7.6 Hz), 7.33 (2H, d, J=4.4 Hz), 7.39 (1H, d, J=7.1 Hz), 7.42-7.50 (1H, m).
MS: m/z=470 [M+H]⁺.

Example 323

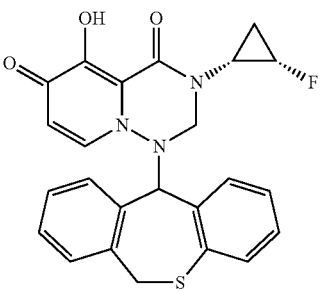 [SMILES: O=C1c2c(O)c(=O)ccn2N(C2c3ccccc3CSc3ccccc32)CN1[C@@H]1C[C@@H]1F]

MS: m/z=450 [M+H]⁺.

Example 324

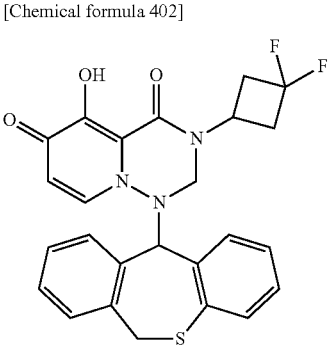

[Chemical formula 402]

MS: m/z=482 [M+H]⁺.

Example 325

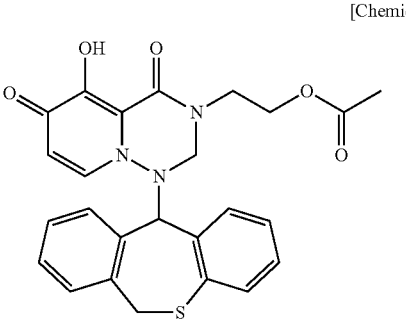

[Chemical formula 403]

¹H-NMR (DMSO-d₆) δ: 1.93 (3H, s), 3.13 (1H, m), 3.86 (1H, d, J=13.6 Hz), 4.06 (3H, m), 4.26 (1H, d, J=13.3 Hz), 5.14 (1H, d, J=13.6 Hz), 5.44 (1H, s), 5.60 (2H, m), 6.82-7.49 (10H, m).
MS: m/z=478 [M+H]⁺.

Example 326

[Chemical formula 404]

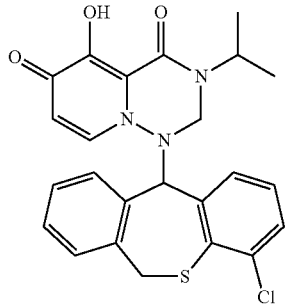

¹H-NMR (CDCl₃) δ: 1.07 (3H, d, J=6.6 Hz), 1.10 (3H, d, J=6.9 Hz), 3.70 (1H, d, J=13.5 Hz), 4.37 (1H, d, J=12.9 Hz), 4.75-4.85 (2H, m), 5.18 (1H, s), 5.76 (1H, d, J=13.2 Hz), 5.82 (1H, d, J=7.8 Hz), 6.67 (1H, dd, J=1.2 Hz, 7.8 Hz), 6.77 (1H, t, J=7.8 Hz), 7.07 (1H, d, J=7.5 Hz), 7.18-7.30 (3H, m), 7.35-7.46 (2H, m).

Example 327

[Chemical formula 405]

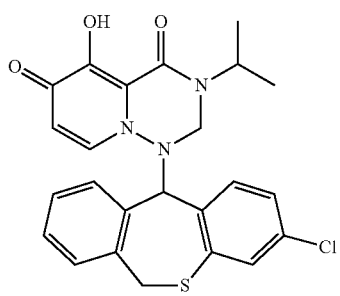

¹H-NMR (CDCl₃) δ: 1.06 (3H, d, J=6.9 Hz), 1.15 (3H, d, J=7.2 Hz), 3.60 (H, d, J=13.5 Hz), 4.36 (1H, d, J=12.9 Hz), 4.75-4.83 (2H, m), 5.10 (1H, s), 5.67 (1H, d, J=13.2 Hz), 5.86 (1H, d, J=7.5 Hz), 6.65 (1H, d, J=8, 1 Hz), 6.78 (1H, dd, J=1.8 Hz, 8.1 Hz), 7.08-7.18 (2H, m), 7.13 (1H, d, J=8.1 Hz), 7.24-7.30 (1H, m), 7.33-7.36 (1H, m), 7.39-7.45 (1H, m).

Example 328

[Chemical formula 406]

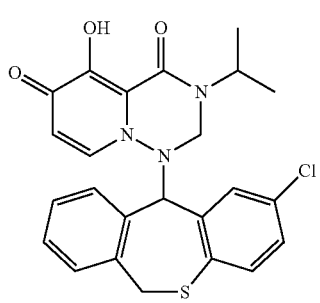

¹H-NMR (CDCl₃) δ: 0.98 (0.4H, d, J=7.2 Hz), 1.07 (2.6H, d, J=6.6 Hz), 1.15 (2.6H, d, J=6.9 Hz), 1.27 (0.4H, d, J=0.6 Hz), 3.62 (0.9H, d, J=13.2 Hz), 3.73 (0.1H, d, J=13.8 Hz), 4.36 (1H, d, J=12.9 Hz), 4.77-4.88 (1H, m), 4.83 (1H, d, J=12.9 Hz), 5.07 (1H, s), 5.62 (1H, d, J=13.2 Hz), 5.77 (0.1H, d, J=7.5 Hz), 5.85 (0.9H, d, J=7.8 Hz), 6.69-6.83 (1H, m), 6.98-7.07 (2H, m), 7.18 (2H, d, J=7.8 Hz), 7.25-7.35 (2H, m), 7.40-7.45 (1H, m).

Example 329

[Chemical formula 407]

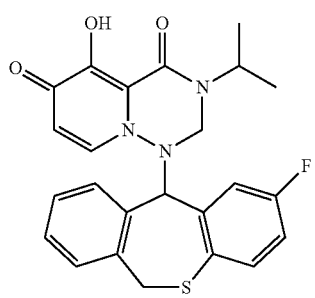

¹H-NMR (CDCl₃) δ: 1.07 (3H, d, J=6.6 Hz), 1.15 (3H, d, J=6.9 Hz), 3.63 (1H, d, J=13.2 Hz), 4.37 (1H, d, J=12.9 Hz), 4.77-4.8 (1H, m), 4.82 (1H, d, J=12.6 Hz), 5.06 (1H, s), 5.60 (1H, d, J=12.9 Hz), 5.85 (1H, d, J=7.8 Hz), 6.53 (1H, dd, J=3.0 Hz, 9.0 Hz), 6.80-6.86 (1H, m), 7.03 (1H, dd, J=4.2 Hz, 9.0 Hz), 7.16-7.30 (3H, m), 7.35 (1H, d, J=6.3 Hz), 7.40-7.45 (1H, m).

Example 330

[Chemical formula 408]

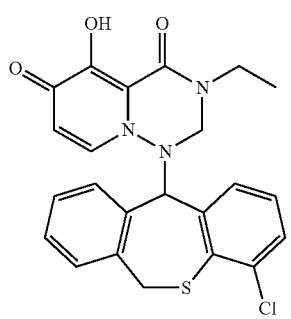

¹H-NMR (DMSO-d₆) δ: 1.02 (3H, t, J=7.2 Hz), 3.07-3.22 (1H, m), 3.44-3.59 (1H, m), 4.00 (1H, d, J=13.4 Hz), 4.21 (1H, d, J=13.4 Hz), 5.06 (1H, d, J=13.3 Hz), 5.47-5.76 (3H, m), 6.84-6.92 (1H, m), 6.92-6.99 (1H, m), 7.04 (1H, d, J=7.6 Hz), 7.10-7.52 (6H, m).
MS: m/z=454 [M+H]⁺.

339

Example 331

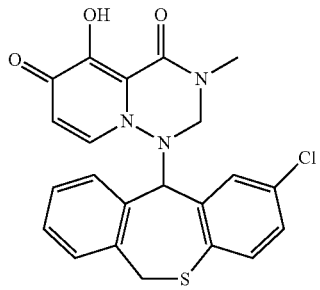

[Chemical formula 409]

$^1$H-NMR (CDCl$_3$) δ: 2.96 (0.79H, s), 3.00 (2.2H, s), 3.59 (0.75H, d, J=13.2 Hz), 3.62 (0.25H, d, J=13.8 Hz), 4.15 (0.25H, d, J=13.2 Hz), 4.21 (0.75H, d, J=12.9 Hz), 4.95-5.01 (2H, m), 5.07 (1H, s), 5.56 (1H, d, J=13.5 Hz), 5.75-5.79 (1H, m), 5.88 (1H, d, J=7.8 Hz), 6.63 (0.36H, d, J=7.8 Hz), 6.73 (1H, d, J=1.8 Hz), 6.83 (0.39H, d, J=7.2 Hz), 7.01-7.46 (7.25H, m).

Example 332

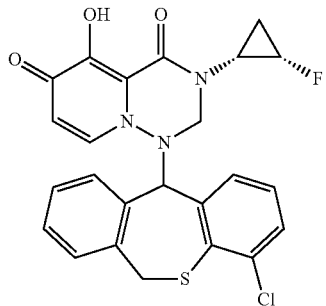

[Chemical formula 410]

MS: m/z=484 [M+H]$^+$.

Example 333

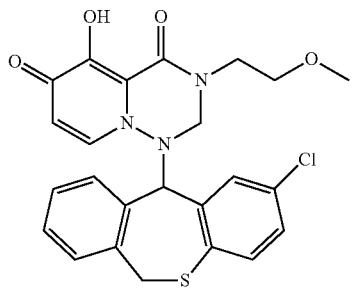

[Chemical formula 411]

MS: m/z=484 [M+H]$^+$.

340

Example 334

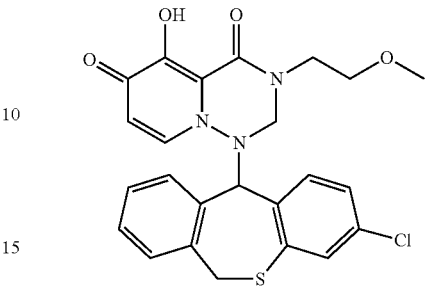

[Chemical formula 412]

$^1$H-NMR (DMSO-d$_6$) δ: 3.01-3.10 (1H, m), 3.16 (3H, s), 3.40 (2H, m), 3.89 (2H, d, J=13.4 Hz), 4.19 (1H, d, J=13.4 Hz), 5.06 (1H, d, J=13.6 Hz), 5.49 (1H, s), 5.58 (1H, d, J=13.4 Hz), 5.70 (1H, d, J=7.8 Hz), 6.89-7.48 (8H, m), 11.36 (1H, s).

Example 335

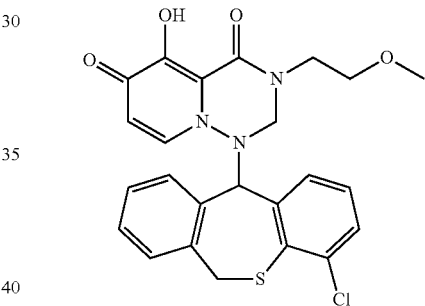

[Chemical formula 413]

$^1$H-NMR (DMSO-d$_6$) δ: 3.00-3.09 (1H, m), 3.15 (3H, s), 3.39 (2H, m), 3.94 (1H, m), 4.00 (1H, d, J=13.2 Hz), 4.20 (1H, d, J=13.4 Hz), 5.06 (1H, d, J=13.4 Hz), 5.54 (1H, s), 5.65 (2H, m), 6.86-7.50 (8H, m), 11.54 (1H, brs).

Example 336

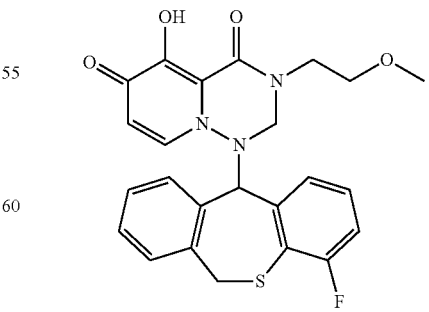

[Chemical formula 414]

$^1$H-NMR (DMSO-d$_6$) δ: 3.01-3.09 (1H, m), 3.15 (3H, s), 3.40 (2H, m), 3.87-3.94 (1H, m), 3.98 (1H, d, J=13.6 Hz), 4.20 (1H, d, J=13.6 Hz), 5.06 (1H, d, J=13.4 Hz), 5.54 (1H, s), 5.62 (1H, d, J=13.6 Hz), 5.67 (1H, d, J=7.6 Hz), 6.78-7.50 (8H, m).
MS: m/z=468 [M+H]+

Example 337

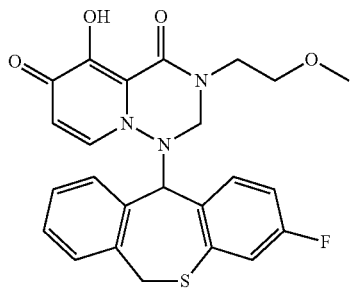

[Chemical formula 415]

¹H-NMR (DMSO-d₆) δ: 3.07 (1H, m), 3.16 (3H, s), 3.41 (2H, s), 3.89 (1H, d, J=13.7 Hz), 3.91 (1H, m), 4.19 (1H, d, J=13.6 Hz), 5.06 (1H, d, J=13.6 Hz), 5.48 (1H, s), 5.61 (1H, d, J=13.3 Hz), 5.69 (1H, d, J=7.6 Hz), 6.70-7.48 (9H, m).
MS: m/z=468 [M+H]+

Example 338

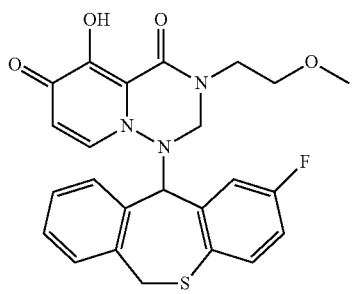

[Chemical formula 416]

MS: m/z=468 [M+H]+

Example 339

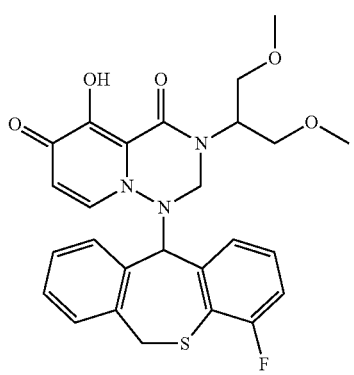

[Chemical formula 417]

¹H-NMR (DMSO-d₆) δ: 3.14 (3H, s), 3.18 (s, 3H), 3.50 (4H, m), 4.00 (1H, d, J=13.1 Hz), 4.49 (1H, d, J=13.3 Hz), 4.77 (1H, m), 4.95 (1H, d, J=13.3 Hz), 5.56 (1H, s), 5.68 (2H, m), 7.14 (8H, m).
MS: m/z=512 [M+H]+

Example 340

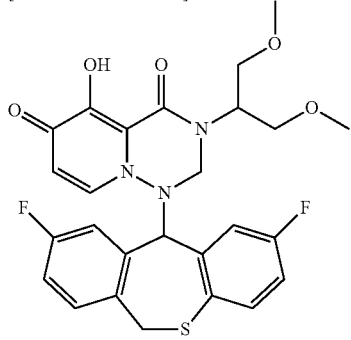

[Chemical formula 418]

¹H-NMR (DMSO-d₆) δ: 3.12 (3H, s), 3.20 (3H, s), 3.51 (4H, m), 3.96 (1H, d, J=13.3 Hz), 4.53 (1H, d, J=13.4 Hz), 4.75 (1H, m), 4.97 (1H, d, J=13.1 Hz), 5.50 (1H, d, J=13.3 Hz), 5.54 (1H, s), 5.67 (1H, d, J=7.8 Hz), 6.87-7.54 (8H, m).
MS: m/z=530 [M+H]+

Example 341

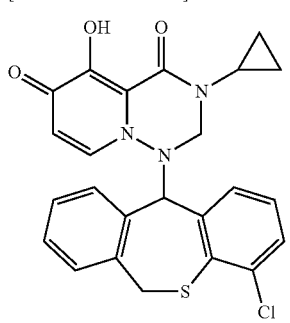

[Chemical formula 419]

MS: m/z=466 [M+H]+

Example 342

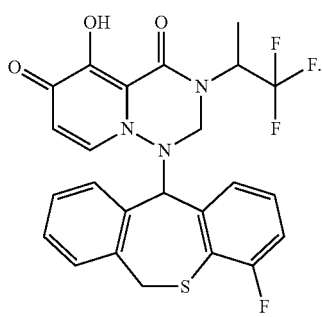

[Chemical formula 420]

MS: m/z=506 [M+H]+

Example 343

[Chemical formula 421]

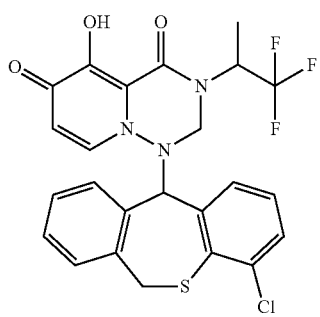

MS: m/z=522 [M+H]+

Example 344

[Chemical formula 422]

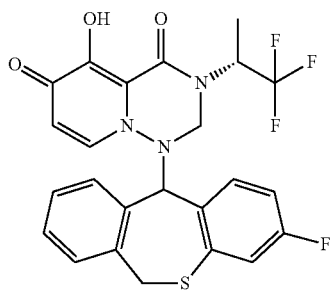

MS: m/z=506 [M+H]+

Example 345

[Chemical formula 423]

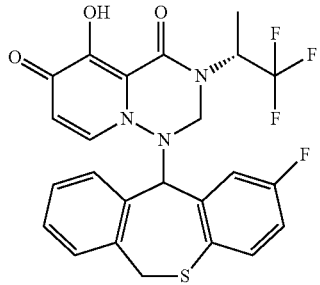

MS: m/z=506 [M+H]+

Example 346

[Chemical formula 424]

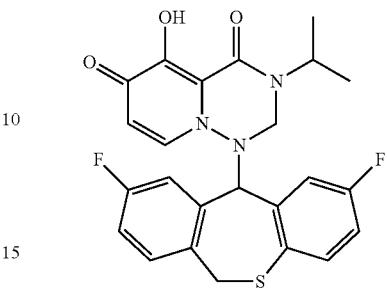

MS: m/z=470 [M+H]+

Example 347

[Chemical formula 425]

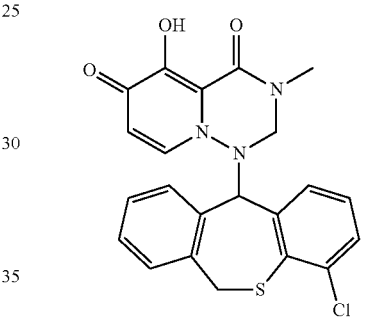

$^1$H-NMR (CDCl$_3$) δ: 2.88 (0.60H, s), 2.99 (2.40H, s), 3.67 (0.80H, d, J=13.8 Hz), 3.73 (0.20H, d, J=14.1 Hz), 4.16 (0.20H, d, J=11.1 Hz), 4.20 (0.80H, d, J=12.9 Hz), 4.97 (0.80H, d, J=12.9 Hz), 4.99 (0.20H, d, J=15 Hz), 5.10 (0.20H, s), 5.18 (0.80H, s), 5.69 (0.80H, d, J=13.5 Hz), 5.79 (0.20H, d, J=7.8 Hz), 5.85 (0.80H, d, J=7.5 Hz), 5.88 (0.20H, J=13.5 Hz), 6.62-6.66 (1H, m), 6.75-6.85 (1H, m), 6.98 (1H, d, J=7.5 Hz), 7.03-7.16 (0.5H, m), 7.19 (1H, d, J=6.9 Hz), 7.24-7.39 (2.5H, m), 7.43-7.48 (1H, m).

Example 348

[Chemical formula 426]

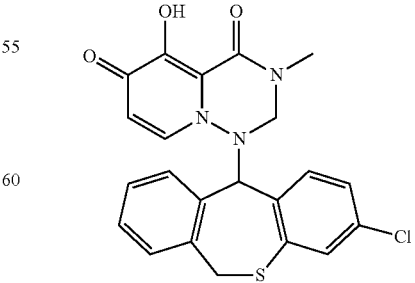

$^1$H-NMR (CDCl$_3$) δ: 2.91 (0.75H, s), 2.99 (2.25H, s), 3.57 (0.75H, d, J=13.8 Hz), 3.63 (0.25H, d, 13.8 Hz), 4.17

(0.25H, d, J=12.9 Hz), 4.10 (0.75H, d, J=12.9 Hz), 4.99 (0.75H, d, J=12.9 Hz), 5.00 (0.25H, s), 5.01 (0.25H, d, J=12.3 Hz), 5.10 (0.75H, s), 5.61 (0.75H, d, J=13.5 Hz), 5.78 (0.25H, J=7.5 Hz), 5.80 (0.25H, J=15 Hz), 5.89 (0.75H, d, J=7.5 Hz), 6.60 (0.75H, d, J=8.4 Hz), 6.64 (0.25H, d, J=7.8 Hz), 6.78 (1H, dd, J=2.1 Hz, 8.1 Hz), 7.03 (1H, d, J=7.8 Hz), 7.04-7.21 (2H, m), 7.26-7.36 (2H, m), 7.41-7.47 (1H, m).

Example 349

[Chemical formula 427]

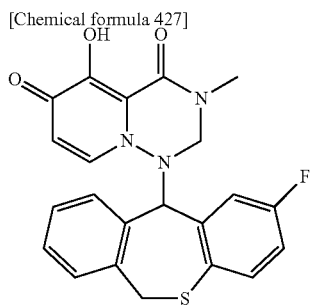

¹H-NMR (CDCl₃) δ: 2.94 (0.66H, s), 3.00 (2.34H, s), 3.60 (0.78H, d, J=13.5 Hz), 3.65 (0.22H, d, J=3.8 Hz), 4.22 (1H, d, J=12.9 Hz), 4.94-5.00 (1H, m), 5.06 (1H, s), 5.54 (0.78H, d, J=13.2 Hz), 5.71 (0.22H, d, J=13.8 Hz), 5.78 (0.22H, d, J=7.5 Hz), 5.88 (0.78H, d, J=7.8 Hz), 6.49 (1H, dd, J=3.0 Hz, 9.0 Hz), 6.66 (0.22H, d, J=7.8 Hz), 6.82-6.88 (1H, m), 6.97-7.13 (2H, m), 7.16-7.21 (1H, m), 7.29-7.36 (2H, m), 7.41-7.46 (1H, m).

Example 350

[Chemical formula 428]

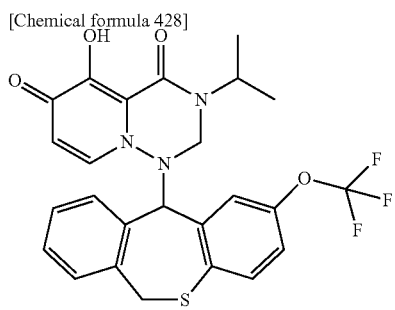

¹H-NMR (CDCl₃) δ: 1.08 (3H, d, J=6.9 Hz), 1.16 (3H, d, J=6.9 Hz), 3.63 (1H, d, J=13.2 Hz), 4.37 (1H, d, J=12.6 Hz), 4.78-4.87 (1H, m), 5.10 (1H, s), 5.67 (1H, d, J=13.2 Hz), 5.82 (1H, d, J=7.8 Hz), 6.65 (1H, d, J=2.1 Hz), 6.96-6.99 (1H, m), 7.08-7.12 (2H, m), 7.17 (1H, d, J=13.5 Hz), 7.25-7.32 (1H, m), 7.35-7.37 (1H, m), 7.42-7.47 (1H, m).

Example 351

[Chemical formula 429]

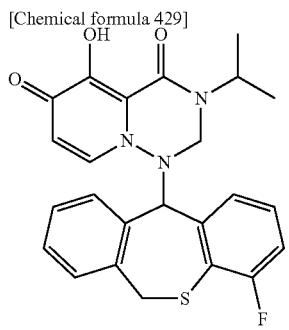

¹H-NMR (CDCl₃) δ: 1.08 (3H, d, J=6.9 Hz), 1.16 (3H, d, J=6.9 Hz), 3.68 (1H, d, J=13.2 Hz), 4.37 (1H, d, J=12.9 Hz), 4.76-4.84 (2H, m), 5.18 (1H, s), 5.72 (1H, d, J=13.5 Hz), 5.81 (1H, dd, J=0.9 Hz, 7.5 Hz), 6.56 (1H, d, J=7.2 Hz), 6.76-6.83 (1H, m), 6.90 (1H, t, J=9.0 Hz), 7.07-7.11 (1H, m), 7.19 (1H, d, J=7.5 Hz), 7.25-7.30 (1H, m), 7.35-7.45 (2H, m).

Example 352

[Chemical formula 430]

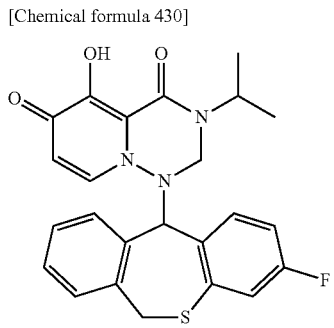

¹H-NMR (CDCl₃) δ: 1.07 (3H, d, J=6.9 Hz), 1.15 (3H, d, J=7.1 Hz), 3.59 (1H, d, J=13.2 Hz), 4.36 (1H, d, J=9.9 Hz), 4.75-4.85 (2H, m), 5.11 (1H, s), 5.70 (1H, d, J=13.2 Hz), 5.84 (1H, d, J=7.8 Hz), 6.48-6.55 (1H, m), 6.71 (1H, dd, J=5.4 Hz, 8.4 Hz), 6.80 (1H, dd, J=2.4 Hz, 9.3 Hz), 7.11 (1H, d, J=7.8 Hz), 7.18 (1H, dd, J=0.9 Hz, 7.5 Hz), 7.25-7.30 (1H, m), 7.32-7.36 (1H, m), 7.39-7.45 (1H, m).

Example 353

[Chemical formula 431]

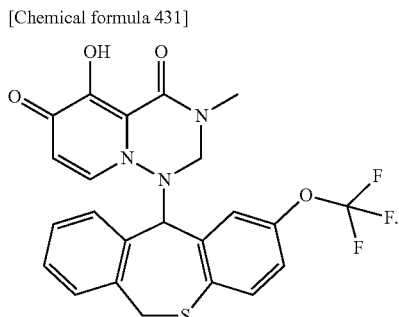

¹H-NMR (CDCl₃) δ: 2.92 (0.66H, s), 3.01 (2.34H, s), 3.59 (0.78H, d, J=13.5 Hz), 3.67 (0.22H, d, J=13.8 Hz), 4.18 (0.22H, d, J=13.2 Hz), 4.21 (0.78H, d, J=12.9 Hz), 5.03 (1H, J=12.9 Hz), 5.05 (0.22H, s), 5.10 (0.78H, s), 5.62 (0.78H, d, J=13.5 Hz), 5.76-5.82 (0.44H, m), 5.87 (0.78H, d, J=7.8 Hz), 6.62 (0.78H, brs), 6.68 (0.22H, d, J=8.1 Hz), 6.85 (0.22H, d, J=7.8 Hz), 6.98-7.04 (1.56H, m), 7.11-7.39 (3H, m), 7.44-7.49 (1H, m).

Example 354

[Chemical formula 432]

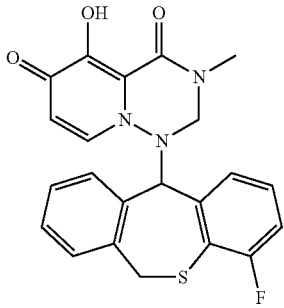

$^1$H-NMR (CDCl$_3$) δ: 2.89 (0.48H, s), 3.00 (2.52H, s), 3.64 (0.84H, d, J=13.5 Hz), 3.71 (0.16H, d, J=13.8 Hz), 4.21 (1H, d, J=12.9 Hz), 4.94 (0.84H, d, J=12.9 Hz), 4.98 (0.16H, d, J=12.9 Hz), 5.10 (0.16H, s), 5.19 (0.84H, s), 5.65 (0.84H, d, J=7.5 Hz), 5.77-5.85 (1.32H, m), 6.52 (0.84H, d, J=7.8 Hz), 6.64 (0.16H, d, J=7.8 Hz), 6.77-6.84 (1H, m), 6.89-6.95 (1H, m), 6.99 (1H, d, J=7.8 Hz), 7.07-7.25 (1H, m), 7.29-7.38 (2H, m), 7.42-7.47 (1H, m).

Example 355

[Chemical formula 433]

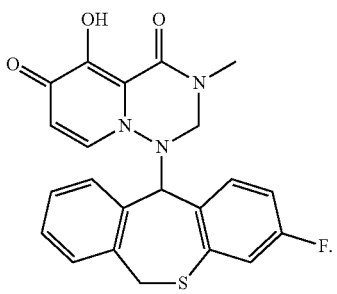

$^1$H-NMR (CDCl$_3$) δ: 2.91 (0.48H, s), 3.00 (2.52H, s), 3.56 (d, J=13.8 Hz), 3.62 (0.16H, d, J=13.8 Hz), 4.18 (0.16H, d, J=12.9 Hz), 4.20 (0.84H, d, J=12.9 Hz), 4.96 (0.84H, d, J=12.9 Hz), 4.98 (0.16H, d, J=13.8 Hz), 5.03 (0.16H, s), 5.12 (0.84H, s), 5.64 (0.84H, d, J=13.5 Hz), 5.78-5.87 (0.32H, m), 5.89 (0.84H, d, J=7.8 Hz), 6.50-6.56 (0.84H, m), 6.63-6.69 (1.16H, m), 6.84 (1H, dd, J=2.4 Hz, 9.3 Hz), 6.94-6.97 (0.16H, m), 7.02 (0.84H, d, J=7.5 Hz), 7.13-7.23 (1H, m), 7.33-7.38 (2H, m), 7.42-7.47 (1H, m).

Example 356

[Chemical formula 434]

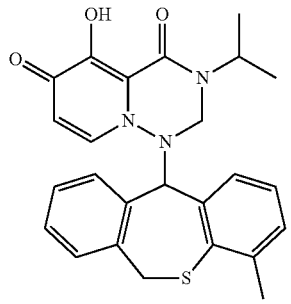

$^1$H-NMR (CDCl$_3$) δ: 1.08 (3H, d, J=6.9 Hz), 1.15 (3H, d, J=6.9 Hz), 2.24 (3H, s), 3.68 (1H, d, J=13.2 Hz), 4.38 (1H, d, J=13.2 Hz), 4.76-4.85 (1H, m), 4.80 (1H, d, J=12.6 Hz), 5.14 (1H, s), 5.72 (1H, d, J=12.9 Hz), 5.76 (1H, d, J=7.8 Hz), 6.59 (1H, d, J=7.5 Hz), 6.72 (1H, t, J=7.5 Hz), 6.99 (1H, d, J=6.9 Hz), 7.07 (1H, d, J=7.8 Hz), 7.17-7.27 (2H, m), 7.33-7.42 (2H, m).

Example 357

[Chemical formula 435]

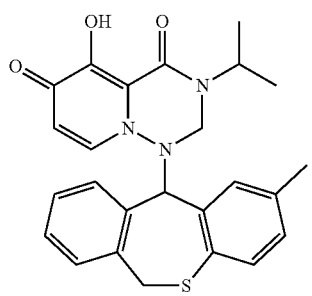

$^1$H-NMR (CDCl$_3$) δ: 1.10 (3H, d, J=6.9 Hz), 1.16 (3H, d, J=6.9 Hz), 3.58 (1H, d, J=13.2 Hz), 4.37 (1H, d, J=12.9 Hz), 4.76-4.87 (1H, m), 4.85 (1H, d, J=12.6 Hz), 5.06 (1H, s), 5.65 (1H, d, J=13.2 Hz), 5.79 (1H, d, J=7.5 Hz), 6.54 (1H, s), 6.89 (1H, dd, J=1.5 Hz, 8.4 Hz), 6.95 (1H, d, J=7.8 Hz), 7.14-7.19 (1H, m), 7.22-7.28 (1H, m), 7.33-7.43 (2H, m).

Example 358

[Chemical formula 436]

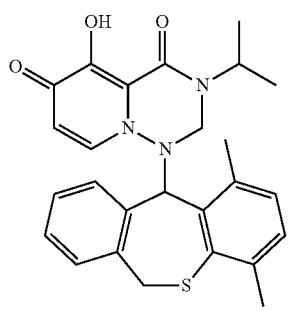

$^1$H-NMR (CDCl$_3$) δ: 1.07 (3H, d, J=6.9 Hz), 1.16 (3H, d, J=6.9 Hz), 2.20 (3H, s), 2.23 (3H, s), 3.77 (1H, d, J=12.6 Hz), 4.47 (1H, d, J=12.9 Hz), 4.78-4.86 (1H, m), 4.88 (1H, 12.9 Hz), 5.49 (1H, d, J=12.9 Hz), 5.83 (1H, d, J=11.1 Hz), 5.85 (1H, d, J=9.0 Hz), 6.64 (1H, d, J=7.8 Hz), 6.86 (1H, J=7.8 Hz), 7.16-7.40 (5H, m).

Example 359

[Chemical formula 437]

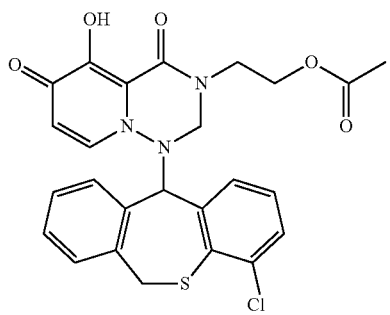

$^1$H-NMR (DMSO-d$_6$) δ: 1.94 (3H, s), 3.07 (1H, m), 3.98-4.12 (4H, m), 4.25 (2H, d, J=13.4 Hz), 5.13 (2H, d, J=13.3 Hz), 5.56 (1H, s), 5.66 (1H, d, J=13.5 Hz), 5.68 (1H, t, J=7.8 Hz), 6.87-7.51 (8H, m).

Example 360

[Chemical formula 438]

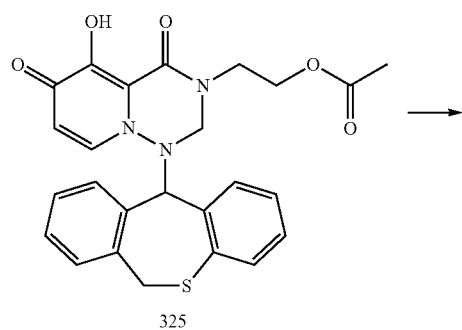

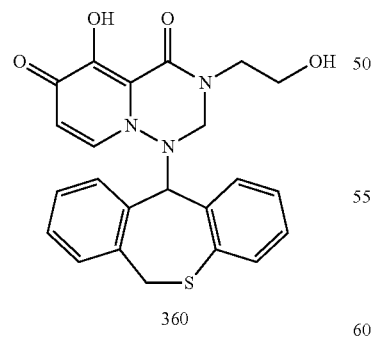

Compound 325 (46.0 mg, 0.0960 mmol) was dissolved in methanol (0.5 ml) and tetrahydrofuran (0.5 ml), a 2N aqueous sodium hydroxide solution (0.241 ml, 0.482 mmol) was added, and the mixture was stirred for 30 minutes. To the reaction solution was added dilute hydrochloric acid to make the solution acidic, and the mixture was extracted with chloroform. The organic layer was dried with sodium sulfate, and the reaction solution was concentrated under reduced pressure. To the resulting compound 360 were added n-hexane-diethyl ether, and the precipitated residue was filtered to obtain 33 mg of a white solid.

$^1$H-NMR (DMSO-d$_6$) δ: 2.85-2.94 (1H, m), 3.52 (2H, m), 3.89 (1H, d, J=13.4 Hz), 3.98 (1H, td, J=9.1, 4.5 Hz), 4.24 (1H, d, J=13.6 Hz), 4.84 (1H, brs), 5.16 (1H, d, J=13.6 Hz), 5.48 (1H, s), 5.65 (2H, m), 6.86-7.55 (9H, m).

MS: m/z=436 [M+H]$^+$.

Using ester bodies synthesized according to Examples 107, 246 and 285, and according to the method of Example 320, compounds 361 to 382 were synthesized.

Example 361

[Chemical formula 439]

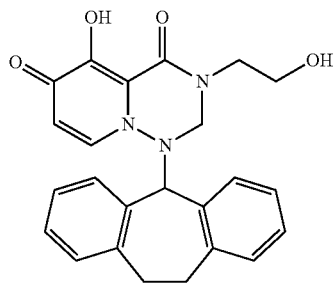

$^1$H-NMR (DMSO-d$_6$) δ: 2.82 (3H, m), 3.49 (1H, brs), 3.71 (1H, dt, J=16.7, 5.0 Hz), 4.03 (1H, t, J=7.8 Hz), 4.08-4.15 (2H, m), 4.79 (1H, brs), 5.01 (1H, d, J=13.4 Hz), 5.25 (1H, s), 5.51 (1H, d, J=7.6 Hz), 6.72-7.41 (9H, m).

Example 362

[Chemical formula 440]

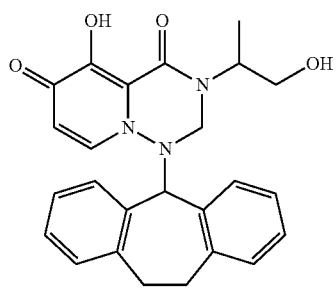

MS: m/z=432 [M+H]$^+$.

Example 363
[Chemical formula 441]
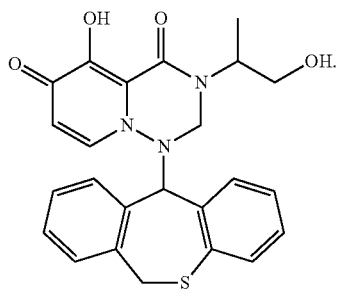
MS: m/z=450 [M+H]+.
Example 364
[Chemical formula 442]
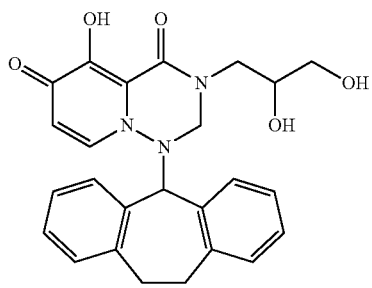
MS: m/z=448 [M+H]+.
Example 365
[Chemical formula 443]
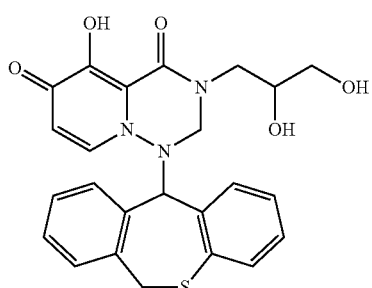
MS: m/z=466 [M+H]+.
Example 366
[Chemical formula 444]
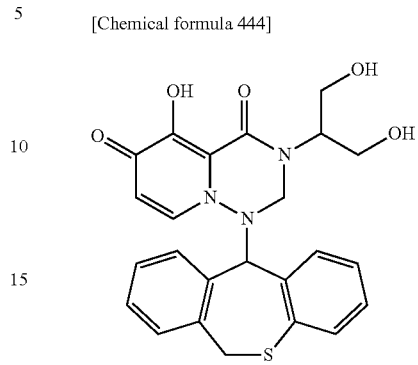
MS: m/z=466 [M+H]+.
Example 367
[Chemical formula 445]
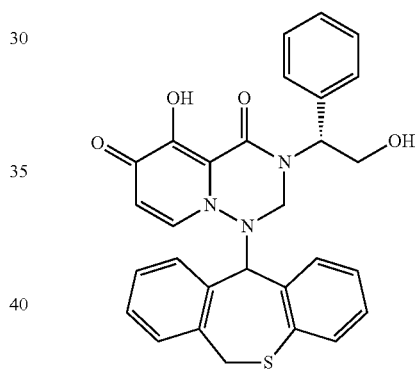
MS: m/z=512 [M+H]+.
Example 368
[Chemical formula 446]
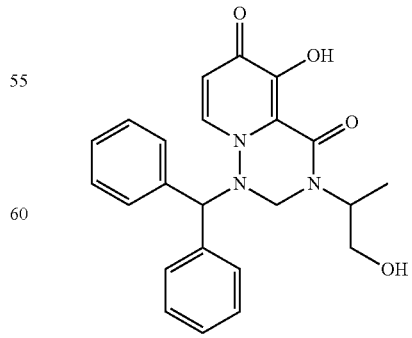
MS: m/z=406 [M+H]+.

Example 369

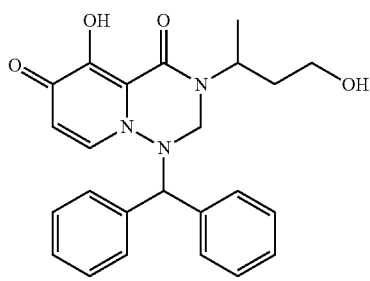

[Chemical formula 447]

MS: m/z=420 [M+H]⁺.

Example 370

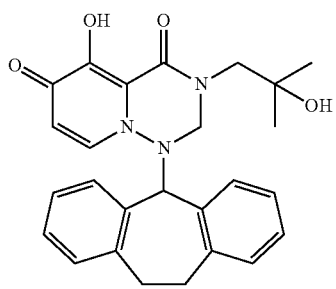

[Chemical formula 448]

¹H-NMR (CDCl₃) δ: 1.23 (3H, s), 1.24 (3H, s), 2.43 (1H, d, J=13.7 Hz), 2.81-2.91 (1H, m), 2.96-3.10 (1H, m), 3.61-3.72 (1H, m), 4.02-4.14 (1H, m), 4.15 (1H, d, J=13.7 Hz), 4.42 (1H, d, J=14.0 Hz), 4.95 (1H, s), 5.15 (1H, d, J=13.5 Hz), 5.74 (1H, d, J=7.7 Hz), 6.54-6.61 (2H, m), 6.86-6.94 (1H, m), 7.11-7.39 (8H, m).
MS: m/z=446 [M+H]⁺.

Example 371

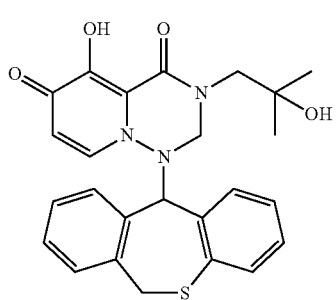

[Chemical formula 449]

¹H-NMR (CDCl₃) δ: 1.24 (3H, s), 1.26 (3H, s), 2.52 (1H, d, J=14.0 Hz), 3.56 (1H, d, J=13.7 Hz), 4.34 (1H, d, J=13.5 Hz), 4.36 (1H, d, J=13.5 Hz), 5.04 (1H, s), 5.23 (1H, d, J=13.7 Hz), 5.63 (1H, d, J=13.5 Hz), 5.84 (1H, d, J=7.7 Hz), 6.65 (1H, d, J=7.7 Hz), 6.76-6.84 (1H, m), 7.03-7.18 (5H, m), 7.27-7.47 (4H, m).
MS: m/z=464 [M+H]⁺.

Example 372

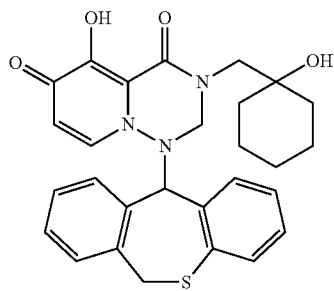

[Chemical formula 450]

¹H-NMR (CDCl₃) δ: 1.21-1.68 (10H, m), 2.47 (1H, d, J=13.7 Hz), 3.55 (1H, d, J=13.5 Hz), 4.34 (1H, d, J=13.6 Hz), 4.35 (1H, d, J=13.6 Hz), 5.03 (1H, s), 5.25 (1H, d, J=13.5 Hz), 5.63 (1H, d, J=13.5 Hz), 5.79 (1H, d, J=7.7 Hz), 6.64 (1H, d, J=7.4 Hz), 6.76-6.84 (1H, m), 7.03 (1H, d, J=7.7 Hz), 7.06-7.10 (2H, m), 7.15 (1H, d, J=7.1 Hz), 7.28-7.37 (2H, m), 7.37-7.46 (1H, m).
MS: m/z=504 [M+H]⁺.

Example 373

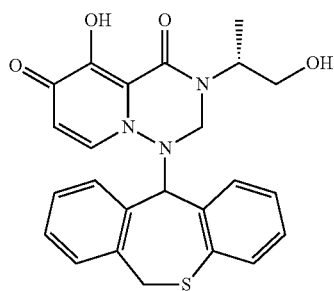

[Chemical formula 451]

MS: m/z=450 [M+H]⁺.

Example 374

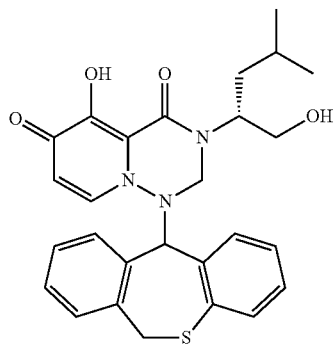

[Chemical formula 452]

MS: m/z=492 [M+H]⁺.

Example 375
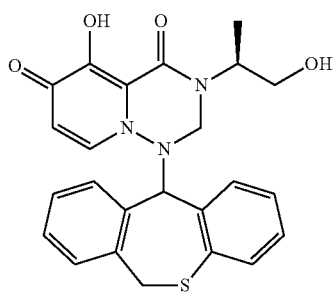
MS: m/z=445 [M+H]+.
Example 376
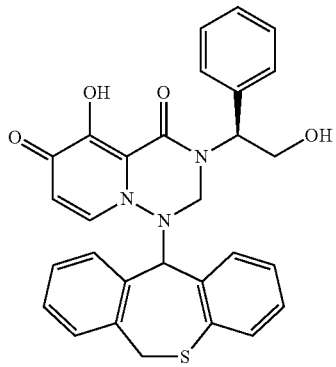
MS: m/z=512 [M+H]+.
Example 377
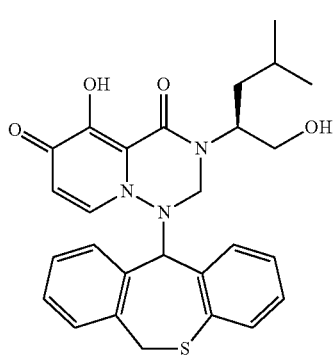
MS: m/z=492 [M+H]+.
Example 378
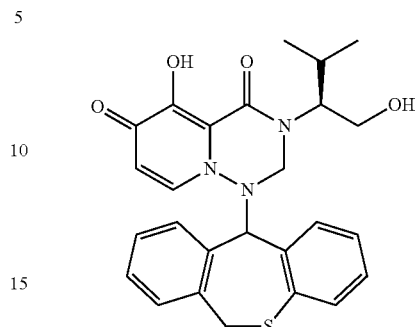
MS: m/z=478 [M+H]+
Example 379
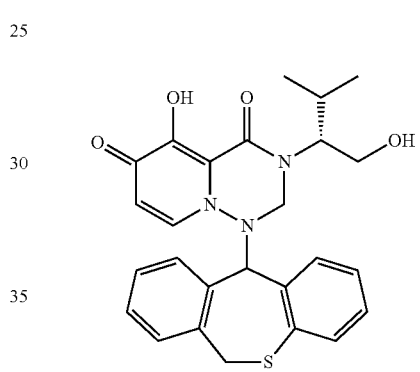
MS: m/z=478 [M+H]+
Example 380
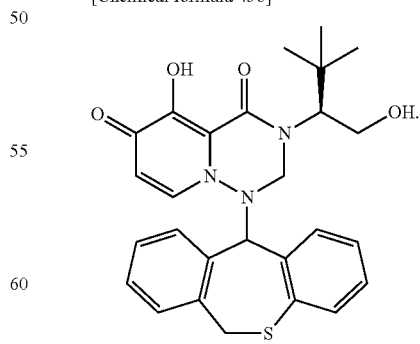
MS: m/z=492 [M+H]+

Example 381

[Chemical formula 459]

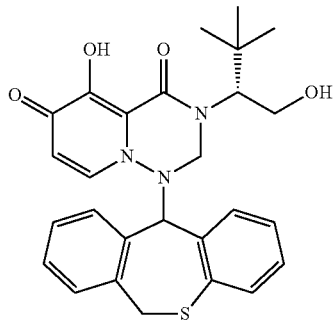

MS: m/z=492 [M+H]⁺

Example 382

[Chemical formula 460]

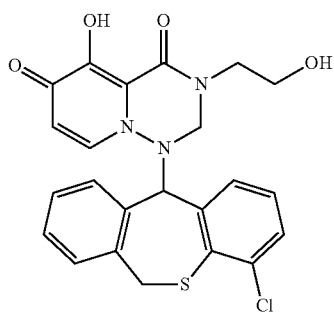

¹H-NMR (DMSO-d₆) δ: 2.76-2.85 (1H, m), 3.58 (2H, m), 3.92 (1H, m), 3.98 (1H, d, J=13.5 Hz), 4.18 (1H, d, J=13.6 Hz), 4.80 (1H, brs), 5.10 (1H, t, J=8.8 Hz), 5.50-5.68 (3H, m), 6.87-7.52 (8H, m).

Example 383

[Chemical formula 461]

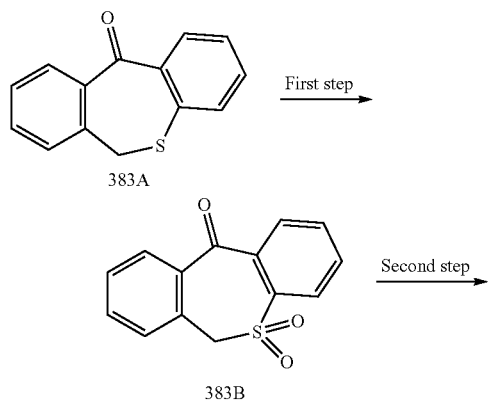

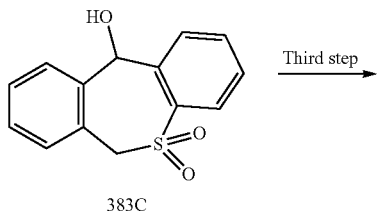

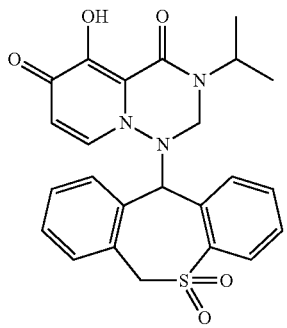

First Step

Compound 383A (1.00 g, 4.42 mmol) was dissolved in dichloromethane (50 ml), mCPBA (2.67 g, 15.5 mmol) was added at 0° C., and the mixture was stirred at room temperature for 4 hours. To the reaction solution was added an aqueous sodium sulfite solution, and the mixture was extracted with dichloromethane. The organic layer was washed with an aqueous sodium bicarbonate solution, and dried with sodium sulfate, and the solvent was distilled off. To the resulting compound were added n-hexane-dichloromethane, and the precipitated residue was filtered to obtain 1.06 g of a white solid 383B.

¹H-NMR (CDCl₃) δ: 4.81 (2H, s), 7.29-8.12 (6H, m).

Second Step

To compound 383B (1.05 g, 4.07 mmol) was added methanol (11 ml), sodium borohydride (185 mg, 4.88 mmol) was added at 0° C., and the mixture was stirred at room temperature for 30 minutes. The reaction solution was poured into water, the mixture was extracted with dichloromethane, the organic layer was dried with sodium sulfate, and the solvent was distilled off. To the resulting compound were added n-hexane-dichloromethane, and the precipitated residue was filtered to obtain 1.01 g of a white solid 383C.

¹H-NMR (CDCl₃) δ: 2.84 (1H, d, J=3.7 Hz), 4.76 (1H, d, J=14.6 Hz), 5.25 (1H, d, J=14.6 Hz), 6.23 (1H, d, J=3.7 Hz), 7.28-7.96 (8H, m).

Third Step

According to Example 107, compound 383 was synthesized by the same procedure.

MS: m/z=466 [M+H]⁺.

Using intermediates corresponding to 383A to 383C which are commercially available or known in the references, and according to the method of Example 383, compounds 384 to 389 were synthesized.

Example 384

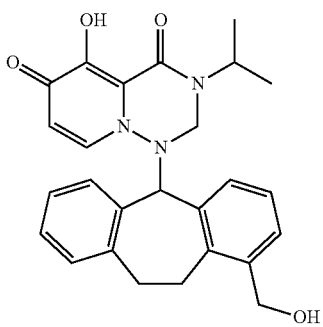

[Chemical formula 462]

$^1$H-NMR (CDCl$_3$) δ: 1.12-1.25 (6H, m), 2.87-3.26 (3H, m), 3.42-3.67 (1H, m), 4.00-4.08 (1H, m), 4.28-4.35 (1H, m), 4.56-4.83 (3H, m), 5.10-5.30 (1H, m), 5.89-6.11 (1H, m), 6.55-6.63 (0.5H, m), 6.71-6.75 (0.5H, m), 6.84-6.94 (1H, m), 7.03-7.47 (4H, m), 8.18-8.20 (0.5H, m), 8.48-8.49 (0.5H, m).

Example 385

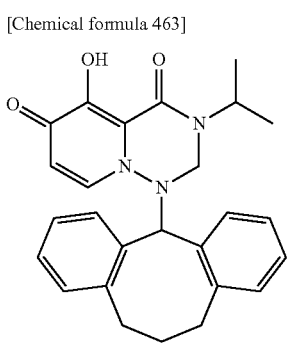

[Chemical formula 463]

$^1$H-NMR (CDCl$_3$) δ: 0.59 (3H, d, J=6.6 Hz), 1.07-1.14 (4H, m), 1.19-1.28 (1H, m), 2.22-2.32 (1H, m), 2.73-3.12 (3H, m), 4.71-4.81 (1H, m), 4.83 (1H, d, J=12.9 Hz), 4.96 (1H, d, J=12.9 Hz), 5.88 (1H, d, J=7.5 Hz), 5.89 (1H, s), 6.89 (1H, m), 7.00-7.04 (2H, m), 7.08-7.18 (2H, m), 7.22-7.27 (1H, m), 7.38 (1H, d, J=7.5 Hz), 7.58-7.61 (1H, m), 7.79 (1H, d, J=7.5 Hz).

Example 386

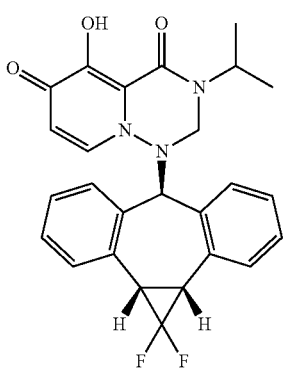

[Chemical formula 464]

$^1$H-NMR (CDCl$_3$) δ: 0.95 (3H, d, J=6.9 Hz), 1.17 (3H, d, 6.9 Hz), 3.34 (2H, d, J=12.3 Hz), 4.39 (1H, d, J=12.9 Hz), 4.56-4.65 (1H, m), 4.85 (1H, d, J=12.9 Hz), 4.93 (1H, m), 5.77 (1H, d, J=7.5 Hz), 6.77-6.81 (1H, m), 6.79 (1H, d, J=7.5 Hz), 7.00-7.05 (1H, m), 7.21-7.29 (2H, m), 7.32-7.42 (3H, m).

Example 387

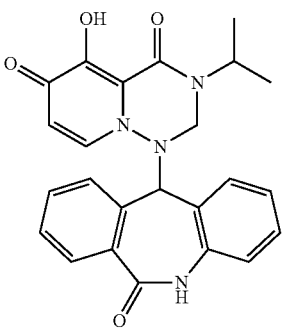

[Chemical formula 465]

$^1$H-NMR (CDCl$_3$) δ: 1.06-1.17 (6H, m), 4.02-4.17 (1H, m), 4.61-4.78 (2H, m), 5.16 (1H, d, J=5.1 Hz), 5.72 (1H, t, J=8.1 Hz), 6.54 (0.5H, d, J=7.8 Hz), 6.84 (0.5H, d, J=7.8 Hz), 6.91-7.08 (2H, m), 7.16-7.47 (4H, m), 7.56-7.59 (1H, m), 8.00 (0.5H, J=6.3 Hz), 8.09-8.12 (0.5H, m), 8.51 (0.5H, s), 8.68 (0.5H, s).

Example 388

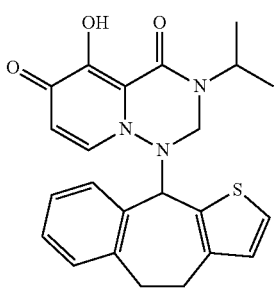

[Chemical formula 466]

$^1$H-NMR (CDCl$_3$) δ: 1.19 (3H, d, J=6.9 Hz), 1.25 (3H, d, J=6.9 Hz), 2.76-2.91 (2H, m), 3.23-3.31 (1H, m), 4.17-4.33 (2H, m), 4, 54-4.84 (2H, m), 5.18 (1H, s), 5.87 (1H, d, J=7.8 Hz), 6.70 (1H, d, J=5.1 Hz), 6.86 (1H, d, J=7.8 Hz), 7.04 (1H, d, J=5.1 Hz), 7.19-7.25 (2H, m), 7.32-7.38 (2H, m).

Example 389

[Chemical formula 467]

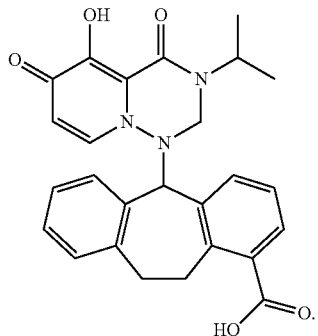

$^1$H-NMR (DMSO-$d_6$) δ: 1.04-1.20 (6H, m), 2.83-3.02 (1H, m), 3.46-3.57 (1H, m), 3.75-3.85 (1H, m), 4.13-4.26 (1H, m), 4.32-4.50 (1H, m), 4.56-4.62 (1H, m), 4.89 (1H, d, J=13.2 Hz), 5.36 (1H, s), 5.44-5.50 (1H, m), 6.73 (1H, d, J=7.8 Hz), 6.86 (1H, t, J=7.5 Hz), 6.95-6.98 (1H, m), 7.09-6.54 (5H, m).

Example 390

[Chemical formula 468]

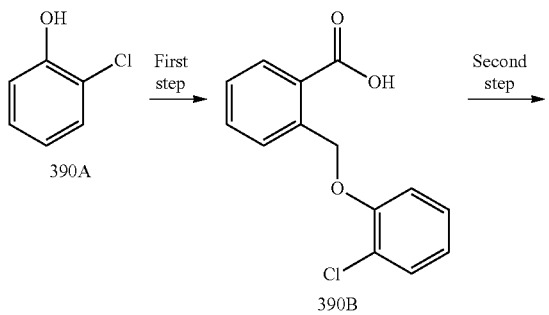

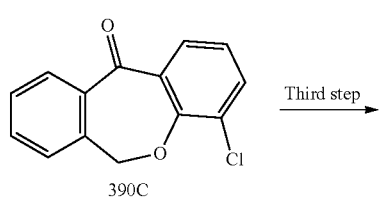

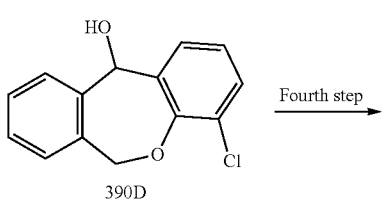

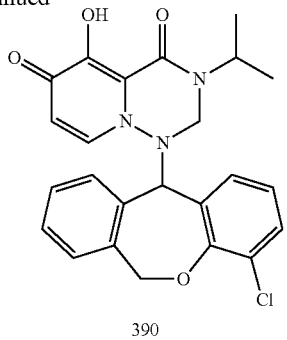

390

First Step.

Compound 390A (14.8 g, 115 mmol) was added to methanol (200 ml), sodium methoxide (28% methanol solution, 22.2 g, 115 mmol) was added at room temperature, and the mixture was stirred for 1 hour. The solvent was distilled off under reduced pressure to obtain 17.3 g of a white solid. To 5.61 g of it was added phthalide (5.00 g, 37.3 mmol), and the mixture was stirred at 200° C. for 1 hour. The reaction solution was poured into water, the mixture was made acidic with hydrochloric acid, and the generated white precipitate was filtered. This was dissolved in chloroform, the solution was dried with sodium sulfate, and the solvent was distilled off. To the resulting compound were added n-hexane-chloroform-diisopropyl ether, and the precipitated residue was filtered to obtain 2.44 g of a pale brown solid 390B.

$^1$H-NMR (CDCl$_3$) δ: 5.61 (2H, s), 6.92 (1H, td, J=7.6, 1.4 Hz), 7.01 (1H, dd, J=8.3, 1.3 Hz), 7.21 (1H, ddd, J=8.7, 7.0, 1.2 Hz), 7.32-7.54 (2H, m), 7.66 (1H, td, J=7.6, 1.4 Hz), 7.92-7.99 (1H, m), 8.17 (1H, dd, J=7.9, 1.3 Hz).

Second Step

Compound 390B (2.44 g, 9.29 mmol) was dissolved in dichloromethane (30 ml), trifluoroacetic acid anhydride (1.44 ml, 10.2 mmol) and boron trifluoride etherate (0.235 ml, 1.86 mmol) were added, and the mixture was stirred at room temperature for 3 hours. The reaction solution was poured into water, the mixture was extracted with dichloromethane, the organic layer was washed with 1N hydrochloric acid and an aqueous saturated sodium chloride solution, and the solvent was distilled off. The resulting crude product was purified by silica gel column chromatography, and eluted with n-hexane-ethyl acetate (4:1, v/v) to obtain 1.76 g of a pale yellow solid 390C.

$^1$H-NMR (CDCl$_3$) δ: 5.36 (2H, s), 7.11 (1H, t, J=8.0 Hz), 7.43-7.66 (4H, m), 7.93 (1H, d, J=6.5 Hz), 8.19 (1H, dd, J=8.1, 1.8 Hz).

Third Step

To compound 390C (1.76 g, 7.19 mmol) was added methanol (20 ml), sodium borohydride (327 mg, 8.63 mmol) was added at 0° C., and the mixture was stirred at room temperature for 30 minutes. The reaction solution was poured into water, the mixture was extracted with dichloromethane, the organic layer was dried with sodium sulfate, and the solvent was distilled off. To the resulting compound were added n-hexane-dichloromethane, and the precipitated residue was filtered to obtain 1.44 g of a white solid 390D.

$^1$H-NMR (CDCl$_3$) δ: 2.75 (1H, d, J=5.0 Hz), 5.18 (1H, d, J=13.6 Hz), 5.69 (1H, d, J=5.0 Hz), 5.89 (1H, d, J=13.6 Hz), 6.93 (1H, t, J=7.9 Hz), 7.19-7.43 (6H, m).

Fourth Step

Compound 390 was synthesized by the same procedure as that of Example 107.

MS: m/z=452 [M+H]$^+$.

Using amines which are commercially available or known in the references and intermediates corresponding to 390A to 390D which are commercially available or known in the references, and according to the method of Example 390, compounds 391 to 412 were synthesized.

Example 391

[Chemical formula 469]

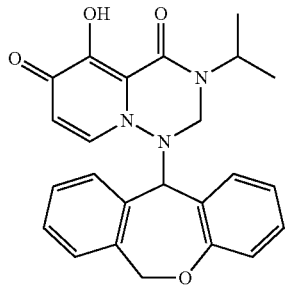

MS: m/z=418 [M+H]$^+$.

Example 392

[Chemical formula 470]

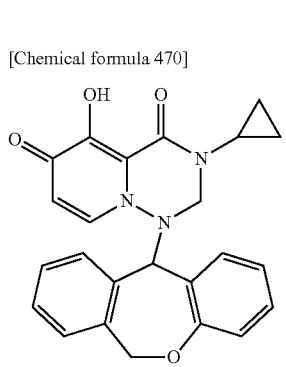 [SMILES: O=C1c2c(O)c(=O)ccn2N(C2c3ccccc3COc3ccccc32)CN1C1CC1]

MS: m/z=416 [M+H]$^+$.

Example 393

[Chemical formula 471]

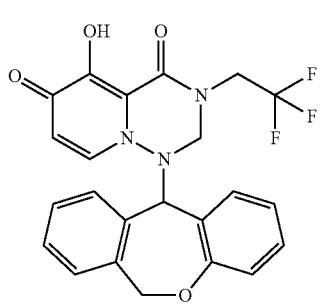

MS: m/z=458 [M+H]$^+$.

Example 394

[Chemical formula 472]

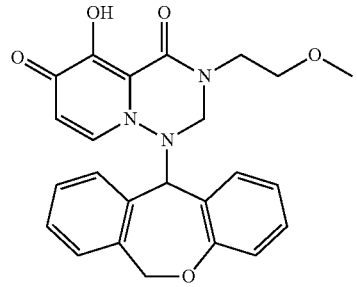

MS: m/z=434 [M+H]$^+$.

Example 395

[Chemical formula 473]

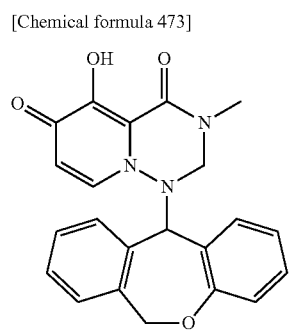 [SMILES: CN1CN(C2c3ccccc3COc3ccccc32)n2ccc(=O)c(O)c2C1=O]

MS: m/z=390 [M+H]$^+$.

Example 396

[Chemical formula 474]

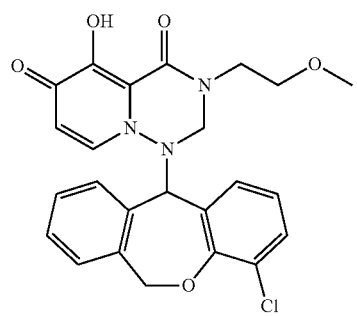

MS: m/z=468 [M+H]$^+$

Example 397
[Chemical formula 475]
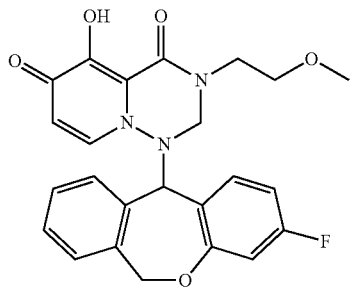
MS: m/z=452 [M+H]+
Example 398
[Chemical formula 476]
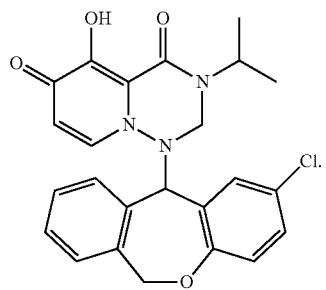
¹H-NMR (CDCl₃) δ: 1.12-1.32 (6H, m), 4.25 (0.52H, d, J=12.9 Hz), 4.41 (0.48H, d, J=13.2 Hz), 4.58-4.79 (2H, m), 4.92-5.03 (2H, m), 5.73 (0.48H, d, J=7.8 Hz), 5.89 (0.52H, d, J=7.8 Hz), 6.12 (0.48H, d, J=12 Hz), 6.46-6.58 (1.52H, m), 6.74-6.78 (1H, m), 6.98 (1H, t, J=7.5 Hz), 7.10-7.14 (1H, m), 7.20-7.50 (4H, m).
Example 399
[Chemical formula 477]
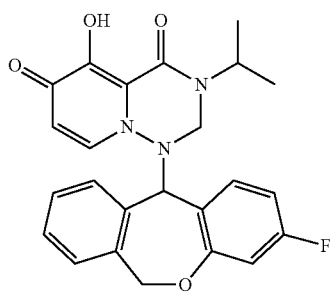
¹H-NMR (CDCl₃) δ: 1.12-1.31 (6H, m), 4.25 (0.75H, d, J=12.9 Hz), 4.43 (0.25H, d, J=12.9 Hz), 4.53-4.60 (0.50H, m), 4.67-4.78 (1.5H, m), 4.90-5.05 (2H, m), 5.70 (0.25H, d, J=7.8 Hz), 5.86 (0.75H, d, J=7.5 Hz), 6.18 (0.25H, d, J=13.5 Hz), 6.36-6.42 (0.75H, m), 6.49-6.56 (2H, m), 6.69-6.80 (1H, m), 6.94 (1H, d, J=7.8 Hz), 7.10-7.19 (0.25H, m), 7.21-7.50 (3.75H, m).
Example 400
[Chemical formula 478]
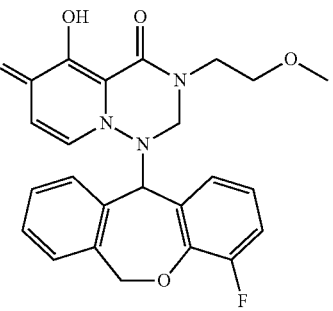
MS: m/z=452 [M+H]+
Example 401
[Chemical formula 479]
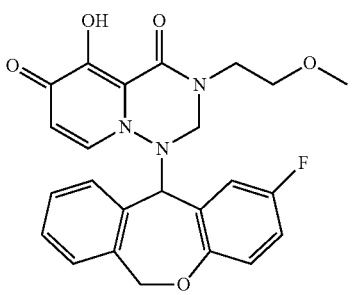
MS: m/z=452 [M+H]+
Example 402
[Chemical formula 480]
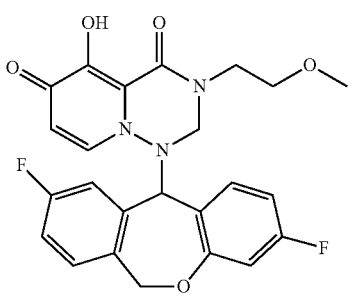
MS: m/z=470 [M+H]+

Example 403
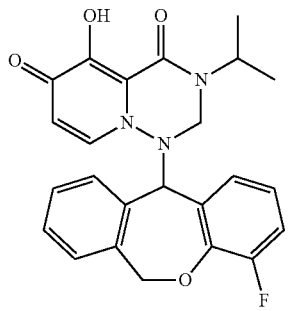
MS: m/z=436 [M+H]⁺
Example 404
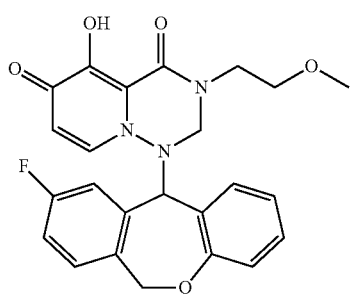
MS: m/z=452 [M+H]⁺
Example 405
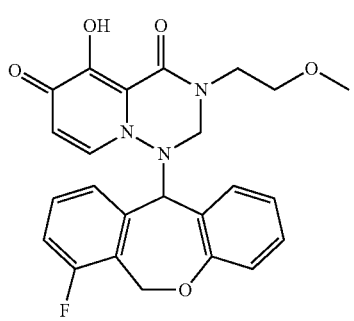
MS: m/z=452 [M+H]⁺
Example 406
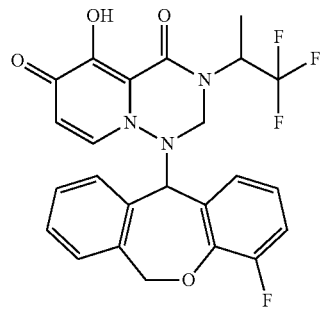
MS: m/z=490 [M+H]⁺
Example 407
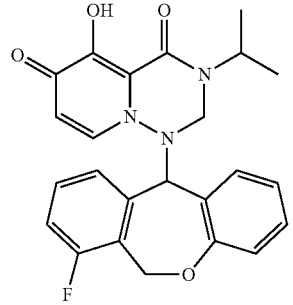
MS: m/z=436 [M+H]⁺
Example 408
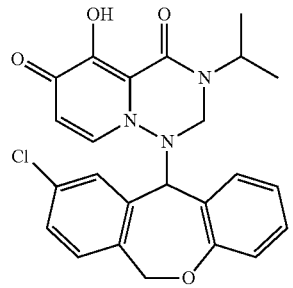
MS: m/z=452 [M+H]⁺

Example 409
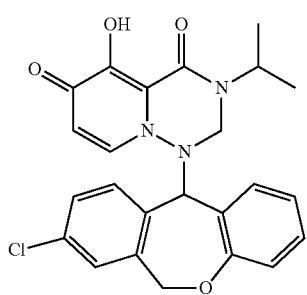
MS: m/z=452 [M+H]+
Example 410
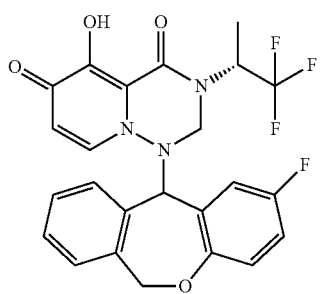
MS: m/z=490 [M+H]+
Example 411
[Chemical formula 489]
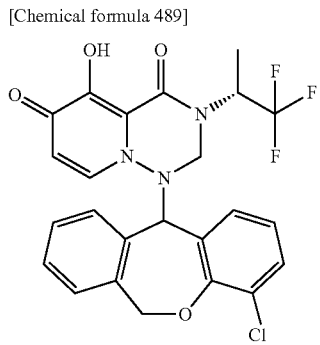 [SMILES: CC(N1CN(C2c3ccccc3COc3c(F)cccc32)n2ccc(=O)c(O)c2C1=O)C(F)(F)F]
MS: m/z=506 [M+H]+
Example 412
[Chemical formula 490]
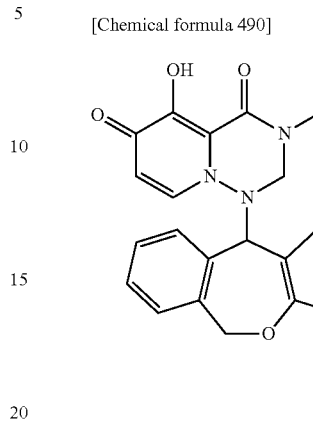
$^1$H-NMR (CDCl$_3$) δ: 1.13-1.31 (12H, m), 3.28-3.37 (0.50H, m), 3.44-3.53 (0.50H, m), 4.29-4.36 (1H, m), 4.65-4.76 (2H, m), 4.98-5.05 (2H, m), 6.37 (0.5H, d, J=12.9 Hz), 6.45 (0.5H, d, J=7.5 Hz), 6.67 (0.5H, t, J=7.8 Hz), 6.81 (0.5H, 7.8 Hz), 6.98-7.08 (2H, m), 7.14 (0.5Hm d, J=7.8 Hz), 7.22-7.45 (2.5H, m).
Example 413, Example 414
[Chemical formula 491]
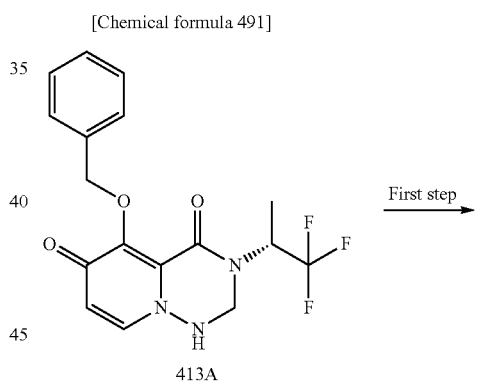
First step →
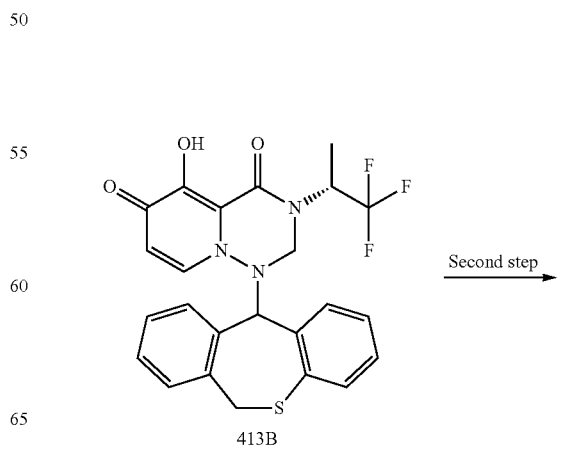
Second step →

371
-continued

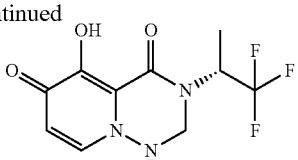

413

+

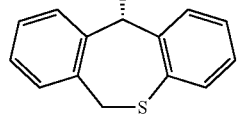

414

First Step

Compound 413A (200 mg, 0.544 mmol) obtained by the same procedure as that of Example 95, and 6,11-dihydrod-ibenzo[b,e]thiepin-11-ol (124 mg 0.554 mmol) were dissolved in acetic acid (8 ml), and concentrated sulfuric acid (2 ml) was added dropwise under water-cooling. After the mixture was stirred at room temperature for 30 minutes, water was added, and the mixture was extracted with ethyl acetate. The organic layer was dried with sodium sulfate, and the solvent was distilled off under reduced pressure to obtain a crude product of 413B.

Second Step

Compound 413B obtained in the first step was dissolved in dichloromethane (2 ml), acetic acid anhydride (0.154 ml, 1.63 mmol), triethylamine (0.226 ml, 1.63 mmol) and 4-(dimethylamino)pyridine (cat.) were added, and the mixture was stirred at room temperature for 30 minutes. The solvent was distilled off, the resulting crude product was purified by silica gel column chromatography, and eluted with chloroform-methanol (97:3, v/v), and diastereomers were resolved. They were dissolved in methanol (1 ml) and tetrahydrofuran (1 ml), respectively, a 2N aqueous sodium hydroxide solution (0.198 ml, 0.397 mmol) was added, and the mixture was stirred at room temperature for 30 minutes. The reaction solution was poured into water, and the mixture was made acidic with hydrochloric acid, and extracted with ethyl acetate. The organic layer was dried with sodium sulfate, and the solvent was distilled off under reduced pressure. To the resulting compound were added ethyl acetate-diethyl ether, and the fractionation-precipitated residue was filtered to obtain compound 413 (22 mg) and compound 414 (20 mg), respectively.

Example 413

$^1$H-NMR (DMSO-d$_6$) δ: 1.20 (3H, d, J=7.4 Hz), 3.92 (1H, d, J=13.6 Hz), 4.45 (1H, d, J=13.4 Hz), 5.12 (1H, d, J=12.8 Hz), 5.60 (4H, m), 6.87-7.60 (9H, m).

MS: m/z=488 [M+H]$^+$

372

Example 414

MS: m/z=488 [M+H]$^+$

According to Example 413, compounds 414 to 475 were synthesized using the same procedure.

Example 415

[Chemical formula 492]

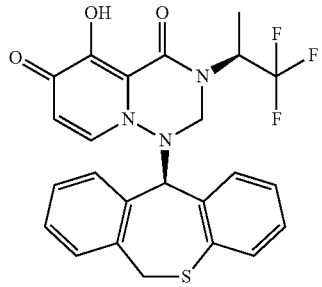

$^1$H-NMR (DMSO-d$_6$) δ: 1.16 (3H, d, J=7.3 Hz), 3.88 (1H, d, J=13.3 Hz), 4.41 (1H, d, J=13.3 Hz), 5.07 (1H, d, J=13.0 Hz), 5.42-5.52 (1H, m), 5.62 (3H, m), 6.82-7.56 (9H, m).

MS: m/z=488 [M+H]$^+$

Example 416

[Chemical formula 493]

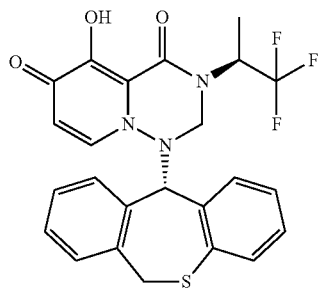

$^1$H-NMR (DMSO-d$_6$) δ: 1.35 (3H, d, J=7.3 Hz), 3.88 (1H, d, J=13.3 Hz), 4.44 (1H, d, J=12.7 Hz), 5.15 (1H, d, J=12.5 Hz), 5.16 (1H, m), 5.29 (1H, s), 5.57 (1H, d, J=13.4 Hz), 5.64 (1H, d, J=7.8 Hz), 6.81-7.45 (9H, m).

MS: m/z=488 [M+H]$^+$

Example 417

[Chemical formula 494]

¹H-NMR (CDCl₃) δ: 1.22 (3H, d, J=7.2 Hz), 4.32 (1H, d, J=13.9 Hz), 4.49 (1H, d, J=13.1 Hz), 4.90 (1H, d, J=13.3 Hz), 5.15 (1H, s), 5.47-5.65 (2H, m), 5.83 (1H, d, J=8.1 Hz), 6.69 (1H, d, J=6.5 Hz), 6.80-6.87 (1H, m), 7.07-7.24 (5H, m), 7.54 (1H, d, J=7.9 Hz).
MS: m/z=522 [M+H]⁺.

Example 418

[Chemical formula 495]

¹H-NMR (CDCl₃) δ: 1.48 (3H, d, J=7.1 Hz), 3.63 (1H, d, J=13.2 Hz), 4.49 (1H, d, J=12.6 Hz), 5.03 (1H, s), 5.28-5.45 (2H, m), 5.53 (1H, d, J=13.5 Hz), 5.73 (1H, d, J=7.7 Hz), 6.50 (1H, dd, J=8.7, 2.6 Hz), 6.79-6.86 (1H, m), 6.90 (1H, d, J=9.1 Hz), 7.02 (1H, dd, J=8.8, 5.2 Hz), 7.10 (1H, ddd, J=8.1, 2.5, 1.2 Hz), 7.25 (1H, d, J=7.7 Hz), 7.30 (1H, dd, J=8.5, 5.5 Hz).
MS: m/z=524 [M+H]⁺.

Example 419

[Chemical formula 496]

¹H-NMR (CDCl₃) δ: 1.50 (3H, d, J=7.1 Hz), 4.28 (1H, d, J=13.7 Hz), 4.50 (1H, d, J=12.4 Hz), 5.17 (1H, s), 5.26-5.44 (2H, m), 5.60-5.69 (2H, m), 6.65 (1H, d, J=7.4 Hz), 6.73-6.80 (1H, m), 7.01-7.21 (5H, m), 7.48 (1H, d, J=8.0 Hz).
MS: m/z=522 [M+H]⁺.

Example 420

[Chemical formula 497]

¹H-NMR (CDCl₃) δ: 1.49 (3H, d, J=7.4 Hz), 3.51 (1H, d, J=13.5 Hz), 4.48 (1H, d, J=12.6 Hz), 5.12 (1H, s), 5.28-5.44 (2H, m), 5.60-5.70 (2H, m), 6.65 (1H, d, J=7.4 Hz), 6.73-6.80 (1H, m), 7.00-7.06 (2H, m), 7.10 (1H, d, J=8.5 Hz), 7.14 (1H, d, J=8.0 Hz), 7.23 (1H, dd, J=8.2, 2.2 Hz), 7.31 (1H, d, J=1.9 Hz).
MS: m/z=522 [M+H]⁺.

Example 421

[Chemical formula 498]

¹H-NMR (CDCl₃) δ: 1.53 (3H, d, J=7.4 Hz), 3.59 (1H, d, J=13.4 Hz), 4.51 (1H, d, J=12.6 Hz), 5.12 (1H, s), 5.30-5.48 (2H, m), 5.62-5.70 (2H, m), 6.71 (1H, d, J=7.7 Hz), 6.80-6.83 (1H, m), 7.07-7.11 (2H, m), 7.18 (1H, d, J=7.7 Hz), 7.22 (1H, s), 7.28 (1H, d, J=8.4 Hz), 7.39 (1H, d, J=8.1 Hz).
MS: m/z=522 [M+H]⁺.

Example 422

[Chemical formula 499]

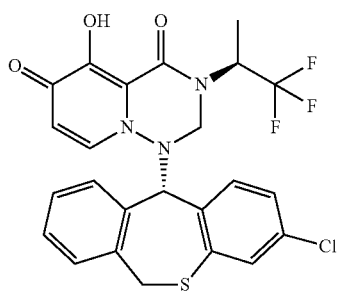

$^1$H-NMR (CDCl$_3$) δ: 1.49 (3H, d, J=7.4 Hz), 3.59 (1H, d, J=13.5 Hz), 4.48 (1H, d, J=12.4 Hz), 5.12 (1H, s), 5.29-5.39 (2H, m), 5.66 (1H, d, J=13.5 Hz), 5.73 (1H, d, J=7.7 Hz), 6.61 (1H, d, J=8.2 Hz), 6.73 (1H, dd, J=8.2, 2.2 Hz), 7.04 (1H, d, J=2.2 Hz), 7.12-7.20 (2H, m), 7.23-7.27 (1H, m), 7.31 (1H, d, J=6.3 Hz), 7.36-7.44 (1H, m).

MS: m/z=522 [M+H]$^+$.

Example 423

[Chemical formula 500]

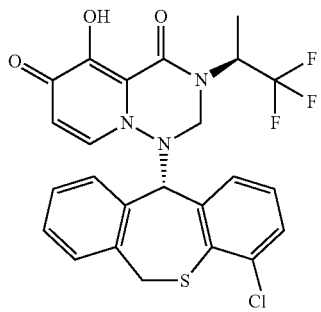

$^1$H-NMR (CDCl$_3$) δ: 1.47 (3H, d, J=7.1 Hz), 3.69 (1H, d, J=13.5 Hz), 4.49 (1H, d, J=12.6 Hz), 5.21 (1H, s), 5.27 (1H, d, J=12.6 Hz), 5.30-5.40 (1H, m), 5.70 (1H, d, J=7.7 Hz), 5.75 (1H, d, J=13.5 Hz), 6.65 (1H, dd, J=7.8, 1.5 Hz), 6.73 (1H, t, J=7.7 Hz), 7.13 (1H, d, J=7.7 Hz), 7.15-7.22 (2H, m), 7.25-7.29 (1H, m), 7.32 (1H, d, J=8.0 Hz), 7.37-7.45 (1H, m).

MS: m/z=522 [M+H]$^+$.

Example 424

[Chemical formula 501]

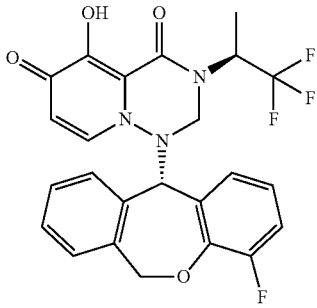

MS: m/z=490 [M+H]$^+$.

Example 425

[Chemical formula 502]

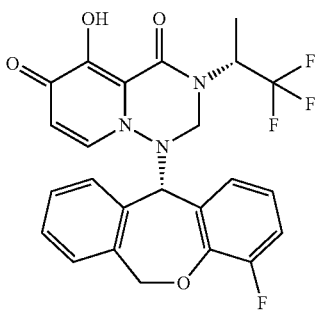

MS: m/z=490 [M+H]$^+$.

Example 426

[Chemical formula 503]

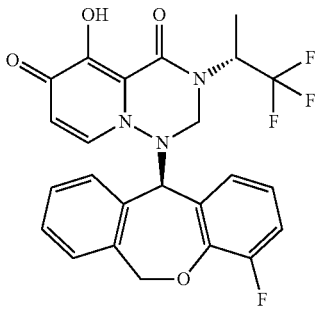

MS: m/z=490 [M+H]$^+$.

Example 427

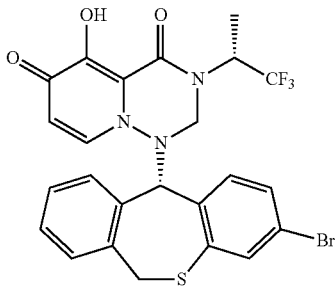
[Chemical formula 504]

¹HNMR (CDCl₃) δ: 1.14 (3H, d, J=6.9 Hz), 3.64 (1H, d, J=13.5 Hz), 4.48 (1H, d, J=12.8 Hz), 4.88 (1H, d, J=12.8 Hz), 5.08 (1H, s), 5.51 (1H, m), 5.60 (1H, d, J=13.5 Hz), 5.93 (1H, d, J=8.1 Hz), 6.58 (1H, d, J=8.1 Hz), 6.95 (1H, dd, J=2.0, 8.1 Hz), 7.18 (2H, m), 7.29 (1H, m), 7.37-7.45 (2H, m).

Example 428

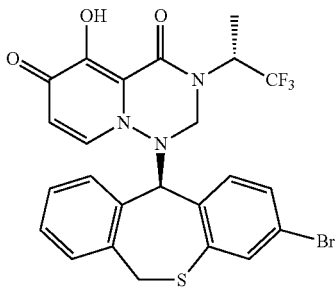
[Chemical formula 505]

¹HNMR (CDCl₃) δ: 1.41 (3H, d, J=7.5 Hz), 3.61 (1H, d, J=13.4 Hz), 4.55 (1H, d, J=12.5 Hz), 5.06 (1H, d, J=12.5 Hz), 5.16 (1H, s), 5.34 (1H, m), 5.63 (1H, d, J=13.4 Hz), 5.87 (1H, d, J=8.1 Hz), 6.61 (1H, d, J=8.1 Hz), 6.93 (1H, dd, J=1.8, 8.1 Hz), 7.16-7.41 (5H, m).

Example 429

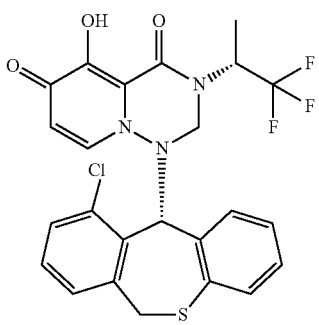
[Chemical formula 506]

¹H-NMR (CDCl₃) δ: 1.15 (3H, d, J=7.4 Hz), 3.64 (1H, d, J=13.5 Hz), 4.44 (1H, d, J=13.2 Hz), 4.87 (1H, d, J=13.2 Hz), 5.44-5.57 (1H, m), 5.68 (1H, d, J=13.2 Hz), 5.83 (1H, d, J=7.7 Hz), 5.94 (1H, s), 6.78-6.91 (2H, m), 7.08-7.18 (3H, m), 7.28-7.38 (3H, m).
MS: m/z=522 [M+H]⁺.

Example 430

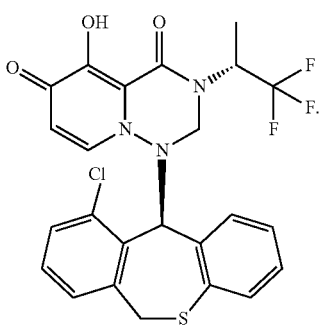
[Chemical formula 507]

MS: m/z=522 [M+H]⁺.

Example 431

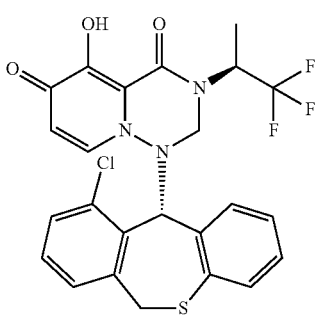
[Chemical formula 508]

MS: m/z=522 [M+H]⁺.

Example 432

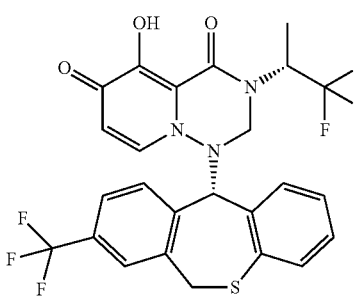
[Chemical formula 509]

¹H-NMR (CDCl₃) δ: 1.21 (3H, d, J=7.4 Hz), 3.70 (1H, d, J=13.5 Hz), 4.43 (1H, d, J=13.2 Hz), 4.93 (1H, d, J=13.2

Hz), 5.21 (1H, s), 5.46-5.60 (1H, m), 5.70 (1H, d, J=13.5 Hz), 5.84 (1H, d, J=7.7 Hz), 6.73 (1H, d, J=7.1 Hz), 6.82-6.89 (1H, m), 7.08-7.17 (2H, m), 7.22 (1H, d, J=7.7 Hz), 7.35 (1H, d, J=8.0 Hz), 7.55 (1H, d, J=8.0 Hz), 7.67 (1H, s).

MS: m/z=071 [M+H]$^+$.

Example 433

[Chemical formula 510]

$^1$H-NMR (CDCl$_3$) δ: 1.22 (3H, d, J=7.1 Hz), 3.56 (1H, d, J=13.5 Hz), 4.48 (1H, d, J=13.2 Hz), 4.90 (1H, d, J=13.2 Hz), 5.09 (1H, s), 5.46-5.60 (1H, m), 5.62 (1H, d, J=13.2 Hz), 5.82 (1H, d, J=7.7 Hz), 6.69 (1H, d, J=7.4 Hz), 6.84 (1H, dt, J=10.0, 3.5 Hz), 7.04-7.14 (3H, m), 7.17 (1H, d, J=7.7 Hz), 7.42 (1H, dd, J=8.0, 1.6 Hz), 7.55 (1H, d, J=1.9 Hz).

MS: m/z=433 [M+H]$^+$.

Example 434

[Chemical formula 511]

$^1$H-NMR (CDCl$_3$) δ: 1.44 (3H, d, J=7.3 Hz), 3.54 (1H, d, J=13.4 Hz), 4.54 (1H, d, J=12.5 Hz), 5.10 (1H, d, J=12.5 Hz), 5.16 (1H, s), 5.31-5.45 (1H, m), 5.65 (1H, d, J=13.3 Hz), 5.73 (1H, d, J=7.8 Hz), 6.71 (1H, d, J=7.8 Hz), 6.77-6.84 (1H, m), 7.03-7.11 (3H, m), 7.22 (1H, d, J=7.6 Hz), 7.40 (1H, dd, J=8.2, 2.0 Hz), 7.48 (1H, d, J=2.0 Hz).

MS: m/z=433 [M+H]$^+$.

Example 435

[Chemical formula 512]

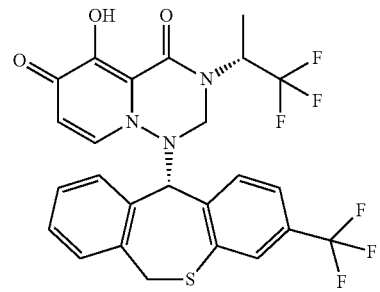

$^1$H-NMR (CDCl$_3$) δ: 1.14 (3H, d, J=7.3 Hz), 3.70 (1H, d, J=13.4 Hz), 4.51 (1H, d, J=13.1 Hz), 4.90 (1H, d, J=12.8 Hz), 5.19 (1H, s), 5.44-5.58 (1H, m), 5.62 (1H, d, J=13.3 Hz), 5.87 (1H, d, J=7.6 Hz), 6.86 (1H, d, J=7.9 Hz), 7.07 (1H, dd, J=8.2, 1.4 Hz), 7.15-7.22 (2H, m), 7.27-7.51 (4H, m).

MS: m/z=433 [M+H]$^+$.

Example 436

[Chemical formula 513]

$^1$H-NMR (CDCl$_3$) δ: 1.48 (3H, d, J=7.4 Hz), 3.71 (1H, d, J=13.3 Hz), 4.60 (1H, d, J=12.6 Hz), 5.21 (1H, d, J=12.6 Hz), 5.29 (1H, s), 5.32-5.46 (1H, m), 5.70 (1H, d, J=13.3 Hz), 5.80 (1H, d, J=7.7 Hz), 6.91 (1H, d, J=7.9 Hz), 7.08 (1H, d, J=7.4 Hz), 7.20-7.29 (2H, m), 7.33-7.51 (4H, m).

MS: m/z=433 [M+H]$^+$.

Example 437

[Chemical formula 514]

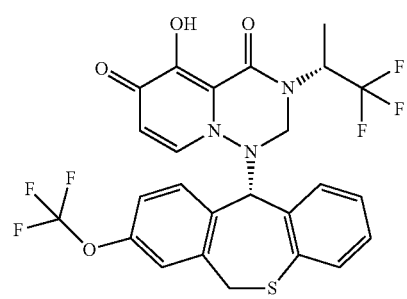

¹H-NMR (CDCl₃) δ: 1.21 (3H, d, J=7.3 Hz), 3.60 (1H, d, J=13.6 Hz), 4.46 (1H, d, J=13.1 Hz), 4.90 (1H, d, J=12.8 Hz), 5.15 (1H, s), 5.47-5.59 (1H, m), 5.68 (1H, d, J=13.4 Hz), 5.83 (1H, d, J=7.6 Hz), 6.70 (1H, d, J=7.3 Hz), 6.80-6.88 (1H, m), 7.07-7.26 (6H, m).

MS: m/z=433 [M+H]⁺.

Example 438

[Chemical formula 515]

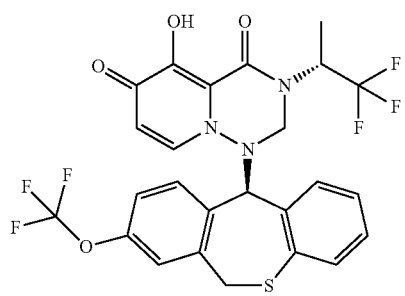

¹H-NMR (CDCl₃) δ: 1.42 (3H, d, J=7.3 Hz), 3.57 (1H, d, J=13.3 Hz), 4.55 (1H, d, J=12.5 Hz), 5.05 (1H, d, J=12.5 Hz), 5.23 (1H, s), 5.32-5.47 (1H, m), 5.70 (1H, d, J=13.4 Hz), 5.77 (1H, d, J=7.6 Hz), 6.74 (1H, d, J=7.8 Hz), 6.79-6.87 (1H, m), 7.04-7.26 (6H, m).

MS: m/z=433 [M+H]⁺.

Example 439

[Chemical formula 516]

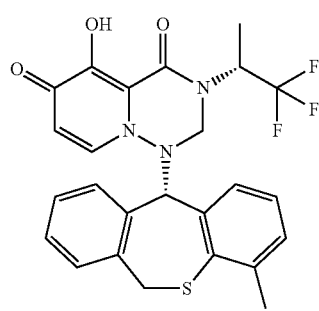

¹H-NMR (CDCl₃) δ: 1.20 (3H, d, J=7.2 Hz), 2.29 (3H, s), 3.76 (1H, d, J=13.3 Hz), 4.54 (1H, d, J=13.1 Hz), 4.92 (1H, d, J=13.1 Hz), 5.18 (1H, s), 5.50-5.62 (1H, m), 5.71 (1H, d, J=13.4 Hz), 5.84 (1H, d, J=7.7 Hz), 6.63 (1H, d, J=7.4 Hz), 6.78 (1H, t, J=7.6 Hz), 7.06 (1H, d, J=7.6 Hz), 7.17 (1H, d, J=7.7 Hz), 7.23 (1H, d, J=7.6 Hz), 7.28-7.34 (1H, m), 7.39-7.51 (2H, m).

MS: m/z=433 [M+H]⁺.

Example 440

[Chemical formula 516]

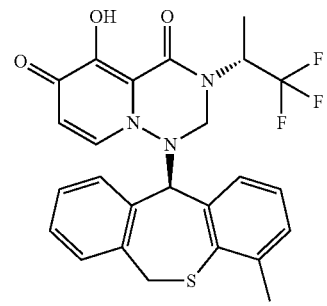

¹H-NMR (CDCl₃) δ: 1.45 (3H, d, J=7.2 Hz), 2.27 (3H, s), 3.74 (1H, d, J=13.3 Hz), 4.61 (1H, d, J=12.4 Hz), 5.07 (1H, d, J=12.4 Hz), 5.27 (1H, s), 5.31-5.44 (1H, m), 5.75 (1H, d, J=13.3 Hz), 5.80 (1H, d, J=7.7 Hz), 6.67 (1H, d, J=7.1 Hz), 6.77 (1H, t, J=7.6 Hz), 7.04 (1H, d, J=7.1 Hz), 7.21-7.47 (5H, m).

MS: m/z=433 [M+H]⁺.

Example 441

[Chemical formula 518]

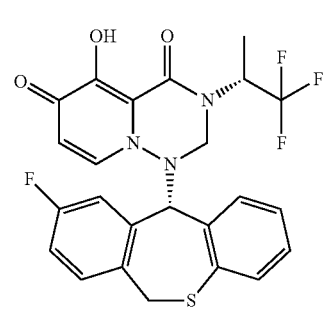

¹H-NMR (DMSO-d₆) δ: 1.22 (3H, d, J=7.2 Hz), 3.94 (1H, d, J=13.3 Hz), 4.45 (1H, d, J=13.4 Hz), 5.08 (1H, d, J=12.8 Hz), 5.56 (4H, dm), 6.84-7.54 (8H, m).

Example 442

[Chemical formula 519]

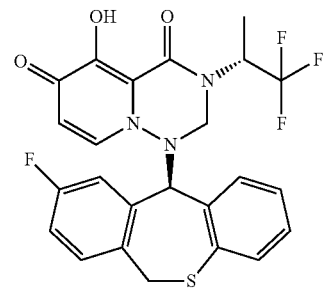

¹H-NMR (DMSO-d₆) δ: 1.37 (3H, d, J=7.2 Hz), 3.98 (1H, d, J=13.4 Hz), 4.48 (1H, d, J=13.1 Hz), 5.21 (1H, d, J=12.9

Hz), 5.22 (1H, m), 5.38 (1H, s), 5.52 (1H, d, J=13.4 Hz), 5.67 (1H, d, J=7.6 Hz), 6.87-7.57 (8H, m).

Example 443

[Chemical formula 520]

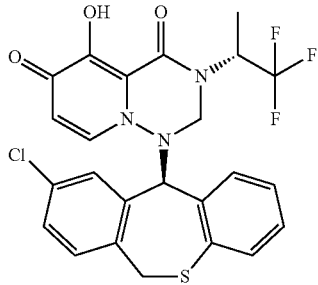

¹H-NMR (DMSO-d₆) δ: 1.19 (3H, d, J=7.2 Hz), 3.92 (1H, d, J=13.4 Hz), 4.43 (1H, d, J=13.1 Hz), 5.05 (1H, d, J=13.0 Hz), 5.54 (4H, m), 7.29 (8H, m).
MS: m/z=522 [M+H]⁺

Example 444

[Chemical formula 521]

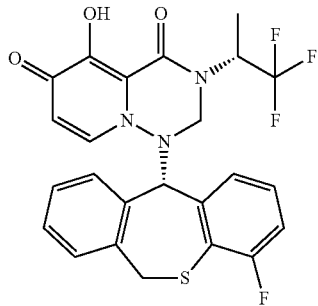

¹H-NMR (DMSO-d₆) δ: 1.13 (3H, d, J=7.0 Hz), 4.00 (1H, d, J=14.2 Hz), 4.40 (1H, d, J=13.3 Hz), 5.05 (1H, d, J=13.3 Hz), 5.44 (1H, m), 5.62-5.71 (3H, m), 6.82-7.56 (8H, m).
MS: m/z=506 [M+H]⁺

Example 445

[Chemical formula 522]

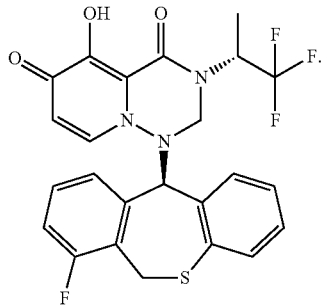

¹H-NMR (DMSO-d₆) δ: 1.23 (3H, d, J=7.2 Hz), 4.14 (1H, d, J=13.8 Hz), 4.60 (1H, d, J=13.6 Hz), 5.10 (1H, d, J=13.3 Hz), 5.48 (1H, d, J=15.6 Hz) 5.49 (1H, m), 5.69 (1H, d, J=7.9 Hz), 5.70 (1H, s), 6.89-7.47 (8H, m).
MS: m/z=506 [M+H]⁺

Example 446

[Chemical formula 523]

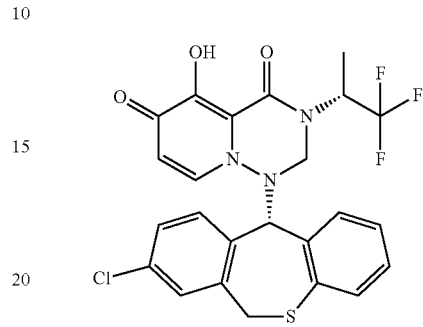

¹H-NMR (DMSO-d₆) δ: 1.22 (3H, d, J=6.9 Hz), 3.93 (1H, d, J=13.1 Hz), 4.49 (1H, d, J=13.4 Hz), 5.05 (1H, d, J=13.7 Hz), 5.57 (4H, m), 6.87-7.61 (8H, m).
MS: m/z=522 [M+H]⁺

Example 447

[Chemical formula 524]

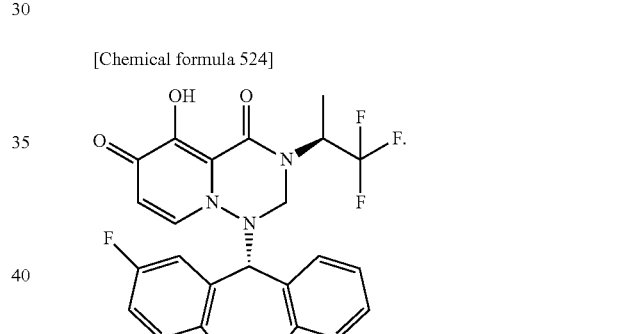

¹H-NMR (DMSO-d₆) δ: 1.41 (3H, d, J=7.2 Hz), 3.98 (1H, d, J=13.3 Hz), 4.48 (1H, d, J=12.9 Hz), 5.21 (1H, d, J=14.4 Hz), 5.22 (1H, m), 5.39 (1H, s), 5.52 (1H, d, J=13.6 Hz), 5.67 (1H, d, J=7.6 Hz), 6.88-7.57 (8H, m).
MS: m/z=506 [M+H]⁺

Example 448

[Chemical formula 525]

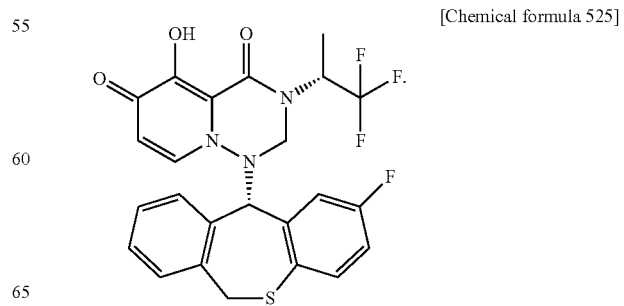

¹H-NMR (DMSO-d₆) δ: 1.19 (3H, d, J=7.2 Hz), 3.94 (1H, d, J=13.3 Hz), 4.44 (1H, d, J=13.3 Hz), 5.12 (1H, d, J=13.1 Hz), 5.46-5.68 (3H, m), 5.76 (1H, d, J=7.6 Hz), 7.27 (8H, m).

MS: m/z=506 [M+H]⁺

Example 449

[Chemical formula 526]

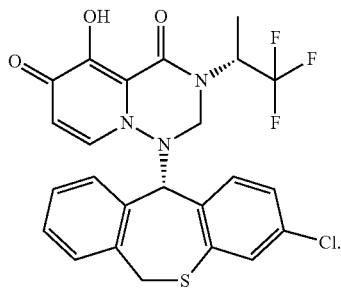

¹H-NMR (DMSO-d₆) δ: 1.14 (3H, d, J=7.2 Hz), 3.93 (1H, d, J=13.3 Hz), 4.40 (1H, d, J=13.1 Hz), 5.07 (1H, d, J=13.0 Hz), 5.46 (1H, m), 5.62 (1H, d, J=15.6 Hz), 5.64 (1H, s), 5.75 (1H, d, J=7.6 Hz), 6.94-7.55 (8H, m).

MS: m/z=522 [M+H]⁺

Example 450

[Chemical formula 527]

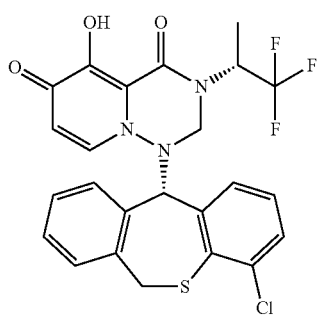

¹H-NMR (DMSO-d₆) δ: 1.14 (3H, d, J=7.2 Hz), 4.03 (1H, d, J=13.3 Hz), 4.41 (1H, d, J=13.3 Hz), 5.06 (1H, d, J=13.0 Hz), 5.46 (1H, m), 5.69 (3H, m), 6.88-7.57 (8H, m).

MS: m/z=522 [M+H]⁺

Example 451

[Chemical formula 528]

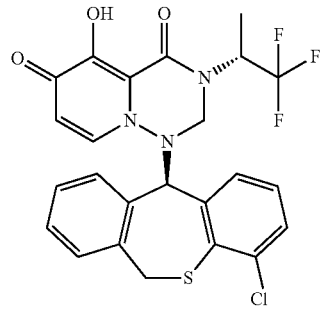

¹H-NMR (DMSO-d₆) δ: 1.35 (3H, d, J=7.2 Hz), 4.03 (1H, d, J=13.3 Hz), 4.43 (1H, d, J=13.0 Hz), 5.14 (1H, t, J=12.6 Hz), 5.15 (1H, m), 5.42 (1H, s), 5.63 (1H, d, J=13.5 Hz), 5.65 (1H, d, J=7.8 Hz), 6.88-7.44 (8H, m).

MS: m/z=522 [M+H]⁺

Example 452

[Chemical formula 529]

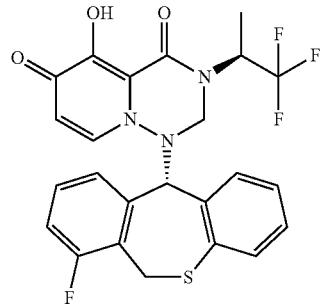

¹H-NMR (DMSO-d₆) δ: 1.42 (3H, d, J=7.2 Hz), 4.14 (1H, d, J=13.9 Hz), 4.57 (1H, d, J=13.1 Hz), 5.14 (1H, d, J=13.0 Hz), 5.15 (1H, m), 5.30 (1H, d, J=13.0 Hz), 5.40 (1H, s), 5.68 (1H, d, J=7.7 Hz), 6.89-7.38 (8H, m).

MS: m/z=506 [M+H]⁺

Example 453

[Chemical formula 530]

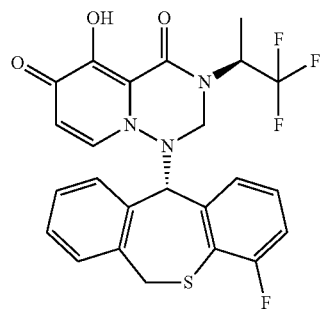

¹H-NMR (DMSO-d₆) δ: 1.40 (3H, d, J=7.4 Hz), 4.05 (1H, d, J=13.4 Hz), 4.47 (1H, d, J=13.1 Hz), 5.18 (1H, m), 5.19 (1H, d, J=13.2 Hz), 5.46 (1H, s), 5.65 (1H, d, J=13.4 Hz), 5.74 (1H, d, J=7.6 Hz), 6.89-7.52 (8H, m).
MS: m/z=506 [M+H]⁺

Example 454

[Chemical formula 531]

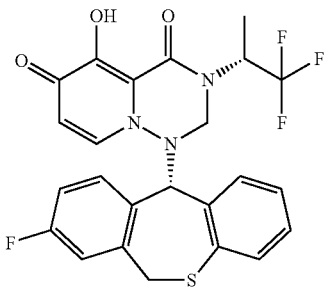

¹H-NMR (DMSO-d₆) δ: 1.20 (3H, d, J=7.2 Hz), 3.89 (1H, d, J=13.4 Hz), 4.46 (1H, d, J=13.4 Hz), 5.05 (1H, d, J=13.4 Hz), 5.44-5.66 (4H, m), 6.83-7.63 (8H, m).
MS: m/z=506 [M+H]⁺

Example 455

[Chemical formula 532]

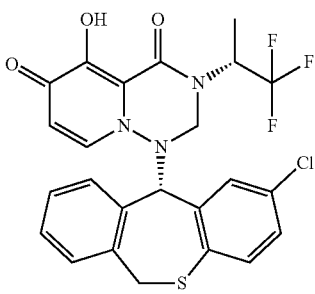

¹H-NMR (DMSO-d₆) δ: 1.16 (3H, d, J=7.5 Hz), 3.92 (1H, d, J=13.3 Hz), 4.39 (1H, d, J=13.1 Hz), 5.07 (1H, d, J=13.3 Hz), 5.47 (1H, m), 5.60 (1H, d, J=13.3 Hz), 5.68 (1H, s), 5.72 (1H, d, J=7.6 Hz), 7.07-7.54 (8H, m).
MS: m/z=522 [M+H]⁺

Example 456

[Chemical formula 533]

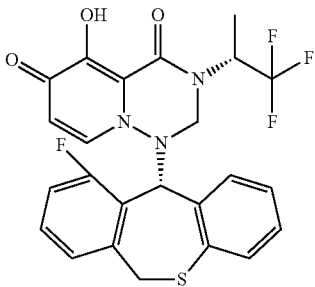

¹H-NMR (DMSO-d₆) δ: 1.13 (5H, d, J=6.3 Hz), 4.00 (1H, d, J=13.4 Hz), 4.52 (1H, d, J=13.6 Hz), 5.09 (1H, d, J=13.3 Hz), 5.49-5.69 (4H, m), 6.84-7.51 (8H, m).
MS: m/z=506 [M+H]⁺

Example 457

[Chemical formula 534]

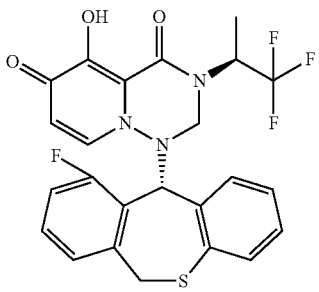

¹H-NMR (DMSO-d₆) δ: 1.40 (3H, d, J=7.2 Hz), 4.02 (1H, d, J=13.1 Hz), 4.53 (1H, d, J=13.3 Hz), 5.20 (1H, d, J=12.9 Hz), 5.26 (1H, m), 5.67 (3H, m), 7.18 (8H, m).
MS: m/z=506 [M+H]⁺

Example 458

[Chemical formula 535]

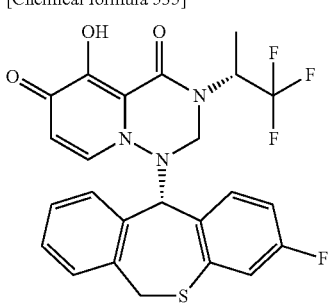

¹H-NMR (DMSO-d₆) δ: 1.15 (3H, d, J=7.3 Hz), 3.91 (1H, d, J=13.4 Hz), 4.39 (1H, d, J=13.3 Hz), 5.06 (1H, d, J=13.3 Hz), 5.45 (1H, m), 5.62 (1H, s), 5.63 (1H, t, J=13.5 Hz), 5.74 (1H, d, J=7.6 Hz), 6.71-7.55 (8H, m).
MS: m/z=506 [M+H]⁺

Example 459

[Chemical formula 536]

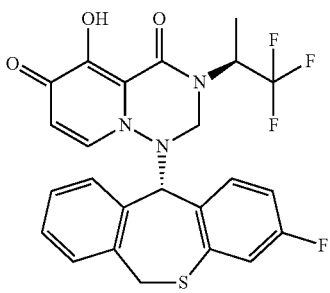

¹H-NMR (DMSO-d₆) δ: 1.39 (3H, d, J=7.4 Hz), 3.95 (1H, d, J=13.4 Hz), 4.46 (1H, d, J=12.9 Hz), 5.19 (1H, d, J=13.1 Hz), 5.20 (1H, m), 5.41 (1H, s), 5.62 (1H, d, J=13.4 Hz), 5.76 (1H, d, J=7.7 Hz), 6.72-7.50 (8H, m).
MS: m/z=506 [M+H]⁺

Example 460

[Chemical formula 537]

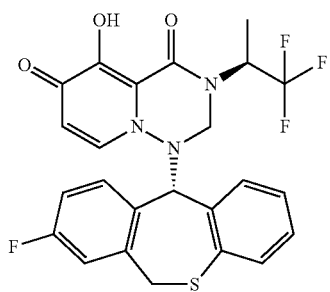

¹H-NMR (DMSO-d₆) δ: 1.42 (3H, d, J=7.2 Hz), 3.94 (1H, d, J=13.3 Hz), 4.50 (1H, d, J=13.1 Hz), 5.17 (1H, d, J=12.4 Hz), 5.18 (1H, m), 5.39 (1H, s), 5.60-5.69 (2H, m), 6.87-7.42 (8H, m).
MS: m/z=506 [M+H]⁺

Example 461

[Chemical formula 538]

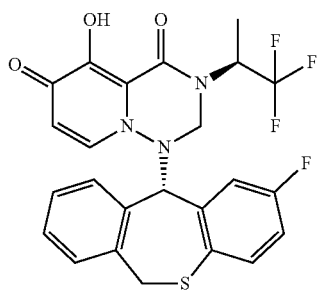

¹H-NMR (DMSO-d₆) δ: 1.35 (3H, d, J=7.2 Hz), 3.91 (1H, d, J=13.0 Hz), 4.43 (1H, d, J=13.1 Hz), 5.15 (1H, d, J=12.8 Hz), 5.16 (1H, m), 5.41 (1H, s), 5.47 (1H, d, J=13.0 Hz), 5.69 (1H, d, J=7.6 Hz), 7.00-7.45 (8H, m).
MS: m/z=506 [M+H]⁺

Example 462

[Chemical formula 539]

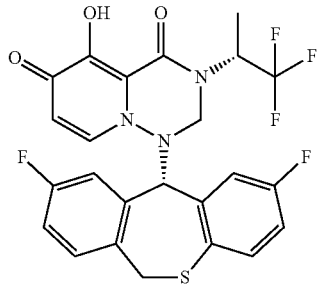

¹H-NMR (DMSO-d₆) δ: 1.21 (3H, d, J=7.3 Hz), 3.97 (1H, d, J=13.3 Hz), 4.46 (1H, d, J=13.1 Hz), 5.09 (1H, d, J=13.6 Hz), 5.50 (1H, m), 5.51 (1H, d, J=12.8 Hz), 5.65 (1H, s), 5.72 (1H, d, J=7.6 Hz), 6.85-7.55 (7H, m).
MS: m/z=524 [M+H]⁺

Example 463

[Chemical formula 540]

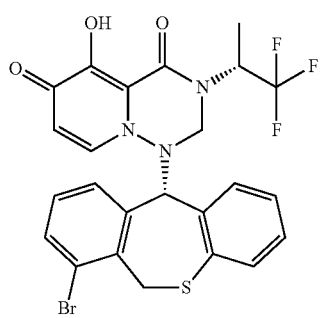

MS: m/z=568 [M+H]⁺

Example 464

[Chemical formula 541]

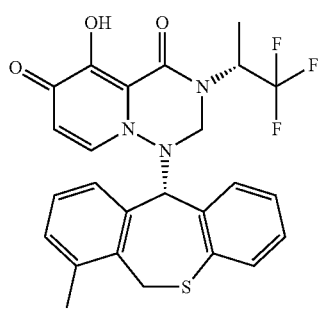

MS: m/z=502 [M+H]⁺.

Example 465

[Chemical formula 542]

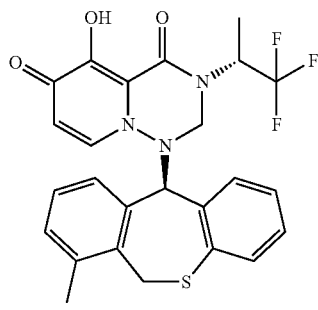

MS: m/z=502 [M+H]⁺

Example 466

[Chemical formula 543]

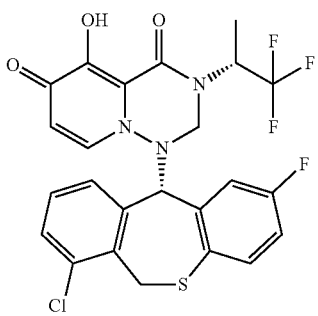

MS: m/z=540 [M+H]+

Example 467

[Chemical formula 544]

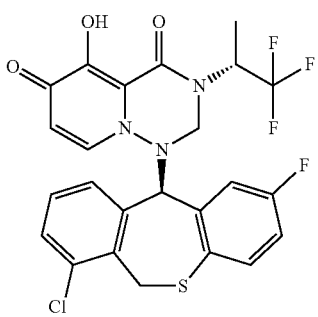

MS: m/z=540 [M+H]+

Example 468

[Chemical formula 545]

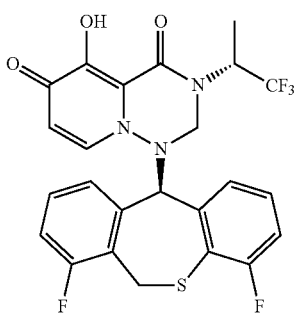

$^1$HNMR (CDCl$_3$) δ: 1.13 (3H, d, J=5.8 Hz), 4.20 (1H, d, J=13.6 Hz), 4.58 (1H, d, J=12.7 Hz), 4.99 (1H, d, J=12.7 Hz), 5.29-5.42 (3H, m), 5.84 (1H, d, J=7.8 Hz), 6.60 (1H, m), 6.79-7.01 (3H, m), 7.19-7.28 (4H, m).
MS: m/z=524 [M+H]+.

Example 469

[Chemical formula 546]

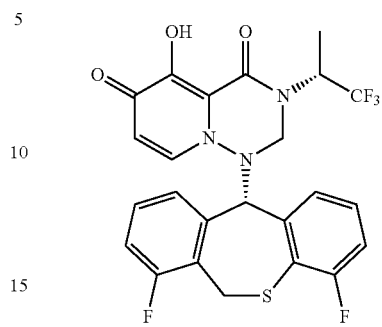

$^1$HNMR (CDCl$_3$) δ: 1.19 (3H, d, J=7.6 Hz), 4.21 (1H, d, J=13.9 Hz), 4.48 (1H, d, J=13.3 Hz), 4.89 (1H, d, J=13.3 Hz), 5.22 (1H, s), 5.37 (1H, dd, J=2.1, 13.9 Hz), 5.52 (1H, m), 5.86 (1H, d, J=7.6), 6.55 (1H, m), 6.83 (1H, m), 6.96 (1H, m), 7.14 (1H, d, J=7.6 Hz), 7.19-7.30 (4H, m).
MS: m/z=524 [M+H]+.

Example 470

[Chemical formula 547]

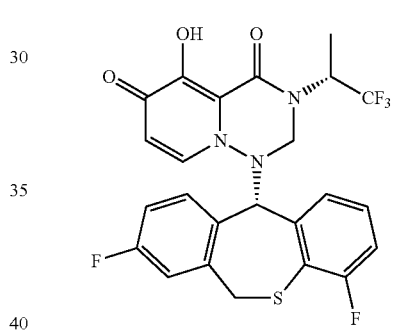

$^1$HNMR (CDCl$_3$) δ: 1.19 (3H, d, J=7.3 Hz), 3.65 (1H, d, J=13.5 Hz), 4.47 (1H, d, J=13.0 Hz), 4.87 (1H, d, J=13.0 Hz), 5.18 (1H, s), 5.50 (1H, m), 5.69 (1H, d, J=13.5 Hz), 5.85 (1H, d, J=7.8 Hz), 6.53 (1H, m), 6.83 (1H, m), 6.91-7.01 (2H, m), 7.11 (1H, d, J=7.6 Hz), 7.10-7.20 (3H, m).
MS: m/z=524 [M+H]+.

Example 471

[Chemical formula 548]

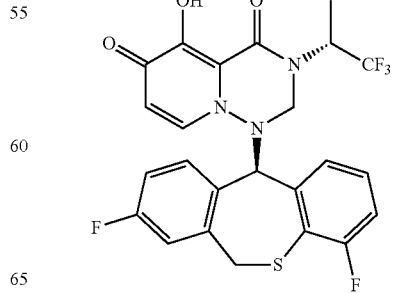

¹HNMR (CDCl₃) δ: 1.13 (3H, d, J=6.1 Hz), 3.63 (1H, d, J=13.5 Hz), 4.56 (1H, d, J=12.5 Hz), 5.02 (1H, d, J=12.5 Hz), 5.26 (1H, s), 5.38 (1H, m), 5.71 (1H, d, J=13.5 Hz), 5.81 (1H, d, J=7.8 Hz), 6.57 (1H, m), 6.81 (1H, m), 6.91 (1H, m), 6.99 (1H, dd, J=2.6, 8.2 Hz), 7.05 (1H, dd, J=2.6, 8.7 Hz), 7.17 (2H, m), 7.19 (1H, d, J=7.6 Hz).

MS: m/z=524 [M+H]⁺.

Example 472

[Chemical formula 549]

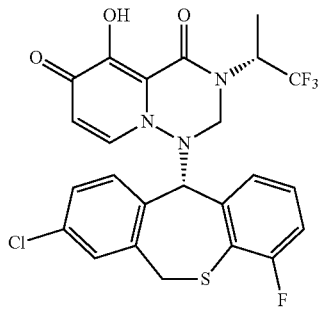

¹HNMR (CDCl₃) δ: 1.21 (3H, d, J=7.4 Hz), 3.66 (1H, d, J=13.5 Hz), 4.47 (1H, d, J=13.3 Hz), 4.88 (1H, d, J=13.3 Hz), 5.17 (1H, s), 5.52 (1H, m), 5.66 (1H, d, J=13.5 Hz), 5.85 (1H, d, J=7.7 Hz), 6.54 (1H, m), 6.83 (1H, m), 6.95 (1H, m), 7.11-7.14 (2H, m), 7.23-7.29 (2H, m), 7.41 (1H, d, J=2.0 Hz).

MS: m/z=540 [M+H]⁺.

Example 473

[Chemical formula 550]

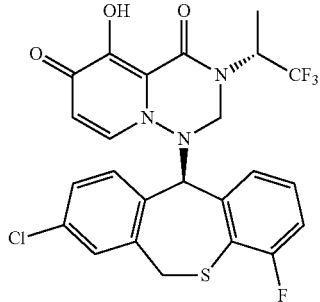

¹HNMR (CDCl₃) δ: 1.13 (3H, d, J=6.2 Hz), 3.63 (1H, d, J=13.5 Hz), 4.55 (1H, d, J=12.6 Hz), 5.04 (1H, d, J=12.6 Hz), 5.25 (1H, s), 5.38 (1H, m), 5.69 (1H, d, J=13.5 Hz), 5.80 (1H, d, J=7.7 Hz), 6.58 (1H, m), 6.82 (1H, m), 6.92 (1H, m), 7.13 (1H, m), 7.19 (1H, d, J=7.7 Hz), 7.24-7.29 (2H, m), 7.34 (1H, d, J=2.2 Hz).

MS: m/z=540 [M+H]⁺.

Example 474

[Chemical formula 551]

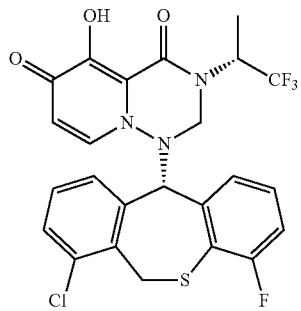

¹HNMR (CDCl₃) δ: 1.19 (3H, d, J=7.3 Hz), 4.40 (1H, d, J=13.9 Hz), 4.59 (1H, d, J=13.0 Hz), 5.02 (1H, d, J=13.0 Hz), 5.31 (1H, s), 5.39 (1H, m), 5.66 (1H, d, J=13.9 Hz), 5.84 (1H, d, J=7.8 Hz), 6.58 (1H, m), 6.82 (1H, m), 6.92 (1H, m), 7.10 (1H, m), 7.19 (1H, dd, J=3.7, 7.9 Hz), 7.20-7.26 (2H, m), 7.51 (1H, m).

MS: m/z=540 [M+H]⁺.

Example 475

[Chemical formula 552]

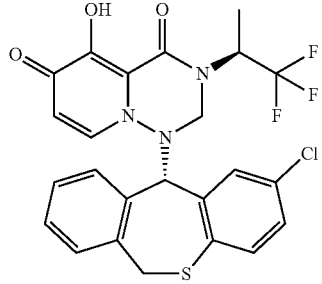

MS: m/z=522 [M+H]⁺.

Example 476

[Chemical formula 553]

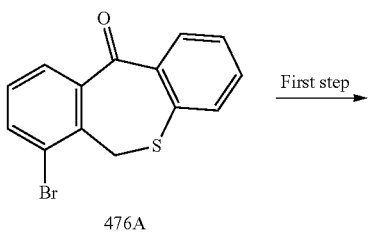

First step →

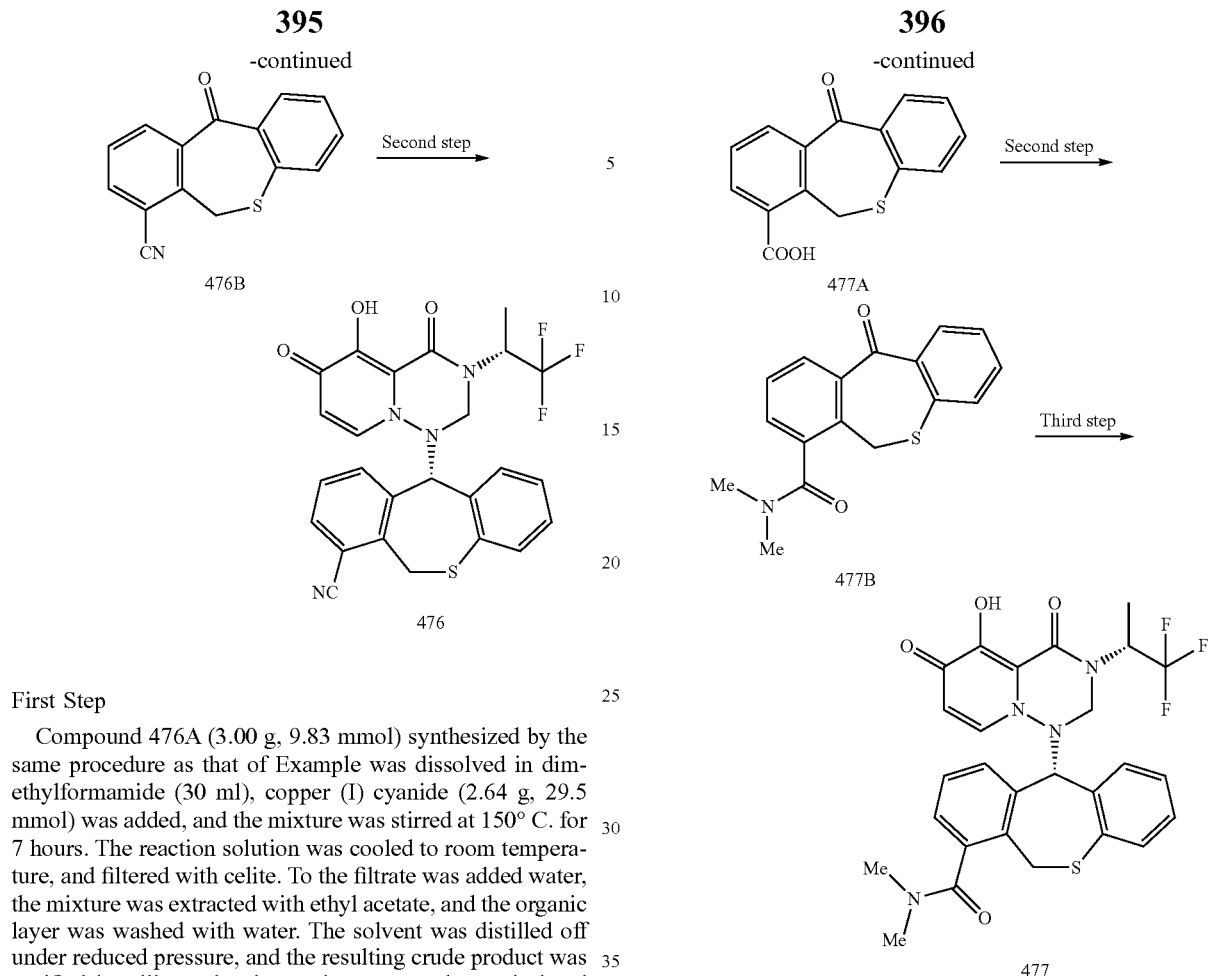

First Step

Compound 476A (3.00 g, 9.83 mmol) synthesized by the same procedure as that of Example was dissolved in dimethylformamide (30 ml), copper (I) cyanide (2.64 g, 29.5 mmol) was added, and the mixture was stirred at 150° C. for 7 hours. The reaction solution was cooled to room temperature, and filtered with celite. To the filtrate was added water, the mixture was extracted with ethyl acetate, and the organic layer was washed with water. The solvent was distilled off under reduced pressure, and the resulting crude product was purified by silica gel column chromatography, and eluted with n-hexane-ethyl acetate (1:1, v/v). To the resulting compound was added n-hexane, and the precipitated residue was filtered to obtain 1.81 g of a white solid 476B.

$^1$H-NMR (CDCl$_3$) δ: 4.29 (2H, s), 7.28-7.48 (4H, m), 7.78 (2H, t, J=7.5 Hz), 8.20 (1H, dd, J=8.1, 1.5 Hz).

Second Step

Compound 476 was synthesized by the same procedure as that of Example 107.

$^1$H-NMR (DMSO-d$_6$) δ: 1.16 (3H, d, J=7.0 Hz), 4.01 (1H, d, J=14.0 Hz), 4.65 (1H, d, J=13.7 Hz), 5.04 (1H, d, J=13.3 Hz), 5.45 (1H, t, J=8.1 Hz), 5.66 (1H, d, J=7.6 Hz), 5.74 (1H, s), 5.84 (1H, d, J=14.0 Hz), 6.87-7.93 (7H, m).

MS: m/z=513 [M+H]$^+$

Example 477

[Chemical formula 554]

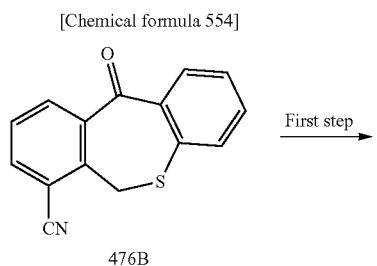

First Step

To compound 476B (859 mg, 3.42 mmol) was added concentrated sulfuric acid (13 ml), and the mixture was stirred at room temperature for 18 hours, and at 60° C. for 2 hours. The reaction solution was added to water, the mixture was extracted with ethyl acetate, and the organic layer was dried with sodium sulfate. The solvent was concentrated under reduced pressure to obtain 387 mg of a pale yellow solid. To the resulting compound was added methanol (10 ml), a 10N aqueous sodium hydroxide solution (6 ml) was added, and the mixture was stirred at 90° C. for 5 hours. The reaction solution was cooled to room temperature, water was added, and the mixture was washed with dichloromethane. To the aqueous layer was added dilute hydrochloric acid, the mixture was extracted with ethyl acetate, and the organic layer was dried with sodium sulfate. The solvent was concentrated under reduced pressure to obtain 296 mg of a yellow solid 477A.

Second Step

Compound 477A (179 mg, 0.662 mmol) obtained in the first step was dissolved in dichloromethane (4 ml), dimethylamine hydrochloride (108 mg, 1.32 mmol), EDCI (190 mg, 0.993 mmol), 1H-benzo[d] [1,2,3]triazol-1-ol (89.0 mg, 0.662 mmol) and triethylamine (0.3 ml) were added, and the mixture was stirred at room temperature for 2 hours. To the reaction solution was added water, the mixture was extracted with ethyl acetate, and the organic layer was washed with an aqueous sodium bicarbonate solution, and dried with sodium sulfate. The solvent was distilled off under reduced pressure, and the resulting crude product was purified by silica gel column chromatography, and eluted with n-hexane-ethyl acetate (1:1, v/v), to obtain 170 mg of a colorless gummy substance 477B.

$^1$H-NMR (CDCl$_3$) δ: 2.99 (3H, s), 3.23 (3H, s), 4.08 (2H, s), 7.28-7.44 (5H, m), 7.58 (1H, t, J=4.4 Hz), 8.22 (1H, dd, J=8.1, 1.5 Hz).

Third Step

Compound 477 was synthesized by the same procedure as that of Example 107.

MS: m/z=559 [M+H]$^+$

Example 478

[Chemical formula 555]

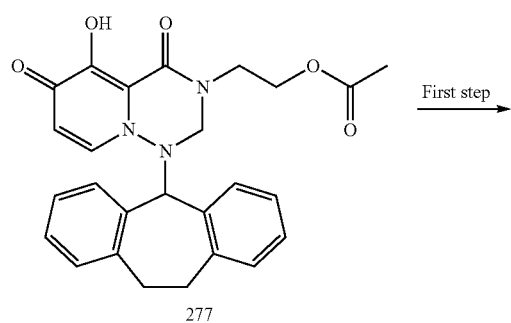
277

First step

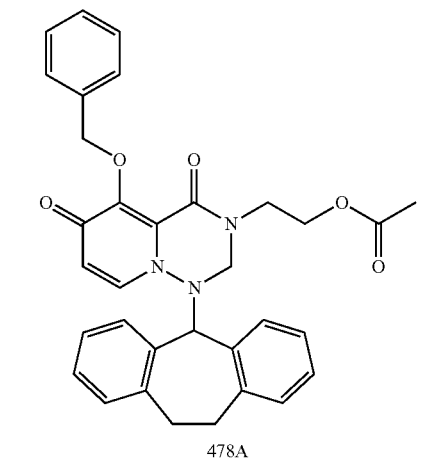
478A

Second step

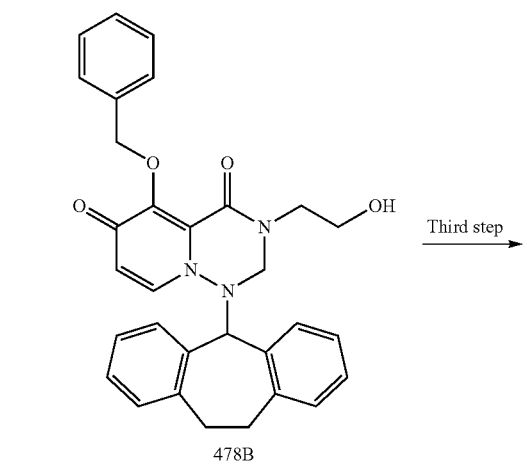
478B

Third step

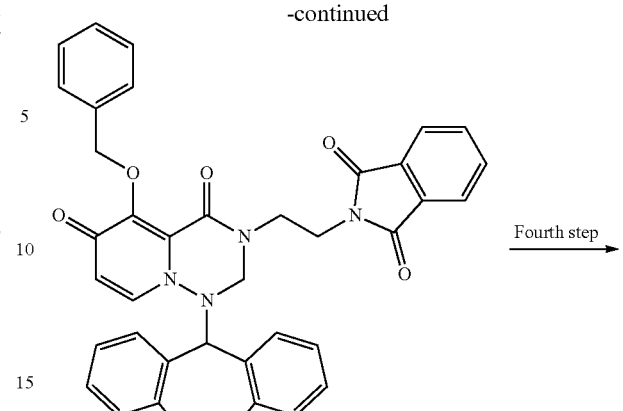
478C

Fourth step

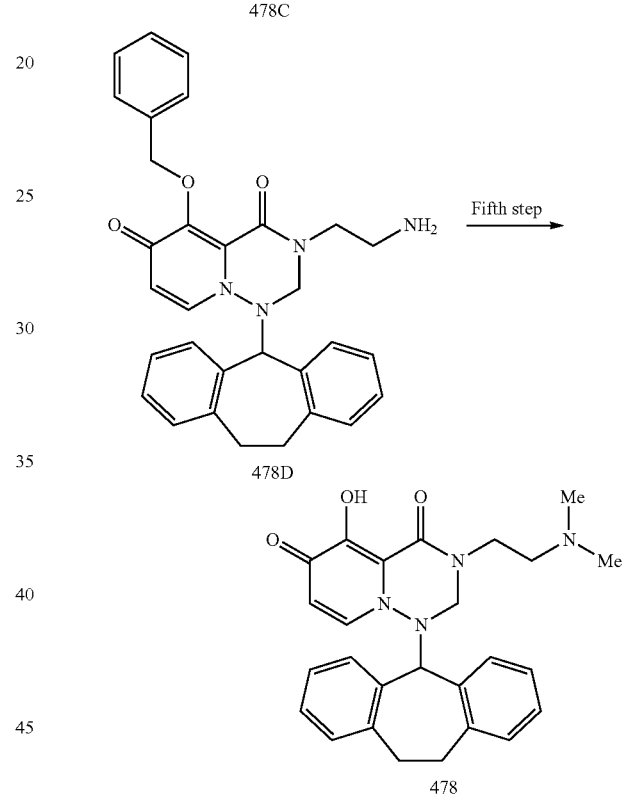
478D

Fifth step

478

First Step

Compound 277 (971 mg, 2.11 mmol) was dissolved in dimethylformamide (10 ml), cesium carbonate (2.75 g, 8.45 mmol) and benzyl bromide (0.753 ml, 6.34 mmol) were added, and the mixture was stirred at room temperature for 4 hours. The reaction solution was poured into water, then extracted with ethyl acetate, and the organic layer was washed with water, and dried with sodium sulfate. The solvent was distilled off under reduced pressure, to the resulting compound were added dichloromethane-diethyl ether, and the precipitated residue was filtered to obtain 740 mg of a white solid 478A.

Second Step

Compound 478A (740 mg, 1.35 mmol) was dissolved in tetrahydrofuran (7 ml) and methanol (7 ml), a 2N aqueous sodium hydroxide solution (3.37 ml, 6.73 mmol) was added, and the mixture was stirred at room temperature for 30 minutes. To the reaction solution was added dilute hydrochloric acid to make the solution acidic, the mixture was extracted with chloroform, and the organic layer was dried with sodium sulfate. The solvent was concentrated under reduced pressure to obtain 618 mg of a white solid 478B.

MS: m/z=508 [M+H]+

Third Step

Compound 478B (505 mg, 0.995 mmol) was dissolved in tetrahydrofuran (10 ml), triphenylphosphine (391 mg, 1.49 mmol), phthalimide (220 mg, 1.49 mmol) and azodicarboxylic acid diisopropyl ester (0.290 ml, 1.49 mmol) were added, and the mixture was stirred at room temperature for 1 hour. The reaction solution was concentrated under reduced pressure, and the resulting crude product was purified by silica gel column chromatography, and eluted with chloroform-methanol (97:3, v/v). To the resulting compound were added dichloromethane-diethyl ether, and the precipitated residue was filtered to obtain 578 mg of a white solid 478C.

MS: m/z=637 [M+H]+.

Fourth Step

To compound 478C (667 mg, 1.05 mmol) was added ethanol (10 ml), hydrazine hydrate (0.254 ml, 5.24 mmol) was added, and the mixture was stirred at 90° C. for 2 hours. The reaction solution was cooled to room temperature, chloroform was added, insolubles were removed by filtration, and the filtrate was concentrated under reduced pressure. The resulting crude product was purified by amino column chromatography, and eluted with chloroform-methanol (97:3, v/v). To the resulting compound were added dichloromethane-diethyl ether, and the precipitated residue was filtered to obtain 462 mg of a white soled 478D.

MS: m/z=507 [M+H]+

Fifth Step

To compound 478D (100 mg, 0.197 mmol) were added formic acid (1.0 ml) and an aqueous formalin solution (1.0 ml), and the mixture was stirred at 80° C. for 1 hour. To the reaction solution was added a 1N aqueous sodium hydroxide solution, the mixture was extracted with dichloromethane, and the organic layer was dried with sodium sulfate. The resulting crude product was purified by amino column chromatography, and eluted with chloroform-methanol (97: 3, v/v), to obtain 56 mg of a colorless oily substance. This compound was dissolved in acetic acid (2.0 ml), concentrated sulfuric acid (0.5 ml) was added dropwise, and the mixture was stirred at room temperature for 30 minutes. The reaction solution was poured into an aqueous sodium bicarbonate solution, and was extracted with chloroform, and the organic layer was dried with sodium sulfate. The solvent was distilled off under reduced pressure, to the resulting crude product were added dichloromethane-ethyl acetate-diethyl ether, and the precipitated residue was filtered to obtain 12 mg of a white solid 478.

MS: m/z=445 [M+H]+

Example 479

[Chemical formula 556]

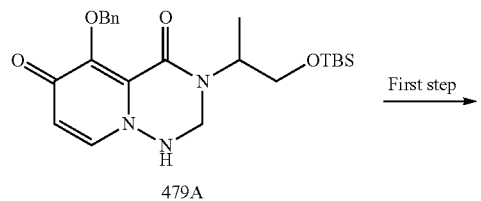

479A

First step

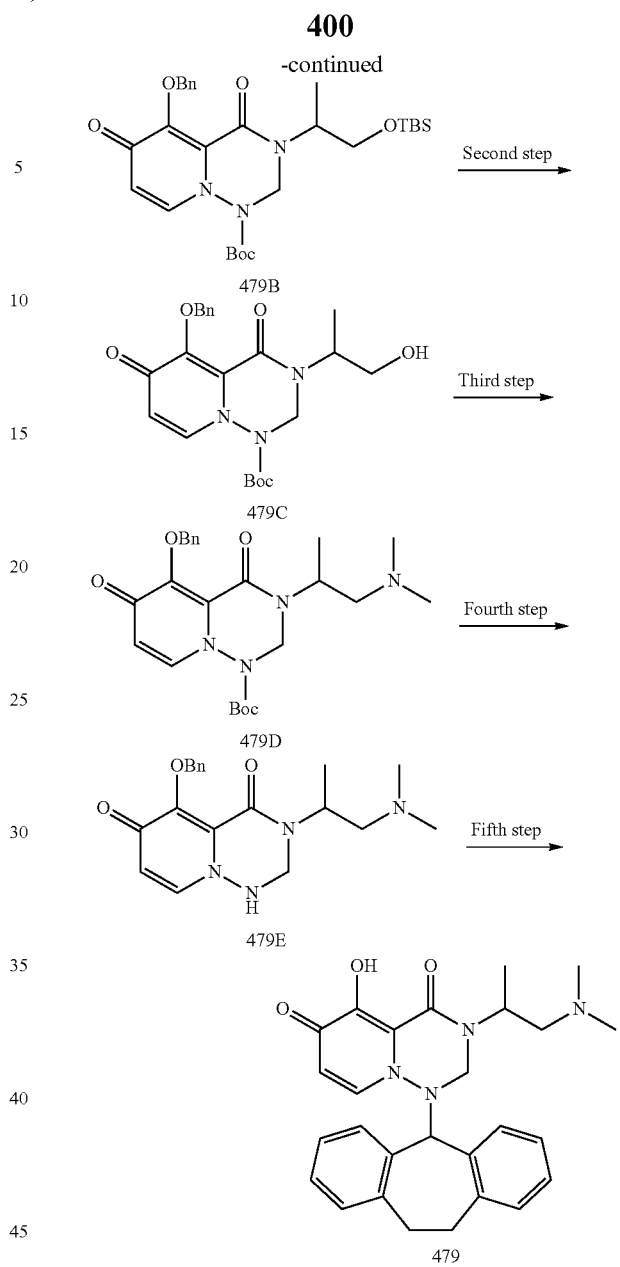

First Step

To a dichloromethane (50 ml) solution of compound 479A (5.25 g, 11.8 mmol) synthesized according to Example 95, DIPEA (6.20 mL, 35.5 mmol) and Boc₂O (5.17 g, 23.7 mmol) was added DMAP (434 mg, 3.55 mmol), and the mixture was stirred at room temperature for 4 hours. After the reaction solution was concentrated under reduced pressure, the residue was dissolved in ethyl acetate. The solution was sequentially washed with 0.5N hydrochloric acid and an aqueous saturated sodium chloride solution, and dried with sodium sulfate. The solvent was distilled off, and the resulting oil was purified by silica gel chromatography. The materials were eluted firstly with chloroform and, then, with chloroform-methanol (97:3, v/v). Concentration of an objective fraction afforded 5.22 g of compound 479B as an oil.

MS: m/z=544 [M+H]+.

Second Step

To a THF (340 mL) solution of compound 479B (29.7 g, 102 mmol) and acetic acid (29.7 g, 102 mmol) was added TBAF (1M THF solution, 23.6 g, 310 mmol) under ice-cooling, and the mixture was stirred at room temperature for 16 hours. To the reaction solution were added ethyl acetate and water, and the ethyl acetate layer was separated, washed with water, and dried with sodium sulfate. The solvent was distilled off, and the resulting oil was solidified by adding dichloromethane-ether, to obtain 2.76 g of compound 479C.

MS: m/z=430 [M+H]$^+$.

Third Step

To an ethyl acetate (20 mL) suspension of compound 479C (500 mg, 1.16 mmol) was added IBX (652 mg, 2.33 mmol), and the mixture was heated to stir for 3 hours. After the reaction solution was diluted with ethyl acetate, insolubles were filtered, and the resulting filtrate was sequentially washed with a 1N aqueous sodium hydroxide solution and water, and dried with sodium sulfate. After the solvent was distilled off, and the resulting oil was dissolved in THF (5 mL), dimethylamine (2M THF solution, 0.873 mL, 1.75 mmol) and NaBH(OAc)$_3$ (370 mg, 1.75 mmol) were added under ice-cooling, and the mixture was stirred at room temperature for 1.5 hours. After 2N hydrochloric acid was added to the reaction solution under ice-cooling, the mixture was made basic with an aqueous sodium bicarbonate solution. This was extracted with chloroform, and dried with sodium sulfate. The solvent was distilled off, and the resulting oil was purified by silica gel chromatography. The materials were eluted first with chloroform and, then, with chloroform-methanol (93:7, v/v). Concentration of an objective fraction afforded 437 mg of compound 479D as an amorphous substance.

MS: m/z=457 [M+H]$^+$.

Fourth Step

Compound 479D (430 mg, 0.942 mmol) was dissolved in acetic acid (10 mL), and the solution was heated to stir for 1 hour. The solvent was distilled off, and the resulting oil was purified by silica gel chromatography. The materials were eluted firstly with chloroform and, then, with chloroform-methanol (95:5, v/v). Concentration of an objective fraction afforded 330 mg of compound 479E as an oil.

MS: m/z=357 [M+H]$^+$.

Fifth Step

To an acetic acid (2 mL) solution of compound 479E (50 mg, 0.140 mmol) and dibenzosuberol (29.5 mg, 0.140 mmol) was added dropwise sulfuric acid (0.5 mL), and the mixture was stirred for 30 minutes. To the reaction solution were added ethyl acetate and water, thereafter, the aqueous layer was separated, and neutralized with an aqueous sodium bicarbonate solution. Extraction was performed using the ethyl acetate layer, and the extract was washed with water, and dried with sodium sulfate. The solvent was distilled off, and the resulting oil was solidified by adding ether, to obtain 17.0 mg of compound 479.

MS: m/z=354 [M+H]$^+$.

According to Example 478 or Example 479, Examples 480 to 490 were synthesized using the same procedure.

Example 480

[Chemical formula 557]

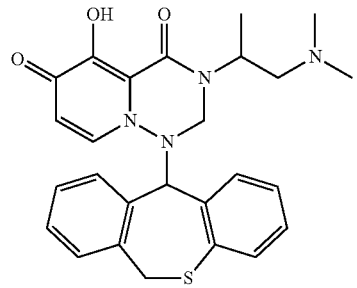

MS: m/z=477 [M+H]$^+$.

Example 481

[Chemical formula 558]

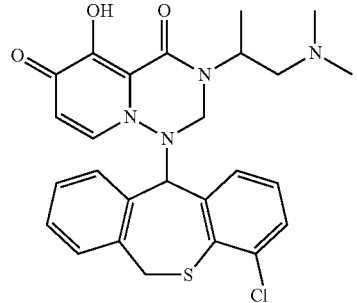

MS: m/z=512 [M+H]$^+$.

Example 482

[Chemical formula 559]

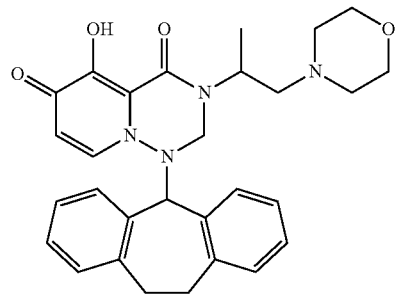

MS: m/z=501 [M+H]$^+$.

Example 483
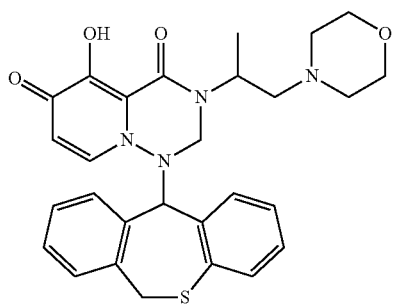
MS: m/z=519 [M+H]⁺.
Example 484
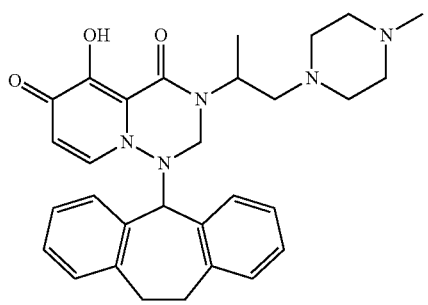
MS: m/z=514 [M+H]⁺.
Example 485
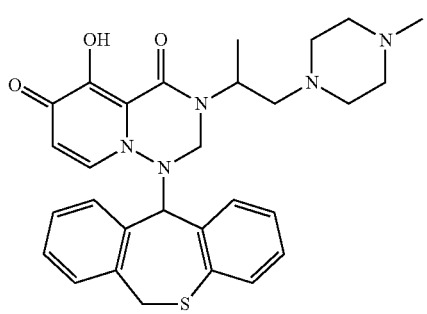
MS: m/z=532 [M+H]⁺
Example 486
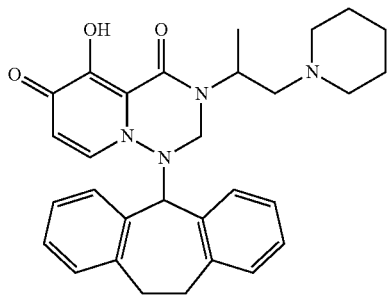
MS: m/z=499 [M+H]⁺.
Example 487
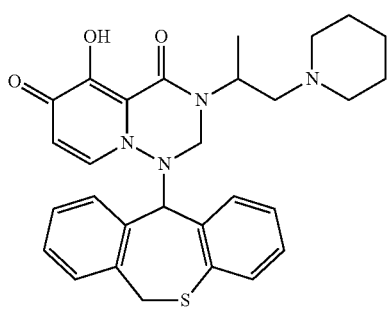
MS: m/z=517 [M+H]⁺.
Example 488
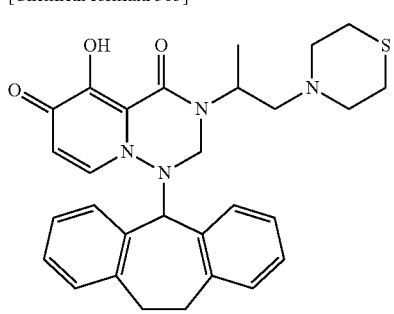
MS: m/z=517 [M+H]⁺.

Example 489

[Chemical formula 566]

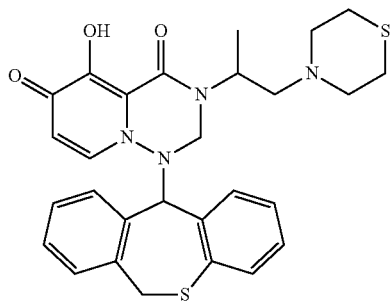

MS: m/z=535 [M+H]⁺.

Example 490

[Chemical formula 567]

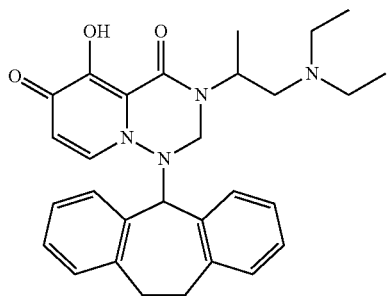

MS: m/z=473 [M+H]⁺

Example 491

[Chemical formula 568]

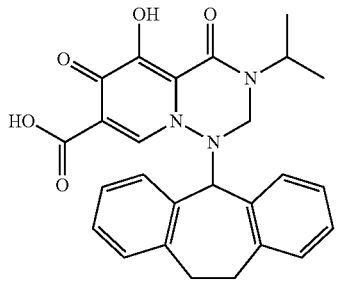

According to Example 65 and Example 107, compound 491 was synthesized by the same procedure.

¹H-NMR (DMSO-d₆) δ: 1.10 (3H, d, J=4.0 Hz), 1.12 (3H, d, J=4.6 Hz), 2.82-3.06 (2H, m), 3.56 (1H, d, J=17.8 Hz), 4.26 (1H, d, J=13.2 Hz), 4.31 (1H, m), 4.51-4.60 (1H, m), 4.97 (1H, d, J=13.1 Hz), 5.39 (1H, s), 6.74-7.52 (8H, m).

MS: m/z=460 [M+H]⁺

Example 492

[Chemical formula 569]

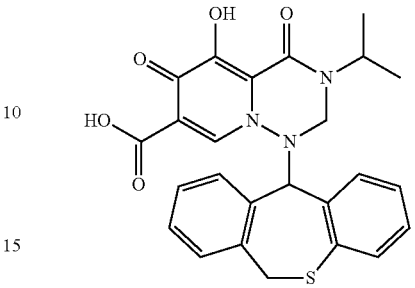

According to Example 65 and Example 107, compound 492 was synthesized by the same procedure.
MS: m/z=478 [M+H]⁺

Example 493

[Chemical formula 570]

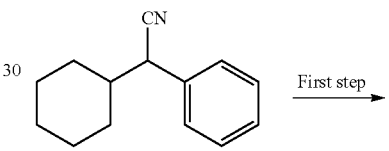

493A

First step →

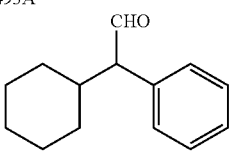

493B

Second step →

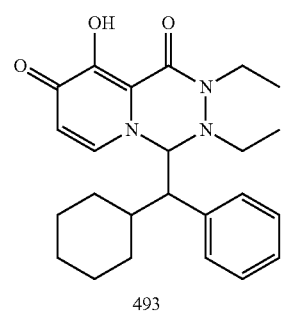

493

First Step

A dichloromethane (5 mL) solution of compound 493A (258 mg, 1.30 mmol) was cooled to −50° C., and a toluene solution (1M, 1.96 mL) of DIBAL-H was added dropwise over 5 minutes while the same temperature was retained. After the reaction solution was stirred at the stirred at the same temperature for 1 hour, temperature was raised to room temperature, and the mixture was stirred for 2.5 hours. To the reaction solution was added an aqueous saturated ammonium chloride solution, thereafter, the mixture was stirred at room temperature for 1 hour, and insolubles were removed by filtration. The dichloromethane layer was separated, and the aqueous layer was extracted with dichloromethane once.

The combined extracts were washed with water three times, washed with an aqueous saturated sodium chloride solution, and dried. The solvent was distilled off, and the resulting oil was subjected to silica gel column chromatography, and eluted with n-hexane-ethyl acetate. Concentration of an objective fraction afforded 148 mg of compound 493B as an oil.

¹HNMR (CDCl₃) δ: 1.03-1.44 (5H, m), 1.63-1.83 (5H, m), 2.05-2.13 (1H, m), 3.25 (1H, dd, J=9.5 Hz, 3.4 Hz), 7.16-7.19 (2H, ms), 7.27-7.38 (3H, m), 9.69 (1H, d, J=3.5 Hz).

Second Step

According to Example 177, compound 493 was synthesized by the same procedure.

MS: m/z=410 [M+H]⁺

Using aldehydes which are commercially available or known in the references and hydrazines which are commercially available or known in the references, and according to Example 493, compounds 494 to 505 were synthesized.

Example 494

[Chemical formula 571]

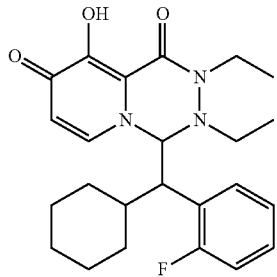

MS: m/z=428 [M+H]⁺

Example 495

[Chemical formula 572]

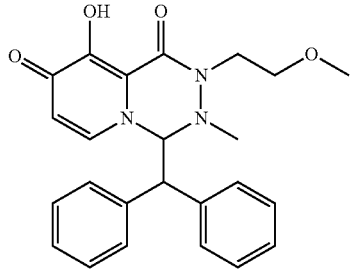

MS: m/z=420 [M+H]⁺.

Example 496

[Chemical formula 573]

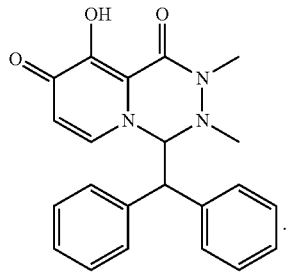

MS: m/z=376 [M+H]⁺.

Example 497

[Chemical formula 574]

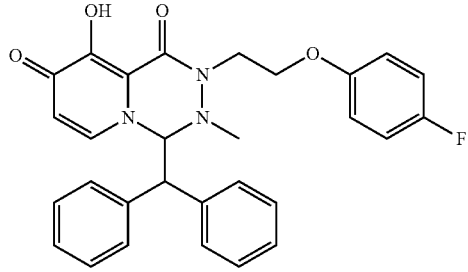

MS: m/z=500 [M+H]⁺.

Example 498

[Chemical formula 575]

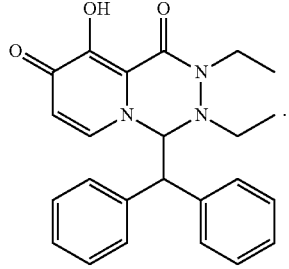

MS: m/z=404 [M+H]⁺.

Example 499
[Chemical formula 576]
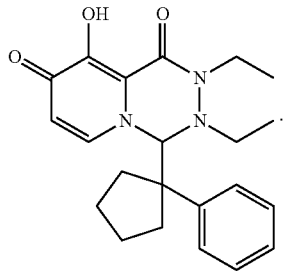
MS: m/z=382 [M+H]⁺.
Example 500
[Chemical formula 577]
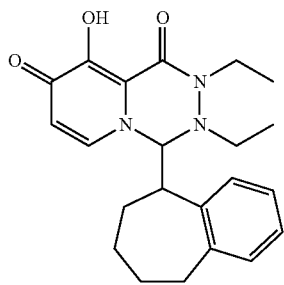
MS: m/z=382 [M+H]⁺.
Example 501
[Chemical formula 578]
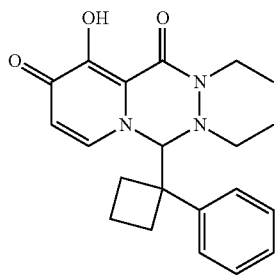
MS: m/z=368 [M+H]⁺.
Example 502
[Chemical formula 579]
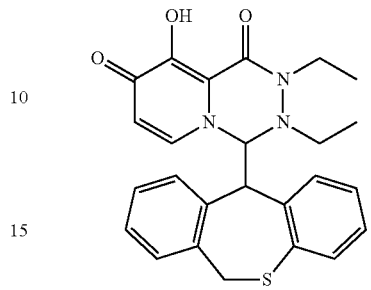
$^1$H-NMR (CDCl$_3$) δ: 0.94 (3H, t, J=7.2 Hz), 1.26 (3H, t, J=7.3 Hz), 2.87-2.94 (2H, m), 3.10-3.22 (1H, m), 3.79-3.89 (1H, m), 3.98 (1H, d, J=16.9 Hz), 4.17 (1H, d, J=16.8 Hz), 4.28 (1H, d, J=9.8 Hz), 6.04 (1H, d, J=7.2 Hz), 6.54 (2H, t, J=8.1 Hz), 6.73 (1H, d, J=9.8 Hz), 6.95-7.33 (6H, m), 7.66 (1H, dd, J=5.3, 3.6 Hz).
MS: m/z=448 [M+H]⁺.
Example 503
[Chemical formula 580]
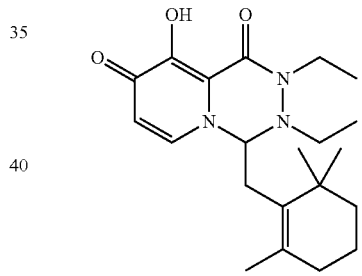
MS: m/z=374 [M+H]⁺.
Example 504
[Chemical formula 581]
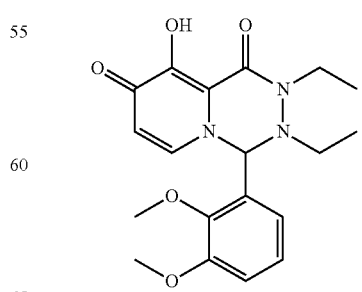
MS: m/z=374 [M+H]⁺.

Example 505
[Chemical formula 582]
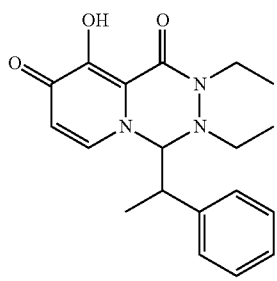
MS: m/z=342 [M+H]⁺.
Example 506
[Chemical formula 583]
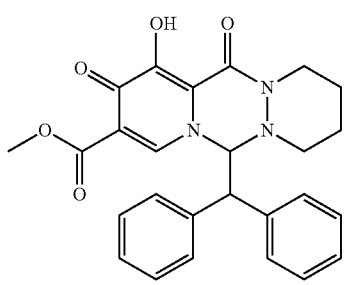
According to Example 177, using compound 65B, compound 506 was synthesized by the same procedure.
MS: m/z=470 [M+H]⁺.
Example 507
[Chemical formula 584]
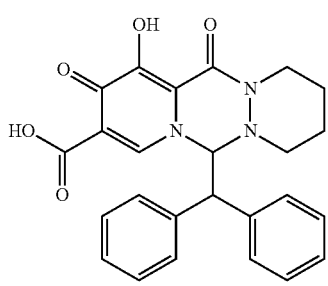
According to Example 65, using compound 506, compound 507 was synthesized by the same procedure.
MS: m/z=446 [M+H]⁺.
Example 508
[Chemical formula 585]
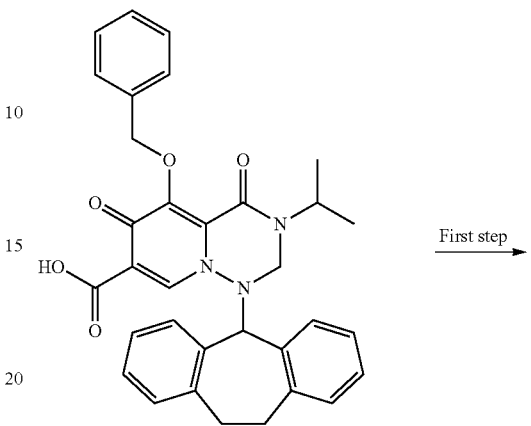
508A
First step →
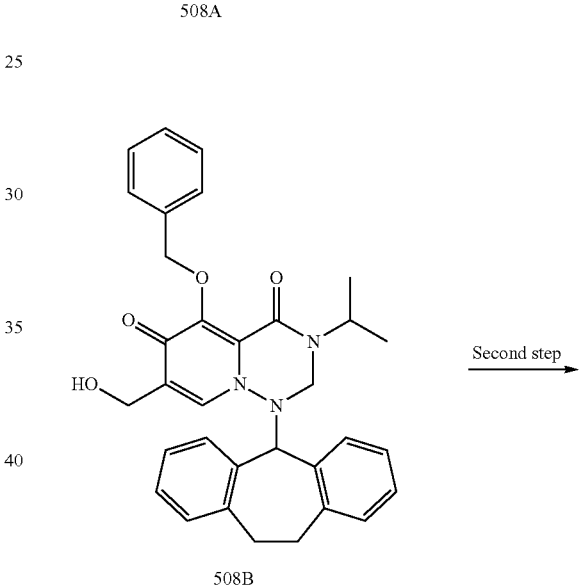
508B
Second step →
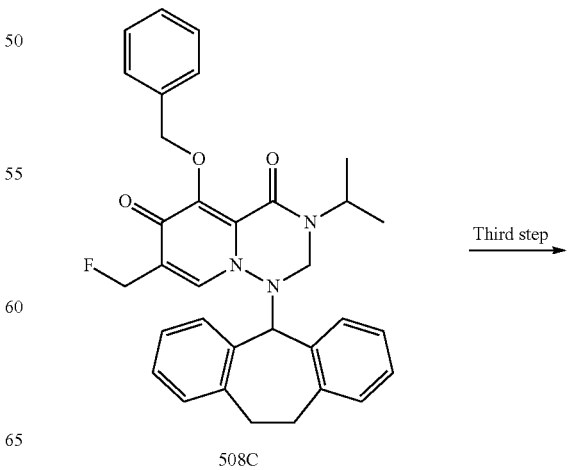
508C
Third step →

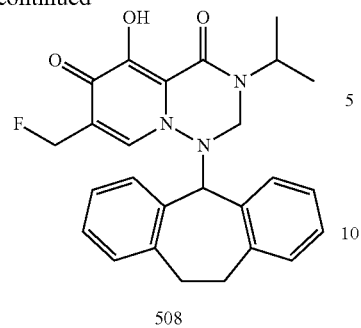

508

First Step

Compound 508A (261 mg, 0.475 mmol) which is a synthetic intermediate of Example 491 was dissolved in dimethyformamide (3 ml), triethylamine (0.132 ml, 0.950 mmol) and ethyl chloroformate (0.0910 ml, 0.950 mmol) were added at 0° C., and the mixture was stirred at room temperature for 20 minutes. An aqueous solution (0.5 ml) of sodium borohydride (71.9 mg, 1.90 mmol) was added at 0° C., and the mixture was stirred for 30 minutes. The reaction solution was poured into water, the mixture was extracted with ethyl acetate, and the organic layer was dried with sodium sulfate. The solvent was distilled off under reduced pressure, and the resulting crude product was purified by silica gel column chromatography, and eluted with chloroform-methanol (97:3, v/v). Diethyl ether was added, and the precipitated residue was filtered to obtain 107 mg of a white solid 508B.

MS: m/z=536 [M+H]$^+$

Second Step

Compound 508B (100 mg, 0.187 mmol) obtained in the first step was dissolved in dichloromethane (1 ml), DAST (33.1 mg, 0.205 mmol) was added at 0° C., and the mixture was stirred for 30 minutes. The reaction solution was poured into water, the mixture was extracted with chloroform, and the organic layer was dried with sodium sulfate. The solvent was distilled off under reduced pressure, and the resulting crude product was purified by silica gel column chromatography, and eluted with chloroform-methanol (97:3, v/v), to obtain 28 mg of a pale yellow gummy substance 508C.

MS: m/z=538 [M+H]$^+$

Third Step

To compound 508C obtained in the second step were added acetic acid (2 ml) and concentrated sulfuric acid (0.5 ml), and the mixture was stirred at room temperature for 20 minutes. The reaction solution was poured into water, the mixture was extracted with ethyl acetate, and the organic layer was dried with sodium sulfate. Diethyl ether was added, and the precipitated residue was filtered to obtain 4.5 mg of a white solid 508.

MS: m/z=448 [M+H]$^+$

Example 509

[Chemical formula 586]

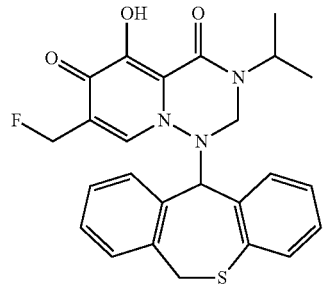

According to Example 508, compound 509 was synthesized by the same procedure.

MS: m/z=466 [M+H]$^+$

Example 510

[Chemical formula 587]

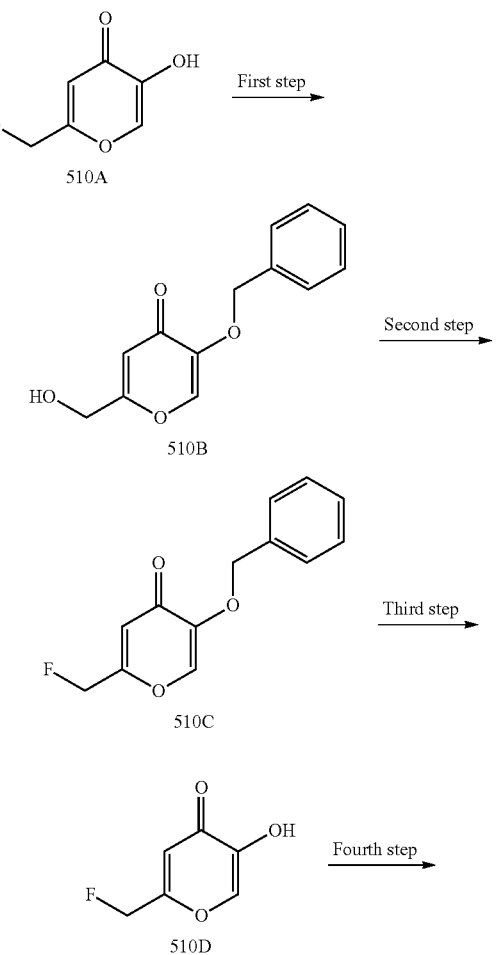

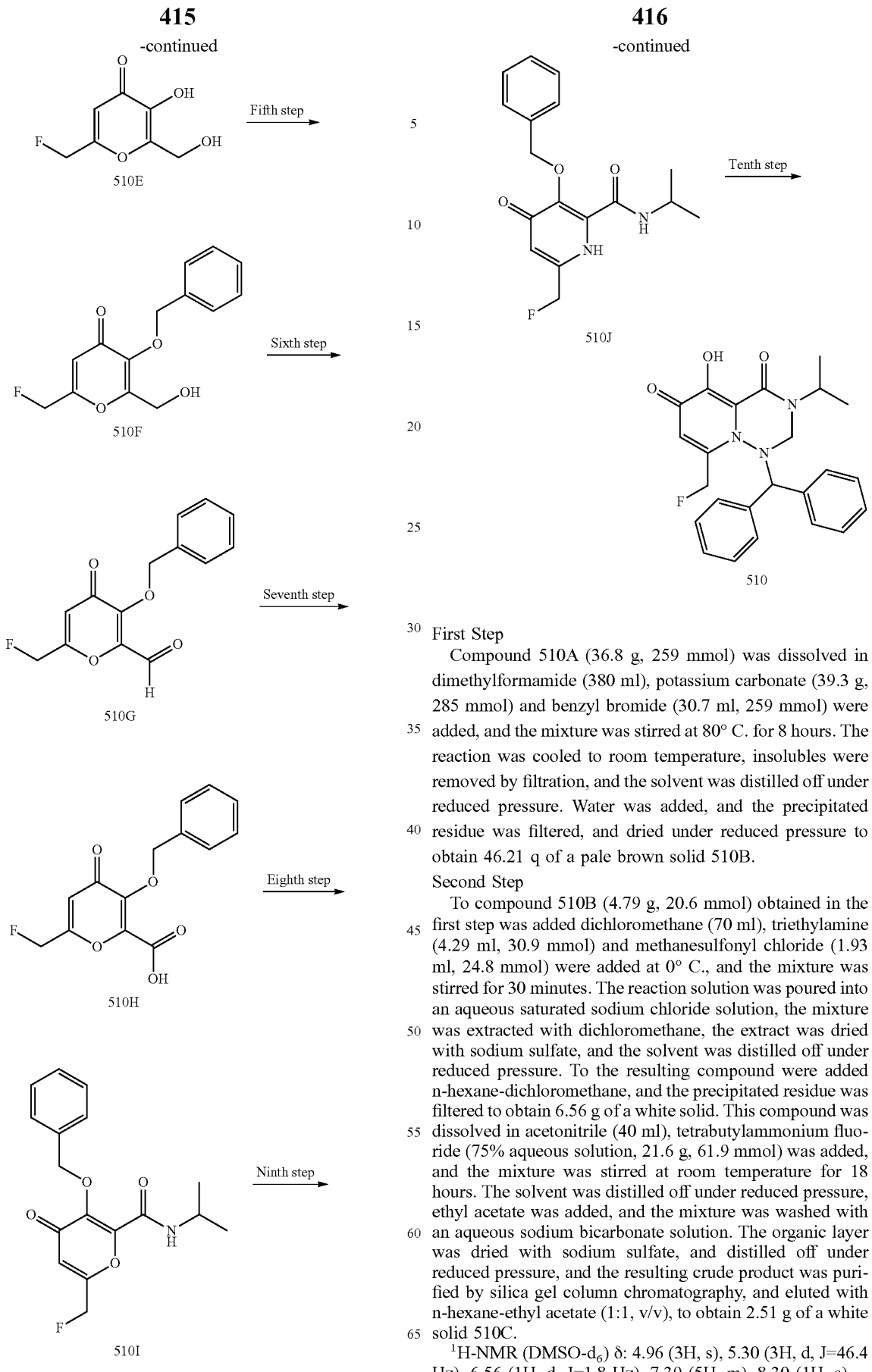

First Step

Compound 510A (36.8 g, 259 mmol) was dissolved in dimethylformamide (380 ml), potassium carbonate (39.3 g, 285 mmol) and benzyl bromide (30.7 ml, 259 mmol) were added, and the mixture was stirred at 80° C. for 8 hours. The reaction was cooled to room temperature, insolubles were removed by filtration, and the solvent was distilled off under reduced pressure. Water was added, and the precipitated residue was filtered, and dried under reduced pressure to obtain 46.21 q of a pale brown solid 510B.

Second Step

To compound 510B (4.79 g, 20.6 mmol) obtained in the first step was added dichloromethane (70 ml), triethylamine (4.29 ml, 30.9 mmol) and methanesulfonyl chloride (1.93 ml, 24.8 mmol) were added at 0° C., and the mixture was stirred for 30 minutes. The reaction solution was poured into an aqueous saturated sodium chloride solution, the mixture was extracted with dichloromethane, the extract was dried with sodium sulfate, and the solvent was distilled off under reduced pressure. To the resulting compound were added n-hexane-dichloromethane, and the precipitated residue was filtered to obtain 6.56 g of a white solid. This compound was dissolved in acetonitrile (40 ml), tetrabutylammonium fluoride (75% aqueous solution, 21.6 g, 61.9 mmol) was added, and the mixture was stirred at room temperature for 18 hours. The solvent was distilled off under reduced pressure, ethyl acetate was added, and the mixture was washed with an aqueous sodium bicarbonate solution. The organic layer was dried with sodium sulfate, and distilled off under reduced pressure, and the resulting crude product was purified by silica gel column chromatography, and eluted with n-hexane-ethyl acetate (1:1, v/v), to obtain 2.51 g of a white solid 510C.

$^1$H-NMR (DMSO-d$_6$) δ: 4.96 (3H, s), 5.30 (3H, d, J=46.4 Hz), 6.56 (1H, d, J=1.8 Hz), 7.39 (5H, m), 8.30 (1H, s).

Third Step

Compound 510C (2.40 g, 10.3 mmol) obtained in the second step was dissolved in dichloromethane (40 ml), boron tribromide (1M dichloromethane solution, 10.3 ml, 10.3 mmol) was added dropwise at 0° C., and the mixture was stirred for 30 minutes. Methanol was added, the solvent was distilled off under reduced pressure, ethyl acetate was added, and the mixture was washed with an aqueous saturated sodium chloride solution. The organic layer was dried with sodium sulfate, the solvent was distilled off under reduced pressure, and the resulting solid was washed with diethyl ether to obtain 940 mg of 510D.

$^1$H-NMR (CDCl$_3$) δ: 5.20 (2H, d, J=46.3 Hz), 6.40 (1H, s), 6.62 (1H, s), 7.91 (1H, s).

Fourth Step

Compound 510D (940 mg, 6.52 mmol) obtained in the third step was dissolved in methanol (8 ml), a 2N aqueous sodium hydroxide solution (3.26 ml, 6.52 mmol) and a 37% aqueous formaldehyde solution (1.46 ml, 19.6 mmol) were added at 0° C., and the mixture was stirred at room temperature for 20 hours. To the reaction solution was added an aqueous saturated ammonium chloride solution, and the solvent was distilled off under reduced pressure. Hydrochloric acid was added, the mixture was extracted with chloroform, and the organic layer was dried with sodium sulfate. The solvent was distilled off under reduced pressure, to the resulting compound were added n-hexane-dichloromethane-ethyl acetate, and the precipitated residue was filtered to obtain 858 mg of a pale yellow solid 510E.

$^1$H-NMR (CDCl$_3$) δ: 4.73 (2H, s), 5.19 (2H, d, J=46.1 Hz), 6.55 (1H, s).

Fifth Step

Compound 510E (855 mg, 4.91 mmol) obtained in the fourth step was dissolved in dimethylformamide (10 ml), potassium carbonate (746 mg, 5.40 mmol) and benzyl bromide (0.583 ml, 4.91 mmol) were added, and the mixture was stirred at 80° C. for 5 hours. Insolubles were removed by filtration, and the filtrate was distilled off under reduced pressure. The resulting crude product was purified by silica gel column chromatography, and eluted with chloroform-methanol (97:3, v/v), to obtain 887 mg of a pale orange solid 510F.

$^1$H-NMR (CDCl$_3$) δ: 1.39 (1H, t, J=7.1 Hz), 4.31 (2H, d, J=7.2 Hz), 5.12 (2H, dd, J=46.3, 0.7 Hz), 5.23 (2H, s), 6.50 (1H, s), 7.33-7.43 (5H, m).

Sixth Step

Compound 510F (887 mg, 3.36 mmol) obtained in the fifth step was dissolved in chloroform, manganese dioxide (2.00 g, 23.0 mmol) was added, and the mixture was stirred at 80° C. for 2 hours. After cooled to room temperature, the mixture was filtered with celite, and the solvent was distilled off under reduced pressure to obtain 812 mg of a white solid 510G.

$^1$H-NMR (CDCl$_3$) δ: 5.18 (2H, dd, J=45.8, 0.8 Hz), 5.52 (2H, s), 6.60 (1H, d, J=0.8 Hz), 7.32-7.38 (5H, m), 9.86 (1H, s).

Seventh Step

To compound 510G (884 mg, 3.37 mmol) obtained in the sixth step were added acetonitrile and water, monosodium dihydrogen phosphate (809 mg, 6.74 mmol) and sodium hypochlorite (1.01 g, 11.1 mmol) were added, and the mixture was stirred at room temperature for 1 hour. The reaction solution was concentrated, pH was adjusted to 3 with hydrochloric acid, the mixture was extracted with chloroform, and the extract was dried with sodium sulfate. The solvent was distilled off under reduced pressure to obtain 404 mg of a white solid 510H.

$^1$H-NMR (DMSO-d$_6$) δ: 5.17 (2H, s), 5.38 (2H, d, J=46.2 Hz), 6.73 (1H, d, J=1.5 Hz), 7.34-7.51 (5H, m).

Eighth Step

Compound 510H (402 mg, 1.45 mmol) obtained in the seventh step was dissolved in dimethylformamide, N1-((ethylimino)methylene)-N3,N3-dimethylpropane-1,3-diamine hydrochloride (554 mg, 2.89 mmol) and 1H-benzo[d][1,2,3]triazol-1-ol (195 mg, 1.45 mmol) were added, and the mixture was stirred at room temperature for 5 minutes. After propan-2-amine (0.149 ml, 1.73 mmol) was added, the mixture was stirred at room temperature for 1 hour. The reaction solution was concentrated under reduced pressure, water was added, the mixture was extracted with ethyl acetate, and the organic layer was washed with an aqueous sodium bicarbonate solution, and dried with sodium sulfate. The reaction solution was distilled off under reduced pressure, to the resulting compound was added n-hexane, and the precipitated residue was filtered to obtain 3.56 g of a white solid 510I.

$^1$H-NMR (CDCl$_3$) δ: 0.98 (6H, d, J=6.6 Hz), 4.05 (1H, m), 5.24 (2H, dd, J=45.9, 0.9 Hz), 5.41 (2H, s), 6.59 (1H, q, J=0.9 Hz), 7.40 (5H, m), 7.56 (1H, brs).

Ninth Step

Compound 510I (392 mg, 1.23 mmol) obtained in the eighth step was dissolved in ethanol (6 ml), aqueous ammonia (4 ml) was added, and the mixture was stirred at room temperature for 15 hours. The reaction solution was concentrated under reduced pressure, and the resulting crude product was purified by silica gel column chromatography, and eluted with chloroform-methanol (97:3, v/v), to obtain 333 mg of a white solid 510J.

MS: m/z=319 [M+H]$^+$

Tenth Step

Compound 510 was synthesized by the same procedure as that of Example 95.

MS: m/z=422 [M+H]$^+$

Example 511

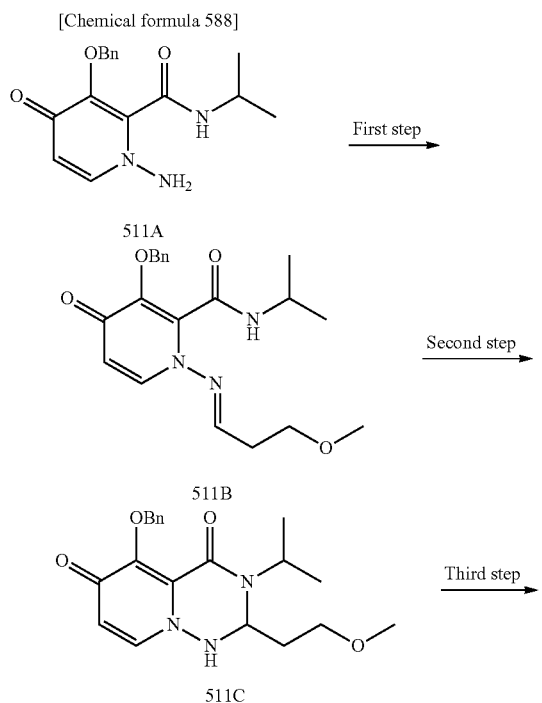

-continued

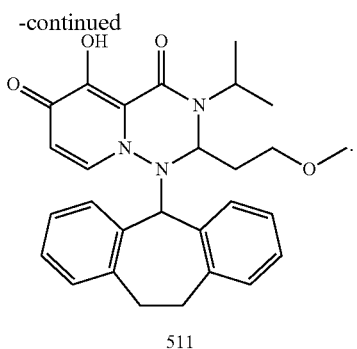

511

First Step

A dichloromethane (90 mL) solution of compound 511A (200 mg, 0.664 mmol) and 1,1,3-trimethoxypropane (178.2 mg, 1.33 mmol) was cooled to 1 to 3° C., and a boron trifluoride diethyl ether complex (113 mg, 0.797 mmol) was added dropwise while the same temperature was retained. After the reaction solution was stirred at the same temperature for 30 minutes, saturated sodium bicarbonate water was added. The dichloromethane layer was separated, and the aqueous layer was extracted with dichloromethane three times. After the combined extracts were dried with sodium sulfate, the solvent was distilled off, and the resulting oil was purified by silica gel column chromatography. The materials were eluted firstly with ethyl acetate and, then, with ethyl acetate-methanol (3:2, v/v). Concentration of an objective fraction afforded 179.2 mg of compound 511B as an oil.

$^1$H-NMR (CDCl$_3$) δ: 1.14 (6H, d, J=6.3 Hz), 2.71 (2H, dd, J=6.0 Hz), 3.34 (3H, s), 3.64 (2H, t, J=6.0 Hz), 4.06-4.17 (1H, m), 5.23 (2H, s), 6.34 (1H, brs), 6.37 (1H, d, J=7.8 Hz), 7.26-7.43 (6H, m), 7.90 (1H, t, J=5.4 Hz).

Second Step

A dimethylformamide (3 ml) solution of compound 511B (179.2 mg, 0.482 mmol) was cooled to 1 to 3° C., cesium carbonate (786 mg, 2.41 mmol) was added while the same temperature was retained, and the mixture was stirred at the same temperature for 15 minutes. The reaction solution was diluted with water, and extracted with chloroform three times. After the combined extracts were dried with sodium sulfate, the solvent was distilled off to obtain 130 mg of compound 511C as a solid.

$^1$H-NMR (CDCl$_3$) δ: 1.22 (3H, d, J=6.9 Hz), 1.28 (3H, d, J=6.9 Hz), 1.59 (2H, brs), 3.22-3.41 (2H, m), 3.12 (3H, s), 4.57-4.70 (2H, m), 5.19 (1H, d, J=10.5 Hz), 5.38 (1H, brs), 5.54 (1H, d, J=10.5 Hz), 6.34 (1H, d, J=7.8 Hz), 7.26-7.32 (4H, m), 7.49-7.52 (2H, m).

Third Step

To an acetic acid (2 ml) solution of compound 511C (130 mg, 0.350 mmol) and dibenzosuberol (368 mg, 1.75 mmol) was added dropwise sulfuric acid (0.4 ml) at room temperature, and the mixture was stirred at the same temperature for 30 minutes. The reaction solution was diluted with water, and extracted with ethyl acetate three times. The extract was washed with water once, and dried with sodium sulfate, thereafter, the solvent was distilled off, and the resulting solid was washed with diisopropyl ether to obtain 65 mg of compound 511 as a solid.

$^1$H-NMR (CDCl$_3$) δ: 1.27 (3H, d, J=6.9 Hz), 1.49 (3H, d, J=6.6 Hz), 1.64-1.74 (1H, m), 1.88-1.99 (1H, m), 2.83 (1H, d, J=4.5 Hz, 4.5 Hz, 9.3 Hz), 3.06 (1H, ddd, J=5.6 Hz, 13.2 Hz, 13.2 Hz), 3.19 (3H, s), 3.30-3.44 (1H, m), 3.50-3.57 (1H, m), 3.78-3.92 (1H, m), 4.28 (1H, ddd, J=4.2 Hz, 13.5 Hz, 13.5 Hz), 4.53 (1H, dd, J=3.3 Hz, 10.8 Hz), 4.96 (1H, s), 5.73 (1H, d, J=7.5 Hz), 6.61 (1H, d, J=7.5 Hz), 6.65 (1H, d, J=7.5 Hz), 6.89-6.93 (1H, m), 7.08-7.36 (6H, m).

Using amines which are commercially available or known in the references and acetals which are commercially available or known in the references, and according to Example 511, compounds 512 to 515 were synthesized.

Example 512

[Chemical formula 589]

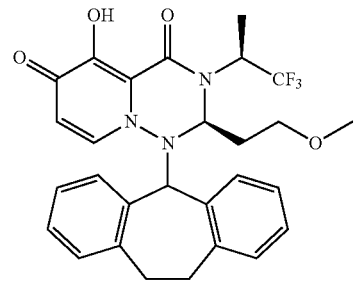

MS: m/z=528 [M+H]$^+$

Example 513

[Chemical formula 590]

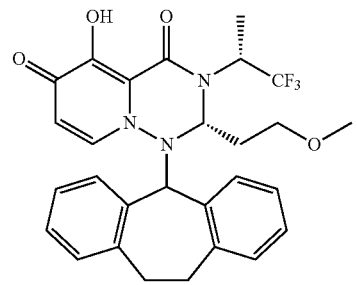

MS: m/z=528 [M+H]$^+$

Example 514

[Chemical formula 591]

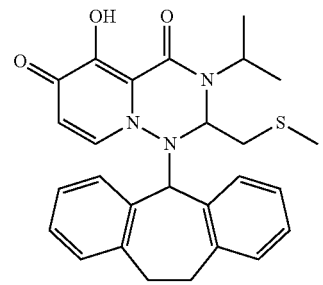

$^1$H-NMR (CDCl$_3$) δ: 1.27 (1H, 3H, d, J=6.9 Hz), 1.48 (3H, d, J=6.6 Hz), 1.95 (3H, s), 2.63-2.68 (2H, m), 2.84 (1H, ddd, J=4.8 Hz, 9.3 Hz, 9.3 Hz), 3.05 (1H, ddd, J=4.2 Hz, 13.2 Hz, 13.2 Hz), 3.60 (1H, ddd, J=4.8 Hz, 4.8 Hz, 17.4 Hz), 3.87-3.98 (1H, m), 4.42 (1H, dd, J=6.6 Hz, 8.1 Hz), 4.59 (1H, ddd, J=4.2 Hz, 13.5 Hz, 13.5 Hz), 4.93 (1H, s), 5.77 (1H, d, J=7.8 Hz), 6.64 (1H, d, J=6.9 Hz), 6.69 (1H, d, J=7.8 Hz), 6.91 (1H, t, J=6.0 Hz), 7.09-7.38 (6H, m).

Example 515

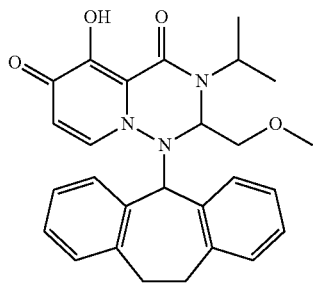

[Chemical formula 592]

$^1$H-NMR (CDCl$_3$) δ: 1.20 (3H, d, J=6.9 Hz), 1.44 (3H, d, J=6.9 Hz), 2.80 (1H, ddd, J=4.5 Hz, 4.5 Hz, 9.3 Hz), 3.07 (1H, ddd, J=4.5 Hz, 13.5 Hz, 13.5 Hz), 3.25 (3H, s), 3.22-3.43 (2H, m), 3.55 (1H, ddd, J=4.2 Hz, 4.2 Hz, 8.7 Hz), 3.85-3.94 (1H, m), 4.36 (1H, dd, J=5.1 Hz, 14.1 Hz), 4.42-4.48 (1H, m), 4.92 (1H, s), 5.78 (1H, d, J=7.5 Hz), 6.59 (1H, d, J=7.8 Hz), 6.64 (1H, d, J=7.5 Hz), 6.91 (1H, t, J=6.9 Hz), 7.09-7.36 (6H, m).

Example 516

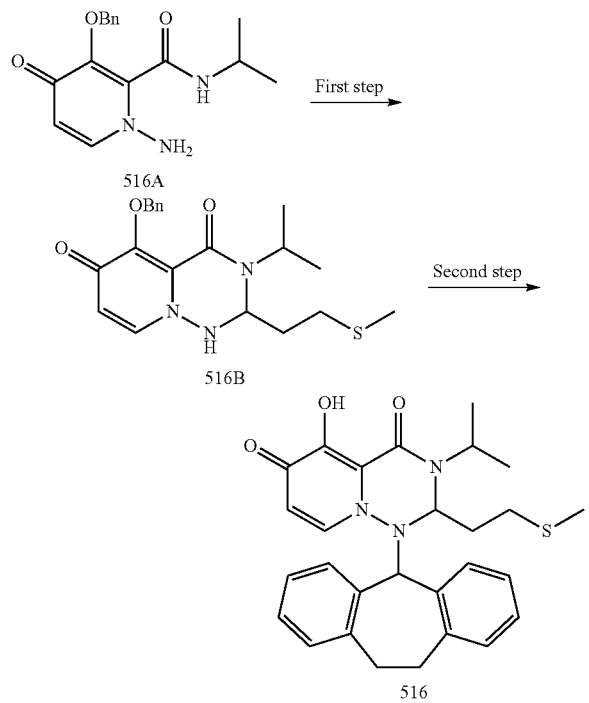

[Chemical formula 593]

First Step

To a toluene (3 ml) solution of compound 516A (100 mg, 0.332 mmol) and 3-(methylthio)propanal (52 mg, 0.498 mmol) was added acetic acid (30 mg, 0.500 mmol), and the mixture was refluxed for 30 minutes. After cooled to room temperature, the solvent was distilled off, and the resulting crude product was dissolved in dimethylformamide (3 ml). The solution was cooled to 1 to 3° C., cesium carbonate (541 mg, 1.66 mmol) was added while the same temperature was retained, and the mixture was stirred at the same temperature for 30 minutes. The reaction solution was diluted with water, and extracted with ethyl acetate three times. The combined extracts were washed with water three times, and dried with sodium sulfate, and the solvent was distilled off. The resulting oil was purified by silica gel column chromatography. The materials were eluted firstly with ethyl acetate and, then, with ethyl acetate-methanol (7:3, v/v). Concentration of an objective fraction afforded 84.7 mg of compound 516B as an oil.

$^1$H-NMR (CDCl$_3$) δ: 1.21 (3H, J=6.9 Hz), 1.28 (3H, d, J=6, 9 Hz), 1.31-1.56 (2H, m), 2.05 (3H, s), 2.46 (2H, dd, J=5.4 Hz, 7.8 Hz), 4.57-4.71 (2H, m), 5.18 (1H, d, J=10.5 Hz), 5.51 (1H, d, J=10.5 Hz), 5.66 (1H, brs), 6.33 (1H, d, J=7.8 Hz), 7.19-7.35 (4H, m), 7.46-7.49 (2H, m).

Second Step

Compound 516 was synthesized by the same procedure as that of Example 511.

$^1$H-NMR (CDCl$_3$) δ: 1.29 (3H, d, J=6.9 Hz), 1.49 (3H, d, J=6.6 Hz), 1.82-1.89 (2H, m), 1.99 (3H, s), 2.41-2.58 (2H, m), 2.86 (1H, ddd, J=4.5 Hz, 4.5 Hz, 14.1 Hz), 2.99-3.11 (1H, m), 3.53 (1H, ddd, J=4.5 Hz, 4.5 Hz, 17.7 Hz), 4.87-3.96 (1H, m), 4.21 (1H, ddd, J=3.9 Hz, 12.9 Hz, 12.9 Hz), 4.53 (1H, dd, J=5.1 Hz, 8.7 Hz), 4.96 (1H, s), 5.74 (1H, d, J=7.5 Hz), 6.62 (1H, d, J=7.5 Hz), 6.64 (1H, d, J=9.0 Hz), 6.89-6.94 (1H, m), 7.07-7.37 (6H, m).

Using amines which are commercially available or known in the references and aldehydes which are commercially available or known in the references, and according to Example 516, compounds 517 to 526 were synthesized.

Example 517

[Chemical formula 594]

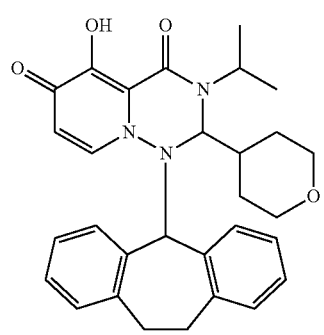

MS: m/z=500 [M+H]$^+$

Example 518

[Chemical formula 595]

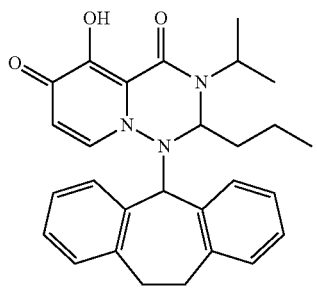

¹H-NMR (CDCl₃) δ: 1.78 (3H, t, J=6.9 Hz), 1.19-1.30 (1H, m), 1.29 (3H, d, J=6.9 Hz), 1.43-1.62 (3H, m), 1.50 (3H, d, J=6.9 Hz), 2.84 (1H, ddd, J=4.5 Hz, 4.5 Hz, 14.1 Hz), 3.00-3.11 (1H, ddd, J=3.9 Hz, 12.9 Hz, 12.9 Hz), 3.52 (1H, ddd, J=4.5 Hz, 4.5 Hz, 17.4 Hz), 3.79-3.88 (1H, m), 4.23-4.35 (2H, m), 4.96 (1H, s), 5.74 (1H, d, J=7.8 Hz), 6.61 (1H, d, J=7.5 Hz), 6.65 (1H, dd, J=1.2 Hz, 7.8 Hz), 6.91 (1H, ddd, J=1.5 Hz, 7.5 Hz, 7.5 Hz), 7.08-7.37 (6H, m).

Example 519

[Chemical formula 596]

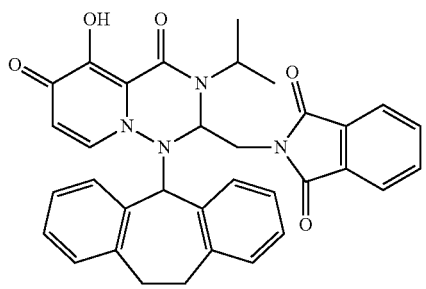

¹H-NMR (CDCl₃) δ: 1.44 (3H, d, J=6.9 Hz), 1.54 (3H, d, J=6.6 Hz), 1.88 (1H, ddd, J=3.9 Hz, 3.9 Hz, 14.4 Hz), 2.72 (1H, ddd, J=3.6 Hz, 14.1 Hz, 14.1 Hz), 3.15 (1H, ddd, J=4.2 Hz, 4.2 Hz, 16.5 Hz), 3.54 (1H, dd, J=3.0 Hz, 14.4 Hz), 3.66 (1H, ddd, J=3.9 Hz, 13.8 Hz, 13.8 Hz), 4.03 (1H, dd, J=10.5 Hz, 14.1 Hz), 4.27-4.26 (1H, m), 4.64 (1H, dd, J=2.7 Hz, 10.5 Hz), 4.92 (1H, s), 5.80 (1H, d, J=7.8 Hz), 6.62-6.70 (2H, m), 6.69 (1H, d, J=7.8 Hz), 6.89 (1H, t, J=7.5 Hz), 6.96 (1H, d, J=7.5 Hz), 7.09-7.25 (4H, m), 7.77-7.89 (4H, m).

Example 520

[Chemical formula 597]

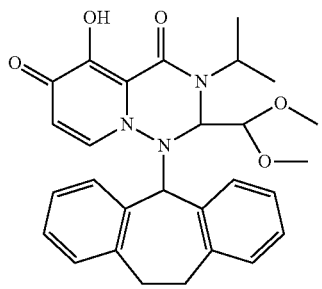

¹H-NMR (CDCl₃) δ: 1.30 (3H, d, J=6.6 Hz), 1.54 (3H, d, J=6.6 Hz), 2.83 (1H, ddd, J=4.8 Hz, 4.8 Hz, 14.1 Hz), 3.03-3.14 (1H, m), 3.21 (3H, s), 3.30 (3H, s), 3.53 (1H, ddd, J=4.5 Hz, 4.5 Hz, 17.7 Hz), 3.61-3.70 (1H, m), 4.18 (1H, d, J=5.4 Hz), 4.26 (1H, d, J=5.4 Hz), 4.45 (1H, ddd, J=4.5 Hz, 13.8 Hz, 13.8 Hz), 4.92 (1H, s), 5.72 (1H, d, J=7.8 Hz), 6.63 (1H, d, J=7.8 Hz), 6.65 (1H, d, J=6.6 Hz), 6.91 (1H, t, J=6.0 Hz), 7.08-7.36 (6H, m).

Example 521

[Chemical formula 598]

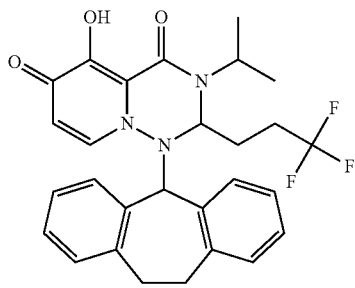

¹H-NMR (CDCl₃) δ: 1.30 (2.52H, d, J=6.9 Hz), 1.36 (0.48H, d, J=6.9 Hz), 1.42 (0.48H, d, J=6.9 Hz), 1.50 (2.52H, d, J=6.9 Hz), 1.74-1.98 (1H, m), 2.00-2.12 (1H, m), 2.16-2.35 (1H, m), 2.89 (1H, ddd, J=5.1 Hz, 5.1 Hz, 13.5 Hz), 3.06 (1H, ddd, J=3.9 Hz, 12.9 Hz, 12.9H), 3.52 (1H, d, J=4.2 Hz, 4.2 Hz, 17.4 Hz), 3.86-3.96 (1H, m), 4.15 (1H, ddd, J=3.9 Hz, 13.5 Hz, 13.5 Hz), 4.32 (1H, dd, J=3.9 Hz, 10.8 Hz), 4.48-4.64 (1H, m), 4.97 (0.84H, s), 5.30 (0.16H, s), 5.73 (0.84H, d, J=7.8 Hz), 6.20 (0.16H, d, J=7.5 Hz), 6.45 (0.16H, brs), 6.61 (1H, d, J=7.5 Hz), 6.64 (0.84H, d, J=8.7 Hz), 6.92 (1H, t, J=6.3 Hz), 7.10 (1H, d, J=7.5 Hz), 7.15-7.39 (3H, m).

Example 522

[Chemical formula 599]

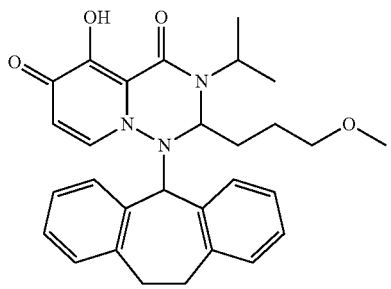

¹H-NMR (CDCl₃) δ: 1.28 (3H, d, J=6.9 Hz), 1.49 (3H, d, J=6.9 Hz), 1.54-1.79 (4H, m), 2.84 (1H, ddd, J=4.8 Hz, 4.8 Hz, 14.1 Hz), 3.05 (1H, ddd, J=4.2 Hz, 13.5 Hz, 13.5 Hz), 3.17 (3H, s), 3.17-3.21 (2H, m), 3.52 (1H, ddd, J=4.2 Hz, 4.2 Hz, 17.7 Hz), 3.83-3.92 (1H, m), 4.22-4.32 (2H, m), 4.96 (1H, s), 5.73 (1H, d, J=7.5 Hz), 6.62 (1H, d, J=7.8 Hz), 6.65 (1H, d, J=8.1 Hz), 6.92 (1H, t, J=7.2 Hz), 7.07-7.37 (6H, m).

Example 523

[Chemical formula 600]

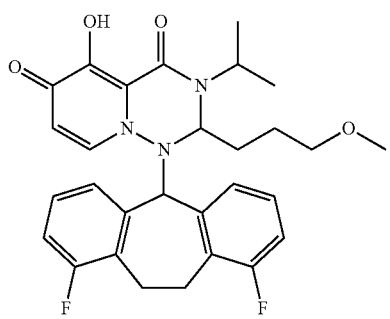

¹H-NMR (CDCl₃) δ: 1.19-1.28 (1H, m), 1.28 (3H, d, J=6.9 Hz), 1.40-1.82 (4H, m), 1.48 (3H, d, J=6.6 Hz), 2.89-3.00 z81H, m), 3.17 (3H, s), 3.20-3.27 (2H, m), 3.31-3.40 (1H, m), 3.44-3.53 (1H, m), 3.86-3.98 (2H, m), 4.38 (1H, dd, J=3.6 Hz, 10.5 Hz), 5.05 (1H, s), 5.84 (1H, d, 7.5 Hz), 6.48-6.50 (1H, m), 6.66-6.69 (1H, m), 6.89-7.00 (2H, m), 7.05 (1H, d, 7.2 Hz), 7.11-7.24 (2H, m).

Example 524

[Chemical formula 601]

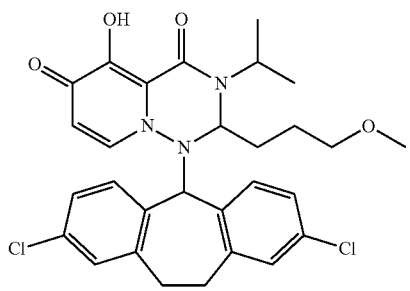

¹H-NMR (CDCl₃) δ: 1.29 (3H, d, J=6.9 Hz), 1.42-1.83 (4H, m), 1.48 (3H, d, J=6.6 Hz), 2.80 (1H, ddd, J=4.5 Hz, 4.5 Hz), 14.4Hz), 2.94-3.11 (1H, m), 3.18 (3H, s), 3.21-3.26 (2H, m), 3.49 (1H, ddd, J=4.2 Hz, 4.2 Hz, 18.0 Hz), 3.82-3.91 (1H, m), 4.20-4.33 (2H, m), 5.83 (1H, s), 5.84 (1Hm d, J=7.8 Hz), 6.58-6.72 (2H, m), 6.91-6.94 (1H, m), 7.11-7.30 (4H, m).

Example 525

[Chemical formula 602]

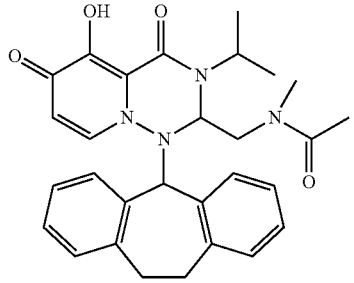

¹H-NMR (CDCl₃) δ: 1.29 (3H, d, J=6.9 Hz), 1.47 (3H, d, J=6.6 Hz), 2.10 (3H, s), 2.78 (1H, ddd, J=4.2 Hz, 4.2 Hz, 13.8 Hz), 2.97 (3H, s), 3.01-3.13 (2H, m), 3.47 (1H, ddd, J=4.2 Hz, 4.2 Hz, 17.7 Hz), 3.65 (1H, dd, J=3.3 Hz, 14.1 Hz), 3.99-4.23 (2H, m), 4.70 (1H, dd, J=3.3 Hz, 10.2 Hz), 4.95 (1H, s), 5.78 (1H, d, J=7.8 Hz), 6.61 (1H, d, J=7.8 Hz), 6.65 (1H, d, J=7.5 Hz), 6.93 (1H, t, J=6.6 Hz), 7.09 (1H, d, J=7.5 Hz), 7.15-7.27 (4H, m), 7.30-7.37 (1H, m).

Example 526

[Chemical formula 603]

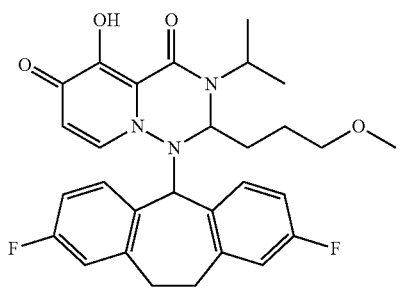

¹H-NMR (CDCl₃) δ: 1.57-1.34 (1H, m), 1.29 (3H, d, J=6.9 Hz), 1.41-1.52 (1H, m), 1.48 (3H, d, J=6.6 Hz), 1.59-1.81 (2H, m), 2.80 (1H, ddd, 4.5 Hz, 4.5 Hz, 14.4 Hz), 3.04 (1H, ddd, J=4.2 Hz, 13.2 Hz, 13.2 Hz), 3.14-3.26 (2H, m), 3.18 (3H, s), 3.49 (1H, ddd, J=4.8 Hz, 4.8 Hz, 17.7 Hz), 3.84-3.93 (1H, m), 4.23-4.34 (2H, m), 4.96 (1H, s), 5.81 (1H, d, J=7.5 Hz), 6.60-6.79 (3H, m), 6.81 (1Hm d, J=9.3 Hz), 6.92 (1H, ddd, J=2.7 Hz, 8.4 Hz, 8.4 Hz), 7.19-7.24 (1H, m).

Example 527

[Chemical formula 604]

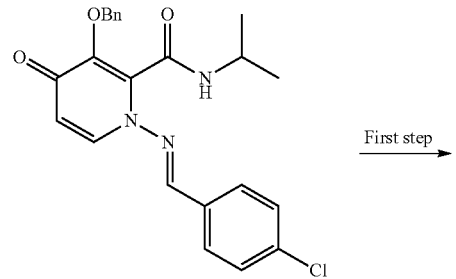

527A

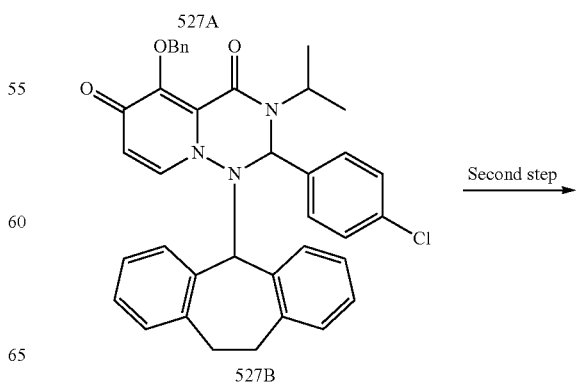

527B

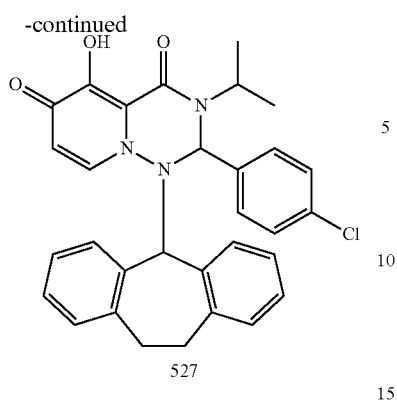

527

First Step

A DMF (0.2 mL) solution of compound 527A (36 mg, 0.09 mmol) synthesized according to the method of synthesizing compound 516 was cooled to 1 to 3° C., 5-chlorodibenzosuberane (97 mg, 0.43 mmol) and cesium carbonate (138 mg, 0.43 mmol) were added, and the mixture was stirred at room temperature overnight. To the reaction solution was added water, and the mixture was distributed between ethyl acetate and water. The organic layer was washed with an aqueous saturated sodium chloride solution, and dried. The solvent was distilled off, and the resulting oil was subjected to silica gel column chromatography, and eluted with chloroform-methanol. Concentration of an objective fraction afforded 19 mg of compound 527B as an oil.

MS: m/z=616 [M+H]$^+$.

Second Step

Compound 527B (19 mg, 0.03 mmol) was dissolved in MeOH (0.6 mL), 10% Pd—C (3 mg) was added, and the mixture was subjected to a catalytic reduction under hydrogen stream. The catalyst was removed by filtration, and the filtrate was concentrated. The resulting oil was subjected to diol silica gel column chromatography, and eluted with chloroform-methanol. Concentration of an objective fraction afforded 7 mg of compound 527 as an oil.

MS: m/z=526 [M+H]$^+$.

Using halides which are commercially available or known in the references and aldehydes which are commercially available or known in the references, and according to the method of Example 527, compounds 528 to 531 were synthesized.

Example 528

[Chemical formula 605]

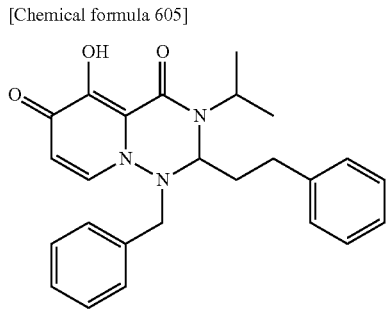 [SMILES: CC(C)N1C(=O)c2c(O)c(=O)ccn2N(Cc2ccccc2)C1CCc1ccccc1]

MS: m/z=418 [M+H]$^+$

Example 529

[Chemical formula 606]

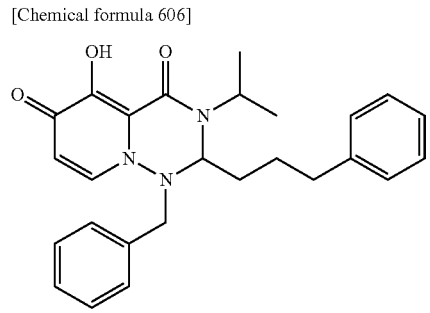 [SMILES: CC(C)N1C(=O)c2c(O)c(=O)ccn2N(Cc2ccccc2)C1CCCc1ccccc1]

MS: m/z=432 [M+H]$^+$

Example 530

[Chemical formula 607]

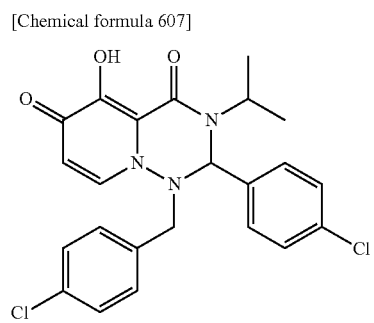

MS: m/z=459 [M+H]$^+$

Example 531

[Chemical formula 608]

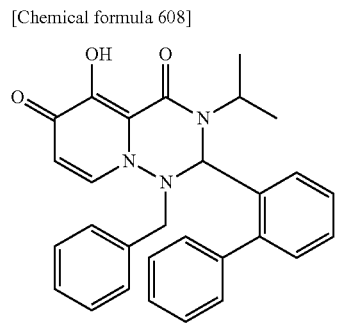 [SMILES: CC(C)N1C(=O)c2c(O)c(=O)ccn2N(Cc2ccccc2)C1c1ccccc1-c1ccccc1]

MS: m/z=466 [M+H]$^+$

Example 532

[Chemical formula 609]

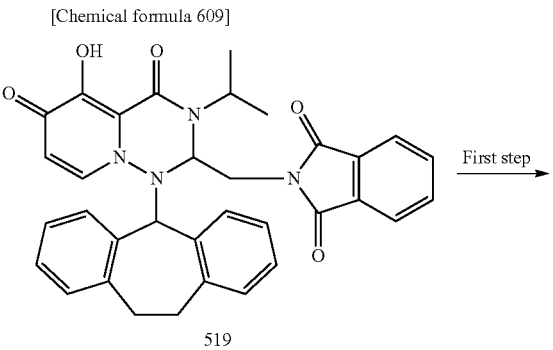

First Step

To a methanol (5 ml) solution of compound 519 (440 mg, 0.766 mmol) was added hydrazine hydrate (383 mg, 7.66 mmol), and the mixture was refluxed for 1 hour. After cooled to room temperature, the precipitated insolubles were filtered off. After the solvent was distilled off, the residue was suspended in ethyl acetate, the insolubles were filtered off, and the solvent was distilled off. The resulting crude product was suspended in chloroform, and insolubles were filtered off. The solvent was distilled off, and the resulting crude product was washed with ethyl acetate-diisopropyl ether to obtain 190 mg of compound 532 as a solid.

$^1$H-NMR (CDCl$_3$) δ: 1.24 (3H, d, J=6.9H), 1.46 (3H, d, J=6.6 Hz), 2.73-2.90 (3H, m), 3.08 (1H, ddd, J=4.2 Hz, 12.9 Hz, 12.9 Hz), 3.54 (1H, ddd, J=4.5 Hz, 4.5 Hz, 17.7 Hz), 3.85-3.94 (1H, m), 4.19 (1H, dd, J=7.2 Hz, 11.1 Hz), 4.35 (1H, ddd, J=4.5 Hz, 13.8 Hz, 13.8 Hz), 4.97 (1H, s), 5.74 (1H, d, J=7.5 Hz), 6.60 (1H, d, J=7.8 Hz), 6.65 (1H, d, J=7.2 Hz), 6.92 (1H, t, J=6.3 Hz), 7.09-7.45 (6H, m).

Example 533

[Chemical formula 610]

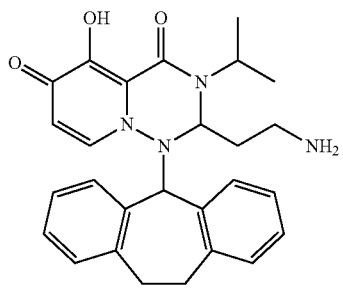

Compound 533 was synthesized by the same procedure as that of Example 532.

$^1$H-NMR (DMSO-d$_6$) δ: 1.22 (3H, d, J=6.6 Hz), 1.40 (3H, d, J=6.6 Hz), 1.45-1.58 (1H, m), 1.62-1.75 (1H, m), 2.61-2.69 (1H, m), 2.71-2.84 (1H, m), 2.88-2.95 (1H, m), 3.16-3.34 (1H, m), 3.60-3.64 (1H, m), 3.92-4.00 (1H, m), 4.24-4.33 (1H, m), 4.42-4.46 (1H, dd, J=3.3 Hz, 10.8 Hz), 5.10 (1H, s), 5.47 (1H, d, J=7.5 Hz), 6.70 (1H, d, J=7.5 Hz), 6.88 (1H, t, J=7.5 Hz), 7.02 (1H, d, J=10.8 Hz), 7.09-7.16 (2H, m), 7.19-7.25 (1H, m), 7.33 (2H, d, 4.2 Hz), 7.42 (1H, d, J=7.5 Hz).

Example 534

[Chemical formula 611]

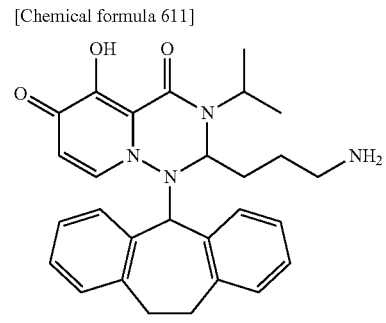

Compound 534 was synthesized by the same procedure as that of Example 532.

$^1$H-NMR (DMSO-d$_6$) δ: 1.25 (3H, d, J=6.9 Hz), 1.44 (3H, d, J=6.6 Hz), 1.32-1.58 (2H, m), 1.77-1.79 (2H, m), 2.64-2.73 (1H, m), 2.79-3.00 (2H, m), 3.88-3.97 (2H, m), 4.19-4.28 (2H, m), 5.15 (1H, s), 5.67 (1H, d, J=7.5 Hz), 5.73 (1H, d, J=7.5 Hz), 6.90 (1H, t, J=6.6 Hz), 7.03 (1H, d, J=7.5 Hz), 7.13-7.32 (3H, m), 7.36 (2H, d, J=4.2 Hz), 7.44 (1H, J=7.2 Hz), 7.75 (1H, brs).

Example 535

[Chemical formula 612]

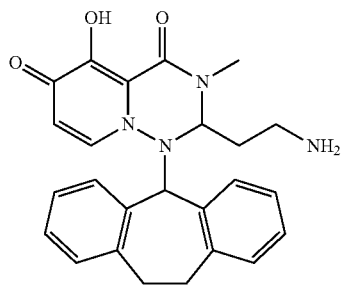

Compound 535 was synthesized by the same procedure as that of Example 532.

$^1$H-NMR (DMSO-d$_6$) δ: 1.40-1.52 (1H, m), 1.61-1.72 (1H, m), 2.40-2.49 (1H, m), 2.58-2.62 (1H, m), 2.78-2.86 (1H, m), 2.89-2.95 (1H, m), 2.95 (3H, m), 3.66-3.74 (1H, m), 4.01-4.13 (1H, m), 4.28-4.32 (1H, m), 5.14 (1H, m), 5.51 (1H, d, J=7.8 Hz), 6.72 (1H, d, J=7.5 Hz), 6.91-6.94 (2H, m), 7.14-7.40 (6H, m).

Example 536

[Chemical formula 613]

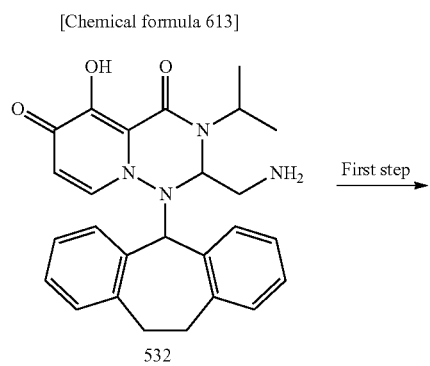

532

First step →

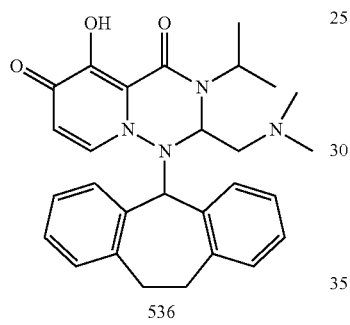

536

First Step

A dichloromethane (1 ml) solution of compound 532 (30 mg, 0.0675 mmol) and a 38% aqueous formalin solution (53.5 mg, 0.675 mmol) was cooled to 1 to 3° C., sodium triacetoxyhydroborate (42.9 mg, 0.293 mmol) and acetic acid (10 mg, 0.166 mmol) were added while the same temperature was retained. After the reaction solution was stirred at the same temperature for 30 minutes, saturated sodium bicarbonate water was added, and the mixture was extracted with ethyl acetate three times. The combined extracts were washed with water once, and dried with sodium sulfate, and the solvent was distilled off. The resulting crude product was washed with ethyl acetate-diisopropyl ether to obtain 20 mg of compound 536 as a solid.

$^1$H-NMR (CDCl$_3$) δ: 1.22 (3H, d, J=6.6 Hz), 1.44 (3H, d, J=6.9 Hz), 2.06 (6H, s), 2.29 (1H, dd, J=4.5 Hz, 13.2 Hz), 4.23 (1H, dd, J=8.4 Hz, 13.2 Hz), 2.78 (1H, ddd, J=4.5 Hz, 4.5 Hz, 14.1 Hz, 3.06 (1H, J=4.2 Hz, 13.5 Hz, 13.5 Hz), 3.55 (1H, ddd, J=4.2 Hz, 4.2 Hz, 17.7 Hz), 3.83-3.92 (1H, m), 4.34 (1H, dd, J=4.5 Hz, 8.4 Hz), 4.54 (1H, ddd, J=4.5 Hz, 13.8 Hz, 13.8 Hz), 4.91 (1H, s), 5.74 (1H, d, J=7.5 Hz), 6.63 (1H, d, J=7.8 Hz), 6.64 (1H, d, J=7.8 Hz), 6.88-6.93 (1H, m), 7.08-7.45 (6H, m).

Example 537

[Chemical formula 614]

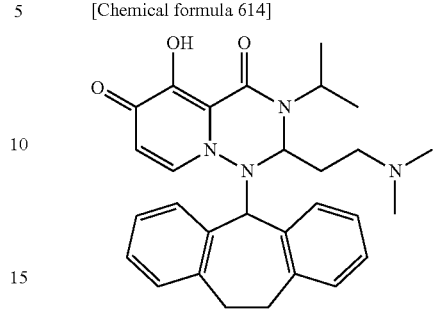

Compound 537 was synthesized by the same procedure as that of Example 536.

$^1$H-NMR (DMSO-d$_6$) δ: 1.25 (3H, d, J=6.6 Hz), 1.40 (3H, d, J=6.6 Hz), 1.46-1.57 (1H, m), 1.68-1.79 (1H, m), 1.98 (6H, s), 2.04-2.11 (1H, m), 2.27-2.41 (1H, m), 2.72-2.94 (2H, m), 3.55-3.64 (1H, m), 3.91-4.00 (1H, m), 4.29-4.44 (2H, m), 5.10 (1H, s), 5.48 (1H, d, J=7.8 Hz), 6.71 (1H, d, J=7.8 Hz), 6.86-6.90 (1H, m), 7.05-7.24 (4H, m), 7.33 (2H, d, J=4.2 Hz), 7.40 (1H, d, J=7.5 Hz).

Example 538

[Chemical formula 615]

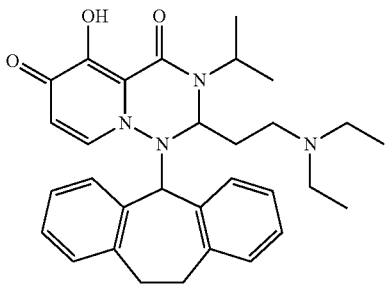

Compound 538 was synthesized by the same procedure as that of Example 536.

$^1$H-NMR (DMSO-d$_6$) δ: 0.75 (6H, t, J=6.6 Hz), 1.28 (3H, d, J=6.6 Hz), 1.41 (3H, d, J=6.6 Hz), 1.45-1.56 (1H, m), 1.67-1.78 (1H, m), 2.22-2.49 (4H, m), 2.74-2.97 (2H, m), 3.94-4.03 (1H, m), 4.29-4.41 (2H, m), 5.11 (1H, s), 5.48 (1H, d, J=7.8 Hz), 6.71 (1H, d, J=6.9 Hz), 6.87 (1H, t, J=7.2 Hz), 7.06-7.25 (4H, m), 7.33 (2H, d, J=7.2 Hz), 7.35 (1H, m).

Example 539

[Chemical formula 616]

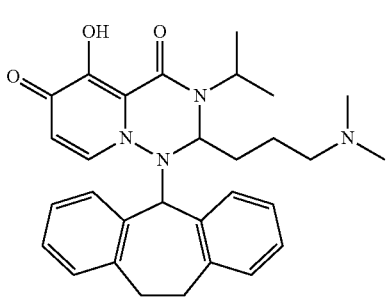

Compound 539 was synthesized by the same procedure as that of Example 536.

¹H-NMR (DMSO-d₆) δ: 1.25 (3H, d, J=6.6 Hz), 1.44 (3H, d, J=6.6 Hz), 1.42-1.51 (2H, m), 1.75-1.91 (2H, m), 2.62-2.67 (1H, m), 2.65 (6H, s), 2.74-2.97 (3H, m), 3.57-3.63 (1H, m), 3.91-3.26 (4H, m), 5.16 (1H, s), 5.73 (1H, d, J=7.5 Hz), 6.71 (1H, d, J=7.2 Hz), 6.89 (1H, t, J=6.9 Hz), 7.12-7.28 (4H, m), 7.33-7.45 (3H, m).

Example 540

[Chemical formula 617]

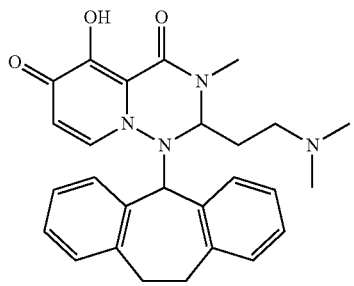

Compound 540 was synthesized by the same procedure as that of Example 536.

¹H-NMR (CDCl₃) δ: 1.58-1.78 (2H, m), 2.06 (6H, s), 2.15-2.35 (2H, m), 2.84-2.93 (1H, m), 2.96-3.11 (1H, m), 3.00 (3H, s), 3.65-3.74 (1H, m), 3.99-4.14 (1H, m), 4.28-4.33 (1H, m), 4.94 (1H, s), 5.78 (1H, d, J=7.5 Hz), 6.56 (1H, d, J=7.8 Hz), 8.66 (1H, d, J=7.2 Hz), 6.95 (t, J=7.2 Hz), 7.13-7.38 (6H, m).

Example 541

[Chemical formula 618]

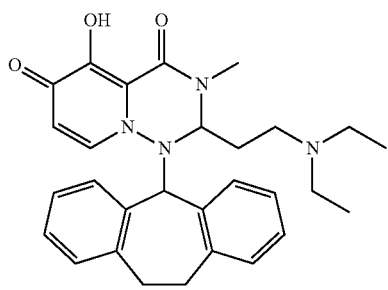

Compound 541 was synthesized by the same procedure as that of Example 536.

¹H-NMR (CDCl₃) δ: 0.846 (6H, t, J=7.2 Hz), 1.49-1.75 (2H, m), 2.30-2.41 (5H, m), 2.43-2.53 (1H, m), 2.85-2.93 (1H, m), 2.98-3.08 (1H, m), 3.01 (3H, s), 3.63-3.74 (1H, m), 3.97-4.07 (1H, m), 4.30 (1H, dd, J=5.1 Hz, 8.1 Hz), 4.95 (1H, s), 5.77 (1H, d, J=6.0 Hz), 6.56 (1H, d, J=7.8 Hz), 6.65 (1H, d, J=7.8 Hz), 6.95 (1H, t, J=6.3 Hz), 7.13-7.38 (6H, m).

Example 542

[Chemical formula 619]

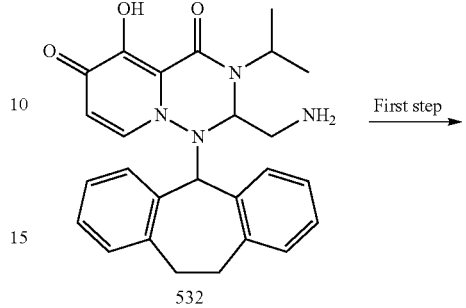

First Step

A dichloromethane (1 ml) solution of compound 532 (30 mg, 0.0675 mmol) and triethylamine (20.5 mg, 0.202 mmol) was cooled to 1 to 3° C., and acetic acid anhydride (10.3 mg, 0.101 mmol) was added while the same temperature was retained. After the reaction solution was stirred at the same temperature for 30 minutes, water was added, and the mixture was extracted with ethyl acetate three times. The combined extracts were washed with water once, and dried with sodium sulfate, and the solvent was distilled off. The resulting crude product was washed with ethyl acetate-diisopropyl ether to obtain 15 mg of compound 542 as a solid.

¹H-NMR (CDCl₃) δ: 1.30 (3H, d, J=6.9 Hz), 1.47 (3H, d, J=6.6 Hz), 2.00 (3H, s), 2.78-2.94 (2H, m), 3.04 (1H, ddd, J=4.2 Hz, 13.5 Hz, 13.5 Hz), 3.48-3.60 (1H, m), 3.98-3.07 (1H, m), 4.36 (1H, ddd, J=4.2 Hz, 13.5 Hz, 13.5 Hz), 4.64 (1H, dd, J=3.9 Hz, 9.3 Hz), 4.87 (1H, s), 5.43 (1H, d, J=7.5 Hz), 6.57 (1H, d, J=7.5 Hz), 6.68 (1H, d, J=7.5 Hz), 6.85 (1H, t, J=6.0 Hz), 7.09-7.36 (6H, m), 7.41 (1H, brs).

Example 543

[Chemical formula 620]

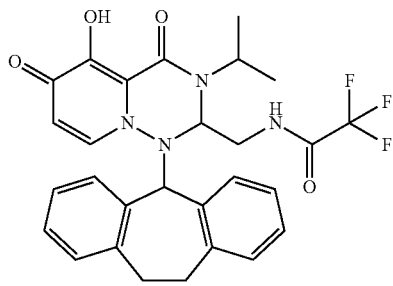

Compound 543 was synthesized by the same procedure as that of Example 542.

$^1$H-NMR (CDCl$_3$) δ: 1.32 (3H, d, J=6.9 Hz), 1.50 (3H, d, J=6.9 Hz), 2.79 (1H, ddd, J=4.2 Hz, 4.2 Hz, 14.4 Hz), 3.01 (1H, ddd, J=3.9 Hz, 13.5 Hz, 13.5 Hz), 3.18-3.28 (1H, m), 3.46-3.59 (2H, m), 4.04-4.18 (1H, m), 4.27 (1H, ddd, J=3.9 Hz, 13.5 Hz, 13.5 Hz), 4.69 (1H, dd, J=3.3 Hz, 9.9 Hz), 4.87 (0.9H, s), 5.17 (0.1H, s), 5.37 (0.9H, d, J=7.8 Hz), 4.50 (0.1H, d, J=7.8H), 6.32 (0.1H, d, J=7.8 Hz), 6.54 (1H, d, J=7.5 Hz), 6.78 (0.9H, d, J=7.5 Hz), 6.84 (1H, t, J=6.6 Hz), 6.91 (0.1H, d, J=6.0 Hz), 7.06-7.51 (6H, m), 9.29 (1H, brs).

Example 544

[Chemical formula 621]

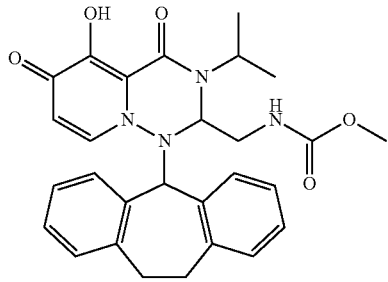

Compound 544 was synthesized by the same procedure as that of Example 542.

$^1$H-NMR (CDCl$_3$) δ: 1.29 (3H, d, J=6.9 Hz), 1.46 (3H, d, J=6.3 Hz), 2.78 (1H, ddd, J=4.5 Hz, 4.5 Hz, 15.9 Hz), 2.94-3.10 (2H, m), 3.19-3.54 (2H, m), 3.64 (3H, s), 3.96-3.11 (1H, m), 4.28 (1H, ddd, J=4.2 Hz, 13.5 Hz, 13.5 Hz), 4.57 (1H, dd, J=3.3 Hz, 9.9 Hz), 4.91 (1H, s), 5.57 (1H, brs), 5.70 (1H, d, J=7.5 Hz), 6.60 (1H, d, J=7.5 Hz), 6.66 (1H, d, J=7.8 Hz), 6.89 (1H, t, J=7.2 Hz), 7.08-7.47 (6H, m).

Example 545

[Chemical formula 622]

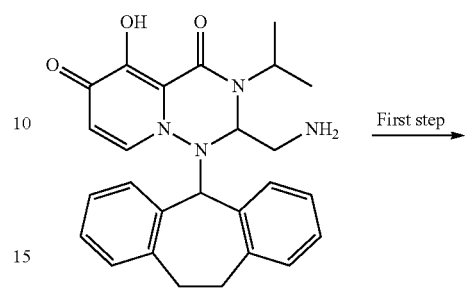

First Step

A dichloromethane (1 ml) solution of compound 532 (30 mg, 0.0675 mmol) and pyridine (16 mg, 0.203 mmol) was cooled to 1 to 3° C., and 2-methoxyacetyl chloride (11 mg, 0.101 mmol) was added while the same temperature was retained. After the reaction solution was stirred at the same temperature for 30 minutes, water was added, and the mixture was extracted with ethyl acetate three times. The combined extracts were washed with water once, and dried with sodium sulfate, and the solvent was distilled off. The resulting crude product was washed with ethyl acetate-diisopropyl ether to obtain 22 mg of compound 545 as a solid.

$^1$H-NMR (CDCl$_3$) δ: 1.31 (3H, d, J=6.9 Hz), 1.49 (3H, d, J=6.9 Hz), 2.77 (1H, ddd, J=4.8 Hz, 4.8 Hz, 14.1 Hz), 2.99-3.11 (2H, m), 3.47 (3H, s), 3.47-3.55 (1H, m), 3.64-3.72 (1H, m), 3.77-3.88 (2H, m), 4.02-4.11 (1H, m), 4.23 (1H, ddd, J=4.2 Hz, 13, 8 Hz, 13.8 Hz), 4.47 (1H, dd, J=3.3 Hz, 9.9 Hz), 4.94 (1H, s), 5.75 (1H, d, J=7.8 Hz), 6.64 (1H, d, J=9.0 Hz), 6.67 (1H, 7.8 Hz), 6.80 (1H, brt), 6.91 (1H, t, J=7.5 Hz), 7.08-7.23 (5H, m), 7.29-7.36 (1H, m).

Example 546

[Chemical formula 623]

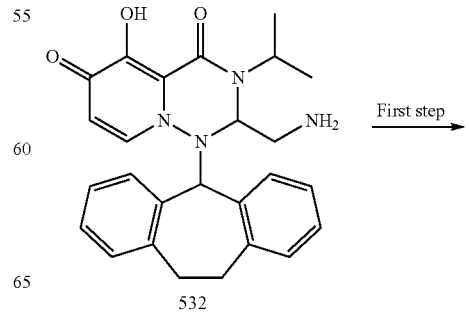

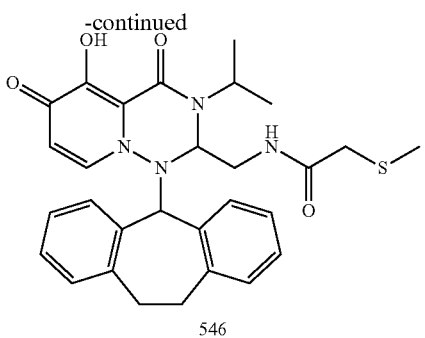

546

First Step

To a dimethylformamide (1 ml) solution of 2-(methylthio) acetic acid (15.7 mg, 0.148 mmol) were added EDCI (28.5 mg, 0.148 mmol) and 1-hydroxy benzotriazole (11.4 mg, 0.0742 mmol) at room temperature, the mixture was stirred at the same temperature for 5 minutes, and compound 532 was added. The reaction solution was stirred at room temperature for 1 hour, and diluted with methanol (3 ml). The solution was cooled to 1 to 30C, a 2N aqueous sodium hydroxide solution (1 ml) was added, the mixture was stirred at the same temperature for 30 minutes, and the mixture was neutralized with 2N hydrochloric acid (1 ml). The reaction solution was extracted with ethyl acetate three times, the combined extracts were washed with water once, and dried with sodium sulfate, and the solvent was distilled off. The resulting crude product was washed with ethyl acetate-diisopropyl ether to obtain 15 mg of compound 546 as a solid.

$^1$H-NMR (CDCl$_3$) δ: 1.32 (3H, d, J=6.9 Hz), 1.50 (3H, J=6.6 Hz), 2.11 (3, s), 2.79 (1H, ddd, J=4.2 Hz, 4.2 Hz, 14.1 Hz), 2.99-3.16 (4H, m), 3.50 (1H, ddd, J=4.5 Hz, 4.5 Hz, 12.9 Hz), 3.68 (1H, d, J=10.2 Hz), 3.97-4.11 (1H, m), 4.26 (1H, ddd, J=4.5 Hz, 13.8 Hz, 13.8 Hz), 4.94 (3H, s), 5.69 (1H, d, J=7.5 Hz), 6.63 (1H, d, J=7.5 Hz), 6.70 (1H, d, J=7.8 Hz), 6.90 (1H, t, J=6.0 Hz), 7.09 (1H, d, J=7.5 Hz), 7.20-7.25 (3H, m), 7.29-7.36 (1H, m), 7.36-7.49 (1H, m).

Example 547

[Chemical formula 624]

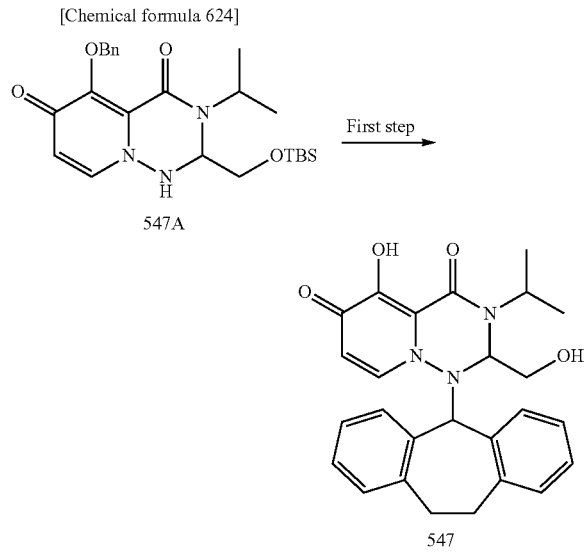

First Step

To an acetic acid (3 ml) solution of compound 547A (367 mg, 0.812 mmol) synthesized by the same procedure as that of Example 516 and dibenzosuberol (205 mg, 0.974 mmol) was added dropwise sulfuric acid (0.6 ml) at room temperature, and the mixture was stirred at the same temperature for 30 minutes. The reaction solution was diluted with water, and extracted with ethyl acetate three times. The extract was washed with water once, and dried with sodium sulfate, and the solvent was distilled off. The resulting crude product was dissolved in methanol (3 ml), a 2N aqueous sodium hydroxide solution (1 ml) was added at room temperature, and the mixture was stirred for 30 minutes. The reaction solution was neutralized with 2N hydrochloric acid (1 ml), and extracted with ethyl acetate three times. The combined extracts were dried with sodium sulfate, and the solvent was distilled off. The resulting crude product was washed with ethyl acetate-diisopropyl ether to obtain 75 mg of compound 547 as a solid.

$^1$H-NMR (CDCl$_3$) δ: 1.22 (3H, d, J=6.9 Hz), 1.45 (3H, d, J=6.3 Hz), 2.80 (1H, ddd, J=4.5 Hz, 4.5 Hz, 14.1 Hz), 2.99-3.11 (1H, m), 3.53 (1H, ddd, J=3.9 Hz, 3, 9 Hz, 17.7 Hz), 3.64 (1H, dd, J=6.9 Hz), 12.3 Hz), 3.82 (1H, dd, J=3.3 Hz, 12.3 Hz), 3.86-3.97 (1H, m), 4.34-4.44 (2H, m), 4.88 (1H, s), 5.35 (1H, d, J=7.5 Hz), 6.52-6.58 (2H, m), 6.82 (1H, dt, J=1.8 Hz, 7.2 Hz), 7.06-7.35 (6H, m).

Example 548

[Chemical formula 625]

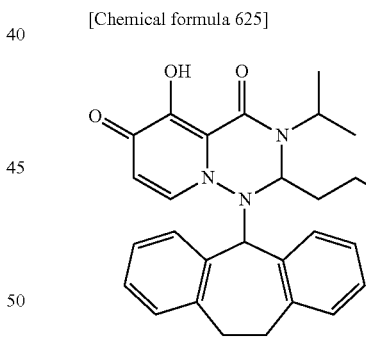

Compound 548 was synthesized by the same procedure as that of Example 547.

$^1$H-NMR (CDCl$_3$) δ: 1.29 (3H, d, J=6.6 Hz), 1.50 (3H, d, J=6.6 Hz), 1.70-1.81 (1H, m), 1.88-2.00 (1H, m), 2.85 (1H, ddd, J=4.5 Hz, 4.5 Hz, 14.1 Hz), 2.99-3.11 (1H, m), 3.48-3.57 (1H, m), 3.68-3.73 (2H, m), 3.83-3.92 (1H, m), 4.3.0 (1H, ddd, J=4.2 Hz, 13.8 Hz, 13.8 Hz), 4.54 (1H, dd, J=3.6 Hz, 11.1 Hz), 4.67 (1H, s), 5.69 (1H, d, J=7.8 Hz), 6.62 (1H, d, J=7.5 Hz), 6.64 (1H, d, J=5.7 Hz), 6.90 (1H, t, J=6.9 Hz), 7.07-7.36 (6H, m).

Example 549

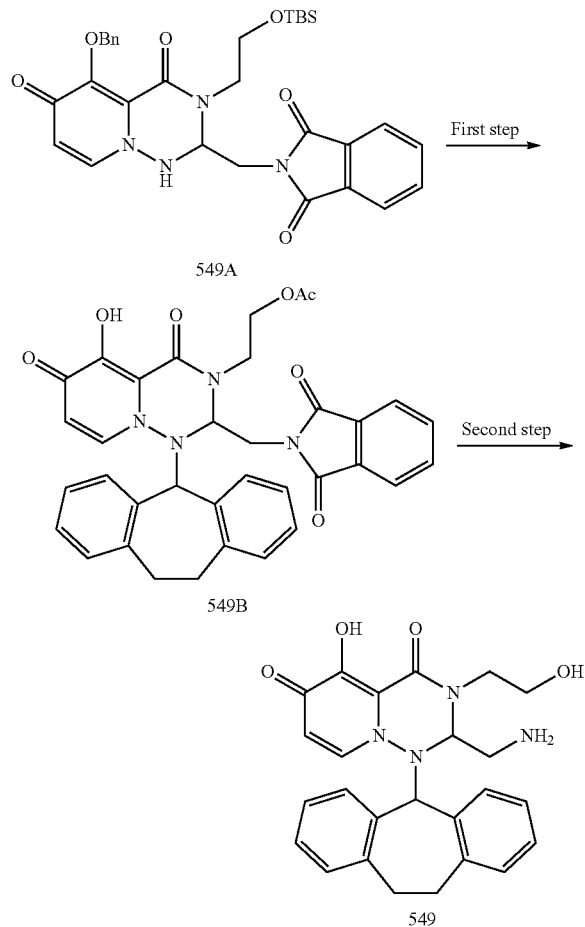

First Step

To an acetic acid (3 ml) solution of compound 549A (997 mg, 1.69 mmol) synthesized by the same procedure as that of Example 516 and dibenzosuberol (1.07 g, 5.08 mmol) was added dropwise sulfuric acid (0.6 ml) at room temperature, and the mixture was stirred at the same temperature for 30 minutes. The reaction solution was diluted with water, and extracted with ethyl acetate three times. The extract was washed with water once, and dried with sodium sulfate, and the solvent was distilled off. The resulting crude product was washed with ethyl acetate-diisopropyl ether to obtain 513 mg of compound 549B.

$^1$H-NMR (CDCl$_3$) δ: 2.09 (3H, s), 2.71 (1H, ddd, J=3.6 Hz, 13.5 Hz, 13.5 Hz), 3.18-3.27 (1H, m), 3.42-3.56 (2H, m), 3.80 (1H, dd, J=2.7 Hz, 14.1 Hz), 4.03 (1H, dd, J=10.2 Hz, 14.1 Hz), 4.15 (1H, ddd, J=4.2 Hz, 4.2 Hz, 9.3 Hz), 4.32-4.40 (1H, m), 4.49-4.53 (2H, m), 4.94 (1H, s), 5/83 (1H, d, J=7.8 Hz), 6.63 (1H, d, J=7.5 Hz), 6.69 (1H, d, J=7.8 Hz), 6.76 (1H, d, J=6.6 Hz), 6.91 (1H, t, J=7.5 Hz), 7.00 (1H, d, J=8.1 Hz), 7.12-7.17 (2H, m), 7.20-7.32 (2H, m), 7.82-7.89 (4H, m).

Second Step

To a methanol (5 ml) solution of compound 549B (513 mg, 0.829 mmol) was added hydrazine hydrate (124.5 mg, 2.49 mmol), and the mixture was refluxed for 2 hours. After cooled to room temperature, to the reaction solution were added 2N hydrochloric acid (30 ml) and ethyl acetate (30 ml). After the layers were separated, the organic layer was extracted with 2N hydrochloric acid two times. The combined aqueous layers were neutralized with sodium bicarbonate water, and extracted with chloroform-methanol three times. The combined organic layers were dried with sodium sulfate, and the solvent was distilled off. The resulting crude product was washed with ethyl acetate-diisopropyl ether to obtain 135 mg of compound 549.

$^1$H-NMR (DMSO-d$_6$) δ: 2.40-2.50 (1H, m), 2.72-2.80 (1H, m), 2.83-2.98 (2H, m), 3.03-3.66 (4H, m), 3.79-3.87 (1H, m), 4.11 (1H, 4.2 Hz), 4.32-4.44 (1H, m), 5.12 (1H, s), 5.51 (1H, 7.5 Hz), 6.69 (d, J=7.5 Hz), 6.84-6.90 (1H, m), 7.07-7.24 (4H, m), 7.30-7.34 (2H, m), 7.39-7.42 (1H, m).

Example 550

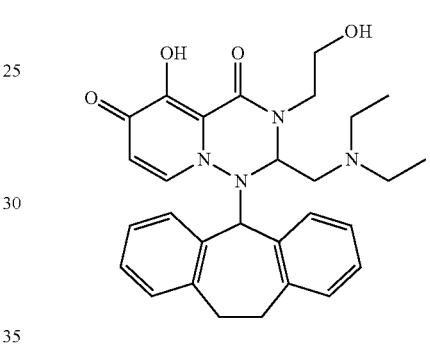

According to Example 536, compound 550 was synthesized from compound 549 by the same procedure.

$^1$H-NMR (DMSO-d$_6$) δ: 0.77 (6H, t, 6.9 Hz), 1.99-2.36 (3H, m), 2.38-2.56 (1H, m), 2.64 (1H, dd, J=3.9 Hz, 14.1 Hz), 2.75 z81H, ddd, J=4.5 Hz, 4.5 Hz, 14.4 Hz), 2.89-3.00 (1H, m), 3.09-3.68 (4H, m), 3.74-3.82 (1H, m), 4.09 (1H, brs), 4.17 (1H, dd, J=3.6 Hz, 8.4 Hz), 5.03 (1H, brs), 5.17 (1H, s), 5.53 (1H, d, J=7.5 Hz), 6.73 (1H, d, J=7.5 Hz), 6.84 (1H, d, J=7.8 Hz), 6.91 (1H, t, J=7.2 Hz), 7.12-7.26 (4H, m), 7.31-7.44 (4H, m), 7.45 (1H, d, J=7.2 Hz).

Example 551

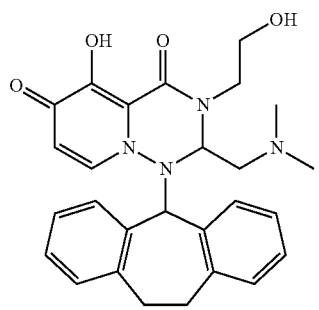

According to Example 536, compound 551 was synthesized from compound 549 by the same procedure.

¹H-NMR (DMSO-d₆) δ: 1.99 (6H, s), 2.27 (1H, brs), 2.51-2.27 (3H, m), 3.56-3.70 (4H, m), 4.03 (2H, brs), 4.36 (1H, brs), 4.94 (2H, brs), 5.29 (1H, brs), 6.54-6.83 (3H, m), 7.11-7.33 (6H, m).

Example 552

[Chemical formula 629]

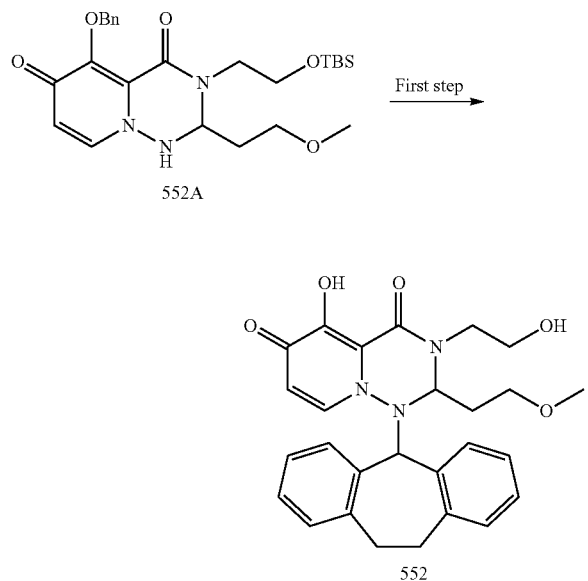

552A

552

First Step

To an acetic acid (2 ml) solution of compound 552A (137 mg, 0.367 mmol) synthesized by the same procedure as that of Example 516 and dibenzosuberol (386 mg, 1.83 mmol) was added dropwise sulfuric acid (0.4 ml) at room temperature, and the mixture was stirred at the same temperature for 30 minutes. The reaction solution was diluted with water, and extracted with ethyl acetate three times. The extract was washed with water once, and dried with sodium sulfate, and the solvent was distilled off. The resulting crude product was dissolved in methanol (5 ml), a 2N aqueous sodium hydroxide solution (2 ml) was added at room temperature, and the mixture was stirred for 30 minutes. The reaction solution was neutralized with 2N hydrochloric acid (2 ml), and extracted with ethyl acetate two times. The combined extracts were dried with sodium sulfate, and the solvent was distilled off. The resulting crude product was washed with ethyl acetate to obtain 62 mg of compound 552.

¹H-NMR (CDCl₃) δ: 1.71-1.82 (1H, m), 2.09-2.21 (1H, m), 2.82-2.90 (1H, m), 3.06 (1H, ddd, J=4.2 Hz, 13.2 Hz, 13.2 Hz), 3.19 (3H, s), 3.22-3.43 (3H, m), 3.60 (1H, ddd, J=10.5 Hz, 10.5 Hz, 17.4 Hz), 3.79-3.96 (3H, m), 4.12-4.21 (1H, m), 4.46 (1H, dd, J=3.3 Hz, 10.2 Hz), 4.98 (1H, s), 5.89 (1H, d, J=7.5 Hz), 6.62 (1H, d, J=6.9 Hz), 6.64 (1H, d, J=7.5 Hz), 6.88-6.93 (1H, m), 7.11-7.37 (6H, m).

Example 553

[Chemical formula 630]

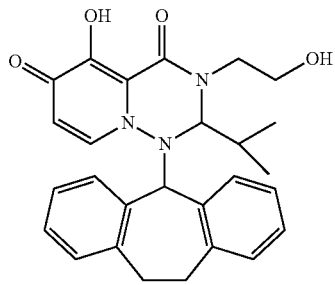

Compound 553 was synthesized by the same procedure as that of Example 552.

¹H-NMR (CDCl₃) δ: 0.80 (3H, d, J=6.6 Hz), 0.94 (3H, d, J=6.9 Hz), 1.94-2.00 (1H, m), 2.82-2.90 (1H, m), 3.00-3.11 (1H, m), 5.31-3.59 (2H, m), 3.64-3.74 (1H, m), 3.94-4.04 (3H, m), 4.25-4.36 (1H, m), 5.04 (1H, s), 5.87 (1H, d, J=7.2 Hz), 6.65 (1H, d, J=7.2 Hz), 7.12 (1H, d, J=7.5 Hz), 6.92 (1H, t, J=8.1 Hz), 7.10 (1H, d, J=7.2 Hz), 7.15-7.38 (5H, m).

Example 554

[Chemical formula 631]

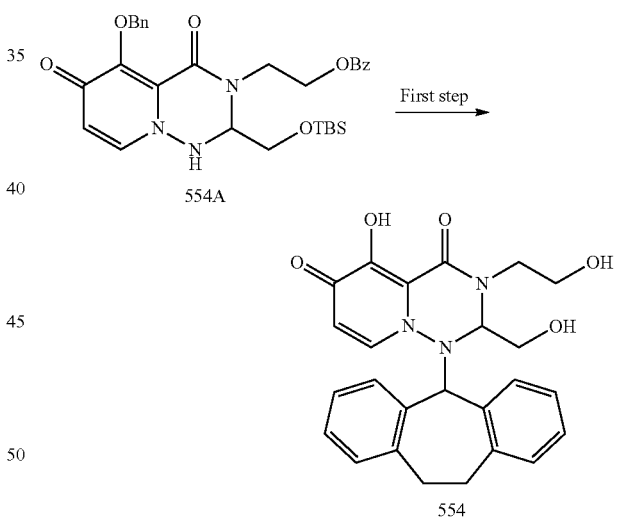

554A

554

First Step

To an acetic acid (2 ml) solution of compound 554A (100 mg, 0.177 mmol) synthesized by the same procedure as that of Example 516 and dibenzosuberol (186 mg, 0.885 mmol) was added dropwise sulfuric acid (0.4 ml) at room temperature, and the mixture was stirred at the same temperature for 30 minutes. The reaction solution was diluted with water, and extracted with ethyl acetate three times. The extract was washed with water once, and dried with sodium sulfate, and the solvent was distilled off. The resulting crude product was dissolved in methanol (5 ml), a 2N aqueous sodium hydroxide solution (2 ml) was added at room temperature, and the mixture was stirred for 30 minutes. The reaction solution was neutralized with an aqueous citric acid solution, and extracted with ethyl acetate two times. The combined extracts were washed with sodium bicarbonate water, and dried with sodium sulfate, and the solvent was distilled off. The resulting crude product was washed with ethyl acetate to obtain 24 mg of compound 554.

$^1$H-NMR (CDCl$_3$) δ: 2.81-2.91 (2H, m), 2.98-3.09 (1H, m), 3.60-3.75 (2H, m), 3.91-4.04 (2H, m), 4.08-4.17 (2H, m), 4.22-4.33 (2H, m), 4.80 (1H, s), 5.69 (1H, d, J=7.8 Hz), 6.48 (1H, d, J=7.5 Hz), 6.59 (1H, d, J=7.5 Hz), 6.80-6.85 (1H, m), 7.13-7.35 (6H, m).

Example 555

[Chemical formula 632]

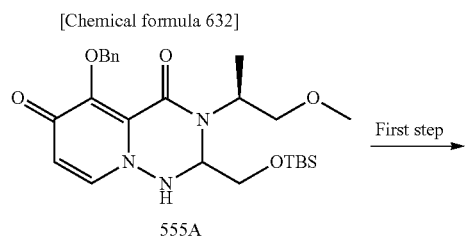

555A

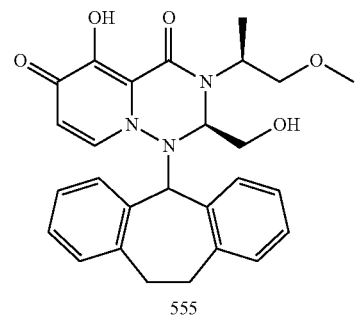

555

To an acetic acid (4 ml) solution of compound 555A (380 mg, 1.11 mmol) synthesized according to Example 516 and dibenzosuberol (1.16 g, 5.52 mmol) was added dropwise sulfuric acid (0.8 ml) at room temperature, and the mixture was stirred at the same temperature for 30 minutes. The reaction solution was diluted with water, and extracted with ethyl acetate three times. The extract was washed with water once, and dried with sodium sulfate, and the solvent was distilled off. The resulting crude product was dissolved in methanol (5 ml), a 2N aqueous sodium hydroxide solution (2 ml) was added at room temperature, and the mixture was stirred for 30 minutes. The reaction solution was neutralized with an aqueous citric acid solution, and extracted with ethyl acetate three times. The combined extracts were dried with sodium sulfate, and the solvent was distilled off. To the resulting crude product were added ethyl acetate-diisopropyl ether, and the precipitated residue was filtered to obtain 22 mg of compound 555.

$^1$H-NMR (CDCl$_3$) δ: 1.62 (3H, d, J=6.9 Hz), 2.81 (1H, ddd, J=4.2 Hz, 4.2 Hz, 14.4 Hz), 3.09 (1H, ddd, J=4.5 Hz, 13.8 Hz, 13.8 Hz), 3.37 (3H, s), 3.37-3.53 (2H, m), 3.70 (1H, d, J=5.4 Hz), 4.23-4.30 (2H, m), 4.33-4.44 (1H, m), 4.94 (1H, s), 5.70 (1H, d, J=7.8 Hz), 6.59 (1H, d, J=7.5 Hz), 6.64 (1H, d, J=7.8 Hz), 6.88-6.92 (1H, m), 7.08-7.37 (6H, m).

Example 556

[Chemical formula 633]

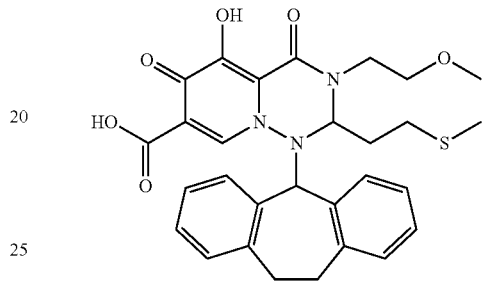

Compound 556 was synthesized by the same procedures as those of Example 65 and Example 516.

$^1$H-NMR (CDCl$_3$) δ: 1.66-1.78 (2H, m), 1.97 (3H, s), 2.19-2.31 (1H, m), 2.35-2.44 (1H, m), 2.49-2.57 (1H, m), 2.85-2.93 (1H, m), 3.06 (1H, J=3.9 Hz, 12.9 Hz, 12.9 Hz), 3.27-3.39 (2H, m), 3.34 (3H, s), 3.58-3.73 (3H, m), 3.96-4.04 (1H, m), 4.08-4.18 (1H, m), 4.60 (1H, dd, J=3.0 Hz, 11.1 Hz), 4.96 (1H, s), 6.52 (1H, d, J=7.5 Hz), 6.87-6.92 (1H, m), 7.18-7.28 (4H, m), 7.31-7.40 (2H, m), 7.65 (1H, s), 12.04 (1H, s), 14.33 (1H, s).

Example 557

[Chemical formula 634]

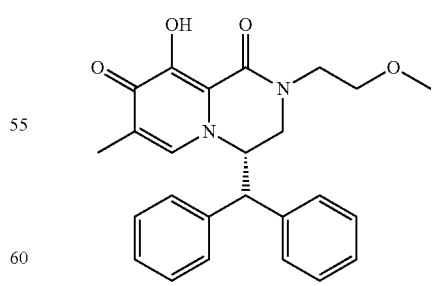

Compound 557 was synthesized by the same procedure as that of Example 149.

MS: m/z=419 [M+H]$^+$.

Example 558

[Chemical formula 635]

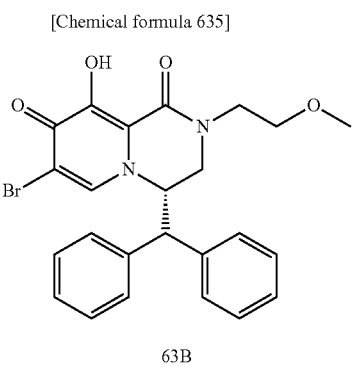

To a DMSO (2 mL) solution of compound 63B (68.8 mg, 0.120 mmol) was added copper chloride (39.2 mg, 0.396 mmol), and the mixture was stirred at 110 degree for 2 hours and, further, at 120 degree for 1 hour. Thereafter, copper chloride (50.0 mg, 0.505 mmol) was added, and the mixture was stirred at 200 degree for 1 hour. The reaction solution was purified using a LCMS fractionating device, the eluted solvent was distilled off, to the concentrated residue was added diethyl ether, and the precipitated white solid was filtered. Washing with diethyl ether, and drying afforded 20.9 mg of compound 558.

MS: m/z=439 [M+H]$^+$.

Example 559

[Chemical formula 636]

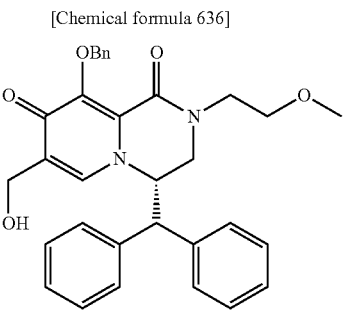

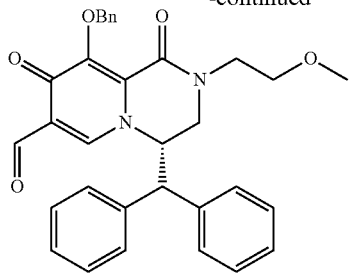

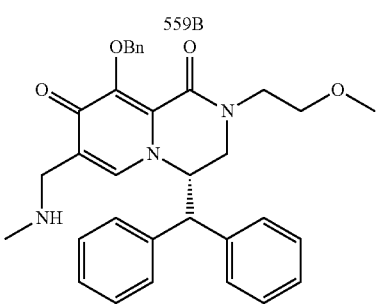

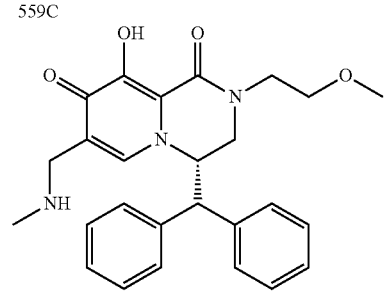

First Step

Compound 48A (43 mg, 0.083 mmol) was dissolved in dichloromethane (6.0 mL), manganese dioxide (120 mg, 1.38 mmol) was added, and the mixture was stirred at room temperature for 3 hours. After the reaction solution was filtered with celite, the filtrate was concentrated to obtain 22.3 mg of compound 559B as a pale yellow solid.

$^1$HNMR (CDCl$_3$) δ: 3.17 (3H, s), 3.41-3.55 (4H, m), 3.95-4.07 (2H, m), 4.28 (1H, d, J=16.1 Hz), 4.53 (1H, d, J=11.8 Hz), 5.49 (2H, d, J=2.0 Hz), 6.97-7.66 (16H, m), 10.07 (1H, s).

Second Step

Compound 559B (22 mg, 0.043 mmol) was dissolved in THF (6.0 mL), a 40% methanamine methanol solution (6.5 ul, 0.064 mmol) and acetic acid (3.7 ul, 0.064 mmol) were added, and the mixture was stirred at room temperature for 5 minutes. The reaction solution was ice-cooled, NaBH(OAc)$_3$ (14 mg, 0.064 mmol) was added, and the mixture was stirred at room temperature overnight. To the reaction solution were added water and chloroform, and the chloroform layer was separated. The aqueous layer was extracted with chloroform, and sodium sulfate was added to the combined extracts to dry them. The solvent was distilled off to obtain 24 mg of compound 559C as a pale yellow solid.

MS: m/z=538 [M+H]$^+$.

Third Step

Compound 559 was synthesized by the same procedure as that of Example 1.

MS: m/z=448 [M+H]$^+$.

Example 560
[Chemical formula 637]
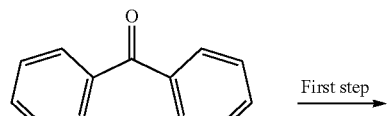
383A
→ First step
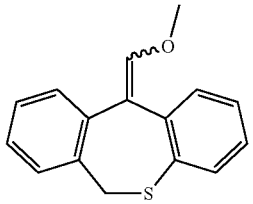
560B
→ Second step
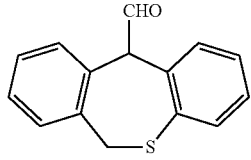
560C
→ Third step
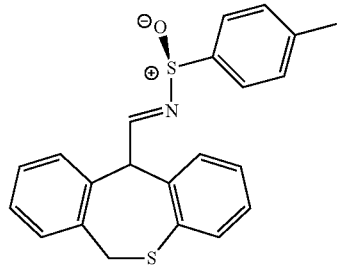
560D
→ Fourth step
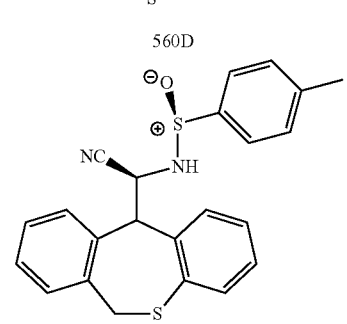
560E
→ Fifth step
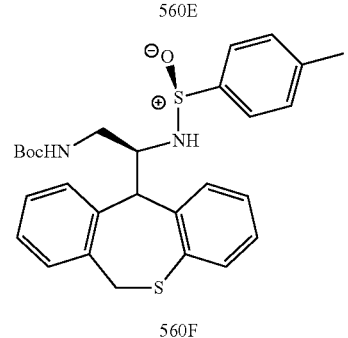
560F
→ Sixth step
-continued
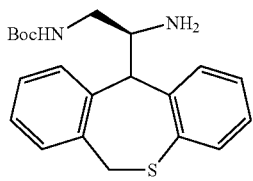
560G
→ Seventh step
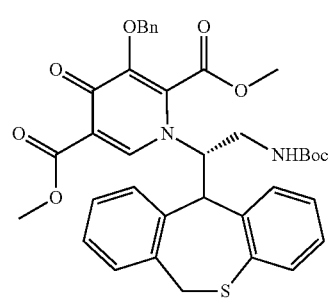
560H
→ Eighth step
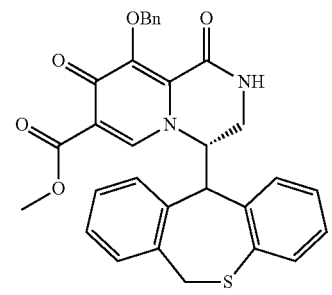
560I
→ Ninth step
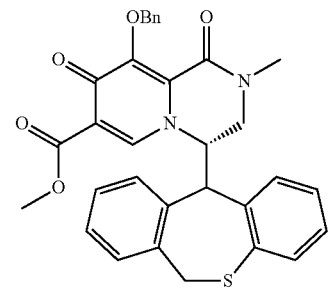
560J
→ Tenth step
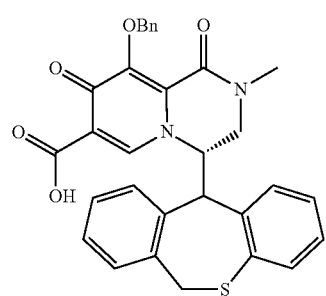
560K
→ Eleventh step -continued

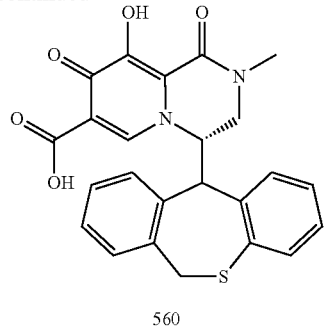

560

First Step

A dioxane (20 mL) mixed solution of (methoxymethyl)triphenylphosphonium chloride (6.73 g, 19.0 mmol) was cooled to 0° C., and a 1.06M NaHMDS toluene solution (18.0 ml, 19.0 mmol) was added dropwise while the same temperature was retained. After the reaction solution was stirred at the same temperature for 30 minutes, compound 383A was added, and the mixture was refluxed for 1 hour and 30 minutes. The reaction solution was returned to room temperature, and water and ethyl acetate were added. The ethyl acetate layer was separated, and the aqueous layer was extracted with ethyl acetate. To the combined extracts was added sodium sulfate to dry them. The solvent was distilled off, and the resulting oil was purified by silica gel column chromatography, and eluted with n-hexane-ethyl acetate (95:5, v/v). Concentration of an objective fraction afforded 2.22 g of compound 560B as an oil.

$^1$H-NMR (CDCl$_3$) δ: 3.68 (3H, s), 3.73 (3H, s), 4.20 (4H, brs), 6.17 (1H, s), 6.39 (1H, s), 6.96-7.07 (6H, m), 7.18-7.32 (9H, m), 7.32-7.46 (1H, m).

Second Step

Compound 560B (1.98 g, 7.78 mmol) was dissolved in dichloromethane (30 mL), a 70% aqueous perchloric acid solution (8.0 ml, 93 mmol) was added, and the mixture was stirred at room temperature overnight. To the reaction solution was added an aqueous saturated sodium carbonate solution, and the dichloromethane layer was separated. The aqueous layer was extracted with dichloromethane, and magnesium sulfate was added to the combined extracts to dry them. The solvent was distilled off, and the resulting oil was purified by silica gel column chromatography, and eluted with n-hexane-ethyl acetate (90:10, v/v). Concentration of an objective fraction afforded 1.80 g of compound 560C as an oil.

$^1$H-NMR (CDCl$_3$) δ: 3.93 (1H, d, J=16.1 Hz), 4.06 (1H, d, J=16.1 Hz), 4.53 (1H, s), 7.11-7.50 (8H, m), 9.89 (1H, s).

MS: m/z=241 [M+H]$^+$.

Third Step

To a dichloromethane (30 mL) solution of compound 560C (2.87 g, 11.9 mmol) were added tetraisopropoxytitanium (17.5 mL, 59.7 mmol) and (S)-4-methylbenzenesulfinamide (2.27 g, 14.3 mmol) at room temperature, then the mixture was refluxed for 3 hours and 30 minutes. The reaction solution was ice-cooled, ice water (30 ml) was added, the mixture was stirred for 1 hour while temperature was retained at the same temperature, and the precipitated solid was filtered using celite. The resulting filtrate was extracted with dichloromethane, and magnesium sulfate was added to the combined extracts to dry them. The solvent was distilled off, and the resulting oil was purified by silica gel column chromatography, and eluted with n-hexane-ethyl acetate (70:30, v/v). Concentration of an objective fraction afforded 3.16 g of compound 560D as a yellow solid.

$^1$H-NMR (CDCl$_3$) δ: 2.39 (6H, s), 3.60 (1H, d, J=15.2 Hz), 3.68 (1H, d, J=14.9 Hz), 3.97 (1H, d, J=15.0 Hz), 4.07 (1H, d, J=15.0 Hz), 4.90 (1H, d, J=2.7 Hz), 4.92 (1H, d, J=2.9 Hz), 7.08-7.26 (20H, m), 7.46-7.51 (4H, m), 8.62 (1H, d, J=2.8 Hz), 8.65 (1H, d, J=2.7 Hz).

MS: m/z=378 [M+H]$^+$.

Fourth Step

A THF (30 mL) suspension of a 1M cyanodiethylaluminum toluene solution (16.7 mL, 16.7 mmol) was cooled to 0 degree, 2-propanol (1.29 mL, 16.7 mmol) was added and, thereafter, the mixture was stirred for 1 hour while temperature was retained at the same temperature. Thereafter, the reaction solution was cooled to −60 degree, a THF (12 mL) solution of compound 560D (3.16 g, 8.37 mmol) was added dropwise, the mixture was stirred for 15 minutes while temperature was retained at the same temperature, thereafter, temperature was raised to room temperature, and the mixture was stirred overnight. The reaction solution was ice-cooled, an aqueous saturated ammonium chloride solution was added, the mixture was stirred at room temperature for 1 hour and 30 minutes and, thereafter, the precipitated solid was filtered using celite, and washed with dichloromethane. The dichloromethane layer of the filtrate was separated, and the aqueous layer was extracted with dichloromethane and, thereafter, sodium sulfate was added to the combined extracts to dry them. The solvent was distilled off, and the resulting oil was purified by silica gel column chromatography, and eluted with chloroform-methanol (97:3, v/v). Concentration of an objective fraction afforded 1.88 g of compound 560E.

MS: m/z=427 [M+Na]$^+$.

Fifth Step

A methanol (4 mL) solution of compound 560E (235 mg, 0.581 mmol) was cooled to 0 degree, cobalt (II) chloride hexahydrate (55.3 mg, 0.232 mmol) was added, and the mixture was stirred at room temperature for 30 minutes. Thereafter, the reaction solution was ice-cooled, a DMF (4 mL) solution of sodium borohydride (88 mg, 2.3 mmol) was added dropwise, and the mixture was stirred at the same temperature for 5 minutes, and at room temperature for 1 hour. Then, Boc$_2$O (0.674 mL, 2.90 mmol) was added, and the mixture was stirred for 30 minutes. To the reaction solution was added water, the mixture was extracted with ethyl acetate, and sodium sulfate was added to the combined extracts to dry them. The solvent was distilled off, and the resulting oil was subjected to silica gel column chromatography, and eluted with chloroform-methanol (98:2, v/v). Concentration of an objective fraction afforded a crude product (211 mg) of compound 560F.

MS: m/z=509 [M+Na]$^+$.

Sixth Step

To a methanol (6 mL) solution of the crude product (211 mg) of compound 560F was added TFA (0.128 mL, 1.66 mmol), and the mixture was stirred at room temperature for 2.5 hours. To the reaction solution was added triethylamine (0.230 mL, 1.66 mmol), the solvent was distilled off, and the resulting crude product of compound 560G was used in a next reaction without purification.

MS: m/z=371 [M+H]$^+$.

Seventh Step

To a toluene (4 mL) solution of the crude product of compound 560G was added dimethyl 3-(benzyloxy)-4-oxo-4H-pyran-2,5-dicarboxylate (132 mg, 0.416 mmol), and the mixture was refluxed for 1 hour and 30 minutes. The reaction solution was subjected to silica gel column chromatography, and eluted with chloroform-methanol (100:0→90:10, v/v). Concentration of an objective fraction afforded a crude product (287 mg) of compound 560H.

MS: m/z=671 [M+H]$^+$.

Eighth Step

To the crude product of compound 560H obtained in the seventh step was added a 4N hydrochloric acid ethyl acetate solution (3 mL), and the mixture was stirred at room temperature for 30 minutes. The solvent was distilled off, to the resulting concentrated residue were added THF (2 mL) and an aqueous saturated sodium bicarbonate solution (2 mL), and the mixture was stirred at room temperature for 45 minutes. To the reaction solution was added water, the mixture was extracted with chloroform, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded 27 mg of compound 560I as a yellow solid.

MS: m/z=539 [M+H]$^+$.

Ninth Step

Compound 560I (27 mg, 0.050 mmol) was dissolved in DMF (2 mL), cesium carbonate (82 mg, 0.25 mmol) and methyl iodide (0.010 mL, 0.16 mmol) were added, and the mixture was stirred at room temperature for 1 hour and 30 minutes. To the reaction solution was added water, the mixture was extracted with ethyl acetate, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded a crude product of compound 560J.

MS: m/z=553 [M+H]$^+$.

Tenth Step

To an EtOH (2 mL) solution of the crude product of compound 560J obtained in the ninth step was added 2N NaOH (1 mL), and the mixture was stirred at room temperature for 40 minutes. To the reaction solution was added a 2N aqueous HCl solution, the mixture was extracted with ethyl acetate, and sodium sulfate was added to the combined extracts to dry them. The solvent was distilled off to obtain 17 mg of compound 560K as a white oil.

MS: m/z=539 [M+H]$^+$.

Eleventh Step

To compound 560K (17 mg, 0.032 mmol) was added TFA (2.0 mL), and the mixture was stirred at room temperature for 35 minutes. The reaction solution was subjected to toluene azeotropy, to the resulting concentrated residue was added isopropyl ether, and the precipitated solid was filtered and washed to obtain 7.1 mg of compound 560 as a pink solid.

MS: m/z=449 [M+H]$^+$.

Example 561

[Chemical formula 638]

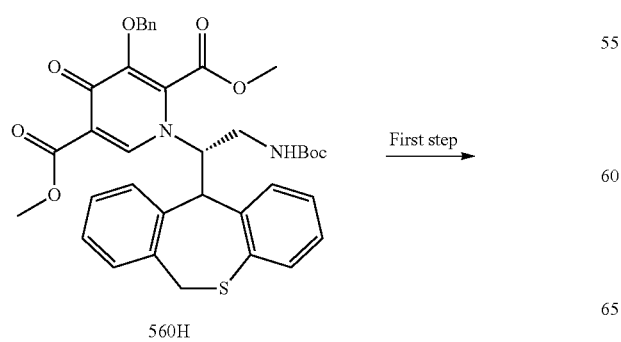

560H

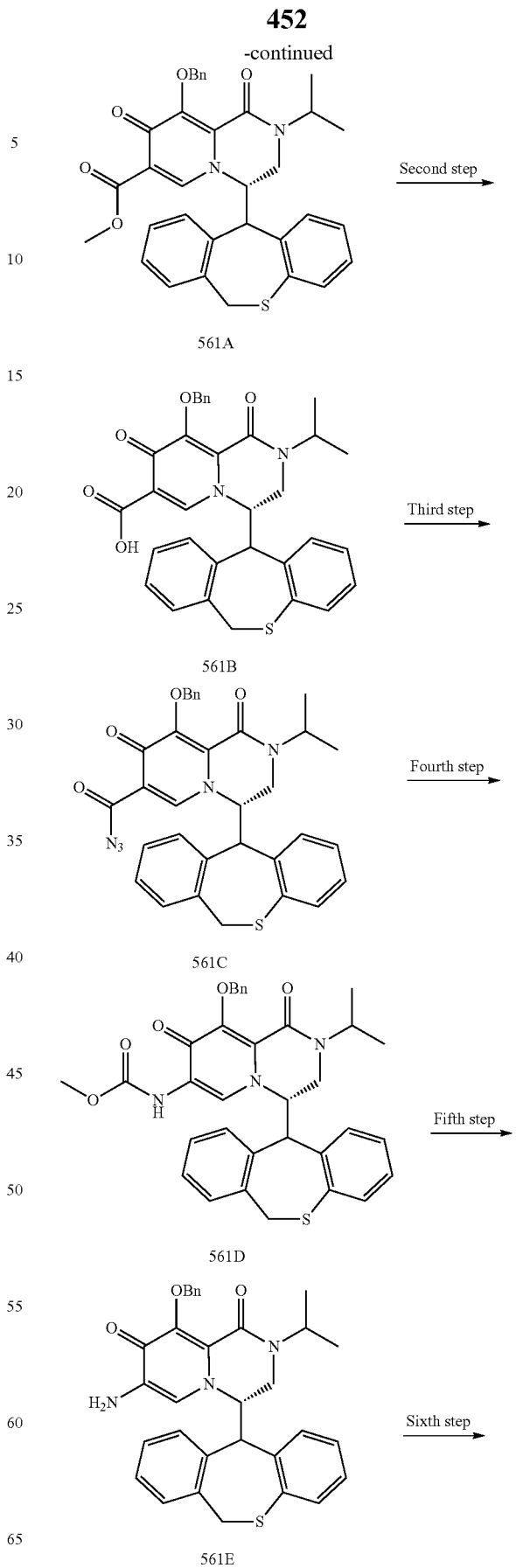

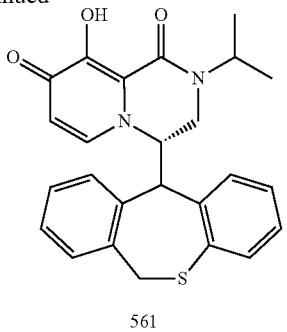

561

First Step

To a crude product (433 mg) of compound 560H was added a 4N hydrochloric acid ethyl acetate solution (3 mL), and the mixture was stirred at room temperature for 1 hour. The solvent was distilled off, to a THF (2 mL) solution of the resulting residue was added acetone (2 mL), the mixture was stirred at room temperature for 20 minutes, NaBH(OAc)$_3$ (70 mg, 0.32 mmol) was added, and the mixture was stirred at room temperature for 1 hour and 30 minutes. Thereafter, to the reaction solution was added an aqueous saturated sodium bicarbonate solution (3 mL), and the mixture was stirred at room temperature overnight. To the reaction solution was added water, the mixture was extracted with chloroform, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded a crude product (79 mg) of compound 561A.

MS: m/z=581 [M+H]$^+$.

Second Step

To an EtOH (4 mL) solution of the crude product (79 mg) of compound 561A was added 2N NaOH (2 mL), and the mixture was stirred at room temperature for 1 hour. To the reaction solution was added a 2N aqueous HCl solution, the mixture was extracted with ethyl acetate, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded compound 561B (53 mg).

MS: m/z=567 [M+H]$^+$.

Third Step

A DMF (2 mL) solution of compound 561B (53 mg, 0.093 mmol) was cooled to 0 degree, triethylamine (0.039 mL, 0.28 mmol) and ethyl chloroformate (0.018 mL, 0.187 mmol) were added, and the mixture was stirred at room temperature for 10 minutes. Thereafter, the reaction solution was cooled to 0 degree, sodium azide (18 mg, 0.28 mmol) was added, and the mixture was stirred for 50 minutes while temperature was retained at the same temperature. To the reaction solution was added water, the mixture was extracted with dichloromethane, and the combined extracts were concentrated to obtain a crude product of compound 561C.

MS: m/z=592 [M+H]$^+$.

Fourth Step

The crude product (55 mg) of compound 561C was dissolved in methanol (2 mL), and the mixture was stirred at 50° C. for 1 hour. The reaction solution was subjected to silica gel column chromatography, and eluted with chloroform-methanol (100:0→94:6, v/v). Concentration of an objective fraction afforded a crude product (43 mg) of compound 561D.

MS: m/z=596 [M+H]$^+$.

Fifth Step

To an EtOH (2 mL) solution of the crude product (43 mg) of compound 561D was added 2N NaOH (4 mL), and the mixture was stirred at 60 degree for 1 hour. The solvent was distilled off, water was added, the mixture was extracted with ethyl acetate and, thereafter, sodium sulfate was added to the combined extracts to dry them. The solvent was distilled off, the resulting oil was subjected to amino column chromatography, and eluted with chloroform-methanol (100:0→80:20, v/v). Concentration of an objective fraction afforded 16 mg of compound 561E as a pale yellow solid.

MS: m/z=538 [M+H]$^+$.

Sixth Step

Compound 561E (16 mg, 0.029 mmol) was dissolved in EtOH (1 mL) and a 48% aqueous tetrafluoroboric acid (1 mL), the reaction solution was cooled to 0 degree, sodium nitrite (15 mg, 0.22 mmol) was added, and the mixture was stirred for 1 hour and 30 minutes while temperature was retained at the same temperature and, further, at room temperature for 2 hours and 30 minutes. To the reaction solution was added water, the mixture was extracted with chloroform, and sodium sulfate was added to the combined extracts to dry them. The solvent was distilled off, to the resulting concentrated residue were added ethyl acetate and isopropyl ether, and the precipitated solid was filtered and washed to obtain 5 mg of compound 561 as a white solid.

$^1$H-NMR (CDCl$_3$) δ: 0.96 (3H, d, J=6.9 Hz), 1.17 (3H, d, J=6.8 Hz), 3.37 (1H, d, J=13.3 Hz), 3.88 (1H, dd, J=13.4, 4.3 Hz), 3.99 (1H, d, J=14.9 Hz), 4.08 (1H, d, J=11.3 Hz), 4.52 (1H, d, J=14.9 Hz), 4.81-4.90 (1H, m), 5.67 (1H, dd, J=11.3, 3.1 Hz), 5.94 (1H, d, J=7.4 Hz), 6.59 (1H, d, J=6.4 Hz), 6.72 (1H, d, J=7.3 Hz), 6.86 (1H, t, J=7.1 Hz), 7.09 (1H, t, J=7.6 Hz), 7.16-7.31 (5H, m).

Example 562

[Chemical formula 639]

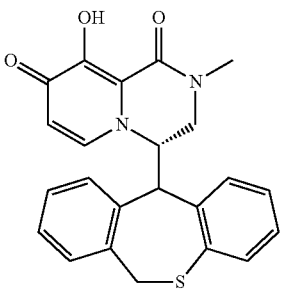

Compound 562 was synthesized by the same procedure as that of Example 561.

$^1$H-NMR (CDCl$_3$) δ: 3.07 (3H, s), 3.21 (1H, d, J=12.3 Hz), 4.00-4.31 (4H, m), 5.78 (1H, d, J=10.5 Hz), 5.94 (1H, d, J=7.4 Hz), 6.54 (1H, d, J=7.3 Hz), 6.69 (1H, d, J=7.5 Hz), 6.98 (1H, t, J=7.6 Hz), 7.14-7.41 (6H, m).

MS: m/z=405 [M+H]$^+$.

Example 563

[Chemical formula 640]

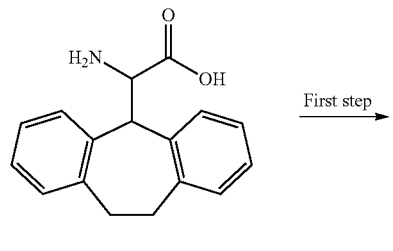

563A

First step →

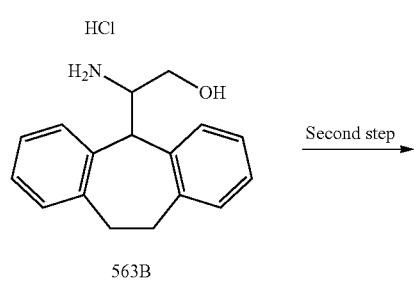

563B

Second step →

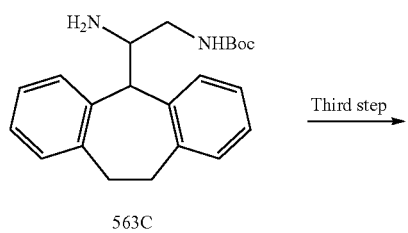

563C

Third step →

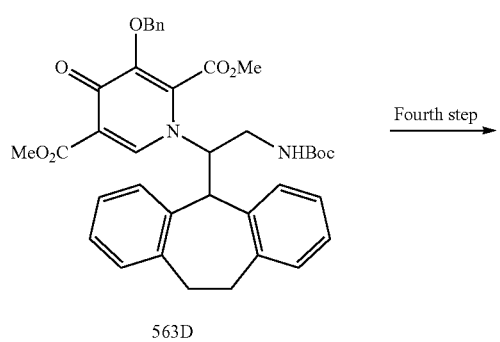

563D

Fourth step →

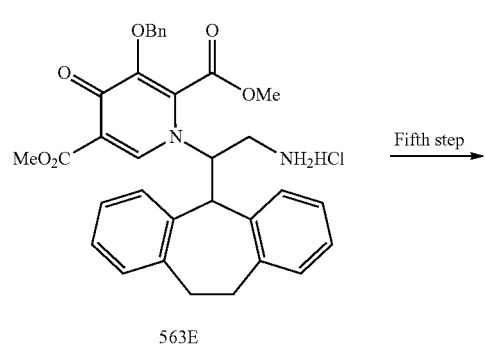

563E

Fifth step →

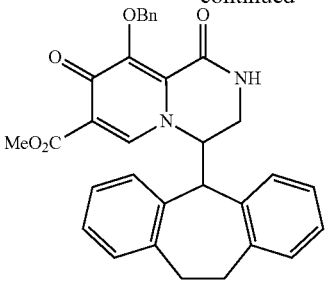

563F

Sixth step →

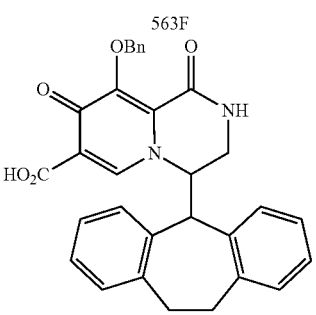

563G

Seventh step →

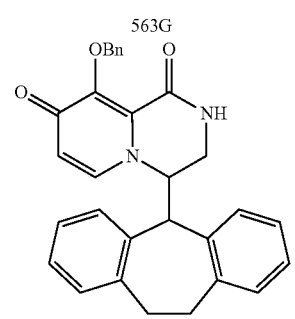

563H

Eighth step →

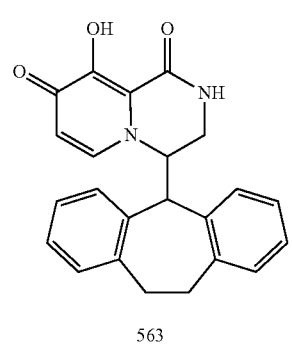

563

First Step

Compound 563A (Tetrahedron Letters, 34, 953-956, 1993, 41.1 g, 154 mmol) was dissolved in THF (300 mL), 1M BH$_3$-THF (770 mL) was slowly added at room temperature, and the mixture was stirred for 18 hours. 3N hydrochloric acid (513 mL) was slowly added, and the mixture was refluxed for 1 hour, and was progressed to a next step without purification.

LC-MS: m/z=254 [M+H]$^+$.

Second Step

Using a solution containing compound 563B, according to Example 12, compound 563C was synthesized.

LC-MS: m/z=353 [M+H]$^+$.

¹H-NMR (DMSO-d₆): 1.40 (9H, s), 2.65-2.72 (1H, m), 2.86-2.92 (3H, m), 3.47-3.56 (3H, m), 3.56-3.69 (1H, m), 6.63 (1H, s), 7.11-7.26 (8H, m).

Third Step

A toluene (30 mL) solution of compound 563C (2.16 g, 6.79 mmol) and dimethyl 3-(benzyloxy)-4-oxo-4H-pyran-2,5-dicarboxylate (2.38 g, 6.75 mmol) was stirred at 100° C. for 4 hours. The reaction solution was distilled off under reduced pressure, and the resulting crude product of compound 563D was used in a next reaction without purification.

MS: m/z=653.05 [M+H]⁺.

Fourth Step

To an ethyl acetate (20 mL) solution of the crude product of compound 563D was added hydrogen chloride (4N ethyl acetate solution, 20 mL) at room temperature, and the mixture was stirred for 30 minutes. The reaction solution was distilled off under reduced pressure, and the resulting crude product of compound 563E was used in a next reaction without purification.

MS: m/z=553.05 [M+H]⁺.

Fifth Step

To a tetrahydrofuran (40 mL) solution of the crude product of compound 563E was added saturated sodium bicarbonate water (5 mL) at room temperature, and the mixture was stirred for 16 hours. To the reaction solution was added water (50 mL), the mixture was extracted with chloroform three times, and the extracts were combined, and dried with sodium sulfate. The solvent was distilled off under reduced pressure, and diethyl ether and chloroform were added to the resulting residue to covert them into a powder, to obtain compound 563F (2.90 g, 70.2%) as a white solid.

MS: m/z=521.05 [M+H]⁺.

Sixth Step

To a methanol (7.5 mL) suspension of compound 563F (523 mg, 1.01 mmol) was added an aqueous sodium hydroxide solution (2 M, 1.5 mL) at room temperature, and the mixture was stirred for 3 hours. To the reaction solution were added hydrochloric acid (2N, 1.5 mL) and water (3 mL) at room temperature and, thereafter, the mixture was stirred at 0° C. for 15 minutes. The precipitated solid was filtered, and washed with water and diethyl ether to obtain compound 563G (418 mg, 82.0%) as a white solid.

MS: m/z=507.00 [M+H]⁺.

Seventh Step

A diphenyl ether (5 mL) suspension of compound 563G (107 mg, 0.211 mmol) was stirred at 240° C. for 1 hour under microwave irradiation. The reaction solution was purified by silica gel column chromatography (methanol/chloroform=0%→5%) to obtain compound 563H (64.4 mg, 65.9%) as a white solid.

MS: m/z=463.05 [M+H]⁺.

Eighth Step

A methanol (30 mL) solution of compound 563H (64.4 mg, 0.139 mmol) was hydrogenated by passing through 10% Pd—C CatCart (H-cube, Full-H₂ mode, 25° C.) for 3 hours. The reaction solution was distilled off under reduced pressure, and ethyl acetate and methanol were added to the resulting residue to convert it into a powder, to obtain compound 563 (31.1 mg, 60.0%) as a gray white solid.

¹HNMR (DMSO-d₆) δ: 2.50-3.03 (3H, m), 3.50-3.72 (3H, m), 4.29 (1H, d, J=11.4 Hz), 5.12 (1H, m), 5.69 (1H, d, J=7.2 Hz), 6.50 (1H, d, J=7.7 Hz), 6.75 (1H, d, J=7.7 Hz), 6.84 (1H, m), 7.14-7.30 (6H, m), 9.16 (1H, d, J=4.8 Hz).

MS: m/z=372.90 [M+H]⁺.

Example 564

[Chemical formula 641]

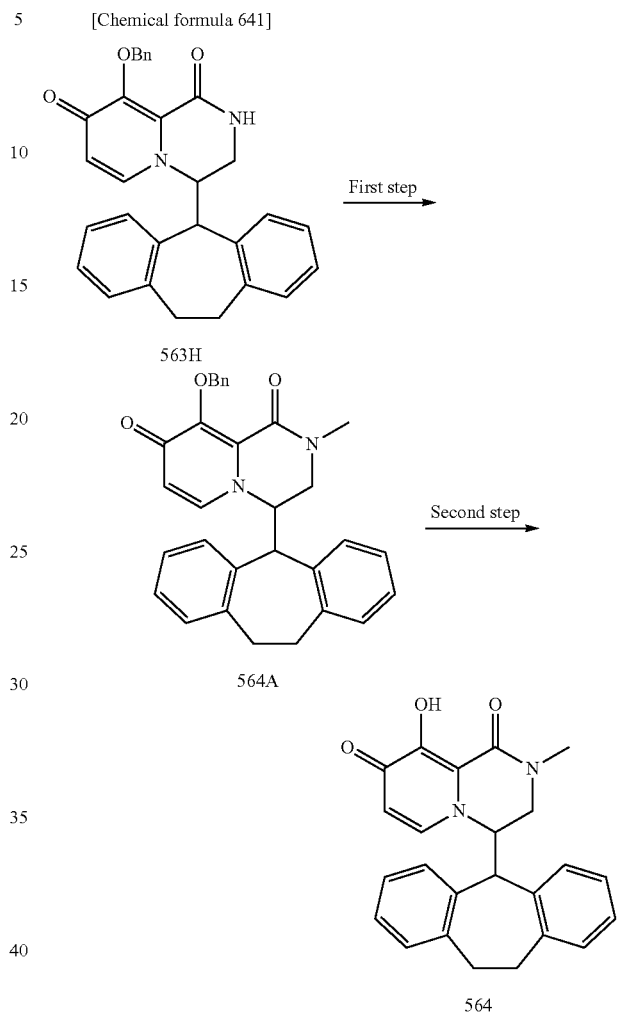

First Step

To a dimethylformamide (2 mL) suspension of compound 563H (64.2 mg, 0.139 mmol) and cesium carbonate (220 mg, 0.675 mmol) was added methyl iodide (0.0430 mL, 0.688 mmol) at room temperature, and the mixture was stirred for 3 hours. To the reaction solution was added water (10 mL) at room temperature, and the mixture was extracted with ethyl acetate (30 mL). The organic layer was washed with water (10 mL) and an aqueous saturated sodium chloride solution (10 mL), and dried with sodium sulfate. The solvent was distilled off under reduced pressure, and the residue was purified by silica gel column chromatography (methanol/chloroform=2.5%→10%) to obtain compound 564A (56.0 mg, 85.0%) as a colorless gummy substance.

MS: m/z=477.00 [M+H]⁺.

Second Step

A solution of compound 564A (56.0 mg, 0.118 mmol) in methanol (10 mL), ethyl acetate (5 mL) and tetrahydrofran (5 mL) was hydrogenated by passing through 10% Pd—C CatCart (H-cube, Full-H₂ mode, 250C) for 75 minutes. The reaction solution was distilled off under reduced pressure,

459 and ethyl acetate and methanol were added to the resulting residue to convert it into a powder, to obtain compound 564 (22.0 mg, 48.4%) as a gray white solid.

$^1$HNMR (DMSO-$d_6$) δ: 2.86-2.98 (6H, m), 3.51-3.58 (2H, m), 3.94 (1H, m), 4.30 (1H, d, J=11.1 Hz), 5.19 (1H, d, J=10.2 Hz), 5.79 (1H, d, J=6.9 Hz), 6.49 (1H, d, J=7.4 Hz), 6.74 (1H, d, J=7.4 Hz), 6.85 (1H, m), 7.14 (2H, m), 7.25 (4H, m), 12.50 (1H, brs).

MS: m/z=387.05 [M+H]$^+$.

Example 565

[Chemical formula 642]

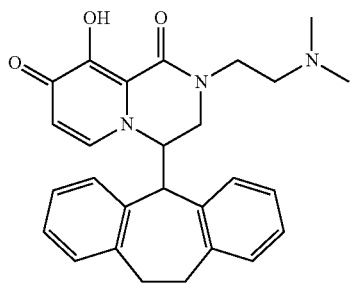

Compound 565 was synthesized by the same procedure as that of Example 564.

MS: m/z=443.95 [M+H]$^+$.

Example 566

[Chemical formula 643]

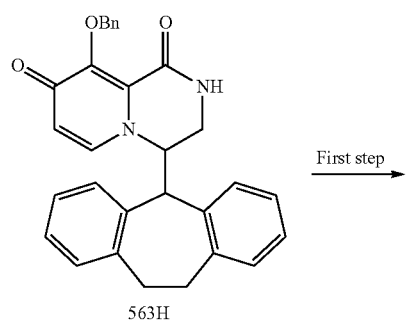
563H

First step →

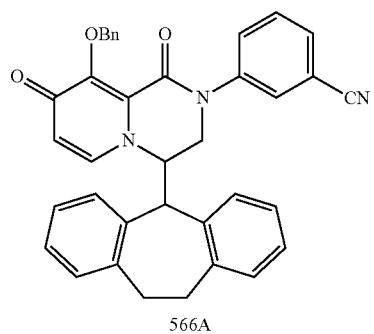
566A

Second step →

460

-continued

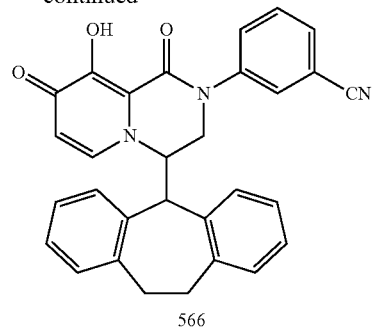
566

First Step

A dimethylformamide (2 mL) suspension of compound 563H (75.4 mg, 0.163 mmol), 3-iodobenzonitrile (124 mg, 0.541 mmol), copper (I) iodide (33.2 mg, 0.174 mmol), potassium carbonate (74.7 mg, 0.540 mmol) and N,N'-dimethylethylenediamine (0.0200 ml, 0.186 mmol) was stirred at 140° C. for 2 hours under microwave irradiation. To the reaction solution were added water (10 mL) and hydrochloric acid (2M, 2 mL) at room temperature, and the mixture was extracted with ethyl acetate. The extract was filtered with celite, and the filtrate was washed with water (10 mL×2) and an aqueous saturated sodium chloride solution (10 mL), and dried with sodium sulfate. The solvent was distilled off under reduced pressure, and the resulting crude product of compound 566A was used in a next reaction without purification.

MS: m/z=564.05 [M+H]$^+$.

Second Step

To a methylene chloride (10 mL) solution of the crude product of compound 566A obtained in the first step was added trifluoroacetic acid (2 mL) at room temperature, and the mixture was stirred for 1 hour. The reaction solution was concentrated under reduced pressure, and the resulting residue was purified by preparative LCMS to obtain compound 566 (30.3 mg, 39.3%) as a yellow solid.

$^1$HNMR (DMSO-$d_6$) δ: 2.81-2.94 (2H, m), 3.38-3.58 (2H, m), 4.54 (1H, d, J=10.5 Hz), 4.64 (1H, d, J=10.5 Hz), 5.35 (1H, d, J=10.5 Hz), 5.76 (1H, m), 6.66-6.71 (3H, m), 6.90 (1H, m), 7.06-7.15 (6H, m), 7.76 (2H, m), 7.90 (2H, m).

MS: m/z=473.90 [M+H]$^+$.

Example 567

[Chemical formula 644]

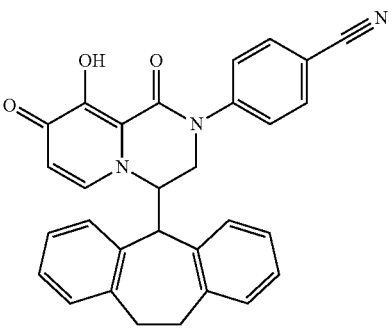

Compound 567 was synthesized by the same procedure as that of Example 566.

¹HNMR (DMSO-d₆) δ: 2.80-3.00 (2H, m), 3.40-3.70 (2H, m), 4.52 (1H, m), 4.64 (1H, m), 5.38 (1H, m), 5.76 (1H, m), 6.60-7.20 (10H, m), 7.60-7.90 (3H, m), 8.11 (1H, m).

MS: m/z=474.00 [M+H]⁺.

Example 568

[Chemical formula 645]

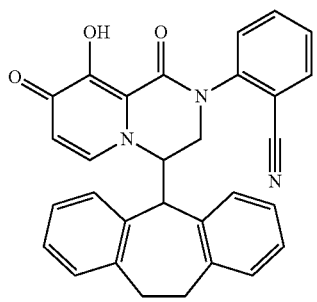

Compound 568 was synthesized by the same procedure as that of Example 566.

¹HNMR (DMSO-d₆) δ: 2.87-2.96 (2H, m), 3.34-3.73 (2H, m), 4.64 (2H, m), 5.33 (1H, m), 5.71 (1H, d, J=7.2 Hz), 6.61 (1H, d, J=7.8 Hz), 6.87-6.95 (3H, m), 7.00-7.27 (6H, m), 7.62 (2H, m), 7.86 (1H, m), 8.07 (1H, m).

MS: m/z=474.00 [M+H]⁺.

Example 569

[Chemical formula 646]

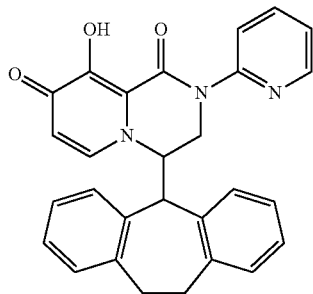

Compound 569 was synthesized by the same procedure as that of Example 566.

MS: m/z=449.95 [M+H]⁺.

Example 570

[Chemical formula 647]

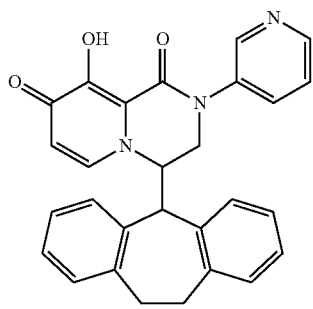

Compound 570 was synthesized by the same procedure as that of Example 566.

¹HNMR (DMSO-d₆) δ: 2.83-2.97 (3H, m), 3.16-3.62 (2H, m), 3.56 (1H, m), 3.66 (1H, d, J=11.1 Hz), 5.35 (1H, d, J=11.1 Hz), 5.73 (1H, d, J=7.4 Hz), 6.68 (1H, d, J=7.4 Hz), 6.92 (1H, m), 7.06-7.21 (5H, m), 7.49 (1H, m), 7.97 (1H, d, J=8.4 Hz), 8.14 (1H, s), 8.50 (1H, d, J=3.6 Hz), 8.81 (1H, d, J=2.1 Hz).

MS: m/z=449.95 [M+H]⁺.

Example 571

[Chemical formula 648]

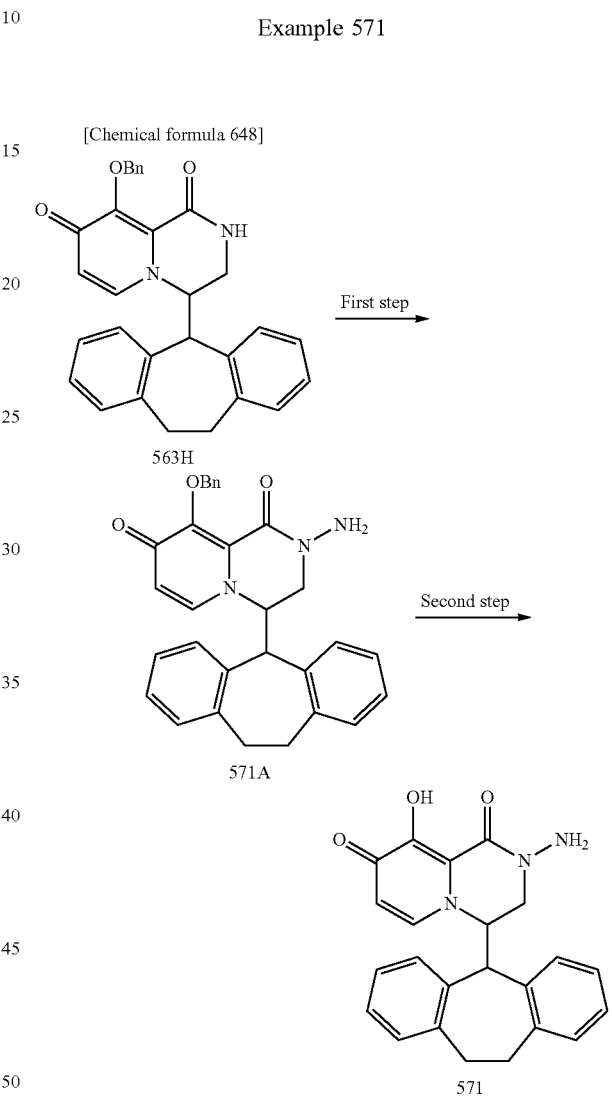

First Step

To a DMF (1 mL) solution of compound 563H (50.0 mg, 0.108 mmol) was added cesium carbonate (176 mg, 0.540 mmol), and the mixture was stirred at room temperature for 10 minutes. To the reaction solution was added O-(2,4-dinitrophenyl)hydroxylamine (64.6 mg, 0.324 mmol), and the mixture was stirred at room temperature for 9 hours. To the reaction solution was added chloroform, and the mixture was washed with water, and dried with sodium sulfate. The solvent was distilled off, and the resulting oil was purified by silica gel column chromatography. The materials were eluted firstly with chloroform and, then, with chloroform-methanol (98:2, v/v). Concentration of an objective fraction afforded 28.3 mg of compound 571A as an amorphous substance.

MS: m/z=478 [M+H]⁺.

Second Step

Compound 571A (27.0 g, 0.057 mmol) was dissolved in a THF-methanol (1 mL, 1:1, v/v) solution, 10% palladium carbon (15.0 mg) was added, and the mixture was stirred at room temperature for 2 hours under hydrogen atmosphere. After dilution with chloroform, insolubles were removed by celite filtration. After the filtrate was concentrated under reduced pressure, the residue was solidified with dichloromethane-ether to obtain 12.0 mg of compound 571.

MS: m/z=388 [M+H]$^+$.

Example 572

[Chemical formula 649]

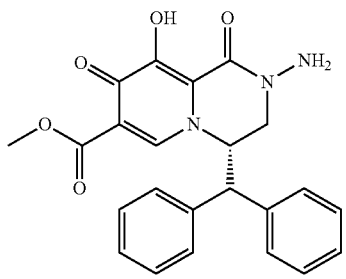

Using compound 12H, and according to Example 571, compound 572 was synthesized by the same procedure.

MS: m/z=420 [M+H]$^+$.

Example 573

[Chemical formula 650]

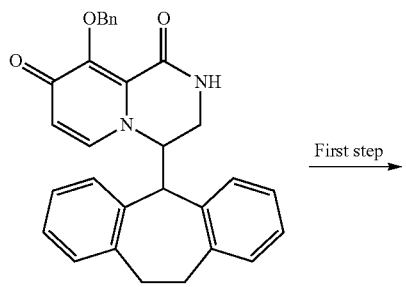

563H

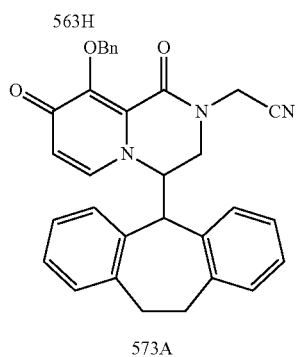

573A

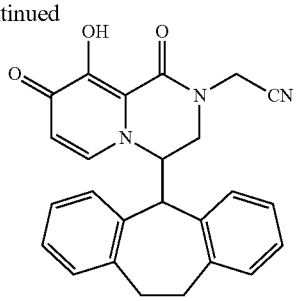

573

First Step

To a dimethylformamide (1.5 mL) solution of compound 563H (83.2 mg, 0.160 mmol) was added sodium hydride (60%, 13.2 mg, 0.330 mmol) under ice-cooling, the mixture was stirred for 30 minutes, thereafter, bromoacetonitrile (0.0190 mL, 0.270 mmol) was added, and the mixture was stirred at room temperature for 1 hour. To the reaction solution was added an aqueous ammonium chloride solution (10%, 3 mL), and the mixture was extracted with ethyl acetate. The organic layer was washed with water (10 mL) and an aqueous saturated sodium chloride solution (10 mL), and dried with sodium sulfate. The solvent was distilled off under reduced pressure, and the resulting crude product of compound 573A was used in a next reaction without purification.

MS: m/z=502.00 [M+H]$^+$.

Second Step

To an acetonitrile (4 mL) suspension of the crude product of compound 573A obtained in the first step and sodium iodide (111 mg, 0.741 mmol) was added chlorotrimethylsilane (0.0920 mL, 0.720 mmol) at room temperature, and the mixture was stirred for 24 hours. To the reaction solution was added an aqueous sodium hydrogen sulfite solution (10%, 10 mL) and, thereafter, the mixture was extracted with chloroform. After the extracts were combined, and dried with sodium sulfate, the solvent was concentrated under reduced pressure, and the resulting residue was purified by preparative LCMS to obtain compound 573 (22.0 mg, 29.7%) as a gray white solid.

$^1$H-NMR (DMSO-d$_6$) δ: 2.86-2.95 (2H, m), 3.45-3.63 (2H, m), 4.01 (1H, m), 4.30 (1H, d, J=10.8 Hz), 4.35 (1H, d, J=17.4 Hz), 4.74 (1H, d, J=17.4 Hz), 5.20 (1H, m), 5.66 (1H, d, J=7.5 Hz), 6.52 (1H, d, J=7.8 Hz), 6.73 (1H, d, J=7.5 Hz), 6.83 (1H, m), 7.11-7.28 (6H, m).

MS: m/z=502.00 [M+H]$^+$.

Example 574

[Chemical formula 651]

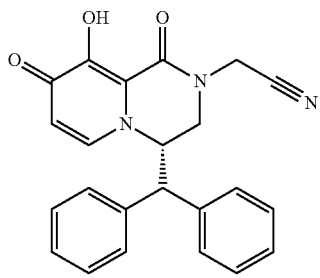

Compound 574 was synthesized by the same procedure as that of Example 573.
$^1$H-NMR (DMSO-$d_6$) δ: 4.16 (1H, dd, J=13.26, 3.53 Hz), 4.36 (1H, d, J=11.58 Hz), 4.52 (2H, dd, J=20.73, 17.54 Hz), 5.44 (1H, d, J=11.41 Hz), 5.65 (1H, d, J=7.39 Hz), 6.99 (1H, d, J=7.55 Hz), 7.11-7.32 (6H, m), 7.36-7.45 (2H, m), 7.58 (2H, d, J=7.39 Hz).
Example 575
[Chemical formula 652]
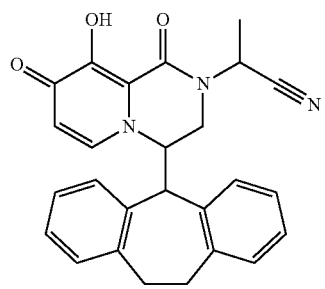
Compound 575 was synthesized by the same procedure as that of Example 573.
MS: m/z=425.95 [M+H]$^+$.
Example 576
[Chemical formula 653]
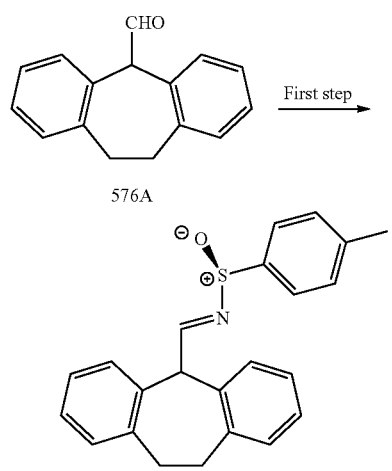
576A
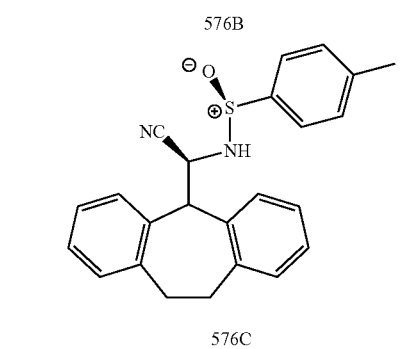
576B
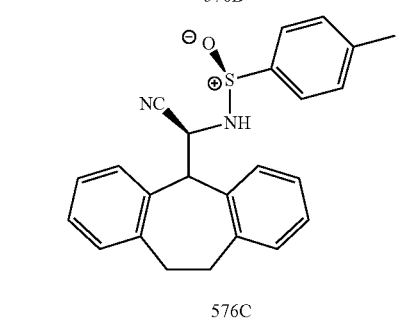
576C
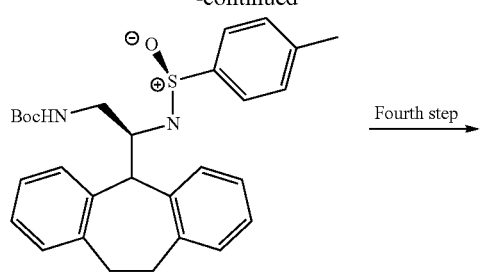
576D
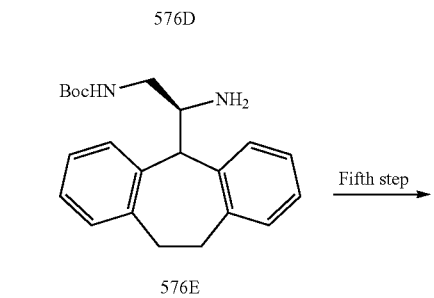
576E
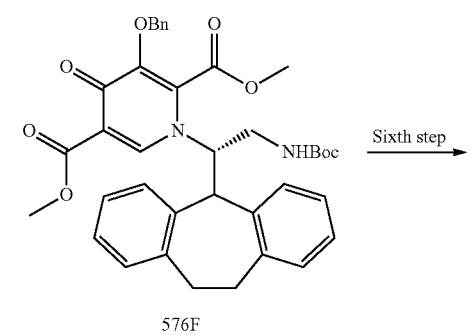
576F
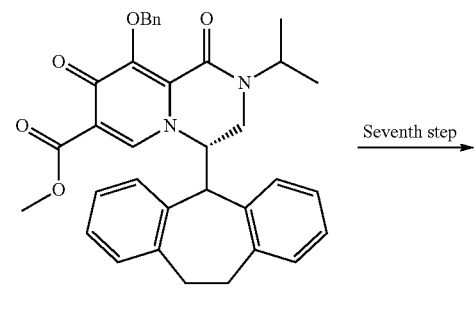
576G
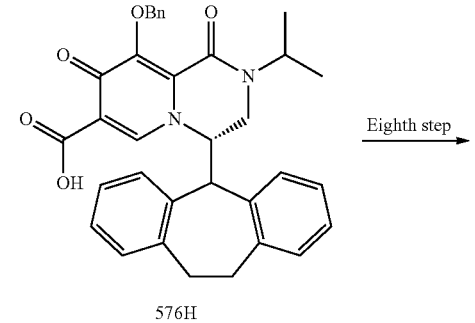
576H

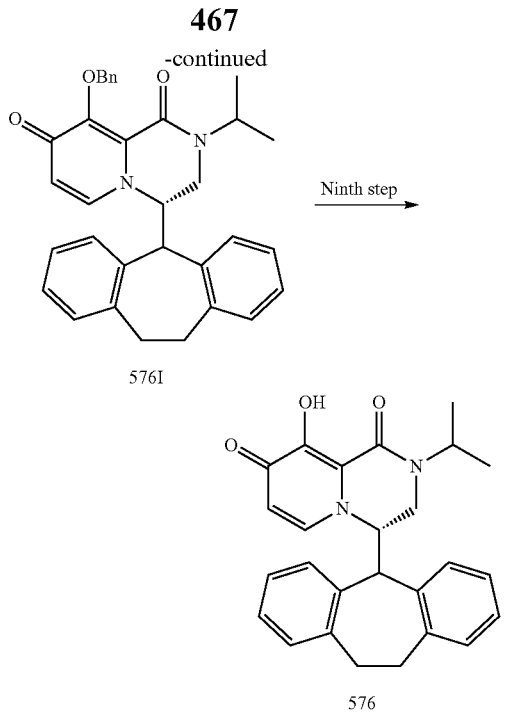

First Step

A dichloromethane (30 mL) solution of compound 576A (Bioorg. Med. Chem., 2003, 11, 197-206) (2.26 g, 10.2 mmol) were added tetraisopropoxytitanium (10.0 mL, 33.1 mmol) and (S)-4-methylbenzenesulfinamide (1.29 g, 8.13 mmol) at room temperature, and the mixture was refluxed for 2 hours. The reaction solution was ice-cooled, ice water (40 ml) was added, the mixture was stirred for 1 hour while temperature was retained at the same temperature, and the precipitated solid was filtered using celite. The resulting filtrate was extracted with dichloromethane, and magnesium sulfate was added to the combined extracts to dry them. The solvent was distilled off, and the resulting oil was purified by silica gel column chromatography, and eluted with n-hexane-ethyl acetate (100:0→70:30, v/v). Concentration of an objective fraction afforded 1.35 g of compound 576B as a yellow solid.

$^1$H-NMR (CDCl$_3$) δ: 2.32 (3H, s), 2.72-2.85 (2H, m), 3.03-3.16 (2H, m), 4.89 (1H, d, J=3.5 Hz), 7.09-7.25 (10H, m), 7.39-7.42 (2H, m), 8.49 (1H, d, J=3.6 Hz).

MS: m/z=360 [M+H]$^+$.

Second Step

A THF (20 mL) solution of a 1M cyanodiethylaluminum toluene solution (7.51 mL, 7.51 mmol) was cooled to 0 degree, 2-propanol (0.579 mL, 7.51 mmol) was added and, thereafter, the mixture was stirred for 1 hour while temperature was retained at the same temperature. Thereafter, the reaction solution was cooled to −60 degree, a THF (14 mL) solution of compound 576B was added dropwise, the mixture was stirred for 15 minutes while temperature was retained at the same temperature, thereafter, temperature was raised to room temperature, and the mixture was stirred overnight. The reaction solution was ice-cooled, an aqueous saturated ammonium chloride solution was added, the mixture was stirred at room temperature for 1 hour and 30 minutes and, thereafter, the precipitated solid was filtered using celite, and washed with dichloromethane. The dichloromethane layer of the filtrate was separated, the aqueous layer was extracted with dichloromethane, and sodium sulfate was added to the combined extracts to dry them. The solvent was distilled off, to the resulting oil were added ethyl acetate and hexane, and the precipitated solid was filtered and washed to obtain 976 mg of compound 576C as a white solid.

$^1$H-NMR (CDCl$_3$) δ: 2.38 (3H, s), 2.92-3.055 (2H, m), 3.41-3.52 (2H, m), 4.25 (1H, d, J=10.8 Hz), 4.28 (1H, d, J=5.6 Hz), 4.94 (1H, dd, J=10.6, 5.7 Hz), 7.14-7.41 (12H, m).

Third Step

A methanol (8 mL) suspension of compound 576C (500 mg, 1.29 mmol) was cooled to 0 degree, cobalt (II) chloride hexahydrate (123 mg, 0.517 mmol) was added, and the mixture was stirred at room temperature for 30 minutes. To the reaction solution was added chloroform (5 mL), thereafter, the mixture was ice-cooled, a DMF (4 mL) solution of sodium borohydride (196 mg, 5.17 mmol) was added dropwise, and the mixture was stirred at the same temperature for 5 minutes, and at room temperature for 2 hours. Then, Boc$_2$O (1.0 mL, 4.3 mmol) was added, and the mixture was stirred at room temperature overnight. To the reaction solution was added water, the mixture was extracted with ethyl acetate, and sodium sulfate was added to the combined extracts to dry them. The solvent was distilled off, and the resulting oil was subjected to silica gel column chromatography, and eluted with chloroform-methanol (100:0→98:2, v/v). Concentration of an objective fraction afforded a crude product (200 mg) of compound 576D.

MS: m/z=491 [M+Na]$^+$.

Fourth Step

To a methanol (6 mL) solution of the crude product (200 mg) of compound 576D obtained in the third step was added TFA (0.188 mL, 2.45 mmol), and the mixture was stirred at room temperature for 2.5 hours. To the reaction solution was added triethylamine (0.399 mL, 2.45 mmol), the solvent was distilled off, and the resulting crude product of compound 576E was used in a next reaction without purification.

MS: m/z=353 [M+H]$^+$.

Fifth Step

To a toluene (4 mL) solution of the crude product of compound 576E obtained in the fourth step was added dimethyl 3-(benzyloxy)-4-oxo-4H-pyran-2,5-dicarboxylate (130 mg, 0.409 mmol), and the mixture was refluxed for 2 hours. The reaction solution was subjected to silica gel column chromatography, and eluted with chloroform-methanol (100:0→90:10, v/v). Concentration of an objective fraction afforded a crude product (268 mg) of compound 576F.

MS: m/z=653 [M+H]$^+$.

Sixth Step

To the crude product (263 mg) of compound 576F obtained in the fifth step was added a 4N hydrochloric acid ethyl acetate solution (3 mL), and the mixture was stirred at room temperature for 1 hour and 30 minutes. The solvent was distilled off, to a THF (4 mL) solution of the resulting concentrated residue was added acetone (1 mL), the mixture was stirred at room temperature for 25 minutes, thereafter, NaBH(OAc)$_3$ (180 mg, 0.807 mmol) was added, and the mixture was stirred at room temperature for 1 hour and 15 minutes. Thereafter, to the reaction solution was added an aqueous saturated sodium bicarbonate solution (7 mL), and the mixture was stirred at room temperature overnight. To the reaction solution was added water, the mixture was extracted with chloroform, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded a crude product (160 mg) of compound 576G.

MS: m/z=563 [M+H]$^+$.

Seventh Step

To an EtOH (4 mL) solution of the crude product (160 mg) of compound 576G obtained in the sixth step was added 2N NaOH (2 mL), and the mixture was stirred at room temperature for 3 hours. To the reaction solution was added a 2N aqueous HCl solution, the mixture was extracted with ethyl acetate, and sodium sulfate was added to the combined extracts to dry them. The solvent was distilled off, and the resulting oil was subjected to silica gel column chromatography, and eluted with chloroform-methanol (100:0→94:6, v/v). Concentration of an objective fraction afforded 78 mg of compound 576H as a yellow solid.

MS: m/z=549 [M+H]$^+$.

Eighth Step

To compound 576H (78 mg, 0.14 mmol) was added diphenyl ether (3 mL), and the mixture was stirred at 245 degree for 1 hour under microwave irradiation. The reaction solution was subjected to silica gel column chromatography, and eluted with chloroform-methanol (100:0→90:10, v/v). Concentration of an objective fraction afforded 43 mg of compound 576I as a bronzed oil.

MS: m/z=505 [M+H]$^+$.

Ninth Step

To compound 576I (42 mg, 0.083 mmol) was added TFA (1.0 mL), and the mixture was stirred at room temperature for 35 minutes. The reaction solution was subjected to toluene azeotropy, to the resulting concentrated residue was added an aqueous saturated sodium bicarbonate solution, and the mixture was extracted with ethyl acetate. Sodium sulfate was added to the combined extracts to dry them. The solvent was distilled off, to the resulting oil were added ethyl acetate and isopropyl ether, and the precipitated solid was filtered and washed to obtain 14 mg of compound 576 as a pale brown solid.

$^1$H-NMR (CDCl$_3$) δ: 1.13 (3H, d, J=6.7 Hz), 1.20 (3H, d, J=6.7 Hz), 2.95-3.13 (2H, m), 3.28 (1H, d, J=13.1 Hz), 3.37-3.59 (2H, m), 3.75 (1H, d, J=10.3 Hz), 4.10 (1H, d, J=10.8 Hz), 4.80-4.87 (2H, m), 5.91 (1H, d, J=5.8 Hz), 6.41 (2H, t, J=6.5 Hz), 6.85 (1H, t, J=6.4 Hz), 7.05-7.35 (6H, m).

MS: m/z=415 [M+H]$^+$.

Example 577

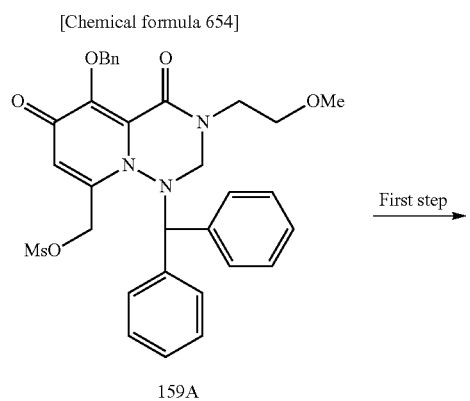

159A

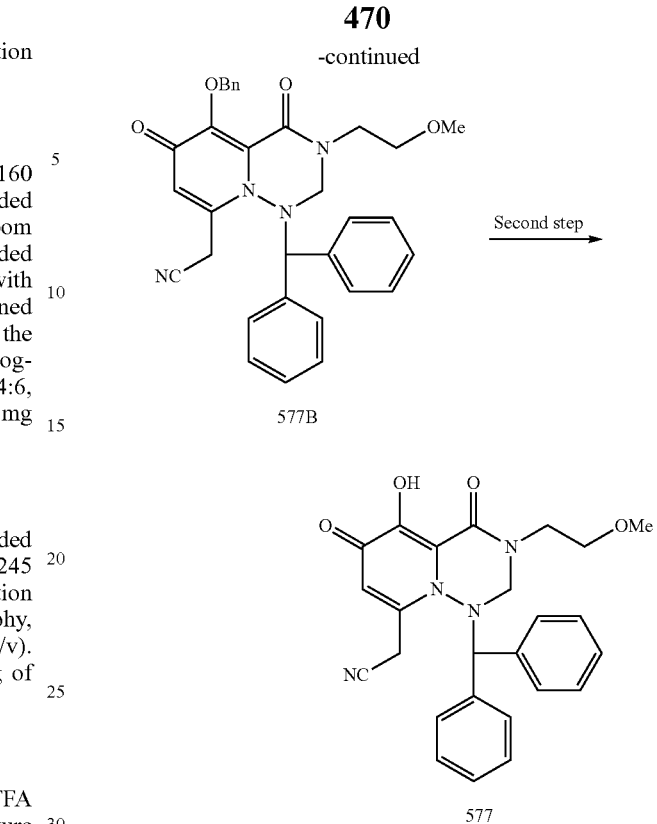

First Step

To a dimethylformamide (3 mL) solution of a crude product (140 mg) of compound 159A was added potassium cyanide (21.0 mg, 0.323 mmol) at room temperature, and the mixture was stirred at 80° C. for 30 minutes, and at 100° C. for 30 minutes. The reaction solution was concentrated under reduced pressure, and the resulting residue was purified by silica gel column chromatography (ethyl acetate/n-hexane=80%→100%) to obtain compound 577B (41.5 mg, 33.5%) as a pale orange foam.

MS: m/z=535.25 [M+H]$^+$.

Second Step

To an acetonitrile (4 mL) solution of compound 577B (41.5 mg, 0.078 mmol) and sodium iodide (45.5 mg, 0.304 mmol) was added chlorotrimethylsilane (0.0400 mL, 0.313 mmol) at room temperature, and the mixture was stirred for 2 hours. To the reaction solution was added water (1 mL), the reaction solution was concentrated under reduced pressure, and the resulting residue was purified by preparative LCMS. Diethyl ether was added to the resulting residue to convert it into a powder, to obtain compound 577 (20.7 mg, 60.0%) as a gray white solid.

$^1$HNMR (DMSO-d$_6$) δ: 3.10 (3H, s), 3.51 (2H, m), 3.70 (1H, d, J=18.9 Hz), 4.03 (1H, d, J=18.9 Hz), 4.46 (1H, d, J=13.4 Hz), 5.04 (1H, d, J=13.4 Hz), 5.56 (1H, s), 5.69 (1H, s), 7.09-7.21 (5H, m), 7.39-7.63 (3H, m), 7.64 (2H, m).

MS: m/z=445.20 [M+H]$^+$.

Example 578

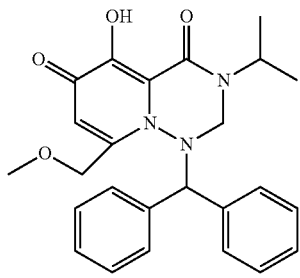

[Chemical formula 655]

Compound 578 was synthesized by the same procedure as that of Example 157.

$^1$HNMR (CDCl$_3$) δ: 0.97 (3H, d, J=6.6 Hz), 1.19 (3H, d, J=6.9 Hz), 3.29 (3H, s), 3.97 (1H, d, J=16.1 Hz), 4.56 (1H, d, J=13.7 Hz), 4.82 (1H, m), 4.96 (1H, d, J=16.1 Hz), 5.34 (1H, s), 5.97 (1H, d, J=13.7 Hz), 6.78 (2H, m), 7.12 (2H, m), 7.44-7.51 (6H, m).

MS: m/z=434.10 [M+H]$^+$.

Example 579

[Chemical formula 656]

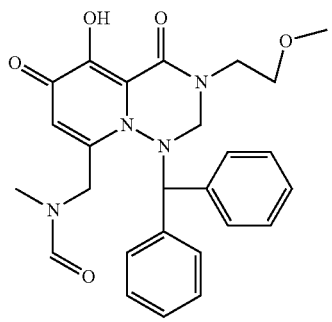

Compound 579 was synthesized by the same procedure as that of Example 163.

MS: m/z=477.25 [M+H]$^+$.

Example 580

[Chemical formula 657]

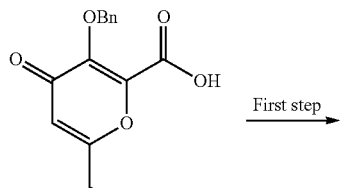

155A

First step →

-continued

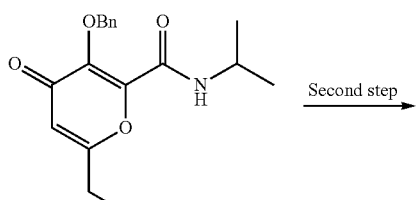

580B

Second step →

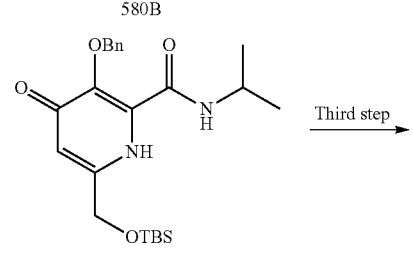

580C

Third step →

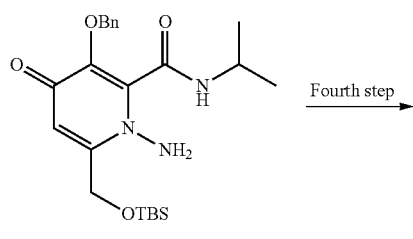

580D

Fourth step →

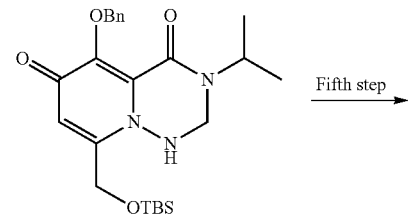

580E

Fifth step →

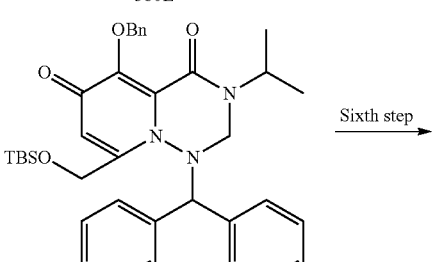

580F

Sixth step →

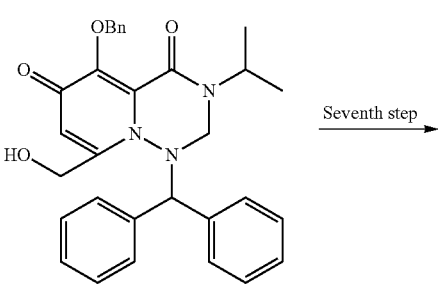

580G

Seventh step →

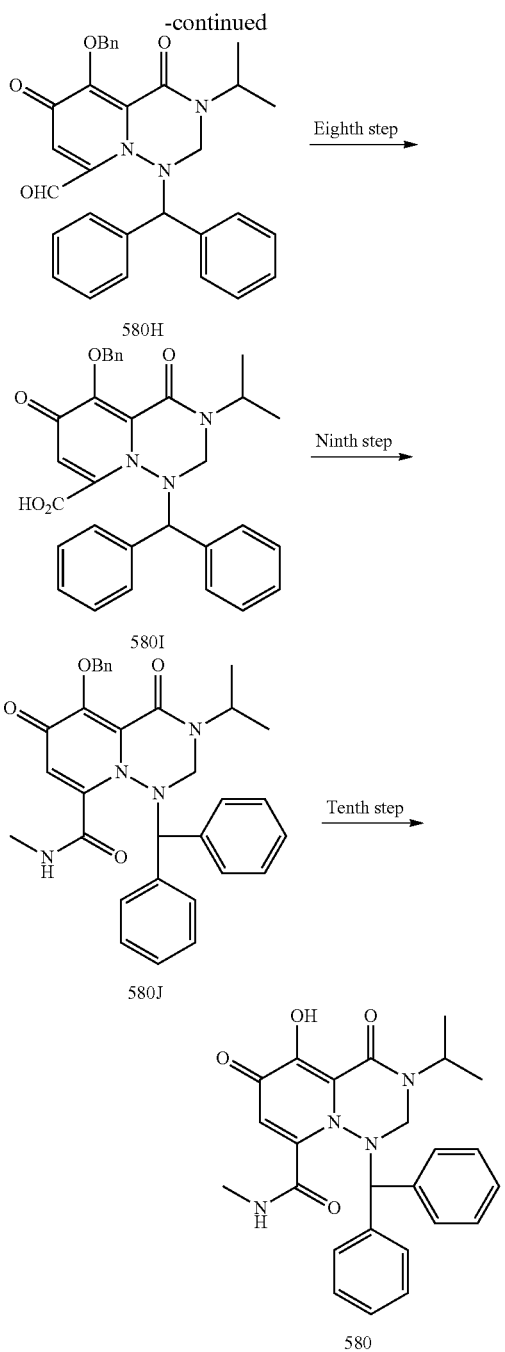

First Step

To a solution of compound 155A (10.5 g, 26.9 mmol), diisopropylethylamine (11.0 mL, 63.0 mmol), 1-methylimidazole (2.60 mL, 32.6 mmol) and isopropylamine (2.80 mL, 32.7 mmol) in toluene (100 mL) and acetonitrile (20 mL) was added dropwise diphenylphosphoric acid chloride (6.80 mL, 32.7 mmol) over 5 minutes under ice-cooling, and the mixture was stirred under ice-cooling for 90 minutes, at room temperature for 90 minutes. To the reaction solution were added tert-butyldimethylsilyl chloride (4.05 g, 26.9 mmol) and triethylamine (4.10 mL, 29.6 mmol) under ice-cooling, the mixture was stirred at room temperature for 80 minutes, 4-dimethylaminopyridine (164 mg, 1.35 mmol) and methylene chloride (100 mL) were added at room temperature, and the mixture was stirred for 15.5 hours. To the reaction solution was added tert-butyldimethylsilyl chloride (2.04 g, 26.9 mmol) at room temperature, and the mixture was stirred for 24 hours. To the reaction solution was added a 10% aqueous acetic acid solution (100 mL) at room temperature, and the mixture was extracted with chloroform, the extracts were combined, washed with saturated sodium bicarbonate water (100 mL), and dried with sodium sulfate. The solvent was concentrated under reduced pressure, and the resulting residue was purified by silica gel column chromatography (ethyl acetate/n-hexane=15%→40%) to obtain compound 580B (6.96 g, 59.9%) as a pale yellow oil.

MS: m/z=432.25 [M+H]$^+$.

Second Step

To an ethanol (50 mL) solution of compound 580B (6.96 g, 16.1 mmol) was added aqueous ammonia (35 mL) at room temperature, and the mixture was stirred for 4 days. The reaction solution was concentrated under reduced pressure, and the resulting residue was purified by silica gel column chromatography (ethyl acetate/n-hexane=75%→100%, methanol/chloroform=0%→15%) to obtain compound 580C (4.50 g, 64.8%) as a pale orange gummy substance.

MS: m/z=431.25 [M+H]$^+$.

Third Step

To a dimethylformamide (90 mL) solution of compound 580C (4.50 g, 10.5 mmol) and potassium carbonate (7.27 g, 52.6 mmol) was added O-(2,4-dinitrophenyl)hydroxylamine (6.29 g, 31.6 mmol) at room temperature, and the mixture was stirred for 2 days. To the reaction solution was added chloroform (180 mL) at room temperature, the precipitated insolubles were filtered off, the filtrated was concentrated under reduced pressure, and the resulting residue was purified by silica gel column chromatography (methanol/chloroform=0%→10%) to obtain compound 580D (5.28 g, quant) as a yellow solid.

MS: m/z=446.25 [M+H]$^+$.

Fourth Step

To an ethanol (15 ml) solution of compound 580D (1.29 g, 2.89 mmol) was added paraformaldehyde (261 mg, 8.68 mmol) at room temperature, and the mixture was stirred at 140° C. for 3 hours under microwave irradiation. The reaction solution was concentrated under reduce pressure, and the resulting residue was purified by silica gel column chromatography (ethyl acetate/n-hexane=50%→100%) to obtain compound 580E (2.47 g, 93.0%) as a pale orange solid.

MS: m/z=458.20 [M+H]$^+$.

Fifth Step

To a DMF (25 mL) solution of compound 580E (2.47 g, 5.40 mmol) were added cesium carbonate (5.28 g, 16.2 mmol) and bromodiphenylmethane (4.02 g, 16.3 mmol) under ice-cooling, and the mixture was stirred at room temperature for 2 days. To the reaction solution was added water (50 mL) under ice-cooling and, thereafter, the mixture was extracted with ethyl acetate (150 mL×2). The extracts were combined, sequentially washed with water (50 mL×2) and an aqueous saturated sodium chloride solution (50 mL), and dried with sodium sulfate. The solvent was concentrated under reduced pressure, and the resulting residue was purified by silica gel column chromatography (ethyl acetate/n-hexane=50%→100%, methanol/chloroform=10%→20%) to obtain compound 580F (1.60 g, 47.5%) as a yellow form.

MS: m/z=624.30 [M+H]$^+$.

Sixth Step

To a methanol (40 mL) solution of compound 580F (1.60 g, 2.56 mmol) was added hydrogen chloride (4N ethyl acetate solution, 20 mL) at room temperature, and the mixture was stirred for 2 hours. The reaction solution was concentrated under reduced pressure, to the resulting residue was added saturated sodium bicarbonate water (20 mL) at room temperature and, thereafter, the mixture was extracted with chloroform three times. The extracts were combined, and dried with sodium sulfate, the solvent was distilled off under reduced pressure, and the resulting residue was purified by silica gel column chromatography (ethyl acetate) to obtain compound 580G (920 mg, 70.4%) as a white foam.

MS: m/z=510.25 [M+H]$^+$.

Seventh Step

To a THF (80 mL) solution of compound 580G (816 mg, 1.60 mmol) was added manganese dioxide (2.39 g, 27.5 mmol) at room temperature, and the mixture was stirred for 19 hours. After the reaction solution was filtered, the filtrate was distilled off under reduced pressure, and the resulting crude product (785 mg) of compound 580H was used in a next reaction without purification.

MS: m/z=508.20 [M+H]$^+$.

Eighth Step

To a solution of the crude product (635 mg, 1.25 mmol) of compound 580H obtained in the seventh step and amidosulfuric acid (425 mg, 4.38 mmol) in methanol (30 mL) and water (10 mL) was added dropwise a solution of sodium chlorite (396 mg, 4.38 mmol) in water (4 mL) over 10 minutes under ice-cooling, the mixture was stirred at room temperature for 30 minutes, and a 5% aqueous sodium hydrogen sulfite solution (10 mL) was added. Methanol was distilled off under reduced pressure, and the resulting residue was extracted with ethyl acetate two times. The extracts were combined, washed with an aqueous saturated sodium chloride solution (10 mL), and dried with sodium sulfate. The filtrated was distilled off under reduced pressure, and the resulting crude product of compound 580I was used in a next reaction without purification.

MS: m/z=524.25 [M+H]$^+$.

Ninth Step

To a methylene chloride (20 mL) solution of the crude product (164 mg, 0.313 mmol) of compound 580I obtained in the eighth step, diisopropylethylamine (0.131 mL, and 0.751 mmol), 1-methylimidazole (0.0300 mL, 0.376 mmol) and methylamine (2.0M tetrahydrofuran solution, 0.188 mL, 0.376 mmol) was added diphenylphosphoric acid chloride (0.0780 mL, 0.375 mmol) at room temperature, the mixture was stirred for 3.5 hours, methylamine hydrochloride (25.0 mg, 0.370 mmol) was added, and the mixture was stirred for 6 days. The reaction solution was distilled off under reduced pressure, and the resulting residue was purified by silica gel column chromatography (ethyl acetate/n-hexane=75%→00%) to obtain compound 580J (45.7 mg, 27.2%) as a white foam.

MS: m/z=537.30 [M+H]$^+$.

Tenth Step

To an acetonitrile (4 mL) solution of compound 580J (45.7 mg, 0.0850 mmol) and sodium iodide (103 mg, 0.687 mmol) was added chlorotrimethylsilane (0.0870 mL, 0.681 mmol) at room temperature, and the mixture was stirred for 20 hours. To the reaction solution was added a 5% aqueous sodium hydrogen sulfite solution (4 mL), and the mixture was extracted with chloroform two times. After the extracts were combined, and dried with sodium sulfate, the residue obtained by concentration under reduced pressure was purified by preparative LCMS. Diethyl ether and n-hexane were added to the resulting residue to convert it into a powder, to obtain compound 580 (17.1 mg, 45.0%) as a white solid.

$^1$HNMR (CDCl$_3$) δ: 0.93 (3H, d, J=6.9 Hz), 1.11 (3H, d, J=6.9 Hz), 2.83 (3H, d, J=4.8 Hz), 4.53 (1H, d, J=13.4 Hz), 4.85 (1H, m), 4.97 (1H, d, J=13.4 Hz), 5.07 (1H, brd), 5.25 (1H, s), 5.86 (1H, s), 6.97 (2H, m), 7.15-7.24 (2H, m), 7.38-7.46 (6H, m).

MS: m/z=447.20 [M+H]$^+$.

Example 581

[Chemical formula 658]

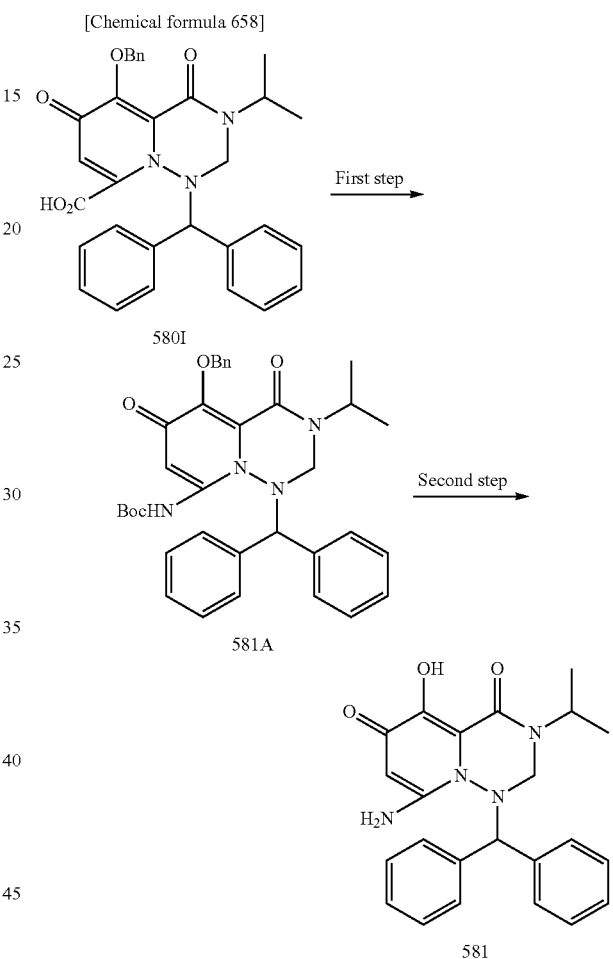

First Step

To a tert-butanol (4 mL) solution of compound 580I (398 mg, 0.760 mmol) were added triethylamine (0.158 mL, 1.14 mmol) and diphenylphosphoric acid azide (0.196 mL, 0.912 mmol) at room temperature, and the mixture was heated to reflux for 20 hours. To the reaction solution was added water (20 mL) at room temperature, and the mixture was extracted with chloroform three times. The extracts were combined, and dried with sodium sulfate. The solvent was distilled off under reduced pressure, and the resulting residue was purified by silica gel column chromatography (methanol/chloroform=0%→10%) to obtain compound 581A (167 mg, 36.9%) as a gray white solid.

MS: m/z=595.10 [M+H]$^+$.

Second Step

To a methylene chloride (2 mL) solution of compound 581A (167 mg, 0.281 mmol) was added trifluoroacetic acid (2 mL) at room temperature, and the mixture was stirred for 1.5 hours. The reaction solution was concentrated under reduced pressure, and the resulting residue was purified by preparative LCMS. Ethyl acetate, diethyl ether, and methanol were added to the resulting residue to convert it into a powder, to obtain compound 581 (29.4 mg, 25.9%) as a white solid.

$^1$HNMR (DMSO-$d_6$) δ: 0.81 (3H, d, J=6.5 Hz), 0.98 (3H, d, J=6.5 Hz), 4.35 (1H, d, J=12.6 Hz), 4.63 (1H, m), 4.68 (1H, d, J=12.6 Hz), 4.80 (1H, s), 5.28 (1H, s), 6.34 (2H, s), 7.10-7.43 (8H, m), 7.81-7.83 (2H, m).

MS: m/z=404.95 [M+H]$^+$.

Example 582

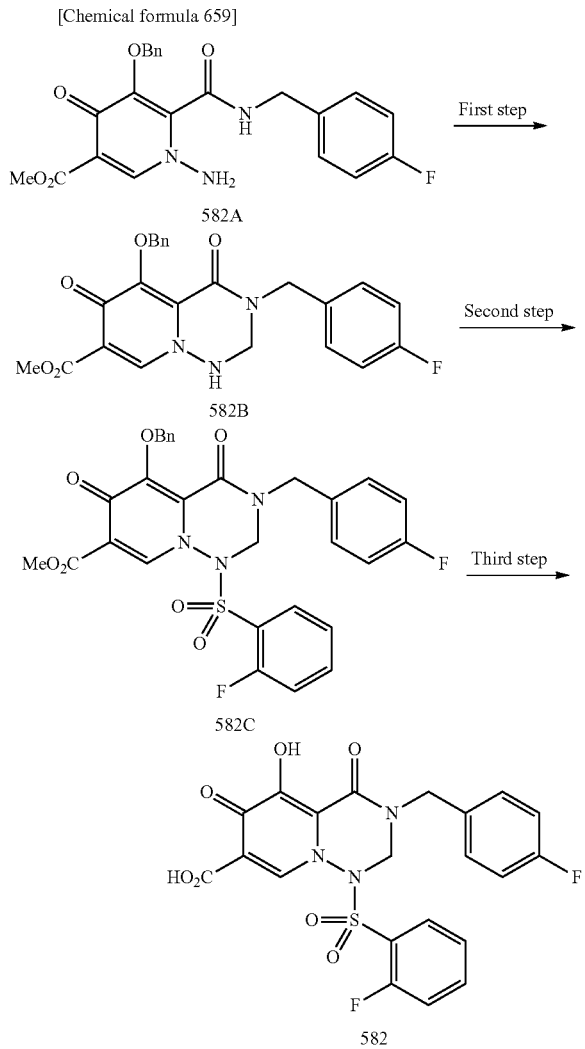

First Step

To an ethanol (4 mL) solution of compound 582A (200 mg, 0.470 mmol) synthesized according to the synthesis method of Example 65 was added paraformaldehyde (14.8 mg, 0.493 mmol) at room temperature, and the mixture was stirred at 140° C. for 45 minutes under microwave irradiation. The reaction solution was distilled off under reduced pressure, and the resulting residue was purified by silica gel column chromatography (ethyl acetate/n-hexane=90%→100%) to obtain compound 582B (173 mg, 84.0%) as a white solid.

MS: m/z=438.15 [M+H]$^+$.

Second Step

To a methylene chloride (4 mL) solution of compound 582B (173 mg, 0.396 mmol), 4-dimethylaminopyridine (5.6 mg, 0.046 mmol) and triethylamine (0.164 mL, 1.18 mmol) was added 2-fluorobenzenesulfonyl chloride (0.0790 mL, 0.597 mmol) at room temperature, and the mixture was stirred for 3 days. The reaction solution was distilled off under reduced pressure, and the resulting residue was purified by silica gel column chromatography (ethyl acetate/n-hexane=60%→80%) to obtain compound 582C (199 mg, 84.0%) as a white solid.

MS: m/z=596.15 [M+H]$^+$.

Third Step

To an acetic acid (2 mL) solution of compound 582C (162 mg, 0.272 mmol) was added 48% aqueous hydrogen bromide (2 mL) at room temperature, and the mixture was stirred at 100° C. for 20 minutes under microwave irradiation. The solvent was distilled off under reduced pressure, and diethyl ether and methanol were added to the resulting residue to convert it into a powder, to obtain compound 582 (160 mg, quant) as a yellow solid.

$^1$HNMR (DMSO-$d_6$) δ: 4.34 (1H, d, J=14.7 Hz), 4.59 (1H, d, J=14.7 Hz), 5.50 (1H, d, J=14.3 Hz), 5.81 (1H, d, J=14.3 Hz), 7.15-7.21 (2H, m), 7.35-7.40 (2H, m), 7.45-7.61 (2H, m), 7.78 (1H, m), 7.93 (1H, m), 8.42 (1H, s).

MS: m/z=492.10 [M+H]$^+$.

Example 583, Example 584

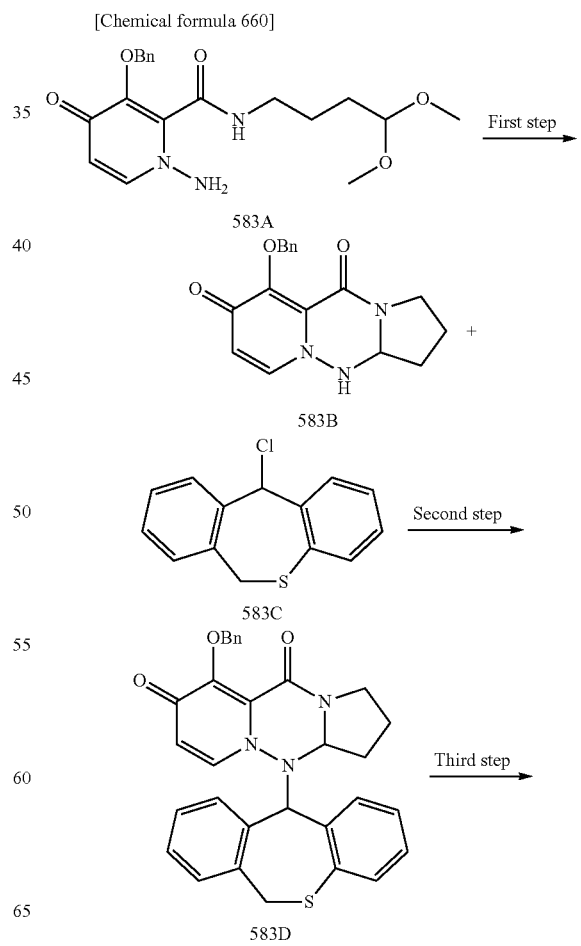

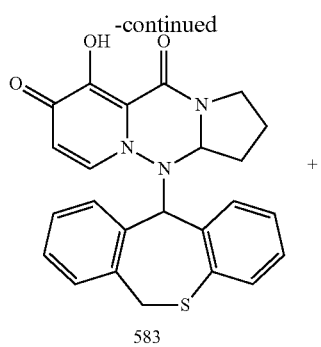

583

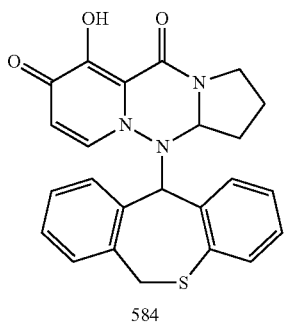

584

First Step

Compound 583A (3.0 g, 0.99 mmol) synthesized according to Example 95 was added to toluene (300 ml) and acetic acid (30.0 ml) to dissolve, and TsOH H$_2$O (0.1 g, 0.526 mmol) was added at room temperature. The reaction mixture was stirred for 3 hours under heat-refluxing. After concentration under reduced pressure, the residue was purified by amino silica gel column chromatography (CHCl$_3$/MeOH 50:1) to obtain compound 583B (1.8 g, 72.4%).

MS: m/z=312 [M+H]$^+$.

Second Step

Compound 583B (233 mg, 0.748 mmol) and compound 583C (197 mg, 0.8 mmol) were suspended in THF (7.5 ml), and NaHMDS (1.123 ml, 1.123 mmol, 1M-THF solution) was added at room temperature under nitrogen stream. After stirring at room temperature for 3 hours, water was added, and the mixture was extracted with ethyl acetate (2×30 mL). The ethyl acetate layer was washed with an aqueous saturated sodium chloride solution, and dried with sodium sulfate, and the solvent was distilled off under reduced pressure. The residue was purified by silica gel column chromatography (CHCl$_3$/MeOH 20:1) to obtain compound 583D (90 mg, 23.1%).

MS: m/z=522 [M+H]$^+$.

Third Step

Compound 583D (90 mg, 0.173 mmol) was dissolved in a mixed solvent of MeOH (3 ml) and THF (3.00 ml), and 10% palladium-carbon (90 mg, 0.846 mmol) was added. The mixture was stirred for 24 hours under hydrogen (2 atm) stream, and insolubles were filtered. The residue was purified using HPLC (MeCN—H$_2$O), and diastereomers were resolved.

First Fraction (Compound 583)

(15 mg, 20.1%)

MS: m/z=432 [M+H]$^+$.

Second Fraction (Compound 584)

(45 mg, 60.4%)

MS: m/z=432 [M+H]$^+$.

Example 585

[Chemical formula 661]

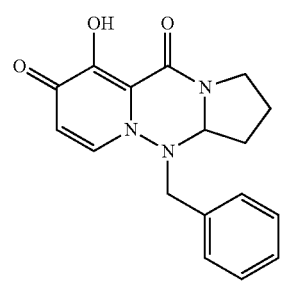

Compound 585 was synthesized by the same procedure as that of Example 403.

$^1$H-NMR (DMSO-d$_6$) δ: 1.87-2.28 (4H, m), 3.40-3.80 (3H, m), 4.32 (1H, d, J=12.96 Hz), 5.34 (1H, t, J=7.32 Hz), 5.65 (1H, d, J=7.63 Hz), 6.90 (1H, d, J=7.78 Hz), 7.10-7.35 (5H, m).

MS: m/z=312 [M+H]$^+$.

Example 586

[Chemical formula 662]

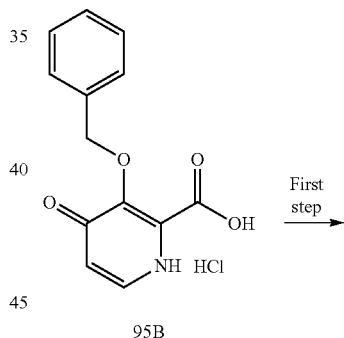

95B

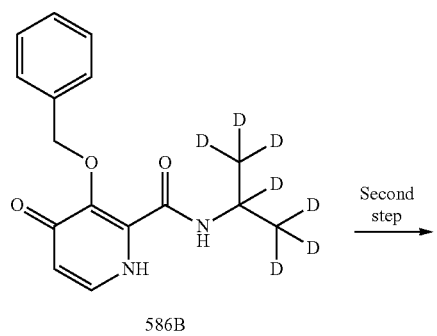

586B

481
-continued

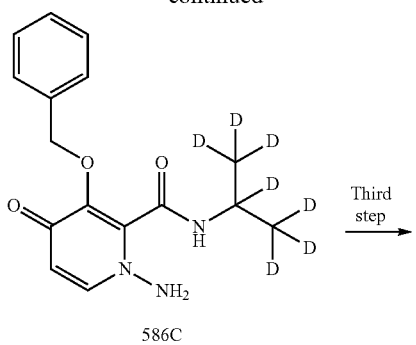
586C

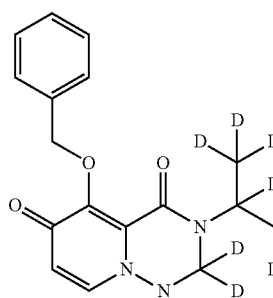
586D

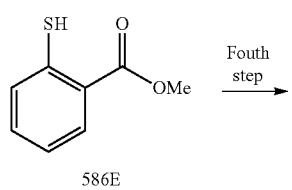
586E

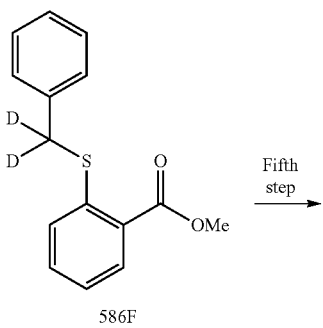
586F

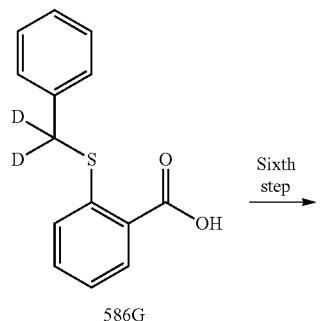
586G

Third step →

Fourth step →

Fifth step →

Sixth step →

482
-continued

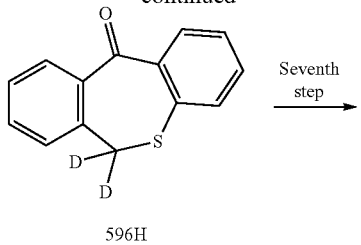
596H

Seventh step →

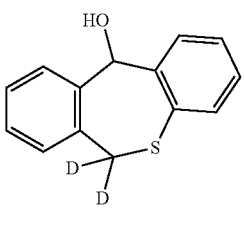
596I

586D + 586I  Eighth step →

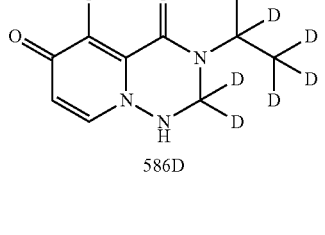
586

First Step

Compound 95B (2.29 g, 8.12 mmol) was dissolved in pyridine (10 ml), iso-propyl-$D_7$-amine hydrochloride (1.00 g, 9.75 mmol), 1H-benzo[d][1,2,3]triazol-1-ol (1.10 g, 8.12 mmol) and N1-((ethylimino)methylene)-N3,N3-dimethylpropane-1,3-diamine hydrochloride (3.11 g, 16.2 mmol) were added, and the mixture was stirred at room temperature for 20 hours. The reaction solution was poured into water, and the mixture was extracted with ethyl acetate, and dried with sodium sulfate. The solvent was distilled off under reduced pressure, and the resulting crude product was purified by silica gel column chromatography, and eluted with chloroform-methanol (97:3, v/v). To the resulting compound was added diethyl ether, and the precipitated residue was filtered to obtain 1.36 g of a white solid 586B.

Second Step

Compound 586B (1.36 g, 4.64 mmol) obtained in the first step was dissolved in dimethylformamide (20 ml), potassium carbonate (3.20 g, 23.2 mmol) was added, and the mixture was stirred at room temperature for 50 minutes. O-(2,4-dinitrophenyl)hydroxylamine (1.85 g, 9.27 mmol) was added, and the mixture was stirred at room temperature for 18 hours. To the reaction solution was added chloroform, the generated precipitate was removed by filtration, and the filtrate was concentrated under reduced pressure. The resulting crude product was purified by amino column chromatography, and eluted with chloroform-methanol (97:3, v/v) to obtain 835 mg of a colorless solid 586C.

¹H-NMR (CDCl₃) δ: 5.28 (2H, s), 5.63 (2H, s), 6.32 (1H, d, J=7.7 Hz), 7.10 (1H, brs), 7.42 (6H, m).
Third Step Compound 586C (581 mg, 1.88 mmol) obtained in the second step and paraformaldehyde-D₂ (181 mg, 5.65 mmol) were added to ethanol (12 ml), and the mixture was stirred at 140° C. for 30 minutes under microwave irradiation. The reaction solution was concentrated under reduced pressure, and the resulting crude product was purified by amino column chromatography, and eluted with chloroform-methanol (97:3, v/v). To the resulting compound was added diethyl ether, and the precipitated residue was filtered to obtain 140 mg of white solid 586D.

¹H-NMR (CDCl₃) δ: 4.39 (2H, d, J=8.1 Hz), 5.36 (2H, s), 5.42 (1H, t, J=8.0 Hz), 6.37 (1H, d, J=7.6 Hz), 7.48 (6H, m).
Fourth Step Compound 586E (972 mg, 5.78 mmol) was dissolved in tetrahydrofuran (10 ml), sodium hydride (60%, 231 mg, 5.78 mmol) and benzyl bromide-D₂ (1.00 g, 5.78 mmol) were added at 0° C., and the mixture was stirred at 60° C. for 30 minutes. The reaction solution was added to dilute hydrochloric acid, the mixture was extracted with ethyl acetate, and the organic layer was washed with an aqueous sodium bicarbonate solution. The solvent was distilled off under reduced pressure to obtain 1.48 g of a white solid 586F.

¹H-NMR (CDCl₃) δ: 3.95 (3H, s), 7.17-7.48 (8H, m), 8.00 (1H, dd, J=7.8, 1.3 Hz).
Fifth Step Compound 586F (1.50 g, 5.76 mmol) obtained in the fourth step was dissolved in methanol (20 ml) and tetrahydrofuran (20 ml), a 2N aqueous sodium hydroxide solution (14.4 ml, 28.8 mmol) was added, and the mixture was stirred at room temperature for 3 hours. To the reaction solution was added dilute hydrochloric acid to make the solution acidic, the mixture was extracted with ethyl acetate, and the organic layer was washed with an aqueous saturated sodium chloride solution, and dried with sodium sulfate. The solvent was distilled off under reduced pressure, to the resulting compound were added n-hexane-ethyl acetate, and the precipitated residue was filtered to obtain 1.17 g of a white solid 586G.

¹H-NMR (CDCl₃) δ: 7.18-7.48 (8H, m), 8.11 (1H, dd, J=7.9, 1.6 Hz).
Sixth Step

To compound 586G (1.15 g, 4.67 mmol) obtained in the fifth step was added toluene (10 ml), dimethylformamide (0.100 ml, 1.29 mmol) and thionyl chloride (0.410 ml, 5.60 mmol) were added, and the mixture was stirred at 130° C. for 1.5 hours. After cooled to room temperature, the reaction solution was concentrated under reduced pressure. To the resulting compound was added n-hexane, and the precipitated residue was filtered to obtain 1.16 g of a white solid. To aluminum chloride (718 mg, 5.38 mmol) were added dichloromethane (10 ml) and nitromethane (0.5 ml), a dichloromethane solution (5 ml) of 500 mg of the compound obtained above was added at 0° C., and the mixture was stirred at room temperature for 5 hours. To the reaction solution was added an aqueous sodium hydroxide solution, and the mixture was extracted with methylene chloride, and the organic layer was dried with sodium sulfate. The solvent was concentrated under reduced pressure, and the resulting crude product was purified by silica gel column chromatography, and eluted with n-hexane-ethyl acetate (4:1, v/v). To the resulting compound was added n-hexane, and the precipitated residue was filtered to obtain 155 mg of a pale yellow solid 586H.

¹H-NMR (CDCl₃) δ: 7.21-7.39 (6H, m), 7.46 (1H, td, J=7.5, 1.4 Hz), 7.59 (1H, dd, J=7.5, 1.4 Hz), 8.21 (1H, dd, J=8.0, 1.0 Hz).
Seventh Step Compound 586H (150 mg, 0.657 mmol) obtained in the sixth step was dissolved in tetrahydrofuran (3 ml), lithium aluminum hydride-D₄ (13.8 mg, 0.329 mmol) was added at 0° C., and the mixture was stirred at room temperature for 2 hours. To the reaction solution was added dilute hydrochloric acid, the mixture was extracted with ethyl acetate, and dried with sodium sulfate, and the solvent was distilled off under reduced pressure. To the resulting compound were added n-hexane-dichloromethane, and the precipitated residue was filtered to obtain 114 mg of a white solid 586I.

¹H-NMR (CDCl₃) δ: 7.17 (6H, m), 7.40-7.52 (2H, m).
Eighth Step

Compound 586D (76.0 mg, 0.236 mmol) and 586I (54.5 mg, 0.235 mmmol) were dissolved in acetic acid (3.2 ml), and concentrated sulfuric acid (0.8 ml) was added dropwise under water-cooling. After the mixture was stirred at room temperature for 30 minutes, the mixture was poured into water, and extracted with ethyl acetate. The organic layer was dried with sodium sulfate, the solvent was distilled off under reduced pressure, to the resulting crude product were added ethyl acetate-diethyl ether, and the precipitated residue was filtered to obtain 32 mg of a white solid 586.

¹H-NMR (DMSO-d₆) δ: 5.57 (1H, d, J=7.3 Hz), 6.82-7.44 (9H, m).

MS: m/z=446 [M+H]⁺.

Using a commercially available heavy hydrogen reagent, and according to Example 586, compounds 587 to 591 were synthesized.

Example 587

[Chemical formula 663]

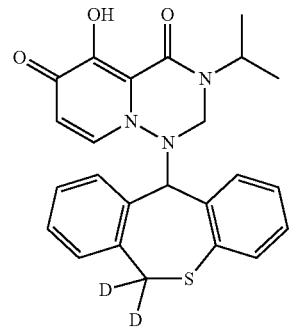

Example 588
MS: m/z = 436 [M + H]+
[Chemical formula 664]
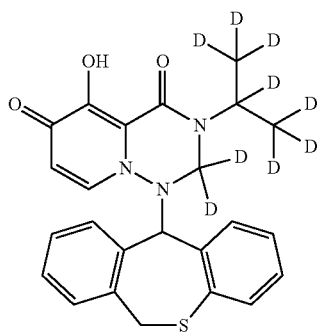
MS: m/z=436 [M+H]+
¹H-NMR (DMSO-d₆) δ: 3.87 (1H, d, J=13.4 Hz), 5.58 (1H, d, J=7.8 Hz), 5.60 (1H, d, J=12.6 Hz), 6.81-7.48 (9H, m).
Example 589
[Chemical formula 665]
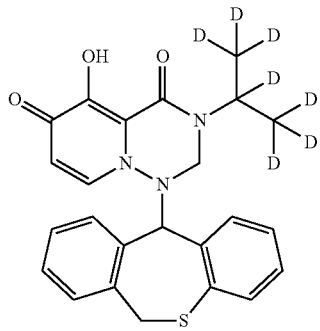
MS: m/z=441 [M+H]+
Example 590
[Chemical formula 666]
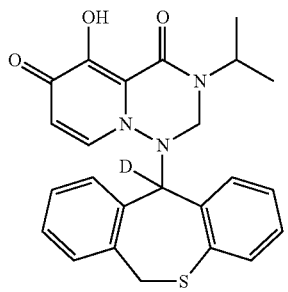
MS: m/z=435 [M+H]+
Example 591
[Chemical formula 667]
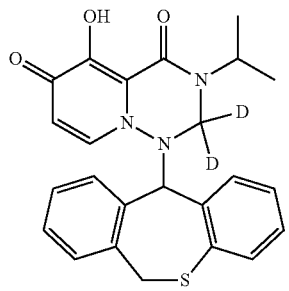
MS: m/z=436 [M+H]+
The following EX-1 to EX-29 can be also synthesized like the Examples, and are a preferable embodiment of the present invention.
[Chemical formula 668]
EX-1
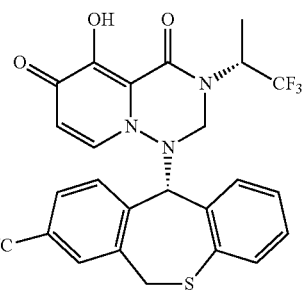
EX-2
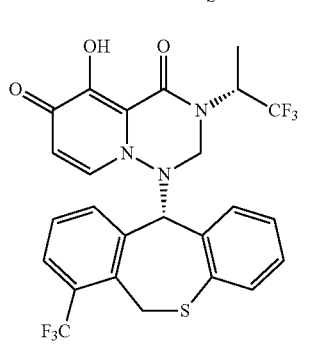
EX-3
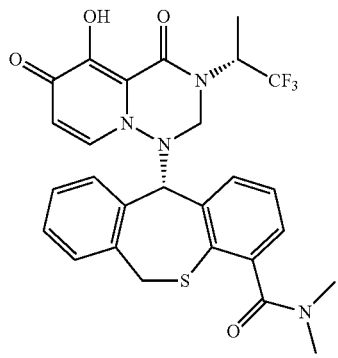

-continued
EX-4
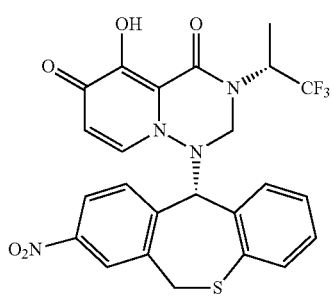
EX-5
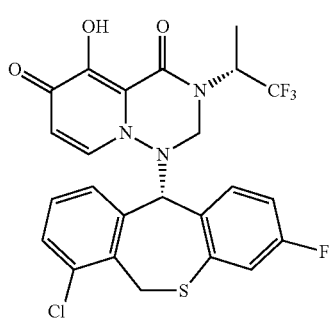
EX-6
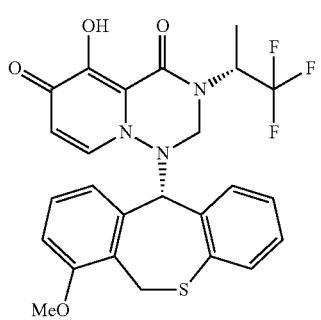
EX-7
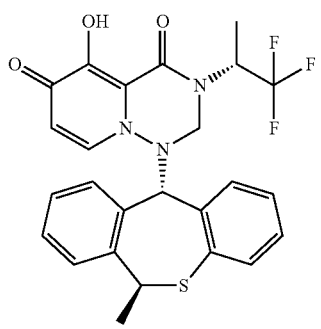
EX-8
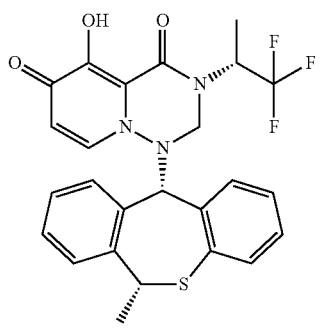
-continued
EX-9
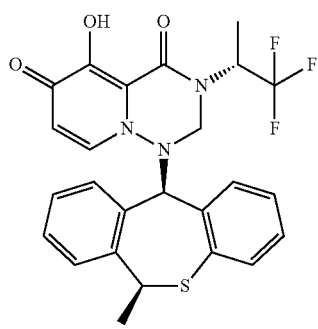
EX-10
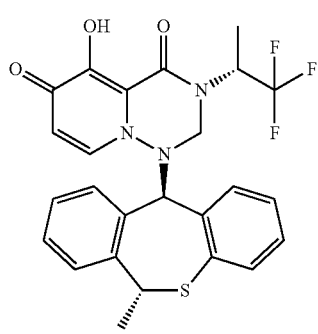
EX-11
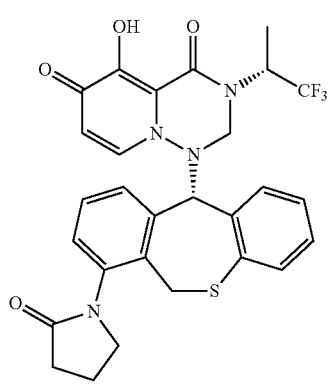
EX-12
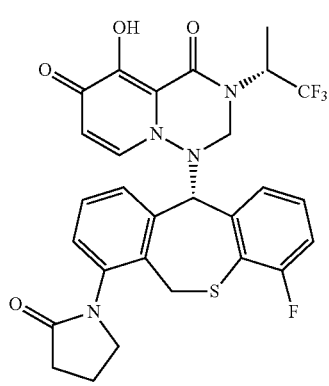

489
-continued
[Chemical formula 669]
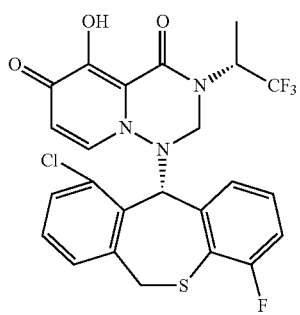
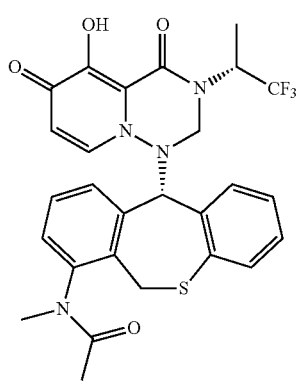
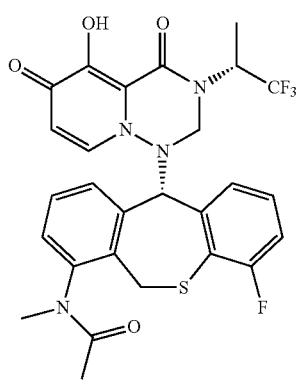
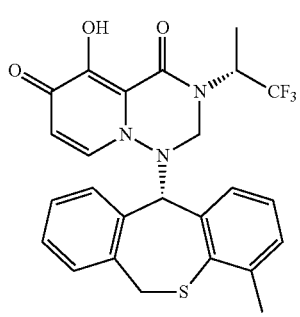
490
-continued
EX-13
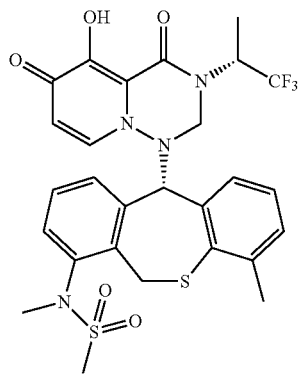  EX-17
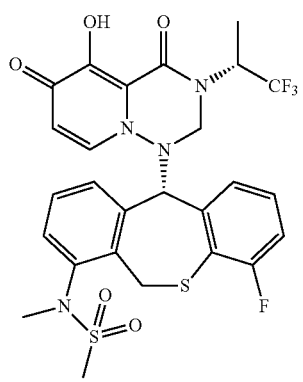  EX-18
EX-14
EX-15
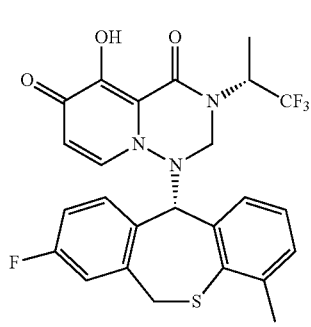  EX-19
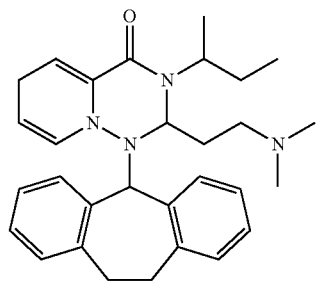  EX-20
EX-16
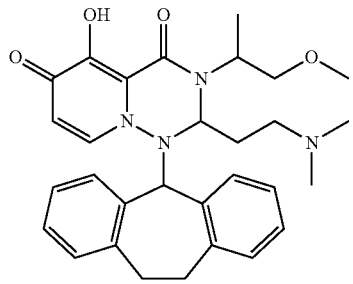  EX-21

EX-22
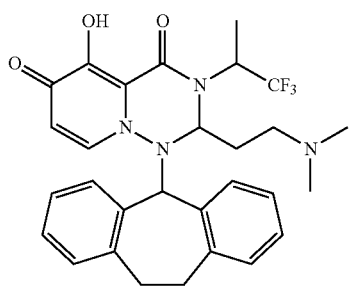
EX-23
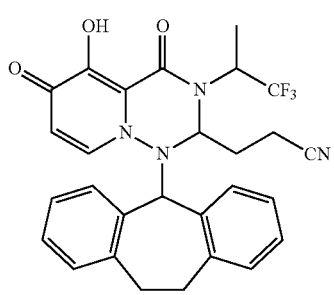
EX-24
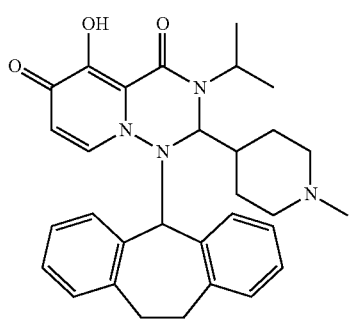
[Chemical formula 670]
EX-25
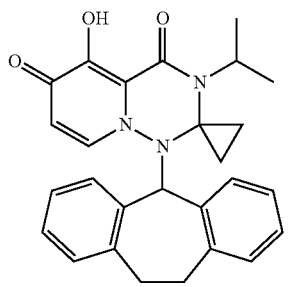
EX-26
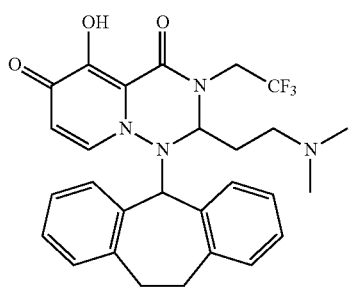
EX-27
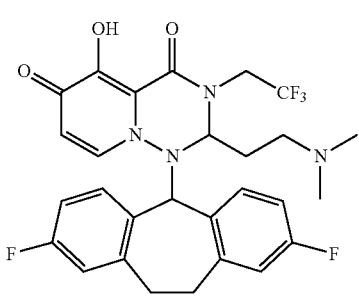
EX-28
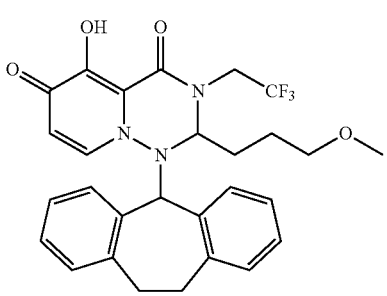
EX-29
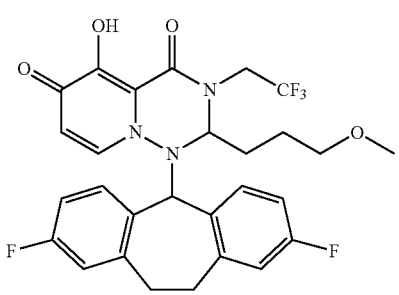
Further, the following combinations of substituents can be also synthesized like the above Examples, and are a preferable embodiment of the present invention.
Compounds in which, in the following formula (I) or (II):
[Chemical formula 671]
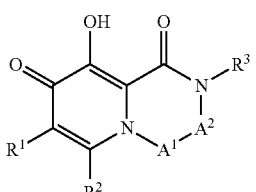
(I)
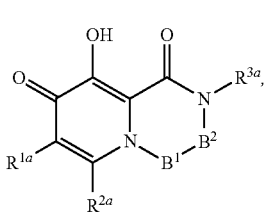
(II)
combinations of $R^3$ or $R^{3a}$, as well as $R^7$ or $R^{7a}$ of the following formula (I') or (II'):

493

[Chemical Formula 672]

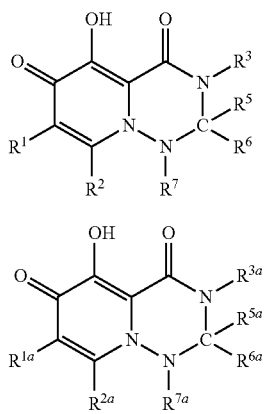

are selected from the following Tables 6 to 10 and Table 11, respectively.

Combinations of ($R^3$, $R^7$) or ($R^{3a}$, $R^{7a}$)=(R3-1, R7-1), (R3-1, R7-2), (R3-1, R7-3), (R3-1, R7-4), (R3-1, R7-5), (R3-1, R7-6), (R3-1, R7-7), (R3-1, R7-8), (R3-1, R7-9), (R3-1, R7-10), (R3-1, R7-11), (R3-1, R7-12), (R3-1, R7-13), (R3-1, R7-14), (R3-1, R7-15), (R3-1, R7-16), (R3-1, R7-17), (R3-1, R7-18), (R3-1, R7-19), (R3-1, R7-20), (R3-1, R7-21), (R3-1, R7-22), (R3-1, R7-23), (R3-1, R7-24), (R3-1, R7-25), (R3-1, R7-26), (R3-1, R7-27), (R3-1, R7-28), (R3-1, R7-29), (R3-1, R7-30), (R3-1, R7-31), (R3-1, R7-32), (R3-1, R7-33), (R3-1, R7-34), (R3-1, R7-35), (R3-1, R7-36), (R3-1, R7-37), (R3-1, R7-38), (R3-1, R7-39), (R3-1, R7-40), (R3-1, R7-41), (R3-1, R7-42), (R3-1, R7-43), (R3-1, R7-44), (R3-1, R7-45), (R3-1, R7-46), (R3-1, R7-47), (R3-1, R7-48), (R3-1, R7-49), (R3-1, R7-50), (R3-1, R7-51), (R3-1, R7-52), (R3-1, R7-53), (R3-1, R7-54), (R3-1, R7-55), (R3-1, R7-56), (R3-1, R7-57), (R3-1, R7-58), (R3-1, R7-59), (R3-1, R7-60), (R3-1, R7-61), (R3-1, R7-62), (R3-1, R7-63), (R3-1, R7-64), (R3-1, R7-65), (R3-1, R7-66), (R3-1, R7-67), (R3-1, R7-68), (R3-1, R7-69), (R3-1, R7-70), (R3-1, R7-71), (R3-1, R7-72), (R3-1, R7-73), (R3-1, R7-74), (R3-1, R7-75), (R3-1, R7-76), (R3-1, R7-77), (R3-2, R7-1), (R3-2, R7-2), (R3-2, R7-3), (R3-2, R7-4), (R3-2, R7-5), (R3-2, R7-6), (R3-2, R7-7), (R3-2, R7-8), (R3-2, R7-9), (R3-2, R7-10), (R3-2, R7-11), (R3-2, R7-12), (R3-2, R7-13), (R3-2, R7-14), (R3-2, R7-15), (R3-2, R7-16), (R3-2, R7-17), (R3-2, R7-18), (R3-2, R7-19), (R3-2, R7-20), (R3-2, R7-21), (R3-2, R7-22), (R3-2, R7-23), (R3-2, R7-24), (R3-2, R7-25), (R3-2, R7-26), (R3-2, R7-27), (R3-2, R7-28), (R3-2, R7-29), (R3-2, R7-30), (R3-2, R7-31), (R3-2, R7-32), (R3-2, R7-33), (R3-2, R7-34), (R3-2, R7-35), (R3-2, R7-36), (R3-2, R7-37), (R3-2, R7-38), (R3-2, R7-39), (R3-2, R7-40), (R3-2, R7-41), (R3-2, R7-42), (R3-2, R7-43), (R3-2, R7-44), (R3-2, R7-45), (R3-2, R7-46), (R3-2, R7-47), (R3-2, R7-48), (R3-2, R7-49), (R3-2, R7-50), (R3-2, R7-51), (R3-2, R7-52), (R3-2, R7-53), (R3-2, R7-54), (R3-2, R7-55), (R3-2, R7-56), (R3-2, R7-57), (R3-2, R7-58), (R3-2, R7-59), (R3-2, R7-60), (R3-2, R7-61), (R3-2, R7-62), (R3-2, R7-63), (R3-2, R7-64), (R3-2, R7-65), (R3-2, R7-66), (R3-2, R7-67), (R3-2, R7-68), (R3-2, R7-69), (R3-2, R7-70), (R3-2, R7-71), (R3-2, R7-72), (R3-2, R7-73), (R3-2, R7-74), (R3-2, R7-75), (R3-2, R7-76), (R3-2, R7-77),

494

(R3-3, R7-1), (R3-3, R7-2), (R3-3, R7-3), (R3-3, R7-4), (R3-3, R7-5), (R3-3, R7-6), (R3-3, R7-7), (R3-3, R7-8), (R3-3, R7-9), (R3-3, R7-10), (R3-3, R7-11), (R3-3, R7-12), (R3-3, R7-13), (R3-3, R7-14), (R3-3, R7-15), (R3-3, R7-16), (R3-3, R7-17), (R3-3, R7-18), (R3-3, R7-19), (R3-3, R7-20), (R3-3, R7-21), (R3-3, R7-22), (R3-3, R7-23), (R3-3, R7-24), (R3-3, R7-25), (R3-3, R7-26), (R3-3, R7-27), (R3-3, R7-28), (R3-3, R7-29), (R3-3, R7-30), (R3-3, R7-31), (R3-3, R7-32), (R3-3, R7-33), (R3-3, R7-34), (R3-3, R7-35), (R3-3, R7-36), (R3-3, R7-37), (R3-3, R7-38), (R3-3, R7-39), (R3-3, R7-40), (R3-3, R7-41), (R3-3, R7-42), (R3-3, R7-43), (R3-3, R7-44), (R3-3, R7-45), (R3-3, R7-46), (R3-3, R7-47), (R3-3, R7-48), (R3-3, R7-49), (R3-3, R7-50), (R3-3, R7-51), (R3-3, R7-52), (R3-3, R7-53), (R3-3, R7-54), (R3-3, R7-55), (R3-3, R7-56), (R3-3, R7-57), (R3-3, R7-58), (R3-3, R7-59), (R3-3, R7-60), (R3-3, R7-61), (R3-3, R7-62), (R3-3, R7-63), (R3-3, R7-64), (R3-3, R7-65), (R3-3, R7-66), (R3-3, R7-67), (R3-3, R7-68), (R3-3, R7-69), (R3-3, R7-70), (R3-3, R7-71), (R3-3, R7-72), (R3-3, R7-73), (R3-3, R7-74), (R3-3, R7-75), (R3-3, R7-76), (R3-3, R7-77).

TABLE 6

| | $R^3$ or $R^{3a}$ |
|---|---|
| R3-1 | ![structure with CF3] |
| R3-2 | ![structure with OH and CF3] |
| R3-3 | ![oxetane structure] |

TABLE 7

| | $R^7$ or $R^{7a}$ |
|---|---|
| R7-1 | ![dibenzothiepine with Cl] |
| R7-2 | ![dibenzothiepine with Br] |
| R7-3 | ![dibenzocycloheptane] |

TABLE 7-continued

R⁷ or R⁷ᵃ

R7-4, R7-5, R7-6, R7-7, R7-8, R7-9, R7-10, R7-11, R7-12, R7-13, R7-14, R7-15, R7-16, R7-17, R7-18

TABLE 8

R⁷ or R⁷ᵃ

R7-19, R7-20

TABLE 8-continued

| | R⁷ or R⁷ᵃ |
|---|---|
| R7-21 | (structure) |
| R7-22 | (structure) |
| R7-23 | (structure) |
| R7-24 | (structure) |
| R7-25 | (structure) |
| R7-26 | (structure) |
| R7-27 | (structure) |
| R7-28 | (structure) |
| R7-29 | (structure) |
| R7-30 | (structure) |
| R7-31 | (structure) |
| R7-32 | (structure) |
| R7-33 | (structure) |
| R7-34 | (structure) |
| R7-35 | (structure) |
| R7-36 | (structure) |

TABLE 9
| | R⁷ or R⁷ᵃ |
|---|---|
| R7-37 | 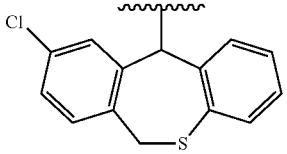 [SMILES: *C1c2cc(Cl)ccc2CSc2ccccc21] |
| R7-38 | 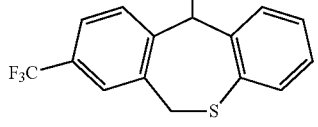 |
| R7-39 | 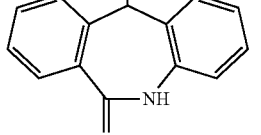 |
| R7-40 | 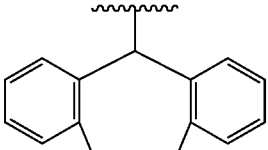 |
| R7-41 | 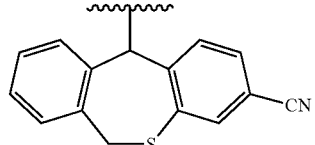 |
| R7-42 | 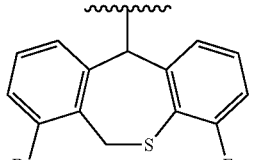 |
| R7-43 | 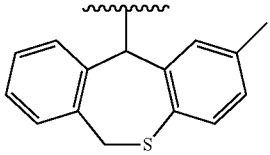 [SMILES: *C1c2ccccc2CSc2ccc(C)cc21] |
| R7-44 | 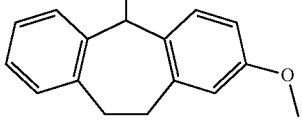 |
| R7-45 | 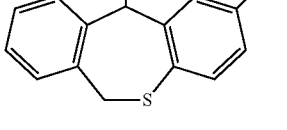 |
TABLE 9-continued
| | R⁷ or R⁷ᵃ |
|---|---|
| R7-46 | 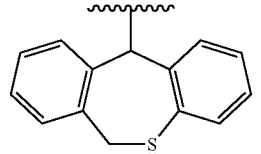 |
| R7-47 | 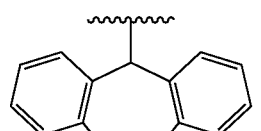 |
| R7-48 | 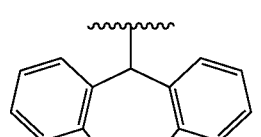 |
| R7-49 | 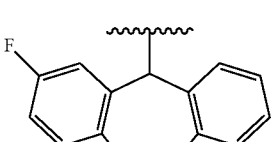 |
| R7-50 | 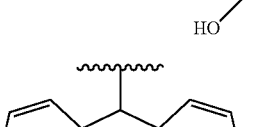 |
| R7-51 | 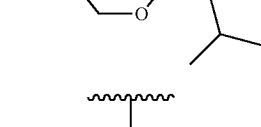 |
| R7-52 | 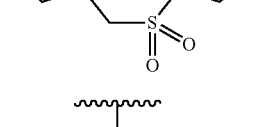 |
| R7-53 | 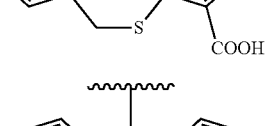 |

TABLE 9-continued

| | $R^7$ or $R^{7a}$ |
|---|---|
| R7-54 | dibenzothiepine with Br and Cl substituents |

TABLE 10

| | $R^7$ or $R^{7a}$ |
|---|---|
| R7-55 | dibenzothiepine with Br and F substituents |
| R7-56 | dibenzothiepine with F and Br substituents |
| R7-57 | dibenzothiepine with Br and F substituents |
| R7-58 | dibenzothiepine with NC and Cl substituents |
| R7-59 | dibenzothiepine with F and Br substituents |
| R7-60 | dibenzothiepine with F and Br substituents |

TABLE 10-continued

| | $R^7$ or $R^{7a}$ |
|---|---|
| R7-61 | dibenzothiepine with NC and F substituents |
| R7-62 | dibenzothiepine with F and CN substituents |
| R7-63 | dibenzothiepine with NC and F substituents |
| R7-64 | dibenzothiepine with NC and Cl substituents |
| R7-65 | dibenzothiepine with F and CN substituents |
| R7-66 | dibenzothiepine with F and NC substituents |
| R7-67 | dibenzothiepine with Br and Cl substituents |
| R7-68 | dibenzothiepine with Cl and Br substituents |

TABLE 10-continued

| | R⁷ or R⁷ᵃ |
|---|---|
| R7-69 | (structure: dibenzothiepine with Br, Cl) |
| R7-70 | (structure: dibenzothiepine with NC) |
| R7-71 | (structure: dibenzothiepine with Cl, Br) |
| R7-72 | (structure: dibenzothiepine with Cl, Br) |

TABLE 11

| | R⁷ or R⁷ᵃ |
|---|---|
| R7-73 | (structure: dibenzothiepine with Cl, CN) |
| R7-74 | (structure: dibenzothiepine with NC, Cl) |
| R7-75 | (structure: dibenzothiepine with Cl, CN) |
| R7-76 | (structure: dibenzoxepine) |

TABLE 11-continued

| | R⁷ or R⁷ᵃ |
|---|---|
| R7-77 | (structure: dibenzothiepine with Cl, NC) |

As Reference Examples, a method for synthesizing intermediates useful for carrying out the present application is shown below.

Reference Example 1

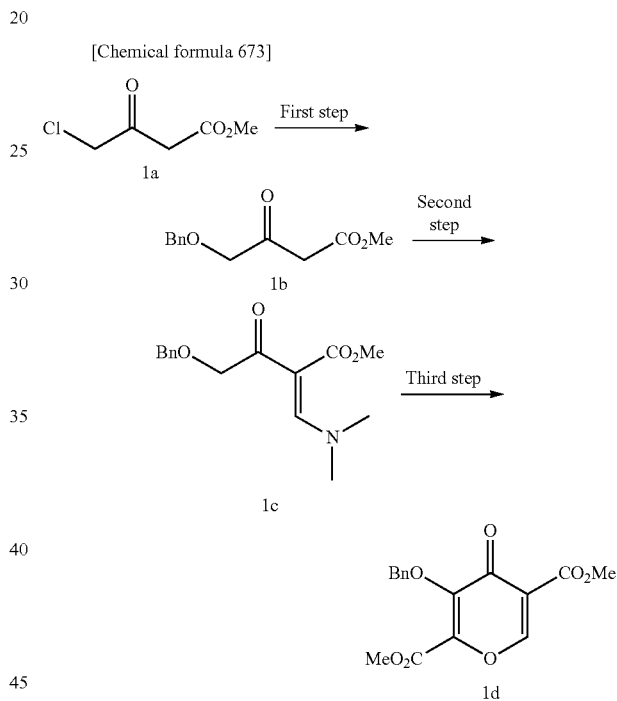

[Chemical formula 673]

First Step

A solution of benzyl alcohol (1.00 g, 9.25 mmol) in THF (3 ml) was added to a suspension of sodium tert-pentoxide (2.55 g, 23.2 mmol) in THF (4 ml) at room temperature under nitrogen atmosphere, and the mixture was stirred at 40° C. for 2 hours. This reaction solution was cooled in an ice bath, and a solution of compound 1a (1.53 g, 10.2 mmol) in THF (3 ml) was added dropwise at 0 to 10° C. After the reaction solution was stirred at room temperature for 2 hours, 2 N hydrochloric acid (15 ml) was added, followed by extraction with ethyl acetate two times. The combined extracts were washed sequentially with water, saturated sodium bicarbonate water, water and saturated sodium chloride water, and then dried with anhydrous sodium sulfate. The solvent was distilled off, and the resulting oil was purified by silica gel column chromatography (n-hexane-ethyl acetate 4:1, v/v) to obtain 1.89 g (yield 92%) of compound 1b as an oil product.

$^1$H-NMR (CDCl$_3$) δ: 3.56 (2H, s), 3.71 (3H, s), 4.14 (2H, s), 4.59 (2H, s), 7.27-7.42 (5H, m).

Second Step

Compound 1b (1.80 g, 8.1 mmol) was dissolved in 1,4-dioxane (18 mL), N,N-dimethylformamide dimethyl acetal (1.45 g, 12.2 mmol) was added, and the mixture was stirred at room temperature for 6 hours. The reaction solution was concentrated under reduced pressure, and the residue was purified by silica gel column chromatography (n-hexane-ethyl acetate 1:4, v/v) to obtain 1.77 g (yield 79%) of compound 1c as an oil product.

$^1$H-NMR (CDCl$_3$) δ: 2.90 (3H, br), 3.25 (3H, br), 3.69 (3H, s), 4.45 (2H, s), 4.59 (2H, s), 7.24-7.40 (5H, m), 7.73 (s, 1H).

Third Step

Sodium tert-butoxide (2.55 g, 23.2 mmol), dimethyl oxalate (639 mg, 5.41 mmol) and DMI (3 ml) were added to a three-neck flask under nitrogen atmosphere, and a solution of compound 1c (0.50 g, 1.80 mmol) in DMI (2 ml) was added dropwise thereto at 25 to 30° C. After stirring at room temperature for 7 hours, 2N hydrochloric acid (10 ml) was added, and the mixture was stirred at room temperature for 15 hours. The reaction solution was extracted with ethyl acetate two times, and the combined extracts were washed sequentially with water, saturated sodium bicarbonate water, water and saturated sodium chloride water, and then dried with anhydrous sodium sulfate. The solvent was distilled off, and the resulting residue was purified by silica gel column chromatography (n-hexane-ethyl acetate 2:1 to 1:1, v/v) to obtain 488 mg (yield 85%) of compound id as a white crystal.

$^1$H-NMR (CDCl$_3$) δ: 3.89 (3H, s), 3.93 (3H, s), 5.34 (2H, s), 7.32-7.40 (3H, m), 7.45-7.49 (2H, m), 8.50 (1H, s).

Reference Example 2

[Chemical formula 674]

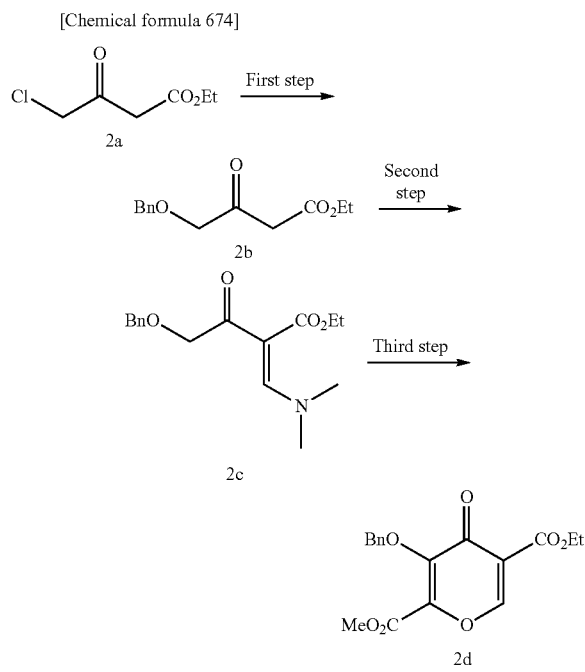

First Step

A solution of benzyl alcohol (0.66 g, 6.1 mmol) in DMI (3 ml) was added to a suspension of sodium tert-pentoxide (1.67 g, 15.2 mmol) in DMI (4 ml) at room temperature under nitrogen atmosphere, and the mixture was stirred at 40° C. for 2 hours. This reaction solution was cooled in an ice bath, and a solution of compound 2a (1.10 g, 6.68 mmol) in DMI (3 ml) was added dropwise at 0 to 10° C. The reaction solution was stirred at 0 to 5° C. for 2 hours, and at room temperature for 3 hours, and 2N hydrochloric acid (15 ml) was added, followed by extraction with ethyl acetate two times. The combined extracts were washed sequentially with water, saturated sodium bicarbonate water, water and saturated sodium chloride water, and then dried with anhydrous sodium sulfate. The solvent was distilled off, and the resulting oil product was purified by silica gel column chromatography (n-hexane-ethyl acetate 4:1, v/v) to obtain 1.29 g (yield 90%) of compound 2b as an oil product.

$^1$H-NMR (CDCl$_3$) δ: 1.25 (3H, t, J=7.2 Hz), 3.54 (2H, s), 4.14 (2H, s), 4.17 (2H, q, J=7.2 Hz), 4.59 (2H, s), 7.28-7.40 (5H, m).

Second Step

Compound 2b (9.73 g, 41.2 mmol) was dissolved in toluene (45 ml), N,N-dimethylformamide dimethyl acetal (7.36 g, 61.8 mmol) was added, and the mixture was stirred at room temperature for 5 hours. Water was added to the reaction solution, followed by extraction with ethyl acetate two times. The combined extracts were washed sequentially with water, and saturated sodium chloride water, and then dried with anhydrous magnesium sulfate. The solvent was distilled off, and the resulting oil product was purified by silica gel column chromatography (n-hexane-ethyl acetate 1:1 to 3:7, v/v) to obtain 7.90 g (yield 66%) of compound 2c as an oil product.

$^1$H-NMR (CDCl$_3$) δ: 1.25 (3H, t, J=7.2 Hz), 2.95 (3H, br), 3.22 (3H, br), 4.15 (2H, q, J=7.2 Hz), 4.45 (2H, s), 4.59 (2H, s), 7.22-7.40 (5H, m), 7.73 (1H, s).

Third Step

Sodium tert-butoxide (495 mg, 5.15 mmol) and DMI (2 ml) were added to a three-neck flask under nitrogen atmosphere, and dimethyl oxalate (608 mg, 5.15 mmol) and a solution of compound 2c (0.50 g, 1.72 mmol) in DMI (3 ml) was added dropwise at 25 to 30° C. After stirring at room temperature for 4 hours, 2N hydrochloric acid (10 ml) was added, and the mixture was stirred at room temperature for 15 hours. The reaction solution was extracted with toluene two times, and the combined extracts were washed sequentially with water, saturated sodium bicarbonate water, water and saturated sodium chloride water, and then dried with anhydrous sodium sulfate. The solvent was distilled off, and the resulting residue was purified by silica gel column chromatography (n-hexane-ethyl acetate 2:1, v/v) to obtain 420 mg (yield 74%) of compound 2d as a white crystal.

$^1$H-NMR (CDCl$_3$) δ: 1.39 (3H, t, J=7.2 Hz), 3.88 (3H, s), 4.39 (2H, q, J=7.2 Hz), 5.34 (2H, s), 7.30-7.41 (3H, m), 7.45-7.50 (2H, m), 8.48 (1H, s).

Reference Example 3

[Chemical formula 675]

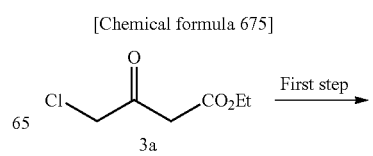

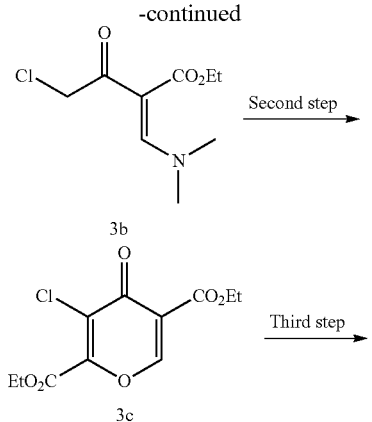

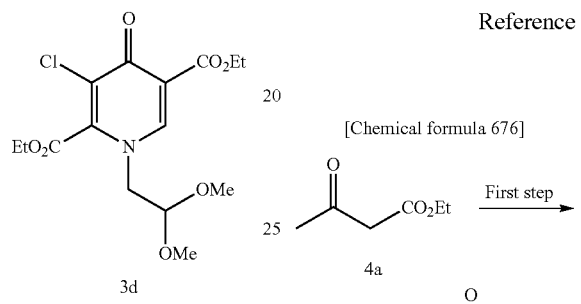

First Step

N,N-dimethylformamide dimethyl acetal (4.9 ml, 36.5 mmol) was added dropwise to compound 3a (5.0 g, 30.4 mmol) at 0° C. under cooling. After stirring at 0° C. for 1 hour, 100 ml of ethyl acetate was added to the reaction solution, followed by washing with 0.5N hydrochloric acid (50 ml). The aqueous layer was separated, and extracted with ethyl acetate (50 ml). The organic layers were combined, washed sequentially with saturated sodium bicarbonate water and saturated sodium chloride water, and then dried with anhydrous sodium sulfate. The solvent was distilled off, and the resulting residue was purified by silica gel column chromatography (n-hexane-ethyl acetate 1:1 (v/v)→ethyl acetate) to obtain 4.49 g (yield 67%) of compound 3b as an oil product.

$^1$H-NMR (CDCl$_3$) δ: 1.32 (3H, t, J=7.1 Hz), 2.90 (3H, br s), 3.29 (3H, br s), 4.23 (2H, q, J=7.1 Hz), 4.54 (2H, s), 7.81 (1H, s).

Second Step

Lithium hexamethyldisilazide (1.0 M toluene solution, 49 ml, 49.0 mmol) was diluted with tetrahydrofuran (44 ml), a solution of compound 3b (4.49 g, 20.4 mmol) in tetrahydrofuran (10 ml) was added dropwise thereto at −78° C. under cooling, and a solution of ethyl oxalyl chloride (3.35 g, 24.5 mmol) in tetrahydrofuran (10 ml) was added dropwise. After stirring at −78° C. for 2 hours, temperature was raised to 0° C. After 2N hydrochloric acid was added to the reaction solution, and the mixture was stirred for 20 minutes, the solution was extracted with ethyl acetate (200 ml×2), and the organic layer was washed with saturated sodium bicarbonate water and saturated sodium chloride water and then dried with anhydrous sodium sulfate. The solvent was distilled off, and the resulting residue was purified by silica gel column chromatography (n-hexane-ethyl acetate 7:3→5:5→0:10 (v/v)) to obtain 1.77 g (yield 31%) of compound 3c as a white solid.

$^1$H-NMR (CDCl$_3$) δ: 1.36-1.46 (6H, m), 4.35-4.52 (8H, m), 8.53 (1H, s).

Third Step

Aminoacetaldehyde dimethyl acetal (0.13 ml, 1.20 mmol) was added to a solution of compound 3c (300 mg, 1.09 mmol) in ethanol (6 ml) at 0° C., and the mixture was stirred at 0° C. for 1 hour and 30 minutes, at room temperature for 18 hours and, then, at 60° C. for 4 hours. After the solvent was distilled off from the reaction solvent under reduced pressure, the resulting residue was purified by silica gel column chromatography (n-hexane-ethyl acetate 5:5→0:10 (v/v)) to obtain 252 mg (yield 64%) of compound 3d as an oil product.

$^1$H-NMR (CDCl$_3$) δ: 1.36-1.47 (6H, m), 3.42 (6H, s), 3.90 (2H, d, J=5.2 Hz), 4.37 (3H, q, J=7.2 Hz), 4.50 (2H, q, J=7.2 Hz), 8.16 (1H, s).

Reference Example 4

[Chemical formula 676]

First Step

N,N-dimethylformamide dimethyl acetal (12.2 ml, 92.2 mmol) was added dropwise to compound 4a (10.0 g, 76.8 mmol) at 0° C. under cooling. After stirring at 0° C. for 1 hour and 30 minutes and, then, at room temperature for 2 hours and 30 minutes, 100 ml of ethyl acetate was added to the reaction solution, and the solvent was distilled off. The resulting residue was purified by silica gel column chromatography (n-hexane-ethyl acetate 5:5→0:10 (v/v)) to obtain 12.45 g (yield 88%) of compound 4b as an oil product.

$^1$H-NMR (CDCl$_3$) δ: 1.32 (3H, t, J=7.1 Hz), 2.33 (3H, s), 3.04 (6H, br s), 4.23 (2H, q, J=7.2 Hz), 7.68 (1H, s).

Second Step

Lithium hexamethyldisilazide (1.0M toluene solution, 24 ml, 24.0 mmol) was diluted with tetrahydrofuran (20 ml), a solution of compound 4b (1.85 g, 10.0 mmol) in tetrahydrofuran (5 ml) was added dropwise thereto at −78° C. under cooling, and a solution of ethyl oxalyl chloride (1.34 ml, 12.0 mmol) in tetrahydrofuran (5 ml) was added dropwise. After stirring at −78° C. for 2 hours, 2N-hydrochloric acid was added to the reaction solution, and the mixture was stirred at room temperature for 20 minutes. The solution was extracted with ethyl acetate, and the organic layer was washed sequentially with saturated sodium bicarbonate water and saturated sodium chloride water, and then dried with anhydrous sodium sulfate. The solvent was distilled off, and the resulting residue was purified by silica gel column chromatography (n-hexane-ethyl acetate 75:25→455:5 (v/v)) to obtain 1.03 g (yield 43%) of compound 4c as a brown oil product.

$^1$H-NMR (CDCl$_3$) δ: 1.38 (3H, t, J=7.1 Hz), 1.42 (3H, t, J=7.4 Hz), 4.33-4.47 (4H, m), 7.19 (1H, s), 8.54 (1H, s).

Third Step

Aminoacetaldehyde dimethyl acetal (0.34 ml, 3.11 mmol) was added to a solution of compound 4c (680 mg, 2.83 mmol) in ethanol (6.8 ml) at 0° C., and it was allowed to stand at room temperature for 16 hours. After the solvent was distilled off from the reaction solution under reduced pressure, the resulting residue was purified by silica gel column chromatography (n-hexane-ethyl acetate 90:10 (v/v)) to obtain 875 mg (yield 94%) of compound 4d as an oil product.

$^1$H-NMR (CDCl$_3$) δ: 1.38 (3H, t, J=7.1 Hz), 1.39 (3H, t, J=7.1 Hz), 3.40 (6H, s), 4.33 (2H, d, J=4.7 Hz), 4.37 (4H, q, J=7.1 Hz), 4.49 (1H, t, J=4.7 Hz), 7.06 (1H, s), 8.17 (1H, s).

Fourth Step

N-bromosuccinimide (1.46 g, 8.18 mmol) was added to a solution of compound 4d (2.68 g, 8.18 mmol) in N,N-dimethylformamide (10 ml), and the mixture was stirred at room temperature for 48 hours. After saturated sodium bicarbonate water was added to the reaction solution, the solution was extracted with ethyl acetate, and the organic layer was washed sequentially with water and saturated sodium chloride water, and then dried with anhydrous sodium sulfate. The solvent was distilled off, and the resulting residue was purified by silica gel column chromatography (n-hexane-ethyl acetate 90:10 (v/v)) to obtain 2.83 g (yield 85%) of compound 4e as an oil product.

$^1$H-NMR (CDCl$_3$) δ: 1.41 (3H, t, J=7.1 Hz), 1.48 (3H, t, J=7.1 Hz), 3.42 (6H, s), 3.90 (2H, d, J=5.0 Hz), 4.39 (2H, q, J=7.1 Hz), 4.53 (3H, q, J=14.3 Hz), 4.54 (3H, s), 4.57 (3H, t, J=5.4 Hz), 8.19 (1H, s).

Reference Example 5

[Chemical formula 677]

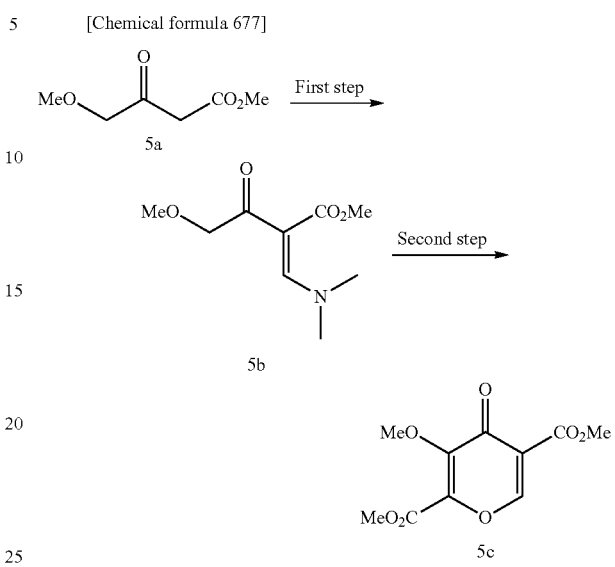

First Step

Compound 5a (598 mg, 4.09 mmol) and N,N-dimethylformamide dimethyl acetal (488 mg, 4.09 mmol) were dissolved in toluene (1 ml), and the mixture was stirred at room temperature for 11 hours. The solvent was distilled off from the reaction solution under reduced pressure, and the resulting residue (containing compound 5b) was used in Second step without purification.

Second Step

Sodium tert-butoxide (400 mg, 4.16 mmol) was suspended in dimethyl imidazolidinone (5 ml), a solution of the crude product obtained in First step in dimethylimidazolidinone (5 ml) was added thereto, a solution of dimethyl oxalate (983 mg, 8.32 mmol) in THF (10 ml) was added dropwise, and the mixture was stirred at room temperature for 45 minutes. The reaction solution was poured into 2N hydrochloric acid-methanol (20 ml), and the mixture was stirred at 0° C. for 20 minutes. Water was added, the solution was extracted with ethyl acetate, and the organic layer was washed sequentially with water, saturated sodium bicarbonate water, and saturated sodium chloride water, and dried with anhydrous sodium sulfate. After the solvent was distilled off, the resulting residue was purified by silica gel column chromatography to obtain 222 mg (yield: 22% from 5a) of compound 5c.

Reference Example 6

[Chemical formula 678]

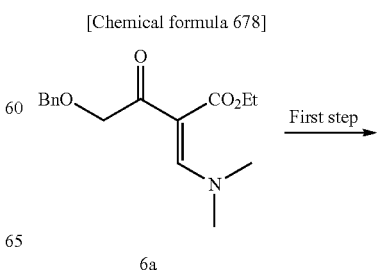

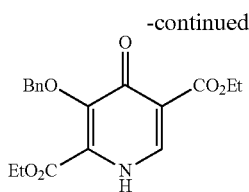

6b

Second step →

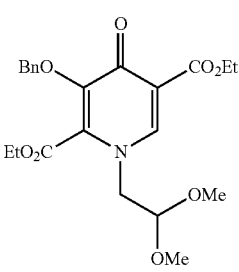

6c

First Step

Lithium hexamethyldisilazide (1.0M toluene solution, 12 ml, 12.0 mmol) was diluted with tetrahydrofuran (11 ml), a solution of compound 6a (1.46 g, 5.0 mmol) in tetrahydrofuran (2 ml) was added dropwise thereto at −78° C. under cooling, and a solution of ethyl oxalyl chloride (0.67 ml, 6.0 mmol) in tetrahydrofuran (2 ml) was added dropwise. After stirring at −78° C. for 2 hours, ammonium acetate (500 mg) and acetic acid (10 ml) were added to the reaction solution, and the mixture was stirred at 65° C. for 1 hour and 30 minutes. Water was added to the reaction solution, the solvent was extracted with ethyl acetate, and the organic layer was washed sequentially with water, and saturated sodium bicarbonate water, and dried with anhydrous sodium sulfate. The solvent was distilled off, and the resulting residue was purified by silica gel column chromatography (N-hexane-ethyl acetate 55:45→45:55 (v/v)) to obtain 505.1 mg of compound 6B as a yellow solid. It was washed with isopropyl ether-hexane (1:2), and dried under reduced pressure to obtain 416.8 mg (yield 24%) of Compound 6b as a yellow crystal.

$^1$H-NMR (CDCl$_3$) δ: 1.35 (3H, t, J=7.1 Hz), 1.46 (3H, t, J=7.1 Hz), 4.40 (2H, q, J=7.2 Hz), 4.50 (2H, q, J=7.1 Hz), 5.20 (2H, s), 7.33-7.41 (3H, m), 7.49-7.52 (2H, m), 8.76 (1H, s), 11.61 (1H, br s).

Second Step

Cesium carbonate (73.3 mg, 0.23 mmol) and bromoacetaldehyde dimethyl acetal (38.0 mg, 0.23 mmol) were added to a solution of compound 6b (51.8 mg, 0.15 mmol) in N,N-dimethylformamide (1 ml), and the mixture was stirred at room temperature overnight. Cesium carbonate (73.3 mg, 0.23 mmol) and bromoacetaldehyde dimethyl acetal (38.0 mg, 0.23 mmol) were further added, and the mixture was further stirred at 100° C. for 20 minutes. After water was added to the reaction solution, the solution was extracted with ethyl acetate, and the organic layer was washed sequentially with water and saturated sodium chloride water, and dried with anhydrous sodium sulfate. The solvent was distilled off, and the resulting residue was purified by silica gel column chromatography (n-hexane-ethyl acetate 50:50→30:70 (v/v)) to obtain 35.3 mg (yield 54%) of compound 6c as a colorless oil product.

$^1$H-NMR (CDCl$_3$) δ: 1.26 (3H, t, J=7.1 Hz), 1.40 (3H, t, J=7.1 Hz), 3.39 (6H, s), 3.91 (2H, d, J=5.0 Hz), 4.29 (2H, q, J=7.1 Hz), 4.40 (2H, q, J=7.2 Hz), 4.50 (1H, t, J=5.0 Hz), 5.30 (2H, s), 7.31-7.37 (3H, m), 7.43-7.46 (2H, m), 8.12 (1H, s).

Reference Example 7

[Chemical formula 679]

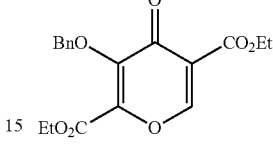

7a

First step →

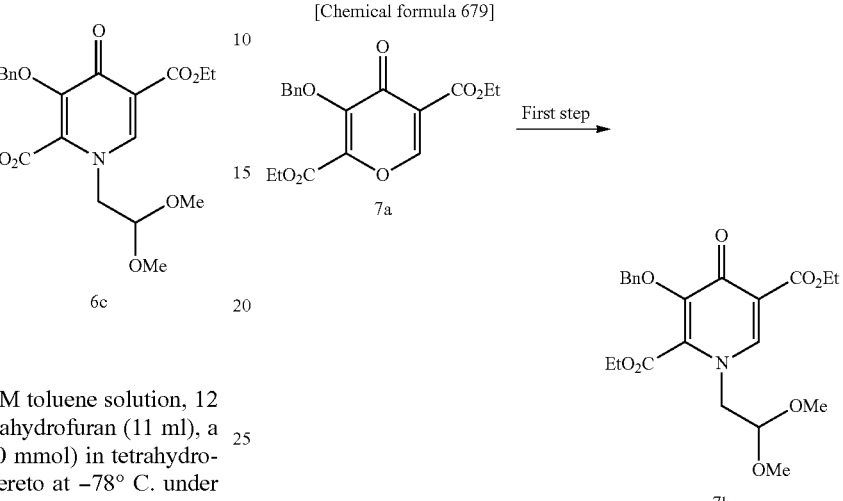

7b

First Step

Aminoacetaldehyde dimethyl acetal (7.80 mmol) was added to a solution of compound 7a (900 mg, 2.60 mmol) in ethanol (5 ml), and the mixture was stirred at room temperature for 22 hours. Ethyl acetate (5 ml) and water (5 ml) were added to the reaction solution, followed by extraction with ethyl acetate (5 ml). After the organic layer was washed with water (10 ml), the solvent was distilled off, and the resulting residue was purified by silica gel column chromatography (n-hexane-ethyl acetate 2:1) to obtain 0.37 g (yield 33%) of compound 7b as a colorless oil product.

$^1$H-NMR (CDCl$_3$) δ: 7.90 (1H, s), 7.45-7.43 (5H, m), 5.30 (2H, s), 4.51 (1H, t, J=5.1 Hz), 4.40 (2H, q, J=7.1 Hz), 4.30 (2H, q, J=7.1 Hz), 3.91 (2H, d, J=5.1 Hz), 3.46 (6H, s), 1.40 (3H, t, J=7.1 Hz), 1.26 (3H, t, J=7.1 Hz).

The compounds in connection with the present invention are useful for symptoms and/or diseases which are induced by influenza virus. For example, they are useful for treating and/or preventing, or improving symptoms of, cold-like symptoms accompanying fever, algor, headache, muscular pain, general malaise etc., airway inflammation symptoms such as pharyngalgia, nasal secretion, nasal congestion, cough, sputum etc., gastrointestinal symptoms such as abdominal pain, vomitus, diarrhea etc. and, further, complications accompanying secondary infection such as acute encephalopathy and pneumonia.

Since the compounds in connection with the present invention have the effects such as inhibitory activity on high cap structure-dependent endonuclease, and high selectivity due to a virus-specific enzyme, they can be medicaments having reduced side effects. Further, since the compounds in connection with the present invention have advantages that metabolism stability is high, solubility is high, oral absorbability is high, good bioavailability is exhibited, good clearance is exhibited, pulmonary transitivity is high, a half life is long, a non-protein binding rate is high, hERG channel inhibition is low, CYP inhibition is low, CPE (CytoPathic Effect) inhibiting effect is recognized, and/or negativity is exhibited in a phototoxicity test, an Ames test and a gene toxicity test, they can be excellent medicaments.

The compounds in connection with the present invention can be administered orally or parenterally. In the case of oral administration, the present compounds can be also used as a normal preparation, for example, as any dosage form of solid preparations such as tablets, powders, granules, capsules etc.; solutions; oleaginous suspensions; or liquid preparations such as syrups or elixirs etc. In the case of parenteral administration, the compounds in connection with the present invention can be used as aqueous or oleaginous suspension injectables, or nose drops. Upon preparation of them, conventional excipients, binders, lubricants, aqueous solvents, oleaginous solvents, emulsifiers, suspending agents, preservatives, stabilizers etc. can be arbitrarily used. The pharmaceutical composition of the present invention can be produced by combining (for example, mixing) a therapeutically effective amount of the present compound with pharmaceutically acceptable carriers or diluents.

A dose of the compounds in connection with the present invention is different depending on an administration method, an age, a weight and the state of a patient, and a kind of a disease and, usually, in the case of oral administration, about 0.05 mg to 3000 mg, preferably about 0.1 mg to 1000 mg per adult a day may be administered, if necessary, by division. In addition, in the case of parenteral administration, about 0.01 mg to 1000 mg, preferably about 0.05 mg to 500 mg per adult a day is administered.

Test Example 1: Measurement of Cap-Dependant Endonuclease (CEN) Inhibitory Activity 1) Preparation of Substrate 30mer RNA(5'-pp-[m2'-O]GAA UAU(-Cy3) GCA UCA CUA GUA AGC UUU GCU CUA-BHQ2-3':manufactured by Japan Bioservice) in which G at a 5' end is diphosphate-modified, a hydroxy group at 2' position is methoxylation-modified, U sixth from a 5' end is labelled with Cy3, and a 3' end is labelled with BHQ2 was purchased, and a cap structure was added using ScriptCap system manufactured by EPICENTRE (a product was m7G [5']-ppp-[5'] [m2'-O] GAA UAU(-Cy3) GCA UCA CUA GUA AGC UUU GCU CUA(-BHQ2)-3'). This was separated and purified by denatured polyacrylamide gel electrophoresis, and used as a substrate.

2) Preparation of Enzyme

RNP was prepared from a virus particle using standard method (Reference Document: VIROLOGY (1976) 73, p 327-338 OLGA M. ROCHOVANSKY). Specifically, A/WSN/33 virus (1×10$^3$ PFU/mL, 200 µL) was innoculated in a 10 days old embryonated chicken egg. After incubation at 37° C. for 2 days, the allantoic fluid of the chicken egg was recovered. A virus particle was purified by ultracentrifugation using 20% sucrose, solubilized using Triton X-100 and lysolecithin, and an RNP fraction (50-70% glycerol fraction) was collected by ultracentrifugation using a 30-70% glycerol density gradient, and was used as an enzyme solution (containing approximately 1 nM PB1•PB2•PA complex).

3) Enzymatic Reaction

An enzymatic reaction solution (2.5 µL) (composition: 53 mM Tris-hydrochloride (pH 7.8), 1 mM MgCl$_2$, 1.25 mM dithiothreitol, 80 mM NaCl, 12.5% glycerol, enzyme solution 0.15 µL) was dispensed into a 384-well plate made of polypropylene. Then, 0.5 µL of a test substance solution which had been serially diluted with dimethyl sulfoxide (DMSO) was added to the plate. As a positive control (PC) or a negative control (NC), 0.5 µL of DMSO was added to the plate respectively. Each plate was mixed well. Then, 2 µL of a substrate solution (1.4 nM substrate RNA, 0.05% Tween20) was added to initiate a reaction. After room temperature incubation for 60 minutes, 1 µL of the reaction solution was collected and added to 10 µL of a Hi-Di formamide solution (containing GeneScan 120 Liz Size Standard as a sizing marker: manufactured by Applied Biosystem (ABI)) in order to stop the reaction. For NC, the reaction was stopped in advance by adding EDTA (4.5 mM) before initiation of the reaction (all concentrations described above are final concentrations).

3) Measurement of Inhibition Ratio (IC$_{50}$ Value)

The solution for which the reaction was stopped was heated at 85° C. for 5 minutes, rapidly cooled on ice for 2 minutes, and analyzed with an ABI PRIZM 3730 genetic analyzer. A peak of the cap-dependent endonuclease product was quantitated by analysis software ABI Genemapper, a CEN reaction inhibition ratio (%) of a test compound was obtained by setting fluorescent intensities of PC and NC to be 0% inhibition and 100% inhibition, respectively, an IC$_{50}$ value was obtained using curve fitting software (XLfit2.0: Model 205 (manufactured IDBS etc.)). The IC$_{50}$ values of test substances are shown in Table 12-21.

Test Example 2: CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound was assessed The reaction conditions were as follows: substrate, 0.5 mol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A$^4$); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and IC$_{50}$ was calculated by reverse presumption by a logistic model using a concentration and an inhibition rate.

Test Example 3: Solubility Test

The solubility of each compound is determined under 1% DMSO addition conditions. A 10 mM solution of the compound is prepared with DMSO, and 6 µL of the compound solution is added to 594 µL of an artificial intestinal juice (water and 118 mL of 0.2 mol/L NaOH reagent are added to 250 mL of 0.2 mol/L potassium dihydrogen phosphate reagent to reach 1000 mL) with pH of 6.8. The mixture is left standing for 16 hours at 25° C., and the mixture is vacuum-filtered. The filtrate is two-fold diluted with methanol/water=1/1, and the compound concentration in the filtrate is measured with HPLC or LC/MS/MS by the absolute calibration method.

Test Example 4: Metabolism Stability Test

Using a commercially available pooled human hepatic microsomes, a test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.

Test Example 5: hERG Test

For the purpose of assessing risk of an electrocardiogram QT interval prolongation, effects on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

Test Example 6: CPE Inhibitory Effect Confirming Assay

<Material>
2% FCS E-MEM (prepared by adding kanamycin and FCS to MEM (Minimum Essential Medium) (Invitrogen))
0.5% BSA E-MEM (prepared by adding kanamycin and BSA to MEM (Minimum Essential Medium) (Invitrogen))
HBSS (Hanks' Balanced Salt Solution)
MDBK cell
Cells were adjusted to the appropriate cell number ($3 \times 10^5$/mL) with 2% FCS E-MEM.
MDCK Cell
After washing with HBSS two times, cells were adjusted to the appropriate cell number ($5 \times 10^5$/mL) with 0.5% BSA E-MEM.
Trypsin Solution
Trypsin from porcine pancreas (SIGMA) was dissolved in PBS(−), and filtrated with a 0.45 µm filter.
EnVision (Perkin Elmer)
WST-8 Kit (Kishida Chemical Co., Ltd.)
10% SDS solution
<Operation Procedure>
Dilution and Dispensation of Test Sample
As a culture medium, 2% FCS E-MEM was used at the use of MDBK cells, and 0.5% BSA E-MEM was used at the use of MDCK cells. Hereinafter, for diluting virus, cells and a-test sample, the same culture medium was used.

A test sample was diluted with a culture medium to a appropriate concentration in advance, and then 2 to 5-fold serial dilution on a 96 well plate (50 µL/well) was prepared. Two plate, one for measuring anti-Flu activity and the another for measuring cytotoxicity, were prepared. Each assay was performed triplicate for each drug.

At the use of MDCK cells, trypsin was added to the cells to be a final concentration of 3 µg/mL only for measuring anti-Flu activity.
Dilution and Dispensation of Influenza Virus
An influenza virus was diluted with a culture medium to a appropriate concentration in advance, and each 50 µL/well was dispensed on a 96-well plate containing a test substance. Each 50 µL/well of a culture medium was dispensed on a plate containing a test substance for measuring cytotoxity.
Dilusion and Dispensation of Cell
Each 100 µL/well of cells which had been adjusted to the appropriate cell number was dispensed on a 96 well plate containing a test substance. This was mixed with a plate mixer, and incubated in a $CO_2$ incubator for 3 days for measuring anti-Flu activity and measuring cytotoxity.
Dispensation of WST 8
The cells in 96-well plate which had been incubated for 3 days was observed visually under a microscope, and appearance of the cells, the presence or absence of a crystal of test substance were checked. The supernatant was removed so that the cells were not absorbed from the plate.

WST-8 Kit was diluted 10-fold with a culture medium, and each 100 µL was dispensed into each well. After mixing with a plate mixer, cells were incubated in a $CO_2$ incubator for 1 to 3 hours.

After incubation, regarding the plate for measuring anti-Flu activity, each 10 L/well of a 10% SDS solution was dispensed in order to inactivate a virus.
Measurement of Absorbance
After the 96-well plate was mixed, absorbance was measured with EnVision at two wavelengthes of 450 nm/620 nm.
<Calculation of Each Measurement Item Value>
The value was calculated using Microsoft Excel or a program having the equivalent calculation and processing ability, based on the following calculation equation. Calculation of effective concentration to achieve 50% CPE inhibition (EC50)

$$EC50 = 10^Z$$

$$Z = (50\% - \text{High \%})/(\text{High \%} - \text{Low \%}) \times \{\log(\text{High conc.}) - \log(\text{Low conc.})\} + \log(\text{High conc.})$$

$IC_{50}$ values of test substances are shown in Table 12-21.

TABLE 12

| Example No. | CEN IC$_{50}$ (μM) | CPE EC$_{50}$ (μM) |
|---|---|---|
| 2 | 0.048 | 0.293 |
| 14 | 0.043 | 0.313 |
| 16 | 0.065 | 0.632 |
| 26 | 0.108 | 0.547 |
| 37 | 0.101 | 0.318 |
| 43 | 0.078 | 1.410 |
| 48 | 0.087 | 10.90 |
| 56 | 0.358 | 3.860 |
| 62 | 0.110 | 1.680 |
| 63 | 0.170 | 2.000 |
| 94 | 0.096 | 1.470 |
| 99 | 0.341 | 2.000 |
| 108 | 0.037 | 0.019 |
| 128 | 0.063 | 0.416 |
| 138 | 0.166 | 0.100 |
| 139 | 0.189 | 0.741 |
| 143 | 0.224 | 0.333 |
| 150 | 0.193 | 0.553 |
| 175 | 0.132 | 0.102 |
| 178 | 0.061 | 0.075 |

TABLE 13

| Example No. | CEN IC$_{50}$ (μM) | CPE EC$_{50}$ (μM) |
|---|---|---|
| 181 | 0.049 | 0.349 |
| 182 | 0.099 | 0.562 |
| 183 | 0.074 | 2.370 |
| 184 | 0.055 | 0.403 |
| 185 | 0.132 | 1.920 |
| 186 | 0.085 | 0.159 |
| 187 | 0.085 | 0.282 |
| 190 | 0.143 | 2.640 |
| 191 | 0.238 | 2.820 |
| 199 | 0.236 | 2.720 |
| 204 | 0.299 | 2.360 |
| 224 | 0.276 | 0.119 |
| 225 | 0.283 | 0.663 |
| 228 | 0.243 | 0.141 |
| 230 | 0.282 | 0.525 |
| 233 | 0.228 | 2.240 |
| 238 | 0.101 | 0.440 |
| 240 | 0.037 | 0.048 |
| 241 | 0.197 | 0.063 |
| 242 | 0.114 | 0.059 |
| 243 | 0.076 | 0.020 |
| 244 | 0.249 | 0.108 |
| 246 | 0.082 | 0.026 |
| 247 | 0.282 | 2.260 |
| 248 | 0.103 | 0.489 |
| 249 | 0.151 | 1.890 |
| 250 | 0.113 | 0.476 |
| 251 | 0.058 | 0.157 |
| 252 | 0.107 | 0.454 |
| 253 | 0.235 | 0.280 |
| 254 | 0.135 | 0.564 |
| 255 | 0.052 | 0.319 |
| 256 | 0.038 | 0.400 |

TABLE 14

| Example No. | CEN IC$_{50}$ (μM) | CPE EC$_{50}$ (μM) |
|---|---|---|
| 257 | 0.041 | 0.055 |
| 258 | 0.042 | 0.028 |
| 259 | 0.066 | 0.026 |
| 260 | 0.091 | 0.065 |
| 261 | 0.058 | 0.047 |
| 262 | 0.032 | 0.038 |
| 263 | 0.085 | 0.075 |
| 264 | 0.064 | 0.128 |
| 265 | 0.172 | 0.036 |
| 266 | 0.043 | 0.085 |
| 267 | 0.029 | 0.063 |
| 268 | 0.018 | 0.074 |
| 269 | 0.073 | 0.417 |
| 270 | 0.058 | 0.129 |
| 271 | 0.073 | 0.102 |
| 272 | 0.082 | 0.030 |
| 273 | 0.016 | 0.084 |
| 274 | 0.038 | 0.016 |
| 274 | 0.157 | 0.056 |
| 276 | 0.053 | 0.089 |
| 277 | 0.039 | 0.071 |
| 278 | 0.205 | 0.074 |
| 279 | 0.056 | 0.119 |
| 280 | 0.068 | 0.145 |
| 281 | 0.026 | 0.018 |
| 282 | 0.036 | 0.029 |
| 283 | 0.028 | 0.021 |
| 284 | 0.042 | 0.019 |
| 285 | 0.044 | 0.017 |
| 286 | 0.161 | 0.121 |
| 287 | 0.154 | 0.268 |
| 288 | 0.299 | 0.085 |
| 289 | 0.031 | 0.419 |

TABLE 15

| Example No. | CEN IC$_{50}$ (μM) | CPE EC$_{50}$ (μM) |
|---|---|---|
| 290 | 0.067 | 0.492 |
| 292 | 0.155 | 2.230 |
| 293 | 0.290 | 0.437 |
| 294 | 0.035 | 0.018 |
| 295 | 0.052 | 0.334 |
| 296 | 0.130 | 0.397 |
| 297 | 0.045 | 0.033 |
| 298 | 0.044 | 0.012 |
| 299 | 0.050 | 0.015 |
| 300 | 0.058 | 0.021 |
| 301 | 0.062 | 0.017 |
| 302 | 0.035 | 0.014 |
| 304 | 0.018 | 0.015 |
| 305 | 0.059 | 0.103 |
| 306 | 0.076 | 0.021 |
| 307 | 0.052 | 0.095 |
| 308 | 0.072 | 0.019 |
| 309 | 0.040 | 0.013 |
| 310 | 0.108 | 0.522 |
| 311 | 0.040 | 0.026 |
| 312 | 0.019 | 0.029 |
| 313 | 0.189 | 0.050 |
| 314 | 0.149 | 0.026 |
| 315 | 0.057 | 0.115 |
| 316 | 0.069 | 0.083 |
| 317 | 0.048 | 0.017 |
| 318 | 0.130 | 0.015 |
| 320 | 0.045 | 0.011 |
| 321 | 0.019 | 0.019 |
| 322 | 0.113 | 0.028 |
| 323 | 0.077 | 0.019 |
| 324 | 0.107 | 0.035 |
| 325 | 0.032 | 0.025 |

TABLE 16

| Example No. | CEN IC$_{50}$ (μM) | CPE EC$_{50}$ (μM) |
|---|---|---|
| 326 | 0.043 | 0.005 |
| 327 | 0.092 | 0.024 |
| 328 | 0.029 | 0.168 |
| 329 | 0.058 | 0.023 |
| 330 | 0.026 | 0.019 |
| 331 | 0.045 | 0.335 |
| 332 | 0.048 | 0.020 |
| 333 | 0.021 | 0.425 |
| 334 | 0.075 | 0.032 |
| 335 | 0.019 | 0.016 |
| 336 | 0.051 | 0.070 |
| 337 | 0.058 | 0.028 |
| 338 | 0.074 | 0.085 |
| 339 | 0.183 | 0.040 |
| 340 | 0.101 | 0.027 |
| 341 | 0.016 | 0.027 |
| 342 | 0.099 | 0.026 |
| 343 | 0.122 | 0.018 |
| 344 | 0.050 | 0.009 |
| 345 | 0.097 | 0.008 |
| 346 | 0.028 | 0.018 |
| 347 | 0.014 | 0.017 |
| 348 | 0.054 | 0.080 |
| 349 | 0.053 | 0.075 |
| 351 | 0.091 | 0.019 |
| 352 | 0.067 | 0.020 |
| 354 | 0.025 | 0.083 |
| 355 | 0.040 | 0.075 |
| 356 | 0.066 | 0.020 |
| 357 | 0.138 | 0.386 |
| 358 | 0.051 | 0.069 |
| 359 | 0.037 | 0.080 |
| 360 | 0.042 | 0.087 |

TABLE 17

| Example No. | CEN IC$_{50}$ (μM) | CPE EC$_{50}$ (μM) |
|---|---|---|
| 361 | 0.039 | 0.145 |
| 362 | 0.084 | 0.067 |
| 363 | 0.058 | 0.067 |
| 364 | 0.112 | 0.515 |
| 365 | 0.041 | 2.250 |
| 366 | 0.090 | 0.838 |
| 368 | 0.140 | 0.470 |
| 369 | 0.294 | 0.434 |
| 370 | 0.113 | 0.061 |
| 371 | 0.161 | 0.074 |
| 372 | 0.164 | 0.146 |
| 373 | 0.065 | 0.050 |
| 374 | 0.137 | 0.154 |
| 375 | 0.037 | 0.073 |
| 376 | 0.063 | 0.092 |
| 377 | 0.024 | 0.022 |
| 378 | 0.047 | 0.022 |
| 380 | 0.123 | 0.018 |
| 381 | 0.200 | 0.034 |
| 382 | 0.032 | 0.094 |
| 384 | 0.153 | 0.293 |
| 386 | 0.075 | 0.096 |
| 387 | 0.300 | 1.150 |
| 388 | 0.133 | 0.063 |
| 390 | 0.095 | 0.029 |
| 391 | 0.264 | 0.071 |
| 392 | 0.153 | 0.025 |
| 394 | 0.087 | 0.064 |
| 395 | 0.043 | 0.089 |
| 396 | 0.056 | 0.060 |
| 397 | 0.055 | 0.077 |
| 398 | 0.034 | 0.118 |
| 399 | 0.105 | 0.061 |

TABLE 18

| Example No. | CEN IC$_{50}$ (μM) | CPE EC$_{50}$ (μM) |
|---|---|---|
| 400 | 0.067 | 0.079 |
| 401 | 0.089 | 0.133 |
| 402 | 0.085 | 0.081 |
| 403 | 0.090 | 0.070 |
| 404 | 0.084 | 0.063 |
| 405 | 0.074 | 0.051 |
| 406 | 0.119 | 0.022 |
| 407 | 0.035 | 0.017 |
| 408 | 0.135 | 0.061 |
| 409 | 0.093 | 0.029 |
| 410 | 0.265 | 0.014 |
| 411 | 0.046 | 0.014 |
| 412 | 0.292 | 0.203 |
| 413 | 0.050 | 0.005 |
| 414 | 1.890 | 0.131 |
| 415 | 0.285 | 0.022 |
| 416 | 0.112 | 0.019 |
| 417 | 0.030 | 0.003 |
| 418 | 0.121 | 0.072 |
| 419 | 0.124 | 0.019 |
| 420 | 0.058 | 0.021 |
| 423 | 0.280 | 0.019 |
| 425 | 0.183 | 0.047 |
| 429 | 0.016 | 0.004 |
| 430 | 0.168 | 0.029 |
| 431 | 0.097 | 0.011 |
| 432 | 0.155 | 0.062 |
| 433 | 0.014 | 0.017 |
| 441 | 0.044 | 0.005 |
| 443 | 0.166 | 0.004 |
| 444 | 0.066 | 0.003 |
| 445 | 0.013 | 0.004 |
| 446 | 0.007 | 0.011 |

TABLE 19

| Example No. | CEN IC$_{50}$ (μM) | CPE EC$_{50}$ (μM) |
|---|---|---|
| 447 | 0.096 | 0.018 |
| 448 | 0.039 | 0.008 |
| 449 | 0.062 | 0.021 |
| 450 | 0.023 | 0.014 |
| 452 | 0.177 | 0.016 |
| 453 | 0.186 | 0.049 |
| 454 | 0.012 | 0.004 |
| 455 | 0.025 | 0.071 |
| 456 | 0.032 | 0.004 |
| 457 | 0.242 | 0.014 |
| 458 | 0.048 | 0.014 |
| 459 | 0.287 | 0.048 |
| 460 | 0.085 | 0.009 |
| 461 | 0.255 | 0.074 |
| 462 | 0.069 | 0.011 |
| 463 | 0.012 | 0.005 |
| 464 | 0.024 | 0.014 |
| 469 | 0.016 | 0.004 |
| 470 | 0.008 | 0.003 |
| 475 | 0.164 | 0.441 |
| 476 | 0.031 | 0.014 |
| 478 | 0.088 | 0.129 |
| 479 | 0.117 | 0.064 |
| 480 | 0.151 | 0.084 |
| 481 | 0.114 | 0.086 |
| 482 | 0.103 | 0.031 |
| 483 | 0.101 | 0.027 |
| 485 | 0.221 | 0.424 |
| 486 | 0.140 | 0.072 |
| 487 | 0.091 | 0.026 |
| 488 | 0.151 | 0.027 |
| 489 | 0.133 | 0.014 |
| 490 | 0.212 | 0.468 |

TABLE 20

| Example No. | CEN IC$_{50}$ (μM) | CPE EC$_{50}$ (μM) |
|---|---|---|
| 491 | 0.069 | 0.099 |
| 492 | 0.121 | 0.160 |
| 493 | 0.112 | 0.101 |
| 495 | 0.277 | 0.310 |
| 496 | 0.170 | 0.177 |
| 497 | 0.215 | 0.511 |
| 498 | 0.161 | 0.351 |
| 502 | 0.042 | 0.142 |
| 506 | 0.247 | 1.620 |
| 507 | 0.063 | 0.197 |
| 508 | 0.036 | 0.056 |
| 509 | 0.015 | 0.014 |
| 511 | 0.175 | 0.015 |
| 514 | 0.049 | 0.018 |
| 515 | 0.197 | 0.019 |
| 516 | 0.039 | 0.017 |
| 518 | 0.049 | 0.024 |
| 520 | 0.212 | 0.017 |
| 521 | 0.191 | 0.015 |
| 522 | 0.039 | 0.014 |
| 523 | 0.035 | 0.014 |
| 524 | 0.057 | 0.026 |
| 525 | 0.141 | 0.090 |
| 526 | 0.044 | 0.019 |
| 527 | 0.127 | 0.088 |
| 532 | 0.098 | 0.075 |
| 533 | 0.065 | 0.391 |
| 534 | 0.165 | 1.200 |
| 536 | 0.071 | 0.027 |
| 537 | 0.152 | 0.022 |
| 538 | 0.196 | 0.030 |
| 544 | 0.168 | 0.051 |
| 546 | 0.202 | 0.124 |

TABLE 21

| Example No. | CEN IC$_{50}$ (μM) | CPE EC$_{50}$ (μM) |
|---|---|---|
| 547 | 0.032 | 0.027 |
| 548 | 0.086 | 0.038 |
| 549 | 0.076 | 2.100 |
| 550 | 0.042 | 0.042 |
| 551 | 0.041 | 0.107 |
| 552 | 0.230 | 0.085 |
| 553 | 0.028 | 0.030 |
| 554 | 0.065 | 0.465 |
| 555 | 0.023 | 0.012 |
| 556 | 0.023 | 0.412 |
| 557 | 0.281 | 2.470 |
| 558 | 0.114 | 0.541 |
| 560 | 0.027 | 0.173 |
| 561 | 0.073 | 0.008 |
| 562 | 0.022 | 0.062 |
| 563 | 0.049 | 0.464 |
| 564 | 0.088 | 0.136 |
| 565 | 0.154 | 0.726 |
| 568 | 0.264 | 2.810 |
| 569 | 0.138 | 1.010 |
| 570 | 0.081 | 2.050 |
| 571 | 0.065 | 0.320 |
| 573 | 0.055 | 0.158 |
| 574 | 0.165 | 0.442 |
| 575 | 0.058 | 0.087 |
| 576 | 0.063 | 0.027 |
| 577 | 0.233 | 0.337 |
| 581 | 0.083 | 0.480 |

Test Example 7: Influenza Virus-Infected Mouse Lethality Inhibitory Test

<Mouse>

BALB/cAnNCrlCrlj (female, 5-week-old; CHARLES RIVER LABORATORIES JAPAN, INC.) was purchased, and 6- to 7-week-old mice were used in the test.

<Preparation of Virus Solution>

A/Victoria/3/75 or B/Maryland/1/59 (ATCC) was passaged in mouse lung to make a mouse-acclimatized virus. A freezing-stored mouse-acclimatized virus solution was rapidly thawed, and diluted with DPBS to an infectivity titer to be used (in the case of A/Victoria/3/75:750 TCID$_{50}$/mouse, in the case of B/Maryland/1/59:100 TCID$_{50}$/mouse).

<Infection>

Under anesthesia with ketamine*xylazine, 100 ul of the prepared virus solution was nasally inoculated to directly infect mouse lung.

<Preparation of Test Sample>

A test sample was dissolved in a 5% DMAA/20% HP-β-CD aqueous solution to a suitable concentration.

<Administration of Test Sample to Infected Mouse>

A suitably diluted test sample was intravenously administered at 200 ul to a mouse immediately after virus infection, by a single dose.

<Drug Efficacy Assessment>

The mouse was reared for 14 days after virus infection, and a necessary dose per day for 50% lethality inhibition, ED$_{50}$ (mg/kg/day), a lethality inhibition rate at a maximum dose (% survival), or days during which the mouse survives 50% as compared with a control at a maximum dose (50% life extension days) was calculated.

<Euthanasia>

The mouse after completion of the test was euthanized by carbon dioxide or halothane excessive administration.

The present compound exhibits the effect of inhibiting lethality of an influenza virus-infected mouse in the above test. Therefore, the present compound is effective in treating and/or preventing an influenza infectious disease.

Formulation Example 1

A granule containing the following ingredients is manufactured.

| Ingredient | A compound shown by formula (I) | 10 mg |
|---|---|---|
| | lactose | 700 mg |
| | cornstarch | 274 mg |
| | HPC-L | 16 mg |
| | | 1000 mg |

A compound shown by formula (I) and lactose are passed through a 60 mesh sieve. Corn starch is passed through a 120 mesh sieve. These are mixed with V-type blender. To the mixture, aqueous HPC-L (low viscosity of hydroxypropylcellulose) is added, then the mixture is kneaded together, granulated (extrusive granulation pore diameter 0.5~1 mm), and dried. The obtained dried granule is passed through vibrating sieve (12/60 mesh) to obtain a granule.

Formulation Example 2

A granule for encapsulation containing the following ingredients is manufactured.

| Ingredient | A compound shown by formula (I) | 15 mg |
|---|---|---|
| | lactose | 90 mg |
| | cornstarch | 42 mg |
| | HPC-L | 3 mg |
| | | 150 mg |

A compound shown by formula (I) and lactose are passed through a 60 mesh sieve. Corn starch is passed through a 120 mesh sieve. These are mixed and aqueous HPC-L (low viscosity of hydroxypropylcellulose) is added thereto, then the mixture is kneaded together, granulated, and dried. The obtained dried granule is trimmed and 150 mg thereof is filled into a No. 4 hard gelatin capsule.

Formulation Example 3

A tablet containing the following ingredients is manufactured.

| Ingredient | A compound shown by formula (I) | 10 mg |
|---|---|---|
| | lactose | 90 mg |
| | microcrystal cellulose | 30 mg |
| | CMC-Na | 15 mg |
| | Magnesium stearate | 5 mg |
| | | 150 mg |

A compound shown by formula (I), lactose, and microcrystal cellulose, CMC-Na (carboxymethylcellulose sodium salt) are passed through a 60 mesh sieve and mixed. Magnesium stearate is added to the mixed powder to obtain a mixture for tablet. The mixture is tabletted directly to obtain a 150 mg tablet.

Formulation Example 4

An injectable solution is manufactured by mixing the following ingredients under warming, followed by sterilization.

| Ingredient | A compound shown by formula (I) | 3 mg |
|---|---|---|
| | non-ion surfactant | 15 mg |
| | Water for injection | 1 ml |

INDUSTRIAL APPLICABILITY

The compound of the present invention has cap-dependent endonuclease (CEN) inhibitory activity. The compound of the present invention can be a useful agent for treatment and/or prevention of symptom and/or disease induced by infection with influenza virus.

The invention claimed is:

1. A compound represented by formula (II), or a pharmaceutically acceptable salt thereof or a solvate thereof:

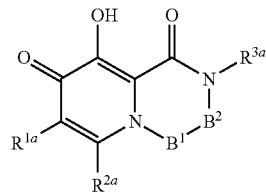

(II)

(wherein
$R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy optionally substituted by substituent group C, heterocycleoxycarbonyl optionally substituted by substituent group C, —Z—N($R^{41}$)($R^{42}$),
—Z—N($R^{43}$)—SO$_2$—($R^{44}$),
—Z—C(=O)—N($R^{45}$)—SO$_2$—($R^{46}$),
—Z—N($R^{47}$)—C(=O)—$R^{48}$,
—Z—S—$R^{49}$,
—Z—SO$_2$—$R^{410}$,
—Z—S(=O)—$R^{411}$,
—Z—N($R^{412}$)—C(=O)—O—$R^{413}$,
—Z—N($R^{414}$)—C(=O)—N($R^{415}$)($R^{416}$),
—Z—C(=O)—N($R^{417}$)—C(=O)—N($R^{418}$)($R^{419}$), or
—Z—N($R^{420}$)—C(=O)—C(=O)—$R^{421}$ (wherein $R^{41}$, $R^{42}$, $R^{43}$, $R^{45}$, $R^{47}$, $R^{48}$, $R^{49}$, $R^{412}$, $R^{413}$, $R^{414}$, $R^{415}$, $R^{416}$, $R^{417}$, $R^{418}$, $R^{419}$, $R^{420}$, and $R^{421}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{44}$, $R^{46}$, $R^{410}$, and $R^{411}$ are each independently selected from a substituent group consisting of, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{A1}$ and $R^{A2}$, $R^{A15}$ and $R^{A16}$, and $R^{A18}$ and $R^{A19}$ each may be taken together with an adjacent atom to form heterocycle, and Z is a bond or straight or branched lower alkylene);

$R^{2a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C, —Z—N($R^{B1}$)—SO$_2$—$R^{B2}$,
—Z—N($R^{B3}$)—C(=O)—$R^{B4}$,
—Z—N($R^{B5}$)—C(=O)—O—$R^{B6}$,
—Z—C(=O)—N($R^{B7}$)($R^{B8}$),
—Z—N($R^{B9}$)($R^{B10}$), or
—Z—SO$_2$—$R^{B11}$ (wherein $R^{B1}$, $R^{B3}$, $R^{B4}$, $R^{B5}$, $R^{B6}$, $R^{B7}$, $R^{B8}$, $R^{B9}$, and $R^{B10}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B2}$ and $R^{B11}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{B7}$ and $R^{B8}$, and $R^{B9}$ and $R^{B10}$ each may be taken together with an adjacent atom to form heterocycle, and Z is a bond or straight or branched lower alkylene);

$B^1$ is $NR^{7a}$ and $B^2$ is $CR^{5a}R^{6a}$, $R^{3a}$ and $R^{6a}$ are taken together with an adjacent atom to form heterocycle optionally substituted by substituent group D, $R^{5a}$ and $R^{7a}$ are each independently selected from a substituent group consisting of hydrogen, carboxy, cyano, lower alkyl optionally substituted by substituent group C, lower alkenyl optionally substituted by substituent group C, lower alkynyl optionally substituted by substituent group C, lower alkyl carbonyl optionally substituted by substituent group C, lower alkyl oxycarbonyl optionally substituted by substituent group C, carbocyclic group optionally substituted by substituent group C, carbocycle lower alkyl optionally substituted by substituent group C, carbocycleoxy lower alkyl optionally substituted by substituent group C, carbocyclecarbonyl optionally substituted by substituent group C, carbocycleoxycarbonyl optionally substituted by substituent group C, heterocyclic group optionally substituted by substituent group C, heterocycle lower alkyl optionally substituted by substituent group C, heterocycleoxy lower alkyl optionally substituted by substituent group C, heterocyclecarbonyl optionally substituted by substituent group C, heterocycleoxycarbonyl optionally substituted by substituent group C, —Y—S—$R^{D1}$,
—Z—S(=O)—$R^{D2}$,
—Z—SO$_2$—$R^{D3}$,
—C(=O)—C(=O)—$R^{D4}$,
—C(=O)—N($R^{D5}$)($R^{D6}$),
—Z—C($R^{D7}$)($R^{D8}$)($R^{D9}$),
—Z—CH$_2$—$R^{D10}$,
—Z—N($R^{D11}$)—C(=O)—O—$R^{D12}$, or
—Z—N($R^{D13}$)—C(=O)—$R^{D14}$ (wherein $R^{D1}$, $R^{D4}$, $R^{D5}$, $R^{D6}$, $R^{D9}$, $R^{D11}$, $R^{D12}$, $R^{D13}$, and $R^{D14}$ are each independently selected from a substituent group consisting of hydrogen, lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D2}$, and $R^{D3}$ are each independently selected from a substituent group consisting of lower alkyl optionally substituted by substituent group C, lower alkenyl optionally substituted by substituent group C, lower alkynyl optionally substituted by substituent group C, carbocyclic group optionally substituted by substituent group C, heterocyclic group optionally substituted by substituent group C, carbocycle lower alkyl optionally substituted by substituent group C, and heterocycle lower alkyl optionally substituted by substituent group C, $R^{D7}$, $R^{D8}$, and $R^{D10}$ are each independently selected from a substituent group consisting of carbocyclic group optionally substituted by substituent group C, heterocyclic group optionally substituted by substituent group C, $R^{D5}$ and $R^{D6}$ may be taken together with an adjacent atom to form heterocycle, Y is straight or branched lower alkylene, and Z is a bond or straight or branched lower alkylene);

$R^{D5}$ and $R^{D6}$ may be taken together with an adjacent atom to form carbocycle;

Substituent group C: halogen, cyano, hydroxy, carboxy, formyl, amino, oxo, nitro, lower alkyl, halogeno lower alkyl, lower alkyloxy, lower alkylthio, hydroxy lower alkyl, carbocyclic group, heterocyclic group, heterocyclic group substituted by oxo, carbocycle lower alkyloxy, carbocycleoxy lower alkyl, carbocycle lower alkyloxy lower alkyl, heterocycle lower alkyloxy, heterocycleoxy lower alkyl, heterocycle lower alkyloxy lower alkyl, halogeno lower alkyloxy, lower alkyloxy lower alkyl, lower alkyloxy lower alkyloxy, lower alkylcarbonyl, lower alkylcarbonyloxy, lower alkyloxycarbonyl, lower alkylamino, lower alkylcarbonylamino, halogeno lower alkyl carbonylamino, lower alkylaminocarbonyl, lower alkylsulfonyl, lower alkylsulfinyl, and lower alkylsulfonylamino;

Substituent group D: halogen, cyano, hydroxy, carboxy, formyl, amino, oxo, nitro, lower alkyl, halogeno lower alkyl, lower alkyloxy, carbocycle lower alkyloxy, heterocycle lower alkyloxy, halogeno lower alkyloxy, lower alkyloxy lower alkyl, lower alkyloxy lower alkyloxy, lower alkylcarbonyl, lower alkyloxycarbonyl, lower alkylamino, lower alkylcarbonylamino, lower alkylaminocarbonyl, lower alkylsulfonyl, lower alkylsulfonylamino, carbocyclic group optionally substituted by substituent group C, heterocyclic group optionally substituted by substituent group C, carbocycle lower alkyl optionally substituted by substituent group C, and heterocycle lower alkyl optionally substituted by substituent group C).

2. The compound according to claim 1, or the pharmaceutically acceptable salt thereof or the solvate thereof, wherein $R^{1a}$ is hydrogen, halogen, hydroxy, carboxy, cyano, formyl, lower alkyl optionally substituted by substituent group C, lower alkenyl optionally substituted by substituent group C, lower alkynyl optionally substituted by substituent group C, lower alkyloxy optionally substituted by substituent group C, lower alkenyloxy optionally substituted by substituent group C, lower alkylcarbonyl optionally substituted by substituent group C, lower alkyloxycarbonyl optionally substituted by substituent group C, carbocyclic group optionally substituted by substituent group C, carbocycle lower alkyl optionally substituted by substituent group C, carbocyclecarbonyl optionally substituted by substituent group C, carbocycleoxy optionally substituted by substituent group C, carbocycleoxycarbonyl optionally substituted by substituent group C, heterocyclic group optionally substituted by substituent group C, heterocycle lower alkyl optionally substituted by substituent group C, heterocyclecarbonyl optionally substituted by substituent group C, heterocycleoxy optionally substituted by substituent group C, heterocycleoxycarbonyl optionally substituted by substituent group C,
—Z—N($R^{41}$)($R^{42}$),
—Z—N($R^{43}$)—$SO_2$—($R^{44}$),
—Z—N($R^{47}$)—C(=O)—$R^{48}$,
—Z—S—$R^{49}$,
—Z—$SO_2$—$R^{410}$,
—Z—N($R^{412}$)—C(=O)—O—$R^{413}$, or
—Z—N($R^{420}$)—C(=O)—C(=O)—$R^{421}$
(substituent group C, $R^{41}$, $R^{42}$, $R^{43}$, $R^{44}$, $R^{47}$, $R^{48}$, $R^{49}$, $R^{410}$, $R^{412}$, $R^{413}$, $R^{420}$, $R^{421}$, and Z are same meaning as those of claim 1).

3. The compound according to claim 1, or the pharmaceutically acceptable salt thereof or the solvate thereof, wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkylcarbonyl optionally substituted by substituent group C, lower alkyloxycarbonyl optionally substituted by substituent group C, heterocyclic group optionally substituted by substituent group C,
—Z—N($R^{41}$)($R^{42}$),
—Z—N($R^{47}$)—C(=O)—$R^{48}$, or
—Z—N($R^{412}$)—C(=O)—O—$R^{413}$
(substituent group C, $R^{41}$, $R^{42}$, $R^{47}$, $R^{48}$, $R^{412}$, $R^{413}$, and Z are same as those of claim 1).

4. The compound according to claim 1, or the pharmaceutically acceptable salt thereof or the solvate thereof, wherein $R^{1a}$ is hydrogen, halogen, hydroxy, carboxy, lower alkyl optionally substituted by substituent group C, lower alkenyl optionally substituted by substituent group C, lower alkyloxy optionally substituted by substituent group C, lower alkyloxycarbonyl optionally substituted by substituent group C, heterocyclic group optionally substituted by substituent group C, or
—Z—N($R^{41}$)($R^{42}$)
(substituent group C, $R^{41}$, $R^{42}$, and Z are same as those of claim 1).

5. The compound according to claim 1, or the pharmaceutically acceptable salt thereof or the solvate thereof, wherein $R^{1a}$ is hydrogen, or carboxy.

6. The compound according to claim 1, or the pharmaceutically acceptable salt thereof or the solvate thereof, wherein $R^{2a}$ is hydrogen, lower alkyl optionally substituted by substituent group C, carbocycle lower alkyl optionally substituted by substituent group C, heterocycle lower alkyl optionally substituted by substituent group C, or
—Z—N($R^{B9}$)($R^{B10}$)
(substituent group C, $R^{B9}$, $R^{B10}$, and Z are same as those of claim 1).

7. The compound according to claim 1, or the pharmaceutically acceptable salt thereof or the solvate thereof, wherein $R^{2a}$ is hydrogen or lower alkyl optionally substituted by substituent group C (substituent group C is same as that of claim 1).

8. The compound according to claim 1, or the pharmaceutically acceptable salt thereof or the solvate thereof, wherein the formula (II) is the formula (II″) represented by

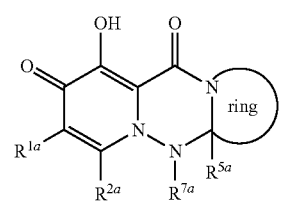

(II″)

wherein ring is a 5- to 7-membered heterocycle ring ($R^{1a}$, $R^{2a}$, $R^{5a}$, $R^{7a}$ and $R^{412}$ are same as those of claim 1).

9. The compound according to claim 8, or the pharmaceutically acceptable salt thereof or the solvate thereof, wherein $R^{7a}$ is the following groups:

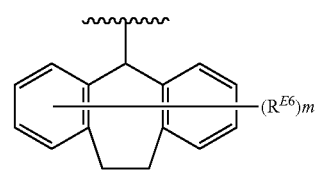

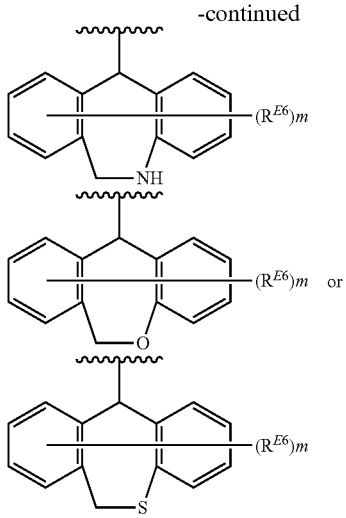

wherein $R^{E6}$ is selected from a substituent group C,
m is an integer of 0 or more.

10. The compound according to claim 1, or the pharmaceutically acceptable salt thereof or the solvate thereof,
wherein substituent group D is carbocyclic group optionally substituted by substituent group C, heterocyclic group optionally substituted by substituent group C, carbocycle lower alkyl optionally substituted by substituent group C, or heterocycle lower alkyl optionally substituted by substituent group C
(wherein substituent group C is same as that of claim 1).

11. A pharmaceutical composition containing a compound according to claim 1, or a pharmaceutically acceptable salt thereof or a solvate thereof, and further comprising at least one pharmaceutically acceptable ingredient.

12. A method for treating influenza infectious disease, the method comprising administering the compound according to claim 1 or the pharmaceutically acceptable salt thereof or the solvate thereof.

* * * * *

UNITED STATES PATENT AND TRADEMARK OFFICE
CERTIFICATE OF CORRECTION

PATENT NO. : 9,815,835 B2  
APPLICATION NO. : 15/252791  
DATED : November 14, 2017  
INVENTOR(S) : Toshiyuki Akiyama et al.

Page 1 of 1

It is certified that error appears in the above-identified patent and that said Letters Patent is hereby corrected as shown below:

Claim 1, Column 525, Lines 1-2, "each ma y be" should read --each may be--.

Signed and Sealed this
Twenty-second Day of May, 2018

Andrei Iancu
*Director of the United States Patent and Trademark Office*